(12) United States Patent
Duncton et al.

(10) Patent No.: US 12,037,357 B2
(45) Date of Patent: Jul. 16, 2024

(54) COMPOUNDS FOR ACTIVATING INVARIANT NATURAL KILLER T-CELLS AND METHODS OF USE IN ELIMINATING INFLAMMATORY SENESCENT CELLS

(71) Applicant: Deciduous Therapeutics, Inc., San Francisco, CA (US)

(72) Inventors: Matthew Duncton, Las Vegas, NV (US); Thomas Bobinski, San Diego, CA (US); Robin Mansukhani, San Francisco, CA (US)

(73) Assignee: Deciduous Therapeutics, Inc., San Francisco, CA (US)

(*) Notice: Subject to any disclaimer, the term of this patent is extended or adjusted under 35 U.S.C. 154(b) by 0 days.

(21) Appl. No.: 18/458,973

(22) Filed: Aug. 30, 2023

(65) Prior Publication Data

US 2024/0025936 A1  Jan. 25, 2024

Related U.S. Application Data

(63) Continuation of application No. PCT/US2022/018151, filed on Feb. 28, 2022.

(60) Provisional application No. 63/155,200, filed on Mar. 1, 2021.

(51) Int. Cl.
*C07H 15/04* (2006.01)
*A61P 37/06* (2006.01)

(52) U.S. Cl.
CPC .............. *C07H 15/04* (2013.01); *A61P 37/06* (2018.01)

(58) Field of Classification Search
CPC ........ C07H 15/04; C07H 15/18; C07H 15/26; C07H 15/06; A61P 37/06; A61P 43/00; A61K 31/7056; A61K 35/17
See application file for complete search history.

(56) References Cited

U.S. PATENT DOCUMENTS

| | | | |
|---|---|---|---|
| 7,645,873 B2 | 1/2010 | Savage et al. |
| 7,928,077 B2 | 4/2011 | Wong et al. |
| 7,989,423 B2 | 8/2011 | Savage et al. |
| 8,163,705 B2 | 4/2012 | Tashiro et al. |
| 8,188,313 B2 | 5/2012 | Cerundolo et al. |
| 8,445,272 B2 | 5/2013 | Savage et al. |
| 8,835,613 B2 | 9/2014 | Berzofsky et al. |
| 9,045,512 B2 | 6/2015 | Savage et al. |
| 9,139,809 B2 | 9/2015 | Porcelli et al. |
| 9,168,291 B2 | 10/2015 | Berzofsky et al. |
| 9,181,292 B2 | 11/2015 | Liang |
| 9,295,722 B2 | 3/2016 | Savage et al. |
| 9,365,496 B2 | 6/2016 | Cerundolo et al. |
| 9,371,352 B2 | 6/2016 | Porcelli et al. |
| 9,821,035 B2 | 11/2017 | Duramad et al. |
| 9,932,402 B2 | 4/2018 | Truneh et al. |
| 10,111,950 B2 | 10/2018 | Porcelli et al. |
| 10,111,951 B2 | 10/2018 | Wong et al. |
| 10,314,796 B2 | 6/2019 | Cerundolo et al. |
| 10,383,932 B2 | 8/2019 | Deisseroth |
| 10,443,041 B2 | 10/2019 | Wang et al. |
| 10,501,541 B2 | 12/2019 | Van der Vliet et al. |
| 10,519,197 B1 | 12/2019 | Hudson et al. |
| 10,654,880 B2 | 5/2020 | Liang |
| 10,765,648 B2 | 9/2020 | Cerundolo et al. |
| 10,918,714 B2 | 2/2021 | Wong et al. |
| 10,919,926 B2 | 2/2021 | Inuki et al. |
| 11,649,211 B2 | 5/2023 | Tazi et al. |
| 2002/0035082 A1 | 3/2002 | Grinstaff et al. |
| 2006/0116332 A1 | 6/2006 | Strober et al. |
| 2009/0162385 A1 | 6/2009 | Serra |
| 2010/0197613 A1 | 8/2010 | Strober et al. |
| 2013/0005669 A1 | 1/2013 | Tashiro et al. |

(Continued)

FOREIGN PATENT DOCUMENTS

| CN | 111320598 A | 6/2020 |
| CN | 113825509 A | 12/2021 |

(Continued)

OTHER PUBLICATIONS

Baek et al., (2010). "Rational Design and Evaluation of a Branched-Chain-Containing Glycolipid Antigen That Binds to CD1d," Chem Asian J., 5(7):1560-1564.

Birkholz et al., (2015). "Lipid and Carbohydrate Modifications of α-Galactosylceramide Differently Influence Mouse and Human Type I Natural Killer T Cell Activation," J Biol Chem., 290(28):17206-17217.

(Continued)

*Primary Examiner* — David Browe
(74) *Attorney, Agent, or Firm* — MORRISON & FOERSTER LLP

(57) ABSTRACT

Compounds as depicted below and structural analogues thereof for activating invariant natural killer T cells (iNKT) cells are provided.

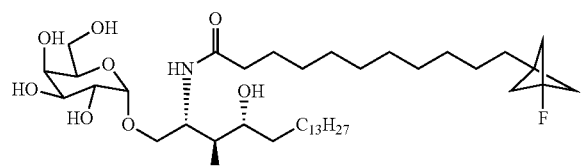

Such compounds may be used to activate iNKT cells and induce an increase in the production of one or more cytokines, such as IFNγ, IL-2, IL-4, IL-6 and TNFα. Activated iNKT cells may be used to selectively reduce the presence of or eliminate inflammatory senescent cells, such as senescent cells having an inflammatory secretome (SASP). Also provided are pharmaceutical compositions comprising such compounds.

18 Claims, 17 Drawing Sheets

(56) References Cited

U.S. PATENT DOCUMENTS

| | | | |
|---|---|---|---|
| 2013/0136735 | A1 | 5/2013 | Truneh et al. |
| 2015/0374734 | A1 | 12/2015 | Trottein et al. |
| 2016/0158258 | A1 | 6/2016 | Chaturvedi |
| 2017/0368002 | A1 | 12/2017 | Cerundolo et al. |
| 2018/0170957 | A1 | 6/2018 | Wong et al. |
| 2018/0250321 | A1* | 9/2018 | Schroeder ............... A61P 35/04 |
| 2019/0119371 | A1 | 4/2019 | Gruber |
| 2019/0125795 | A1 | 5/2019 | Rosen et al. |
| 2019/0255119 | A1 | 8/2019 | Marban et al. |
| 2020/0046820 | A1 | 2/2020 | Deisseroth |
| 2020/0115450 | A1 | 4/2020 | Van der Vliet et al. |
| 2021/0060064 | A1 | 3/2021 | Wong |
| 2021/0369862 | A1 | 12/2021 | De Smedt et al. |

FOREIGN PATENT DOCUMENTS

| | | |
|---|---|---|
| EP | 3139675 A1 | 3/2017 |
| WO | WO-2003016326 A1 | 2/2003 |
| WO | WO-2004072091 A1 | 8/2004 |
| WO | WO-2006083671 A2 | 8/2006 |
| WO | WO-2007004705 A1 | 1/2007 |
| WO | WO-2007049819 A1 | 5/2007 |
| WO | WO-2007050668 A1 | 5/2007 |
| WO | WO-2007099999 A1 | 9/2007 |
| WO | WO-2009060086 A2 | 5/2009 |
| WO | WO-2009101475 A2 | 8/2009 |
| WO | WO-2010023498 A1 | 3/2010 |
| WO | WO-2010040710 A1 | 4/2010 |
| WO | WO-2010055340 A1 | 5/2010 |
| WO | WO-2012088414 A1 | 6/2012 |
| WO | WO-2013022985 A2 | 2/2013 |
| WO | WO-2013022996 A2 | 2/2013 |
| WO | WO-2013022997 A2 | 2/2013 |
| WO | WO-2013023000 A2 | 2/2013 |
| WO | WO-2013079687 A1 | 6/2013 |
| WO | WO-2014030708 A1 | 2/2014 |
| WO | WO-2014067995 A1 | 5/2014 |
| WO | WO-2014069655 A1 | 5/2014 |
| WO | WO-2015174278 A1 | 11/2015 |
| WO | WO-2015178288 A1 | 11/2015 |
| WO | WO-2017099079 A1 | 6/2017 |
| WO | WO-2017163808 A1 | 9/2017 |
| WO | WO-2018050782 A1 | 3/2018 |
| WO | WO-2019033119 A1 | 2/2019 |
| WO | WO-2019053142 A1 | 3/2019 |
| WO | WO-2019107431 A1 | 6/2019 |
| WO | WO-2020047462 A2 | 3/2020 |
| WO | WO-2020252441 A2 | 12/2020 |
| WO | WO-2021152129 A1 | 8/2021 |
| WO | WO-2021216934 A1 | 10/2021 |
| WO | WO-2022097287 A1 | 5/2022 |
| WO | WO-2022118913 A1 | 6/2022 |
| WO | WO-2022187141 A1 | 9/2022 |

OTHER PUBLICATIONS

Kim et al., (2014). "Phase transfer agent assisted biphasic CuAAC reaction," RSC Advances, 4:26516-26523.

Lee et al., (2007). "Synthesis and Evaluation of 1,2,3-Triazole Containing Analogues of the Immunostimulant α-GalCer," Journal of Medicinal Chemistry, 50(3):585-589.

Lee at al., (2011). "An α-GalCer analogue with branched acyl chain enhances protective immune responses in a nasal influenza vaccine," Vaccine, 29(3):417-425.

Li et al., (2010). "Design of a potent CD1d-binding NKT cell ligand as a vaccine adjuvant," Proc Natl Acad Sci USA, 107(29):13010-13015.

Li et al., (2015). "Colocalization of a CD1d-Binding Glycolipid with a Radiation-Attenuated Sporozoite Vaccine in Lymph Node-Resident Dendritic Cells for a Robust Adjuvant Effect," J Immunol., 195(6):2710-2721.

Li et al., (2017). "Co-localization of a CD1d-binding glycolipid with an adenovirus-based malaria vaccine for a potent adjuvant effect," Vaccine, 35(24):3171-3177, 15 pages.

Liang et al., (2008). "Quantitative Microarray Analysis of Intact Glycolipid-CD1d Interaction and Correlation with Cell-Based Cytokine Production," Journal of the American Chemical Society, 130(37):12348-12354.

Lin et al., (2010). "In vivo protection provided by a synthetic new alpha-galactosyl ceramide analog against bacterial and viral infections in murine models," Antimicrobial Agents and Chemotherapy, 54(10):4129-4136.

Panza et al., (2019). "A versatile synthesis of aGalCer and its analogues exploiting a cyclic carbonate as phytosphingosine 3,4-diol protecting group," Carbohydrate Research, 472:50-57.

Sakai et al., (1999). "Syntheses of Biotinylated α-Galactosylceramides and Their Effects on the Immune System and CD1 Molecules," J Med Chem, 42(10):1836-1841. Abstract only, 8 pages.

Scherrer et al., (2022). "Demonstration of the Antitumor Activity of the iNKT Agonist ABX196, a Novel Enhancer of Cancer Immunotherapy, in Melanoma and Hepatocarcinoma Mouse Models," Mol Cancer Ther, 21(12):1788-1797.

Seki et al., (2019). "A Potent CD1d-binding Glycolipid for iNKT-Cell-based Therapy Against Human Breast Cancer," Anticancer Res., 39(2):549-555.

Stepan et al., (2012). "Application of the Bicyclo[1.1.1]pentane Motif as a Nonclassical Phenyl Ring Bioisostere in the Design of a Potent and Orally Active γ-Secretase Inhibitor," Journal of Medicinal Chemistry, 55(7):3414-3424.

Tefit et al., (2014). "Efficacy of ABX196, a new NKT agonist, in prophylactic human vaccination," Vaccine, 32:6138-6145.

Xu et al., (2014). "Effective cancer vaccine platform based on attenuated *Salmonella* and a type III secretion system," Cancer Res., 74(21):6260-6270.

International Preliminary Report on Patentability received for International Patent Application No. PCT/US2022/018151 mailed on Aug. 29, 2023, 7 pages.

Waldowska et al., (2017). "A brief review of clinical trials involving manipulation of invariant NKT cells as a promising approach in future cancer therapies," Cen Eur J Immunol, 42(2):181-195.

Bhushan, (2021). "Uncovering immune and senescent cell interactions in disease," Med, 2(8):895-898.

Birkholz et al., (2015). "A novel glycolipid antigen for NKT cells that preferentially induces IFN-γ production," J Immunol, 195(3):924-933, 26 pages.

International Search Report and Written Opinion received for International Patent Application No. PCT/US2022/018151 mailed on Jun. 29, 2022, 10 pages.

Jervis et al., (2013). "Design, Synthesis, and Functional Activity of Labeled CD1d Glycolipid Agonists," Bioconjugate Chemistry, 24(4):586-594.

King et al., (2018). "CD1d-Invariant Natural Killer T Cell- Based Cancer Immunotherapy: α-Galactosylceramide and Beyond," Frontiers in Immunology, 9:1519, 7 pages.

Pauwels et al., (2011). "Divergent synthetic approach to 6"-modified a-GalCer analogues," Org. Biomol. Chem., 9:8413-8421, 20 pages.

Pubchem, (2016). "(11-Tetradecyl-3,6,9-trioxaheptacosane)-1-yl 2-(acetylamino)-2-deoxy-beta-D-glucopyranoside; SID: 272705555," available online at <https://pubchem.ncbi.nlm.nih.gov/substance/272705555>, 5 pages.

Pubchem, (2018). "525-37-1; SID: 374391972," available online at <https://pubchem.ncbi.nlm.nih.gov/substance/374391972>, 4 pages.

Tse et al., (2020). "Nonclassical Phenyl Bioisosteres as Effective Replacements in a Series of Novel Open-Source Antimalarials," J Med Chem, 63(20):11585-11601.

UCSF Health, (2022). "Activating Immune Surveillance Mechanisms Shows Promise for Treating Diabetes and Pulmonary Fibrosis," available online at <https://medconnection.ucsfhealth.org/news/activating-immune-surveillance-mechanisms-shows-promise-for-treating-diabetes-and-pulmonary-fibrosis>, 4 pages.

Clinicaltrials.gov, (2015). "NCT01783691: Safety, Pharmacokinetic, and Pharmacodynamic Study of NKTT120 in Adult Patients With Stable Sickle Cell Disease (SCD)," available online at <https://clinicaltrials.gov/study/NCT01783691?intr=NKTT120&rank=1>, 8 pages.

(56) References Cited

OTHER PUBLICATIONS

Diaz et al., (2009). "Synthesis of threitol ceramide and [14C]threitol ceramide, non-glycosidic analogues of the potent CD1d antigen α-galactosyl ceramide," Tetrahedron: Asymmetry, 20:747-753.

Hsieh et al., (2012). "Synthesis and Evaluation of Acyl-Chain- and Galactose-6"-Modified Analogues of α-GalCer for NKT Cell Activation," ChemBioChem, 13(11):1689-1697.

Kratzer et al., (1998). "Synthesis of D-erythro-Ceramide-1-phosphoinositol and Its Aminoglucosylated Derivative—Intermediates in GPI-Anchor Biosynthesis," Eur. J. Org. Chem, 1998(12):291-298.

\* cited by examiner

Example 2. *In vitro* Activation of Human iTCR through a Jurkat Reporter Cell Line

| Molecule | EC50 (μg/mL) |
|---|---|
| DCD127 | 0.02406 |
| DCD141 | 0.04923 |
| DCD143 | 0.05 |
| DCD144 | 0.05036 |
| DCD136 | 0.05152 |
| DCD133 | 0.06454 |
| DCD122 | 0.06455 |
| DCD155 | 0.07507 |
| DCD118 | 0.08269 |
| DCD121 | 0.08341 |
| DCD101 | 0.0999 |
| DCD138 | 0.1134 |
| DCD153 | 0.126 |
| DCD119 | 0.1338 |
| DCD149 | 0.1612 |
| DCD150 | 0.2071 |
| DCD139 | 0.2182 |
| DCD125 | 0.2531 |
| DCD148 | 0.2537 |
| DCD103 | 0.2847 |
| DCD113 | 0.2992 |
| DCD106 | 0.308 |
| DCD114 | 0.3427 |
| DCD151 | 0.362 |
| DCD137 | 0.3939 |
| DCD128 | 0.427 |
| DCD156 | 0.4283 |
| DCD104 | 0.5047 |
| DCD130 | 0.5314 |
| DCD140 | 0.5607 |
| DCD157 | 0.5616 |
| αGalCer | 0.5973 |

| Molecule | EC50 (μg/mL) |
|---|---|
| DCD129 | 0.6665 |
| DCD105 | 0.6849 |
| DCD147 | 1.009 |
| DCD154 | 1.491 |
| DCD146 | 1.666 |
| DCD123 | 1.981 |
| DCD131 | 2.045 |
| DCD120 | 2.435 |
| DCD126 | 2.686 |
| DCD132 | 3.097 |
| DCD145 | 4.341 |
| DCD134 | 4.769 |
| DCD158 | 5.177 |
| DCD116 | 5.334 |
| DCD102 | 8.596 |
| DCD124 | 12.33 |
| DCD108 | 13.14 |
| DCD135 | 14.81 |
| DCD142 | 14.87 |
| DCD115 | 20.07 |
| DCD152 | 37.81 |
| DCD112 | 74.58 |
| DCD159 | 178.8 |

Figure 1

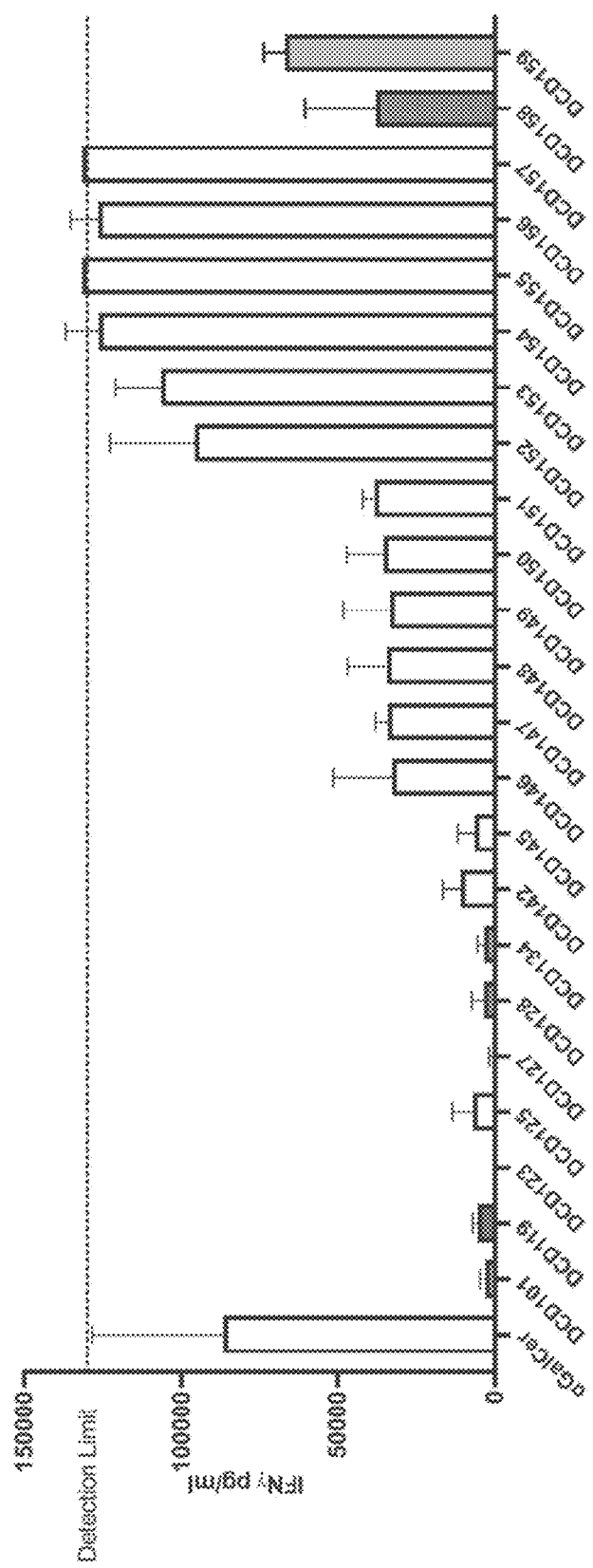

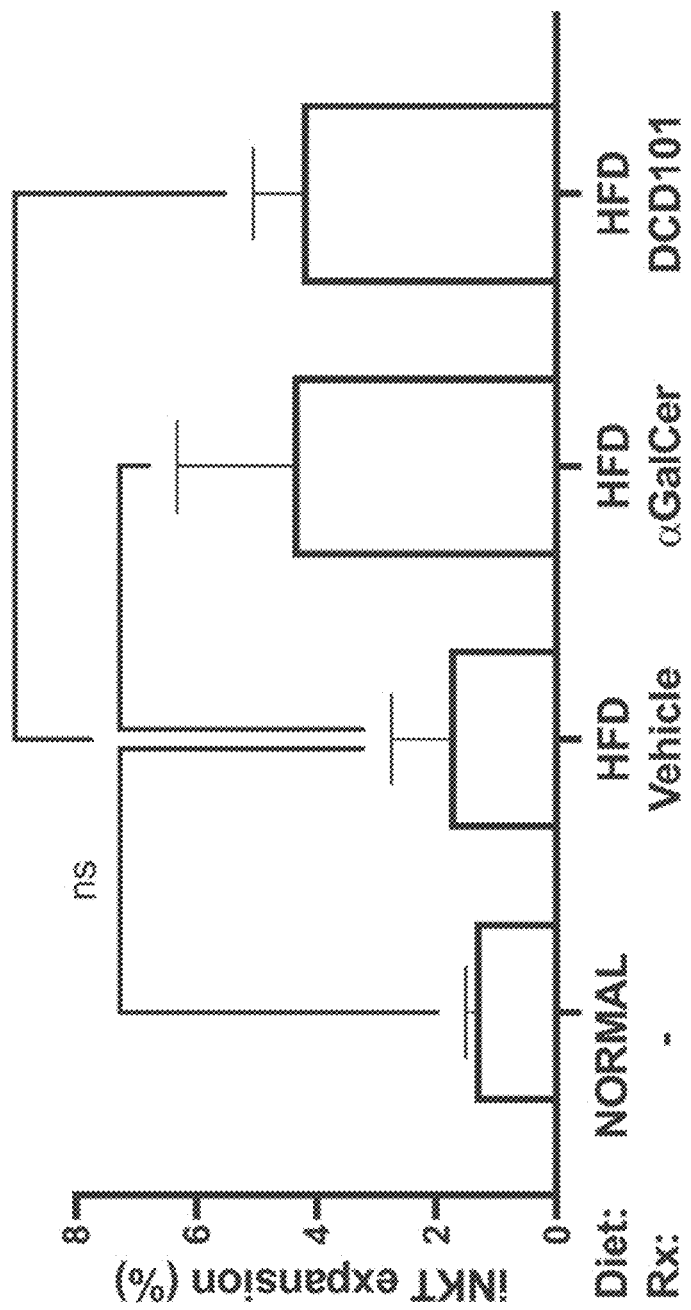

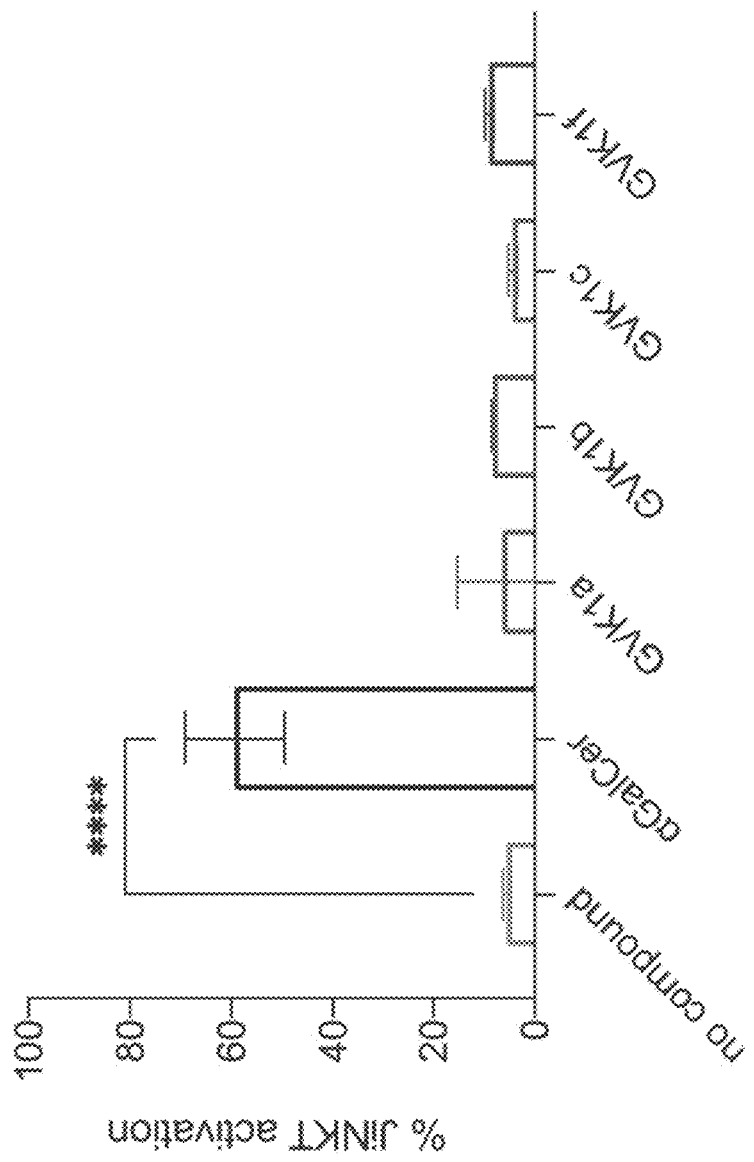

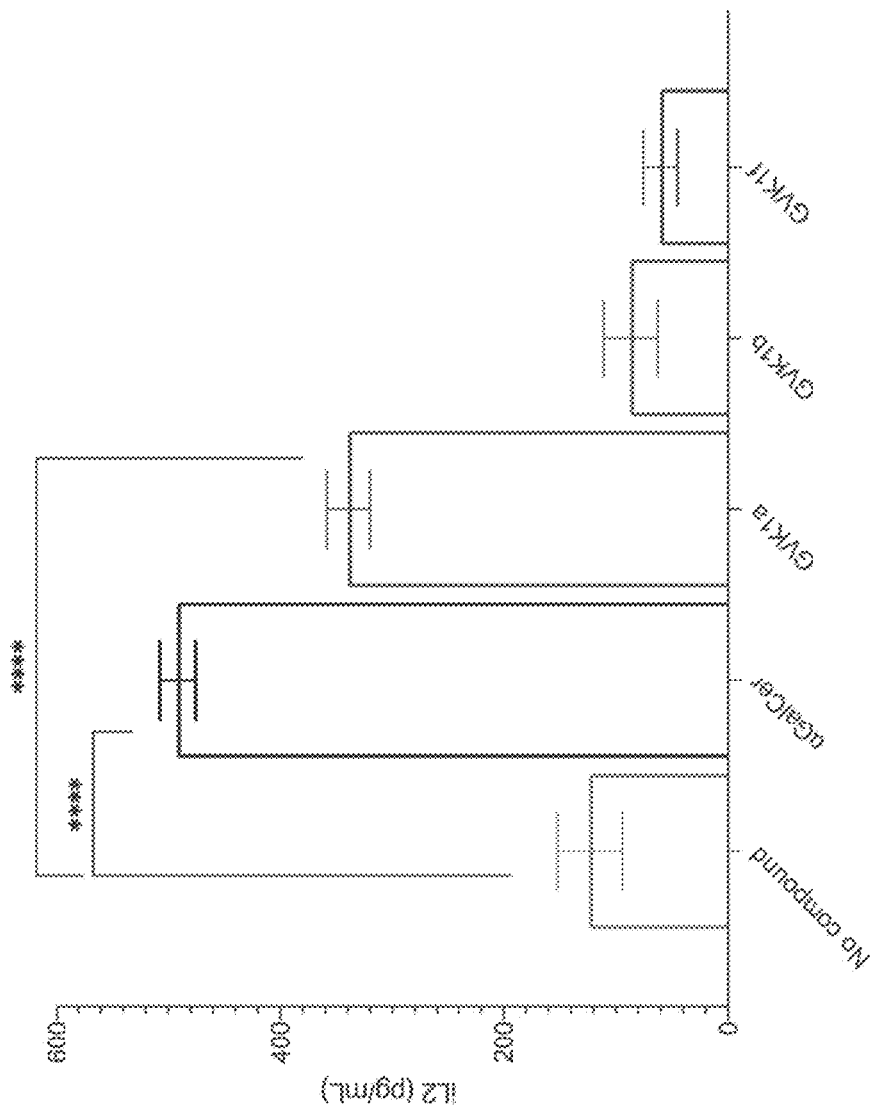

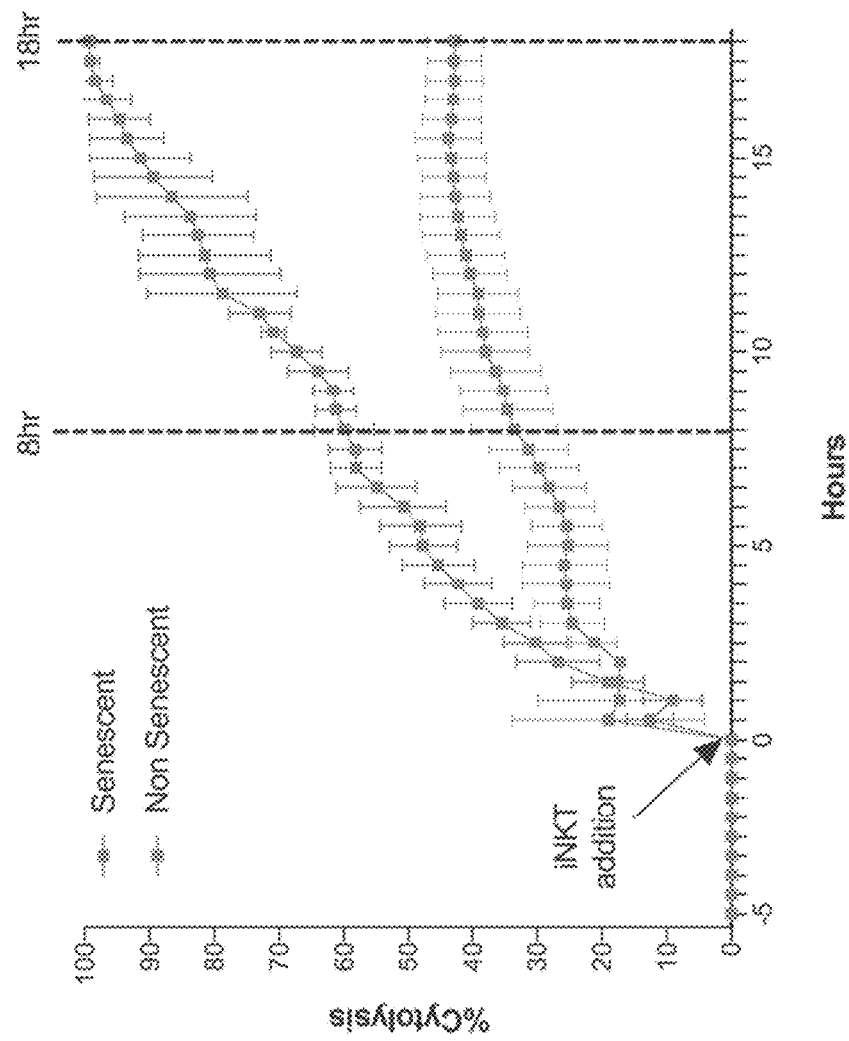

Example 8. In vitro killing assay

COMPOUNDS FOR ACTIVATING INVARIANT NATURAL KILLER T-CELLS AND METHODS OF USE IN ELIMINATING INFLAMMATORY SENESCENT CELLS

CROSS-REFERENCE TO RELATED APPLICATIONS

This application is a continuation application of International Application No. PCT/US2022/018151, filed internationally on Feb. 28, 2022, which claims priority to U.S. Application No. 63/155,200, filed on Mar. 1, 2021.

INTRODUCTION

In a healthy system, the immune system naturally (endogenously) clears senescent cells. When this immune function is compromised, senescent cells build up and can propagate into a multitude of different diseases. Invariant natural killer T (iNKT) cells are a subset of T cells that recognize glycolipid antigens bound to the cluster of differentiation (CD)1d molecule expressed by surface antigen presenting cells. Recognition of exogenous and endogenous lipids can aid in immune response to maladies such as autoimmune disease, allergic disease, metabolic syndrome, cancer and pathogen infection. Although iNKT cells have been shown to mediate immune responses based on cytokine release, iNKT cells can also function as effectors by cell cytotoxicity.

SUMMARY

Compounds for activating invariant natural killer T cells (INKT) cells are provided. Compounds according to certain embodiments activate iNKT cells and induce an increase in the production of one or more cytokines, such as IFNγ, IL-2, IL-4, IL-6 and TNFα. In some embodiments, activated iNKT cells are used to selectively reduce the presence of or eliminate inflammatory senescent cells, such as senescent cells having an inflammatory secretome (SASP). Methods for activating iNKT cells by contacting an iNKT cell with an amount of the subject compounds and selectively reducing the presence of or eliminating senescent cells with activated iNKT cells are also described. Compositions for practicing the subject methods are also described.

In some embodiments, compounds of interest include a compound of formula DCD-(I):

wherein:

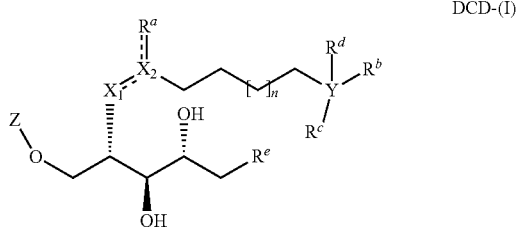

DCD-(I)

Z is selected from:

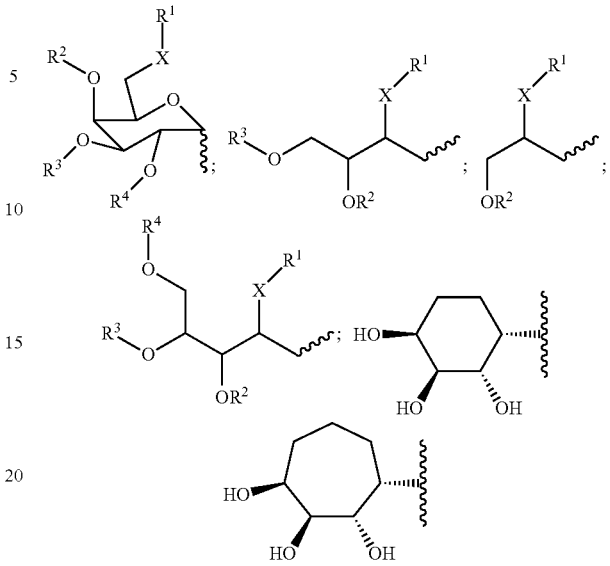

wherein ∼∼∼ indicates the Z—O bond;

wherein X is —NHCO— or oxygen;

$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

$X_1$ and $X_2$ are each independently selected from —C, —$NR^j$, —O, —$SR^k$, —Si, wherein $R^j$ and $R^k$ are each independently selected from hydrogen, alkyl or substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

$R^a$ is selected from hydrogen, oxygen, fluorine, —$CF_3$, or together with $X_2$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

wherein ==== indicates a double or single bond;

n is an integer from 2 to 25;

Y is selected from carbon, nitrogen or silicon;

$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^e$ and $R^d$ together with Y form a cycloalkyl, substituted cycloalkyl, aryl, substituted aryl, heteroaryl or substituted heteroaryl group; and $R^e$ is alkyl or substituted alkyl, or salt, solvate or hydrate thereof.

In some instances, $R^1$ is hydrogen. In some instances, $R^2$ is hydrogen. In some instances, $R^3$ is hydrogen. In some instances, $R^4$ is hydrogen. In some instances, each of $R^1$, $R^2$, $R^3$, $R^4$ are each hydrogen.

In certain instances, R¹ is:

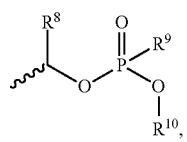

wherein ~~~ represents the R¹—O bond;

R⁸ is hydrogen, alkyl or substituted alkyl; In some instances, R⁸ is selected from hydrogen, methyl, ethyl and cyclopropyl.

R⁹ is —NR$^f$ or —OR$^f$, wherein R$^f$ is alkyl, substituted alkyl, acyl, alkylacyl or substituted alkylacyl, or wherein R$^f$ together with R¹⁰ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and R¹⁰ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein R¹⁰ together with R$^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In certain instances, R¹ is selected from:

1)

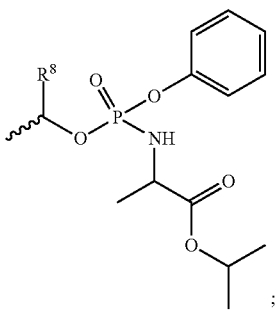

2)

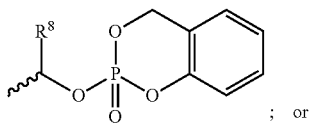
; or

3)

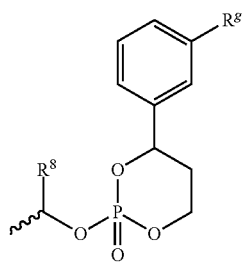

wherein ~~~ represents the R¹—O bond;

R⁸ is hydrogen, alkyl, substituted alkyl; and

R⁹ is hydrogen or a halogen selected from fluorine, chlorine, bromine or iodine.

In certain instances, R¹ is:

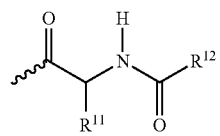

wherein:

R¹¹ is alkyl or substituted alkyl;

R¹² is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, R¹¹ is selected from methyl, ethyl, n-propyl, iso-propyl, n-butyl, iso-butyl, t-butyl. In certain instances, R¹¹ is iso-propyl.

In certain instances, R¹ is:

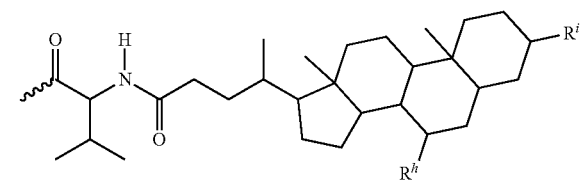

wherein R$^h$ and R$^i$ are each independently selected from hydrogen, hydroxyl or halogen. In some instances, R$^h$ is hydroxyl. In some instances, R$^h$ is F. In some instances, R$^h$ is Cl. In some instances, R$^h$ is I. In some instances, R$^h$ is Br. In some instances, R$^i$ is hydroxyl. In some instances, R$^i$ is F. In other instances, R$^i$ is Cl. In other instances, R$^i$ is I. In other instances, R$^i$ is Br.

In some embodiments, $X_1$ is —NH. In some instances, $X_1$, $X_2$ and R$^a$ together form an amide, such as where $X_1$ is —NH, $X_2$ is carbon and R$^a$ is oxygen. In other instances, $X_1$, $X_2$ and R$^a$ together form a sulfoximine, such as where $X_1$ is —NH, $X_2$ is —SR$^k$ and R$^a$ is oxygen. In some instances, R$^k$ is selected from methyl, ethyl, n-propyl, iso-propyl, n-butyl, iso-butyl, t-butyl. In certain instances, R$^k$ is methyl. In other instances, $X_1$, $X_2$ and R$^a$ together form a trifluoromethyl aminomethyl, such as where $X_1$ is —NH, $X_2$ is carbon and R$^a$ is trifluoromethyl. In other instances, $X_1$, $X_2$ and R$^a$ together form a vinylfluoride, such as where $X_1$ is carbon, $X_2$ is carbon and R$^a$ is fluorine. In certain instances, $X_1$, $X_2$ and R$^a$ together form an aminooxetane, such as where $X_1$ is —NH and R$^a$ together with $X_2$ forms an oxacyclobutane.

In embodiments, R$^e$ may be alkyl or substituted alkyl. In some instances, R$^e$ is a C8 to C20 alkyl. In some instances, R$^e$ is a substituted C8 to C20 alkyl. In certain instances, R$^e$ is a C13 alkyl.

In some embodiments, R$^b$ is hydrogen. In some instances, R$^b$ is a C1 to C16 alkyl. In some instances, R$^b$ is selected from the group consisting of methyl, ethyl, propyl, isopropyl, n-butyl, isobutyl, tert-butyl, pentyl, hexyl, heptyl and octyl. In some instances, R$^b$ is selected from:

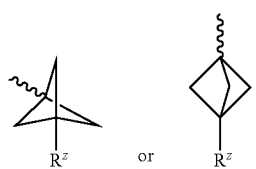

wherein ⌇ indicates a bond to Y and $R^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, $R^z$ is alkyl, such as a C1 to C16 alkyl or C1 to C16 substituted alkyl.

In some embodiments, $R^e$ is a C1 to C16 alkyl. In some instances, $R^e$ is selected from methyl, ethyl, propyl, isopropyl, n-butyl, isobutyl, tert-butyl, pentyl, hexyl, heptyl and octyl.

In some embodiments, $R^d$ is a C5 to C25 alkyl or a C5 to C25 alkyl substituted with a cycloalkyl group, substituted cycloalkyl group, heterocycloalkyl group, substituted heterocycloalkyl group, aryl group, substituted aryl group, arylalkyl group, substituted arylalkyl group, heteroaryl group, substituted heteroaryl group, heteroarylalkyl group, or substituted heteroarylalkyl group. In some instances, $R^d$ is a C5 to C25 alkyl substituted with a moiety selected from the group consisting of:

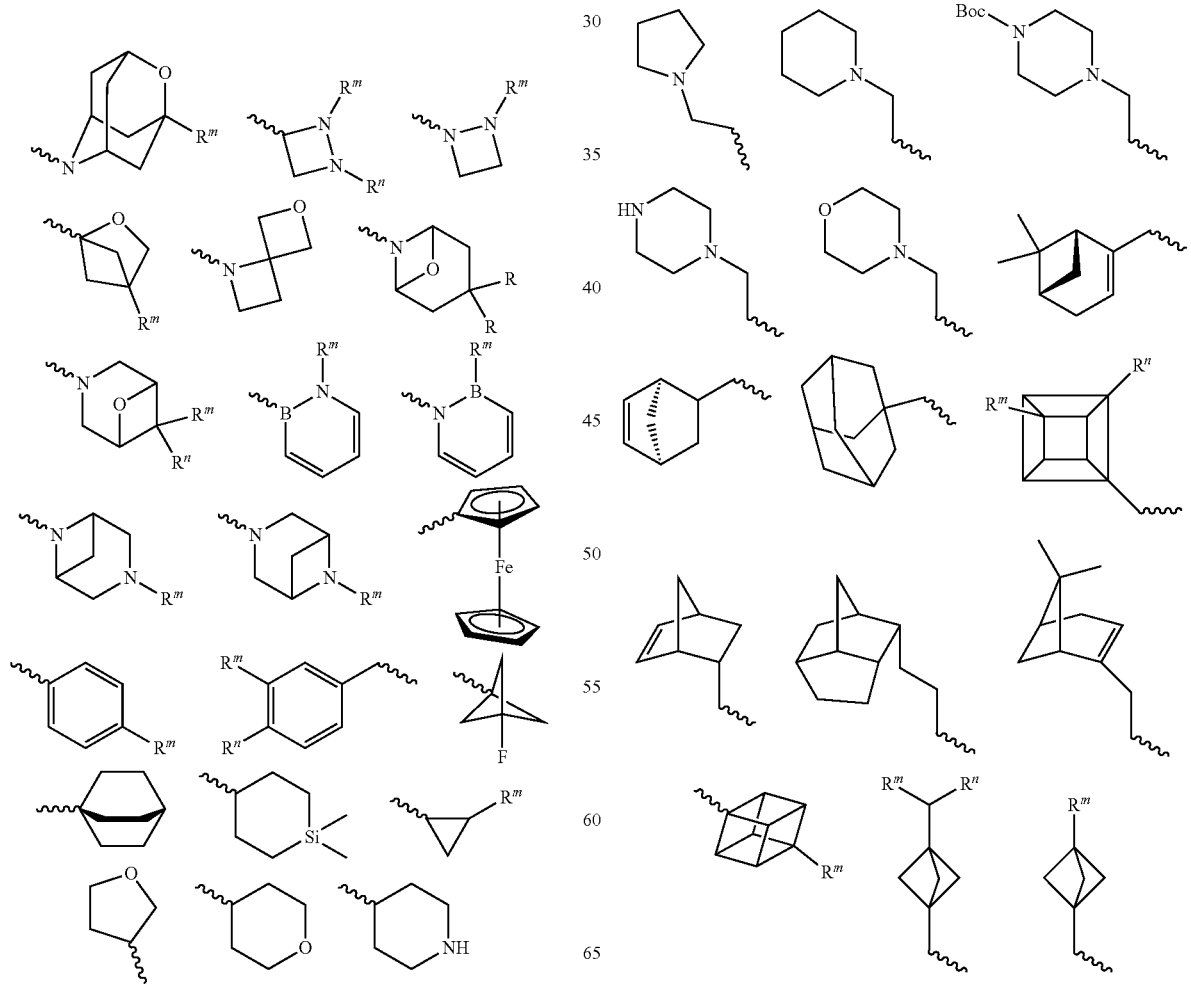

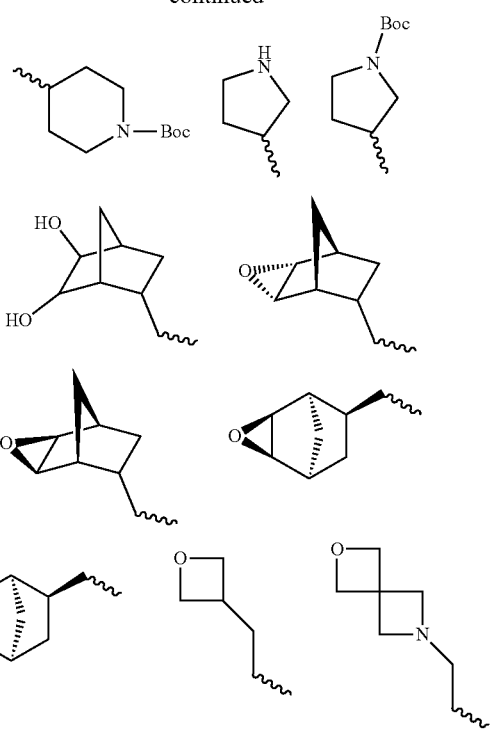

-continued

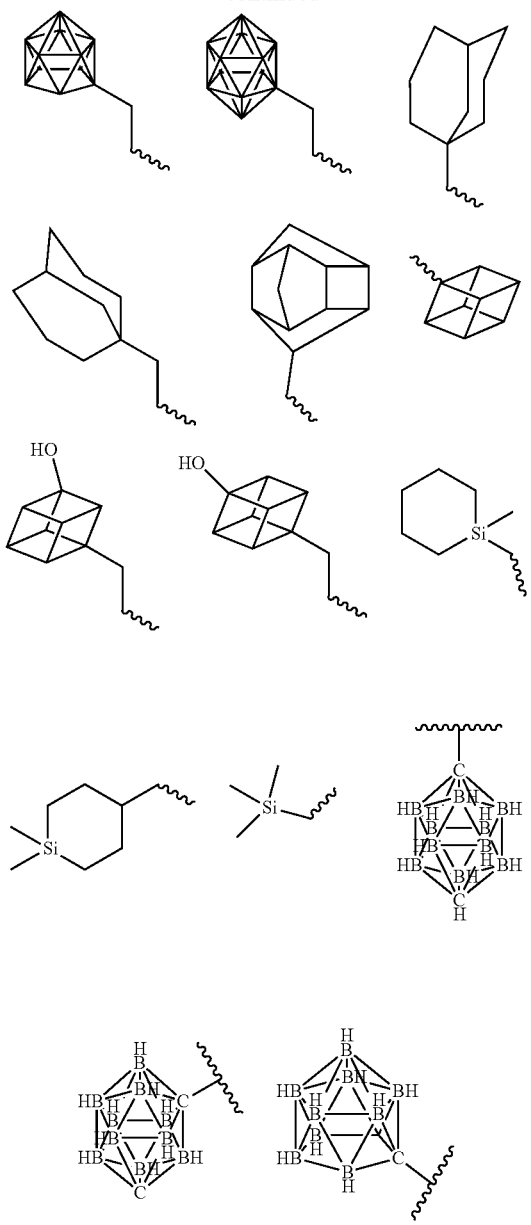

wherein ∿ indicates the bond to the C5 to C25 alkyl; and R''' and R'' are independently selected from hydrogen, halogen, hydroxyl, substituted hydroxyl, amino, substituted amino, thiol, substituted thiol, sulfoxide, substituted sulfoxide, sulfone, substituted sulfone, sulfoximine, substituted sulfoximine. Acyl, aminoacyl, alkyl, substituted alkyl; heteroalkyl, substituted heteroalkyl, cycloalkyl, substituted cycloalkyl, spiroalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, R''' is hydrogen. In some instances, R''' is halogen. In some instances, R''' is selected from fluorine, bromine or iodine. In some instances, R'' is hydrogen. In some instances, R'' is halogen. In some instances, R'' is fluorine, bromine or iodine.

In some embodiments, compounds of interest include a compound of formula DCD-(II):

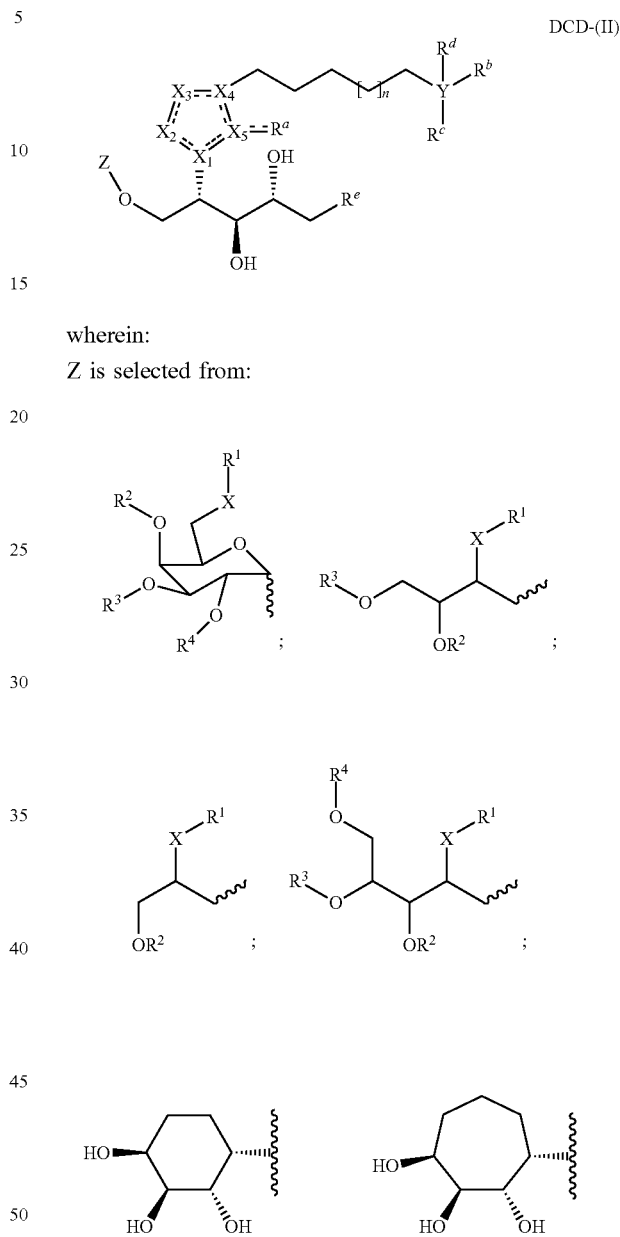

DCD-(II)

wherein:
Z is selected from:

wherein ∿ indicates the Z—O bond;

wherein X is —NHCO— or oxygen $R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

$X_1$, $X_2$, $X_3$, $X_4$ and $X_5$ are each independently selected from carbon, nitrogen, oxygen or sulfur;

$R^a$ is optionally absent or when present is selected from hydrogen or oxygen;

In certain instances, $R^1$ is selected from:

1)

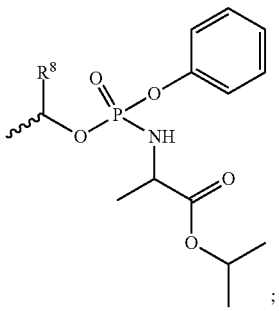
;

2)

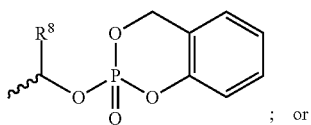
; or

3)

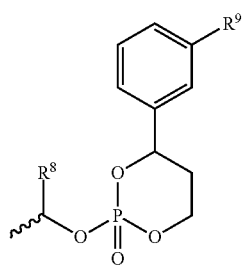

wherein ∼∼ represents the $R^1$—O bond;

$R^8$ is hydrogen, alkyl, substituted alkyl; and $R^8$ is hydrogen or a halogen selected from fluorine, chlorine, bromine or iodine.

In certain instances, $R^1$ is:

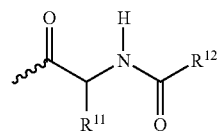

wherein:

$R^{11}$ is alkyl or substituted alkyl;

$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^{11}$ is selected from methyl, ethyl, n-propyl, iso-propyl, n-butyl, iso-butyl, t-butyl. In certain instances, $R^{11}$ is iso-propyl.

In certain instances, $R^1$ is:

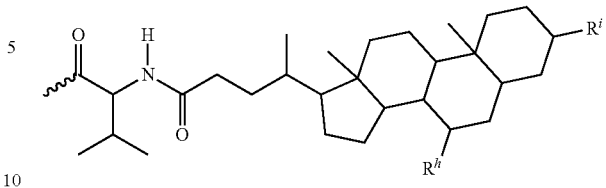

wherein $R^h$ and $R^i$ are each independently selected from hydrogen, hydroxyl or halogen. In some instances, $R^h$ is hydroxyl. In some instances, $R^h$ is F. In some instances, $R^h$ is Cl. In some instances, $R^h$ is I. In some instances, $R^h$ is Br. In some instances, Riis hydroxyl. In some instances, $R^i$ is F. In other instances, $R^i$ is Cl. In other instances, Riis I. In other instances, $R^i$ is Br.

In some embodiments, $X_1$, $X_2$, $X_3$, $X_4$ and $X_5$ together form a pyrazole, such as where $X_1$ is carbon, $X_2$ is nitrogen, $X_3$ is nitrogen, $X_4$ is carbon and $X_5$ is carbon. In other embodiments, $X_1$, $X_2$, $X_3$, $X_4$ and $X_5$ together form an imidazole, such as where $X_1$ is carbon, $X_2$ is nitrogen, $X_3$ is carbon, $X_4$ is carbon and $X_5$ is nitrogen. In other embodiments, $X_1$, $X_2$, $X_3$, $X_4$ and $X_5$ together form a tetrazole, such as where $X_1$ is nitrogen, $X_2$ is nitrogen, $X_3$ is nitrogen, $X_4$ is nitrogen and $X_5$ is carbon. In certain embodiments, $X_1$, $X_2$, $X_3$, $X_4$ and $X_5$ together form a tetrazoline, such as where $X_1$ is nitrogen, $X_2$ is nitrogen, $X_3$ is nitrogen, $X_4$ is nitrogen, $X_5$ is carbon and $R^a$ is oxygen.

In embodiments, $R^e$ may be alkyl or substituted alkyl. In some instances, $R^e$ is a C8 to C20 alkyl. In some instances, $R^e$ is a substituted C5 to C20 alkyl. In certain instances, $R^e$ is a C13 alkyl.

In some embodiments, $R^b$ is hydrogen. In some instances, $R^b$ is a C1 to C16 alkyl. In some instances, $R^b$ is selected from the group consisting of methyl, ethyl, propyl, isopropyl, n-butyl, isobutyl, tert-butyl, pentyl, hexyl, heptyl and octyl. In some instances, $R^a$ is selected from.

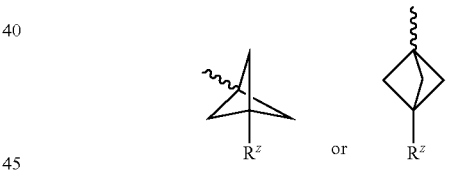

wherein ∼∼ indicates a bond to Y and $R^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, $R^z$ is alkyl, such as a C1 to C16 alkyl or C1 to C16 substituted alkyl.

In some embodiments, $R^c$ is a C1 to C16 alkyl. In some instances, $R^c$ is selected from the group consisting of methyl, ethyl, propyl, isopropyl, n-butyl, isobutyl, tert-butyl, pentyl, hexyl, heptyl and octyl.

In some embodiments, $R^d$ is a C5 to C25 alkyl or a C5 to C25 alkyl substituted with a cycloalkyl group, substituted cycloalkyl group, heterocycloalkyl group, substituted heterocycloalkyl group, aryl group, substituted aryl group, arylalkyl group, substituted arylalkyl group, heteroaryl group, substituted heteroaryl group, heteroarylalkyl group, or substituted heteroarylalkyl group. In some instances, $R^d$ is a C5 to C25 alkyl substituted with a moiety selected from the group consisting of:

-continued
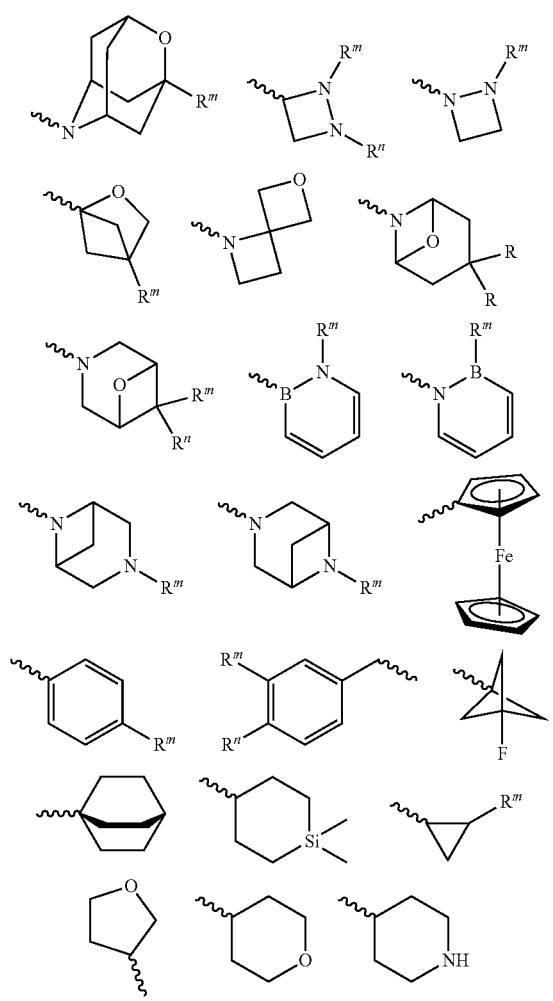
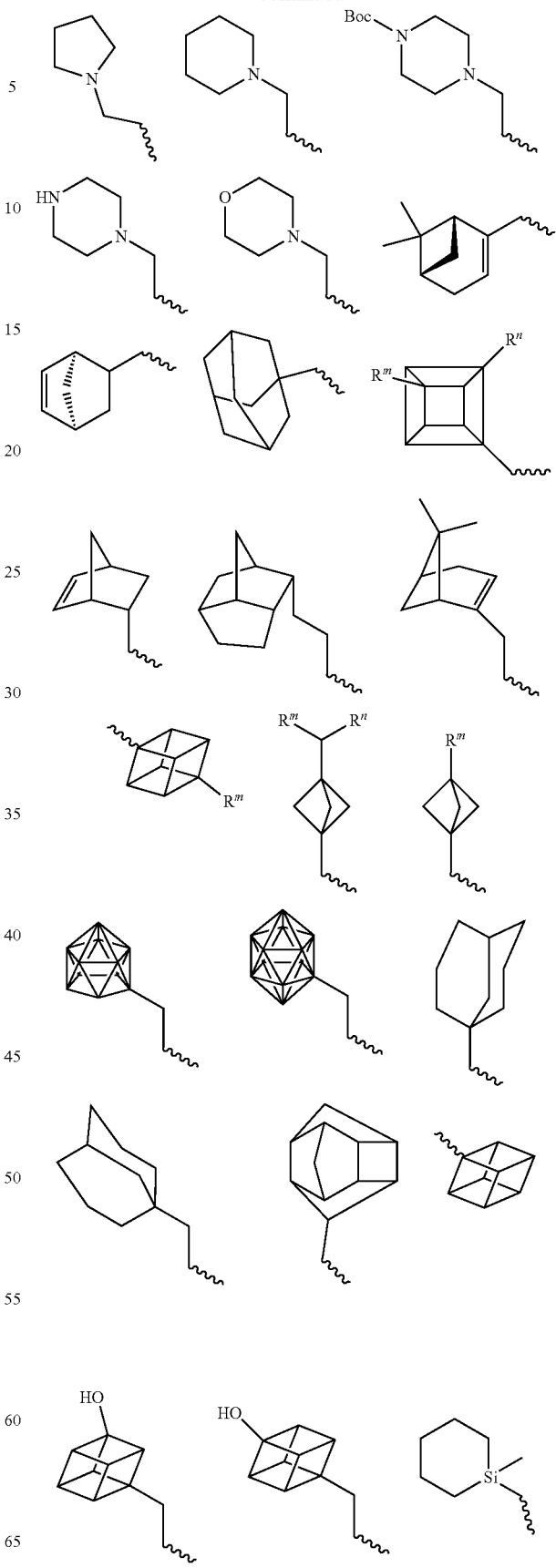

-continued

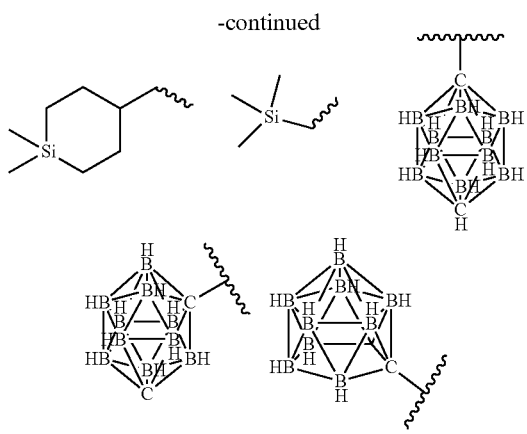

wherein ~~~ indicates the bond to the C5 to C25 alkyl; and $R'''$ and $R''$ are independently selected from hydrogen, halogen, hydroxyl, substituted hydroxyl, amino, substituted amino, thiol, substituted thiol, sulfoxide, substituted sulfoxide, sulfone, substituted sulfone, sulfoximine, substituted sulfoximine. Acyl, aminoacyl, alkyl, substituted alkyl, heteroalkyl, substituted heteroalkyl, cycloalkyl, substituted cycloalkyl, spiroalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R'''$ is hydrogen. In some instances, $R'''$ is halogen. In some instances, $R'''$ is selected from fluorine, bromine or iodine. In some instances, $R''$ is hydrogen. In some instances, $R''$ is halogen. In some instances, $R''$ is fluorine, bromine or iodine.

Aspects of the disclosure also include methods for activing an iNKT cell by contacting the iNKT cell with an amount of the subject compounds or a pharmaceutically acceptable salt thereof. In some instances, the iNKT cell is contacted with the compound in vitro. In other instances, the iNKT cell is contacted with the compound in vivo. In some instances, methods include contacting one or more of the compounds described herein with iNKT cells in a manner sufficient to induce a $T_H1$-type cytokine response (e.g., increase production of one or more cytokines selected from IFNγ, IL-1β, IL-2, IL-3, IL-8, IL-12, IL-15, TNFα, GM-CSF, RANTES, MIP-1α and MCP-1). In other instances, methods include contacting one or more of the compounds described herein with iNKT cells in a manner sufficient to induce a $T_H2$-type cytokine response (e.g., increase production of one or more cytokines selected from IL-4, IL-6, IL-8, IL-10, IL-13, RANTES, MIP-1α and MCP-1) In some instances, the compound forms a complex with a CD1 molecule on an antigen-presenting cell. In certain instances, the CD1 molecule is a CD1d molecule. In some instances, the receptor on the T lymphocyte is a T cell receptor. In some instances, the compound stimulates at least one other lymphocyte to produce the cytokine response in some instances the at least one other lymphocyte is a T helper cell.

In certain instances, methods include contacting activated iNKT cells with a composition comprising senescent cells where contacting the activated iNKT cells reduces the presence of or eliminates the senescent cells in the composition. In some embodiments, the senescent cells have an inflammatory secretome. In some embodiments, the composition further includes healthy cells. In some instances, contacting the activated iNKT cells reduces the presence of or eliminates the senescent cells in the composition without reducing the presence of the healthy cells. For example, contacting the activated iNKT cells reduces the presence of or eliminates the senescent cells in the composition and the presence of healthy cells is reduced by 5% or less when the composition is contacted with the activated iNKT cells.

In some embodiments, methods include administering one or more of the compounds described herein to a subject, such as to reduce the presence of or eliminate senescent cells in the subject. In some instances, methods include administering one or more of the compounds to treat the subject for an autoimmune disease, fibrotic disorders (lung, kidney, liver), an allergic disease, a metabolic syndrome, type 2 diabetes, NAFLD, NASH, cancer, an eye disease, heart disease, kidney disease, pathogen infection, rheumatoid arthritis, ulcerative colitis, multiple sclerosis, familial hypercholesteremia, giant cell arteritis, idiopathic pulmonary fibrosis, systemic lupus erythematosus, cachexia, glaucoma, chronic obstructive pulmonary disease, systemic sclerosis, pulmonary arterial hypertension, lipodystrophy, sarcopenia, alopecia, post myocardial infarction, vitiligo, POTS, MCAD, Sjogren's, Scleroderma, Hashimoto Disease, Ankylosing Spondylitis, Fibromyalgia, Sarcoidosis. Hepatitis, Raynauld's Syndrome, Mold Illness, Celiac, Crohn's, Pemphigus. SPS, PBC, Psoriatic Arthritis, CIDP, motor neuron disease, GPA, ALS, myasenthia gravis, and presbyopia.

BRIEF DESCRIPTION OF THE FIGURES

FIG. 1 depicts the EC50 of the dose responses of cells at different concentrations of compounds DCD-101, DCD-102, DCD-103, DCD-104, DCD-105, DCD-106, DCD-108, DCD-112, DCD-113, DCD-114, DCD115, and DCD-116, DCD118, DCD-119, DCD-120, DCD-121, DCD-122, DCD-123, DCD-124, DCD-125, DCD-126, DCD-127, DCD-128, DCD-129, DCD-130, DCD-131, DCD-132, DCD-133, DCD-134, DCD-135, DCD-136, DCD-137, DCD-138, DCD-139, DCD-140, DCD-141, DCD-142, DCD-143, DCD-144, DCD-145, DCD-146, DCD-147, DCD-148, DCD-149, DCD-150, DCD-151, DCD-152, DCD-153, DCD-154, DCD-155, DCD-156, DCD-157, DCD-158, DCD-159 and α-GalCer at varying concentrations.

FIG. 4A depicts the activation of C57BL/6J immune cells, as measured by the serum IFNγ using ELISA, in response to injection of the compounds DCD-101, DCD-119, DCD-123, DCD125, DCD127, DCD-128, DCD-134, DCD-142, DCD-145, DCD-146, DCD-147, DCD-148, DCD-149, DCD-150, DCD-151, DCD-152, DCD-153, DCD-154, DCD-155, DCD-156, and DCD-157, DCD-158, and DCD-159 with comparison to αGalCer twenty hours after injection.

FIG. 5A depicts the expansion of iNKT cells caused by αGalCer or DCD-101 in a HFD model mouse spleen, as measured by flow cytometry.

FIG. 6A depicts expression of GFP in response to incubation with compound GVK1a, GVK1b, GVK1c, and GVK1f with BWSTIM cells and JiNKT cells.

FIG. 6B depicts IL-2 expression by compounds GVK1a, GVK1b, and GVK1f in the DN3.2 cell line when loaded on BWSTIM CD1d.

FIG. 7A depicts the effect of activated iNKT cells on senescent cells and non-senescent cells over a period of 18 hours.

DEFINITIONS

Figure 2:
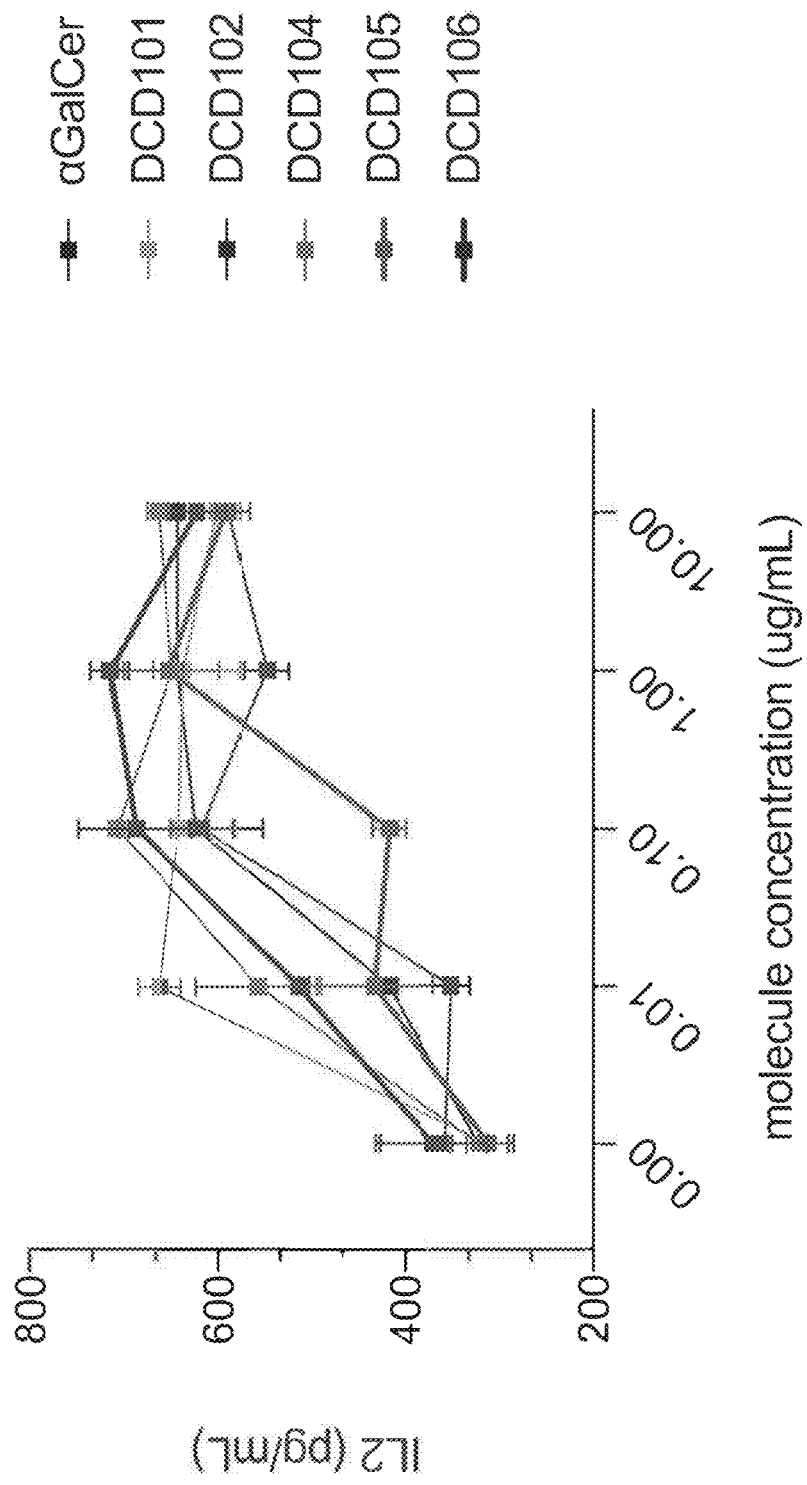
FIG. 2 depicts the amount of interleukin-2 (IL-2) secretion in response to a 48 hour incubation with compounds DCD-101, DCD-102, DCD-104, DCD-105, DCD-106 and α-GalCer in a dose response of 0.01, 0.1, 1, and 10 ug/mL.

The following terms have the following meaning unless otherwise indicated. Any undefined terms have their art recognized meanings.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), aggregate-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc., butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical. e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, aggregate e, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyndine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —O—, =O, —$OR^{60}$, —$SR^{60}$, —$S^-$, =S, —$NR^{60}R^{61}$, —$NR^{60}$, —$CF_3$, —CN, —OCN, —SCN, —NO, —$NO_2$, =$N_2$, —$N_3$, —$S(O)_2O$—, —$S(O)_2OH$, —$S(O)_2R^{60}$, —$OS(O)_2O$—, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O$—, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2^-$, —$OS(O)_2R^{60}$, —$P(O)(O^-)_2$, —$P(O)(OR(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O$—, —$NR^{60}$, $C(O)NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)$ $NR^{60}R^{61}$, —$C(O)O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})OR)$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

"Pharmaceutically acceptable carrier" refers to a diluent, adjuvant, excipient or vehicle with, or in which a compound is administered.

"Treating" or "treatment" of any condition, such as an autoimmune, metabolic, allergic, cancer or infectious disease, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically. (e.g., stabilization of a discernible symptom), physiologically, (e.g., stabilization of a physical parameter), or both. In certain embodiments, "treating" or "treatment" refers to delaying the onset of the condition.

"Therapeutically effective amount" means the amount of a compound that, when administered to a patient for preventing or treating a condition such as an autoimmune, metabolic, allergic, cancer or infectious disease, is sufficient to effect such treatment. The "therapeutically effective amount" will vary depending on the compound, the condition and its severity and the age, weight, etc., of the patient.

DETAILED DESCRIPTION

Compounds for activating invariant natural killer T cells (iNKT) cells are provided. Compounds according to certain embodiments activate iNKT cells and induce an increase in the production of one or more cytokines, such as IFNγ, IL-2, IL-4, IL-6 and TNFα. In some embodiments, activated iNKT cells are used to selectively reduce the presence of or eliminate inflammatory senescent cells, such as senescent cells having an inflammatory secretome (SASP). Methods for activating iNKT cells by contacting an iNKT cell with an amount of the subject compounds and selectively reducing the presence of or eliminating senescent cells with activated iNKT cells are also described. Compositions for practicing the subject methods are also described.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely." "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the compounds and methods have or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed m the embodiments describing such variables are also specifically embraced by the present invention and are disclosed herein just as if each and every such sub-combination of chemical groups was individually and explicitly disclosed herein.

Reference will now be made in detail to various embodiments. It will be understood that the invention is not limited to these embodiments. To the contrary, it is intended to cover alternatives, modifications, and equivalents as may be included within the spirit and scope of the allowed claims.

Compounds for Activating iNKT Cells and Selectively Eliminating Senescent Cells

Formula DCD-(I)

Aspects of the present disclosure according to certain embodiments include a compound of formula DCD-(I):

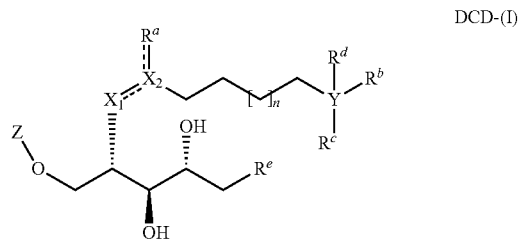

DCD-(I)

wherein:
Z is selected from:

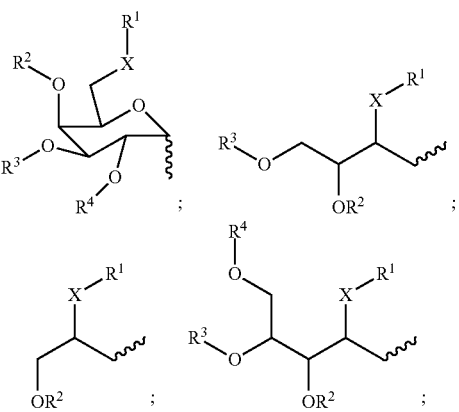

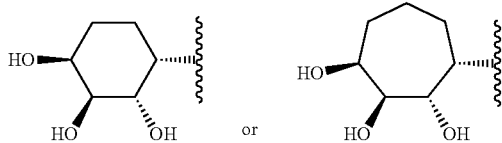

wherein ⌇⌇⌇ indicates the Z—O bond;
wherein X is —NHCO— or oxygen
R¹, R², R³ and R⁴ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
$X_1$ and $X_2$ are each independently selected from —C, —NR$^j$, —O, —SR$^k$, —Si, wherein R$^j$ and R$^k$ are each independently selected from hydrogen, alkyl or substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
R$^a$ is selected from hydrogen, oxygen, fluorine, —CF₃, or together with $X_2$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
wherein ⎓ indicates a double or single bond;
n is an integer from 2 to 25;
Y is selected from carbon, nitrogen or silicon;
R$^b$, R$^c$ and R$^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, R$^d$ is not present, or wherein R$^c$ and R$^d$ together with Y form a cycloalkyl, substituted cycloalkyl, aryl, substituted aryl, heteroaryl or substituted heteroaryl group; and
R$^e$ is alkyl or substituted alkyl,
or salt, solvate or hydrate thereof.

In embodiments, "salts" of the compounds of the present disclosure may include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The term "solvate" as used herein refers to a complex or aggregate formed by one or more molecules of a solute, e.g. a compound of DCD-(I) or a salt thereof, and one or more molecules of a solvent. Such solvates may be crystalline solids having a substantially fixed molar ratio of solute and solvent. Representative solvents include by way of example, water, methanol, ethanol, isopropanol, acetic acid, and the like. When the solvent is water, the solvate formed is a hydrate.

Formula DCD-(IA-1)

Aspects of the present disclosure according to certain embodiments include a compound of formula DCD-(IA-1):

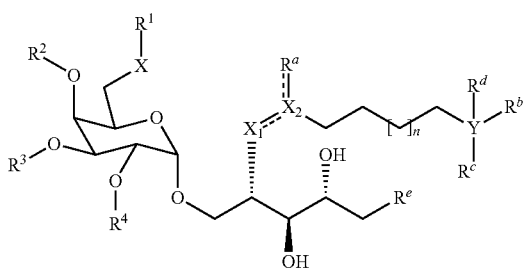

DCD-(IA-1)

wherein:
wherein X is —NHCO— or oxygen
R¹, R², R³ and R⁴ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
$X_1$ and $X_2$ are each independently selected from —C, —NR$^j$, —O, —SR$^k$, —Si, wherein R$^j$ and R$^k$ are each independently selected from hydrogen, alkyl or substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
R$^a$ is selected from hydrogen, oxygen, fluorine, —CF₃, or together with $X_2$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
wherein ⎓ indicates a double or single bond;
n is an integer from 2 to 25;
Y is selected from carbon, nitrogen or silicon;
R$^b$, R$^c$ and R$^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, R$^d$ is not present, or wherein R$^c$ and R$^d$ together with Y form a cycloalkyl, substituted cycloalkyl, aryl, substituted aryl, heteroaryl or substituted heteroaryl group; and $R^e$ is alkyl or substituted alkyl, or salt, solvate or hydrate thereof.

In some instances, $R^1$ is hydrogen. In some instances, $R^2$ is hydrogen. In some instances, $R^3$ is hydrogen. In some instances, $R^4$ is hydrogen. In certain instances, each of $R^1$, $R^2$, $R^3$ and $R^4$ are hydrogen.

In other instances, $R^1$ is:

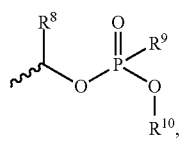

wherein ⌇ represents the $R^1$—O bond;

$R^8$ is hydrogen, alkyl or substituted alkyl; In some instances, $R^8$ is selected from hydrogen, methyl, ethyl and cyclopropyl.

$R^9$ is —$NR^f$ or —$OR^f$ wherein $R^f$ is alkyl, substituted alkyl, acyl, alkylacyl or substituted alkylacyl, or wherein $R^f$ together with $R^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and $R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with $R^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In certain instances, $R^1$ is selected from:

1)

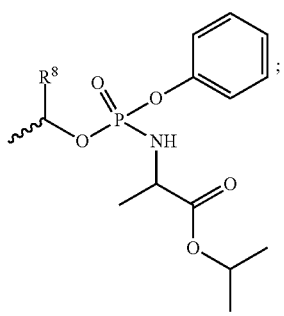

2)

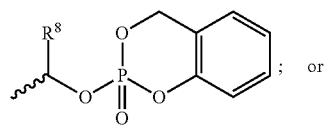

; or

3)

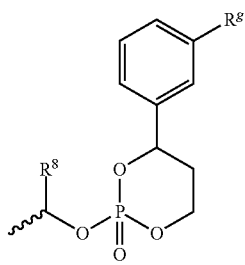

wherein ⌇ represents the $R^1$—O bond;

$R^8$ is hydrogen, alkyl, substituted alkyl; and $R^9$ is hydrogen or a halogen selected from fluorine, chlorine, bromine or iodine.

In other instances, $R^1$ is:

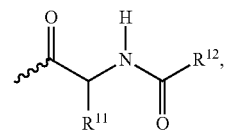

wherein:

$R^{11}$ is alkyl or substituted alkyl;

$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^{11}$ is selected from methyl, ethyl, n-propyl, iso-propyl, n-butyl, iso-butyl, t-butyl. In certain instances, $R^{11}$ is iso-propyl.

In certain instances, $R^1$ is:

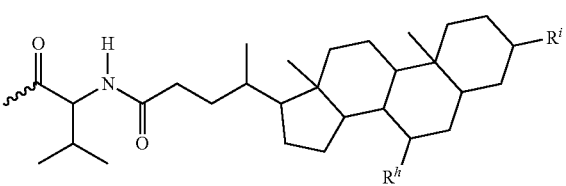

wherein $R^h$ and $R^i$ are each independently selected from hydrogen, hydroxyl or halogen. In some instances, $R^h$ is hydroxyl. In some instances, $R^h$ is F. In some instances, $R^h$ is Cl. In some instances, $R^h$ is I. In some instances, $R^h$ is Br. In some instances, $R^i$ is hydroxyl. In some instances, $R^i$ is F. In other instances, $R^i$ is Cl. In other instances, $R^i$ is I. In other instances, $R^i$ is Br.

Formula DCD-(IA-2)

Aspects of the present disclosure according to certain embodiments include a compound of formula DCD-(IA-2):

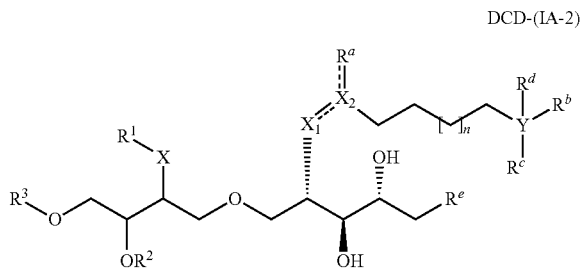

DCD-(IA-2)

wherein:
wherein X is —NHCO— or oxygen;
$R^1$, $R^2$ and $R^3$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
$X_1$ and $X_2$ are each independently selected from —C, —$NR^j$, —O, —$SR^k$, —Si, wherein $R^j$ and $R^k$ are each independently selected from hydrogen, alkyl or substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
$R^a$ is selected from hydrogen, oxygen, fluorine, —$CF_3$, or together with $X_2$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
wherein ---- indicates a double or single bond;
n is an integer from 2 to 25;
Y is selected from carbon, nitrogen or silicon;
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and
$R^e$ is alkyl or substituted alkyl,
or salt, solvate or hydrate thereof.
In some instances, $R^1$ is hydrogen. In some instances, $R^2$ is hydrogen. In some instances. $R^3$ is hydrogen. In certain instances, each of $R^1$, $R^2$ and $R^3$ are hydrogen.
In other instances, $R^1$ is:

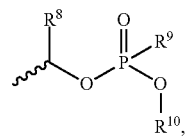

wherein ∿∿ represents the $R^1$—O bond;
$R^8$ is hydrogen, alkyl or substituted alkyl; In some instances, $R^8$ is selected from hydrogen, methyl, ethyl and cyclopropyl
$R^9$ is —$NR^f$ or —OR, wherein $R^f$ is alkyl, substituted alkyl, acyl, alkylacyl or substituted alkylacyl, or wherein $R^f$ together with $R^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and
$R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with $R^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.
In certain instances, $R^1$ is selected from:

1)

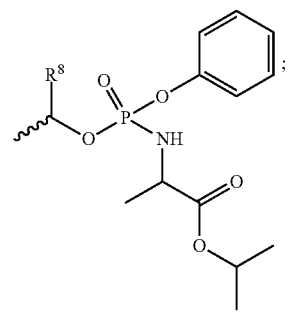

2)

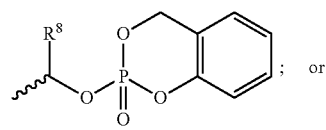

; or

3)

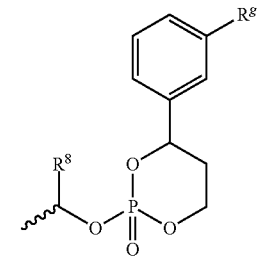

wherein ∿∿ represents the $R^1$—O bond;
$R^8$ is hydrogen, alkyl, substituted alkyl; and
$R^g$ is hydrogen or a halogen selected from fluorine, chlorine, bromine or iodine.
In other instances, $R^1$ is:

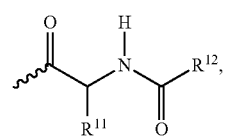

wherein:

$R^{11}$ is alkyl or substituted alkyl;

$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^{11}$ is selected from methyl, ethyl, n-propyl, iso-propyl, n-butyl, iso-butyl, t-butyl. In certain instances, $R^{11}$ is iso-propyl.

In certain instances, $R^1$ is:

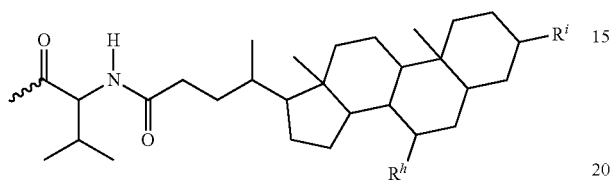

wherein $R^h$ and $R^i$ are each independently selected from hydrogen, hydroxyl or halogen. In some instances, $R^h$ is hydroxyl. In some instances, $R^h$ is F. In some instances, $R^h$ is Cl. In some instances, $R^h$ is I. In some instances, $R^h$ is Br. In some instances, $R^i$ is hydroxyl. In some instances, $R^i$ is F. In other instances, $R^i$ is Cl. In other instances, $R^i$ is I. In other instances, $R^i$ is Br.

Formula DCD-(IA-3)

Aspects of the present disclosure according to certain embodiments include a compound of formula DCD-(IA-3):

DCD-(IA-3)

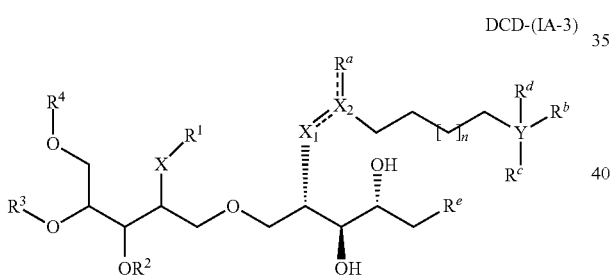

wherein:

wherein X is —NHCO— or oxygen;

$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

$X_1$ and $X_2$ are each independently selected from —C, —NR$^j$, —O, —SR$^k$, —Si, wherein R$^j$ and R$^k$ are each independently selected from hydrogen, alkyl or substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

$R^a$ is selected from hydrogen, oxygen, fluorine, —CF$_3$, or together with $X_2$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

wherein ≡ indicates a double or single bond;

n is an integer from 2 to 25,

Y is selected from carbon, nitrogen or silicon;

$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and $R^e$ is alkyl or substituted alkyl, or salt, solvate or hydrate thereof.

In some instances, $R^1$ is hydrogen. In some instances, $R^2$ is hydrogen. In some instances, $R^3$ is hydrogen. In some instances, $R^4$ is hydrogen. In certain instances, each of $R^1$, $R^2$, $R^3$ and $R^4$ are hydrogen.

In other instances, $R^1$ is:

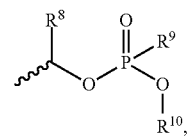

wherein ⌇ represents the $R^1$—O bond;

$R^8$ is hydrogen, alkyl or substituted alkyl; In some instances, $R^8$ is selected from hydrogen, methyl, ethyl and cyclopropyl.

$R^9$ is —NR$^f$ or —OR$^f$, wherein R$^f$ is alkyl, substituted alkyl, acyl, alkylacyl or substituted alkylacyl, or wherein R$^f$ together with $R^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and $R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with R$^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In certain instances, $R^1$ is selected from:

1)

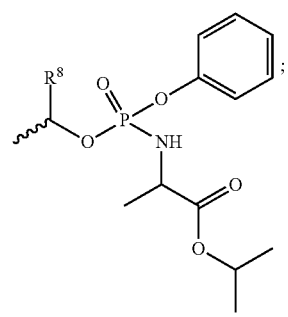

2)

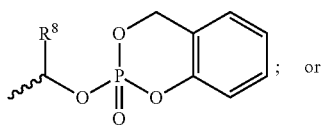

; or

3)

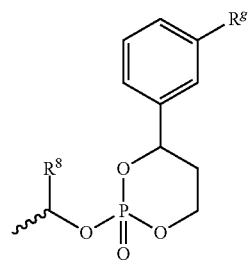

wherein ∼∼∼ represents the R¹—O bond;
R⁸ is hydrogen, alkyl, substituted alkyl; and
R^g is hydrogen or a halogen selected from fluorine, chlorine, bromine or iodine.

In other instances, R¹ is:

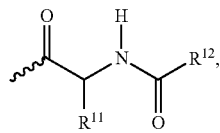

wherein:

$R^{11}$ is alkyl or substituted alkyl;

$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^{11}$ is selected from methyl, ethyl, n-propyl, iso-propyl, n-butyl, iso-butyl, t-butyl. In certain instances, $R^{11}$ is iso-propyl.

In certain instances, R¹ is:

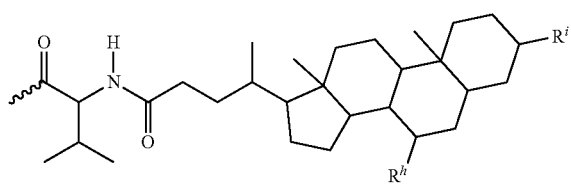

wherein $R^h$ and $R^i$ are each independently selected from hydrogen, hydroxyl or halogen. In some instances, $R^h$ is hydroxyl. In some instances, $R^h$ is F. In some instances, $R^h$ is Cl. In some instances, $R^h$ is I. In some instances, $R^h$ is Br. In some instances, $R^i$ is hydroxyl. In some instances, $R^h$ is F. In other instances, $R^h$ is Cl. In other instances, $R^i$ is I.

In other instances, $R^i$ is Br.

Formula DCD-(IA-4)

Aspects of the present disclosure according to certain embodiments include a compound of formula DCD-(IA-4):

DCD-(IA-4)

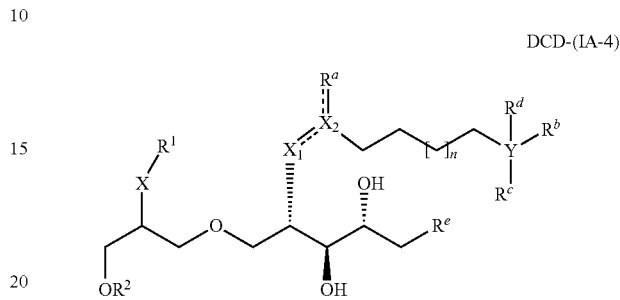

wherein:

wherein X is —NHCO— or oxygen;

R¹ and R² are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

$X_1$ and $X_2$ are each independently selected from —C, —NR^j, —O, —SR^k, —Si, wherein $R^j$ and $R^k$ are each independently selected from hydrogen, alkyl or substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

$R^a$ is selected from hydrogen, oxygen, fluorine, —CF₃, or together with $X_2$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

wherein ═══ indicates a double or single bond;

n is an integer from 2 to 25;

Y is selected from carbon, nitrogen or silicon;

$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and $R^e$ is alkyl or substituted alkyl, or salt, solvate or hydrate thereof.

In some instances, R¹ is hydrogen. In some instances, R² is hydrogen. In some instances, each of R¹ and R² are each hydrogen.

In other instances, $R^1$ is:

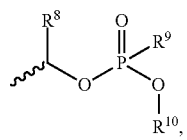

wherein ⌇ a represents the $R^1$—O bond;

$R^8$ is hydrogen, alkyl or substituted alkyl; In some instances, $R^8$ is selected from hydrogen, methyl, ethyl and cyclopropyl.

$R^9$ is —$NR^f$ or —$OR^f$, wherein $R^f$ is alkyl, substituted alkyl, acyl, alkylacyl or substituted alkylacyl, or wherein $R^1$ together with $R^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and $R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with $R^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In certain instances, $R^1$ is selected from:

1)

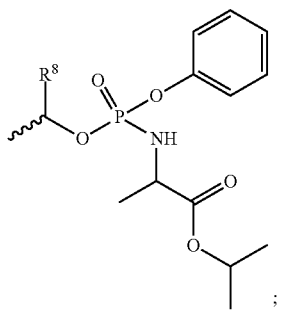

2)

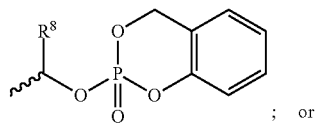

; or

3)

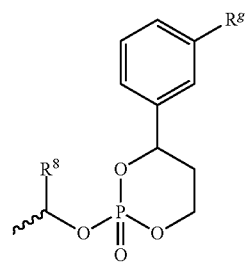

wherein ⌇ represents the $R^1$—O bond;
$R^8$ is hydrogen, alkyl, substituted alkyl; and
$R^g$ is hydrogen or a halogen selected from fluorine, chlorine, bromine or iodine.

In other instances, $R^1$ is:

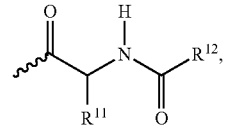

wherein:
$R^{11}$ is alkyl or substituted alkyl;
$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^{11}$ is selected from methyl, ethyl, n-propyl, iso-propyl, n-butyl, iso-butyl, t-butyl. In certain instances, $R^{11}$ is iso-propyl.

In certain instances, $R^1$ is:

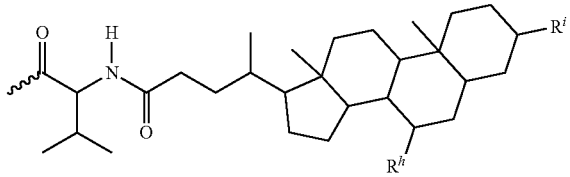

wherein $R^h$ and $R^i$ are each independently selected from hydrogen, hydroxyl or halogen. In some instances, $R^h$ is hydroxyl. In some instances, $R^h$ is F. In some instances, $R^h$ is Cl. In some instances, $R^h$ is I. In some instances, $R^h$ is Br. In some instances, $R^i$ is hydroxyl. In some instances, $R^i$ is F. In other instances, $R^i$ is Cl. In other instances, $R^i$ is I. In other instances, $R^i$ is Br.

Formula DCD-(IB-1)

Aspects of the present disclosure according to certain embodiments include a compound of formula DCD-(IB-1):

DCD-(IB-1)

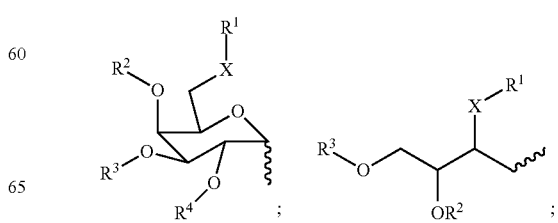

wherein:
Z is selected from:

-continued

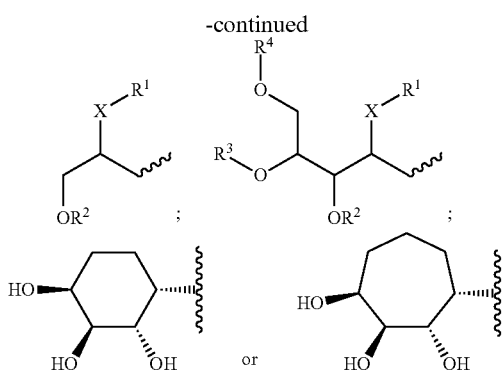

wherein ∼∼∼ indicates the Z—O bond;
wherein X is —NHCO— or oxygen;
$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
n is an integer from 2 to 25;
Y is selected from carbon, nitrogen or silicon
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and
$R^e$ is alkyl or substituted alkyl,
or salt, solvate or hydrate thereof.

Formula DCD-(IB-2)

Aspects of the present disclosure according to certain embodiments include a compound of formula DCD-(IB-2):

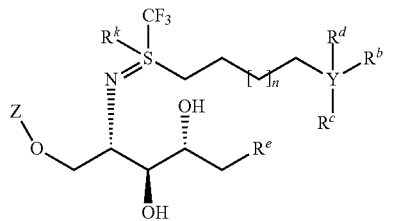

DCD-(IB-2)

wherein:
Z is selected from:

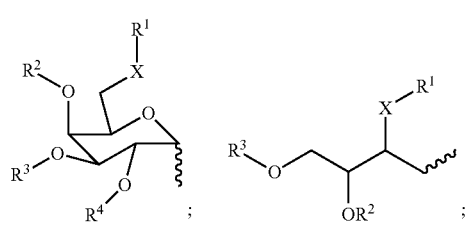

-continued

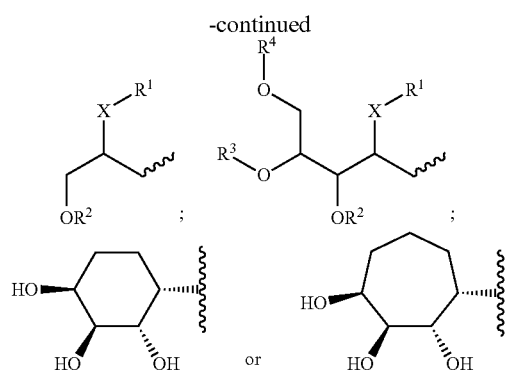

wherein ∼∼∼ indicates the Z—O bond;
wherein X is —NHCO— or oxygen;
$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
$R^k$ is selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In some instances, $R^k$ is selected from methyl, ethyl, n-propyl, iso-propyl, n-butyl, iso-butyl, t-butyl. In certain instances, $R^k$ is methyl.
N is an integer from 2 to 25;
Y is selected from carbon, nitrogen or silicon;
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and
$R^e$ is alkyl or substituted alkyl,
or salt, solvate or hydrate thereof.

Formula DCD-(IB-3)

Aspects of the present disclosure according to certain embodiments include a compound of formula DCD-(IB-3):

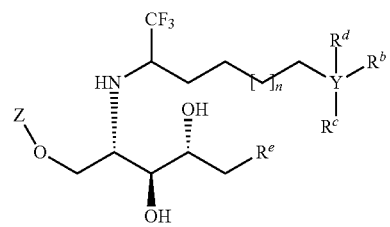

DCD-(IB-3)

wherein:
Z is selected from:

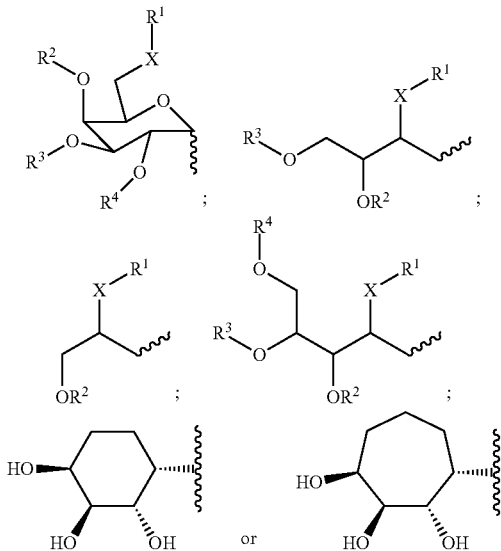

wherein ∼∼∼ indicates the Z—O bond;
wherein X is —NHCO— or oxygen;
$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
n is an integer from 2 to 25;
Y is selected from carbon, nitrogen or silicon;
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and
$R^e$ is alkyl or substituted alkyl,
or salt, solvate or hydrate thereof.
Formula DCD-(IB-4)
Aspects of the present disclosure according to certain embodiments include a compound of formula DCD-(IB-4):

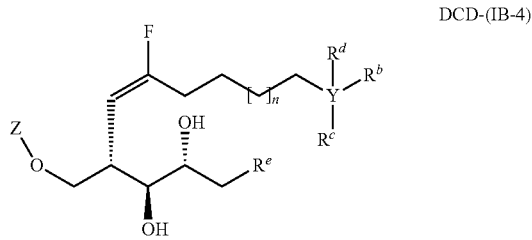

DCD-(IB-4)

wherein:
Z is selected from:

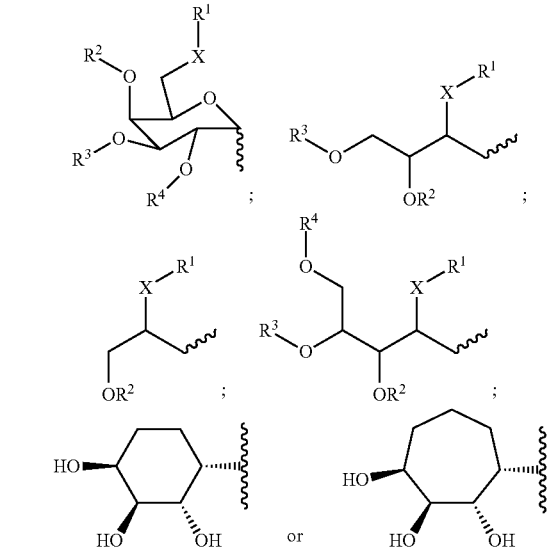

wherein ∼∼∼ indicates Z—O bond;
wherein X is —NHCO— or oxygen;
$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
n is an integer from 2 to 25;
Y is selected from carbon, nitrogen or silicon;
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and
$R^e$ is alkyl or substituted alkyl,
or salt, solvate or hydrate thereof.
Formula DCD-(IX-5)
Aspects of the present disclosure according to certain embodiments include a compound of formula DCD-(IB-5):

DCD-(IB-5)

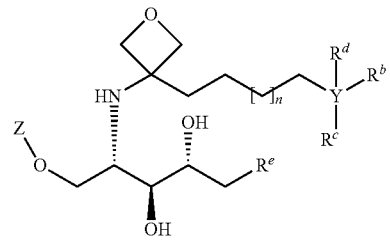

wherein:

Z is selected from:

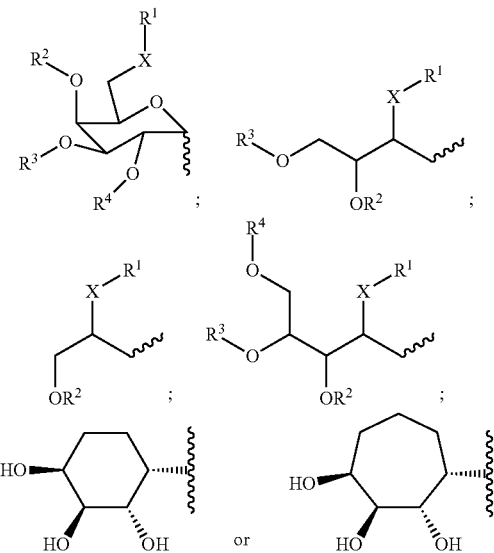

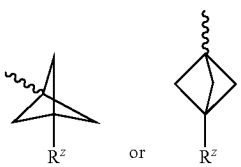

wherein ∿∿ indicates the Z—O bond;
wherein X is —NHCO— or oxygen;
R¹, R², R³ and R⁴ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
n is an integer from 2 to 25;
Y is selected from carbon, nitrogen or silicon;
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and $R^e$ is alkyl or substituted alkyl, or salt, solvate or hydrate thereof.

In embodiments of compounds of formulae DCD-(I), DCD-(IA) and DCD-(IB), in some instances, $R^e$ may be alkyl or substituted alkyl. In some instances, $R^e$ is a C8 to C20 alkyl. In some instances, $R^e$ is a substituted C8 to C20 alkyl. In certain instances, $R^e$ is a C13 alkyl.

In some instances n is an integer from 2 to 25, such as where n is selected from 2, 3, 4, 5, 6, 7, 8, 9, 10, 11, 12, 13, 14, 15, 16, 17, 18, 19, 20, 21, 22, 23, 24 and 25.

In some instances, Y is carbon. In some instances, Y is nitrogen. In some instances, Y is silicon.

In some instances, $R^b$ is hydrogen. In some instances, $R^b$ is alkyl. In some instances, $R^b$ is a $C_1$-$C_{16}$ alkyl. In some instances, $R^b$ is selected from methyl, ethyl, propyl, isopropyl, n-butyl, isobutyl, tert-butyl, pentyl, hexyl, heptyl and octyl. In some instances, $R^b$ is selected from:

Wherein ∿∿ indicates a bond to Y and $R^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, $R^z$ is alkyl, such as a C1 to C16 alkyl or C1 to C16 substituted alkyl.

In some instances, $R^c$ is hydrogen. In some instances, $R^c$ is alkyl. In some instances, $R^c$ is a C1-C16 alkyl. In some instances, $R^c$ is selected from methyl, ethyl, propyl, isopropyl, n-butyl, isobutyl, tert-butyl, pentyl, hexyl, heptyl and octyl.

In some embodiments, $R^d$ is a C5 to C25 alkyl or a C5 to C25 alkyl substituted with a cycloalkyl group, substituted cycloalkyl group, heterocycloalkyl group, substituted heterocycloalkyl group, aryl group, substituted aryl group, arylalkyl group, substituted arylalkyl group, heteroaryl group, substituted heteroaryl group, heteroarylalkyl group, or substituted heteroarylalkyl group. In some instances, $R^d$ is a C5 to C25 alkyl substituted with a moiety selected from the group consisting of

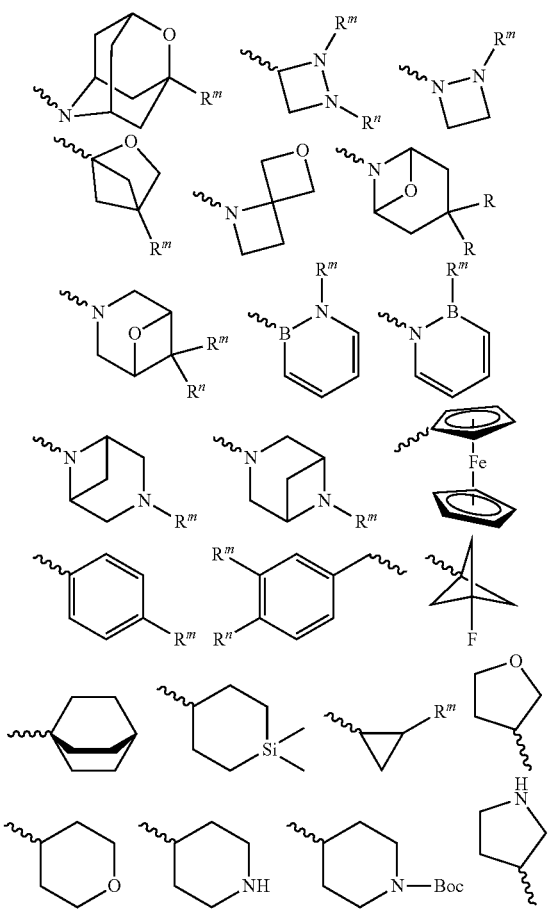

-continued

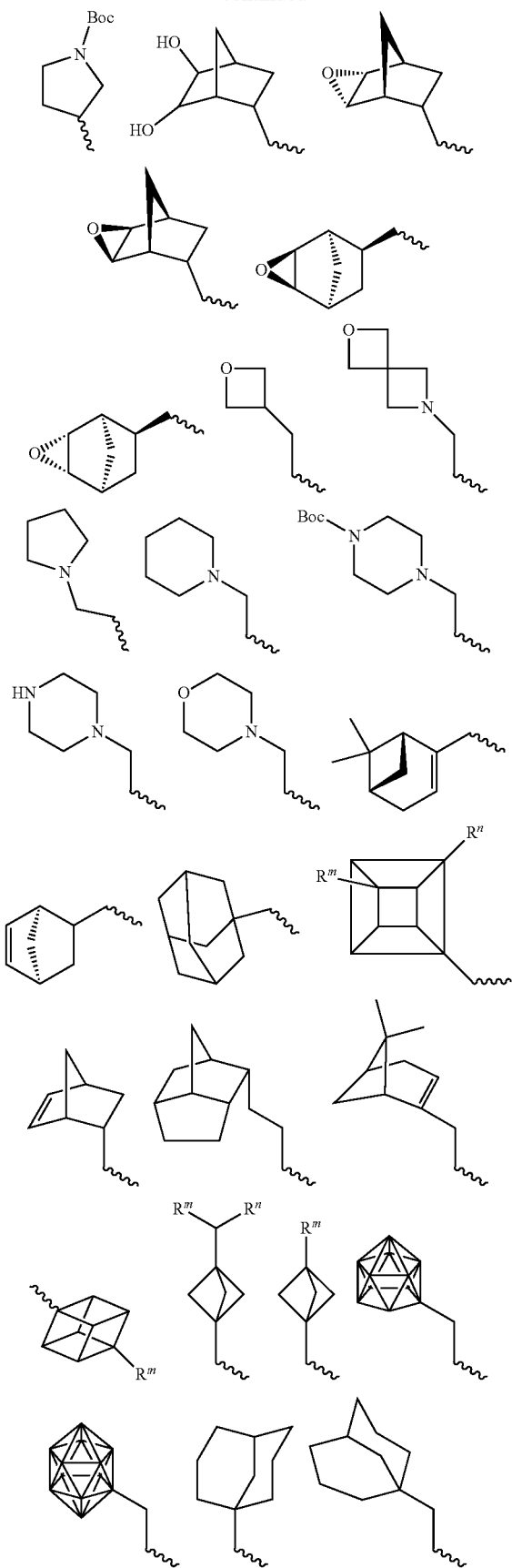

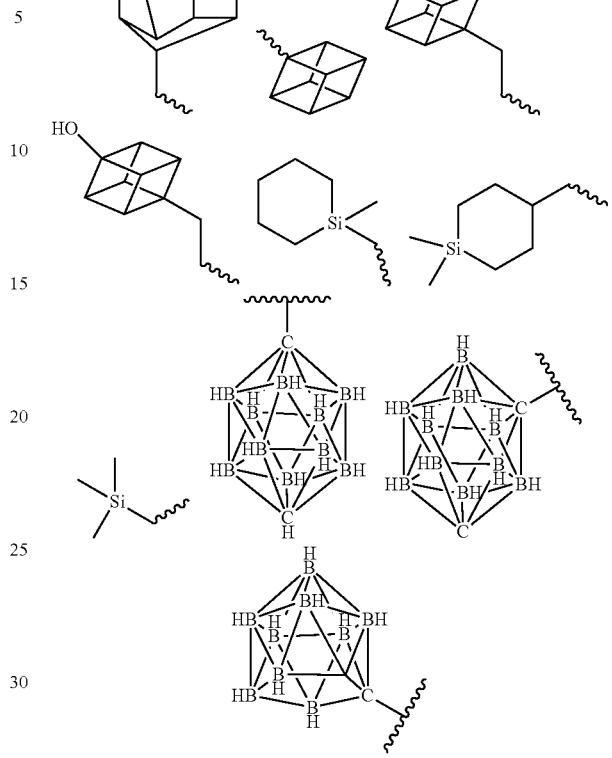

wherein ～ indicates the bond to the C5 to C25 alkyl; and $R^m$ and $R^n$ are independently selected from hydrogen, halogen, hydroxyl, substituted hydroxyl, amino, substituted amino, thiol, substituted thiol, sulfoxide, substituted sulfoxide, sulfone, substituted sulfone, sulfoximine, substituted sulfoximine, acyl, aminoacyl, alkyl, substituted alkyl, heteroalkyl, substituted heteroalkyl, cycloalkyl, substituted cycloalkyl, spiroalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^m$ is hydrogen. In some instances, $R^m$ is halogen. In some instances, $R^m$ is selected from fluorine, bromine or iodine. In some instances, $R^n$ is hydrogen. In some instances, $R^n$ is halogen. In some instances, $R^n$ is fluorine, bromine or iodine.

Formula DCD-(II)

Aspects of the present disclosure according to certain embodiments include a compound of formulae DCD-(II):

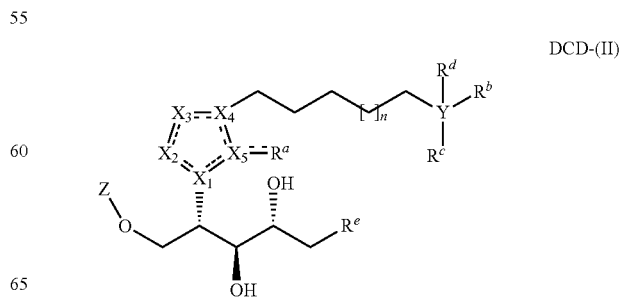

DCD-(II)

wherein:

Z is selected from:

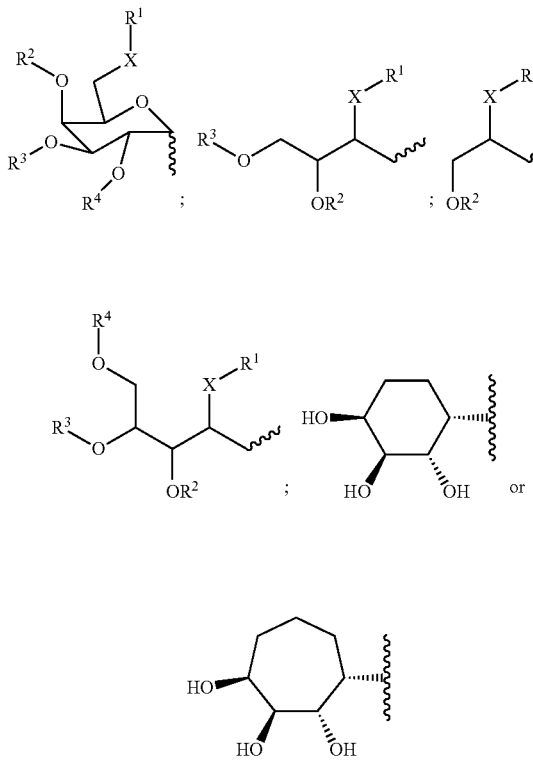

wherein ⁓ indicates the Z—O bond;

wherein X is —NHCO— or oxygen;

R$^1$, R$^2$, R$^3$ and R$^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

X$_1$, X$_2$, X$_3$, X$_4$ and X$_5$ are each independently selected from carbon, nitrogen, oxygen or sulfur;

R$^a$ is optionally absent or when present is selected from hydrogen or oxygen;

wherein ═══ indicates a double or single bond;

n is an integer from 2 to 25;

Y is selected from carbon, nitrogen or silicon;

R$^b$, R$^c$ and R$^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, R$^d$ is not present, or wherein R$^c$ and R$^d$ together with Y form a cycloalkyl, substituted cycloalkyl, aryl, substituted aryl, heteroaryl or substituted heteroaryl group; and R$^e$ is alkyl or substituted alkyl, or salt, solvate or hydrate thereof.

Formula DCD-(IIA-1)

Aspects of the present disclosure according to certain embodiments include a compound of formula DCD-(IIA-1):

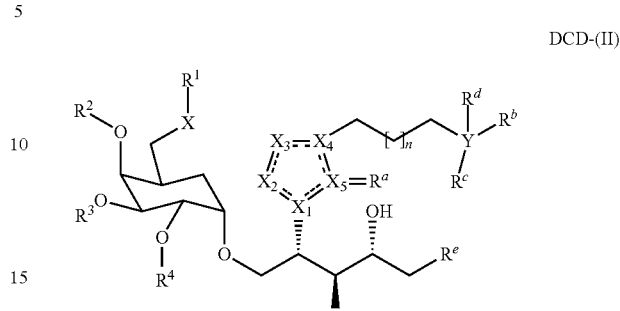

DCD-(II)

wherein X is —NHCO— or oxygen;

R$^1$, R$^2$, R$^3$ and R$^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

X$_1$, X$_2$, X$_3$, X$_4$ and X$_5$ are each independently selected from carbon, nitrogen, oxygen or sulfur;

R$^a$ is optionally absent or when present is selected from hydrogen or oxygen;

wherein ═══ indicates a double or single bond;

n is an integer from 2 to 25;

Y is selected from carbon, nitrogen or silicon;

R$^b$, R$^c$ and R$^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, R$^d$ is not present, or wherein R$^c$ and R$^d$ together with Y form a cycloalkyl, substituted cycloalkyl, aryl, substituted aryl, heteroaryl or substituted heteroaryl group; and R$^e$ is alkyl or substituted alkyl, or salt, solvate or hydrate thereof.

In some instances, R$^1$ is hydrogen. In some instances, R$^2$ is hydrogen. In some instances, R$^3$ is hydrogen. In some instances, R$^4$ is hydrogen. In certain instances, each of R$^1$, R$^2$, R$^3$ and R$^4$ are hydrogen.

In other instances, R$^1$ is:

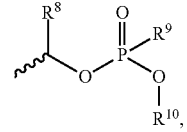

wherein ⁓ represents the R$^1$—O bond;

R$^8$ is hydrogen, alkyl or substituted alkyl; In some instances, R$^8$ is selected from hydrogen, methyl, ethyl and cyclopropyl.

R$^9$ is —NR$^f$ or —OR$^f$, wherein Rr is alkyl, substituted alkyl, acyl, alkylacyl or substituted alkylacyl, or wherein R$^f$ together with R$^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and $R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with $R^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In certain instances, $R^1$ is selected from.

1)

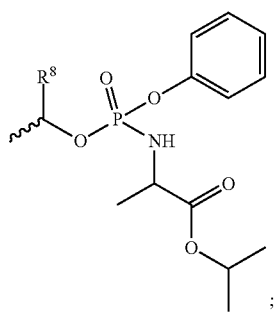

2)

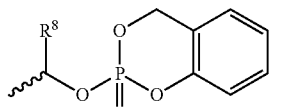

; or

3)

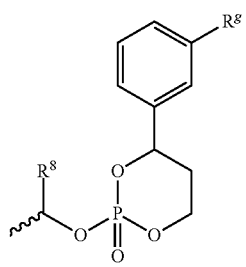

wherein ∽ represents the $R^1$—O bond;

$R^8$ is hydrogen, alkyl, substituted alkyl; and $R^g$ is hydrogen or a halogen selected from fluorine, chlorine, bromine or iodine.

In other instances, $R^1$ is:

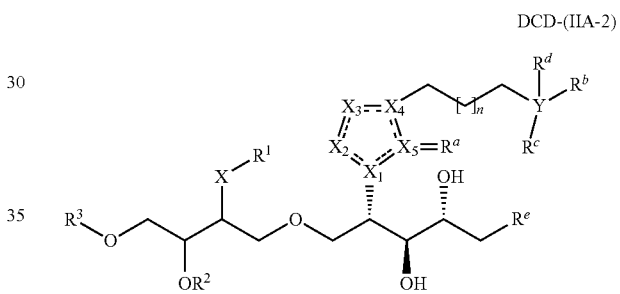

wherein:

$R^{11}$ is alkyl or substituted alkyl;

$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^{11}$ is selected from methyl, ethyl, n-propyl, iso-propyl, n-butyl, iso-butyl, t-butyl. In certain instances, $R^{11}$ is iso-propyl.

In certain instances, $R^1$ is:

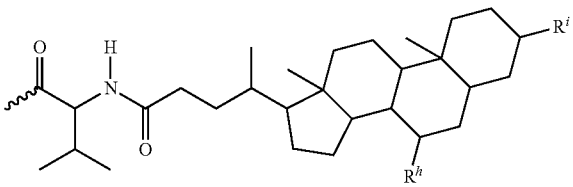

wherein $R^h$ and $R^i$ are each independently selected from hydrogen, hydroxyl or halogen. In some instances, $R^h$ is hydroxyl. In some instances, $R^h$ is F. In some instances, $R^h$ is Cl. In some instances, $R^h$ is I. In some instances, $R^h$ is Br. In some instances, $R^i$ is hydroxyl. In some instances, $R^i$ is F. In other instances, $R^i$ is Cl. In other instances, $R^i$ is I. In other instances, $R^i$ is Br.

Formula DCD-(IIA-2)

Aspects of the present disclosure according to certain embodiments include a compound of formula DCD-(IIA-2):

DCD-(IIA-2)

wherein X is —NHCO— or oxygen;

$R^1$, $R^2$ and $R^3$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

$X_1$, $X_2$, $X_3$, $X_4$ and $X_5$ are each independently selected from carbon, nitrogen, oxygen or sulfur;

$R^a$ is optionally absent or when present is selected from hydrogen or oxygen;

wherein ═══ indicates a double or single bond;

n is an integer from 2 to 25.

Y is selected from carbon, nitrogen or silicon;

$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and $R^e$ is alkyl or substituted alkyl, or salt, solvate or hydrate thereof.

In some instances, $R^1$ is hydrogen. In some instances, $R^2$ is hydrogen. In some instances, $R^3$ is hydrogen. In certain instances, each of $R^1$, $R^2$ and $R^3$ are hydrogen.

In other instances, $R^1$ is:

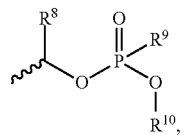

wherein ⁓⁓⁓ represents the $R^1$—O bond;

$R^8$ is hydrogen, alkyl or substituted alkyl. In some instances, $R^8$ is selected from hydrogen, methyl, ethyl and cyclopropyl.

$R^9$ is —$NR^f$ or —$OR^f$, wherein $R^f$ is alkyl, substituted alkyl, acyl, alkylacyl or substituted alkylacyl, or wherein $R^f$ together with $R^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and $R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with $R^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In certain instances, $R^1$ is selected from:

1)

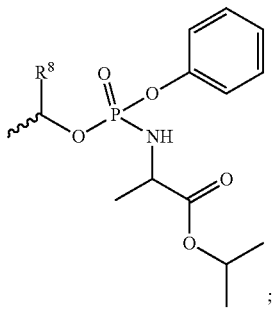

;

2)

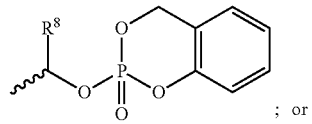

; or

3)

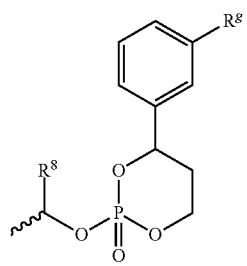

wherein ⁓⁓⁓ represents the $R^1$—O bond, $R^8$ is hydrogen, alkyl, substituted alkyl; and $R^g$ is hydrogen or a halogen selected from fluorine, chlorine, bromine or iodine.

In other instances, $R^1$ is:

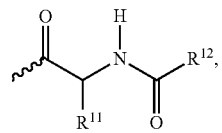

wherein:

$R^{11}$ is alkyl or substituted alkyl;

$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^{11}$ is selected from methyl, ethyl, n-propyl, iso-propyl, n-butyl, iso-butyl, t-butyl. In certain instances, $R^{11}$ is iso-propyl.

In certain instances, $R^1$ is:

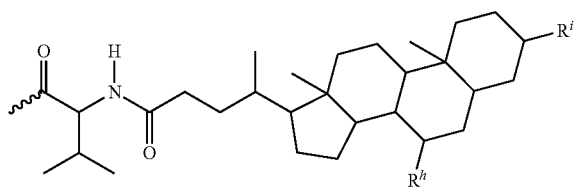

wherein $R^h$ and $R^i$ are each independently selected from hydrogen, hydroxyl or halogen. In some instances, $R^h$ is hydroxyl. In some instances, $R^h$ is F. In some instances, $R^h$ is Cl. In some instances, $R^h$ is I. In some instances, $R^a$ is Br. In some instances, $R^i$ is hydroxyl. In some instances, $R^i$ is F. In other instances, $R^i$ is Cl. In other instances, $R^i$ is I.

In other instances, $R^i$ is Br.

Formula DCD-(IIA-3)

Aspects of the present disclosure according to certain embodiments include a compound of formula DCD-(IIA-3):

DCD-(IIA-3)

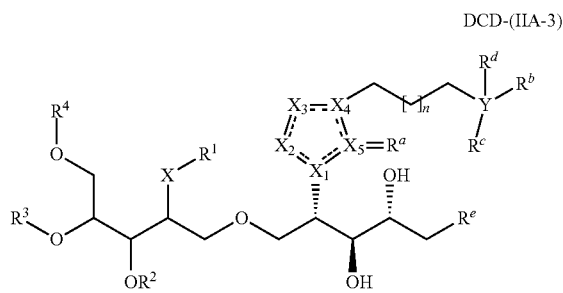

wherein X is —NHCO— or oxygen.

$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;

$X_1$, $X_2$, $X_3$, $X_4$ and $X_5$ are each independently selected from carbon, nitrogen, oxygen or sulfur;

R is optionally absent or wen present is selected from hydrogen or oxygen;

wherein ⁝⁝⁝ a indicates a double or single bond;

n is an integer from 2 to 25;

Y is selected from carbon, nitrogen or silicon;

$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and $R^e$ is alkyl or substituted alkyl, or salt, solvate or hydrate thereof.

In some instances, $R^1$ is hydrogen. In some instances, $R^2$ is hydrogen. In some instances, $R^3$ is hydrogen. In some instances, $R^4$ is hydrogen. In certain instances, each of $R^1$, $R^2$, $R^3$ and $R^4$ are hydrogen.

In other instances, $R^1$ is:

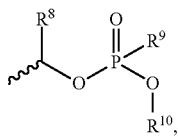

wherein ∼∼ represents the $R^1$—O bond;

$R^8$ is hydrogen, alkyl or substituted alkyl; In some instances, $R^8$ is selected from hydrogen, methyl, ethyl and cyclopropyl.

$R^9$ is —$NR^f$ or —$OR^f$, wherein $R^f$ is alkyl, substituted alkyl, acyl, alkylacyl or substituted alkylacyl, or wherein Rr together with $R^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and $R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with $R^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In certain instances, $R^1$ is selected from:

1)

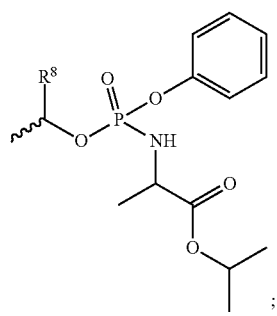

2)

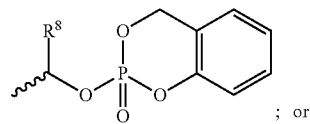

; or

3)

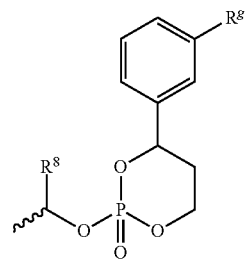

wherein ∼∼ represents the $R^1$—O bond;

$R^8$ is hydrogen, alkyl, substituted alkyl; and $R^g$ is hydrogen or a halogen selected from fluorine, chlorine, bromine or iodine.

In other instances, $R^1$ is:

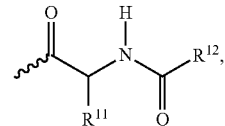

wherein:

$R^{11}$ is alkyl or substituted alkyl;

$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^{11}$ is selected from methyl, ethyl, n-propyl, iso-propyl, n-butyl, iso-butyl, t-butyl. In certain instances, $R^{11}$ is iso-propyl.

In certain instances, $R^1$ is:

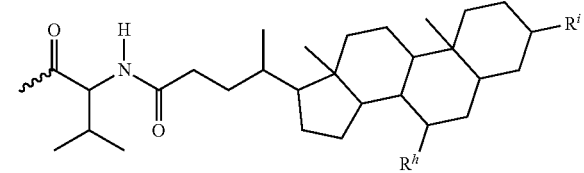

wherein $R^h$ and $R^i$ are each independently selected from hydrogen, hydroxyl or halogen. In some instances, $R^h$ is hydroxyl. In some instances, $R^h$ is F. In some instances, R is Cl. In some instances, $R^h$ is I. In some instances, $R^h$ is Br. In some instances, $R^i$ is hydroxyl. In some instances, $R^i$ is F. In other instances, $R^i$ is Cl. In other instances, $R^i$ is I. In other instances, $R^i$ is Br.

Formula DCD-(IIA-4)

Aspects of the present disclosure according to certain embodiments include a compound of formula DCD-(IIA-4):

DCD-(IIA-4)

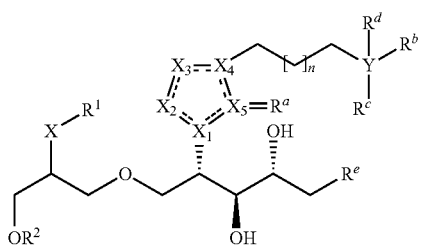

wherein X is —NHCO— or oxygen;
$R^1$ and $R^2$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
$X_1$, $X_2$, $X_3$, $X_4$ and $X_5$ are each independently selected from carbon, nitrogen, oxygen or sulfur;
$R^1$ is optionally absent or when present is selected from hydrogen or oxygen;
wherein ≈ indicates a double or single bond;
n is an integer from 2 to 25;
Y is selected from carbon, nitrogen or silicon;
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, amyl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and
$R^e$ is alkyl or substituted alkyl,
or salt, solvate or hydrate thereof.

In some instances, $R^1$ is hydrogen. In some instances, $R^2$ is hydrogen. In certain instances, each of $R^1$ and $R^2$ are hydrogen.

In other instances, $R^1$ is:

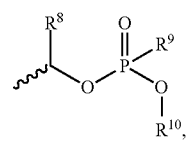

wherein ⌇ represents the $R^1$—O bond;
$R^8$ is hydrogen, alkyl or substituted alkyl; In some instances, $R^8$ is selected from hydrogen, methyl, ethyl and cyclopropyl.

$R^9$ is —$NR^f$ or —OR wherein $R^f$ is alkyl, substituted alkyl, acyl, alkylacyl or substituted alkylacyl, or wherein $R^f$ together with $R^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and
$R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with $R^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In certain instances, $R^1$ is selected from:

1) 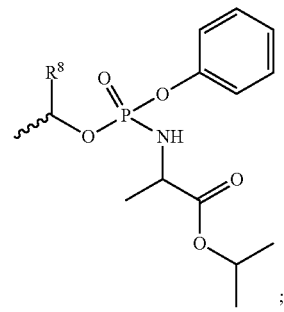

2) 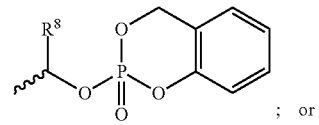

; or

3) 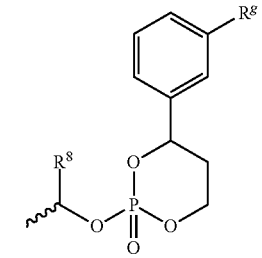

wherein ⌇ represents the $R^1$—O bond;
$R^8$ is hydrogen, alkyl, substituted alkyl; and
$R^g$ is hydrogen or a halogen selected from fluorine, chlorine, bromine or iodine.

In other instances, $R^1$ is:
wherein:

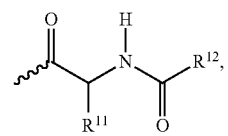

$R^{11}$ is alkyl or substituted alkyl.
$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, $R^{11}$ is selected from methyl, ethyl, n-propyl, iso-propyl, n-butyl, iso-butyl, t-butyl. In certain instances, $R^{11}$ is iso-propyl.

In certain instances, $R^1$ is:

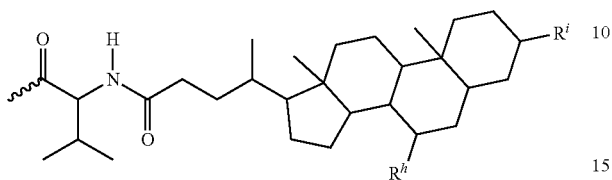

wherein $R^h$ and $R^i$ are each independently selected from hydrogen, hydroxyl or halogen. In some instances, $R^h$ is hydroxyl. In some instances, $R^h$ is F. In some instances, $R^h$ is Cl. In some instances, $R^h$ is I. In some instances, $R^h$ is Br. In some instances, $R^i$ is hydroxyl. In some instances, $R^i$ is F. In other instances, $R^i$ is Cl. In other instances, $R^i$ is I.

In other instances, $R^i$ is

Formula DCD-(IIB-1)

Aspects of the present disclosure according to certain embodiments include a compound of formula DCD-(IIB-1):

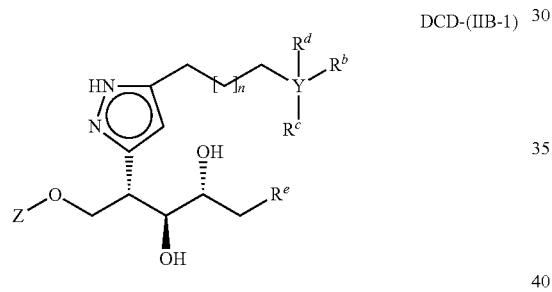

DCD-(IIB-1)

wherein:
Z is selected from:

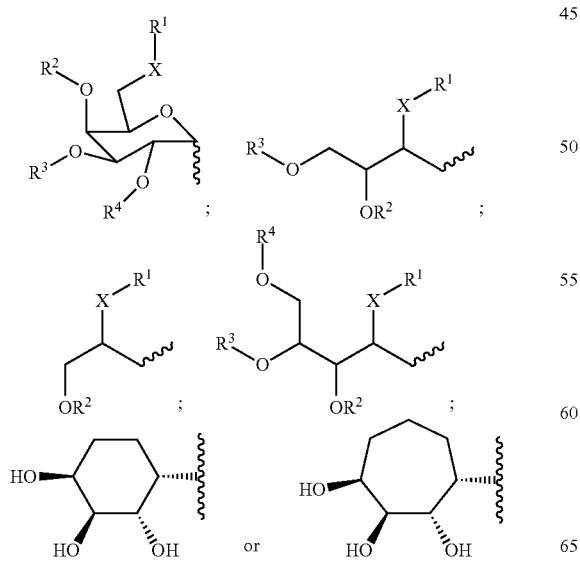

wherein ∼∼∼ indicates the Z—O bond;
wherein X is —NHCO— or oxygen;
$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
n is an integer from 2 to 25;
Y is selected from carbon, nitrogen or silicon;
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and
$R^e$ is alkyl or substituted alkyl,
or salt, solvate or hydrate thereof.

Formula DCD-(IIB-2)

Aspects of the present disclosure according to certain embodiments include a compound of formula DCD-(IIB-2):

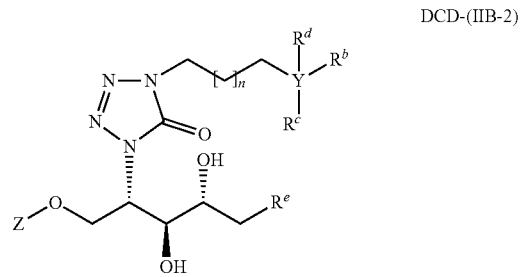

DCD-(IIB-2)

wherein:
Z is selected from:

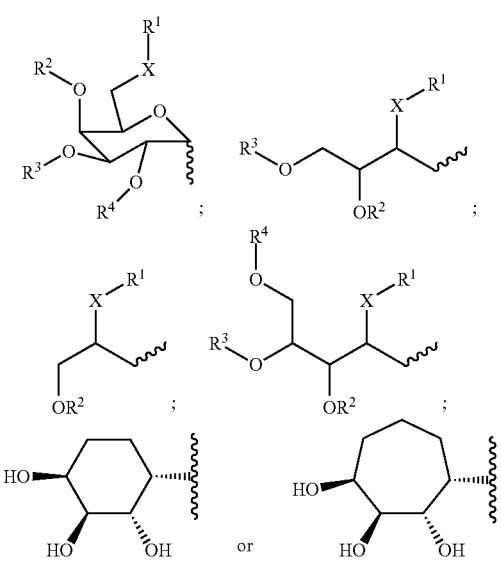

wherein ∼∼∼ indicates the Z—O bond
wherein X is —NHCO— or oxygen;
R$^1$, R$^2$, R$^3$ and R$^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
n is an integer from 2 to 25;
Y is selected from carbon, nitrogen or silicon;
R$^b$, R$^c$ and R$^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, R$^d$ is not present, or wherein R$^c$ and R$^d$ together with Y form a cycloalkyl, substituted cycloalkyl, aryl, substituted aryl, heteroaryl or substituted heteroaryl group; and
R$^e$ is alkyl or substituted alkyl,
or salt, solvate or hydrate thereof.
Formula DCD-(IIB-3)

Aspects of the present disclosure according to certain embodiments include a compound of formula DCD-(IIB-3):

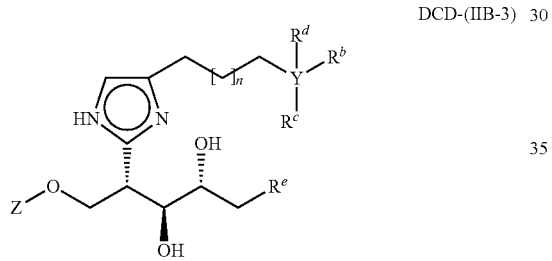

DCD-(IIB-3)

wherein:
Z is selected from:

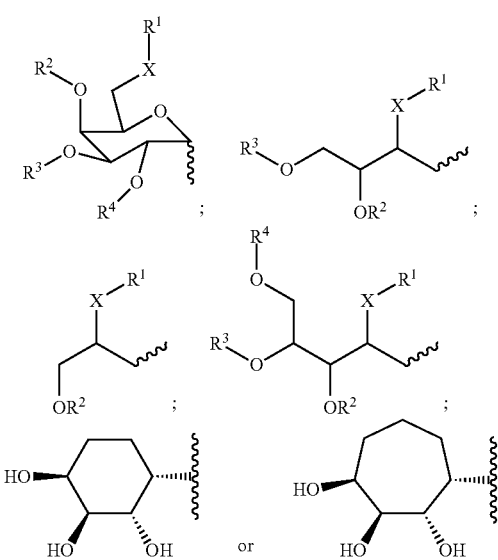

wherein ∼∼∼ indicates the Z—O bond;
wherein X is —NHCO— or oxygen;
R$^1$, R$^2$, R$^3$ and R$^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
n is an integer from 2 to 25;
Y is selected from carbon, nitrogen or silicon,
R$^b$, R$^c$ and R$^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, R$^d$ is not present, or wherein R$^c$ and R$^d$ together with Y form a cycloalkyl, substituted cycloalkyl, aryl, substituted aryl, heteroaryl or substituted heteroaryl group; and
R$^e$ is alkyl or substituted alkyl.
or salt, solvate or hydrate thereof.

In embodiments of compounds of formulae DCD-(II), DCD-(IIA) and DCD-(IIB), in some instances, R$^e$ may be alkyl or substituted alkyl. In some instances, R$^e$ is a C8 to C20 alkyl. In some instances, R$^e$ is a substituted C8 to C20 alkyl. In certain instances, R$^e$ is a C13 alkyl.

In some instances n is an integer from 2 to 25, such as where n is selected from 2, 3, 4, 5, 6, 7, 8, 9, 10, 11, 12, 13, 14, 15, 16, 17, 18, 19, 20, 21, 22, 23, 24 and 25.

In some instances, Y is carbon. In some instances, Y is nitrogen. In some instances, Y is silicon.

In some instances, R$^b$ is hydrogen. In some instances, R$^b$ is alkyl. In some instances, R$^b$ is a C1-C16 alkyl. In some instances, R$^b$ is selected from methyl, ethyl, propyl, isopropyl, n-butyl, isobutyl, tert-butyl, pentyl, hexyl, heptyl and octyl. In some instances, R$^b$ is selected from:

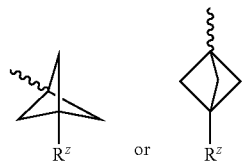

wherein ∼∼∼ indicates a bond to Y and R$^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, R$^z$ is alkyl, such as a C1 to C16 alkyl or C1 to C16 substituted alkyl.

In some instances, R$^c$ is hydrogen. In some instances, R$^c$ is alkyl. In some instances, R$^c$ is a C1-C16 alkyl. In some instances, R$^c$ is selected from methyl, ethyl, propyl, isopropyl, n-butyl, isobutyl, tert-butyl, pentyl, hexyl, heptyl and octyl.

In some embodiments, R$^d$ is a C5 to C25 alkyl or a C5 to C25 alkyl substituted with a cycloalkyl group, substituted cycloalkyl group, heterocycloalkyl group, substituted heterocycloalkyl group, aryl group, substituted aryl group, arylalkyl group, substituted arylalkyl group, heteroaryl group, substituted heteroaryl group, heteroarylalkyl group, or substituted heteroarylalkyl group. In some instances, $R^d$ is a C5 to C25 alkyl substituted with a moiety selected from the group consisting of:
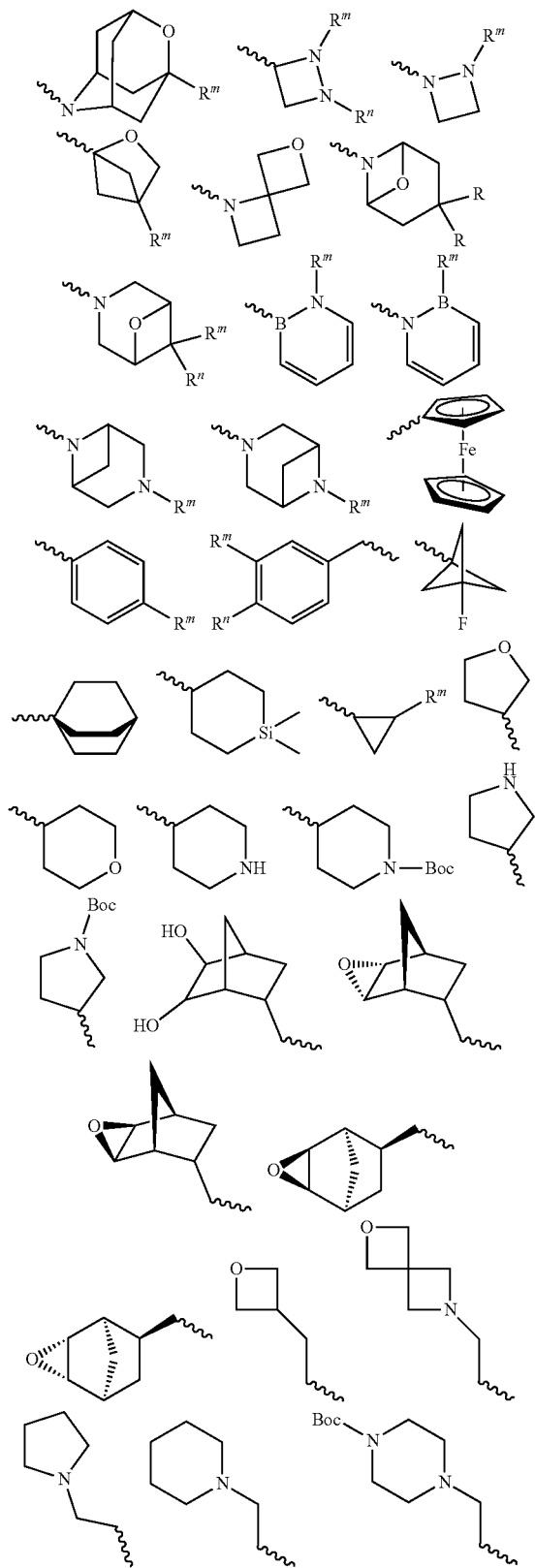
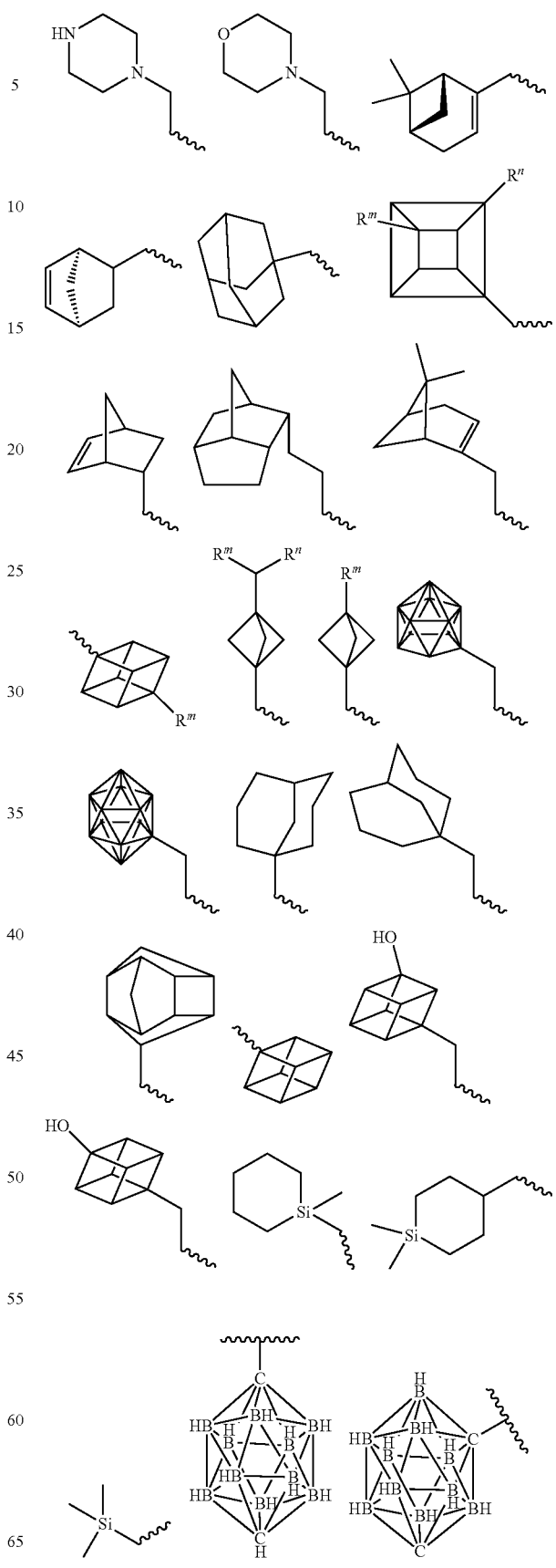

-continued

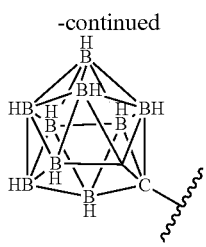

wherein ⁓ indicates the bond to the C5 to C25 alkyl; and R''' and R'' are independently selected from hydrogen, halogen, hydroxyl, substituted hydroxyl, amino, substituted amino, thiol, substituted thiol, sulfoxide, substituted sulfoxide, sulfone, substituted sulfone, sulfoximine, substituted sulfoximine, acyl, aminoacyl, alkyl, substituted alkyl, heteroalkyl, substituted heteroalkyl, cycloalkyl, substituted cycloalkyl, spiroalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, R''' is hydrogen. In some instances, R''' is halogen. In some instances, R''' is selected from fluorine, bromine or iodine. In some instances, R'' is hydrogen. In some instances, R'' is halogen. In some instances, R'' is fluorine, bromine or iodine.

In some embodiments, compounds of interest include those shown in Tables 1-9, which are not to be construed as limitative.

TABLE 1

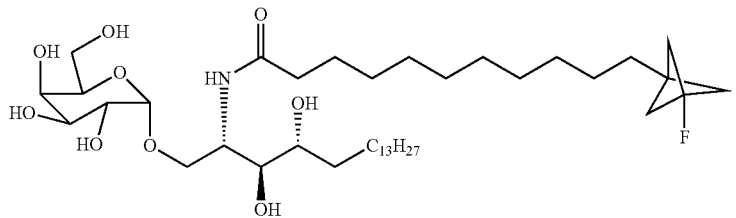

DCD-101

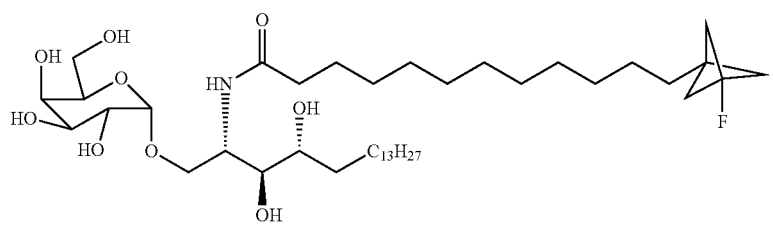

DCD-113

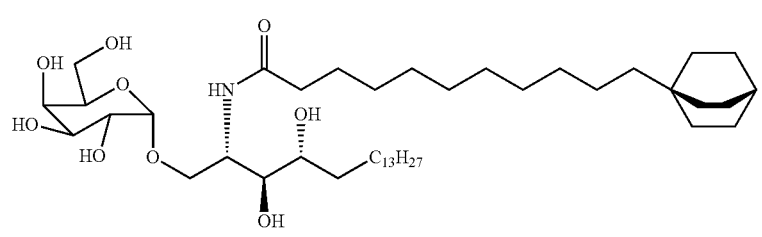

DCD-102

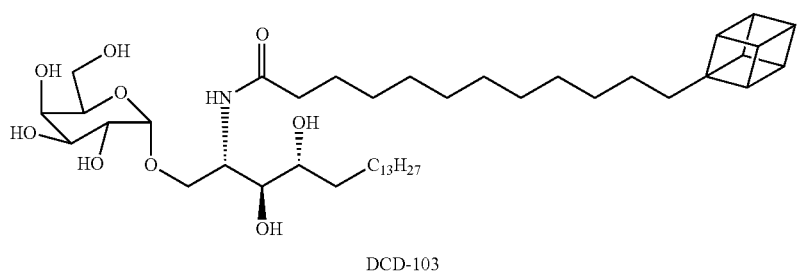

DCD-103

TABLE 1-continued
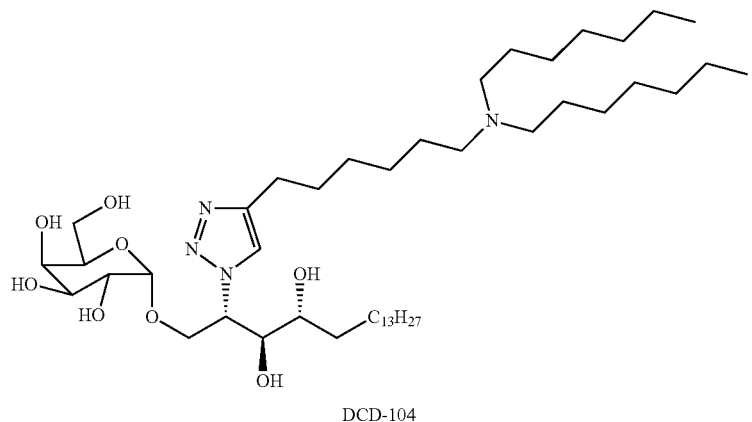
DCD-104
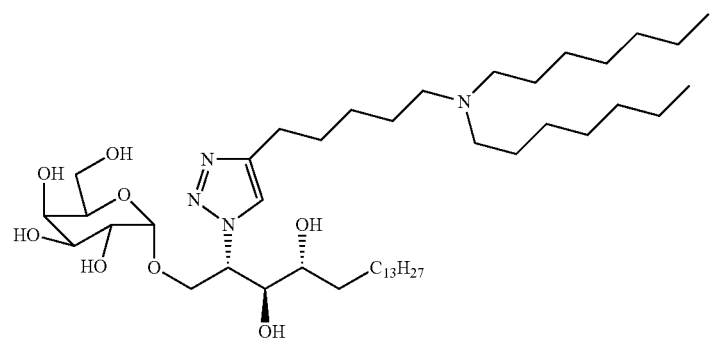
DCD-105
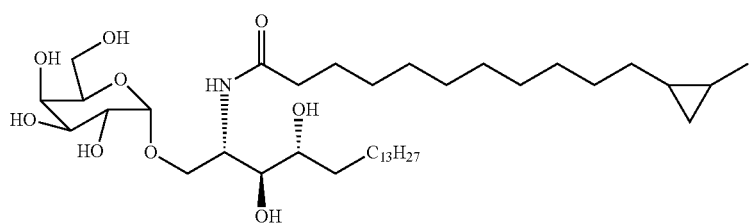
DCD-106
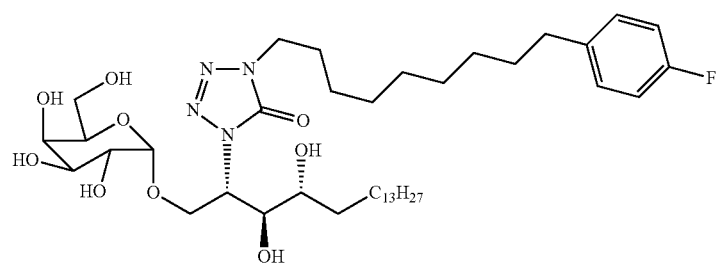
DCD-107

TABLE 1-continued
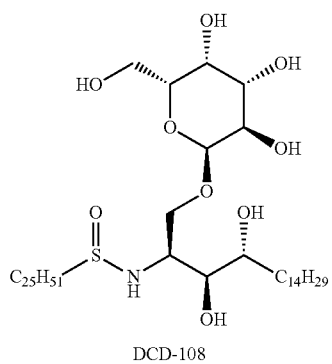
DCD-108
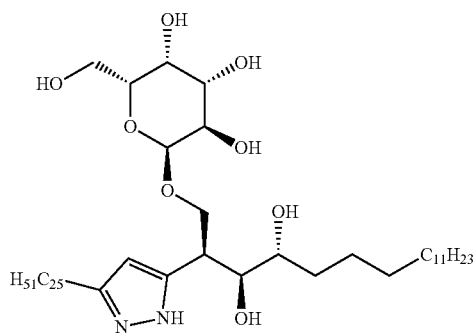
DCD-109
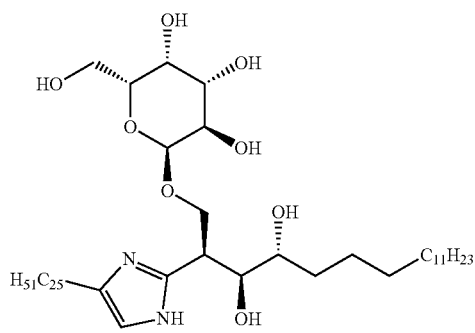
DCD-110
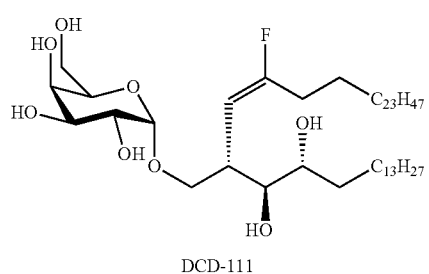
DCD-111

TABLE 1-continued
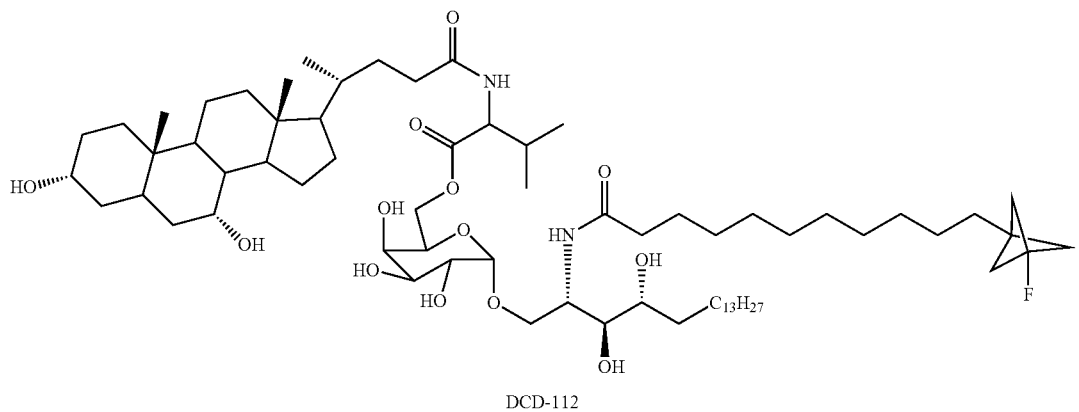
DCD-112
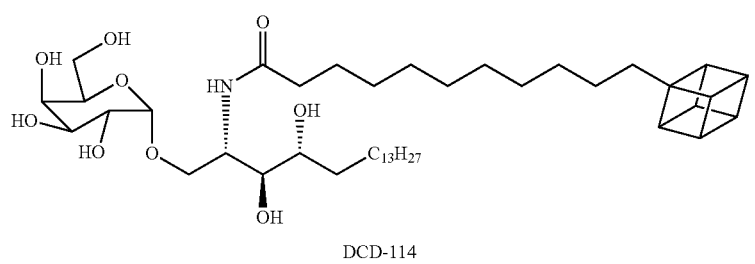
DCD-114
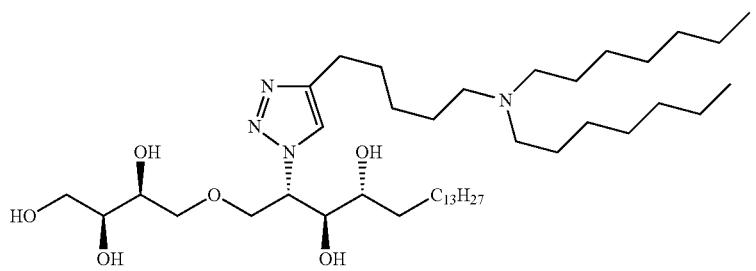
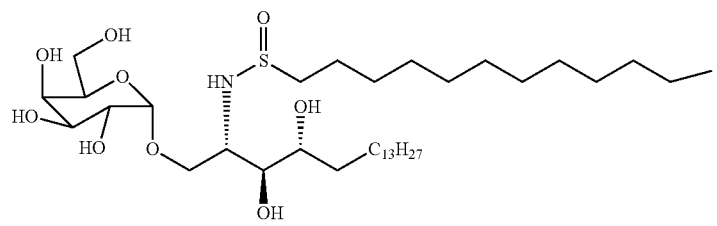
DCD-115
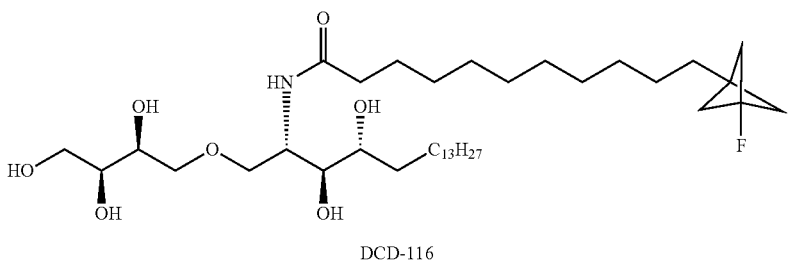
DCD-116

TABLE 1-continued
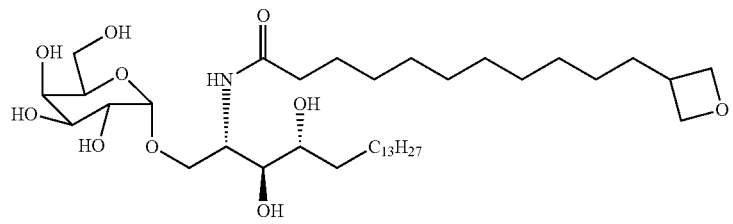
DCD-118
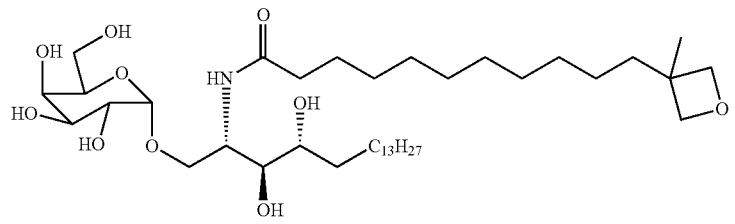
DCD-119
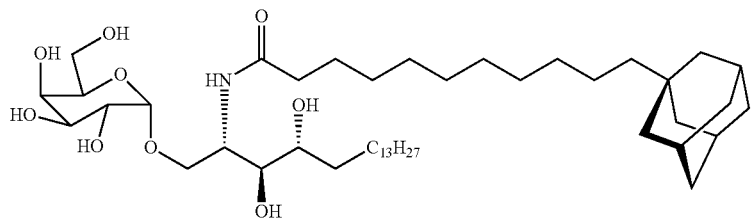
DCD-120
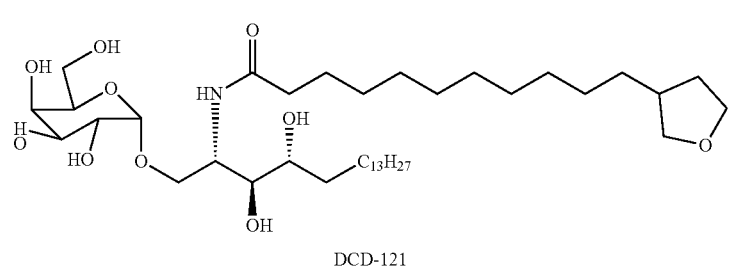
DCD-121
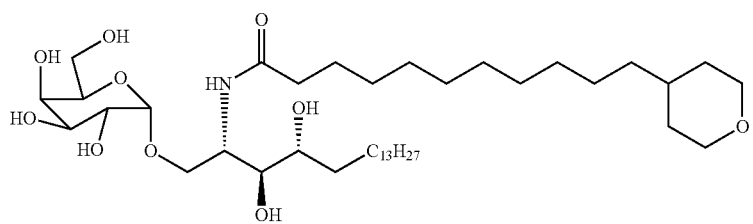
DCD-122
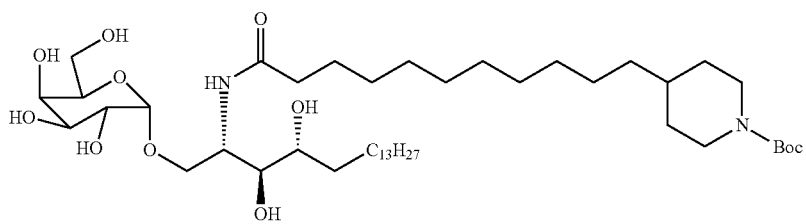
DCD-123

TABLE 1-continued
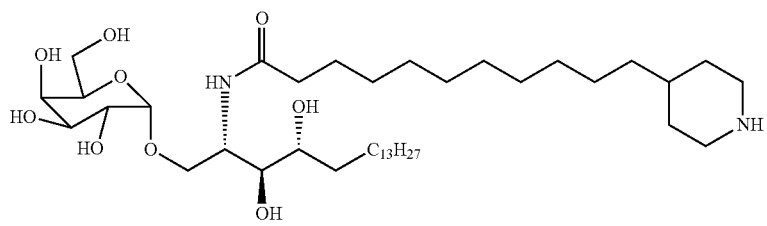
DCD-124
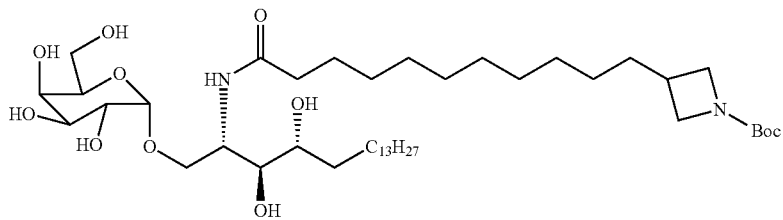
DCD-125
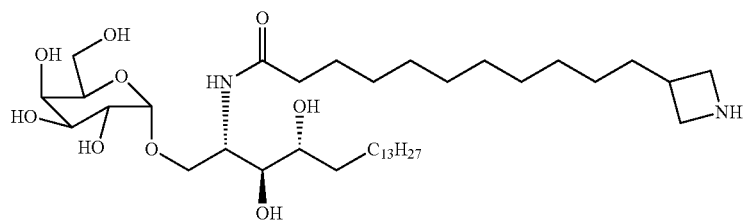
DCD-126
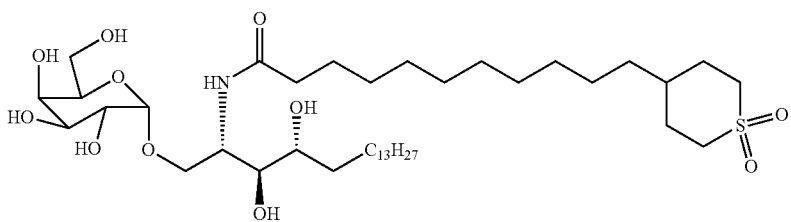
DCD-127
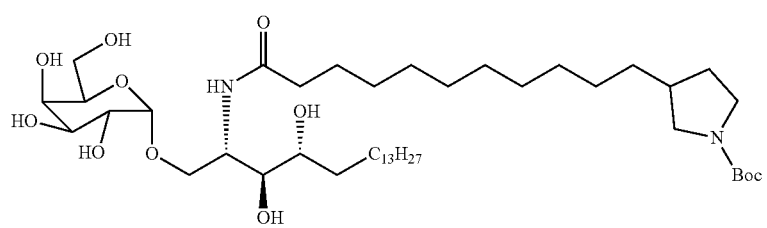
DCD-128
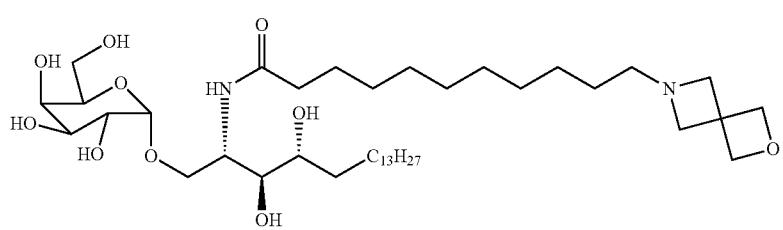
DCD-129

TABLE 1-continued
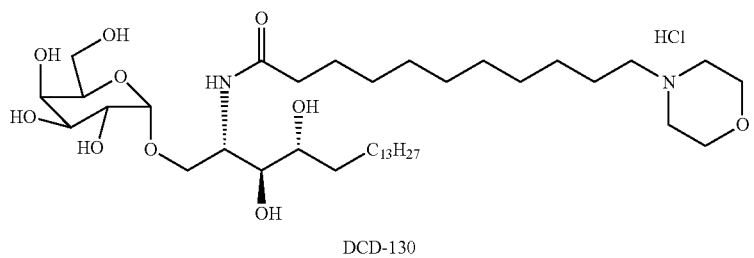
DCD-130
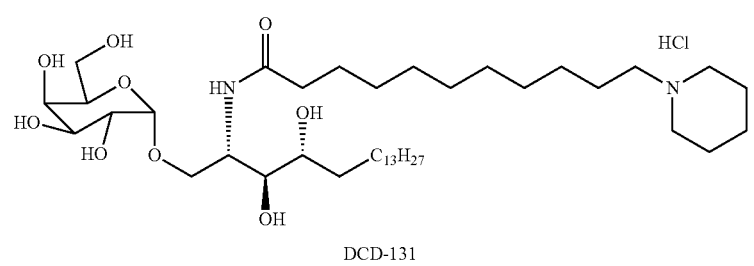
DCD-131
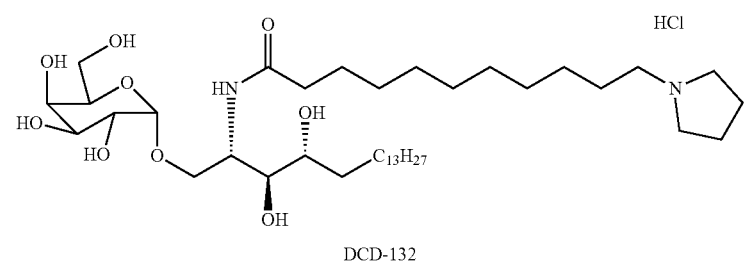
DCD-132
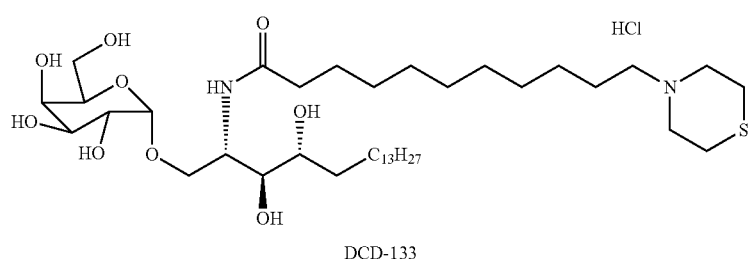
DCD-133
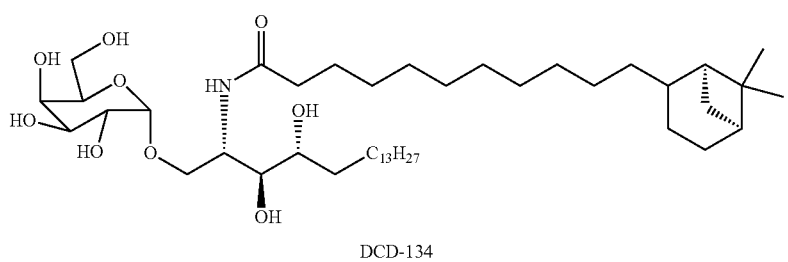
DCD-134
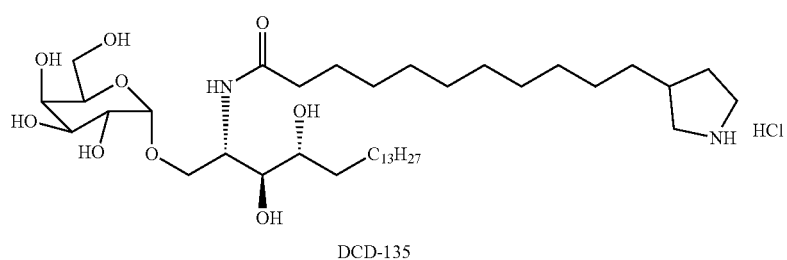
DCD-135

TABLE 1-continued
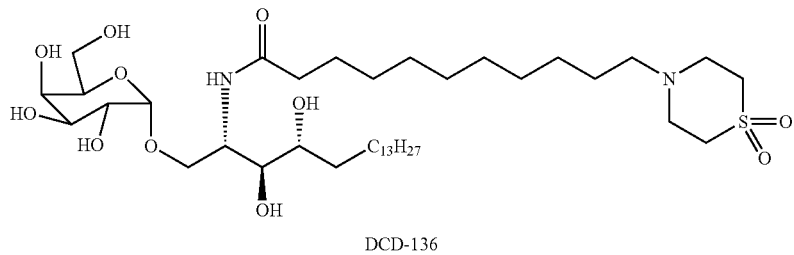
DCD-136
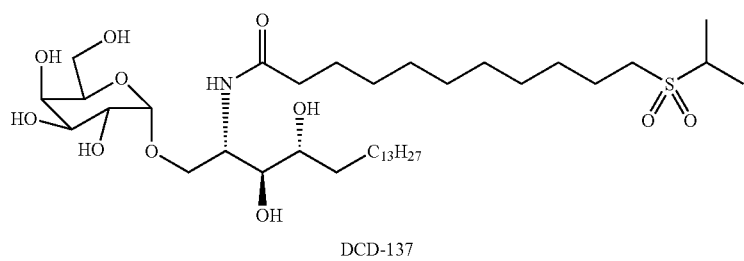
DCD-137
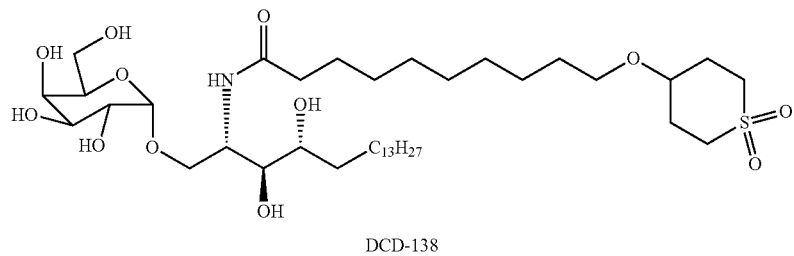
DCD-138
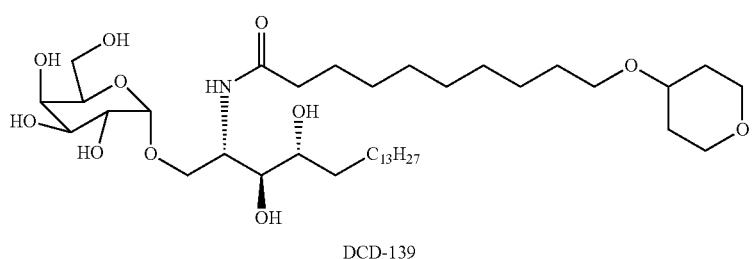
DCD-139
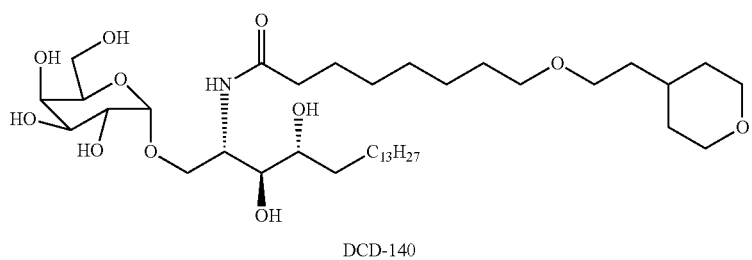
DCD-140
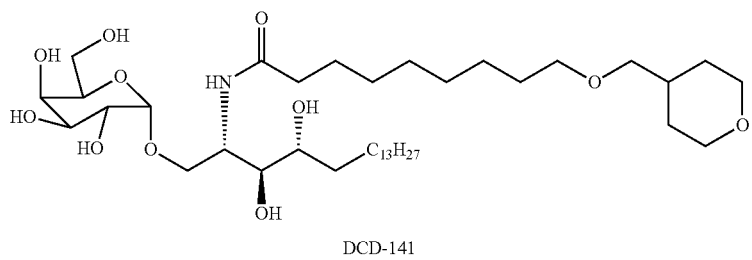
DCD-141

TABLE 1-continued
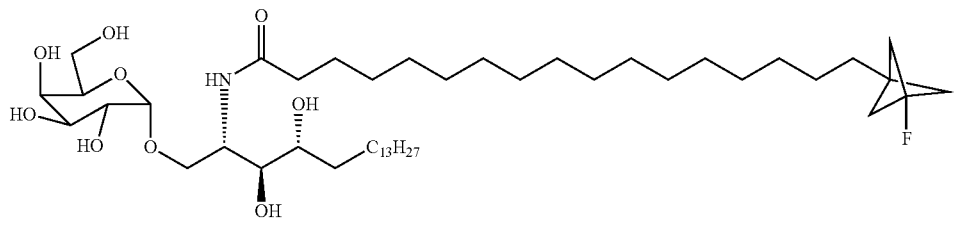
DCD-142
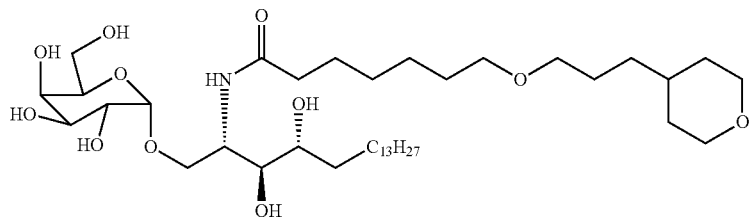
DCD-143
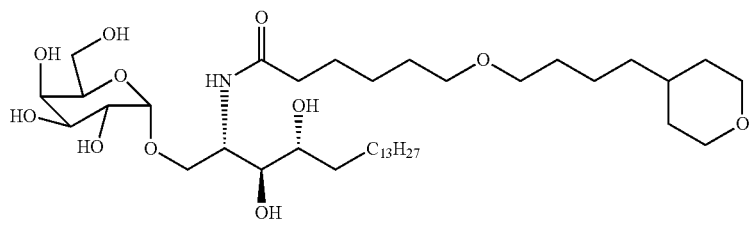
DCD-144
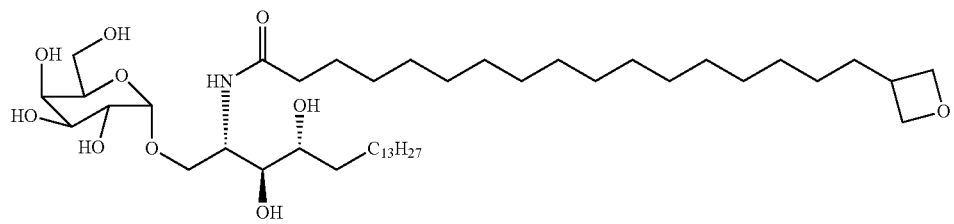
DCD-145
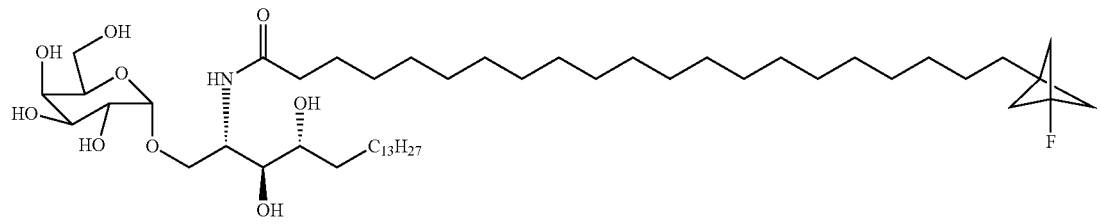
DCD-146
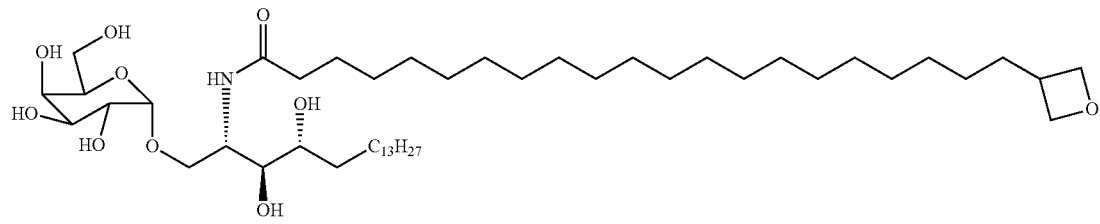
DCD-147

TABLE 1-continued
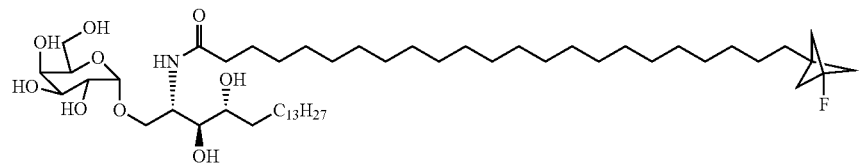
DCD-148
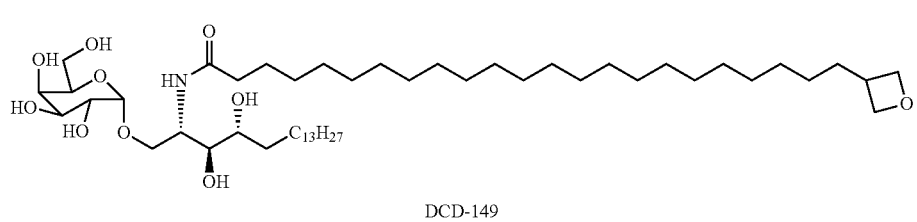
DCD-149
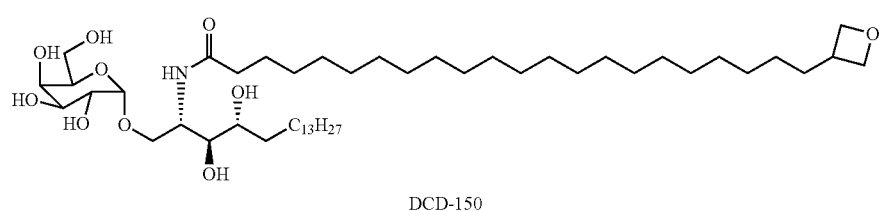
DCD-150
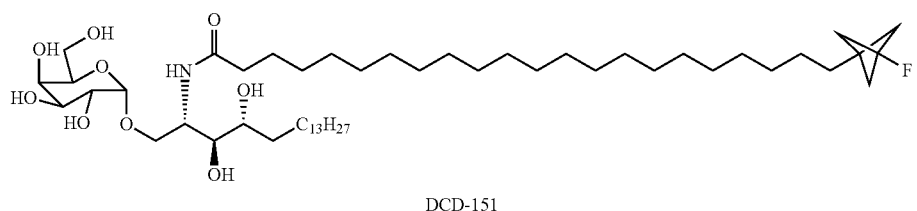
DCD-151
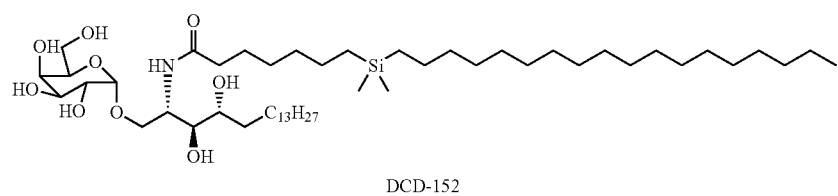
DCD-152
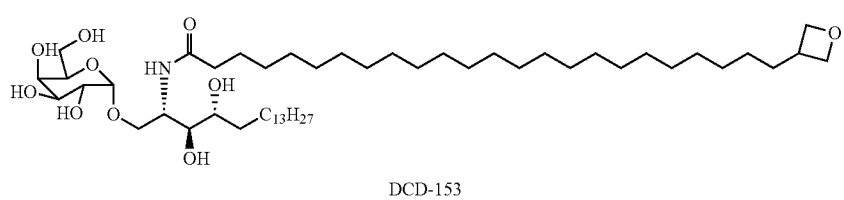
DCD-153
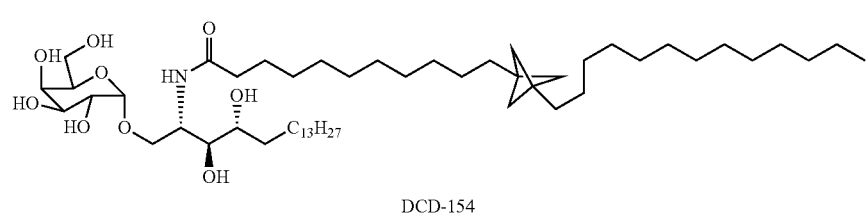
DCD-154

TABLE 1-continued
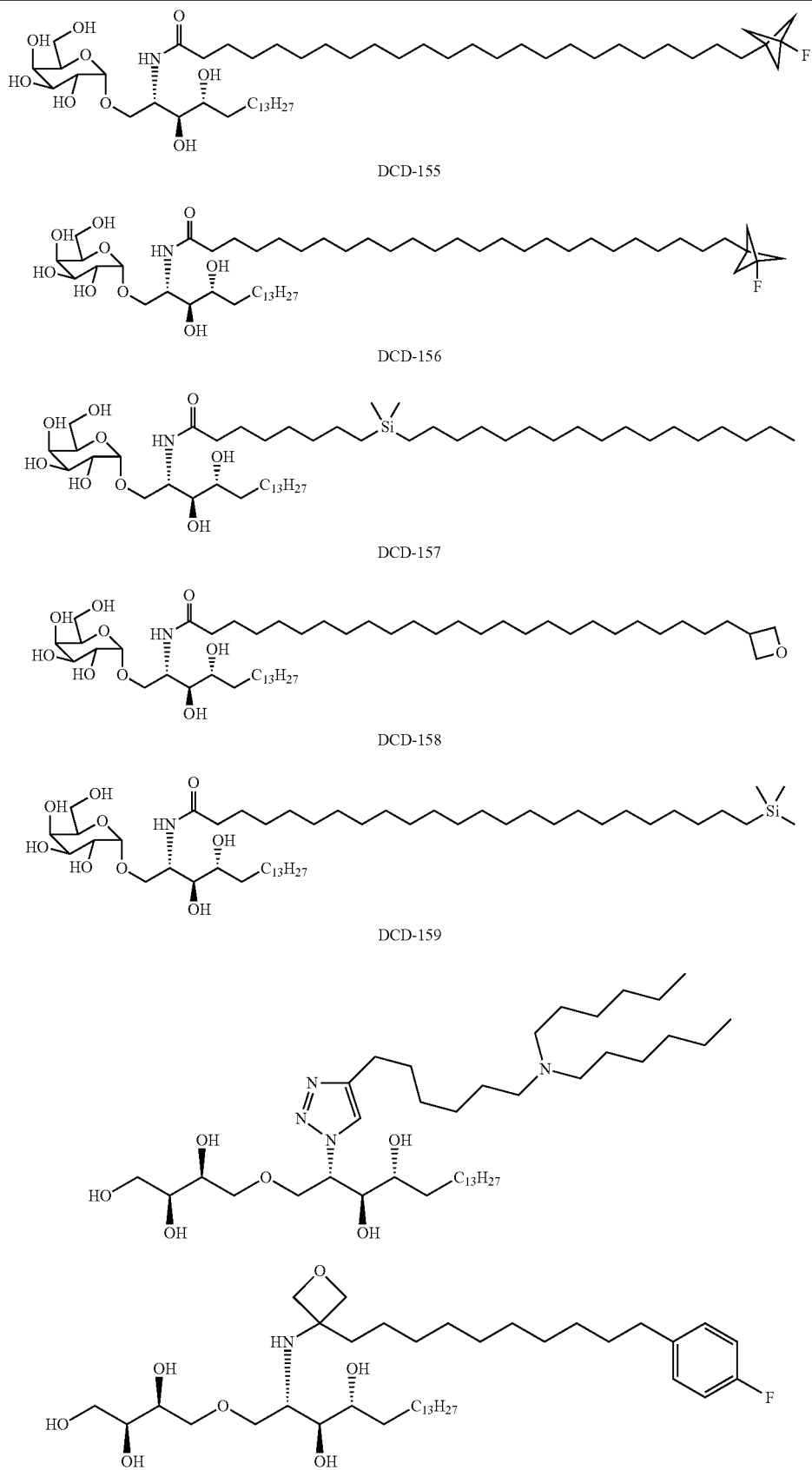

TABLE 1-continued
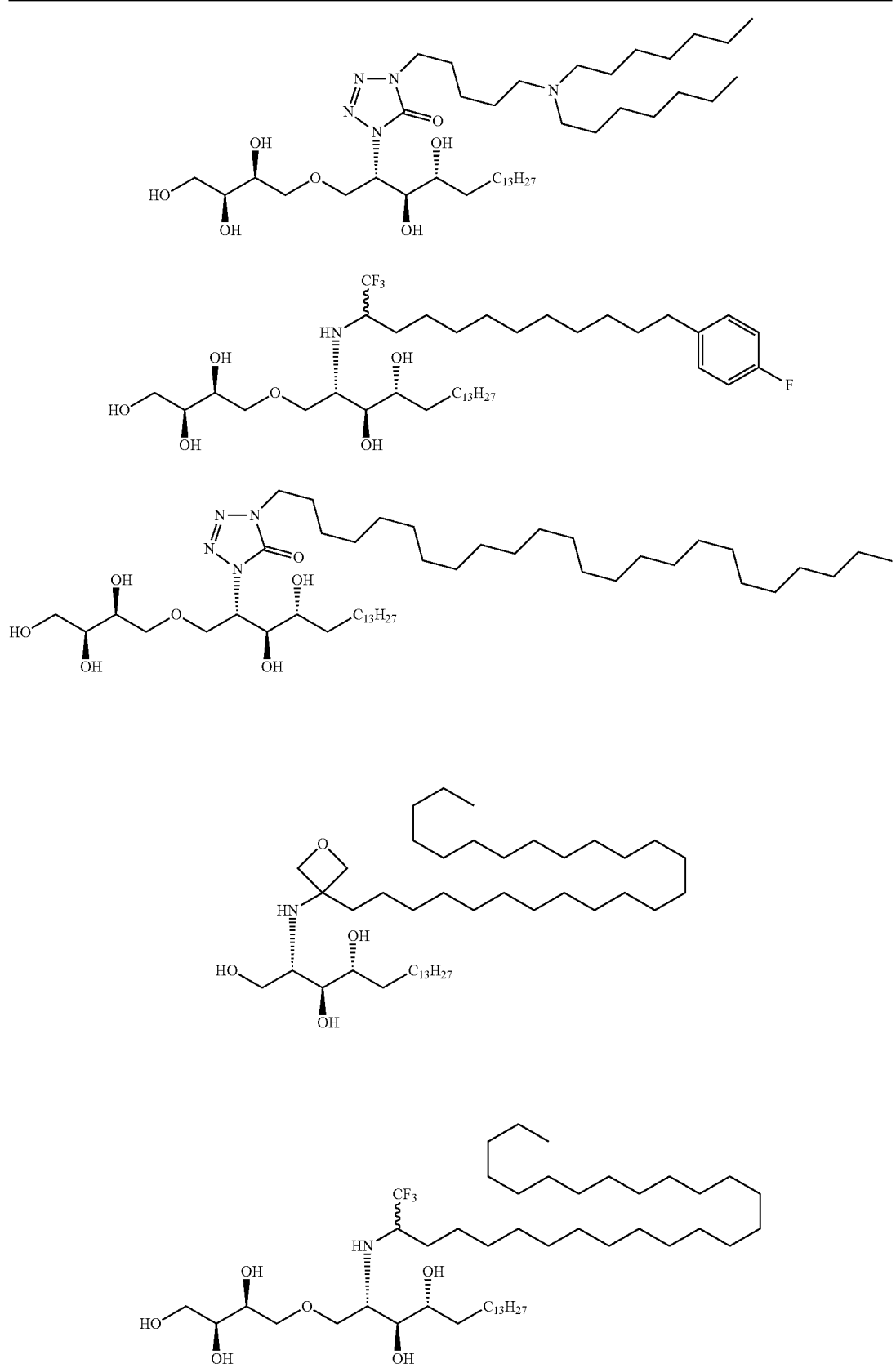

TABLE 1-continued
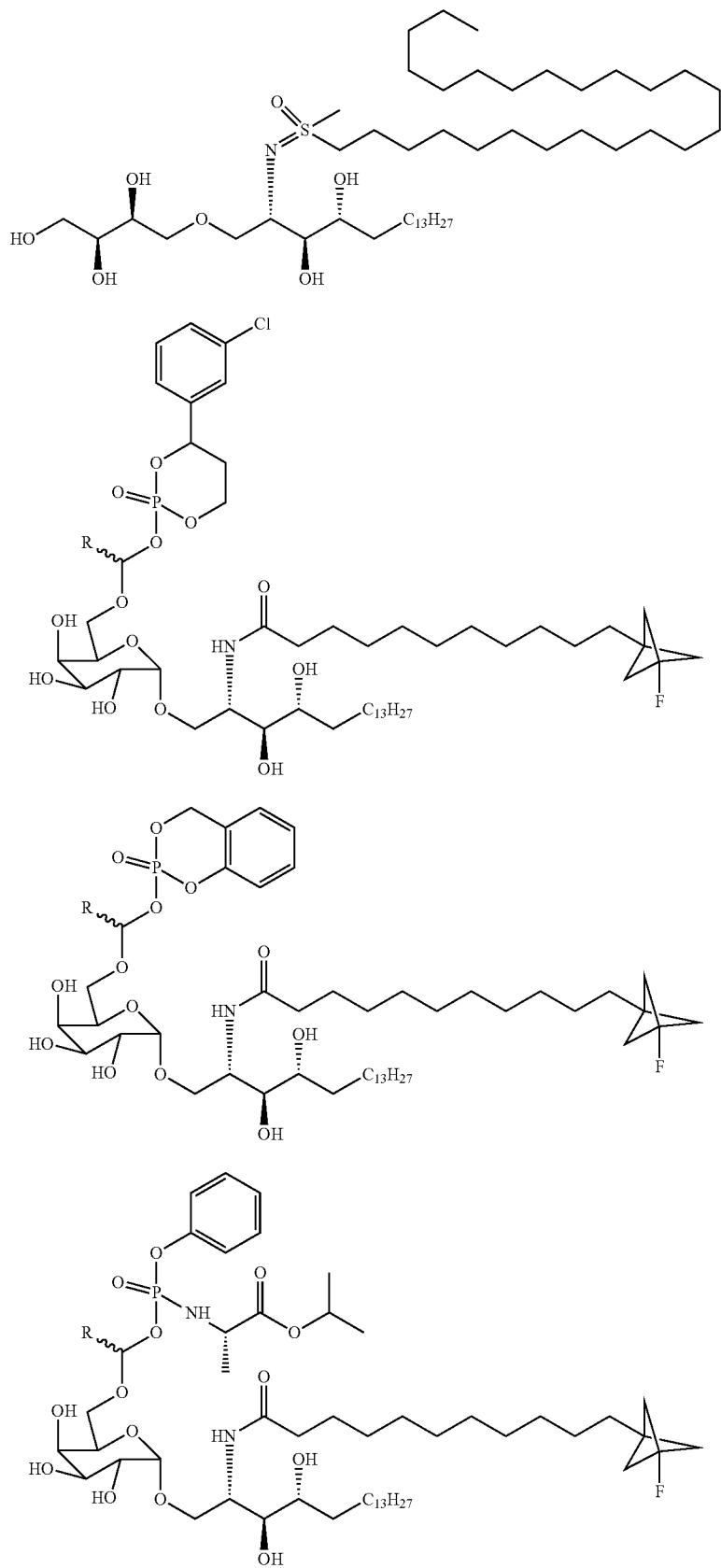

TABLE 2
| Amide Analogs |
|---|
| 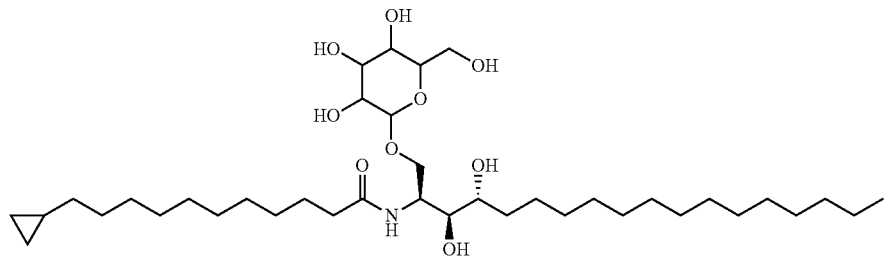 [SMILES: CCCCCCCCCCCCCC[C@@H](O)[C@@H](O)[C@H](COC1OC(CO)C(O)C(O)C1O)NC(=O)CCCCCCCCCCC1CC1] |
| 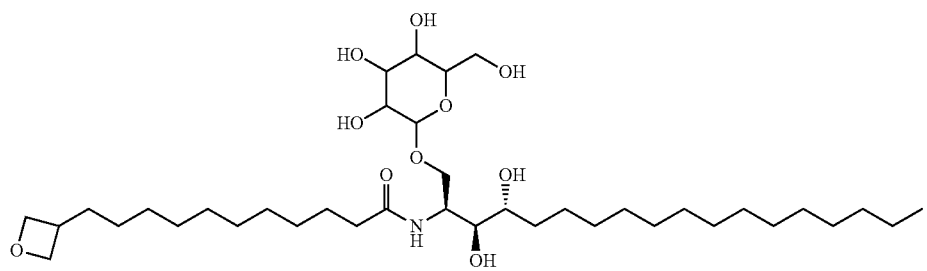 [SMILES: CCCCCCCCCCCCCC[C@@H](O)[C@@H](O)[C@H](COC1OC(CO)C(O)C(O)C1O)NC(=O)CCCCCCCCCCC1COC1] |
| 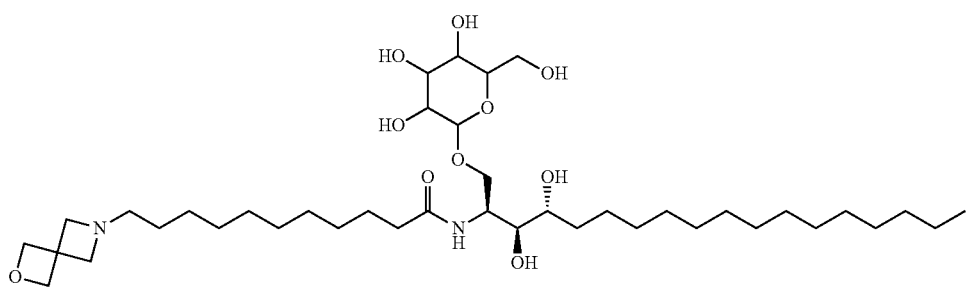 [SMILES: CCCCCCCCCCCCCC[C@@H](O)[C@@H](O)[C@H](COC1OC(CO)C(O)C(O)C1O)NC(=O)CCCCCCCCCCN1CC2(COC2)C1] |
| 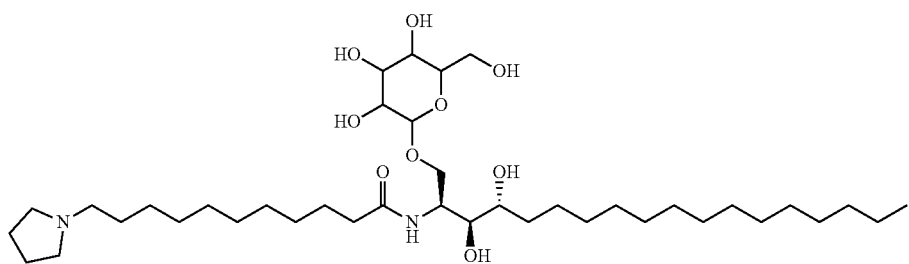 [SMILES: CCCCCCCCCCCCCC[C@@H](O)[C@@H](O)[C@H](COC1OC(CO)C(O)C(O)C1O)NC(=O)CCCCCCCCCCN1CCCC1] |
| 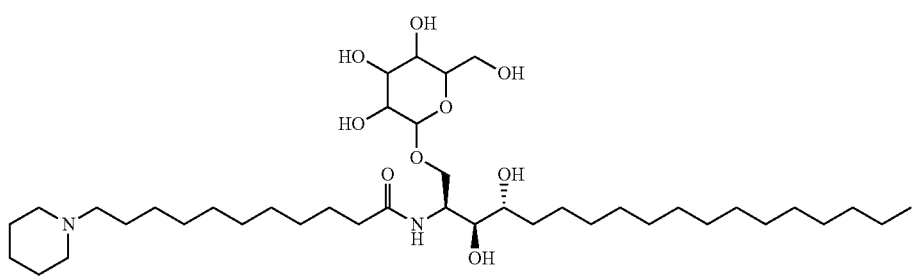 [SMILES: CCCCCCCCCCCCCC[C@@H](O)[C@@H](O)[C@H](COC1OC(CO)C(O)C(O)C1O)NC(=O)CCCCCCCCCCN1CCCCC1] |

TABLE 2-continued
Amide Analogs

TABLE 2-continued
Amide Analogs
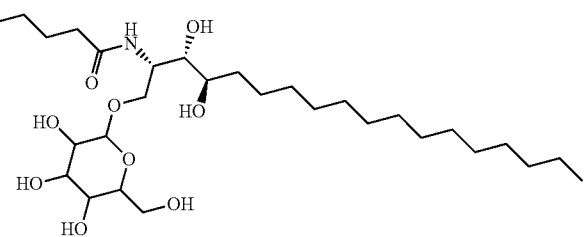
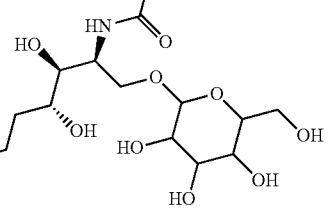
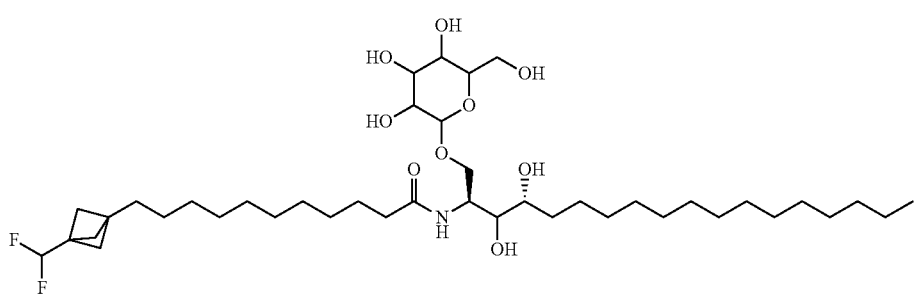 [SMILES: CCCCCCCCCCCCCC[C@@H](O)C(O)[C@H](COC1OC(CO)C(O)C(O)C1O)NC(=O)CCCCCCCCCCC12CC(C(F)F)(C1)C2]

TABLE 2-continued
Amide Analogs
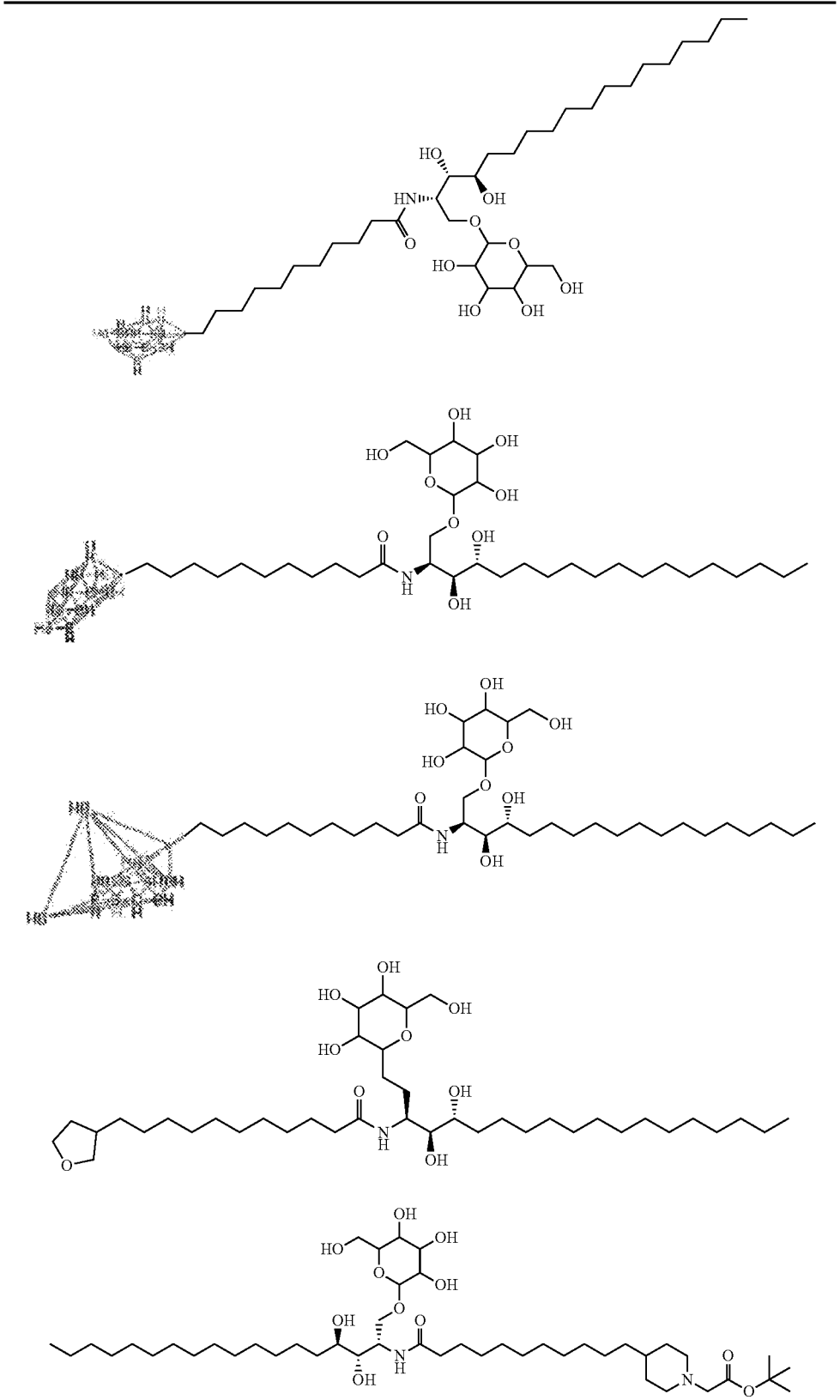

TABLE 2-continued
Amide Analogs
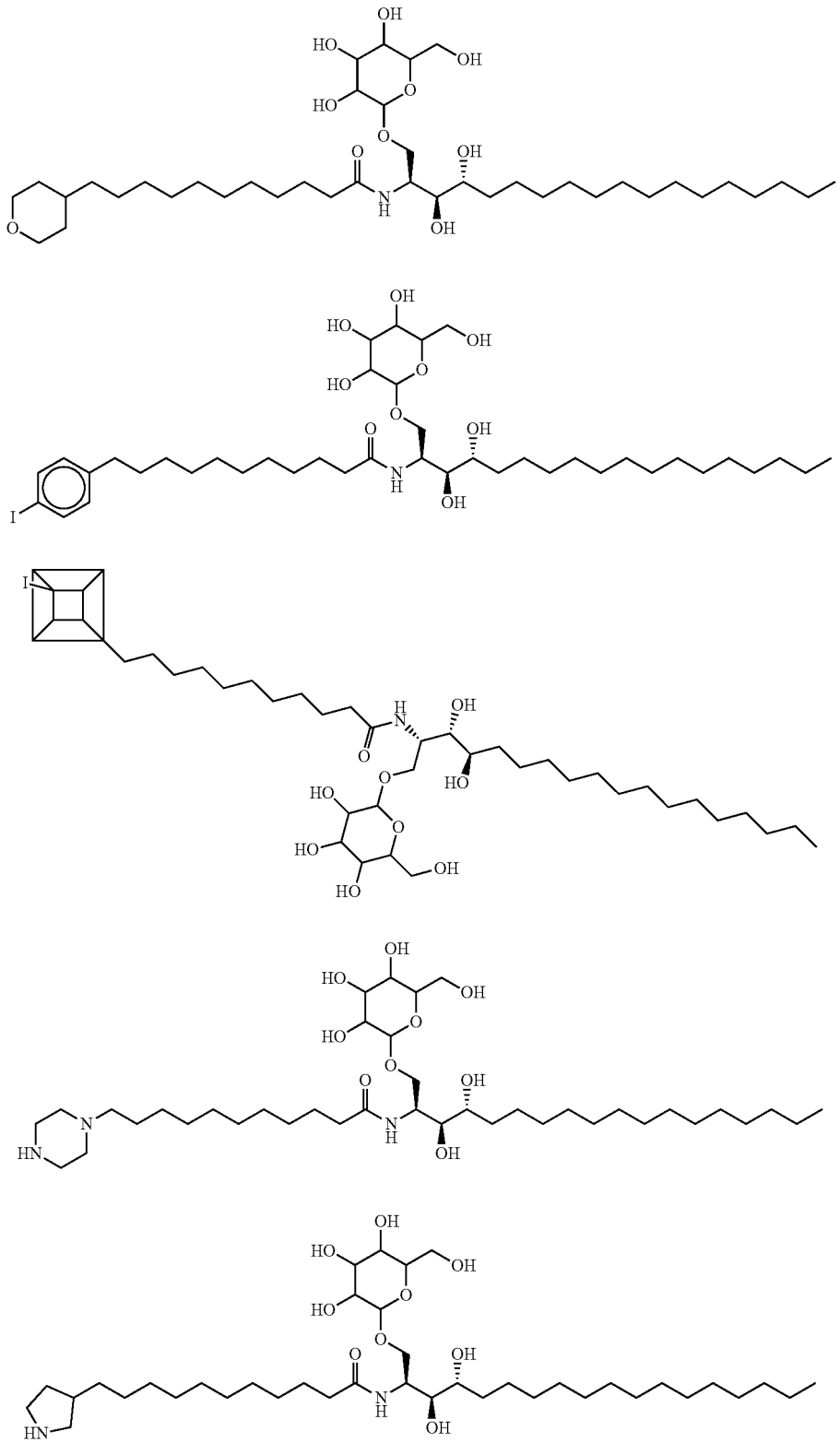

TABLE 2-continued
Amide Analogs
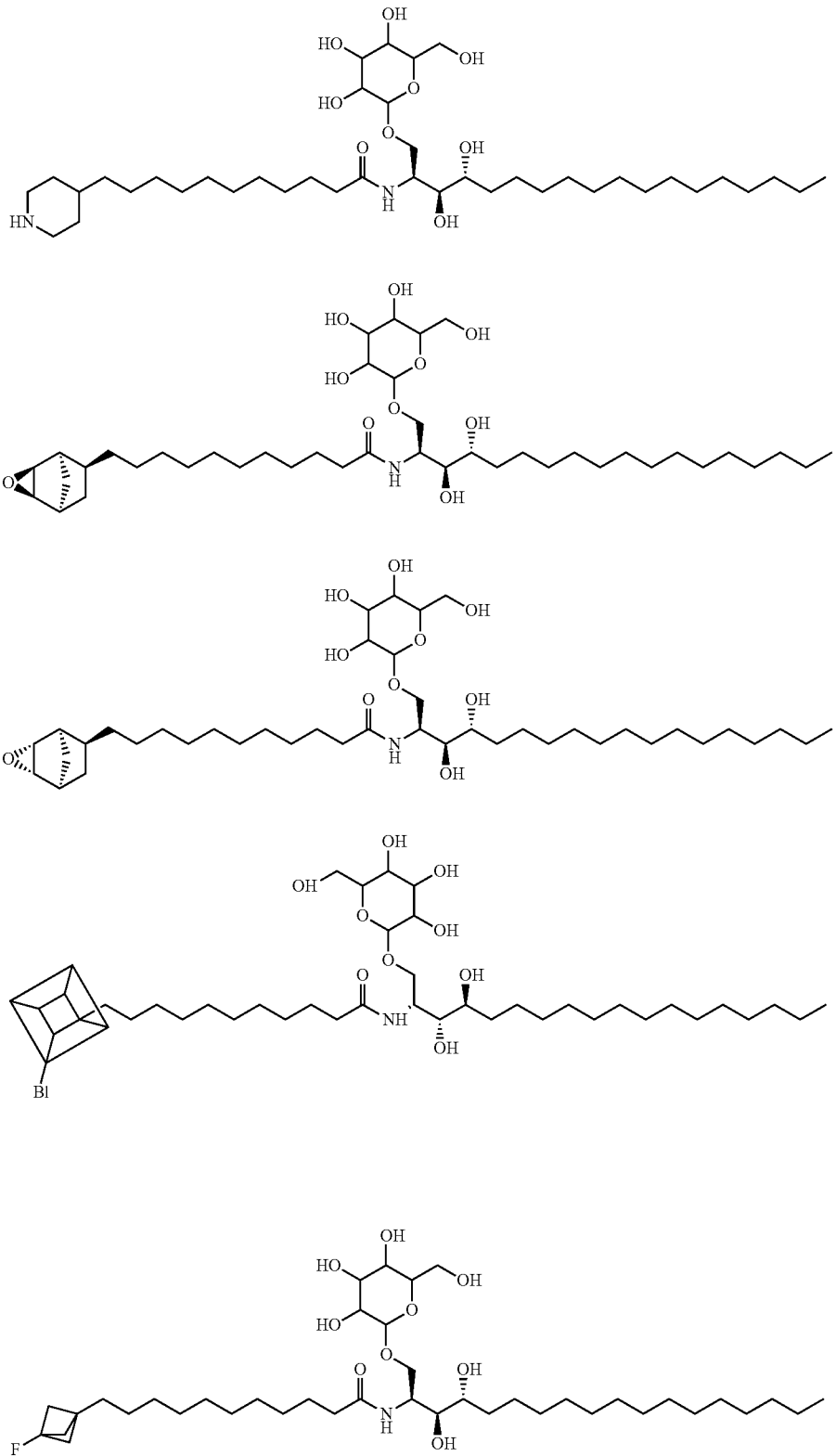

TABLE 2-continued
Amide Analogs
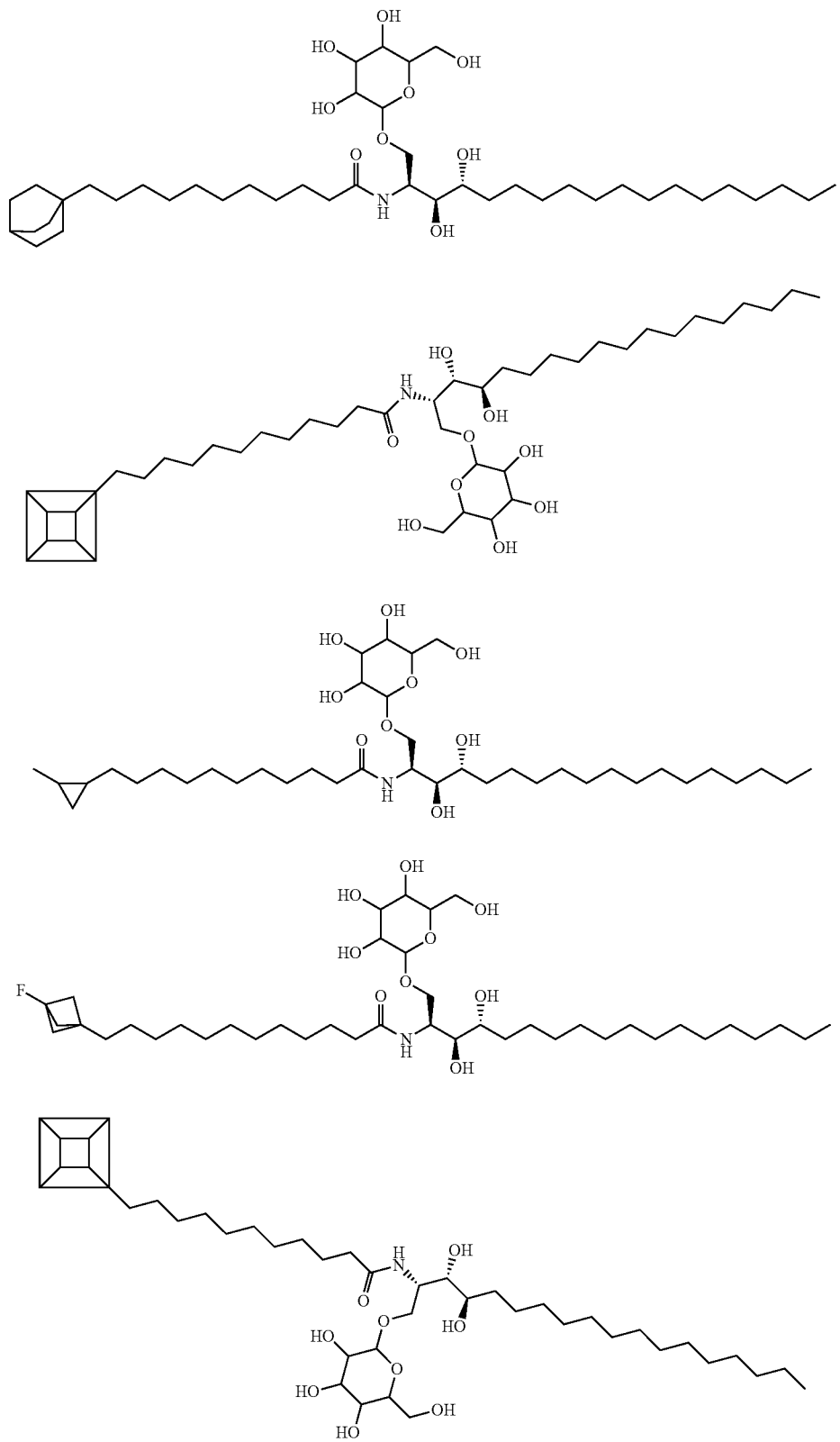

TABLE 2-continued
Amide Analogs
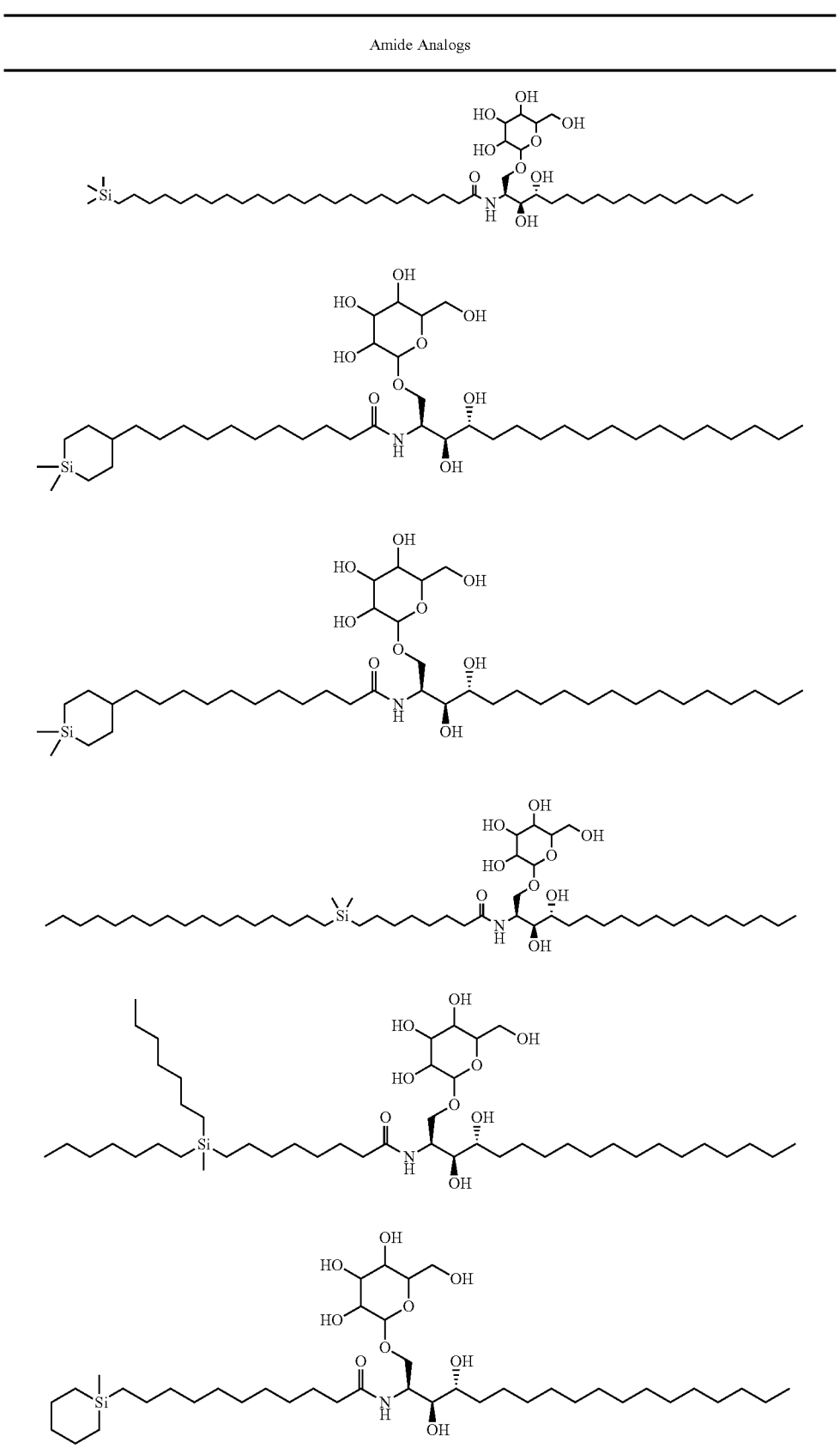

TABLE 2-continued
Amide Analogs
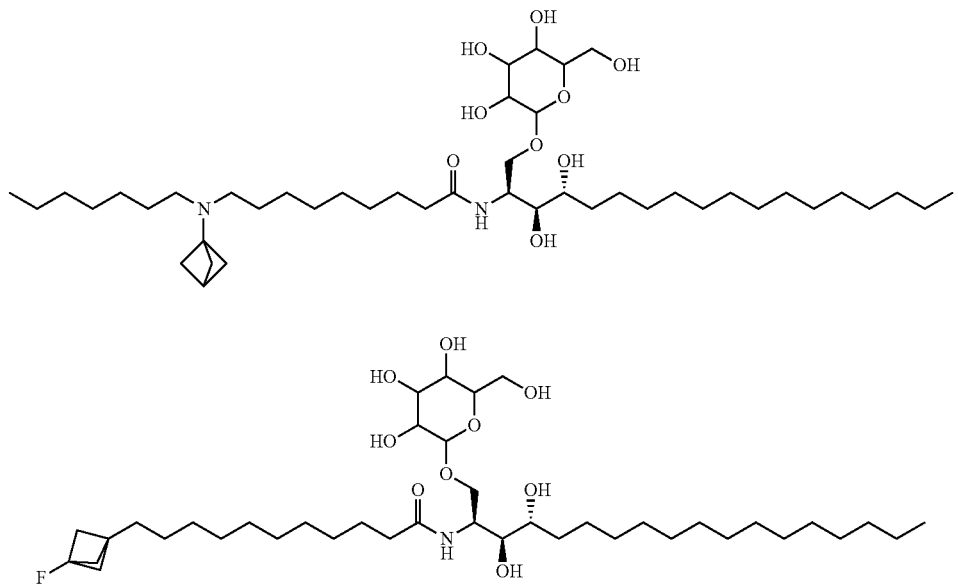
TABLE 3
Trifluoromethyl Aminomethyl Analogs
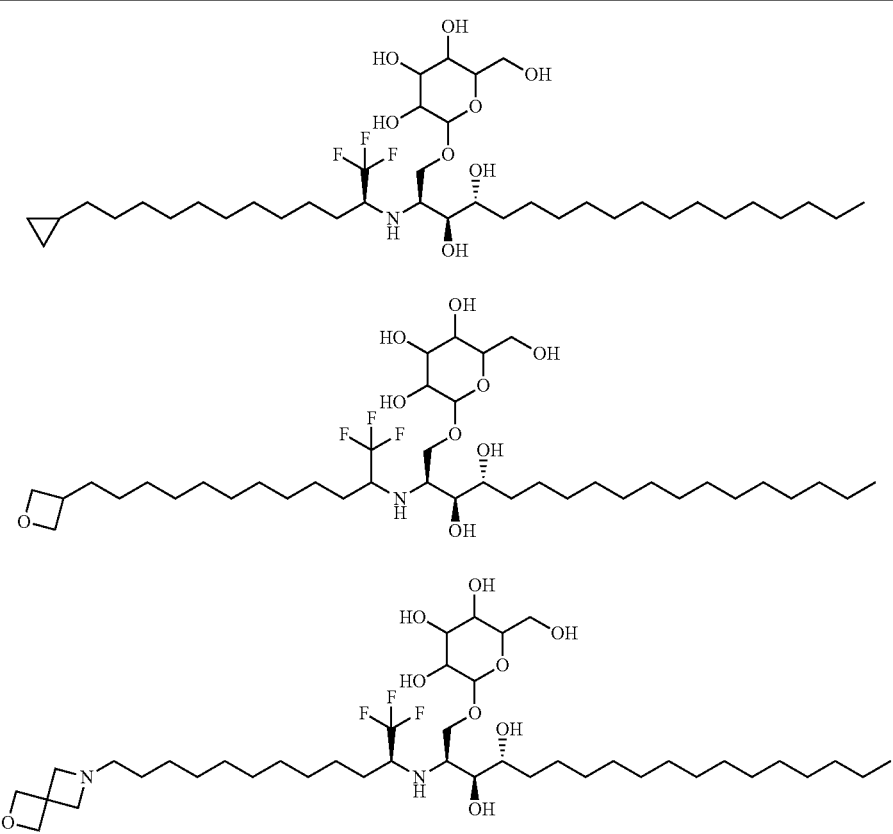

TABLE 3-continued
Trifluoromethyl Aminomethyl Analogs
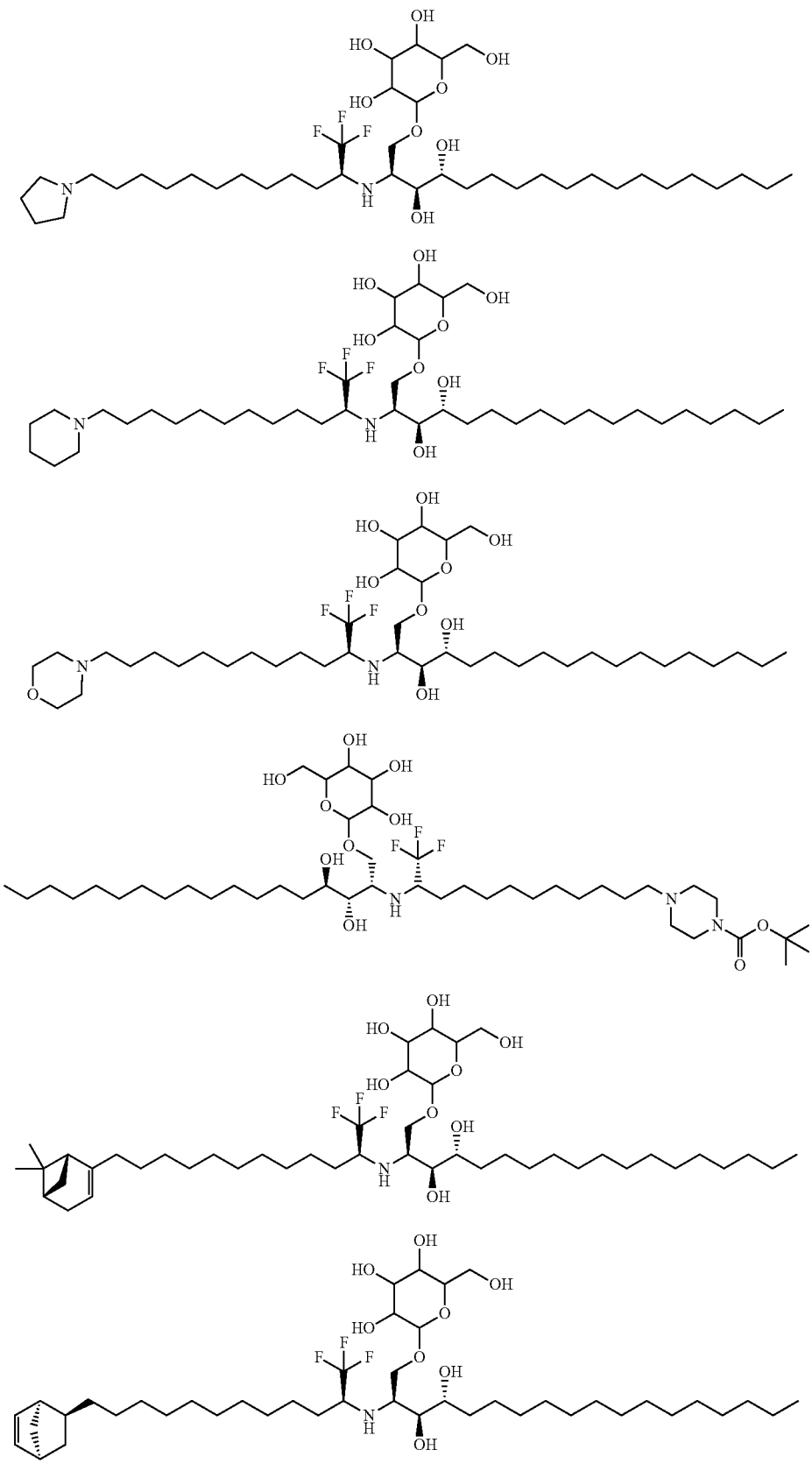

TABLE 3-continued
Trifluoromethyl Aminomethyl Analogs
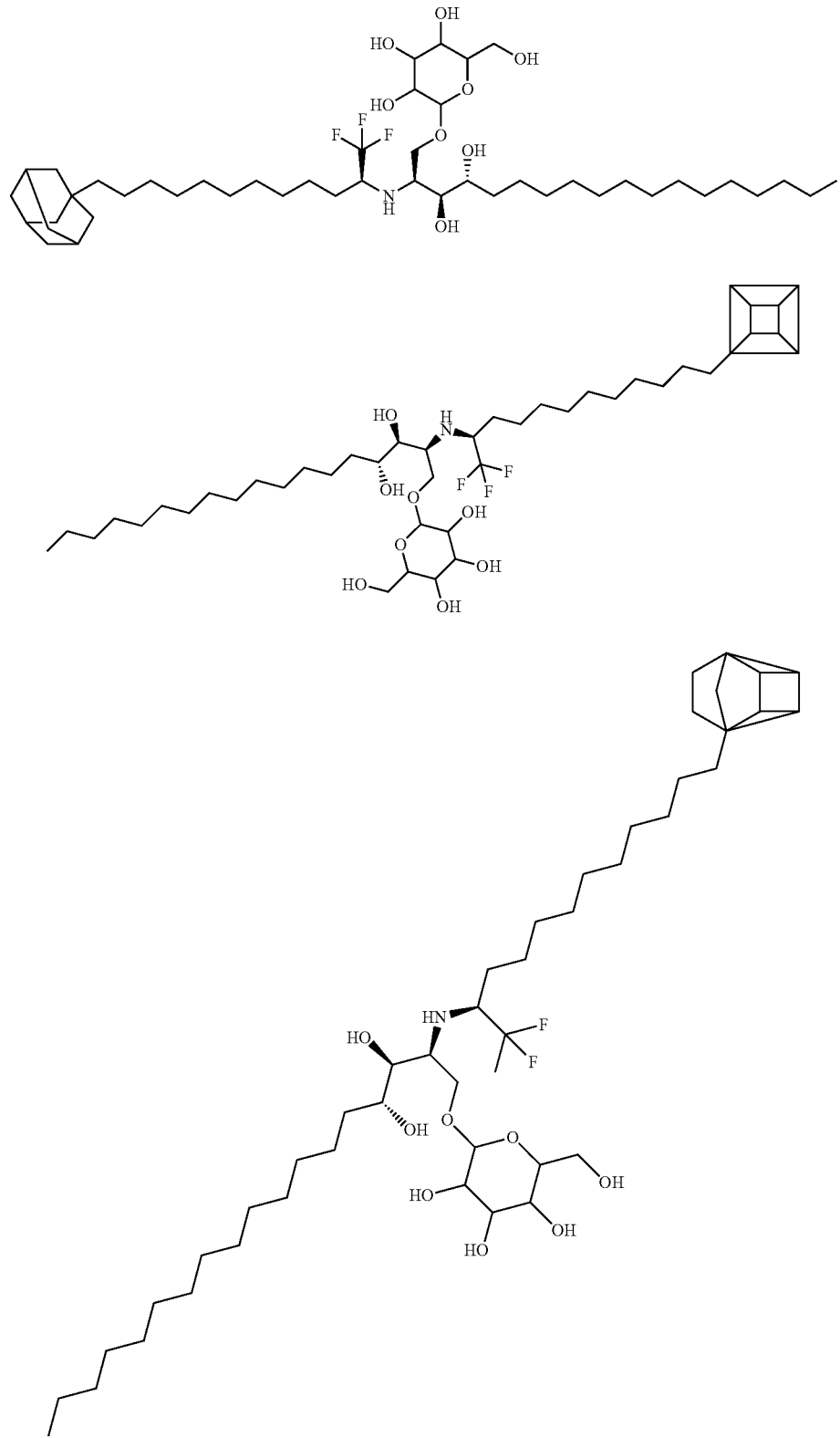

TABLE 3-continued
Trifluoromethyl Aminomethyl Analogs
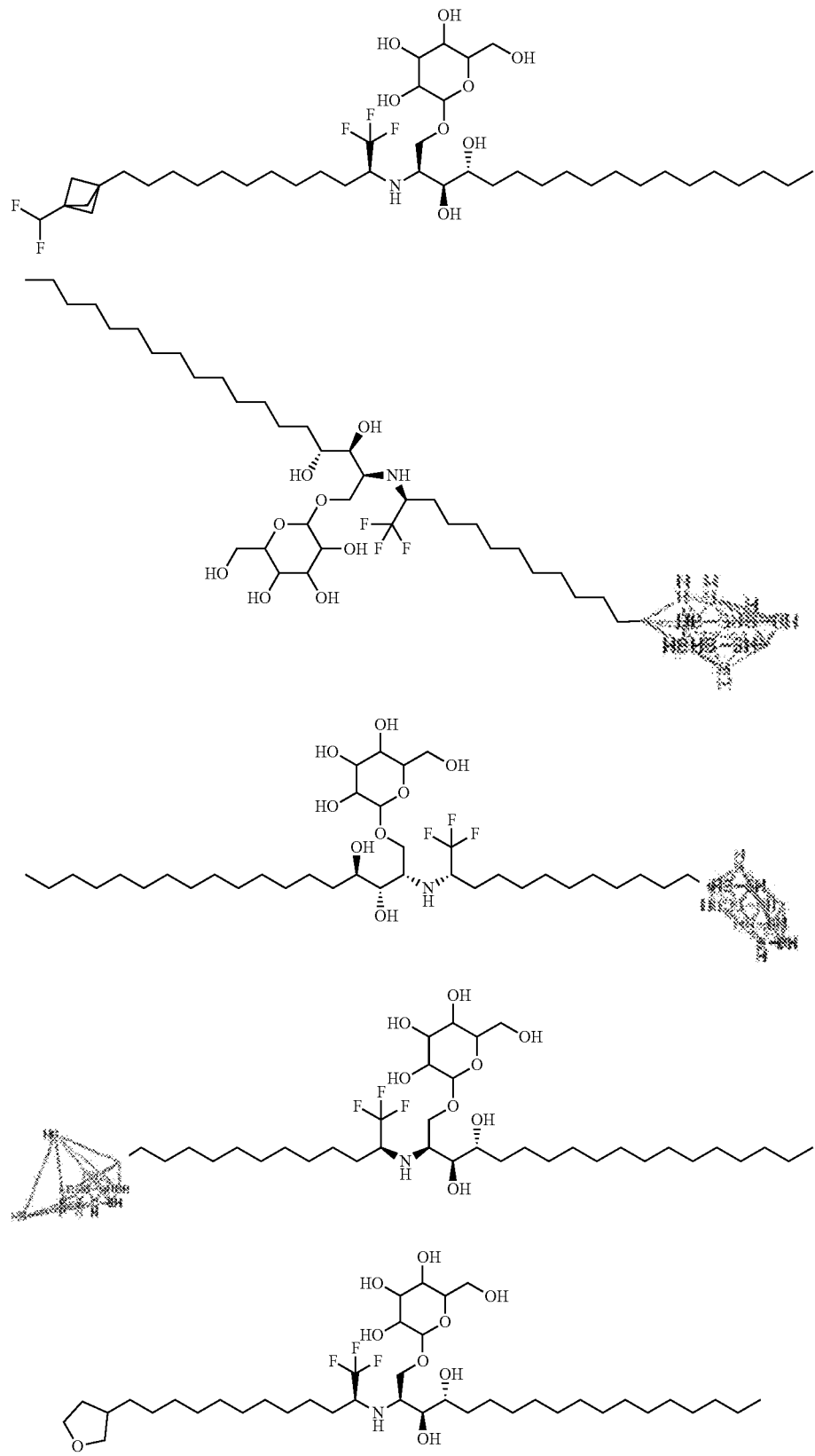

TABLE 3-continued
Trifluoromethyl Aminomethyl Analogs
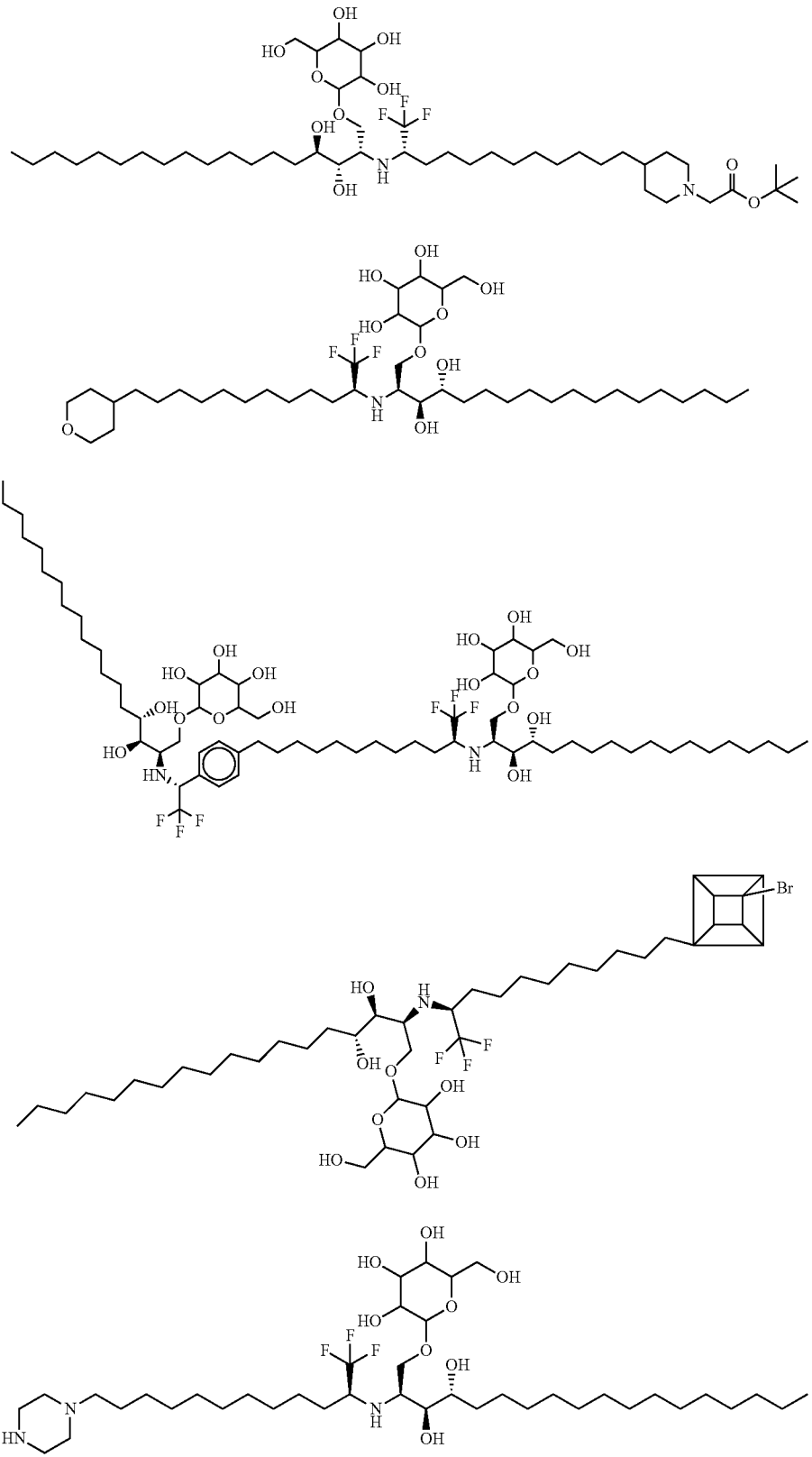

TABLE 3-continued
Trifluoromethyl Aminomethyl Analogs
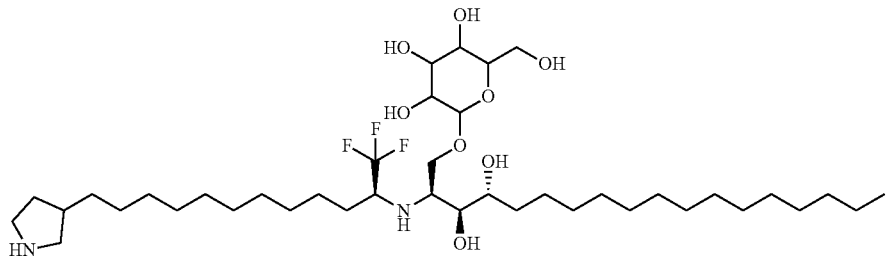 [SMILES: CCCCCCCCCCCCCC[C@@H](O)[C@@H](O)[C@H](COC1OC(CO)C(O)C(O)C1O)N[C@@H](CCCCCCCCCCC1CCNC1)C(F)(F)F]
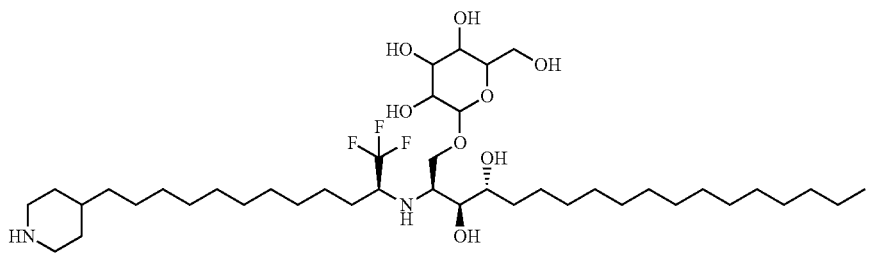 [SMILES: CCCCCCCCCCCCCC[C@@H](O)[C@@H](O)[C@H](COC1OC(CO)C(O)C(O)C1O)N[C@@H](CCCCCCCCCCC1CCNCC1)C(F)(F)F]
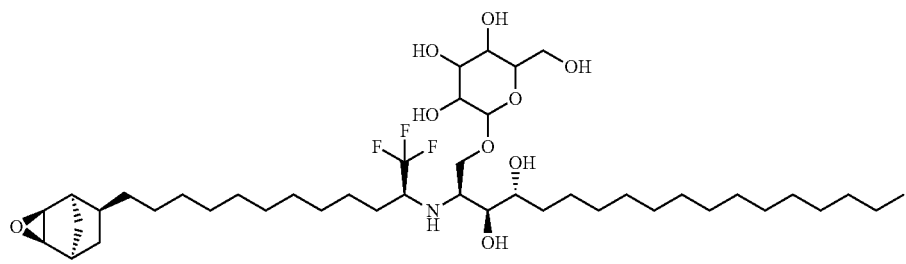 [SMILES: CCCCCCCCCCCCCC[C@@H](O)[C@@H](O)[C@H](COC1OC(CO)C(O)C(O)C1O)N[C@@H](CCCCCCCCCC[C@H]1C[C@@H]2C[C@H]1[C@@H]1O[C@H]21)C(F)(F)F]
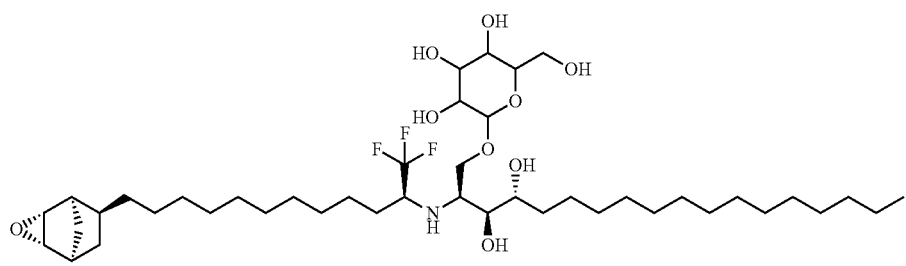 [SMILES: CCCCCCCCCCCCCC[C@@H](O)[C@@H](O)[C@H](COC1OC(CO)C(O)C(O)C1O)N[C@@H](CCCCCCCCCC[C@H]1C[C@@H]2C[C@H]1[C@H]1O[C@@H]21)C(F)(F)F]

TABLE 3-continued
Trifluoromethyl Aminomethyl Analogs
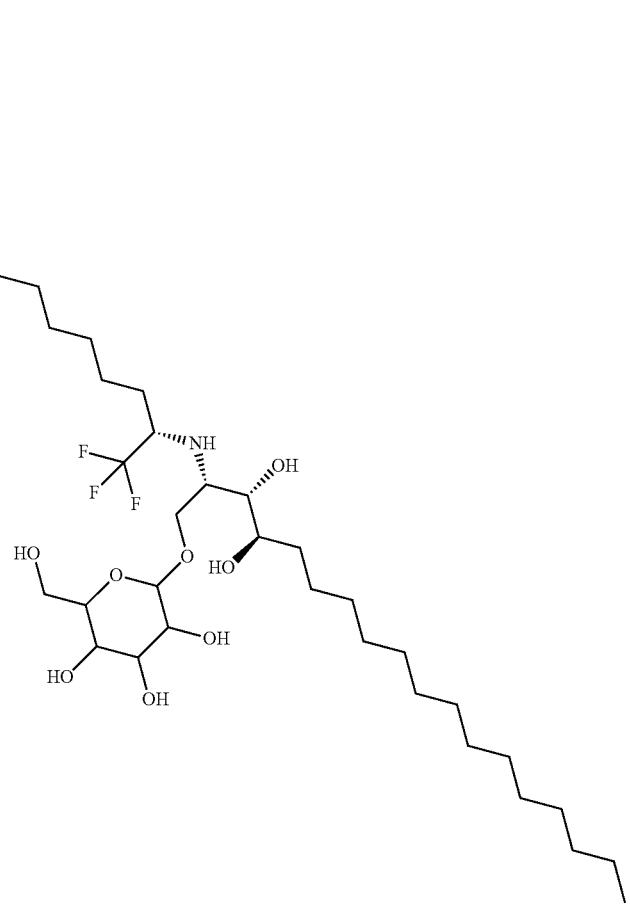
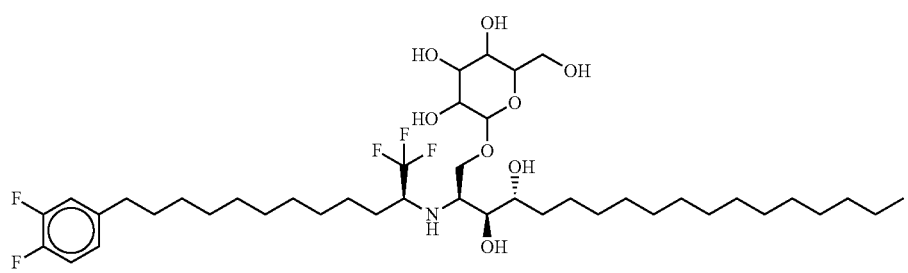
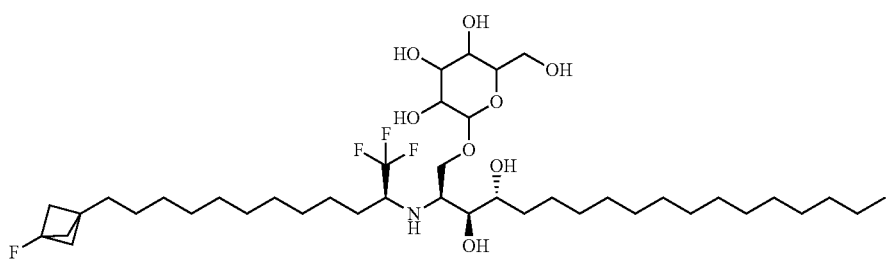 [SMILES: CCCCCCCCCCCCCC[C@@H](O)[C@@H](O)[C@H](COC1OC(CO)C(O)C(O)C1O)N[C@@H](CCCCCCCCCCC12CC(F)(C1)C2)C(F)(F)F]

TABLE 3-continued
Trifluoromethyl Aminomethyl Analogs
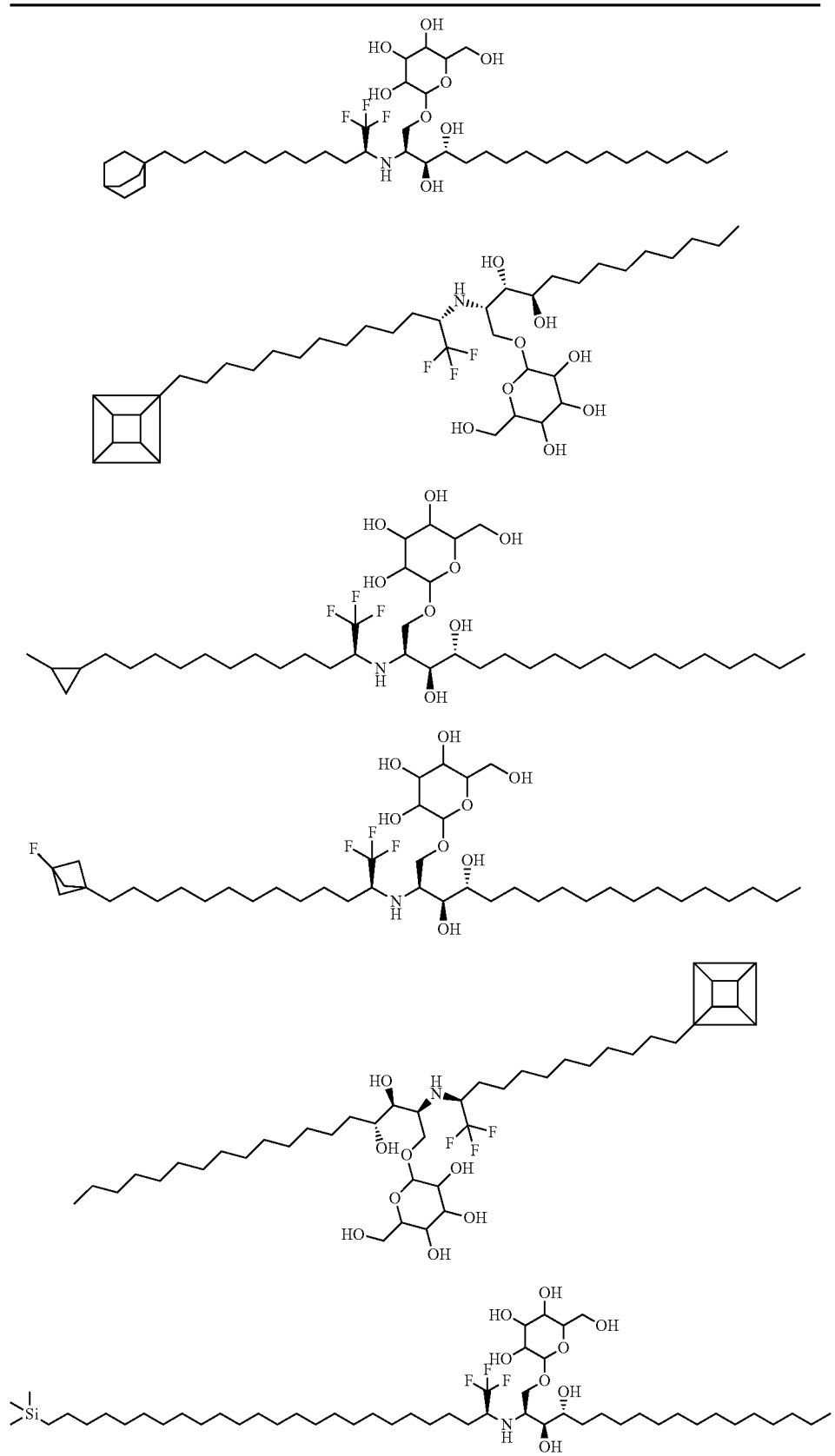

TABLE 3-continued
Trifluoromethyl Aminomethyl Analogs
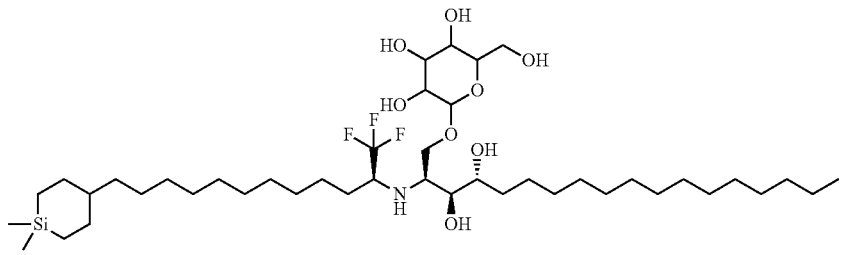 [SMILES: CCCCCCCCCCCCCC[C@@H](O)[C@@H](O)[C@H](COC1OC(CO)C(O)C(O)C1O)N[C@@H](CCCCCCCCCCC1CC[Si](C)(C)CC1)C(F)(F)F]
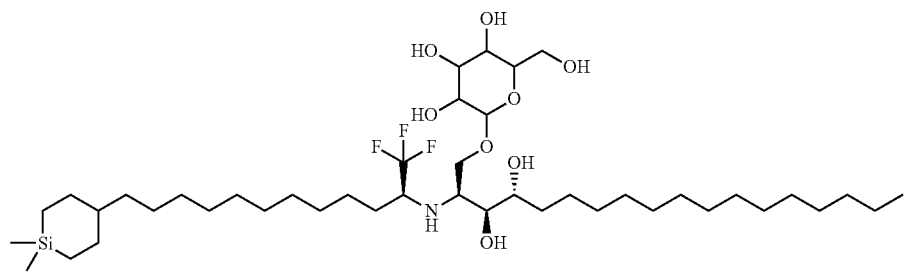 [SMILES: CCCCCCCCCCCCCC[C@@H](O)[C@@H](O)[C@H](COC1OC(CO)C(O)C(O)C1O)N[C@@H](CCCCCCCCCCC1CC[Si](C)(C)CC1)C(F)(F)F]
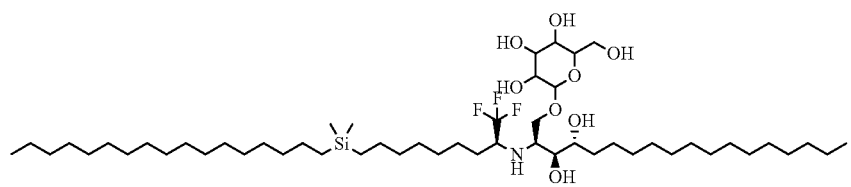 [SMILES: CCCCCCCCCCCCCCCCC[Si](C)(C)CCCCCCC[C@H](N[C@@H](COC1OC(CO)C(O)C(O)C1O)[C@H](O)[C@H](O)CCCCCCCCCCCCCC)C(F)(F)F]
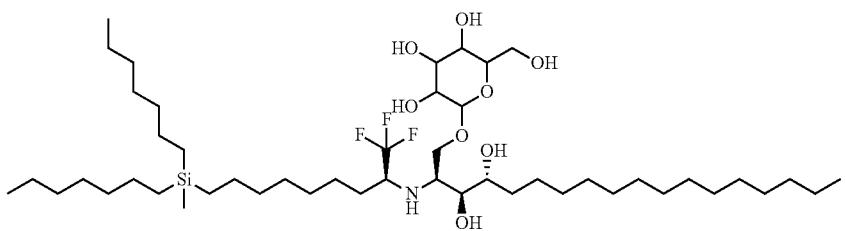 [SMILES: CCCCCCCCCCCCCC[C@@H](O)[C@@H](O)[C@H](COC1OC(CO)C(O)C(O)C1O)N[C@@H](CCCCCCC[Si](C)(CCCCCCC)CCCCCCC)C(F)(F)F]
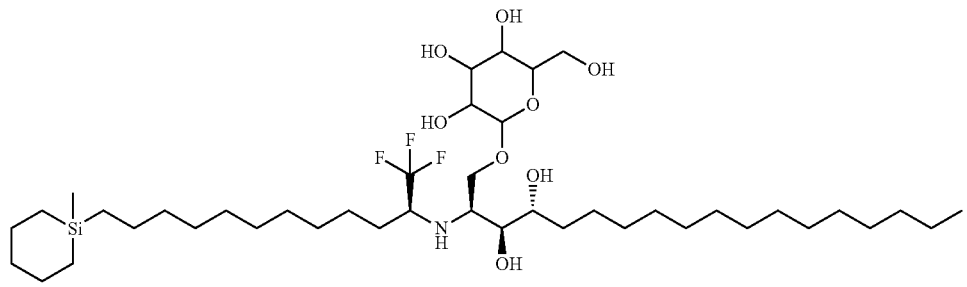 [SMILES: CCCCCCCCCCCCCC[C@@H](O)[C@@H](O)[C@H](COC1OC(CO)C(O)C(O)C1O)N[C@@H](CCCCCCCCCC[Si]1(C)CCCCC1)C(F)(F)F]
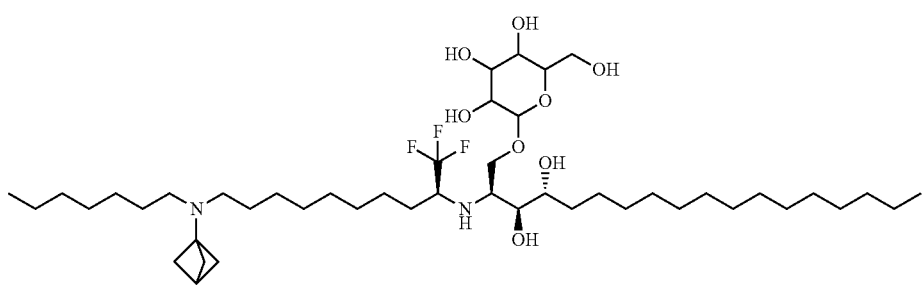 [SMILES: CCCCCCCCCCCCCC[C@@H](O)[C@@H](O)[C@H](COC1OC(CO)C(O)C(O)C1O)N[C@@H](CCCCCCCCN(CCCCCCC)C12CC(C1)C2)C(F)(F)F]

TABLE 4
Sulfoximine Analogs
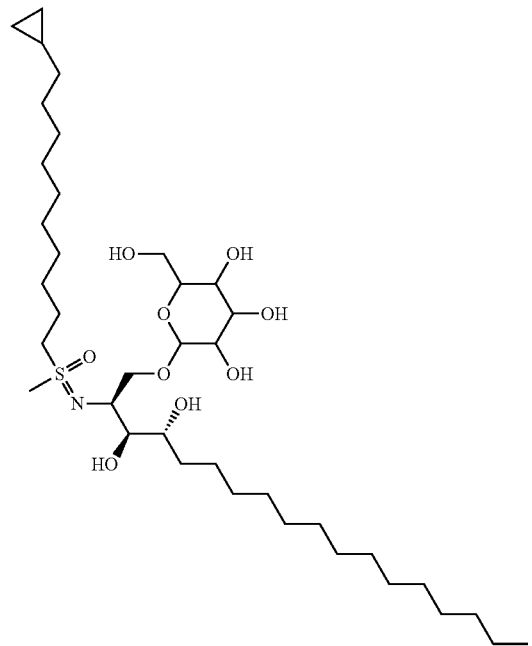 [SMILES: CCCCCCCCCCCCCC[C@@H](O)[C@@H](O)[C@H](COC1OC(CO)C(O)C(O)C1O)N=S(C)(=O)CCCCCCCCCCC1CC1]
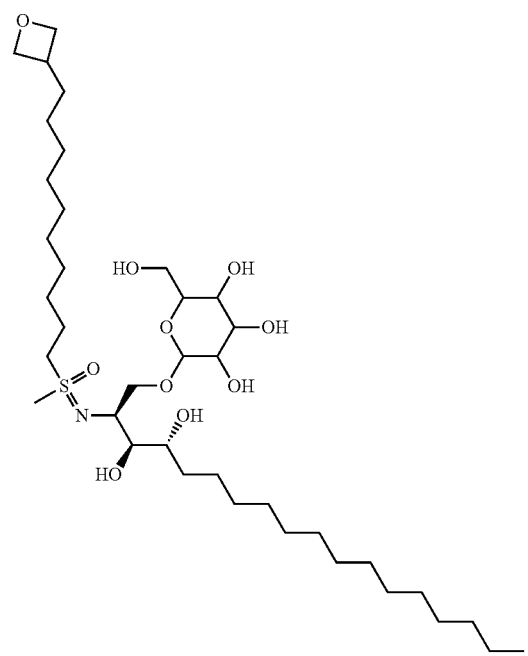 [SMILES: CCCCCCCCCCCCCC[C@@H](O)[C@@H](O)[C@H](COC1OC(CO)C(O)C(O)C1O)N=S(C)(=O)CCCCCCCCCCC1COC1]

TABLE 4-continued
Sulfoximine Analogs
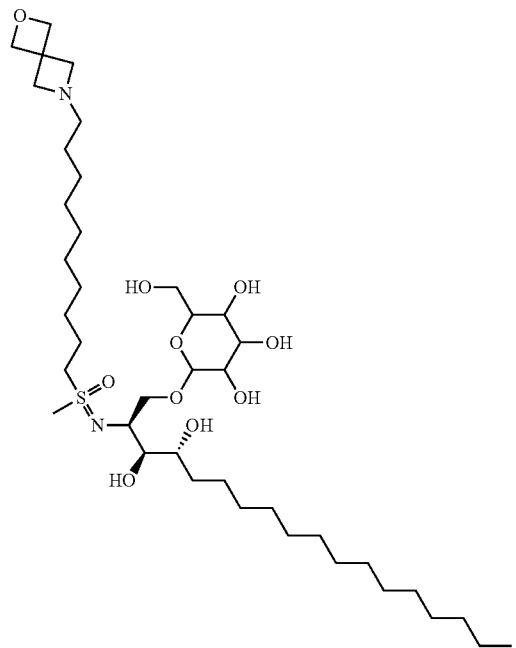 [SMILES: CCCCCCCCCCCCCC[C@@H](O)[C@@H](O)[C@H](COC1OC(CO)C(O)C(O)C1O)N=S(C)(=O)CCCCCCCCCCN1CC2(COC2)C1]
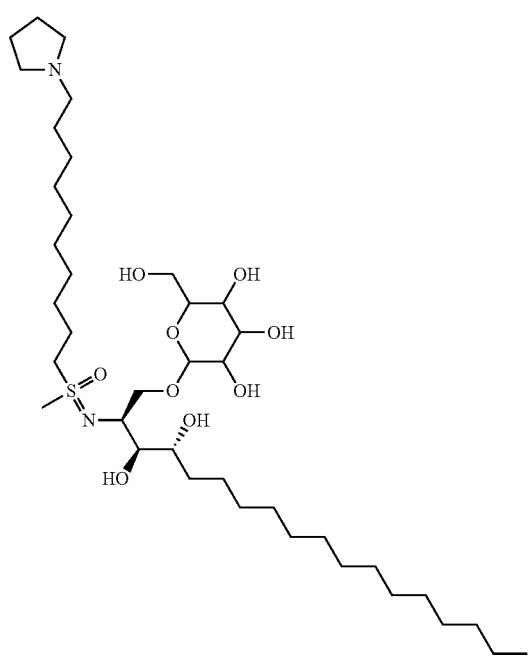 [SMILES: CCCCCCCCCCCCCC[C@@H](O)[C@@H](O)[C@H](COC1OC(CO)C(O)C(O)C1O)N=S(C)(=O)CCCCCCCCCCN1CCCC1]

TABLE 4-continued
Sulfoximine Analogs
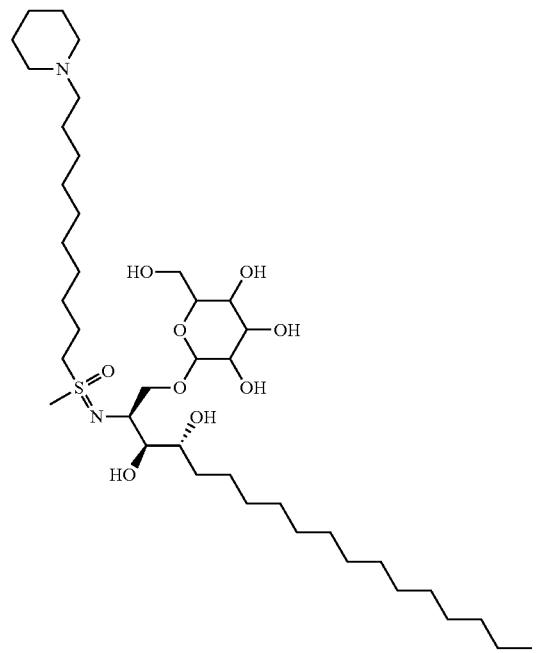 [SMILES: CCCCCCCCCCCCCC[C@@H](O)[C@@H](O)[C@H](COC1OC(CO)C(O)C(O)C1O)N=S(C)(=O)CCCCCCCCCCN1CCCCC1]
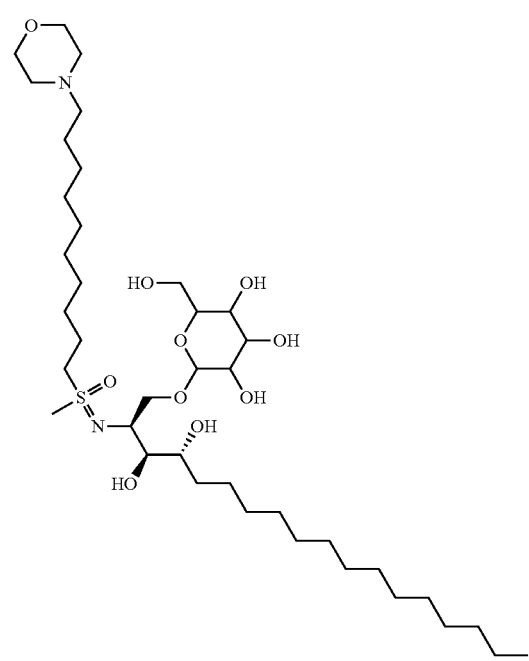 [SMILES: CCCCCCCCCCCCCC[C@@H](O)[C@@H](O)[C@H](COC1OC(CO)C(O)C(O)C1O)N=S(C)(=O)CCCCCCCCCCN1CCOCC1]

TABLE 4-continued
Sulfoximine Analogs
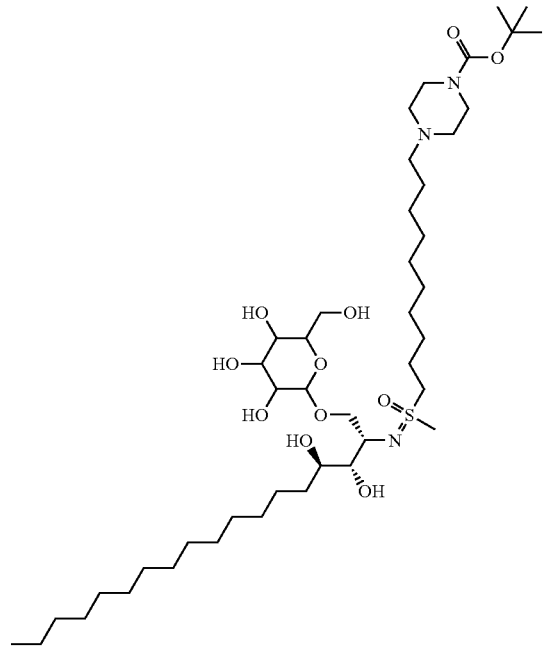 [SMILES: CCCCCCCCCCCCCC[C@@H](O)[C@@H](O)[C@H](COC1OC(CO)C(O)C(O)C1O)N=S(C)(=O)CCCCCCCCCCN1CCN(C(=O)OC(C)(C)C)CC1]
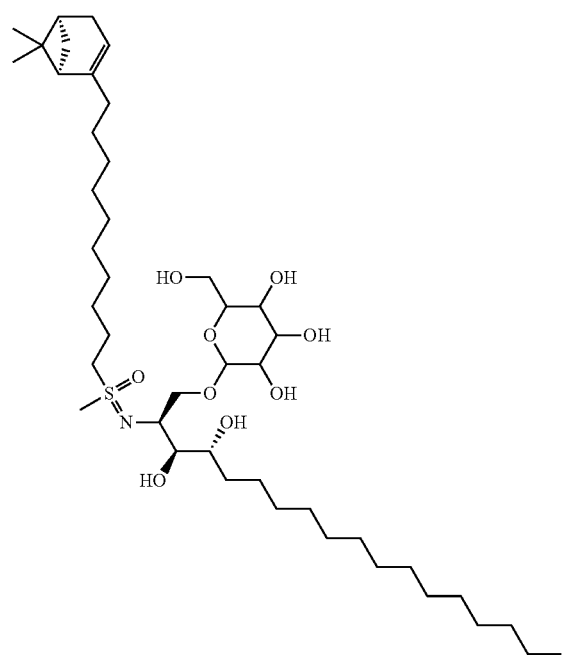 [SMILES: CCCCCCCCCCCCCC[C@@H](O)[C@@H](O)[C@H](COC1OC(CO)C(O)C(O)C1O)N=S(C)(=O)CCCCCCCCCCC1=CC[C@H]2C[C@@H]1C2(C)C]

TABLE 4-continued
Sulfoximine Analogs
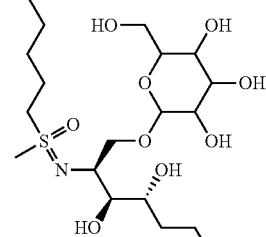
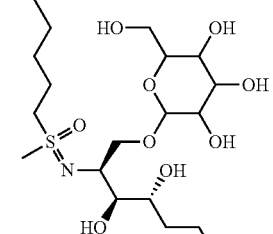

TABLE 4-continued
Sulfoximine Analogs
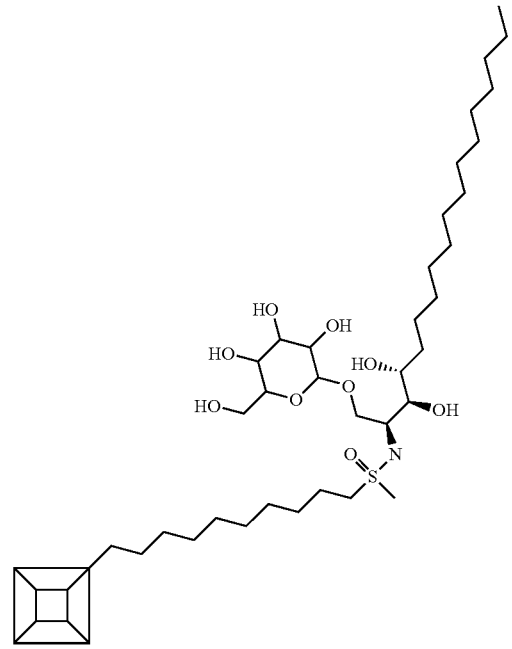
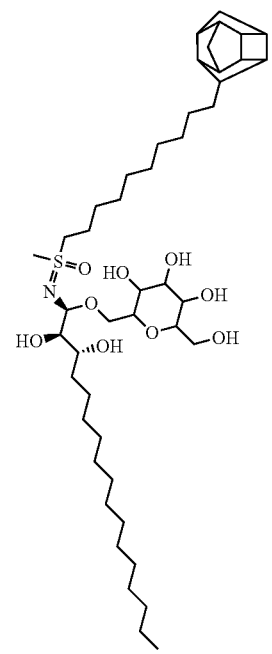 [SMILES: CCCCCCCCCCCCCC[C@@H](O)[C@@H](O)[C@@H](N=S(C)(=O)CCCCCCCCCCC1C2C3CC4C5C3CC2C5C14)OCC1OC(CO)C(O)C(O)C1O]

TABLE 4-continued
Sulfoximine Analogs
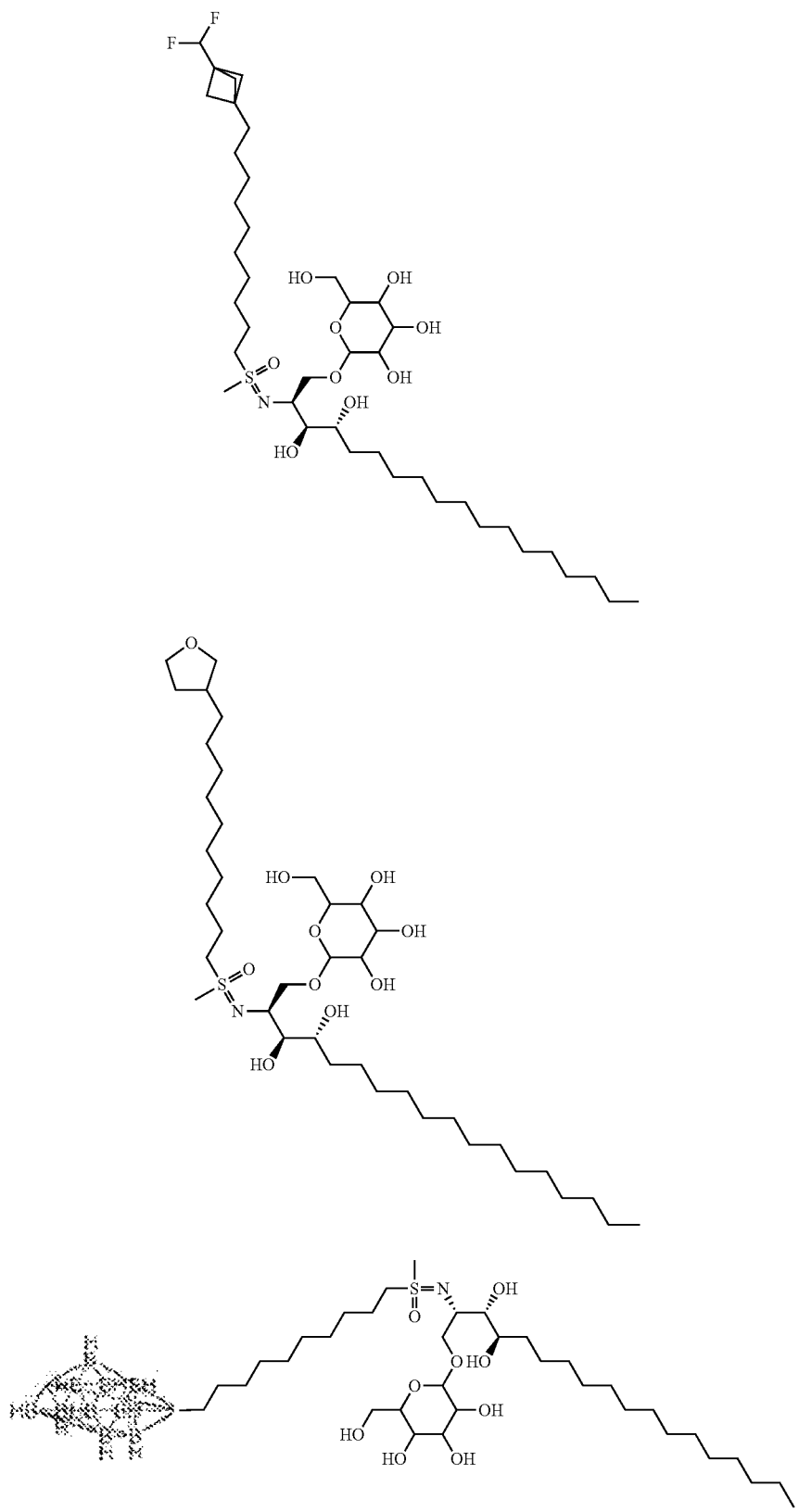

TABLE 4-continued
Sulfoximine Analogs
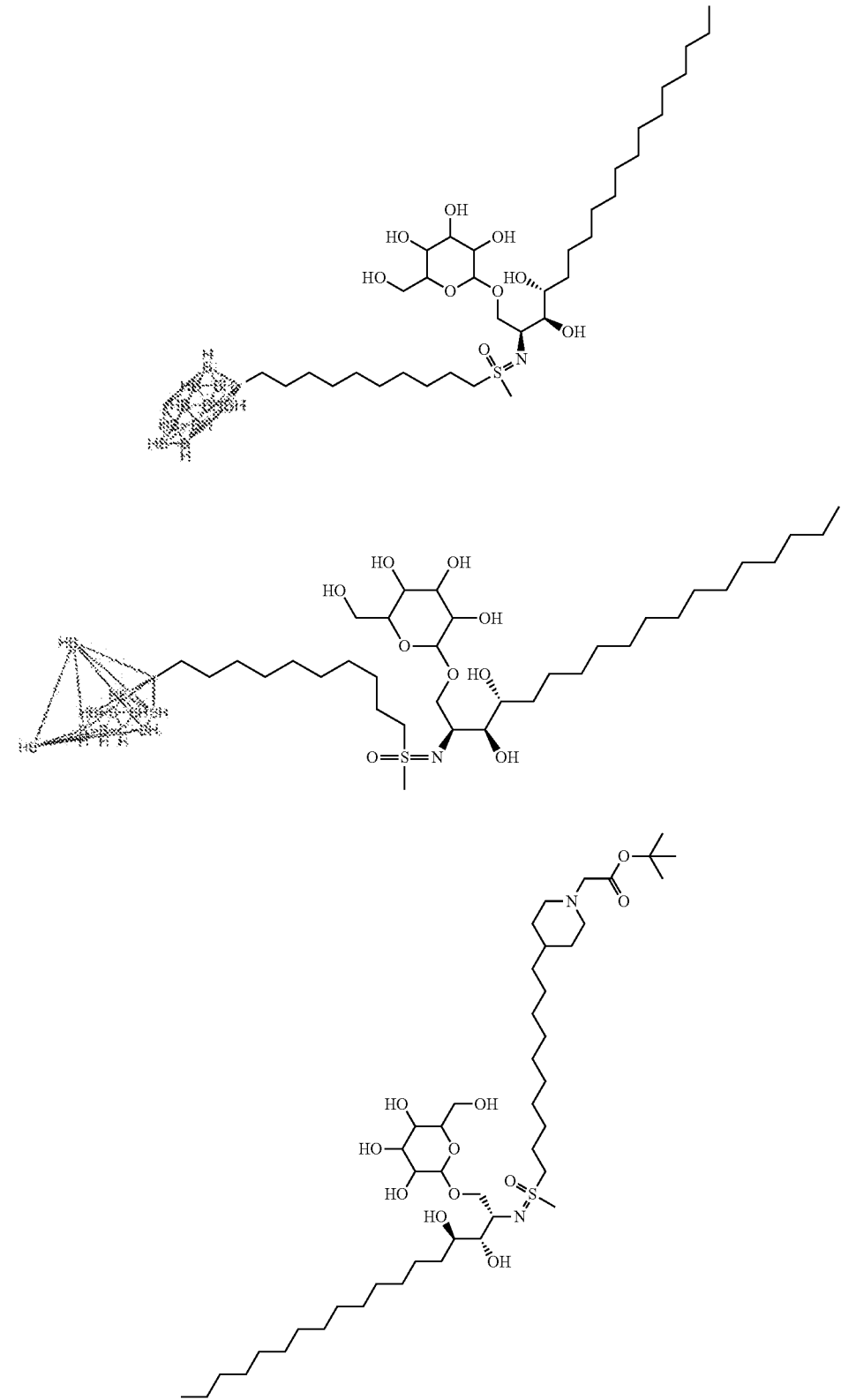

TABLE 4-continued
Sulfoximine Analogs
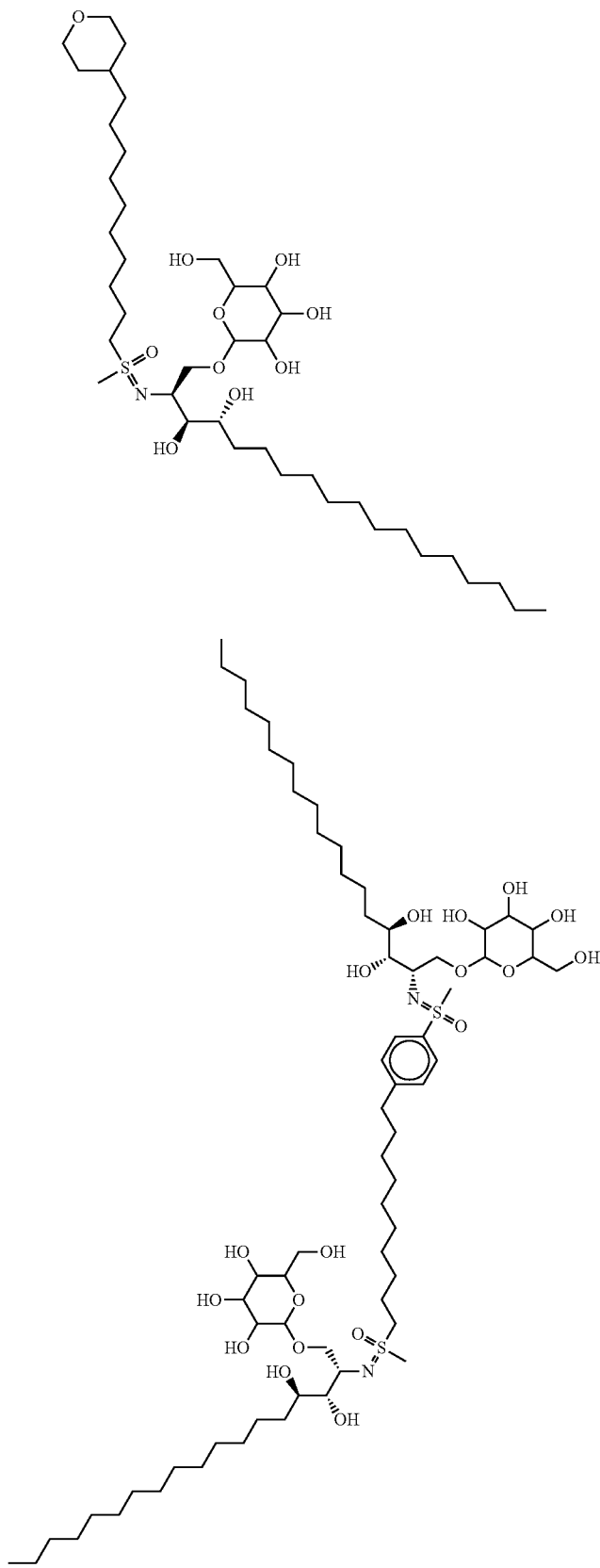

TABLE 4-continued
Sulfoximine Analogs
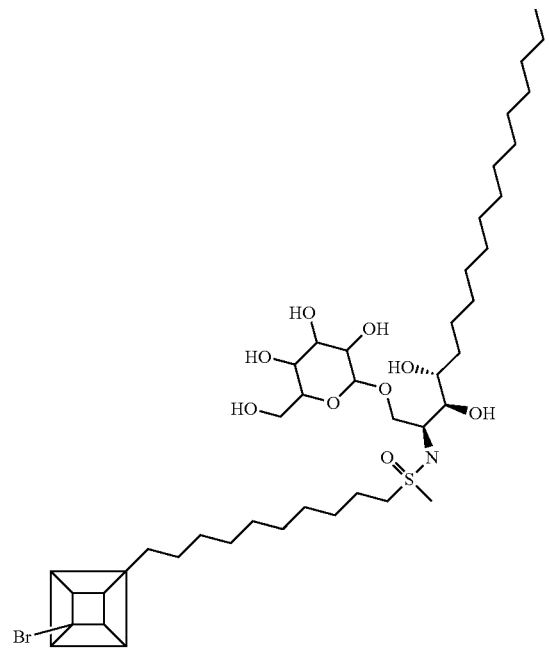
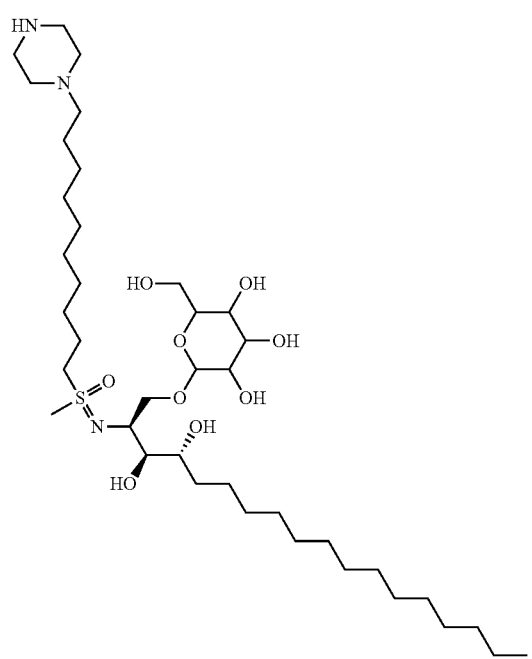 [SMILES: CCCCCCCCCCCCCC[C@@H](O)[C@@H](O)[C@H](COC1OC(CO)C(O)C(O)C1O)N=S(C)(=O)CCCCCCCCCCN1CCNCC1]

TABLE 4-continued
Sulfoximine Analogs
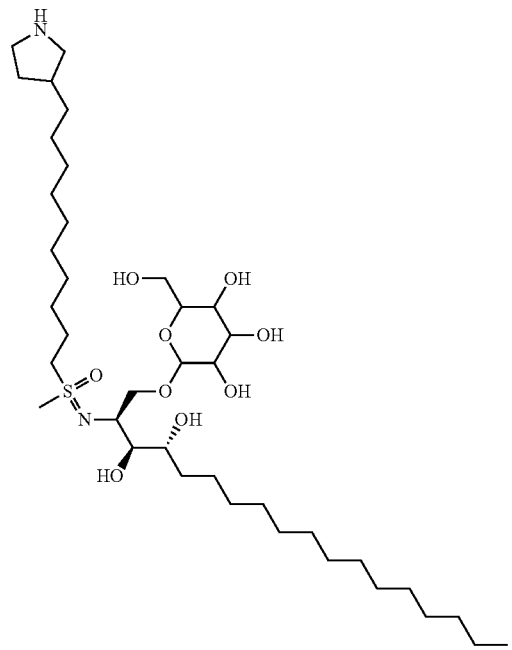 [SMILES: CCCCCCCCCCCCCC[C@@H](O)[C@@H](O)[C@H](COC1OC(CO)C(O)C(O)C1O)N=S(C)(=O)CCCCCCCCCCC1CCNC1]
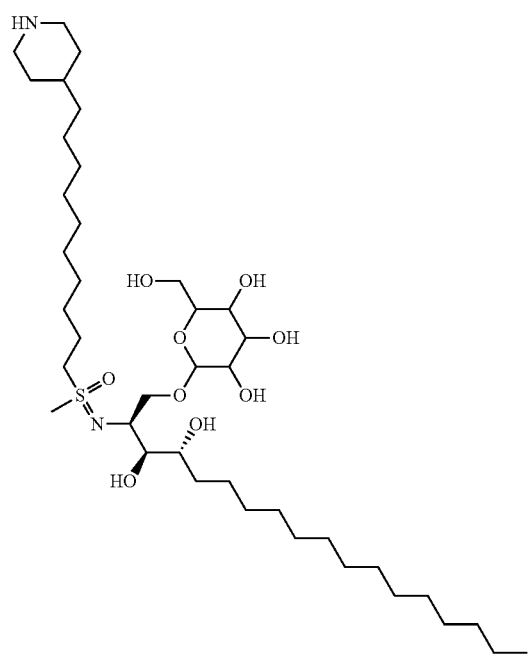 [SMILES: CCCCCCCCCCCCCC[C@@H](O)[C@@H](O)[C@H](COC1OC(CO)C(O)C(O)C1O)N=S(C)(=O)CCCCCCCCCCC1CCNCC1]

TABLE 4-continued
Sulfoximine Analogs
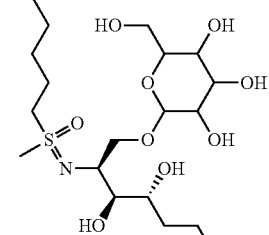
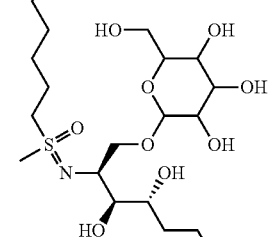

143 144
TABLE 4-continued
Sulfoximine Analogs
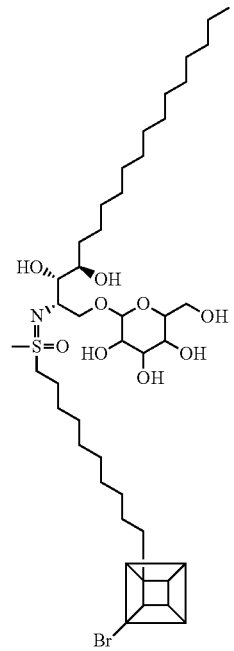 [SMILES: CCCCCCCCCCCCCC[C@@H](O)[C@@H](O)[C@H](COC1OC(CO)C(O)C(O)C1O)N=S(C)(=O)CCCCCCCCCCC12C3C4C5C3C1C5(Br)C42]
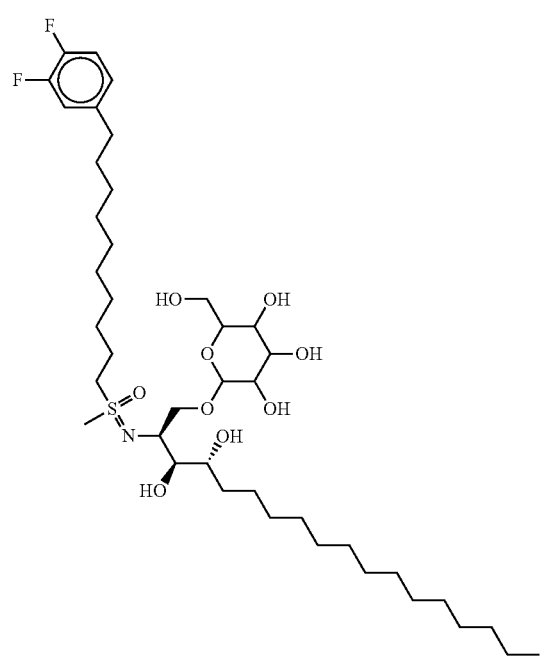

TABLE 4-continued
Sulfoximine Analogs
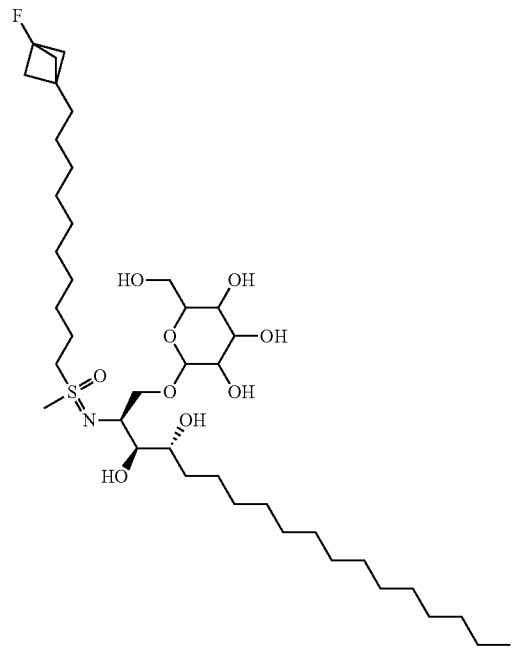 [SMILES: CCCCCCCCCCCCCC[C@@H](O)[C@@H](O)[C@H](COC1OC(CO)C(O)C(O)C1O)N=S(C)(=O)CCCCCCCCCCC12CC(F)(C1)C2]
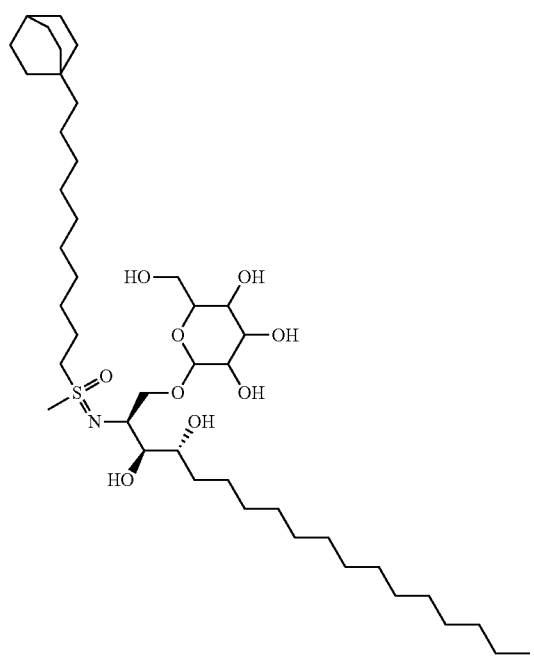 [SMILES: CCCCCCCCCCCCCC[C@@H](O)[C@@H](O)[C@H](COC1OC(CO)C(O)C(O)C1O)N=S(C)(=O)CCCCCCCCCCC12CCC(CC1)CC2]

TABLE 4-continued
Sulfoximine Analogs
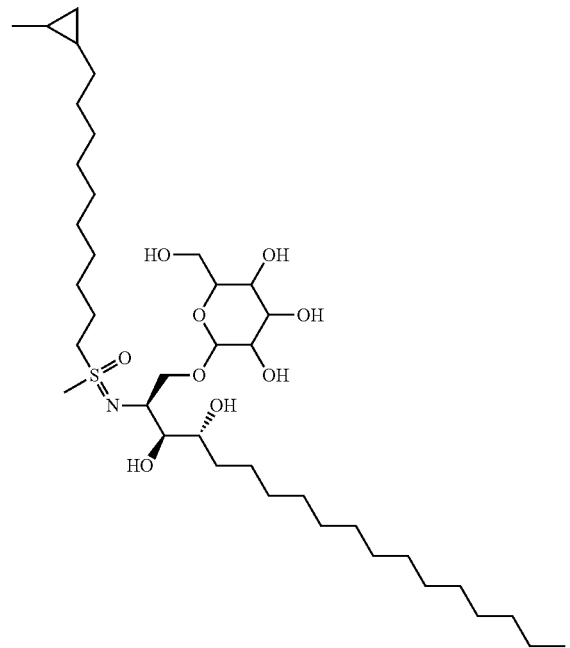 [SMILES: CCCCCCCCCCCCCC[C@@H](O)[C@@H](O)[C@H](COC1OC(CO)C(O)C(O)C1O)N=S(C)(=O)CCCCCCCCCCC1CC1C]
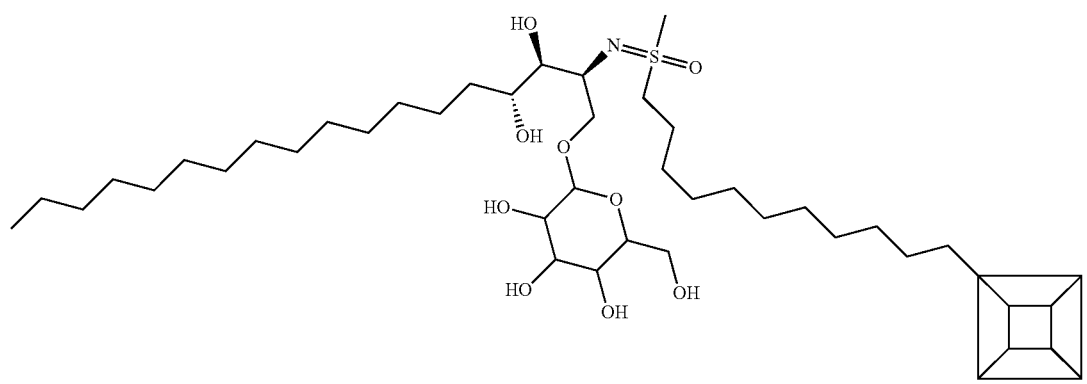 [SMILES: CCCCCCCCCCCCCC[C@@H](O)[C@@H](O)[C@H](COC1OC(CO)C(O)C(O)C1O)N=S(C)(=O)CCCCCCCCCCCC12C3C4C5C3C1C5C42]

TABLE 4-continued
Sulfoximine Analogs
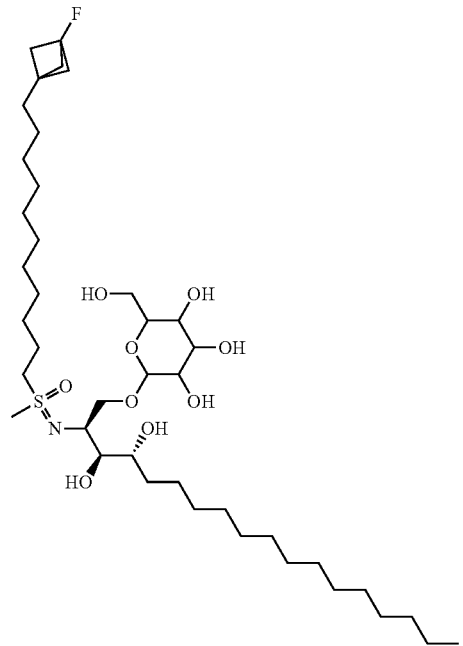 [SMILES: CCCCCCCCCCCCCC[C@@H](O)[C@@H](O)[C@H](COC1OC(CO)C(O)C(O)C1O)N=S(C)(=O)CCCCCCCCCCCC12CC(F)(C1)C2]
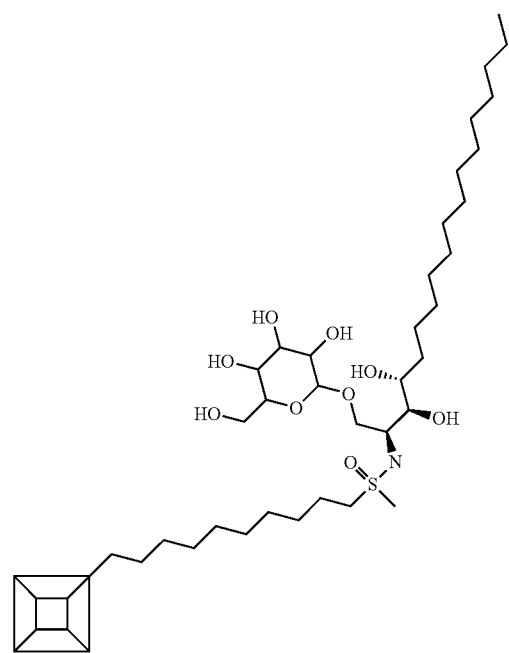

TABLE 4-continued
Sulfoximine Analogs
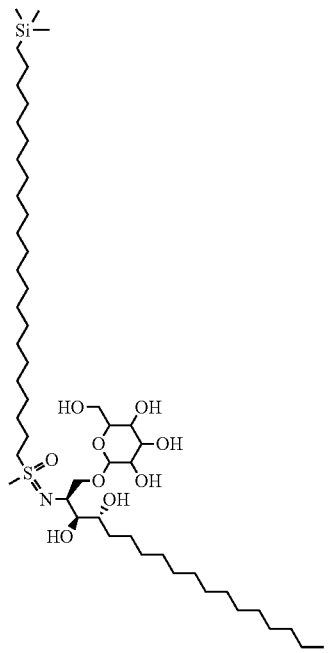 [SMILES: CCCCCCCCCCCCCC[C@@H](O)[C@@H](O)[C@H](COC1OC(CO)C(O)C(O)C1O)N=S(C)(=O)CCCCCCCCCCCCCCCCCCCCCCC[Si](C)(C)C]
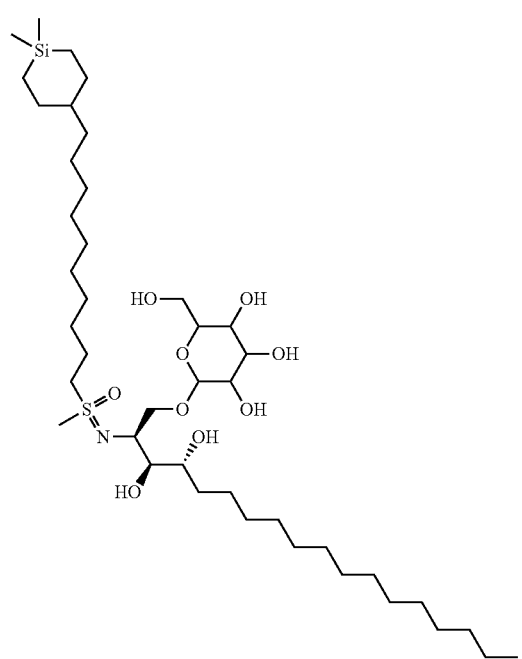 [SMILES: CCCCCCCCCCCCCC[C@@H](O)[C@@H](O)[C@H](COC1OC(CO)C(O)C(O)C1O)N=S(C)(=O)CCCCCCCCCCC1CC[Si](C)(C)CC1]

TABLE 4-continued
Sulfoximine Analogs
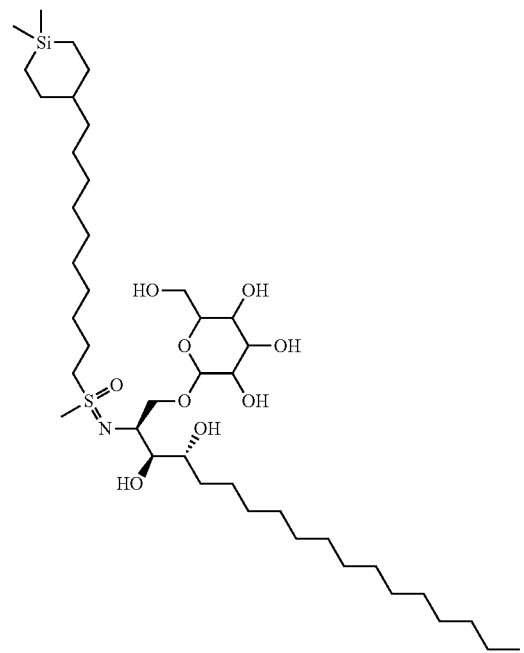 [SMILES: CCCCCCCCCCCCCC[C@@H](O)[C@@H](O)[C@H](COC1OC(CO)C(O)C(O)C1O)N=S(C)(=O)CCCCCCCCCCC1CC[Si](C)(C)CC1]
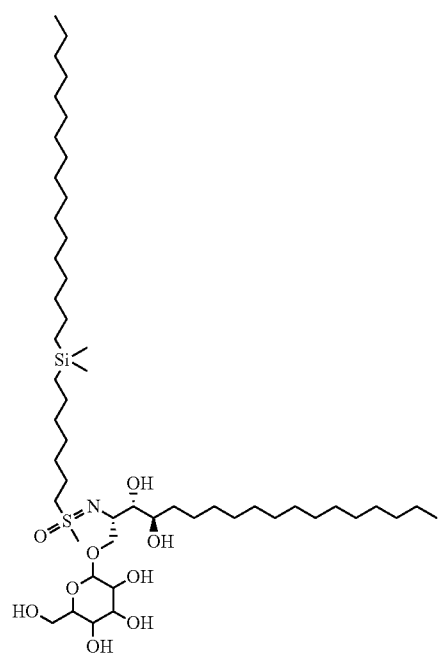 [SMILES: CCCCCCCCCCCCCCCCC[Si](C)(C)CCCCCCCS(C)(=O)=N[C@@H](COC1OC(CO)C(O)C(O)C1O)[C@H](O)[C@H](O)CCCCCCCCCCCCCC]

TABLE 4-continued
Sulfoximine Analogs
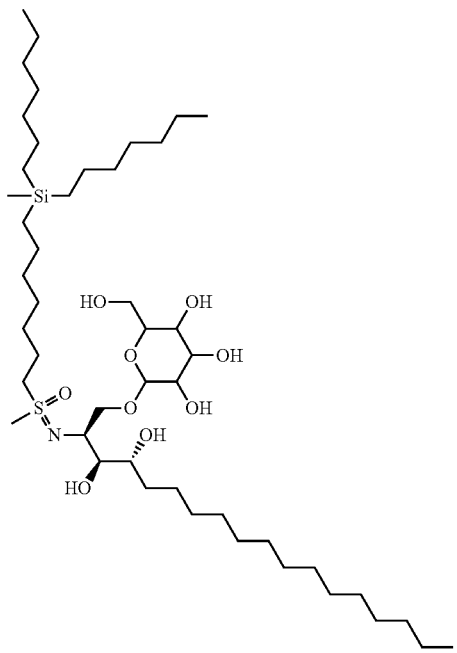 [SMILES: CCCCCCCCCCCCCC[C@@H](O)[C@@H](O)[C@H](COC1OC(CO)C(O)C(O)C1O)N=S(C)(=O)CCCCCCC[Si](C)(CCCCCCC)CCCCCCC]
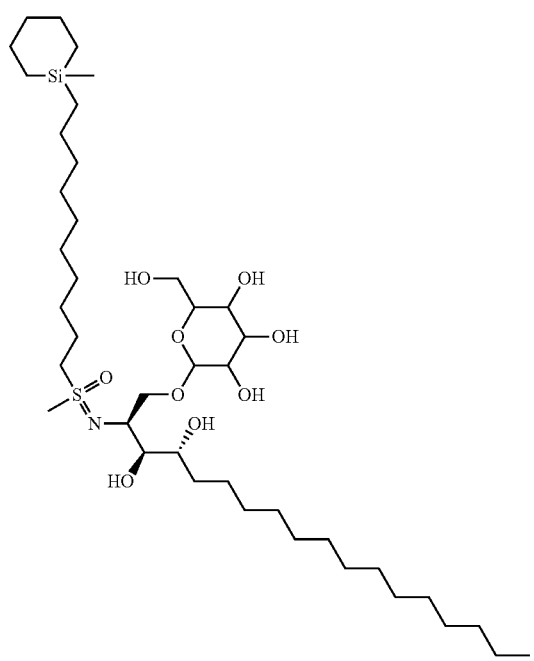 [SMILES: CCCCCCCCCCCCCC[C@@H](O)[C@@H](O)[C@H](COC1OC(CO)C(O)C(O)C1O)N=S(C)(=O)CCCCCCCCCC[Si]1(C)CCCCC1]

TABLE 4-continued
Sulfoximine Analogs
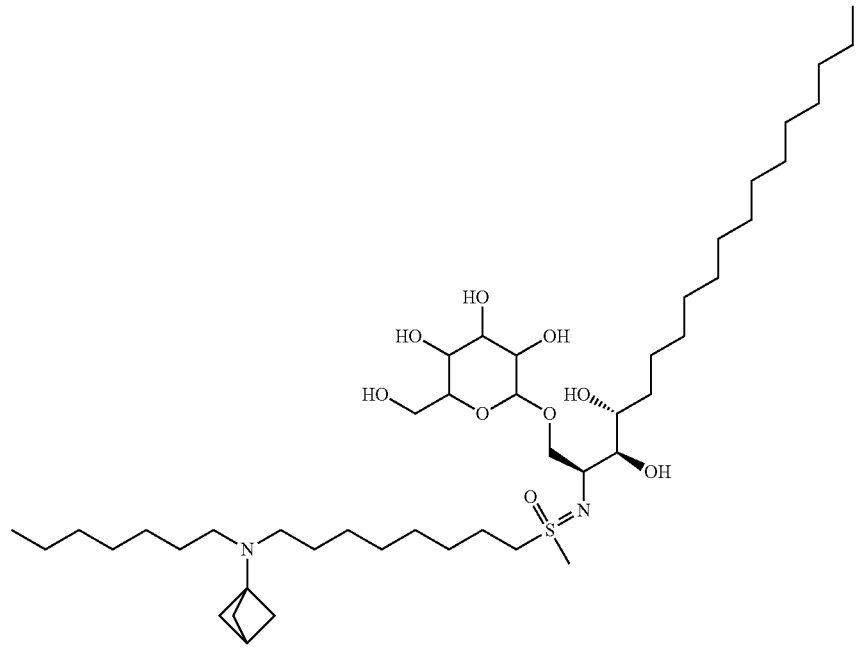 [SMILES: CCCCCCCCCCCCCC[C@@H](O)[C@@H](O)[C@H](COC1OC(CO)C(O)C(O)C1O)N=S(C)(=O)CCCCCCCCN(CCCCCCC)C12CC(C1)C2]
TABLE 5
Vinylfluoride Analogs
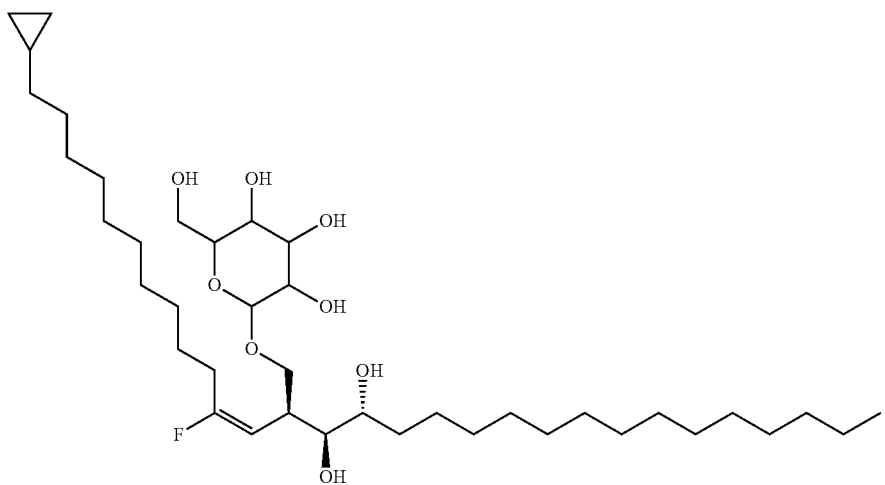 [SMILES: CCCCCCCCCCCCCC[C@@H](O)[C@@H](O)[C@@H](/C=C(/F)CCCCCCCCCCC1CC1)COC1OC(CO)C(O)C(O)C1O]

TABLE 5-continued
Vinylfluoride Analogs
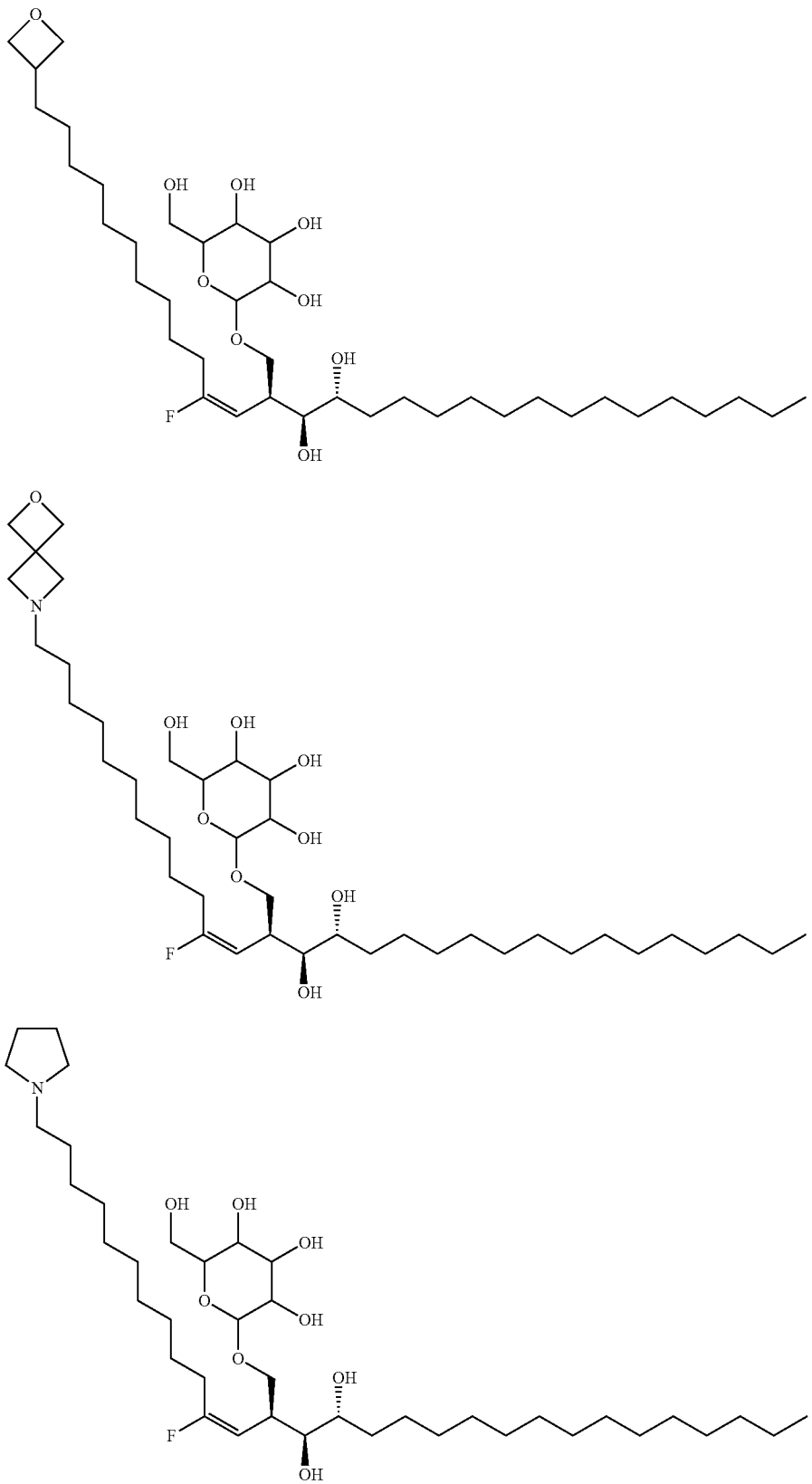

TABLE 5-continued
Vinylfluoride Analogs
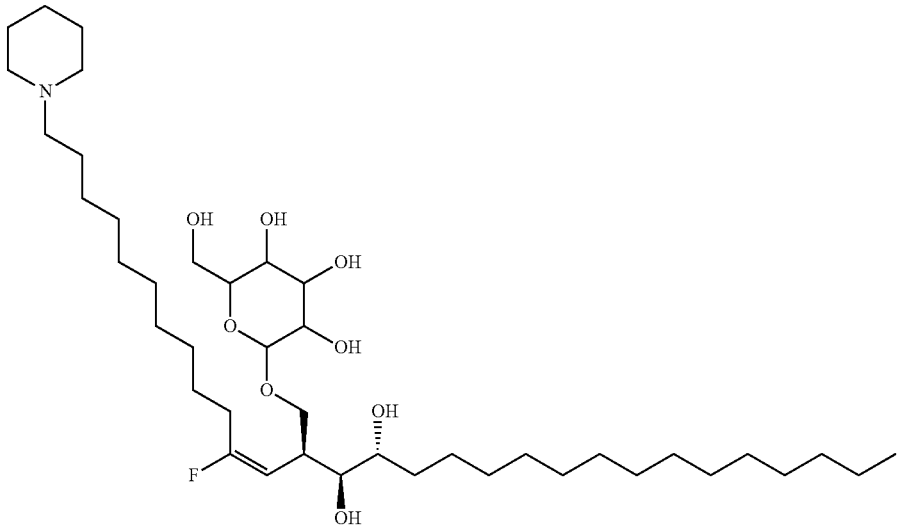
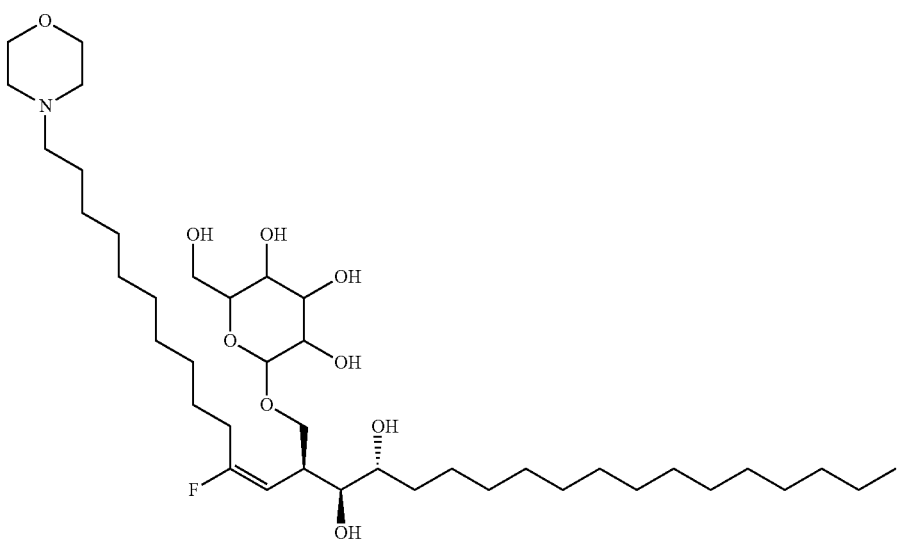

TABLE 5-continued
Vinylfluoride Analogs
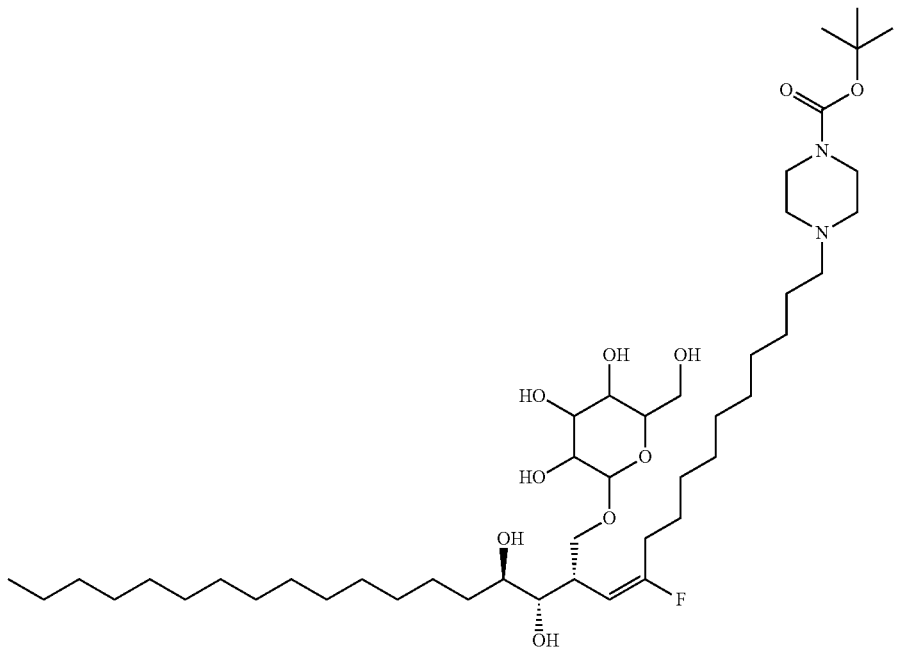 [SMILES: CCCCCCCCCCCCCC[C@@H](O)[C@@H](O)[C@@H](/C=C(/F)CCCCCCCCCCN1CCN(C(=O)OC(C)(C)C)CC1)COC1OC(CO)C(O)C(O)C1O]
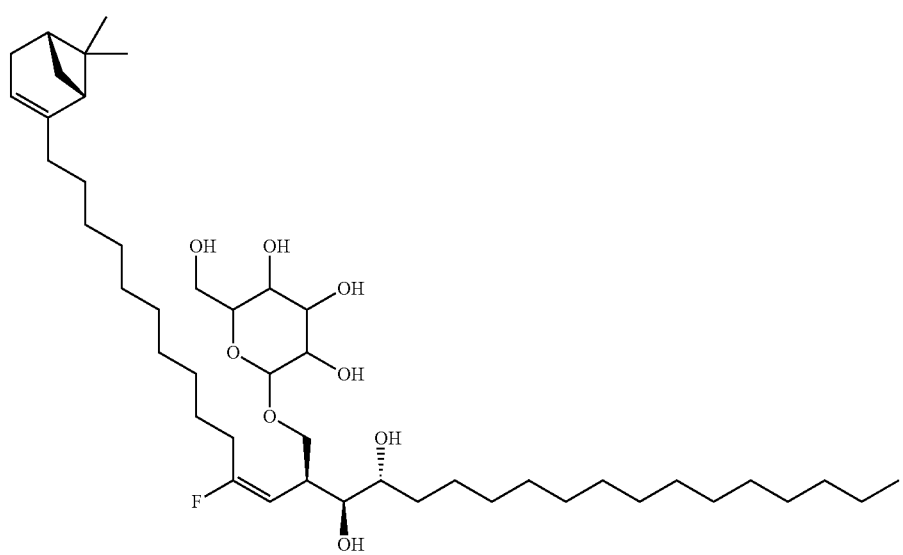 [SMILES: CCCCCCCCCCCCCC[C@@H](O)[C@@H](O)[C@@H](/C=C(/F)CCCCCCCCCCC1=CC[C@H]2C[C@@H]1C2(C)C)COC1OC(CO)C(O)C(O)C1O]

TABLE 5-continued
Vinylfluoride Analogs
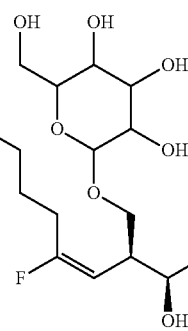
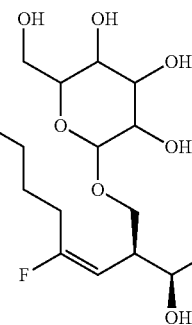
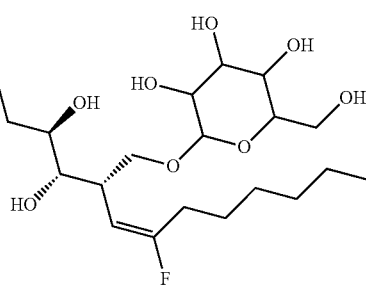

TABLE 5-continued
Vinylfluoride Analogs
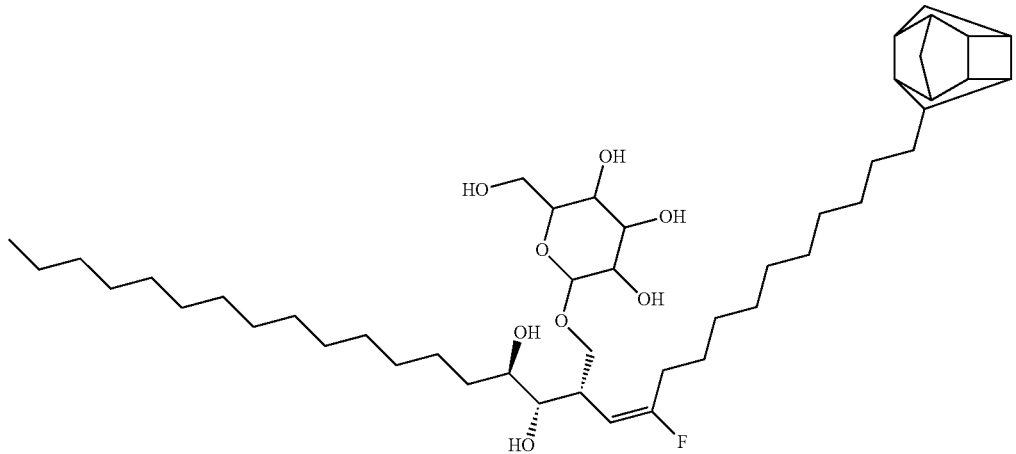 [SMILES: CCCCCCCCCCCCCC[C@@H](O)[C@@H](O)[C@@H](/C=C(/F)CCCCCCCCCCC1C2C3CC4C5C3CC2C5C14)COC1OC(CO)C(O)C(O)C1O]
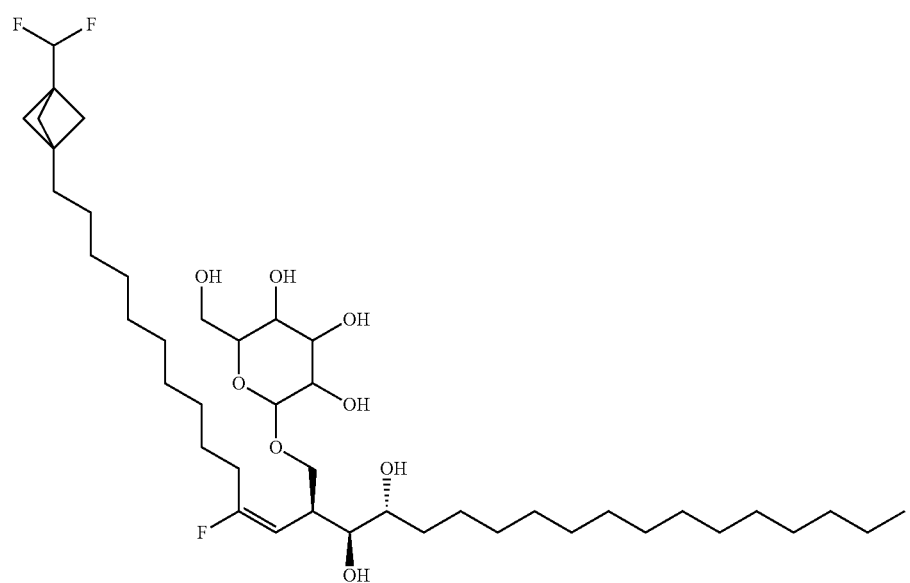 [SMILES: CCCCCCCCCCCCCC[C@@H](O)[C@@H](O)[C@@H](/C=C(/F)CCCCCCCCCCC12CC(C(F)F)(C1)C2)COC1OC(CO)C(O)C(O)C1O]

TABLE 5-continued
Vinylfluoride Analogs
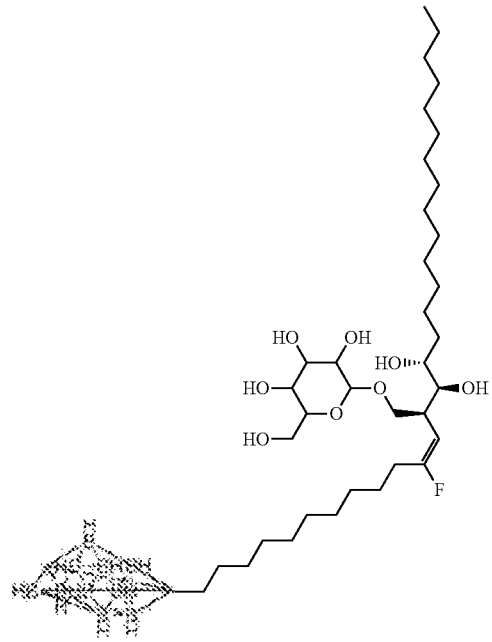 [SMILES: CCCCCCCCCCCCCC[C@@H](O)[C@@H](O)[C@@H](/C=C(/F)CCCCCCCCCCC)COC1OC(CO)C(O)C(O)C1O]
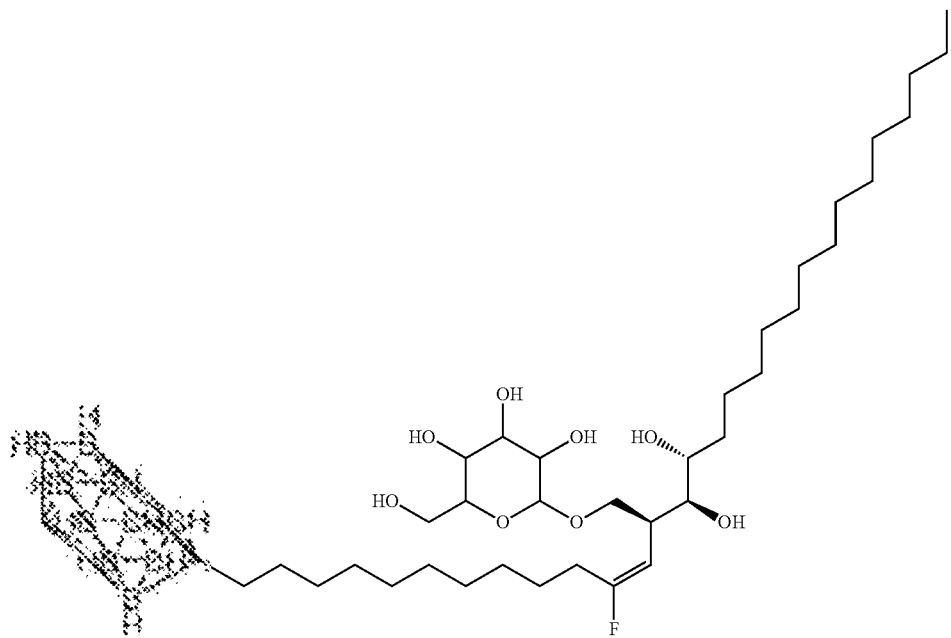 [SMILES: CCCCCCCCCCCCCC[C@@H](O)[C@@H](O)[C@@H](/C=C(/F)CCCCCCCCCCC)COC1OC(CO)C(O)C(O)C1O]

TABLE 5-continued
Vinylfluoride Analogs
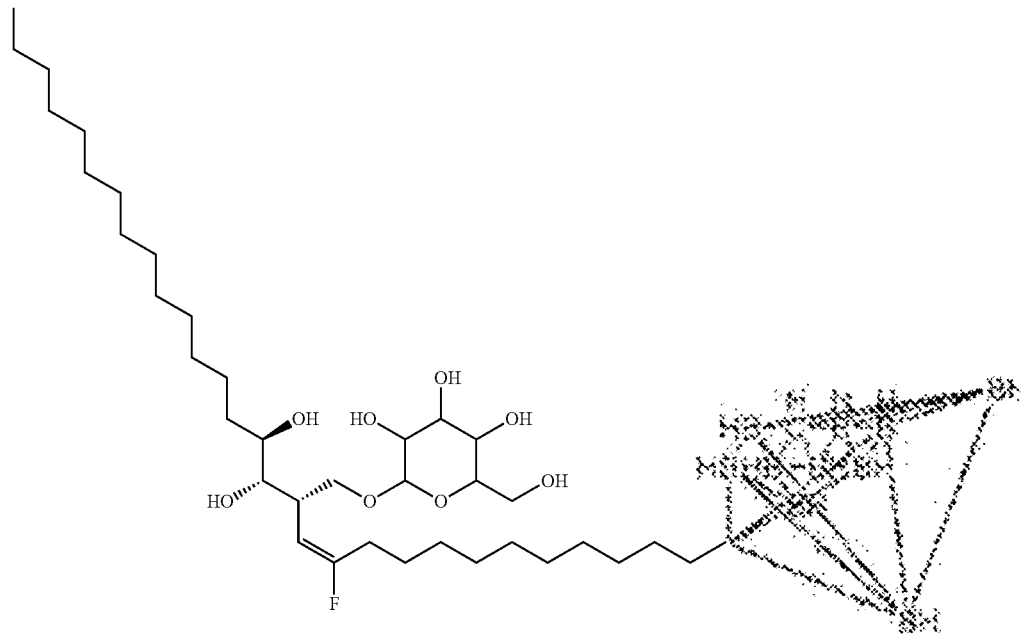 [SMILES: CCCCCCCCCCCCCC[C@@H](O)[C@@H](O)[C@@H](/C=C(/F)CCCCCCCCCCC)COC1OC(CO)C(O)C(O)C1O]
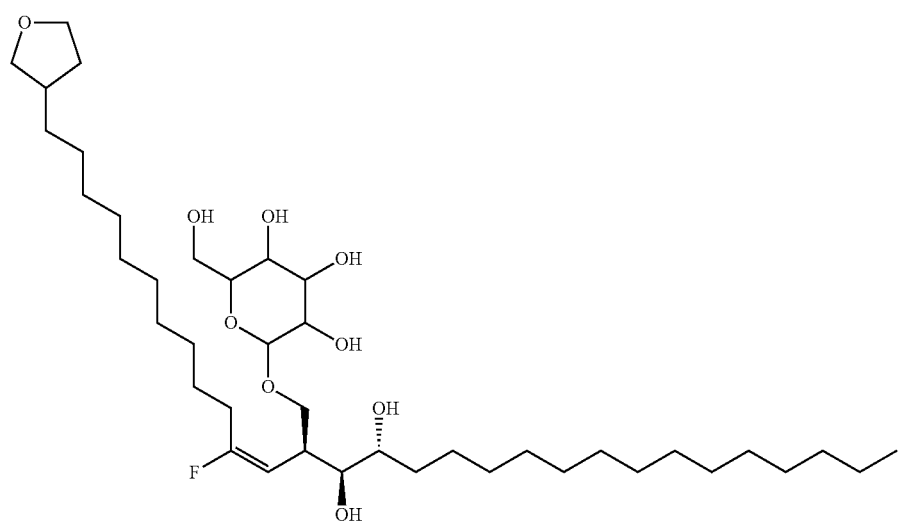 [SMILES: CCCCCCCCCCCCCC[C@@H](O)[C@@H](O)[C@@H](/C=C(/F)CCCCCCCCCCC1CCOC1)COC1OC(CO)C(O)C(O)C1O]

TABLE 5-continued
Vinylfluoride Analogs
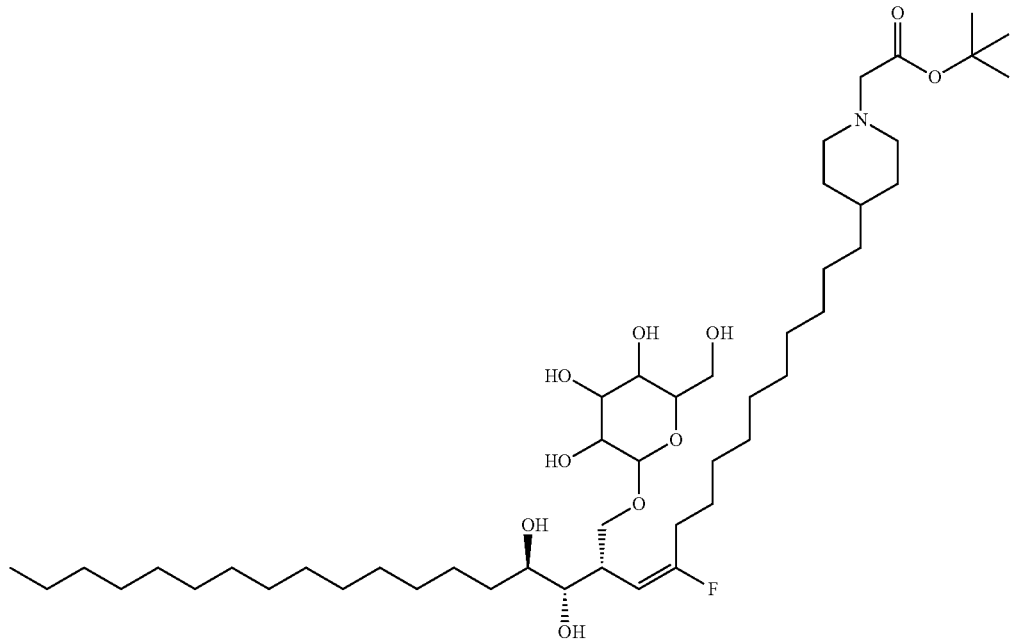 [SMILES: CCCCCCCCCCCCCC[C@@H](O)[C@@H](O)[C@@H](/C=C(/F)CCCCCCCCCCC1CCN(CC(=O)OC(C)(C)C)CC1)COC1OC(CO)C(O)C(O)C1O]
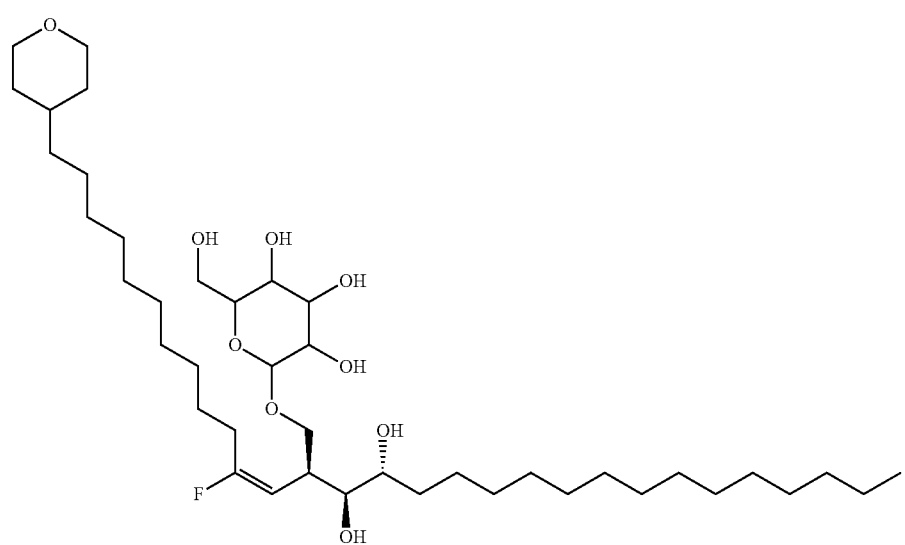 [SMILES: CCCCCCCCCCCCCC[C@@H](O)[C@@H](O)[C@@H](/C=C(/F)CCCCCCCCCCC1CCOCC1)COC1OC(CO)C(O)C(O)C1O]

TABLE 5-continued
Vinylfluoride Analogs
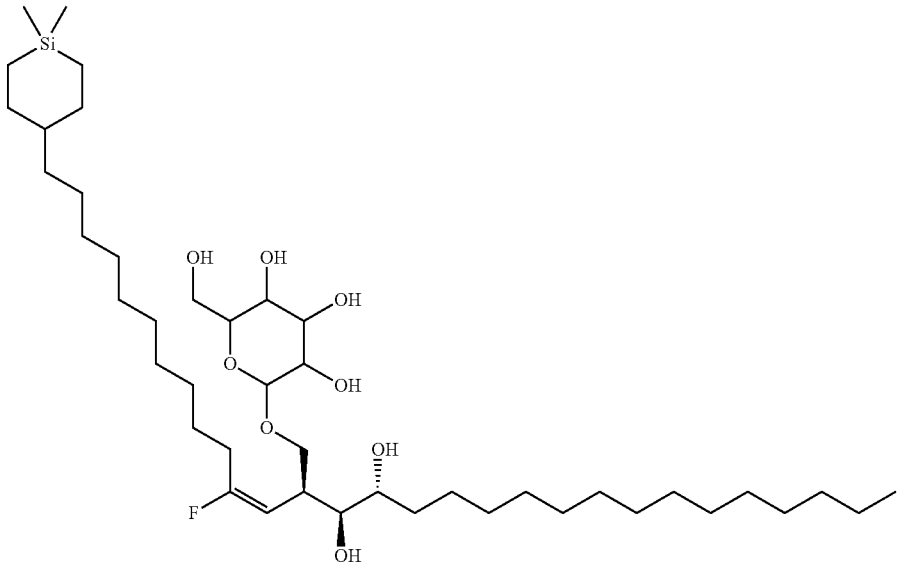 [SMILES: CCCCCCCCCCCCCC[C@@H](O)[C@@H](O)[C@@H](/C=C(/F)CCCCCCCCCCC1CC[Si](C)(C)CC1)COC1OC(CO)C(O)C(O)C1O]
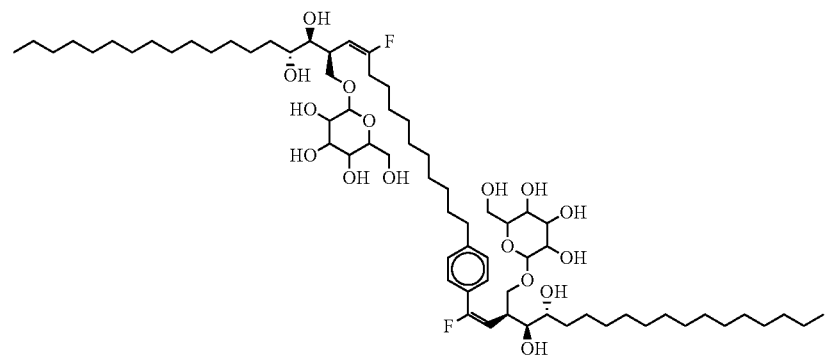
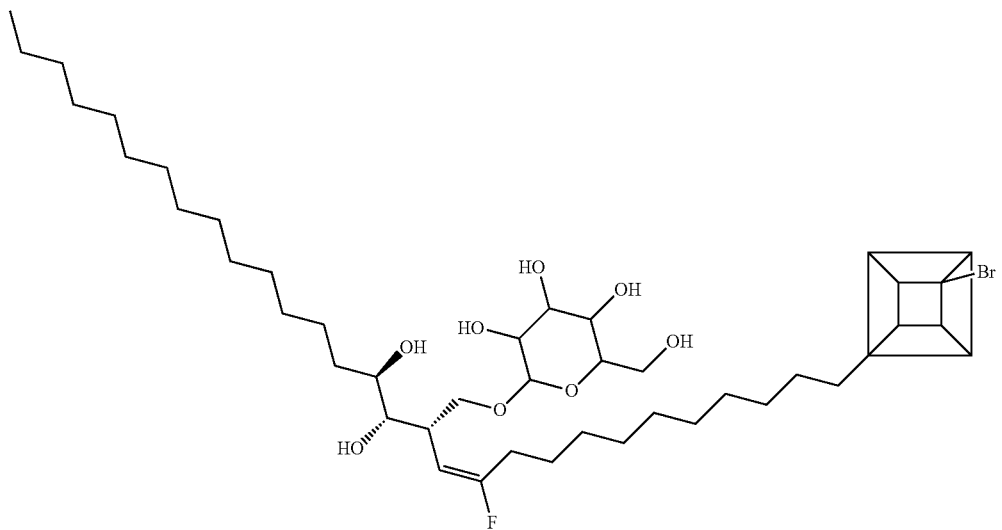 [SMILES: CCCCCCCCCCCCCC[C@@H](O)[C@@H](O)[C@@H](/C=C(/F)CCCCCCCCCCC12C3C4C1C1C2C3C41Br)COC1OC(CO)C(O)C(O)C1O]

TABLE 5-continued
Vinylfluoride Analogs
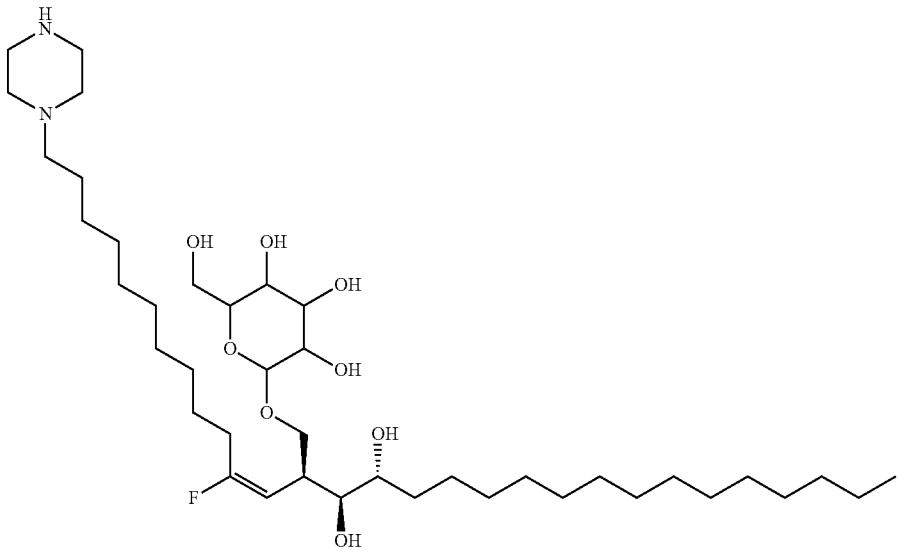 [SMILES: CCCCCCCCCCCCCC[C@@H](O)[C@@H](O)[C@@H](/C=C(/F)CCCCCCCCCCN1CCNCC1)COC1OC(CO)C(O)C(O)C1O]
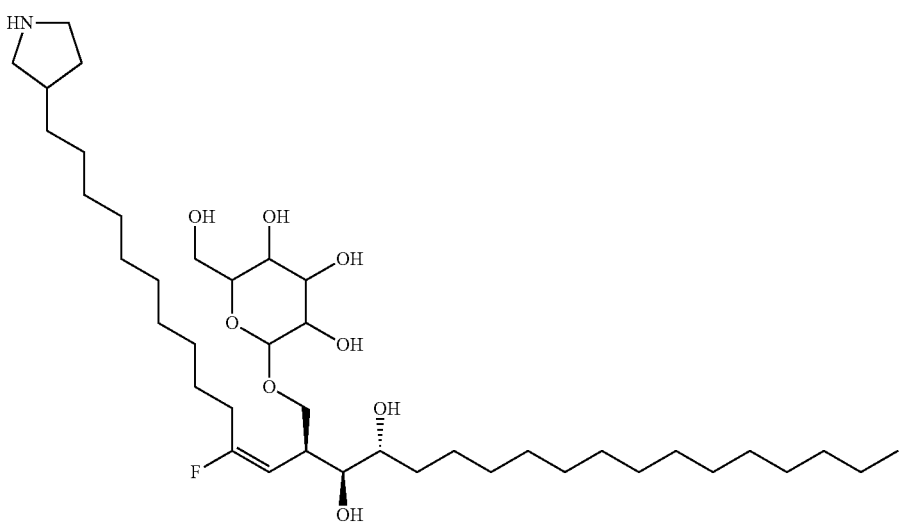 [SMILES: CCCCCCCCCCCCCC[C@@H](O)[C@@H](O)[C@@H](/C=C(/F)CCCCCCCCCCC1CCNC1)COC1OC(CO)C(O)C(O)C1O]
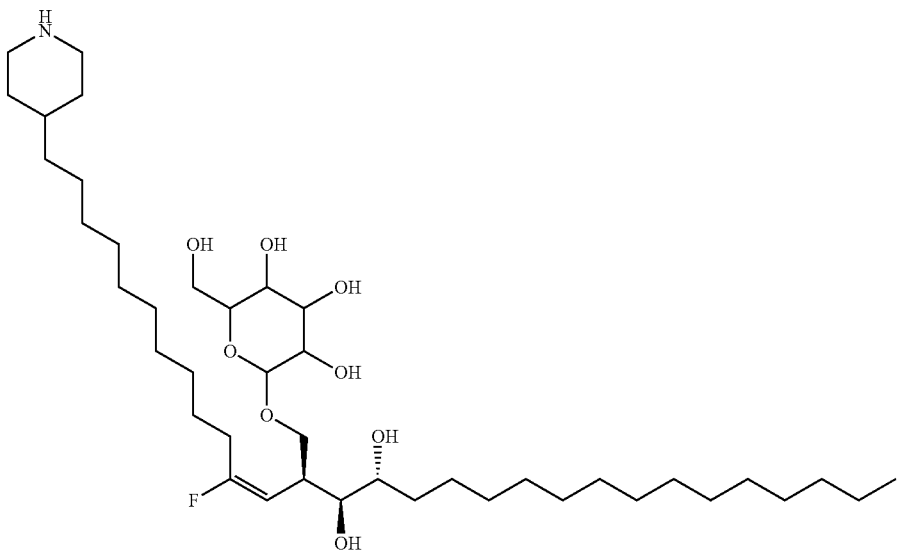 [SMILES: CCCCCCCCCCCCCC[C@@H](O)[C@@H](O)[C@@H](/C=C(/F)CCCCCCCCCCC1CCNCC1)COC1OC(CO)C(O)C(O)C1O]

TABLE 5-continued
Vinylfluoride Analogs
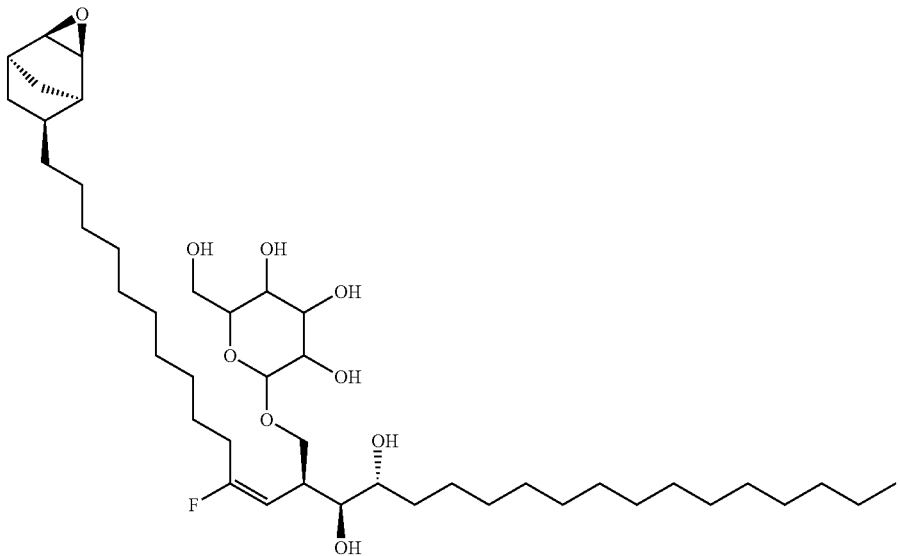 [SMILES: CCCCCCCCCCCCCC[C@@H](O)[C@@H](O)[C@@H](/C=C(/F)CCCCCCCCCC[C@H]1C[C@@H]2C[C@H]1[C@@H]1O[C@H]21)COC1OC(CO)C(O)C(O)C1O]
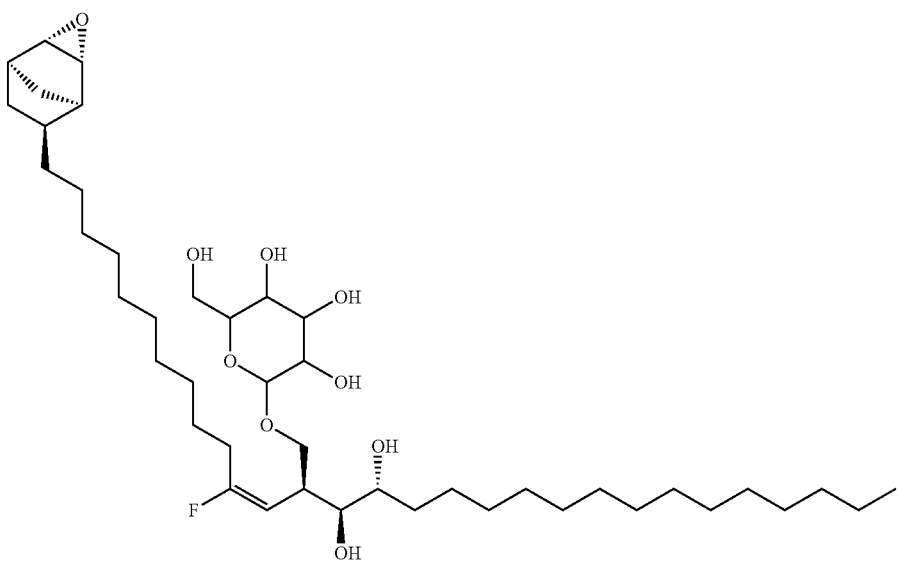 [SMILES: CCCCCCCCCCCCCC[C@@H](O)[C@@H](O)[C@@H](/C=C(/F)CCCCCCCCCC[C@H]1C[C@@H]2C[C@H]1[C@H]1O[C@@H]21)COC1OC(CO)C(O)C(O)C1O]
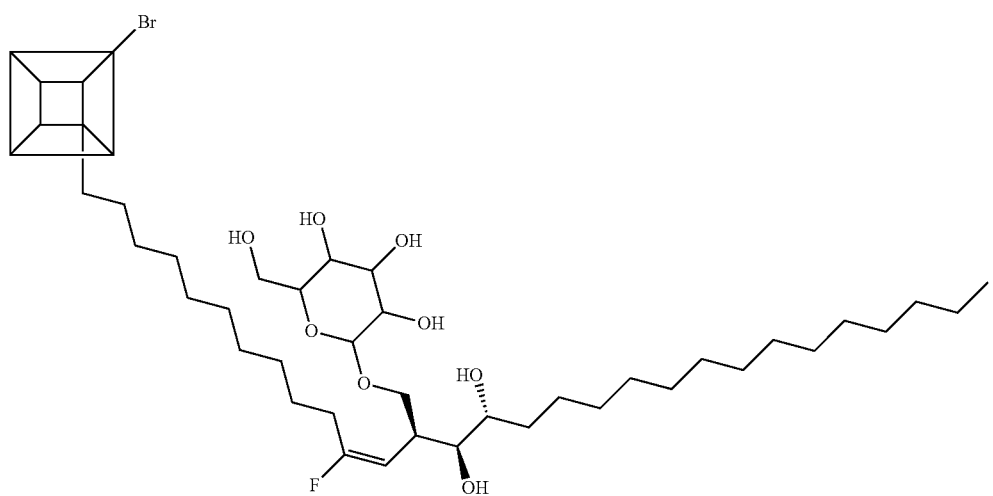 [SMILES: CCCCCCCCCCCCCC[C@@H](O)[C@@H](O)[C@@H](/C=C(/F)CCCCCCCCCCC12C3C4C5C3C1C5(Br)C42)COC1OC(CO)C(O)C(O)C1O]

TABLE 5-continued
Vinylfluoride Analogs
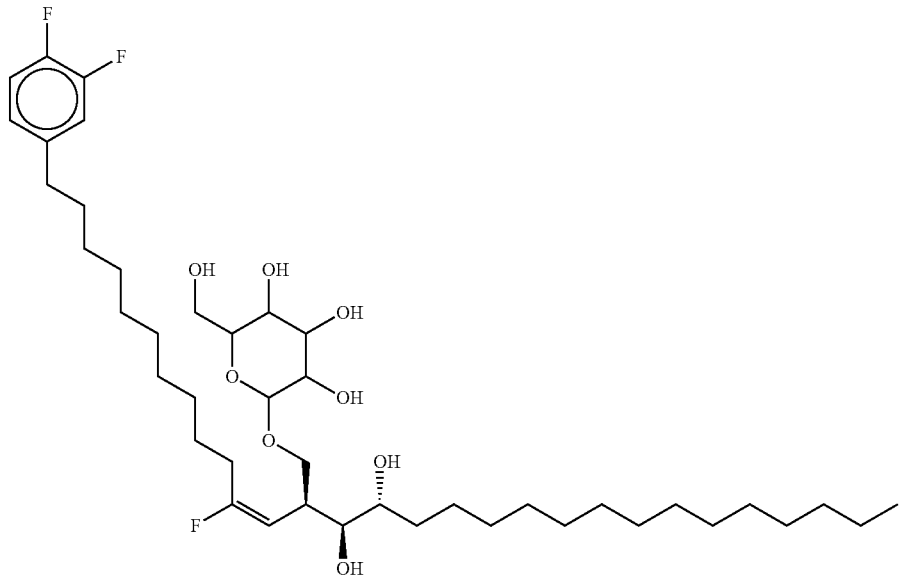
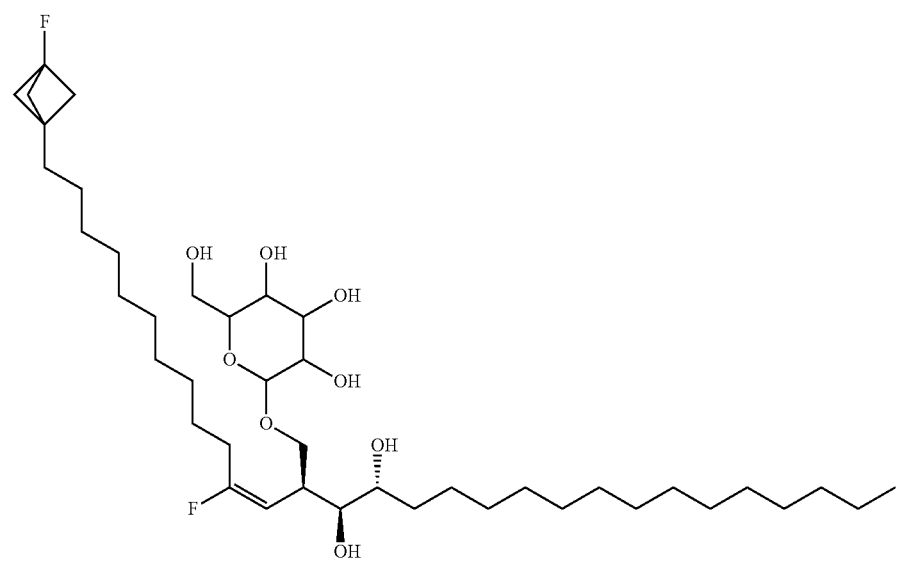 [SMILES: CCCCCCCCCCCCCC[C@@H](O)[C@@H](O)[C@@H](/C=C(/F)CCCCCCCCCCC12CC(F)(C1)C2)COC1OC(CO)C(O)C(O)C1O]

TABLE 5-continued
Vinylfluoride Analogs
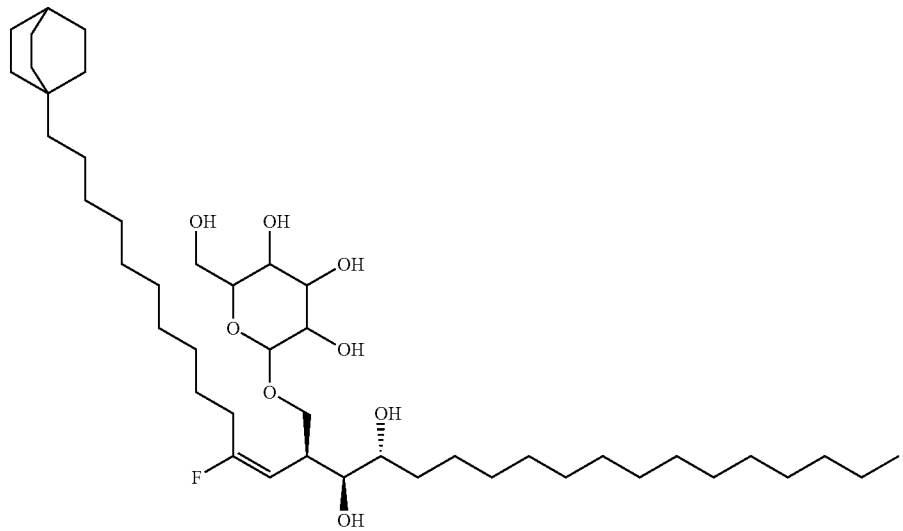 [SMILES: CCCCCCCCCCCCCC[C@@H](O)[C@@H](O)[C@@H](/C=C(/F)CCCCCCCCCCC12CCC(CC1)CC2)COC1OC(CO)C(O)C(O)C1O]
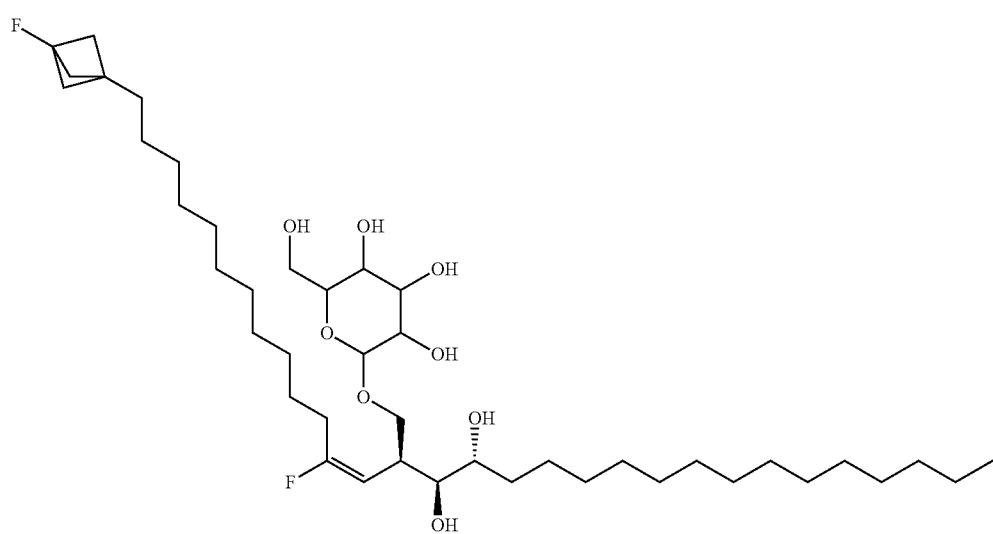 [SMILES: CCCCCCCCCCCCCC[C@@H](O)[C@@H](O)[C@@H](/C=C(/F)CCCCCCCCCCCC12CC(F)(C1)C2)COC1OC(CO)C(O)C(O)C1O]
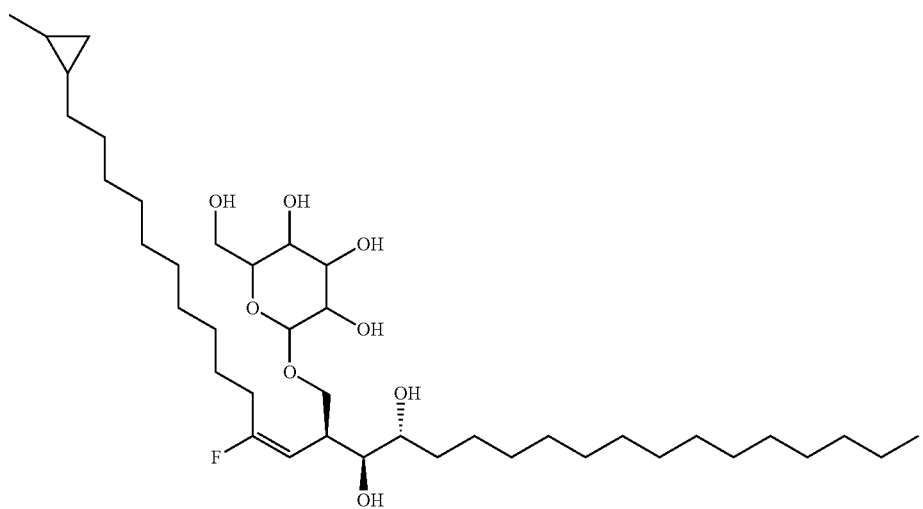 [SMILES: CCCCCCCCCCCCCC[C@@H](O)[C@@H](O)[C@@H](/C=C(/F)CCCCCCCCCCC1CC1C)COC1OC(CO)C(O)C(O)C1O]

TABLE 5-continued
Vinylfluoride Analogs
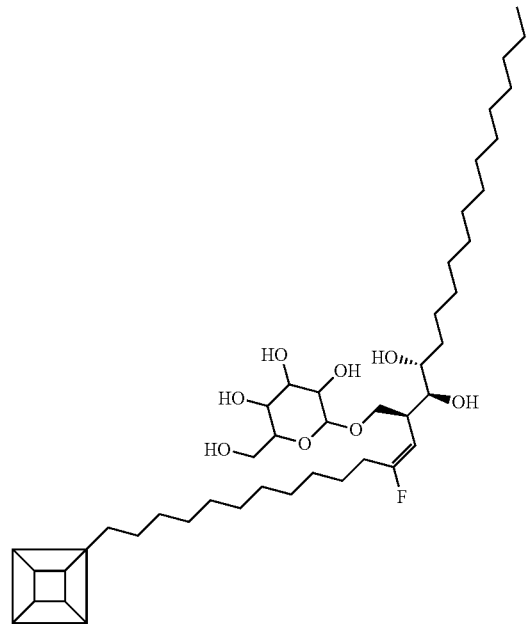 [SMILES: CCCCCCCCCCCCCC[C@@H](O)[C@@H](O)[C@@H](/C=C(/F)CCCCCCCCCCCC12C3C4C5C3C1C5C42)COC1OC(CO)C(O)C(O)C1O]
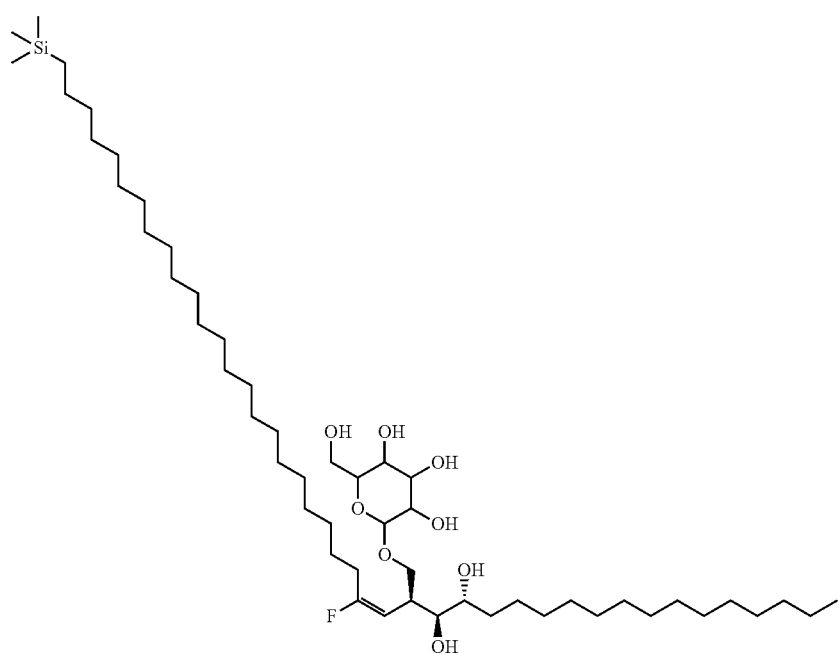 [SMILES: CCCCCCCCCCCCCC[C@@H](O)[C@@H](O)[C@@H](/C=C(/F)CCCCCCCCCCCCCCCCCCCCCCC[Si](C)(C)C)COC1OC(CO)C(O)C(O)C1O]

TABLE 5-continued
Vinylfluoride Analogs
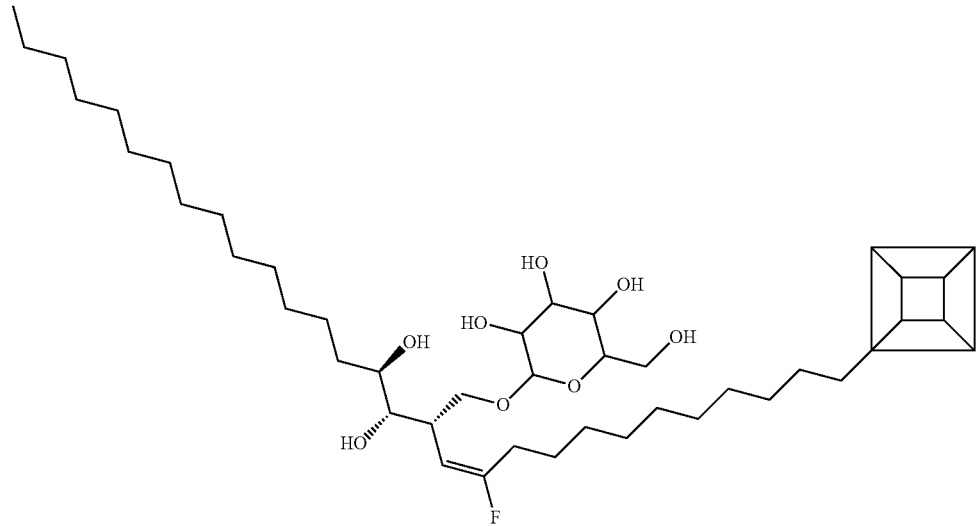 [SMILES: CCCCCCCCCCCCCC[C@@H](O)[C@@H](O)[C@@H](/C=C(/F)CCCCCCCCCCC12C3C4C5C3C1C5C42)COC1OC(CO)C(O)C(O)C1O]
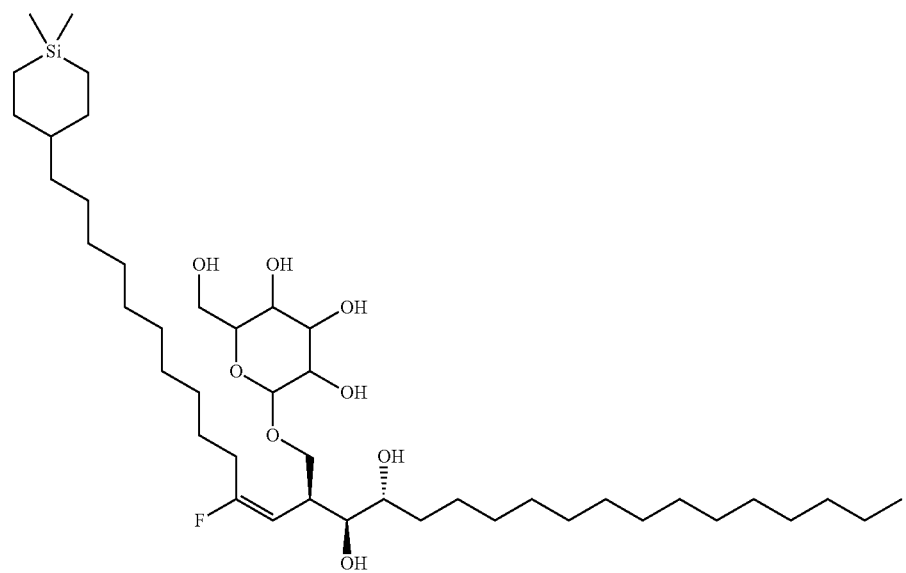 [SMILES: CCCCCCCCCCCCCC[C@@H](O)[C@@H](O)[C@@H](/C=C(/F)CCCCCCCCCCC1CC[Si](C)(C)CC1)COC1OC(CO)C(O)C(O)C1O]

TABLE 5-continued
Vinylfluoride Analogs
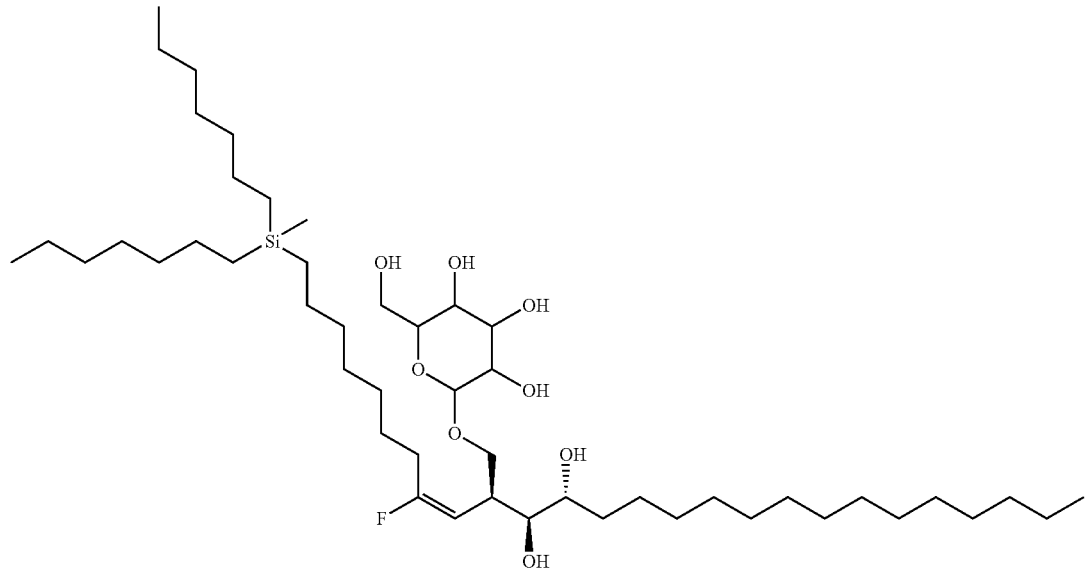 [SMILES: CCCCCCCCCCCCCC[C@@H](O)[C@@H](O)[C@@H](/C=C(/F)CCCCCCC[Si](C)(CCCCCCC)CCCCCCC)COC1OC(CO)C(O)C(O)C1O]
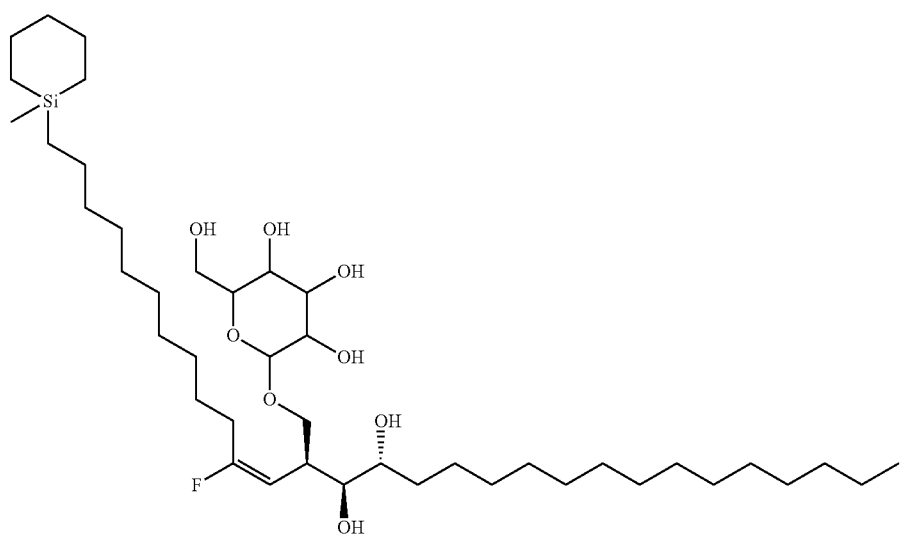 [SMILES: CCCCCCCCCCCCCC[C@@H](O)[C@@H](O)[C@@H](/C=C(/F)CCCCCCCCCC[Si]1(C)CCCCC1)COC1OC(CO)C(O)C(O)C1O]

TABLE 5-continued
Vinylfluoride Analogs
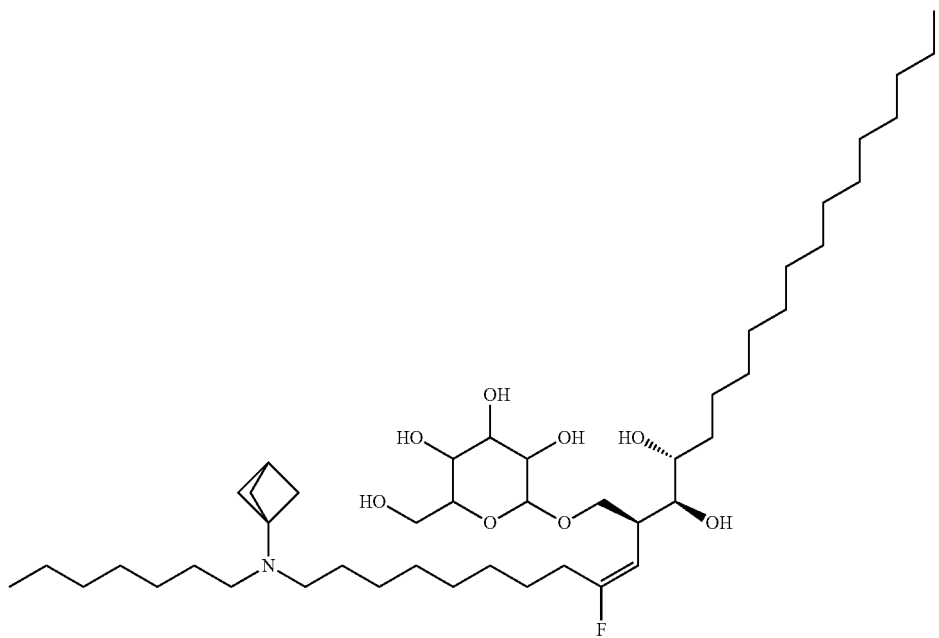 [SMILES: CCCCCCCCCCCCCC[C@@H](O)[C@@H](O)[C@@H](/C=C(/F)CCCCCCCCN(CCCCCCC)C12CC(C1)C2)COC1OC(CO)C(O)C(O)C1O]
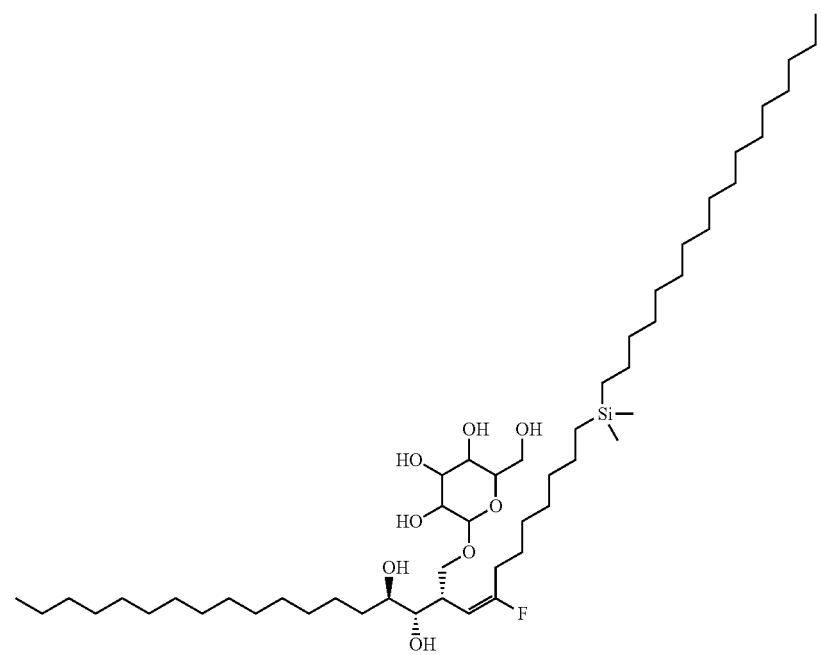 [SMILES: CCCCCCCCCCCCCCCCC[Si](C)(C)CCCCCCC/C(F)=C\[C@@H](COC1OC(CO)C(O)C(O)C1O)[C@H](O)[C@H](O)CCCCCCCCCCCCCC]

TABLE 6
Aminooxetane Analogs
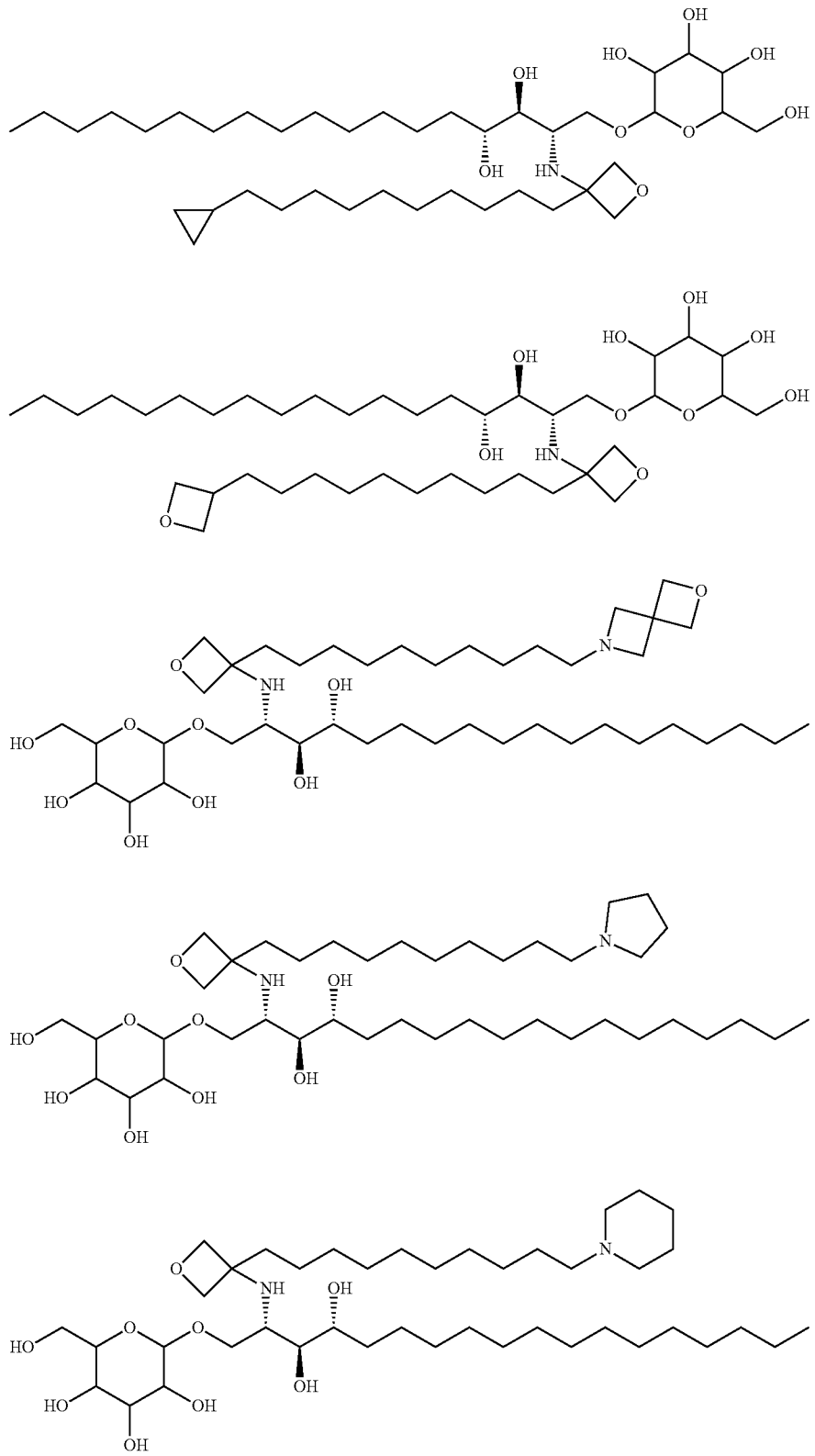

TABLE 6-continued
Aminooxetane Analogs
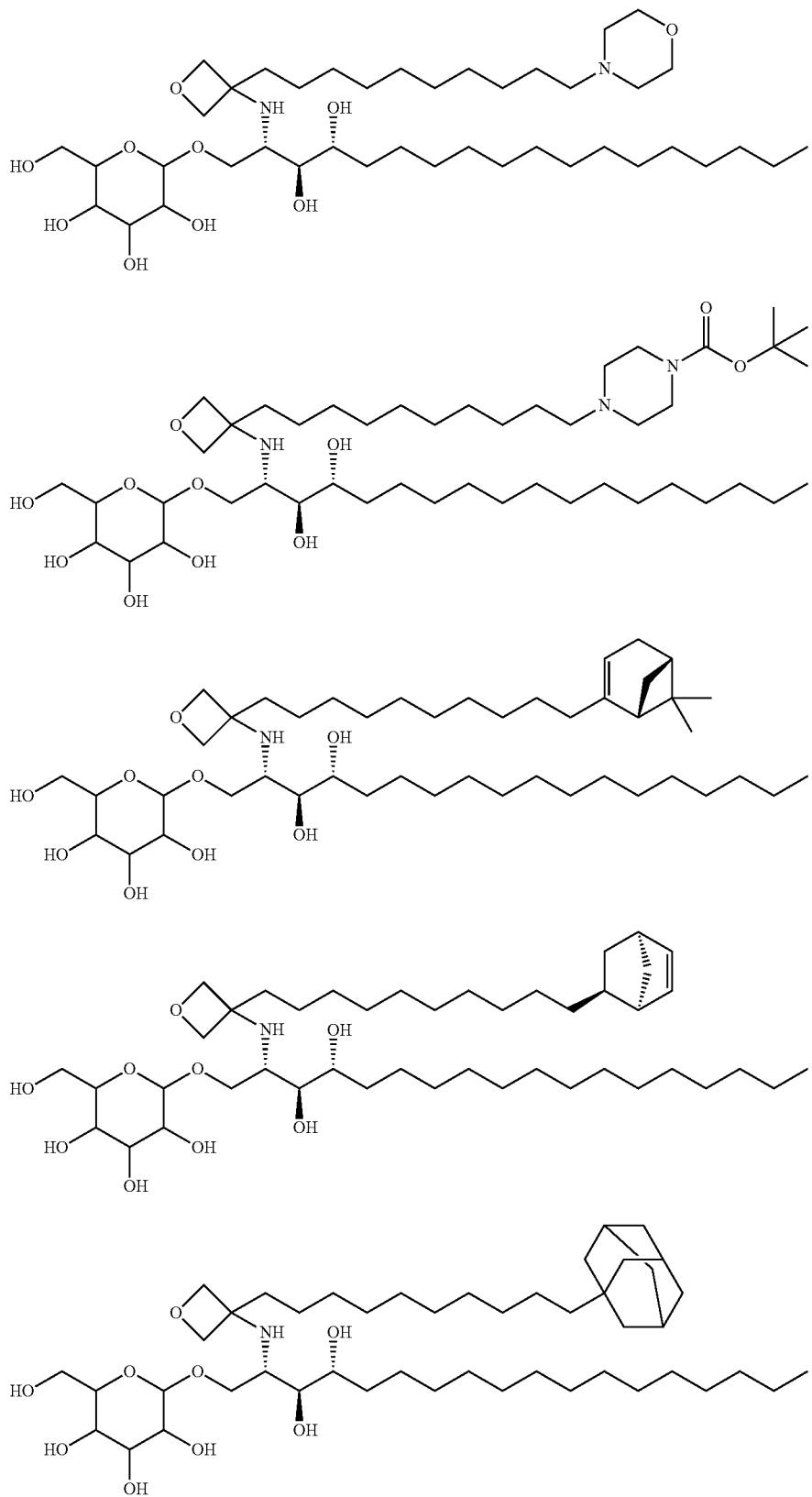

TABLE 6-continued
Aminooxetane Analogs
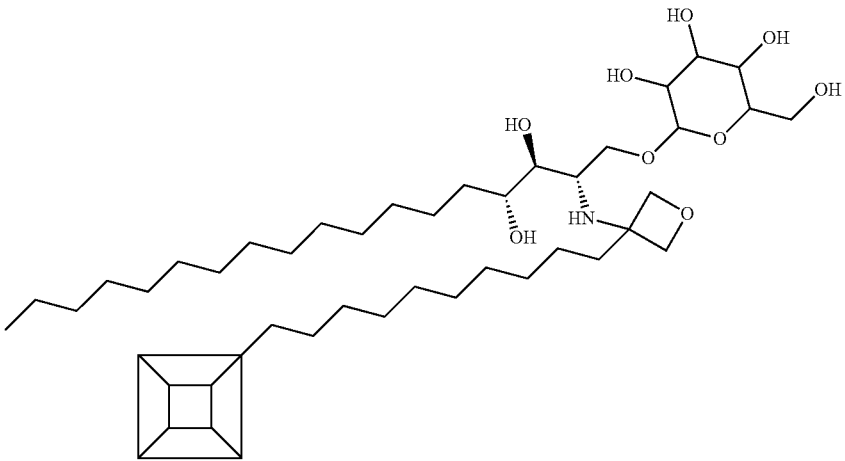 [SMILES: CCCCCCCCCCCCCC[C@@H](O)[C@@H](O)[C@H](COC1OC(CO)C(O)C(O)C1O)NC1(CCCCCCCCCCC23C4C5C6C4C2C6C53)COC1]
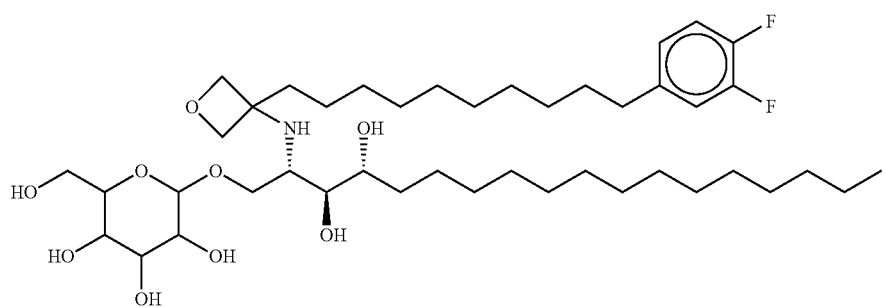
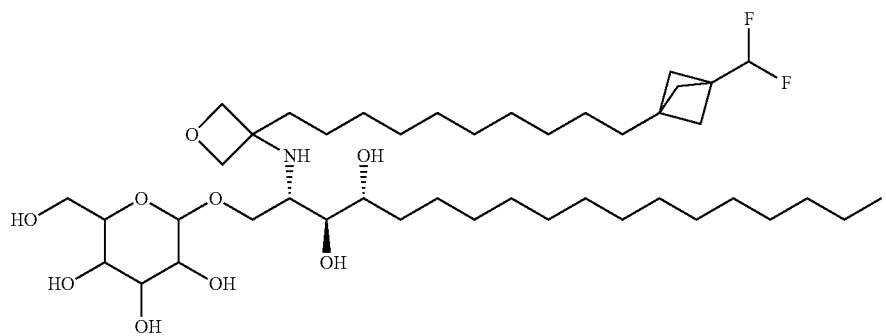 [SMILES: CCCCCCCCCCCCCC[C@@H](O)[C@@H](O)[C@H](COC1OC(CO)C(O)C(O)C1O)NC1(CCCCCCCCCCC23CC(C(F)F)(C2)C3)COC1]

TABLE 6-continued
Aminooxetane Analogs
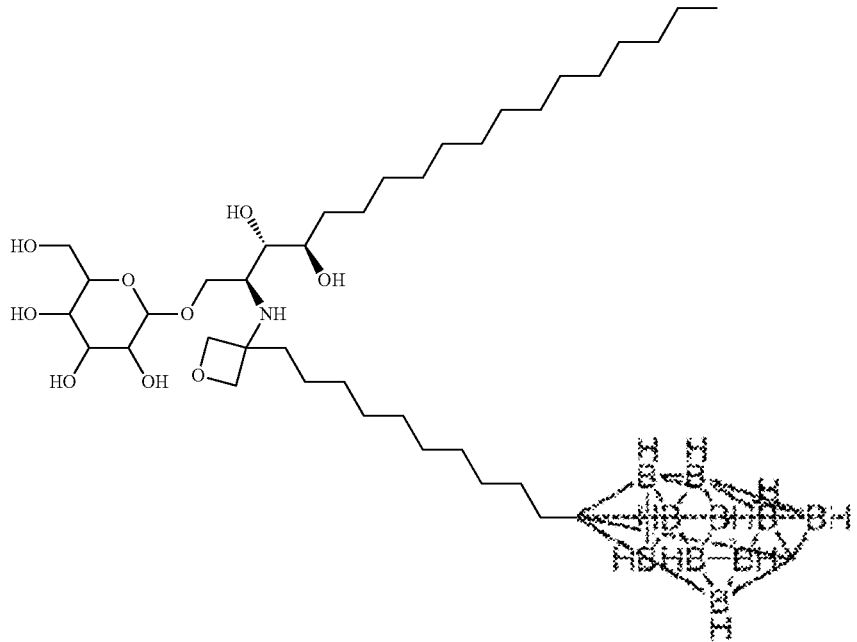 [SMILES: CCCCCCCCCCCCCC[C@@H](O)[C@@H](O)[C@H](COC1OC(CO)C(O)C(O)C1O)NC1(CCCCCCCCCCC)COC1]
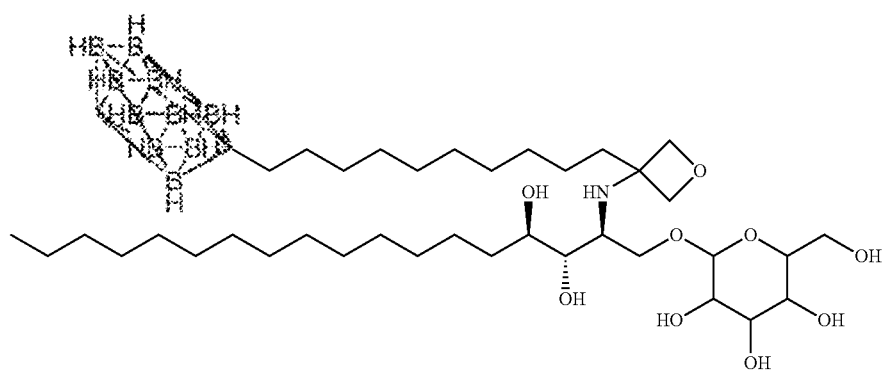 [SMILES: CCCCCCCCCCCCCC[C@@H](O)[C@@H](O)[C@H](COC1OC(CO)C(O)C(O)C1O)NC1(CCCCCCCCCCC)COC1]
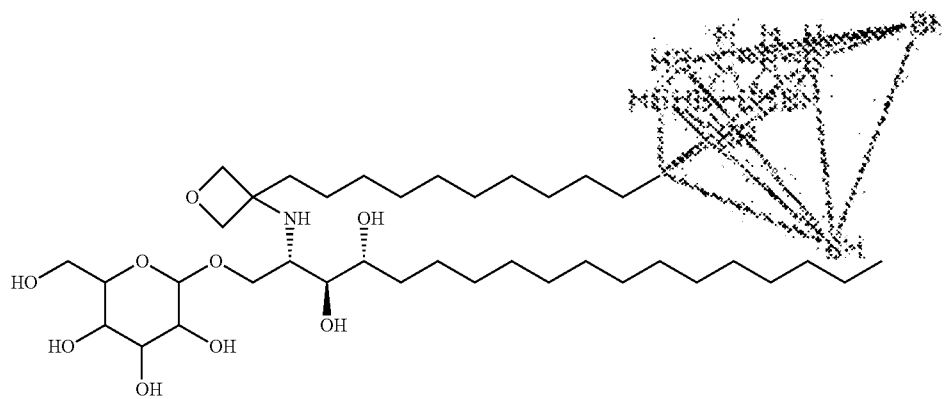 [SMILES: CCCCCCCCCCCCCC[C@@H](O)[C@@H](O)[C@H](COC1OC(CO)C(O)C(O)C1O)NC1(CCCCCCCCCCC)COC1]

TABLE 6-continued
Aminooxetane Analogs
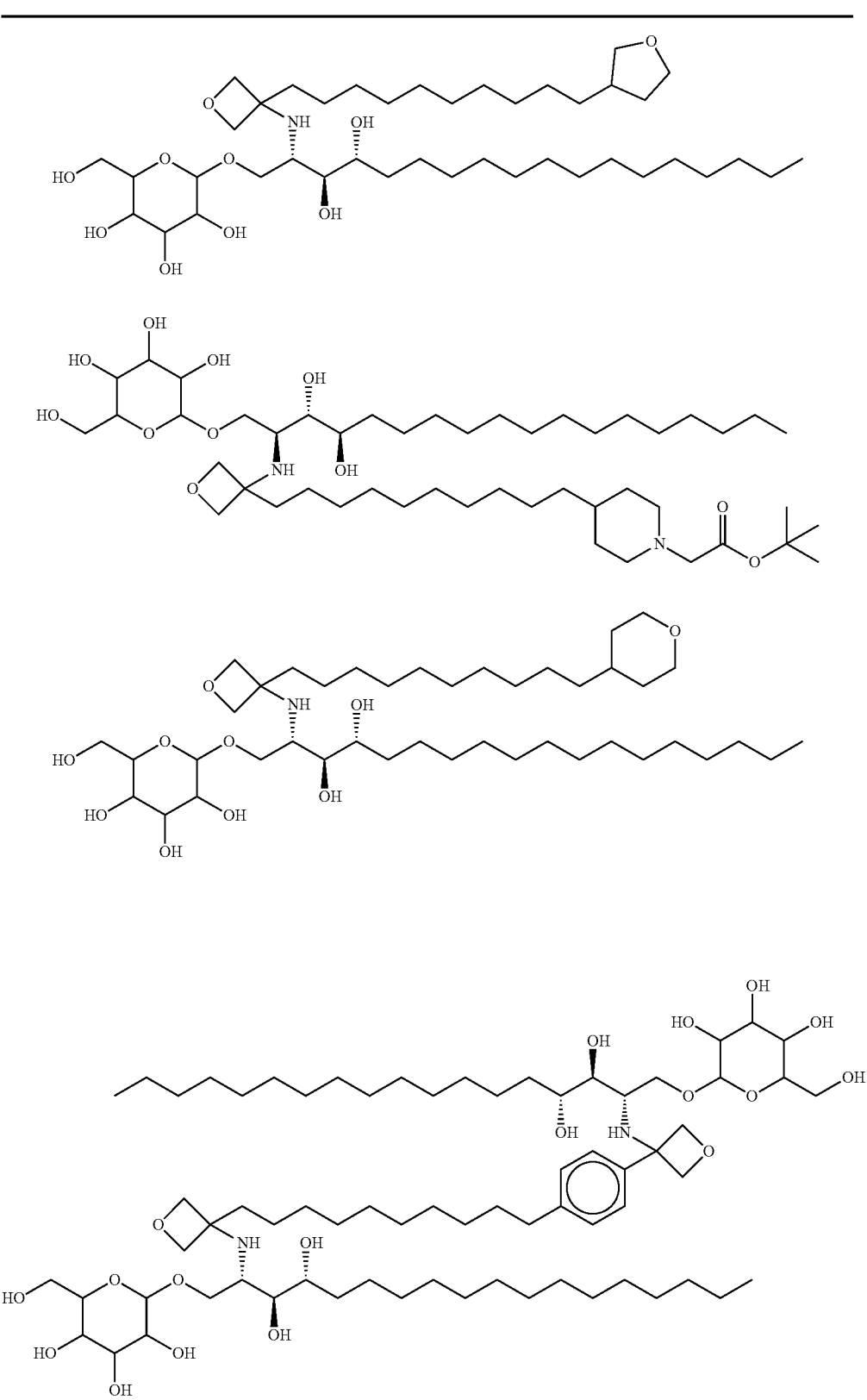

TABLE 6-continued
Aminooxetane Analogs
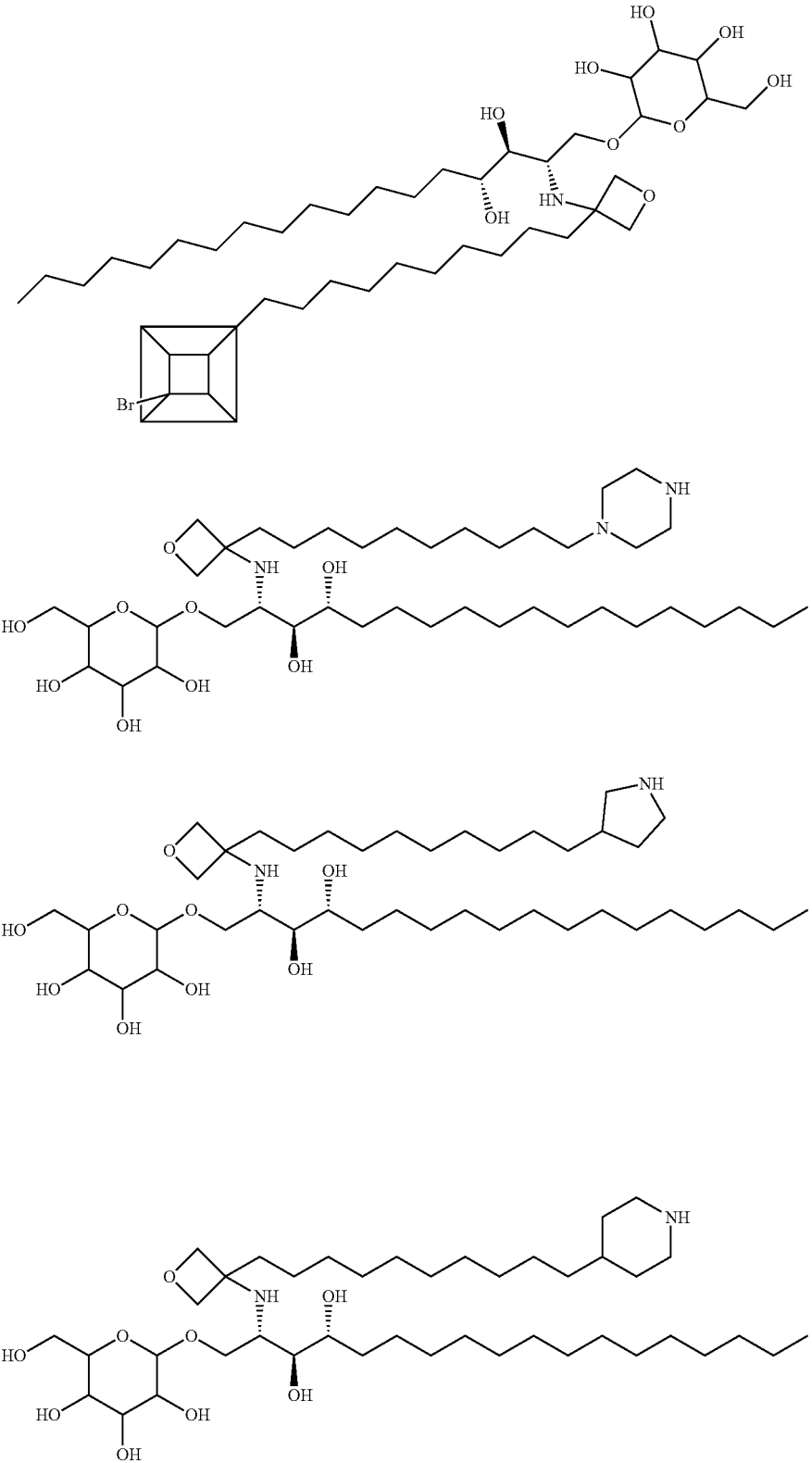

TABLE 6-continued
Aminooxetane Analogs
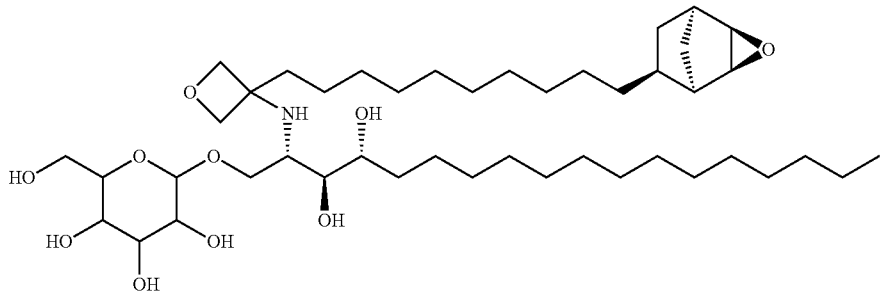 [SMILES: CCCCCCCCCCCCCC[C@@H](O)[C@@H](O)[C@H](COC1OC(CO)C(O)C(O)C1O)NC1(CCCCCCCCCC[C@H]2C[C@@H]3C[C@H]2[C@@H]2O[C@H]32)COC1]
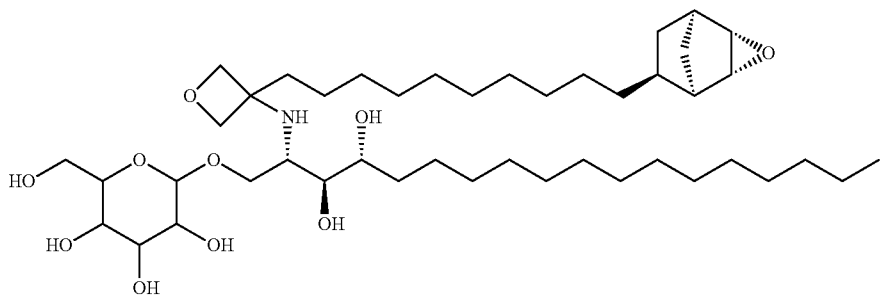 [SMILES: CCCCCCCCCCCCCC[C@@H](O)[C@@H](O)[C@H](COC1OC(CO)C(O)C(O)C1O)NC1(CCCCCCCCCC[C@H]2C[C@@H]3C[C@H]2[C@H]2O[C@@H]32)COC1]
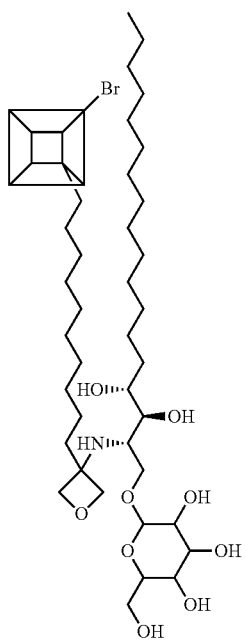 [SMILES: CCCCCCCCCCCCCC[C@@H](O)[C@@H](O)[C@H](COC1OC(CO)C(O)C(O)C1O)NC1(CCCCCCCCCCC23C4C5C6C4C2C6(Br)C53)COC1]

TABLE 6-continued
Aminooxetane Analogs
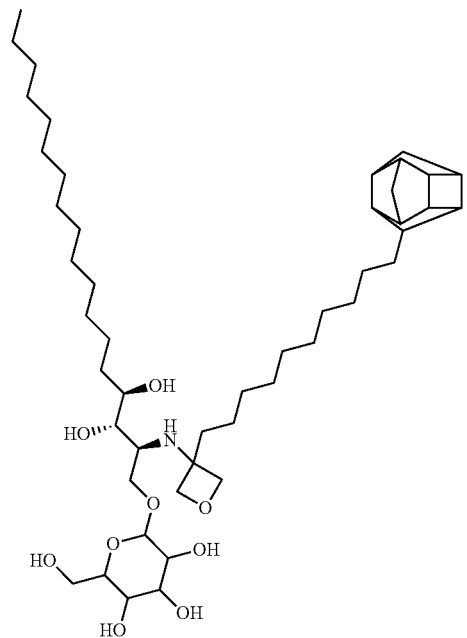 [SMILES: CCCCCCCCCCCCCC[C@@H](O)[C@@H](O)[C@H](COC1OC(CO)C(O)C(O)C1O)NC1(CCCCCCCCCCC2C3C4CC5C6C4CC3C6C25)COC1]
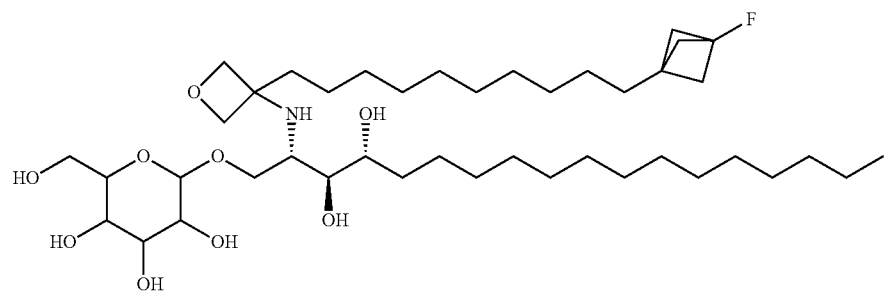 [SMILES: CCCCCCCCCCCCCC[C@@H](O)[C@@H](O)[C@H](COC1OC(CO)C(O)C(O)C1O)NC1(CCCCCCCCCCC23CC(F)(C2)C3)COC1]
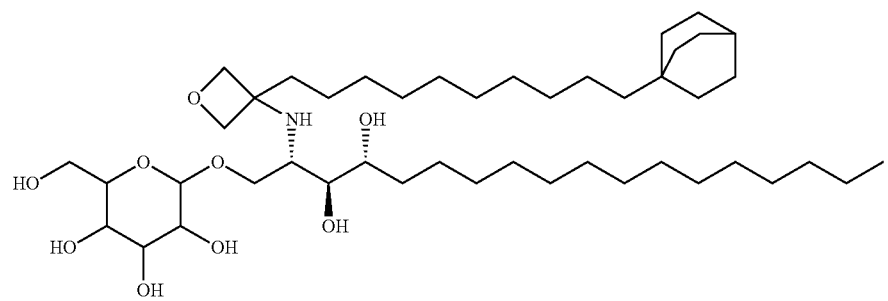 [SMILES: CCCCCCCCCCCCCC[C@@H](O)[C@@H](O)[C@H](COC1OC(CO)C(O)C(O)C1O)NC1(CCCCCCCCCCC23CCC(CC2)CC3)COC1]

TABLE 6-continued
Aminooxetane Analogs
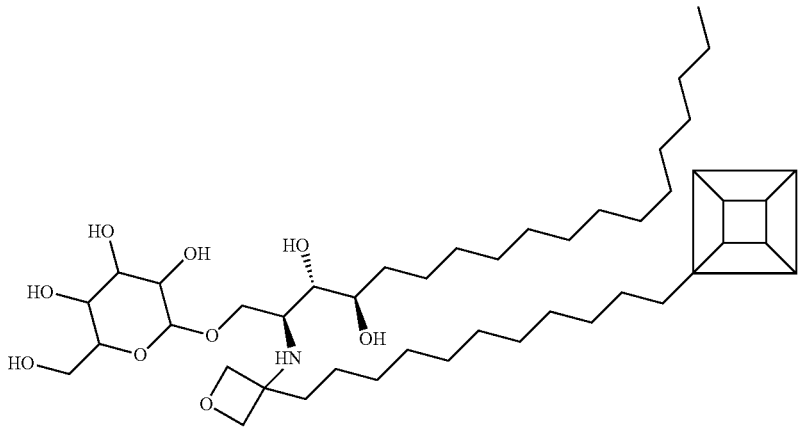 [SMILES: CCCCCCCCCCCCCC[C@@H](O)[C@@H](O)[C@H](COC1OC(CO)C(O)C(O)C1O)NC1(CCCCCCCCCCCC23C4C5C6C4C2C6C53)COC1]
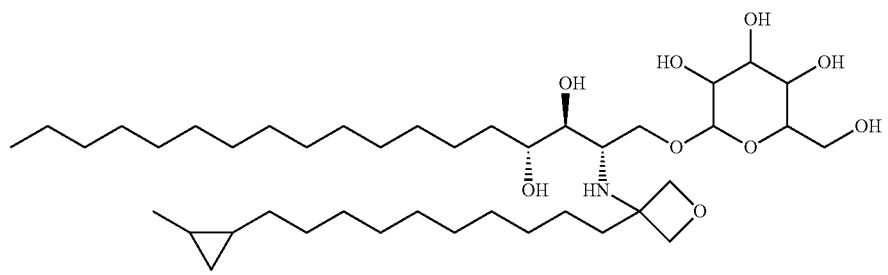 [SMILES: CCCCCCCCCCCCCC[C@@H](O)[C@@H](O)[C@H](COC1OC(CO)C(O)C(O)C1O)NC1(CCCCCCCCCCC2CC2C)COC1]
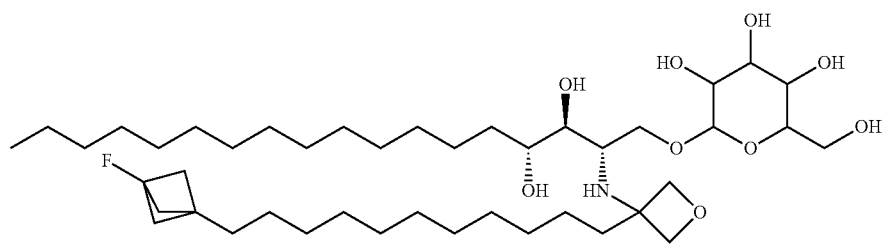 [SMILES: CCCCCCCCCCCCCC[C@@H](O)[C@@H](O)[C@H](COC1OC(CO)C(O)C(O)C1O)NC1(CCCCCCCCCCCC23CC(F)(C2)C3)COC1]
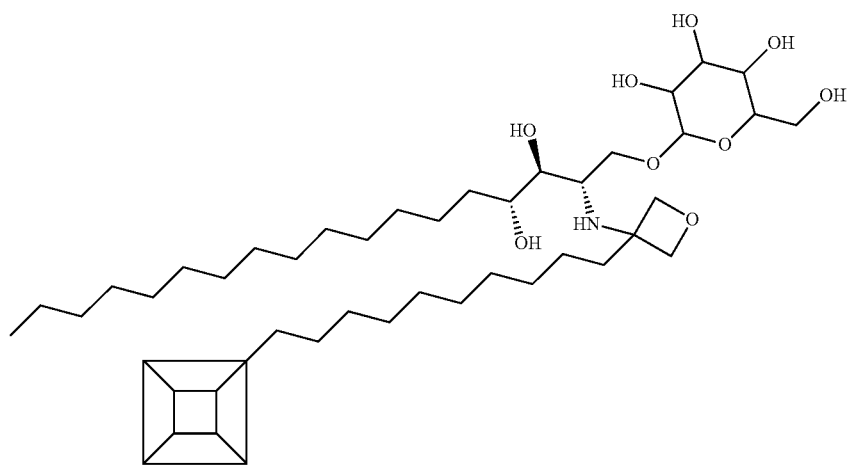 [SMILES: CCCCCCCCCCCCCC[C@@H](O)[C@@H](O)[C@H](COC1OC(CO)C(O)C(O)C1O)NC1(CCCCCCCCCCC23C4C5C6C4C2C6C53)COC1]

TABLE 6-continued
Aminooxetane Analogs
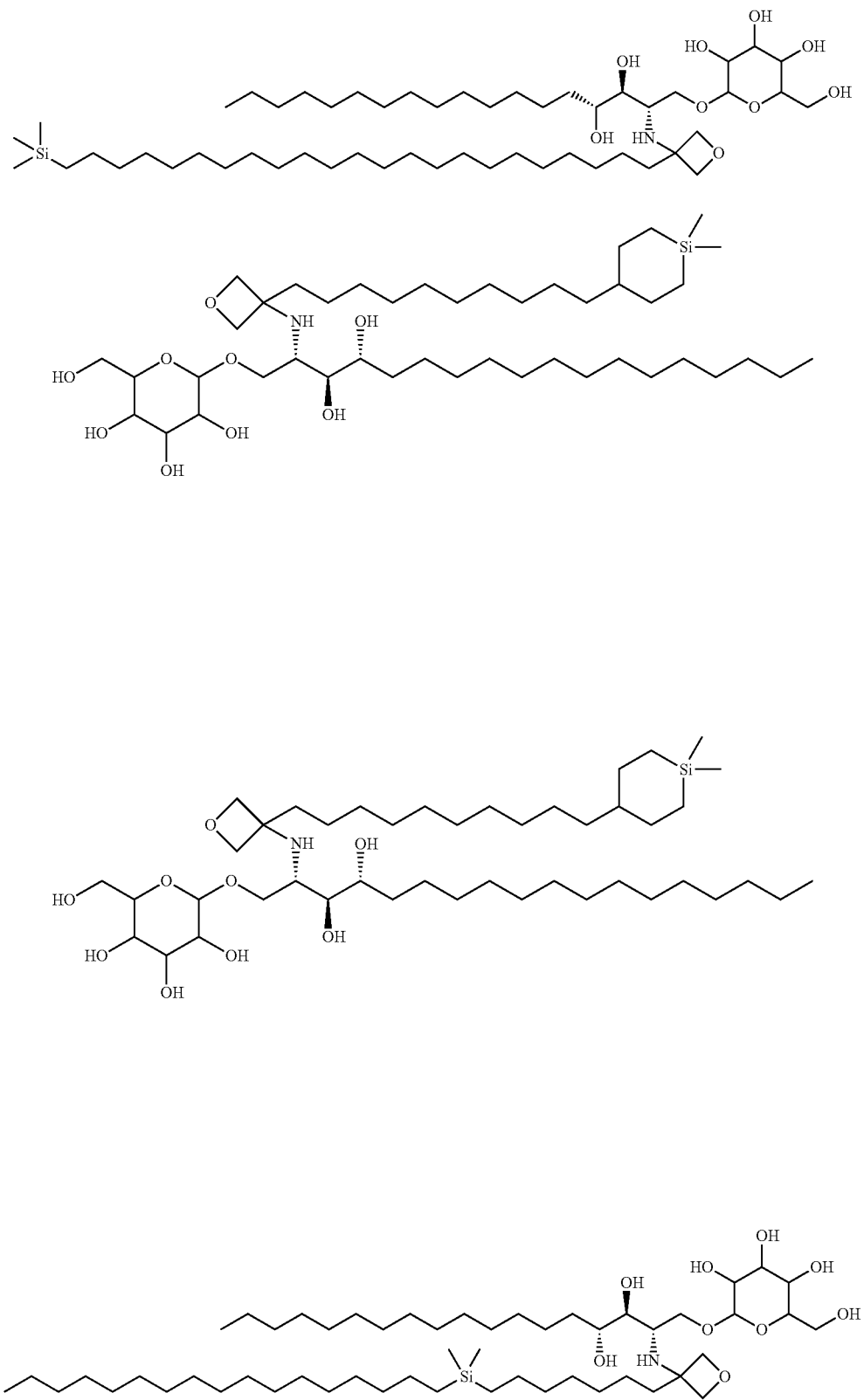

TABLE 6-continued
Aminooxetane Analogs
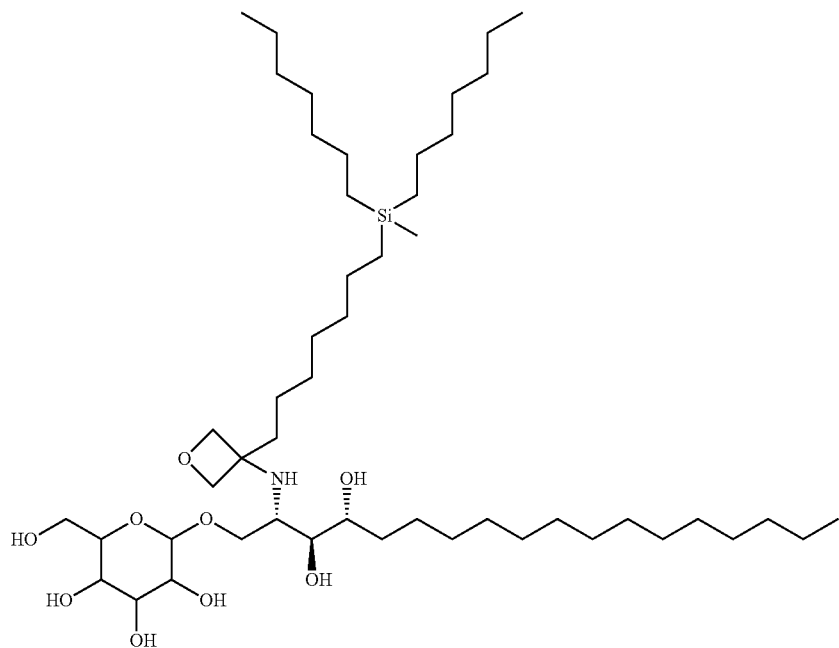 [SMILES: CCCCCCCCCCCCCC[C@@H](O)[C@@H](O)[C@H](COC1OC(CO)C(O)C(O)C1O)NC1(CCCCCCC[Si](C)(CCCCCCC)CCCCCCC)COC1]
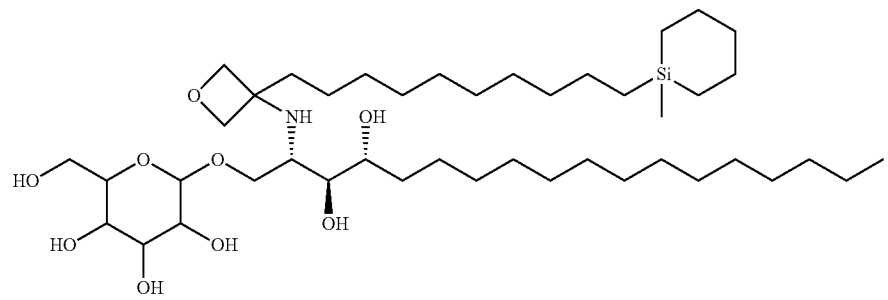 [SMILES: CCCCCCCCCCCCCC[C@@H](O)[C@@H](O)[C@H](COC1OC(CO)C(O)C(O)C1O)NC1(CCCCCCCCCC[Si]2(C)CCCCC2)COC1]
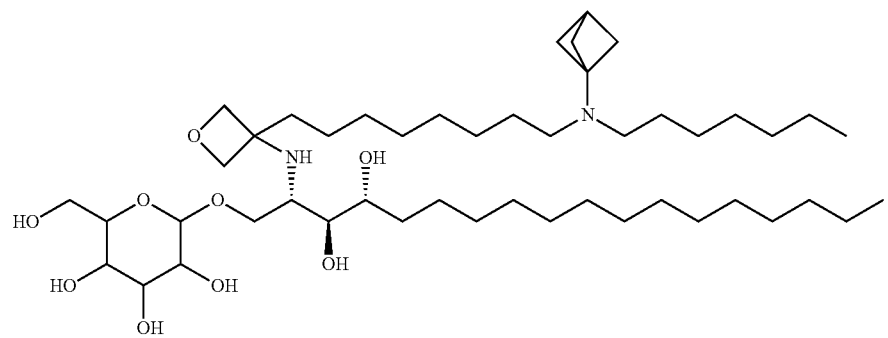 [SMILES: CCCCCCCCCCCCCC[C@@H](O)[C@@H](O)[C@H](COC1OC(CO)C(O)C(O)C1O)NC1(CCCCCCCCN(CCCCCCC)C23CC(C2)C3)COC1]

TABLE 7
Pyrazole Analoge
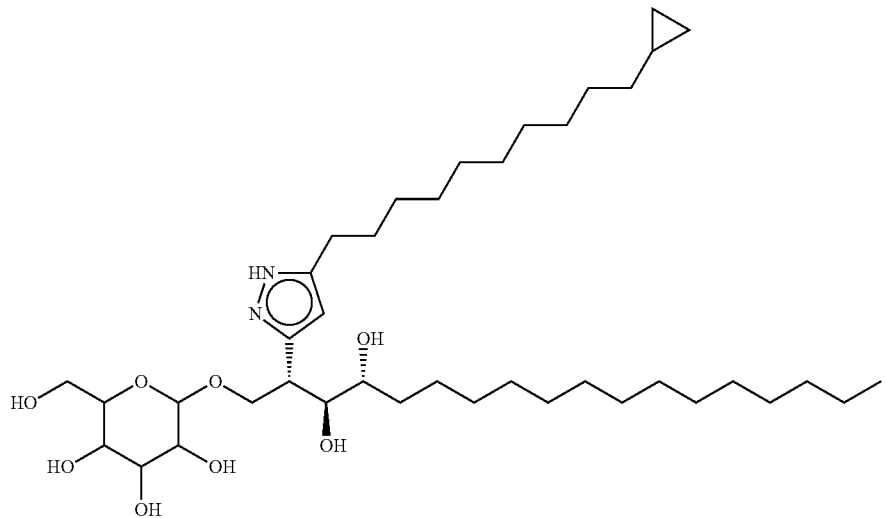
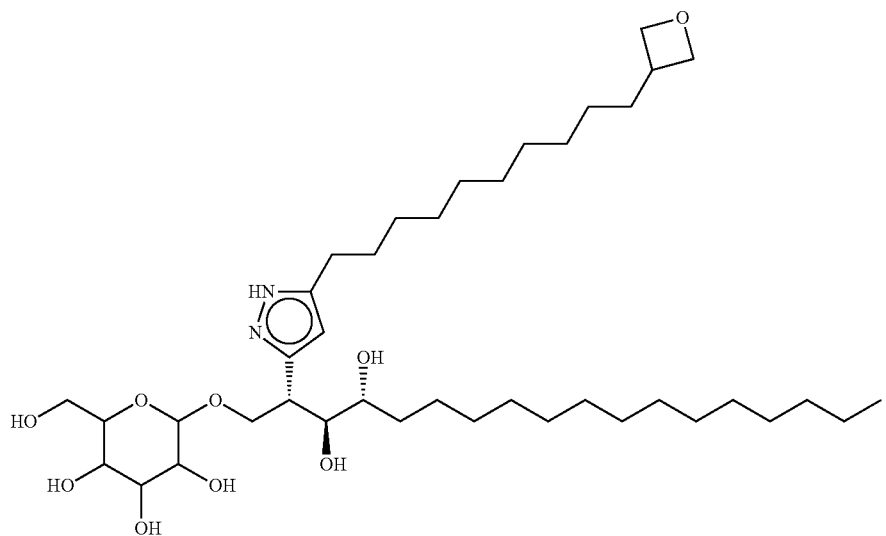

TABLE 7-continued
Pyrazole Analoge
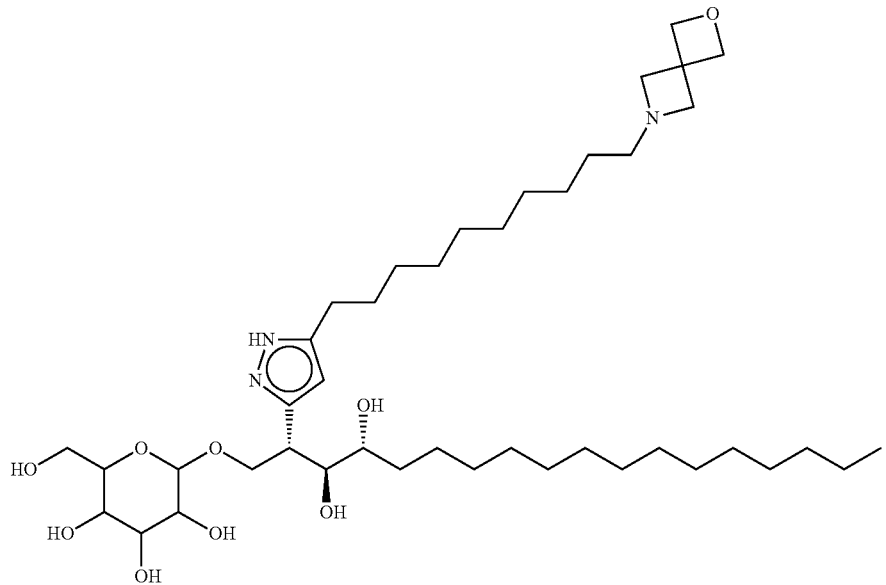
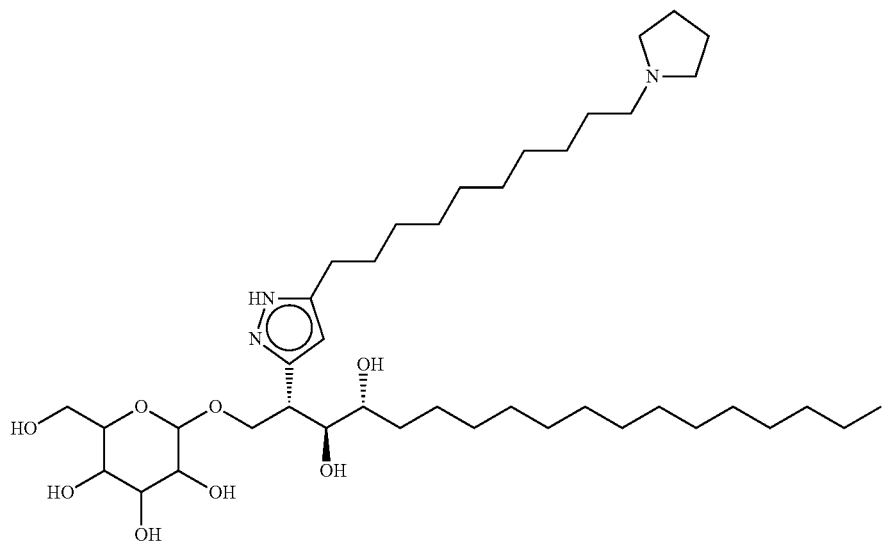

TABLE 7-continued
Pyrazole Analoge
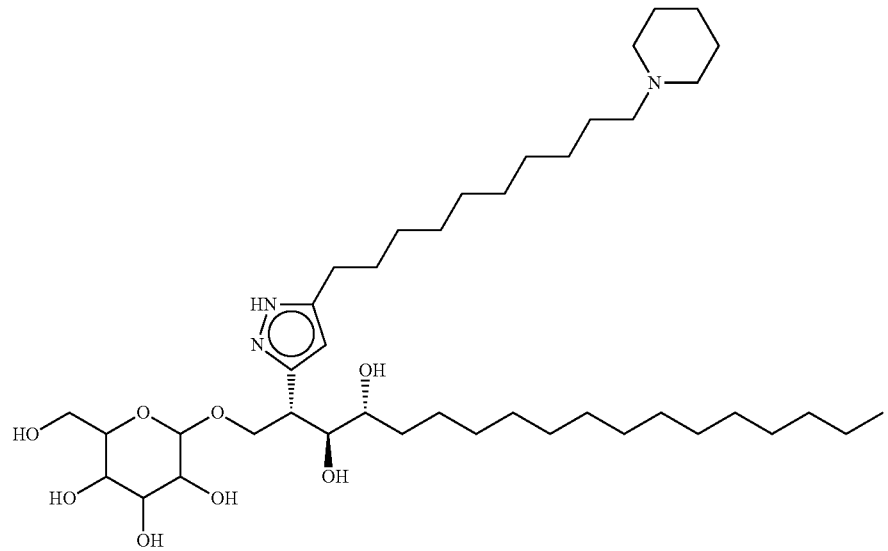
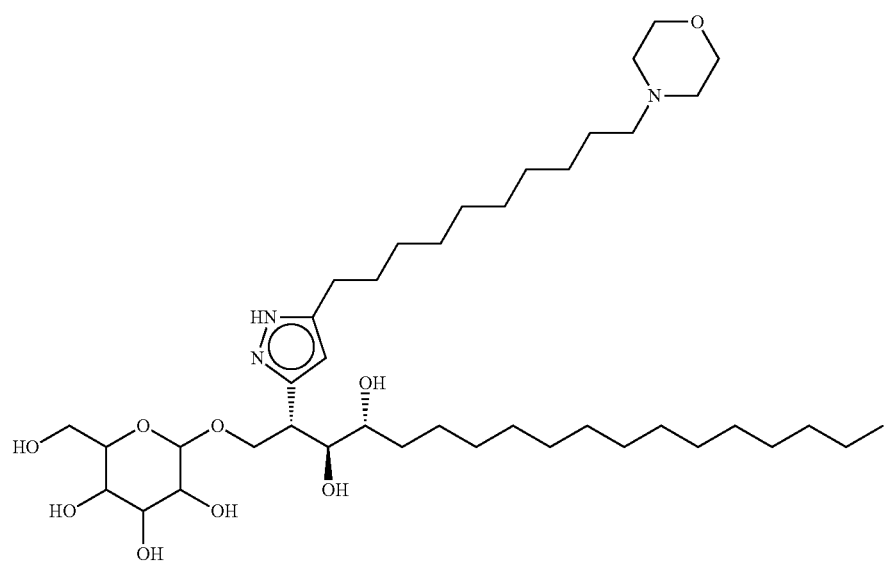

TABLE 7-continued
Pyrazole Analoge
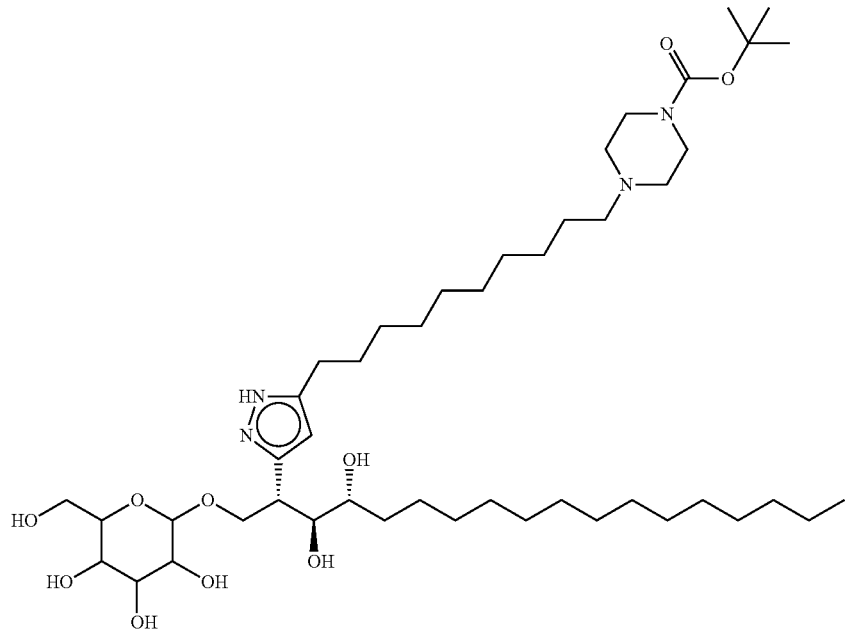
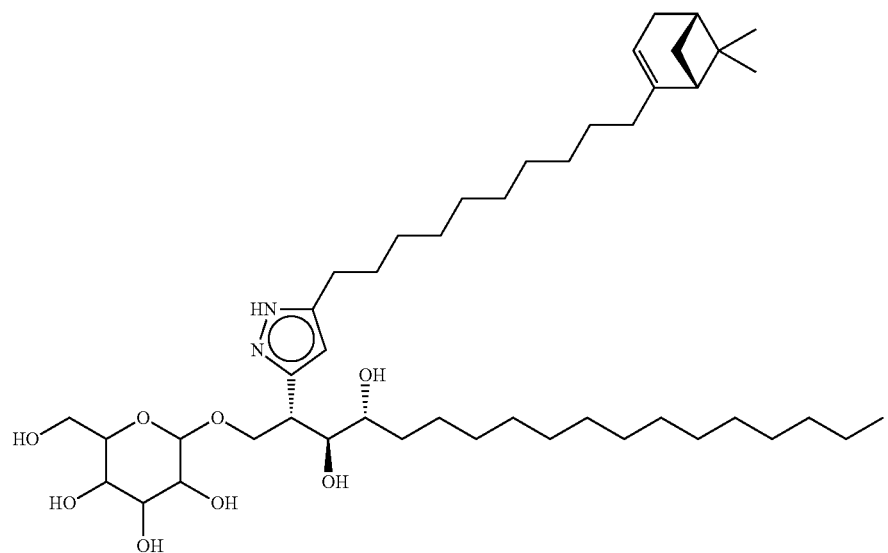

TABLE 7-continued
Pyrazole Analoge
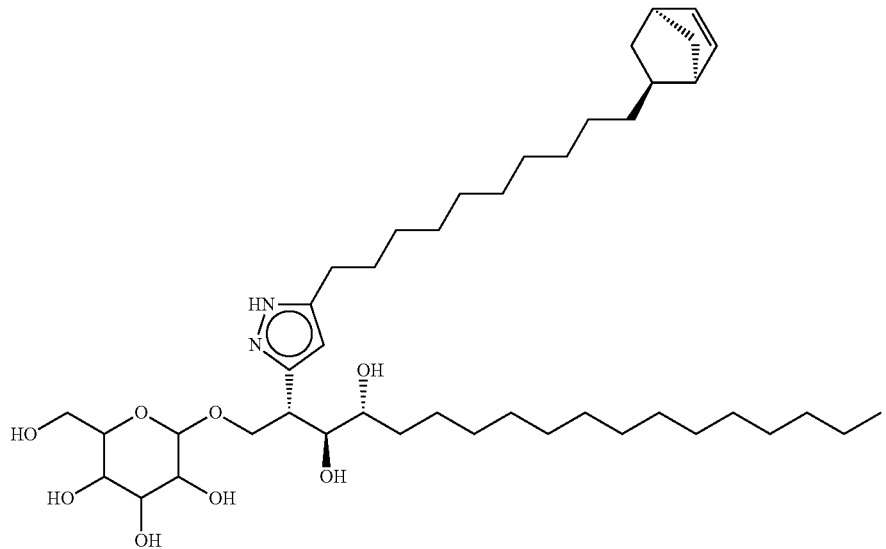
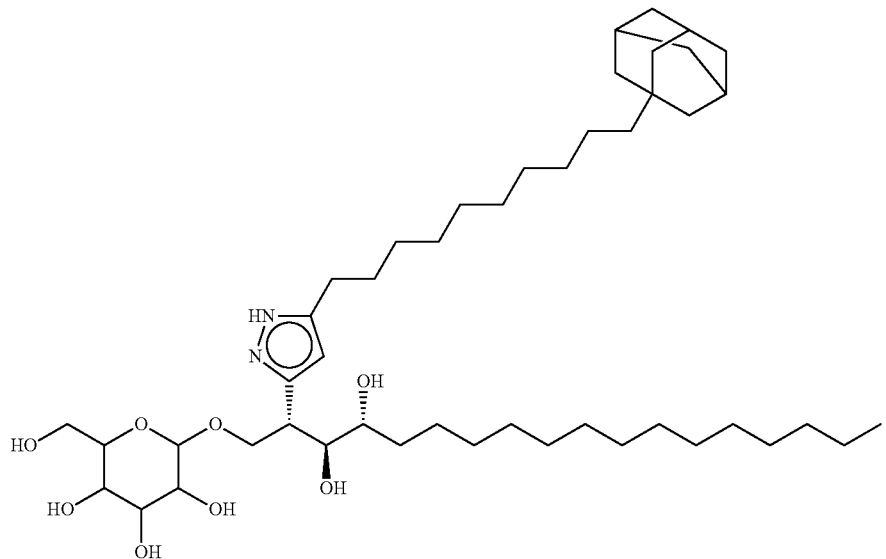

TABLE 7-continued
Pyrazole Analoge
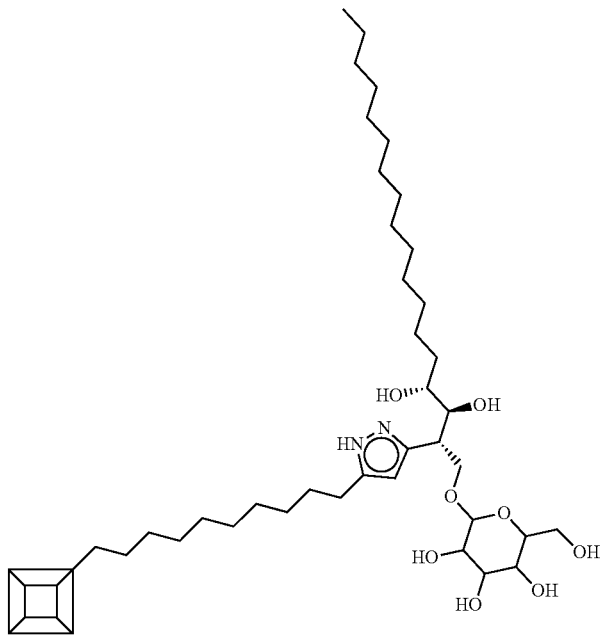
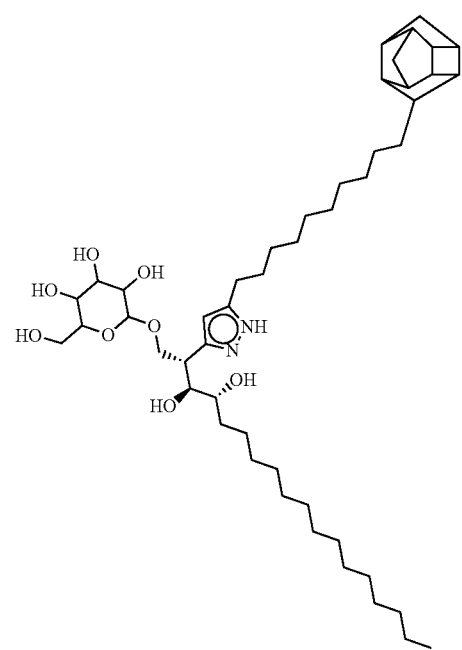

TABLE 7-continued
Pyrazole Analoge
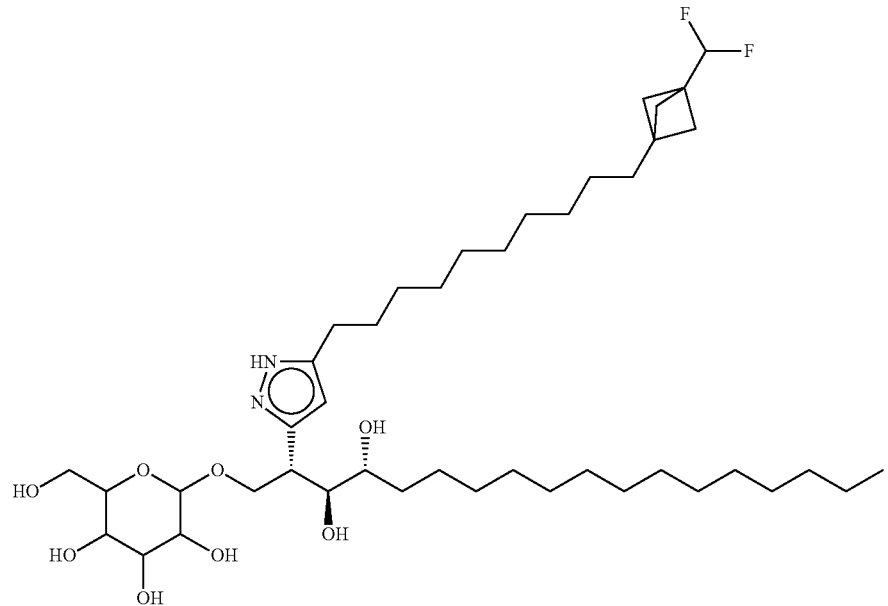
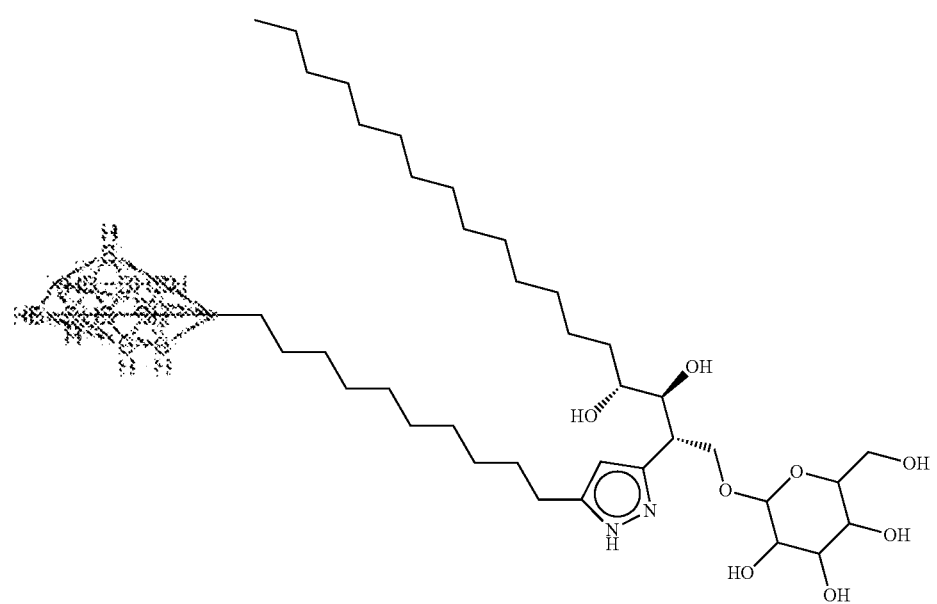

TABLE 7-continued
Pyrazole Analoge
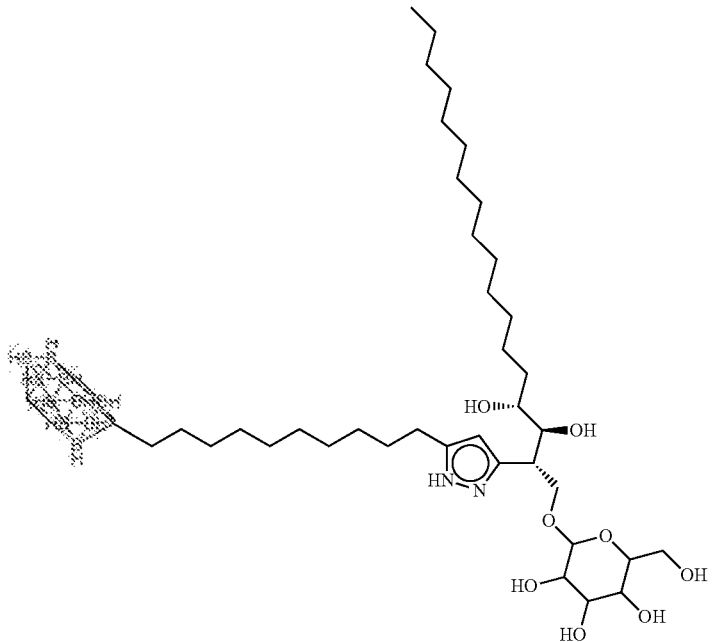
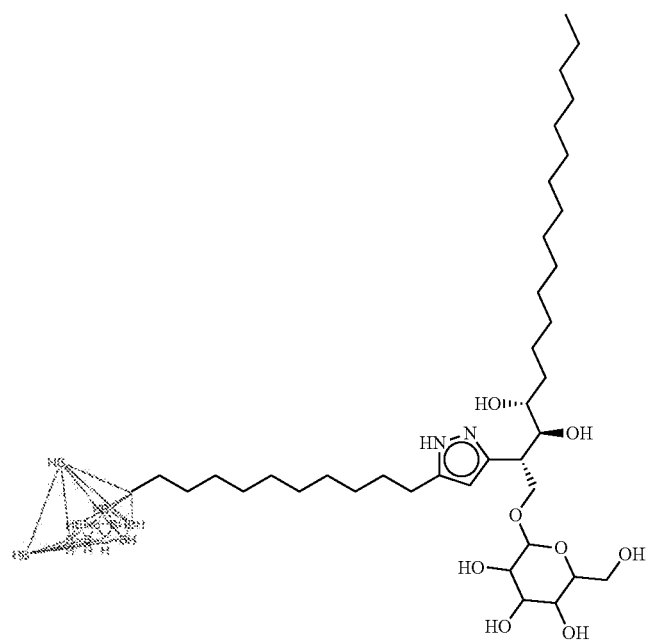

TABLE 7-continued
Pyrazole Analoge
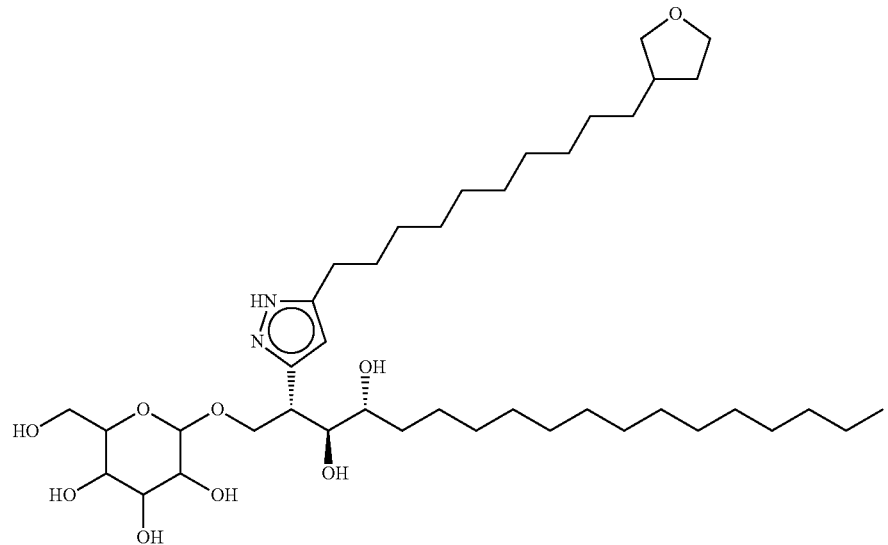
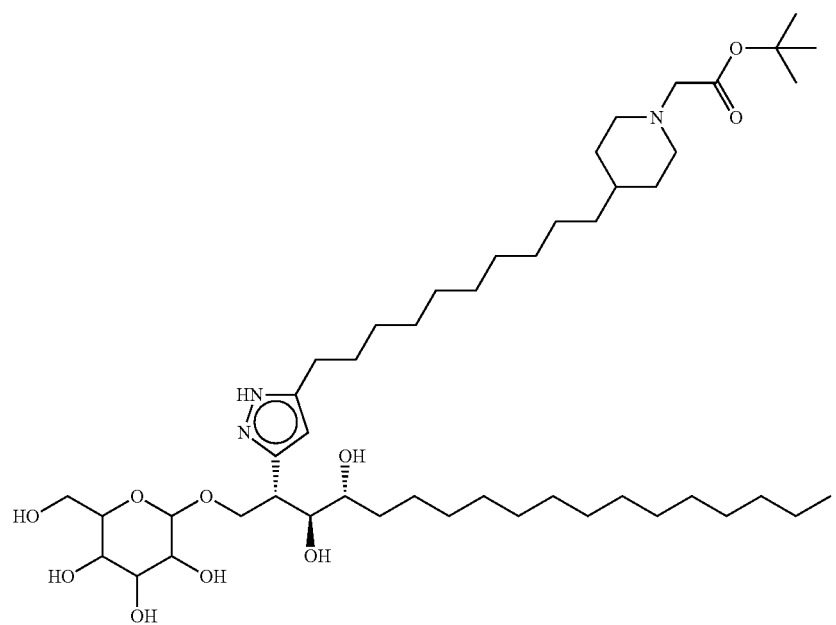

TABLE 7-continued
Pyrazole Analoge
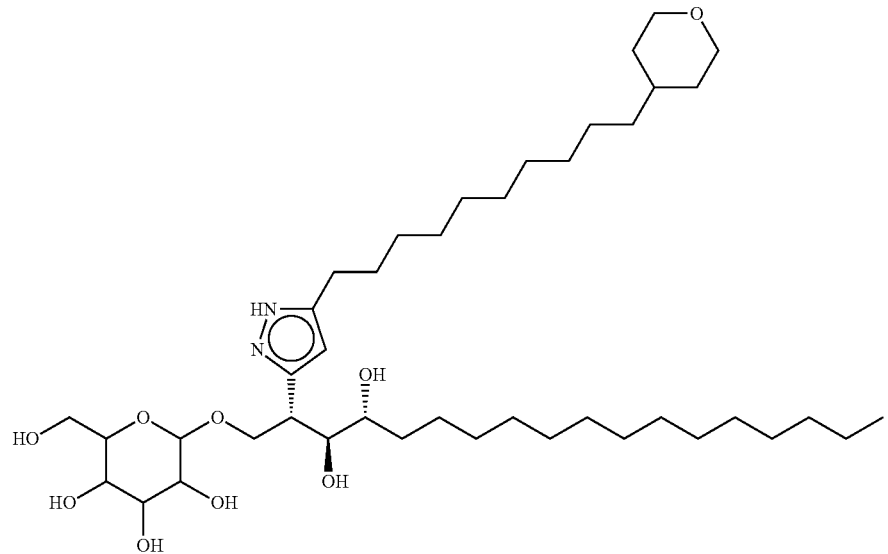
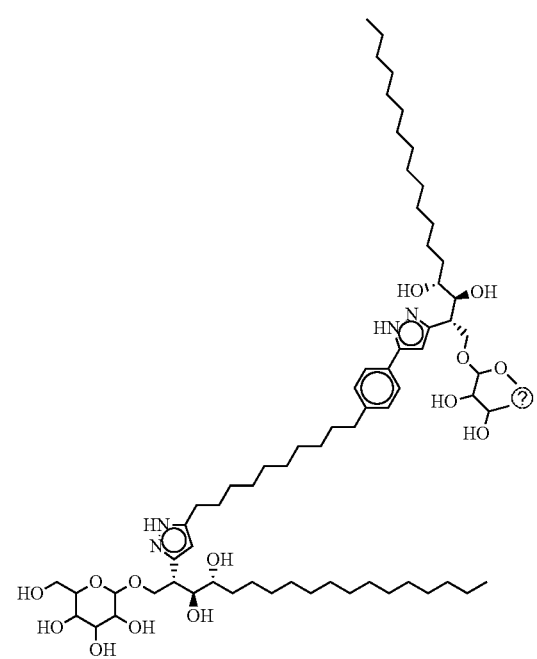

TABLE 7-continued
Pyrazole Analoge
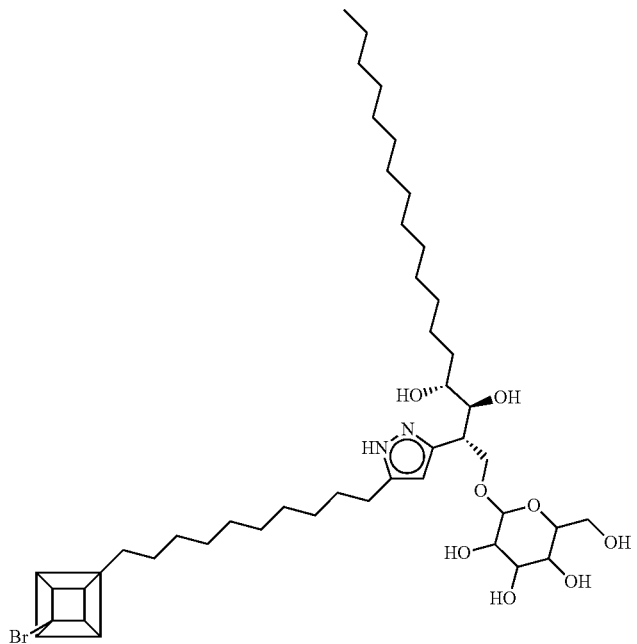
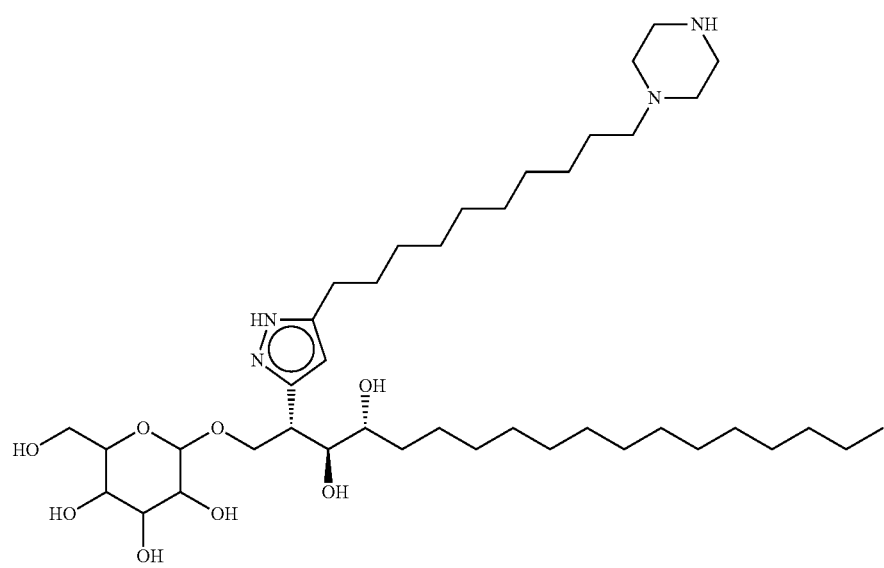

TABLE 7-continued
Pyrazole Analoge
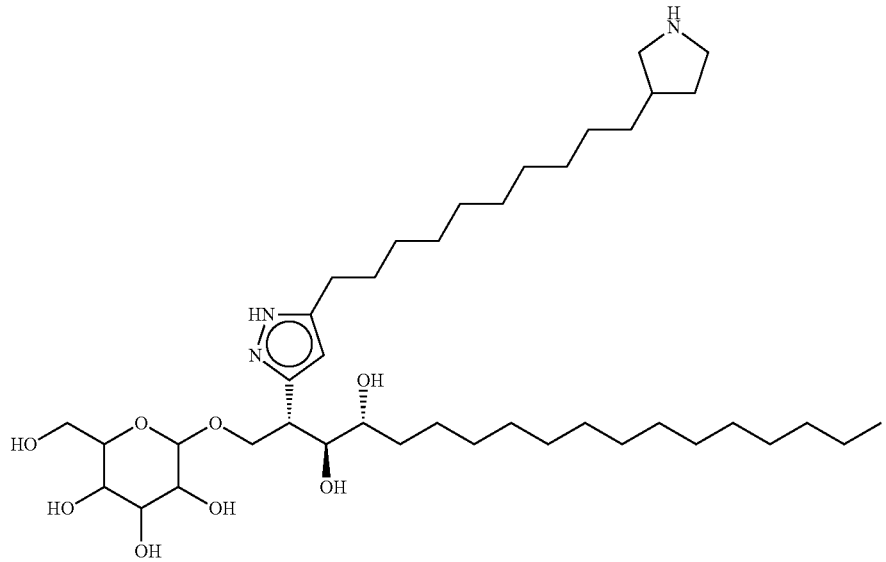
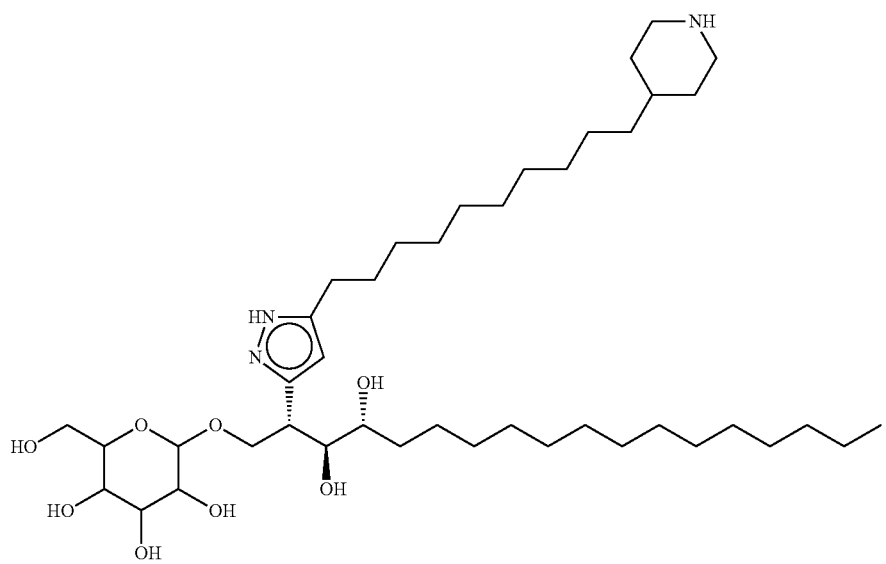

TABLE 7-continued
Pyrazole Analoge
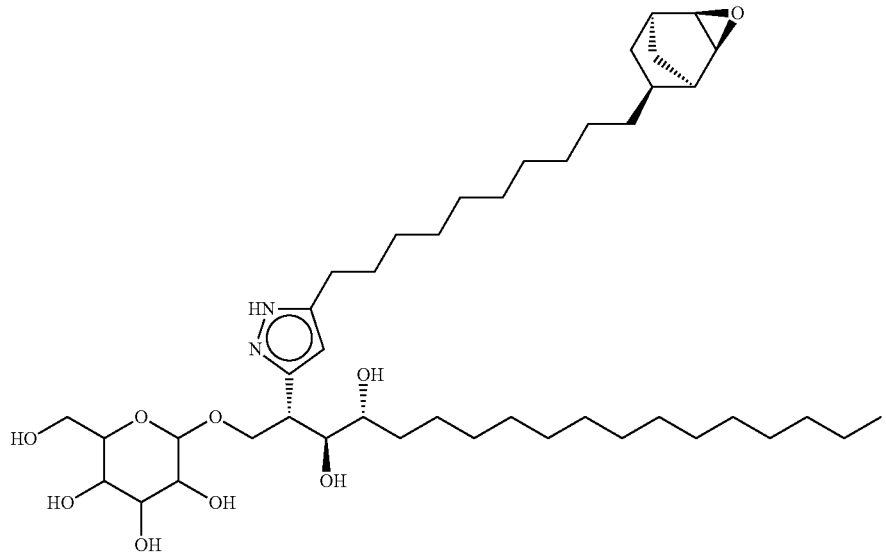
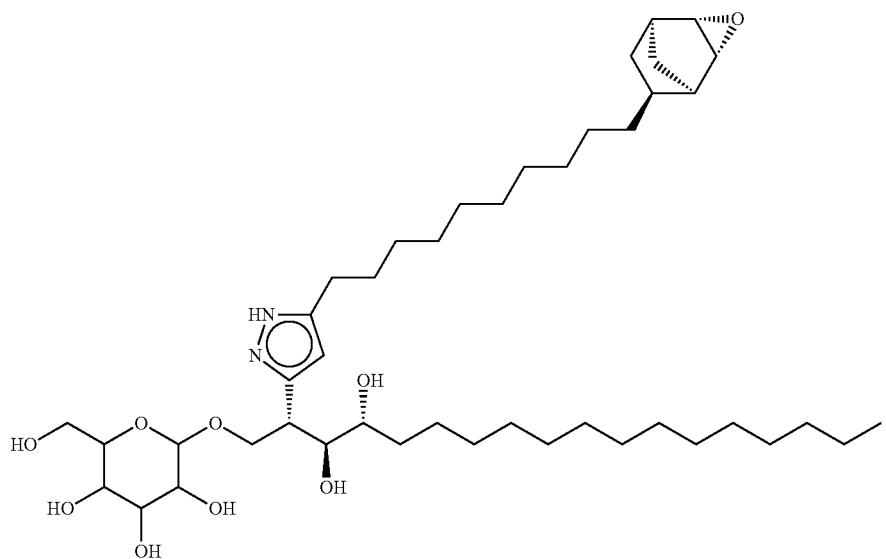

TABLE 7-continued
Pyrazole Analoge
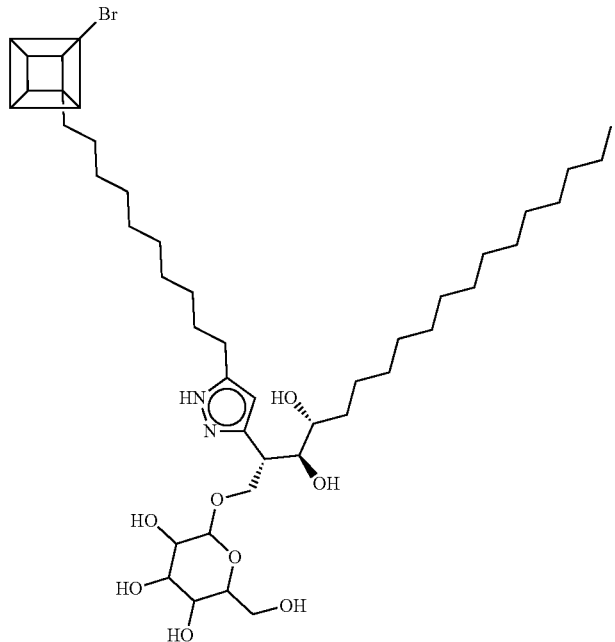
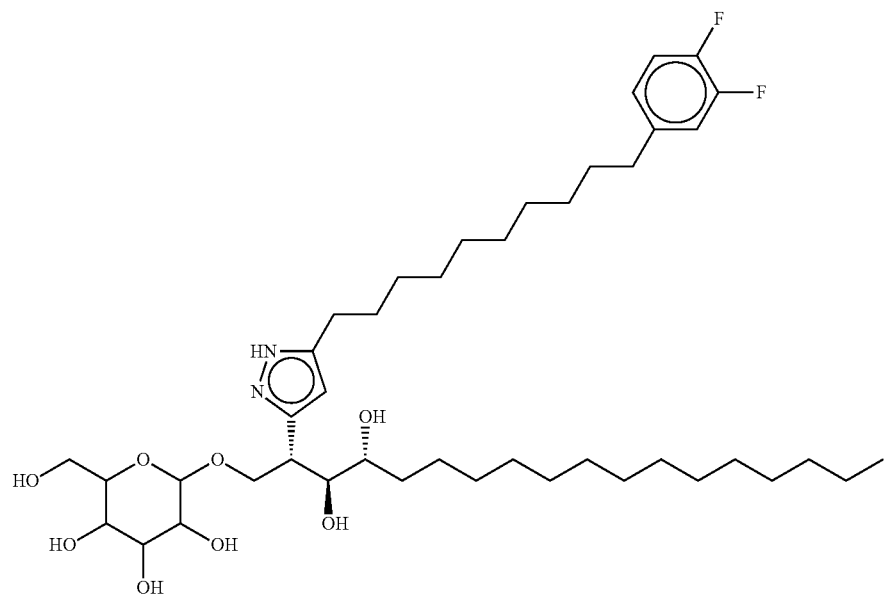

TABLE 7-continued
Pyrazole Analoge
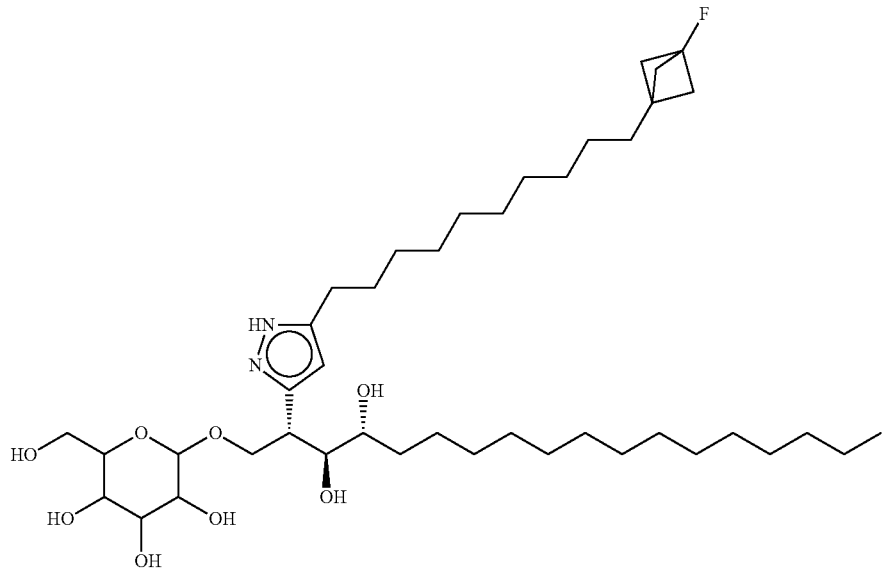
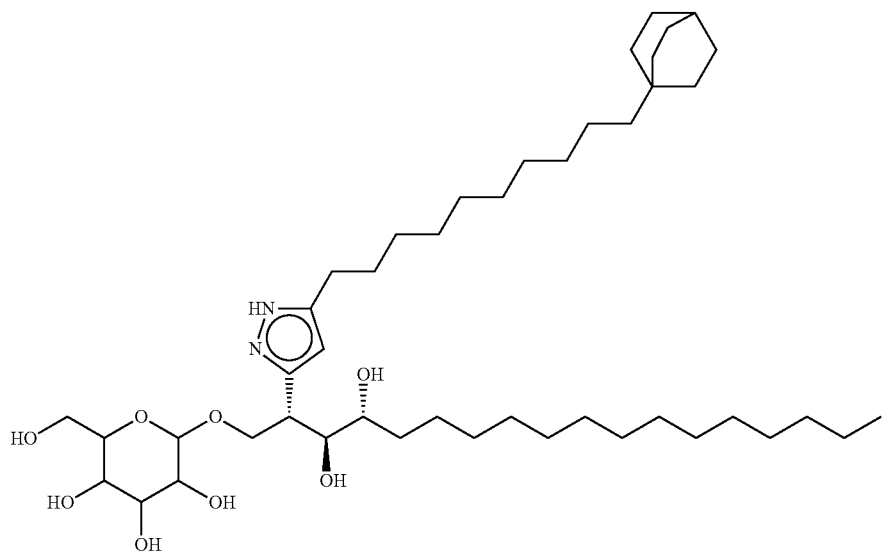

TABLE 7-continued
Pyrazole Analoge
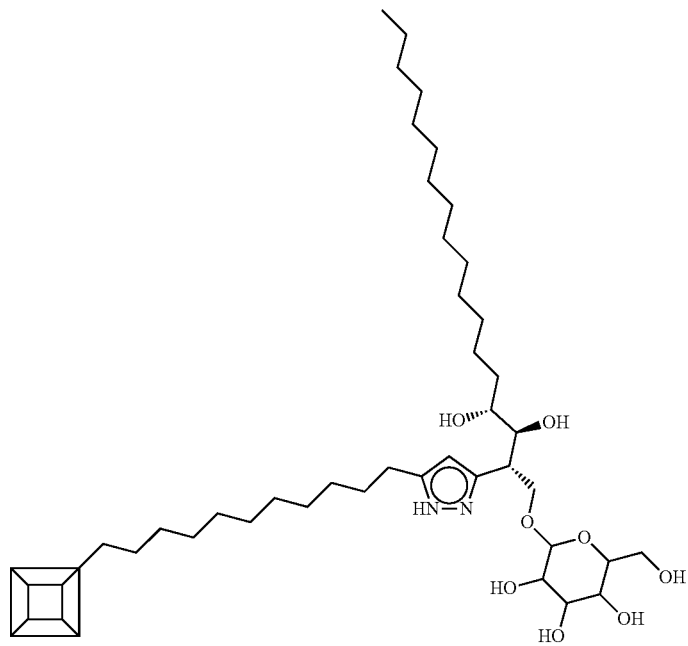
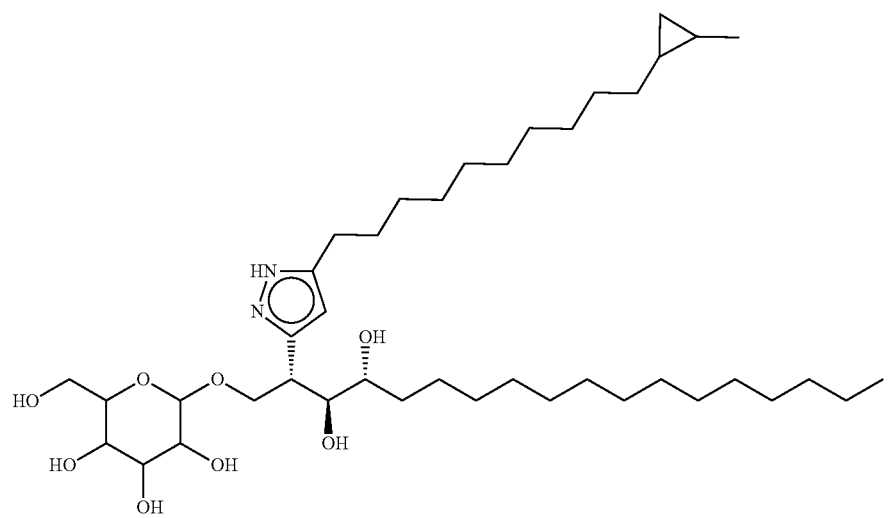

TABLE 7-continued
Pyrazole Analoge
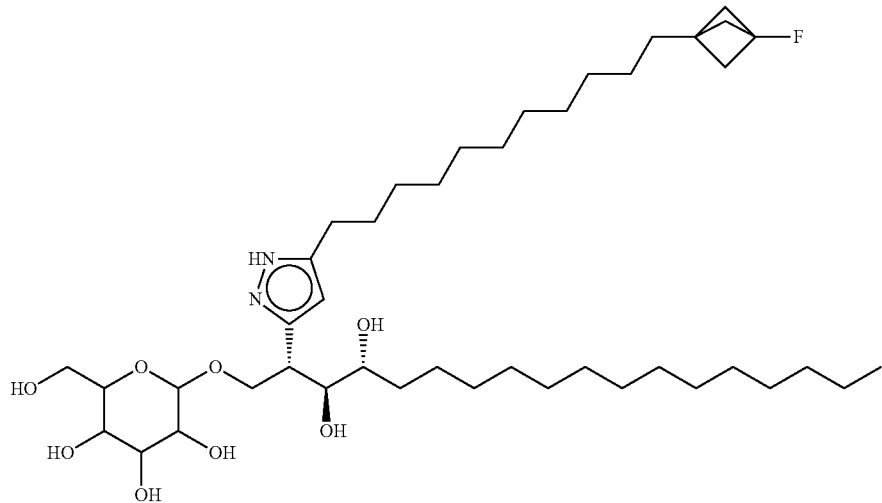
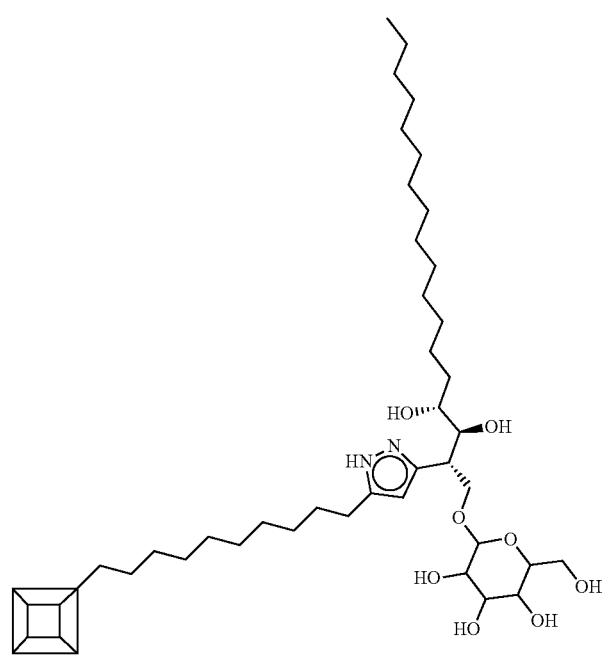

TABLE 7-continued
Pyrazole Analoge
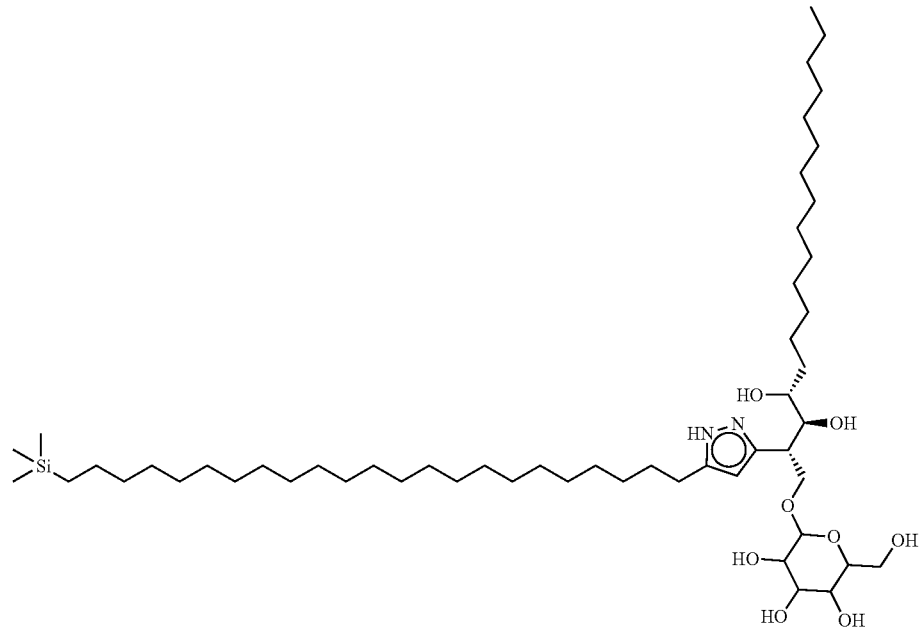
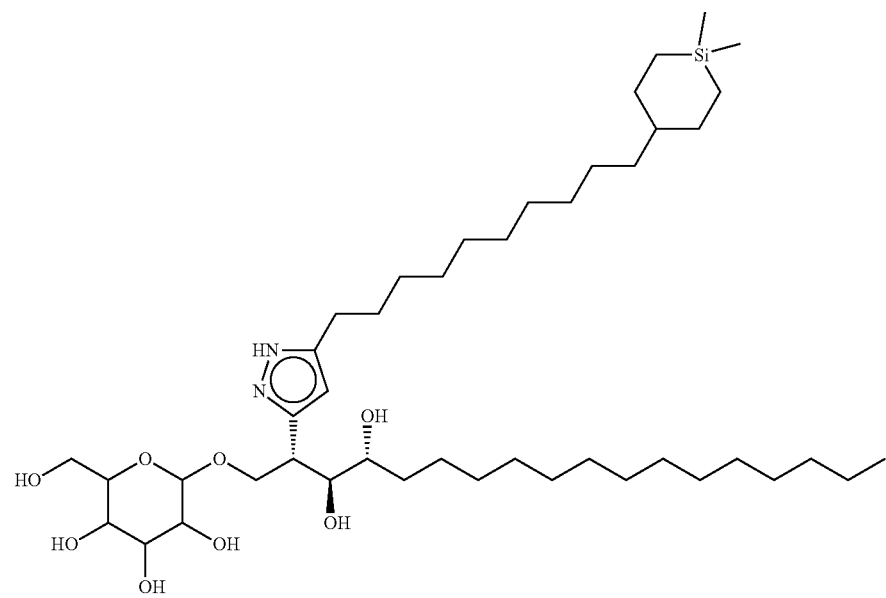

TABLE 7-continued
Pyrazole Analoge
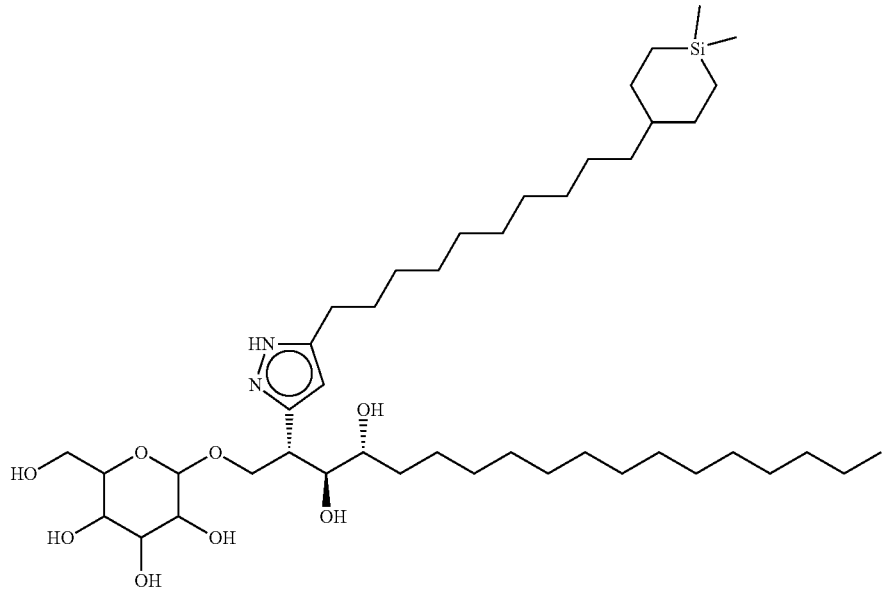
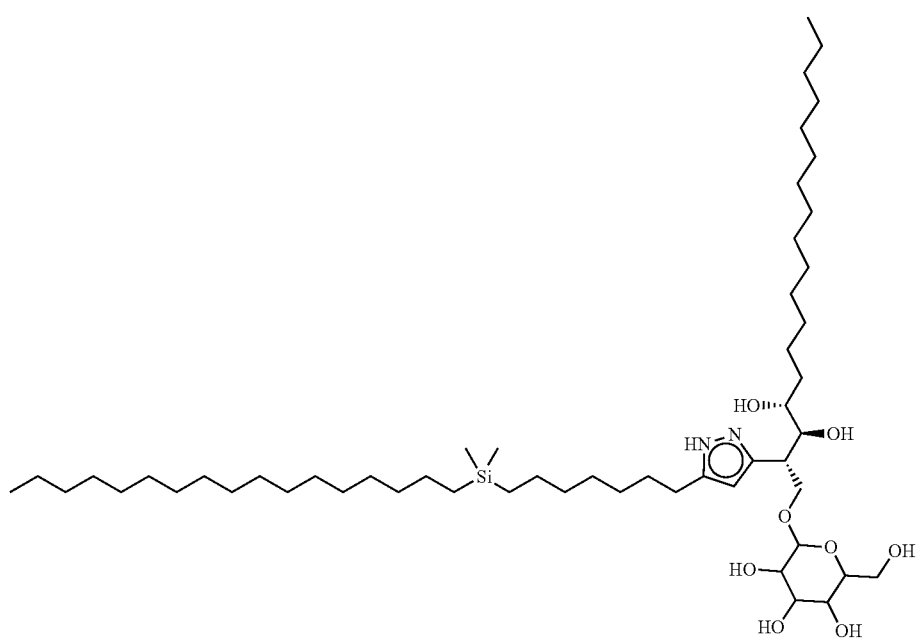

TABLE 7-continued
Pyrazole Analoge
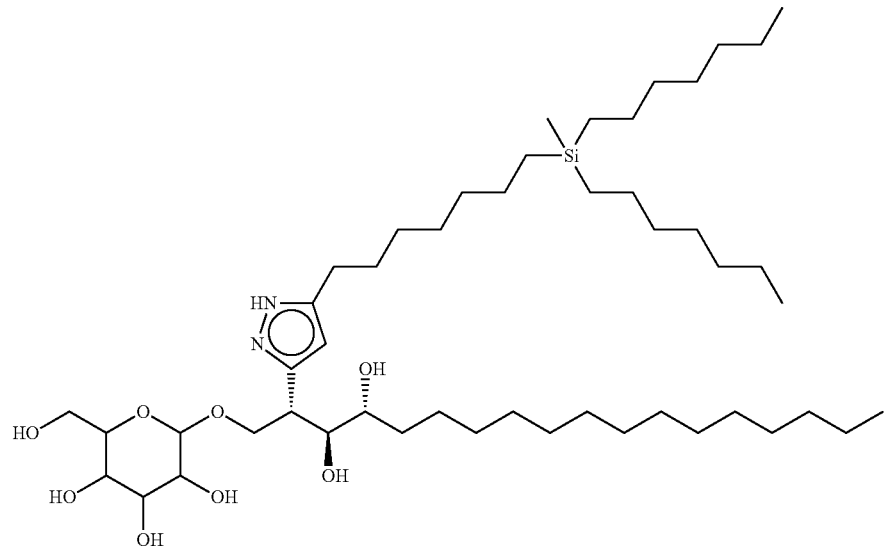
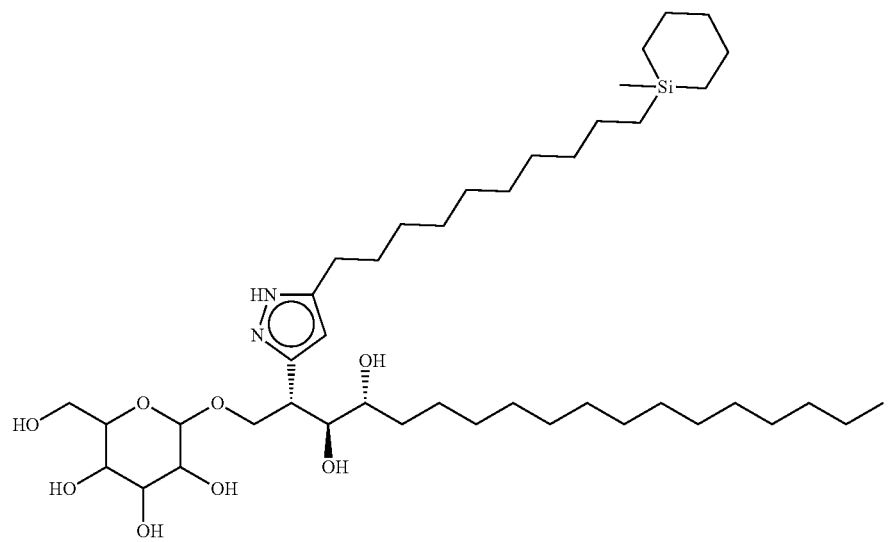

TABLE 7-continued
Pyrazole Analoge
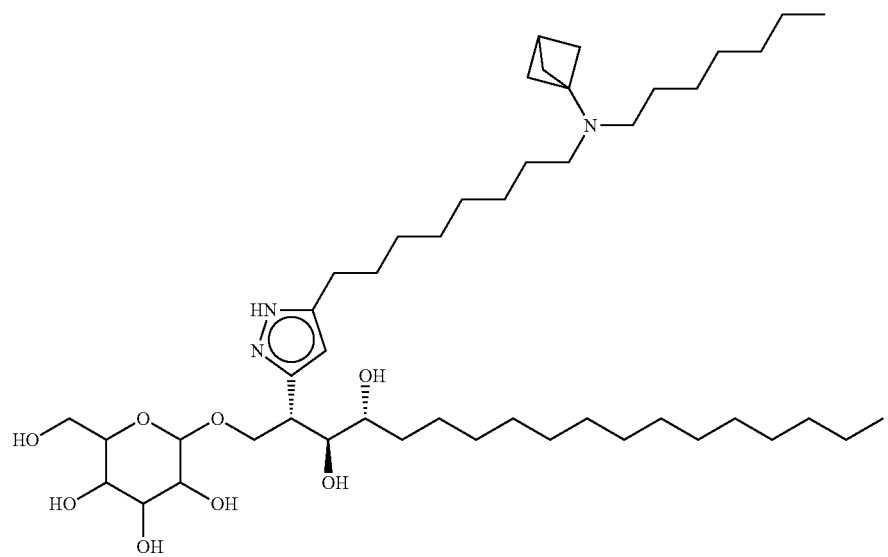
TABLE 8
Tetrazolone Analogs
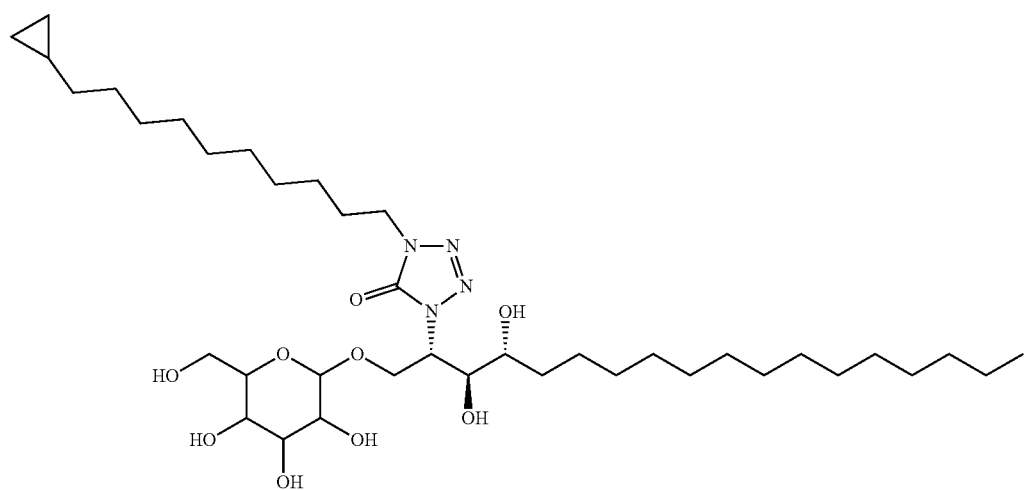 [SMILES: CCCCCCCCCCCCCC[C@@H](O)[C@@H](O)[C@H](COC1OC(CO)C(O)C(O)C1O)n1nnn(CCCCCCCCCCC2CC2)c1=O]

TABLE 8-continued
Tetrazolone Analogs
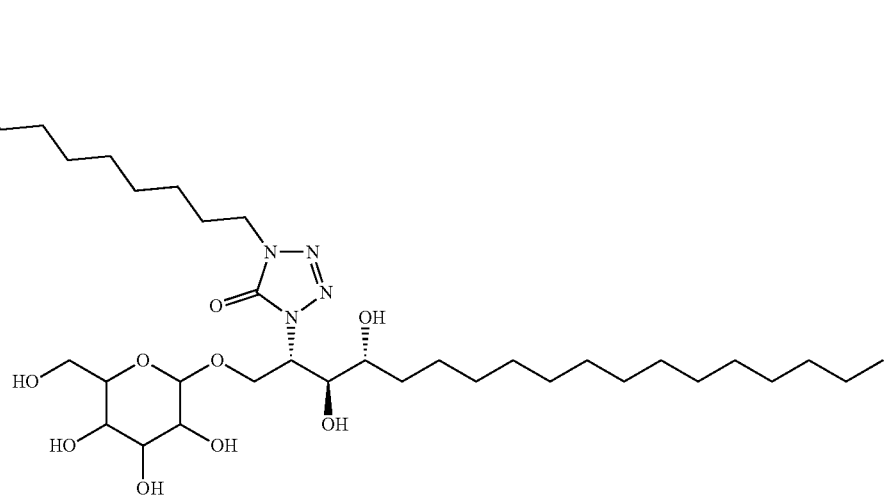
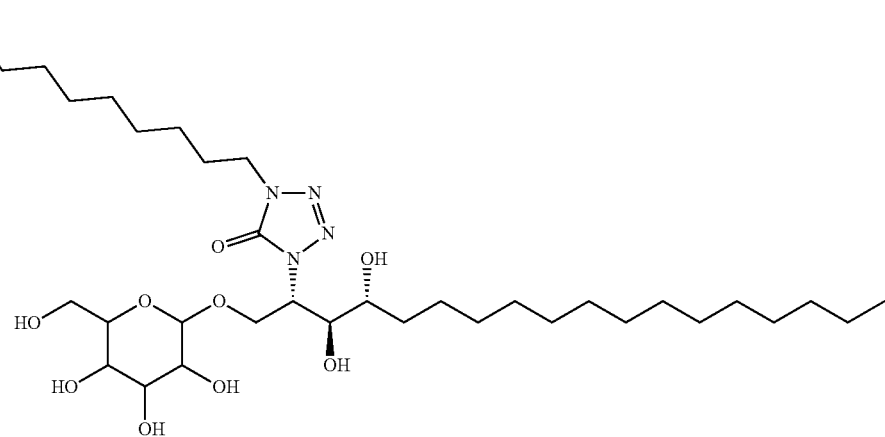
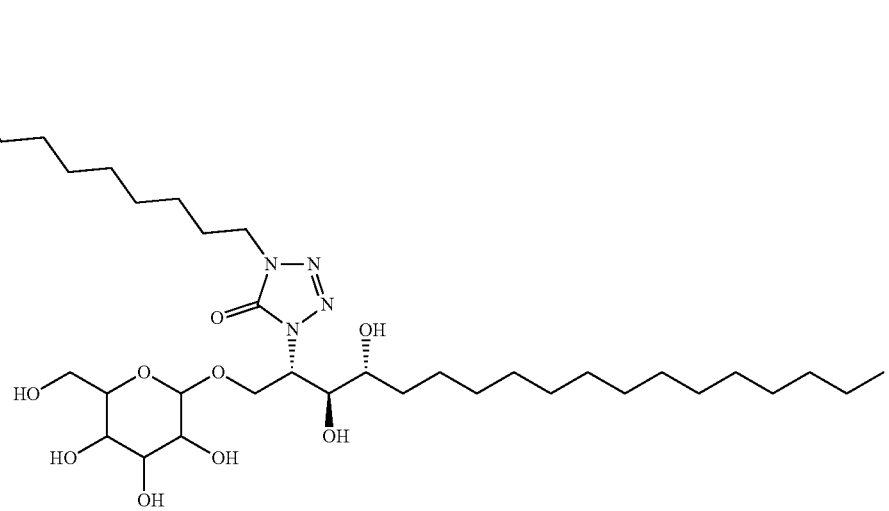

TABLE 8-continued
Tetrazolone Analogs
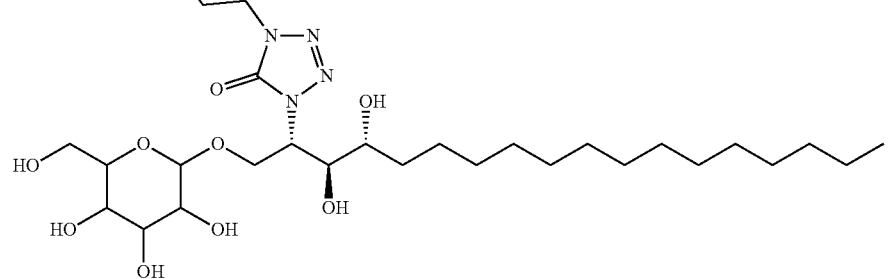
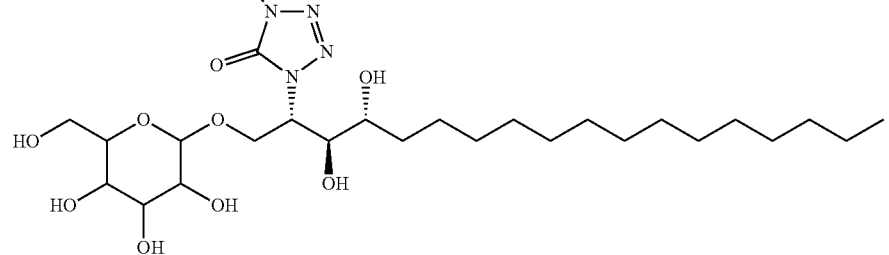
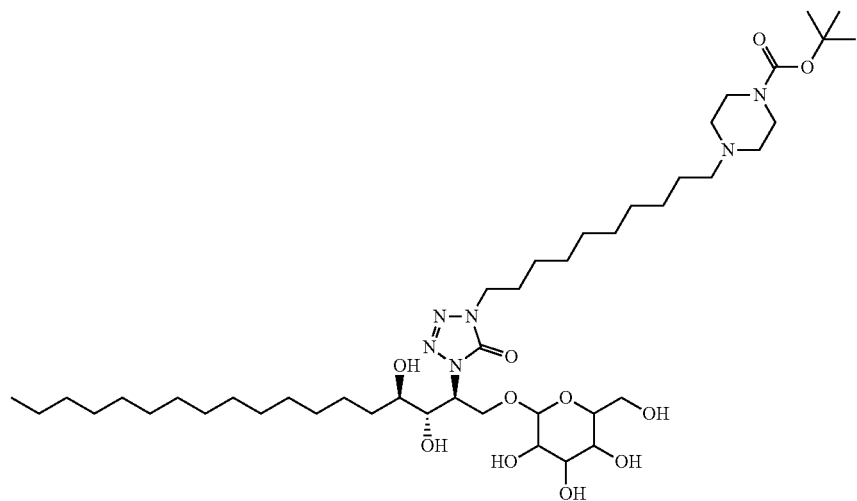 [SMILES: CCCCCCCCCCCCCC[C@@H](O)[C@@H](O)[C@H](COC1OC(CO)C(O)C(O)C1O)n1nnn(CCCCCCCCCCN2CCN(C(=O)OC(C)(C)C)CC2)c1=O]

TABLE 8-continued
Tetrazolone Analogs
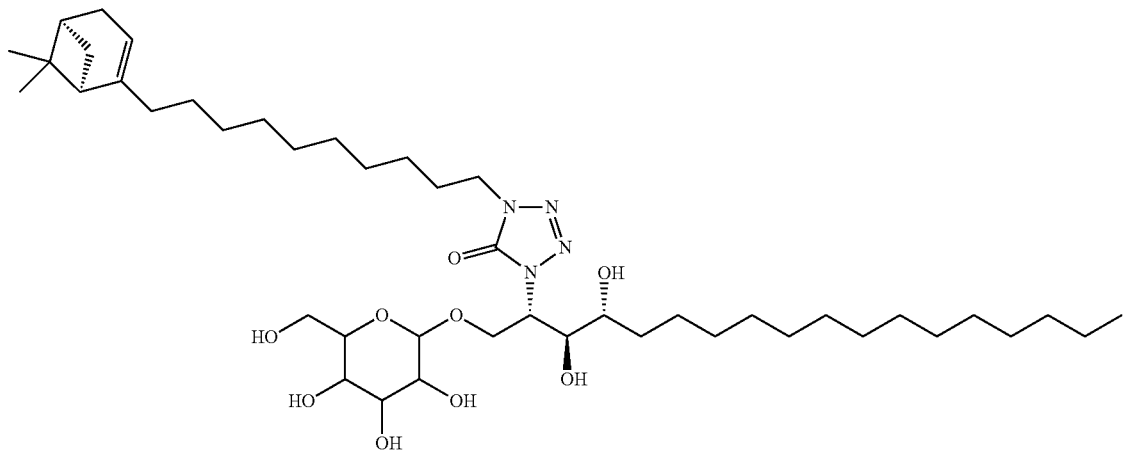 [SMILES: CCCCCCCCCCCCCC[C@@H](O)[C@@H](O)[C@H](COC1OC(CO)C(O)C(O)C1O)n1nnn(CCCCCCCCCCC2=CC[C@H]3C[C@@H]2C3(C)C)c1=O]
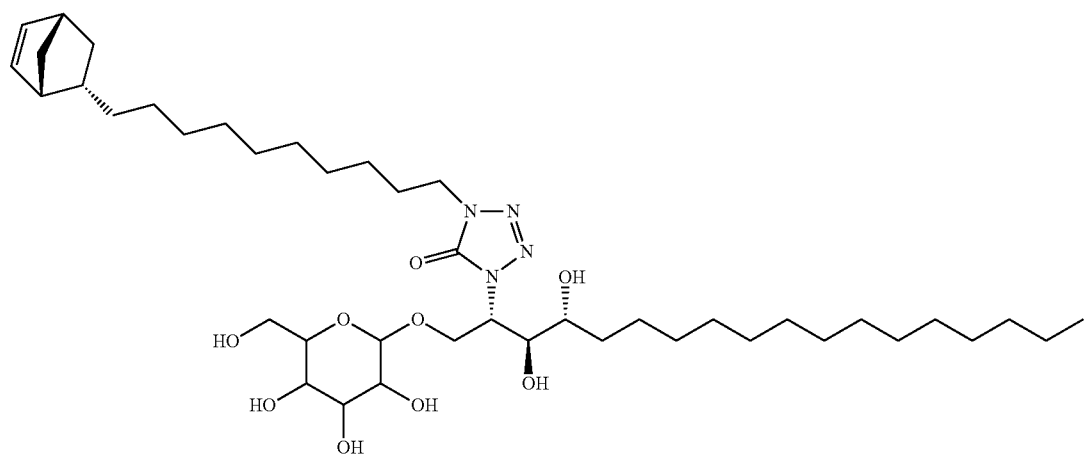 [SMILES: CCCCCCCCCCCCCC[C@@H](O)[C@@H](O)[C@H](COC1OC(CO)C(O)C(O)C1O)n1nnn(CCCCCCCCCC[C@H]2C[C@H]3C=C[C@@H]2C3)c1=O]
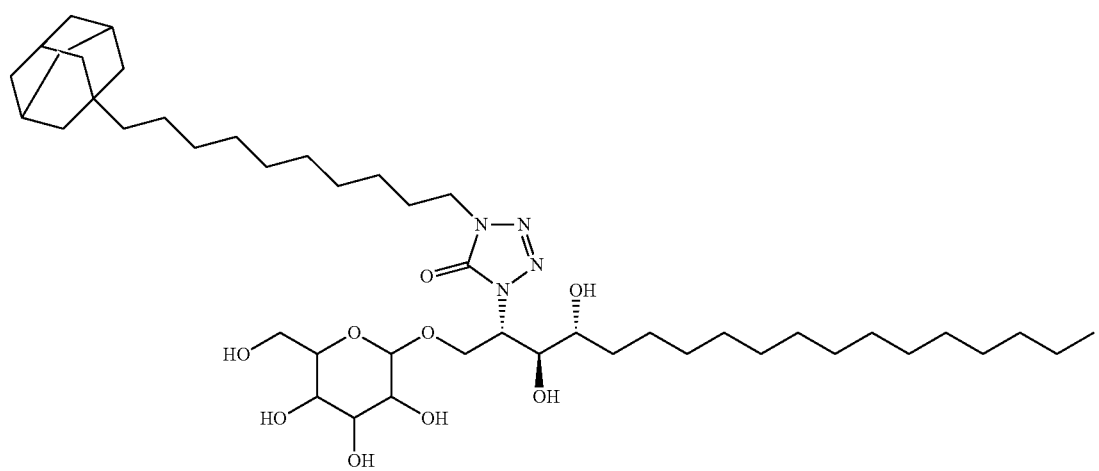 [SMILES: CCCCCCCCCCCCCC[C@@H](O)[C@@H](O)[C@H](COC1OC(CO)C(O)C(O)C1O)n1nnn(CCCCCCCCCCC23CC4CC(CC(C4)C2)C3)c1=O]

TABLE 8-continued
Tetrazolone Analogs
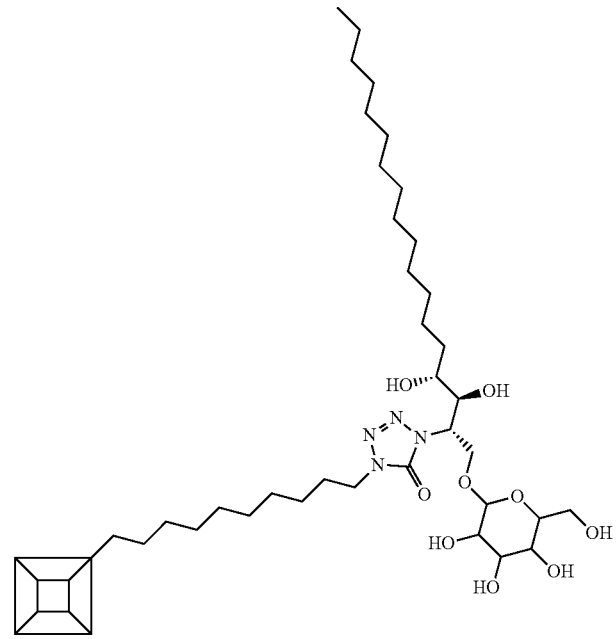 [SMILES: CCCCCCCCCCCCCC[C@@H](O)[C@@H](O)[C@H](COC1OC(CO)C(O)C(O)C1O)n1nnn(CCCCCCCCCCC23C4C5C6C4C2C6C53)c1=O]
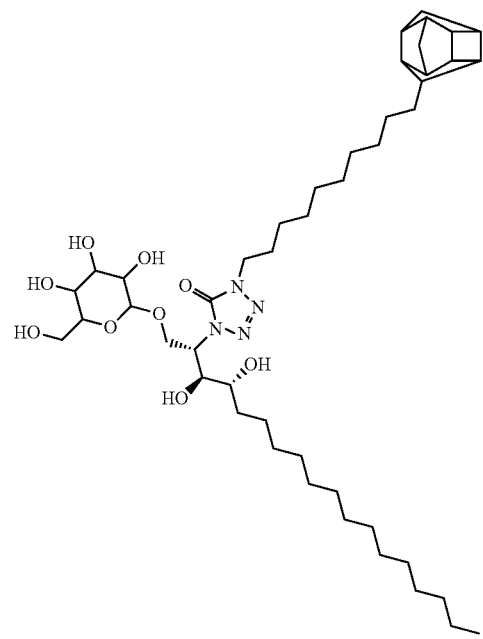 [SMILES: CCCCCCCCCCCCCC[C@@H](O)[C@@H](O)[C@H](COC1OC(CO)C(O)C(O)C1O)n1nnn(CCCCCCCCCCC2C3C4CC5C6C4CC3C6C25)c1=O]

TABLE 8-continued
Tetrazolone Analogs
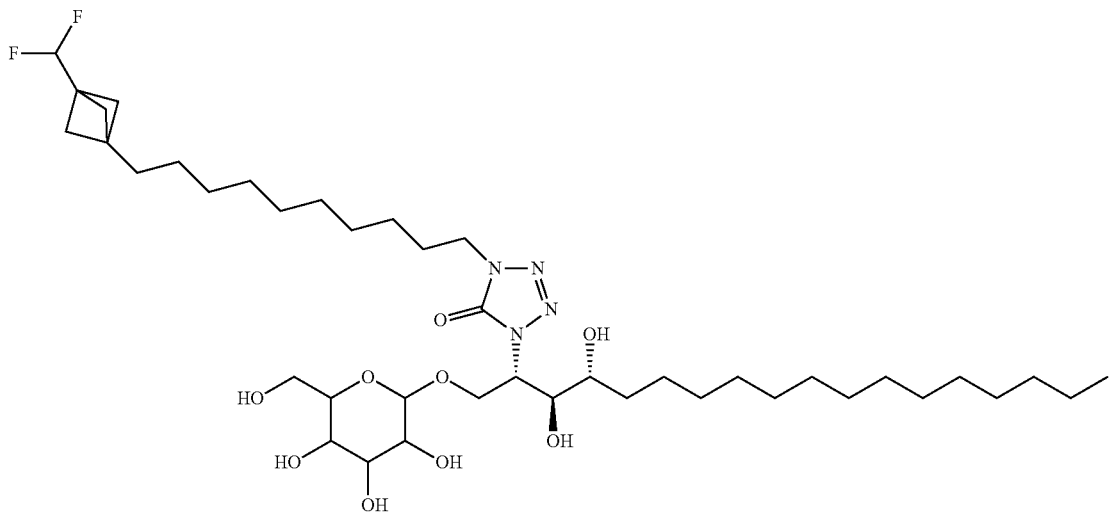 [SMILES: CCCCCCCCCCCCCC[C@@H](O)[C@@H](O)[C@H](COC1OC(CO)C(O)C(O)C1O)n1nnn(CCCCCCCCCCC23CC(C(F)F)(C2)C3)c1=O]
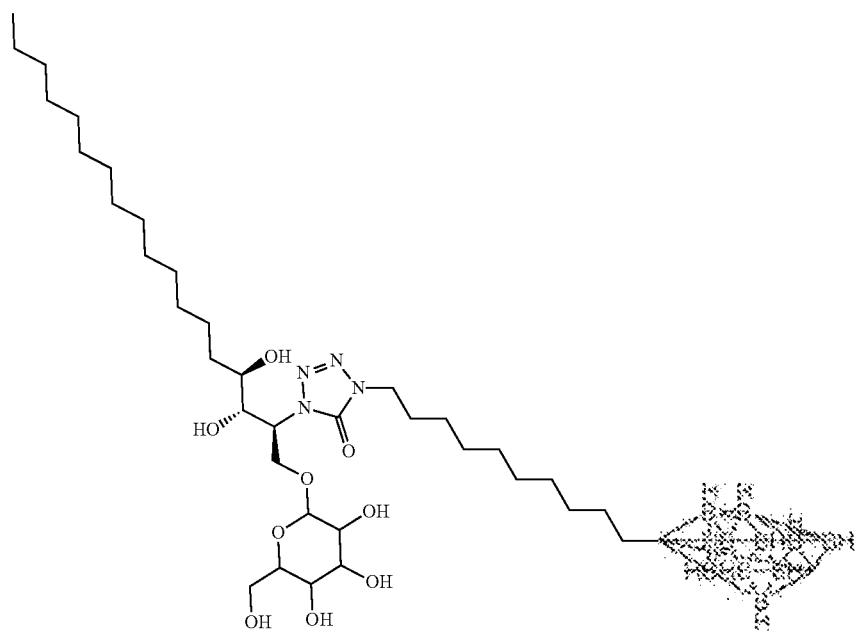 [SMILES: CCCCCCCCCCCCCC[C@@H](O)[C@@H](O)[C@H](COC1OC(CO)C(O)C(O)C1O)n1nnn(CCCCCCCCCCC)c1=O]

TABLE 8-continued
Tetrazolone Analogs
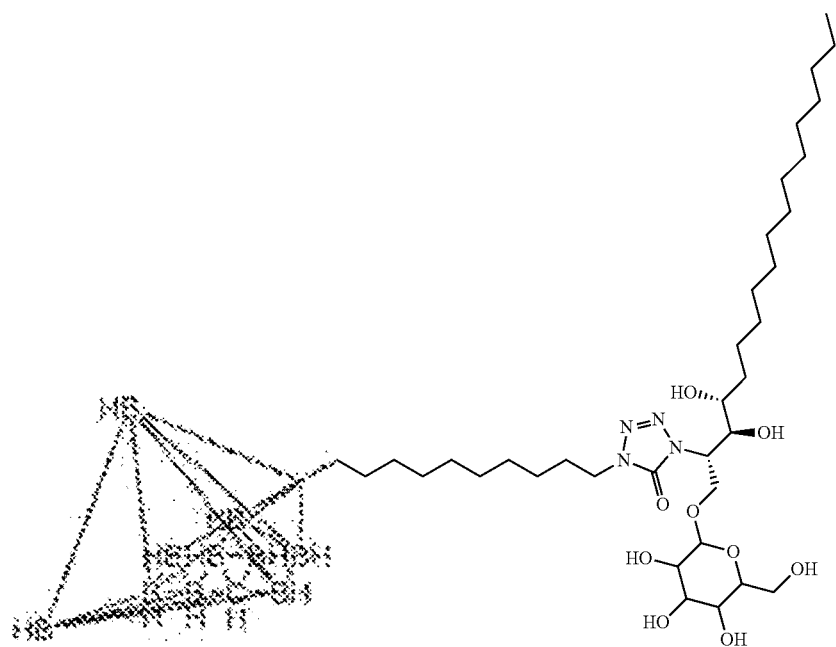 [SMILES: CCCCCCCCCCCCCC[C@@H](O)[C@@H](O)[C@H](COC1OC(CO)C(O)C(O)C1O)n1nnn(CCCCCCCCCC)c1=O]

TABLE 8-continued
Tetrazolone Analogs
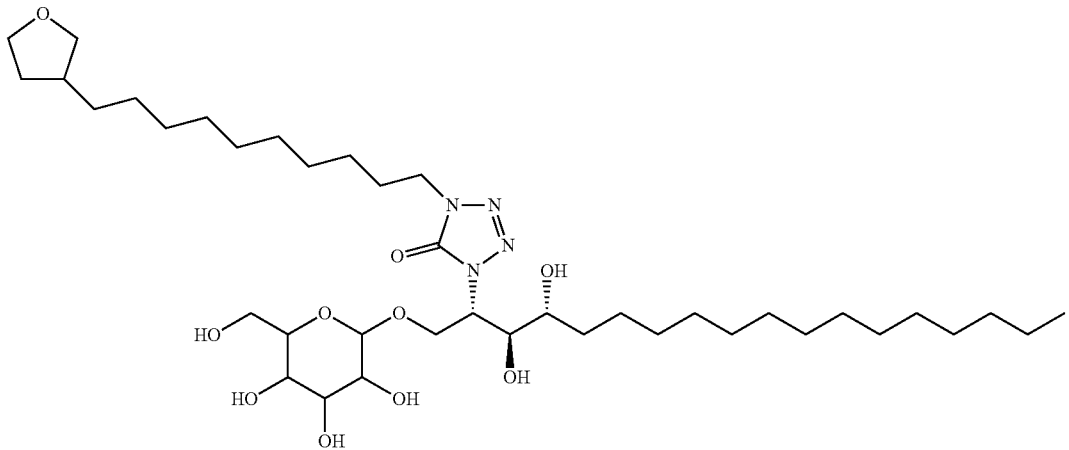 [SMILES: CCCCCCCCCCCCCC[C@@H](O)[C@@H](O)[C@H](COC1OC(CO)C(O)C(O)C1O)n1nnn(CCCCCCCCCCC2CCOC2)c1=O]
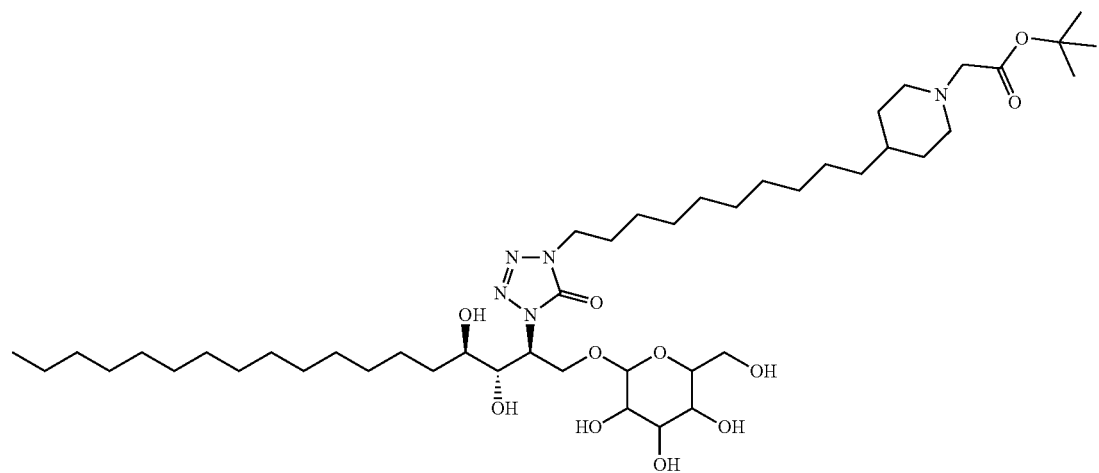 [SMILES: CCCCCCCCCCCCCC[C@@H](O)[C@@H](O)[C@H](COC1OC(CO)C(O)C(O)C1O)n1nnn(CCCCCCCCCCC2CCN(CC(=O)OC(C)(C)C)CC2)c1=O]

TABLE 8-continued
Tetrazolone Analogs
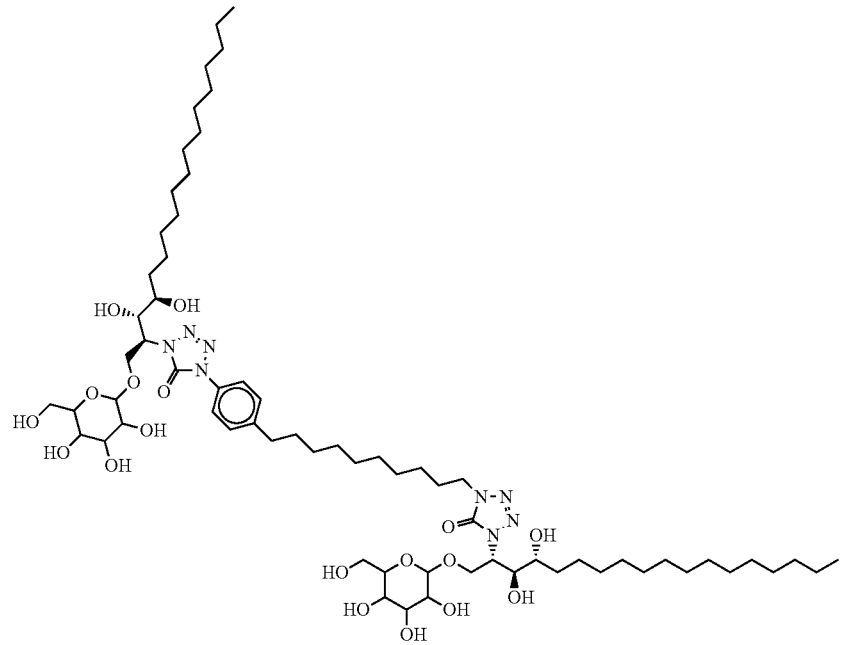
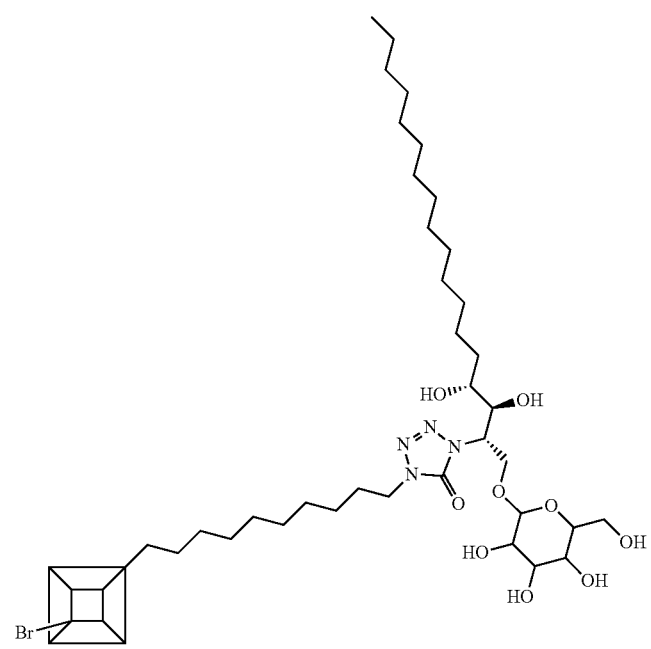 [SMILES: CCCCCCCCCCCCCC[C@@H](O)[C@@H](O)[C@H](COC1OC(CO)C(O)C(O)C1O)n1nnn(CCCCCCCCCCC23C4C5C2C2C3C4C52Br)c1=O]

TABLE 8-continued
Tetrazolone Analogs
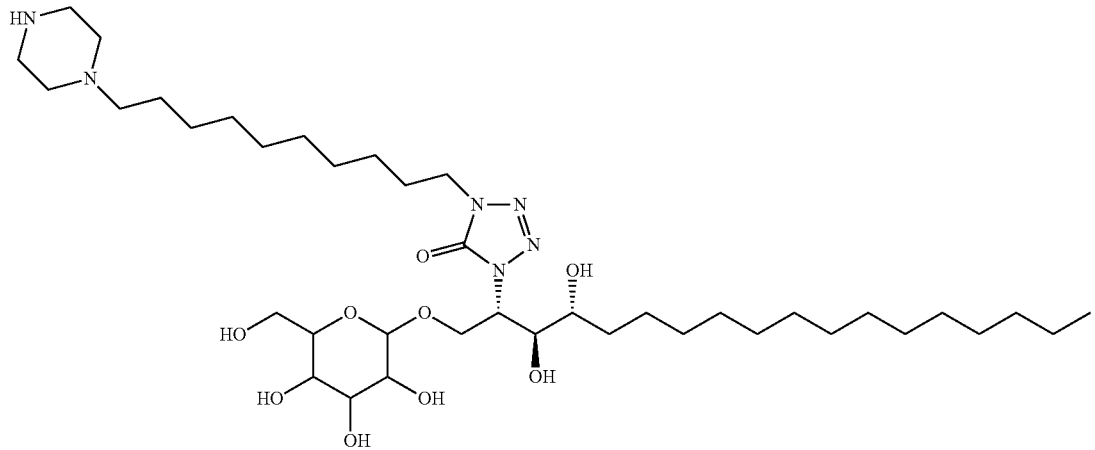 [SMILES: CCCCCCCCCCCCCC[C@@H](O)[C@@H](O)[C@H](COC1OC(CO)C(O)C(O)C1O)n1nnn(CCCCCCCCCCN2CCNCC2)c1=O]
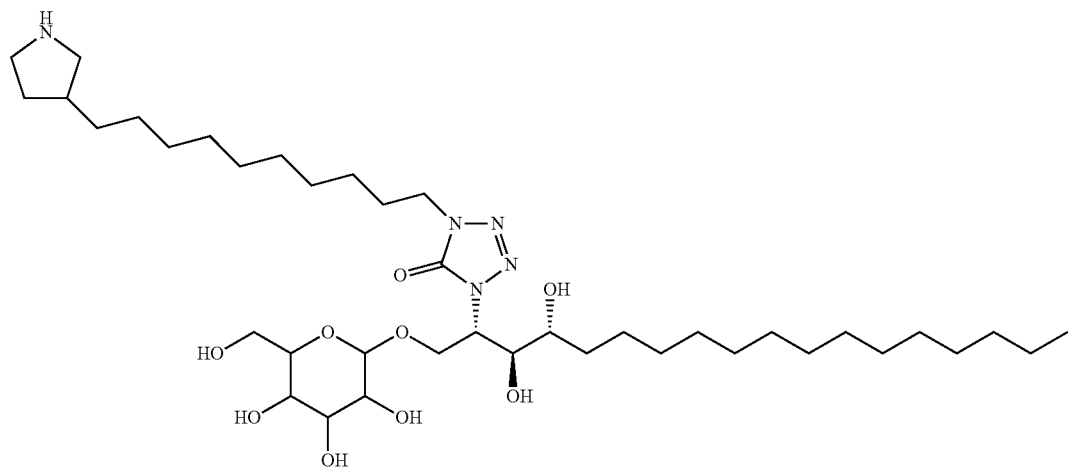 [SMILES: CCCCCCCCCCCCCC[C@@H](O)[C@@H](O)[C@H](COC1OC(CO)C(O)C(O)C1O)n1nnn(CCCCCCCCCCC2CCNC2)c1=O]
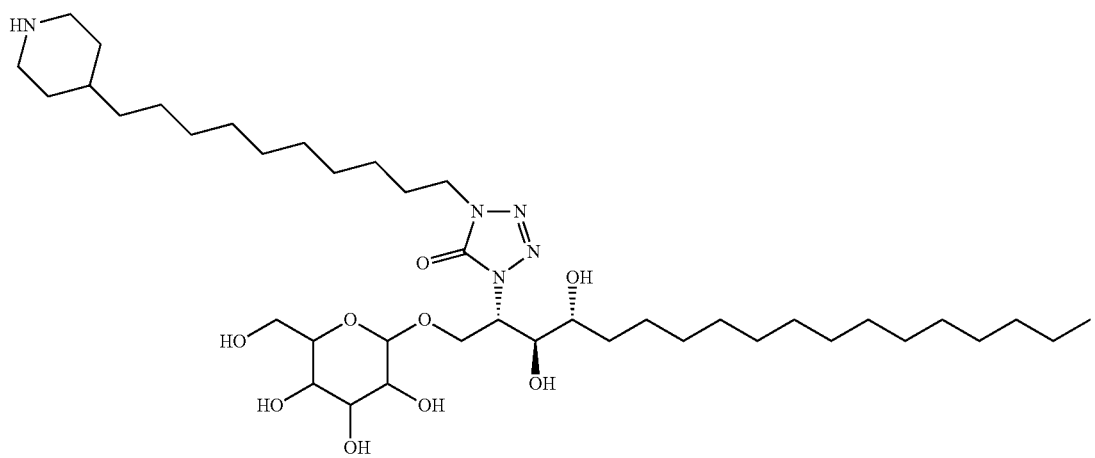

TABLE 8-continued
Tetrazolone Analogs
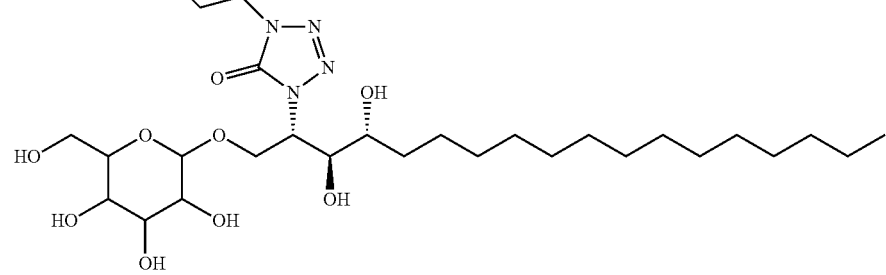
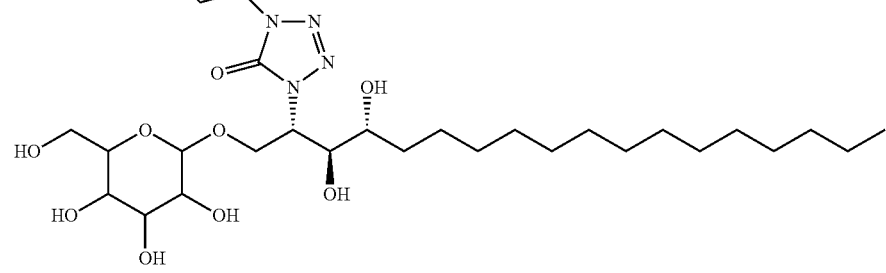
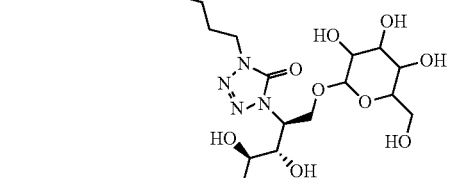

TABLE 8-continued
Tetrazolone Analogs
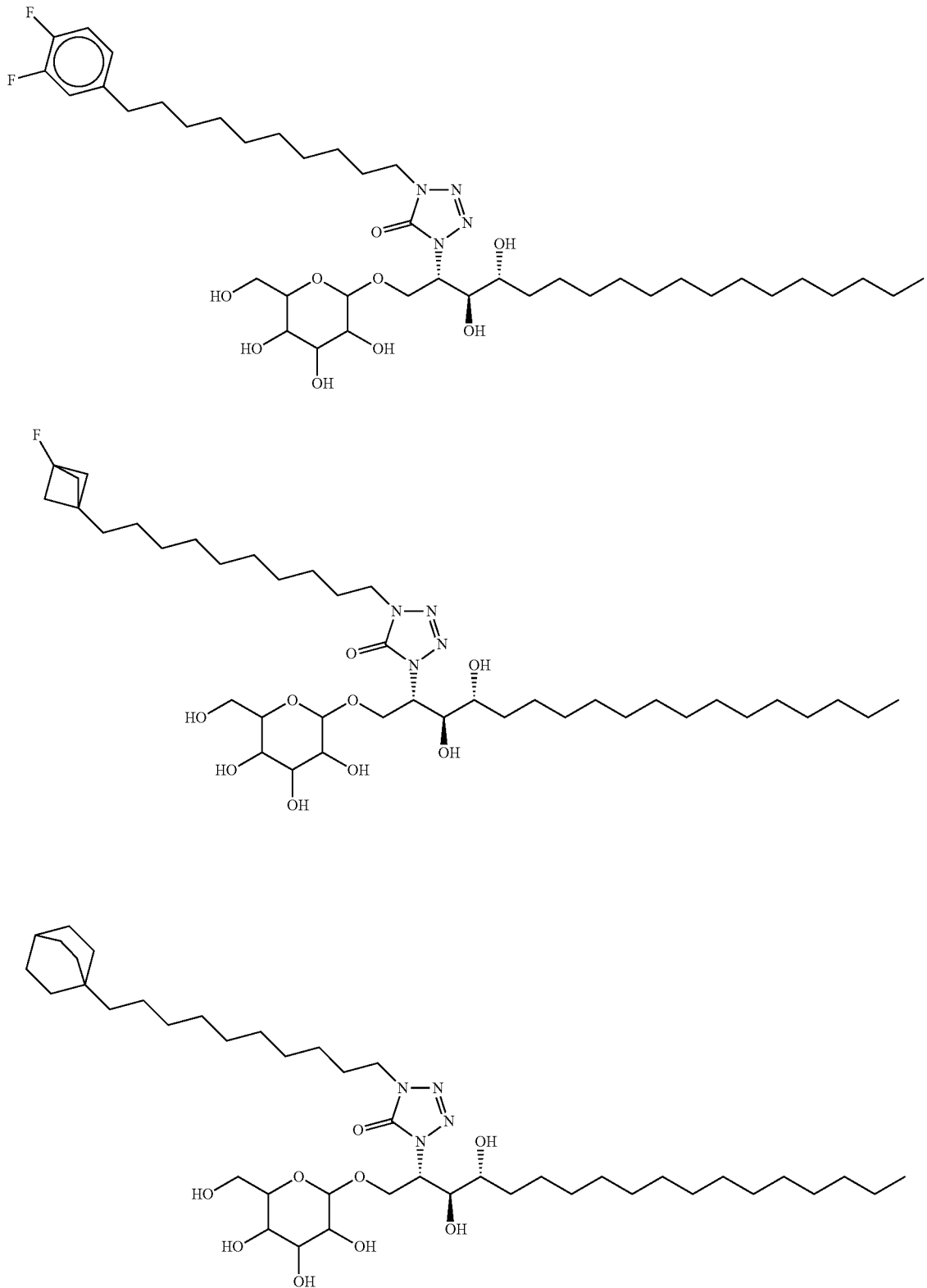

TABLE 8-continued
Tetrazolone Analogs
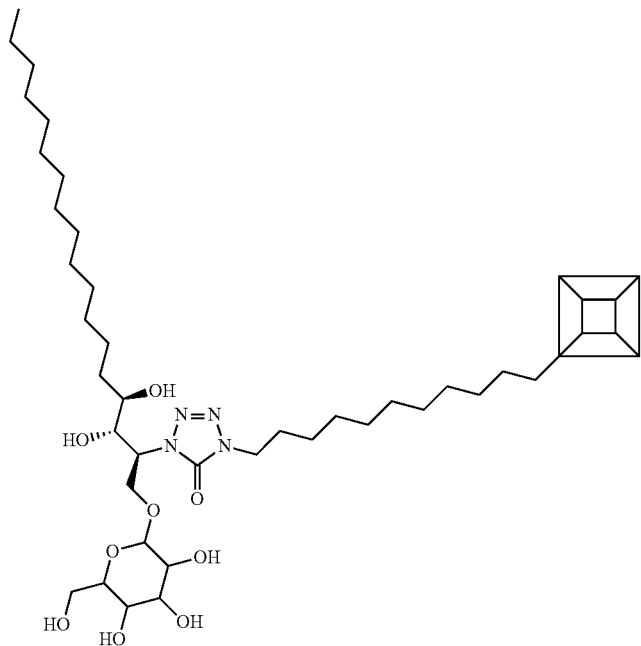 [SMILES: CCCCCCCCCCCCCC[C@@H](O)[C@@H](O)[C@H](COC1OC(CO)C(O)C(O)C1O)n1nnn(CCCCCCCCCCCC23C4C5C6C4C2C6C53)c1=O]
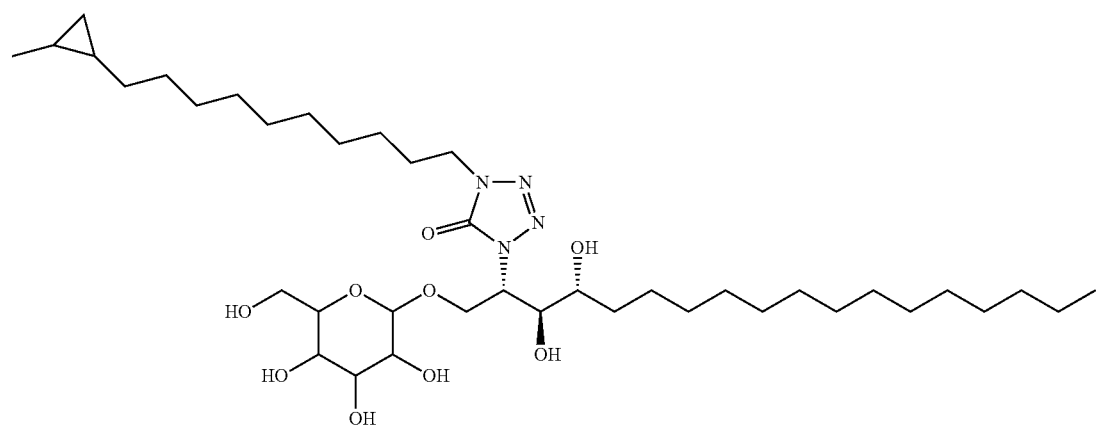 [SMILES: CCCCCCCCCCCCCC[C@@H](O)[C@@H](O)[C@H](COC1OC(CO)C(O)C(O)C1O)n1nnn(CCCCCCCCCCC2CC2C)c1=O]
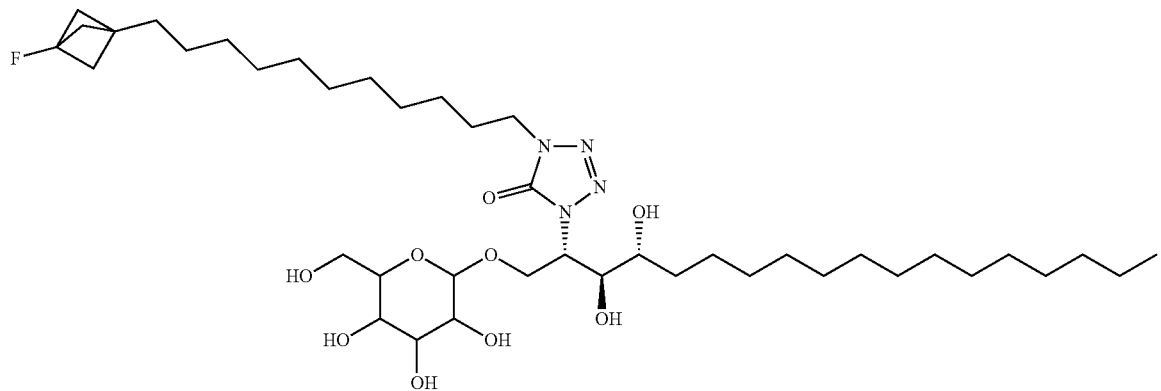 [SMILES: CCCCCCCCCCCCCC[C@@H](O)[C@@H](O)[C@H](COC1OC(CO)C(O)C(O)C1O)n1nnn(CCCCCCCCCCCC23CC(F)(C2)C3)c1=O]

TABLE 8-continued
Tetrazolone Analogs
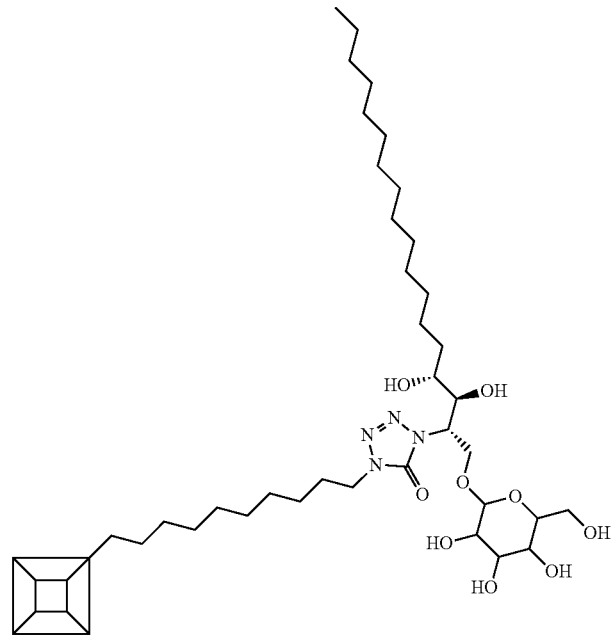 [SMILES: CCCCCCCCCCCCCC[C@@H](O)[C@@H](O)[C@H](COC1OC(CO)C(O)C(O)C1O)n1nnn(CCCCCCCCCCC23C4C5C6C4C2C6C53)c1=O]
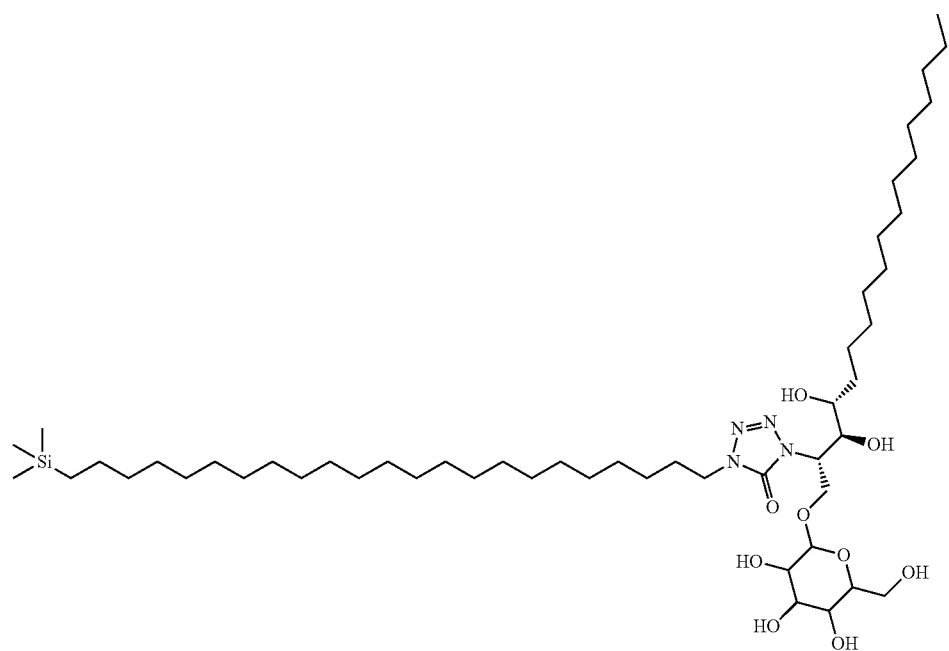 [SMILES: CCCCCCCCCCCCCC[C@@H](O)[C@@H](O)[C@H](COC1OC(CO)C(O)C(O)C1O)n1nnn(CCCCCCCCCCCCCCCCCCCCCCC[Si](C)(C)C)c1=O]

TABLE 8-continued
Tetrazolone Analogs
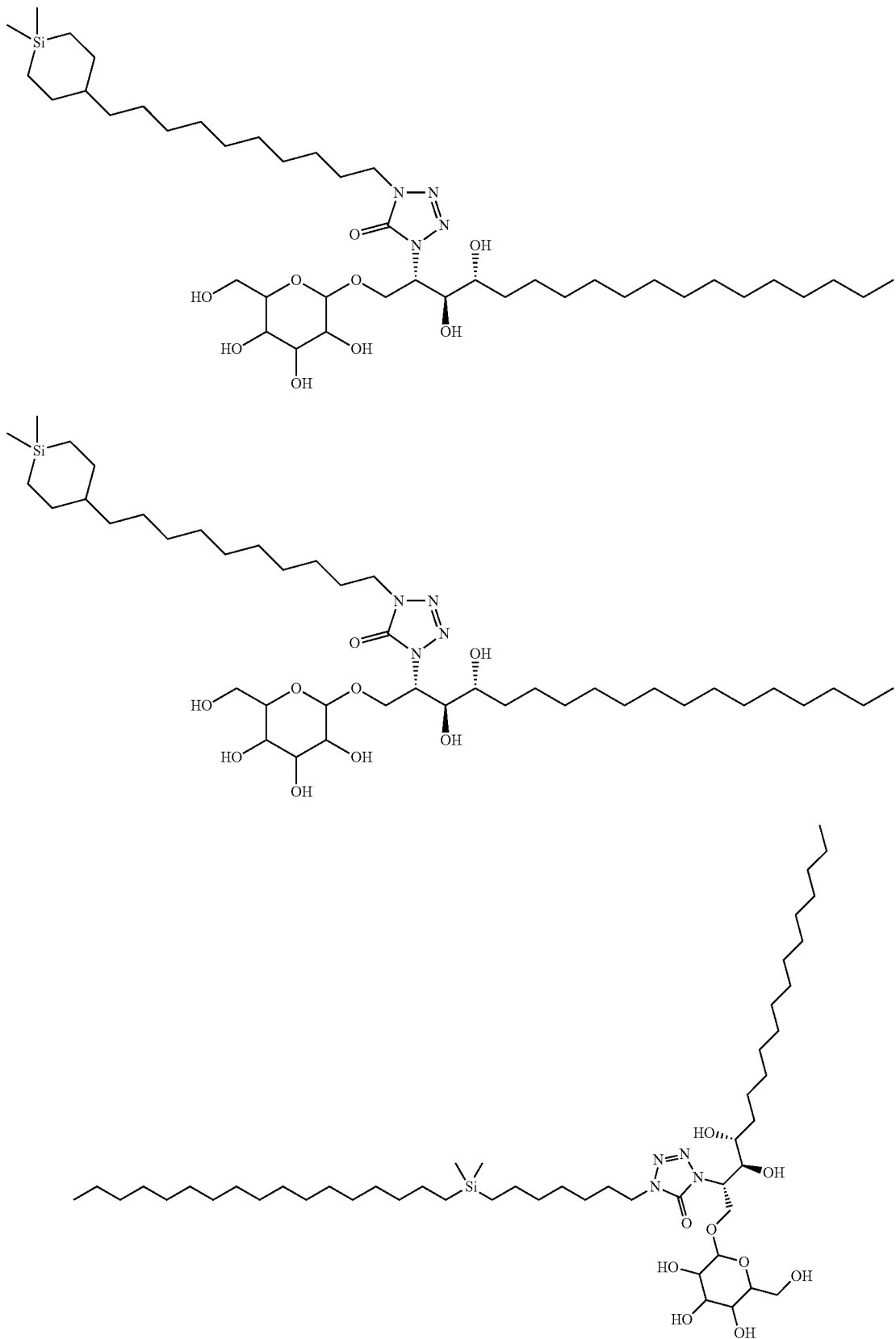

TABLE 8-continued
Tetrazolone Analogs
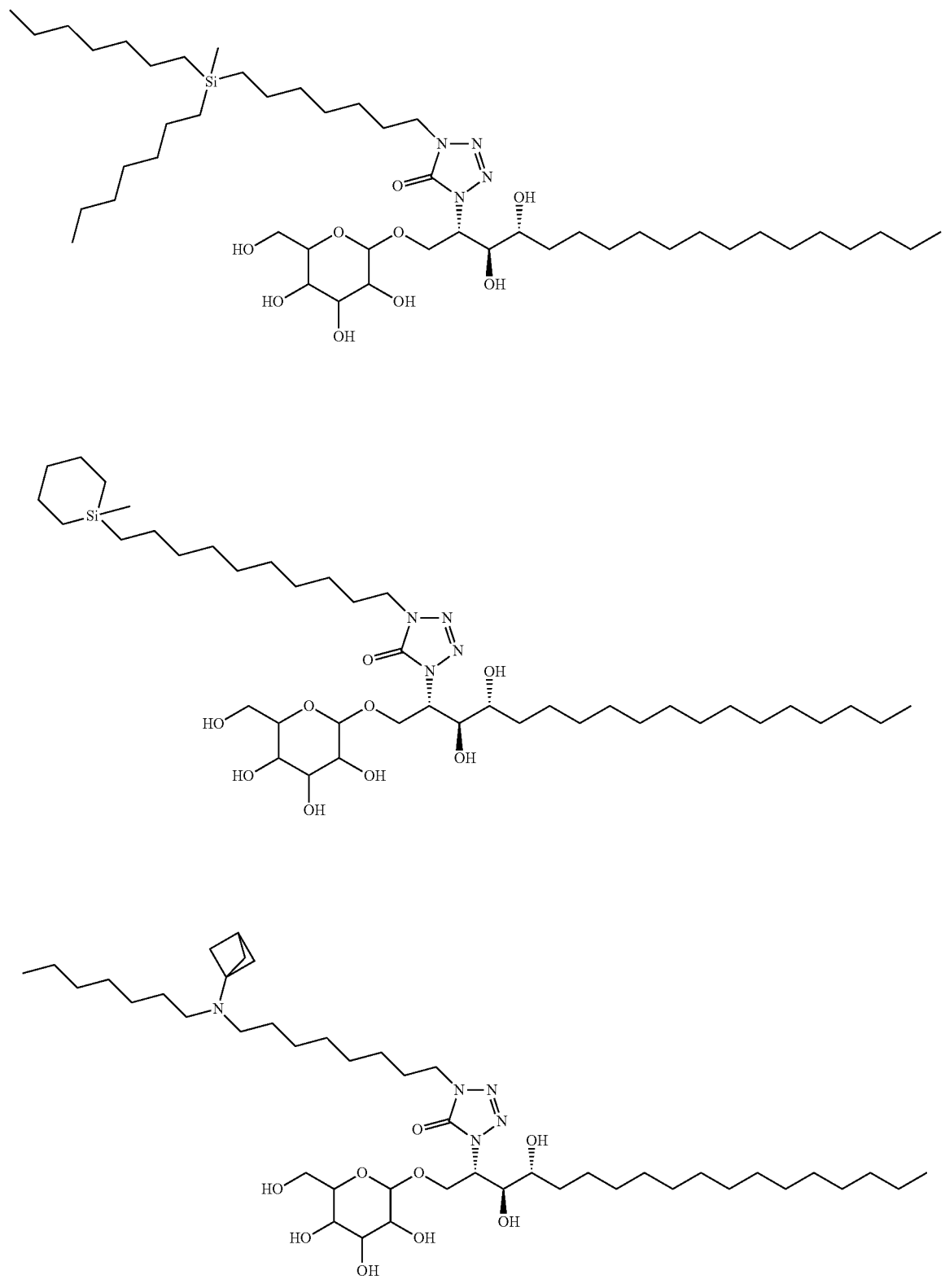

TABLE 9
Imidazole Analogs
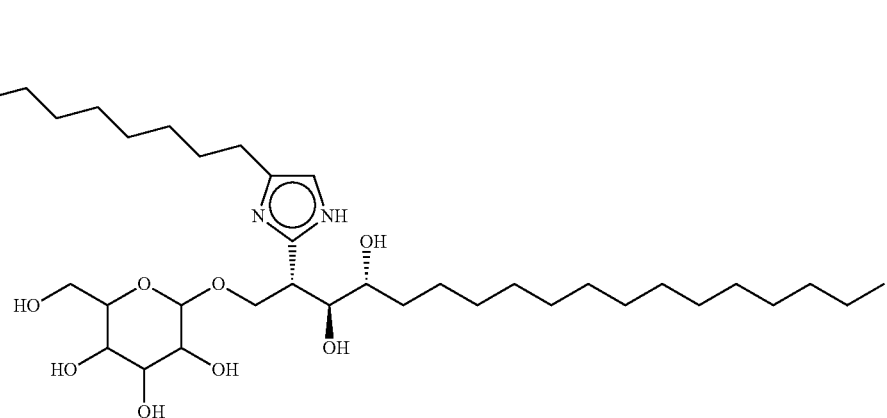
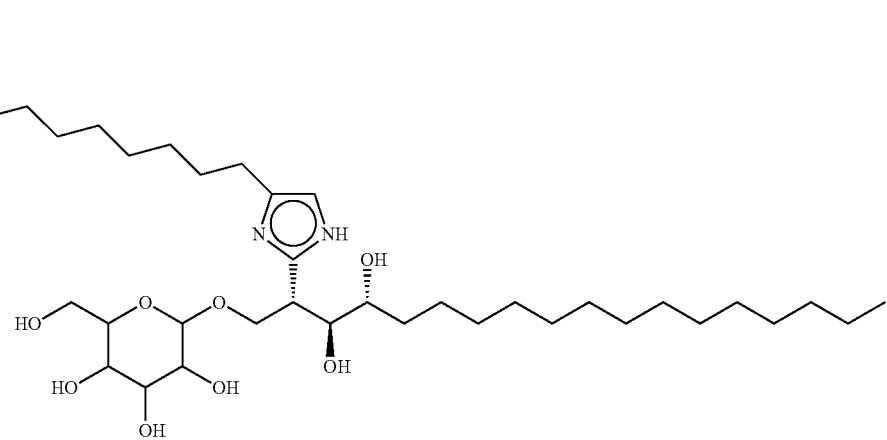
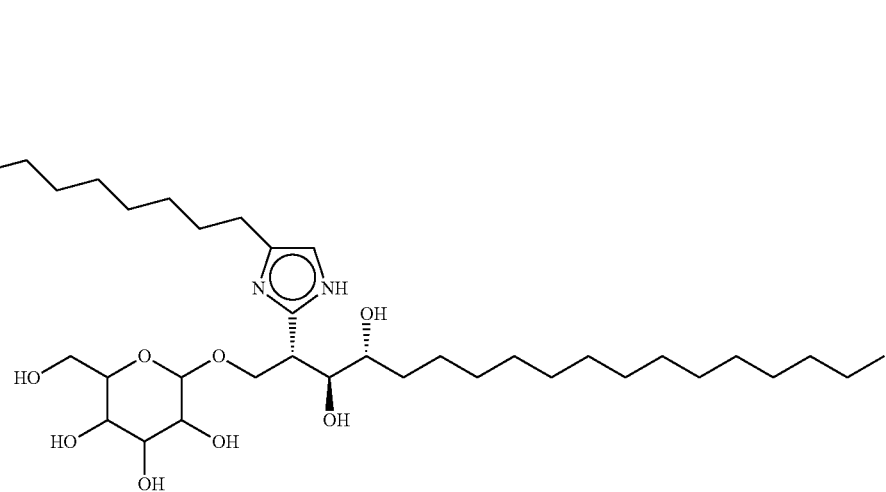

TABLE 9-continued
Imidazole Analogs
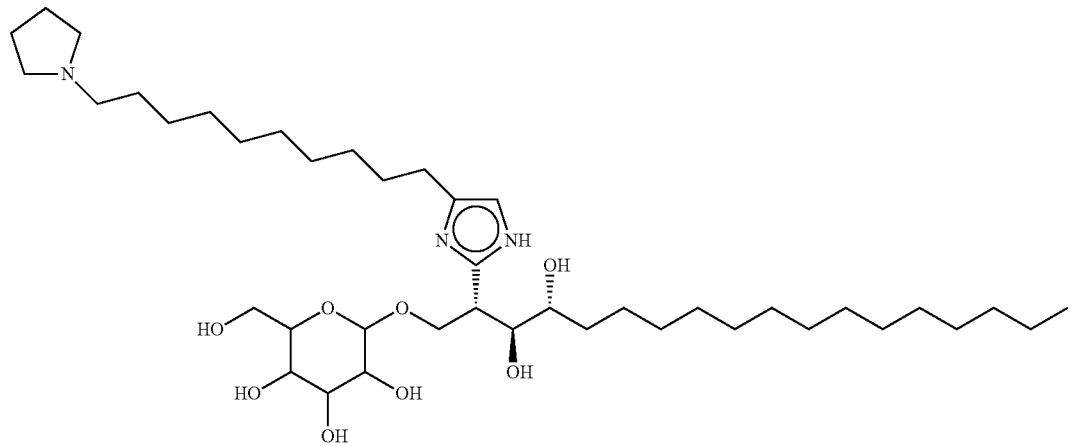
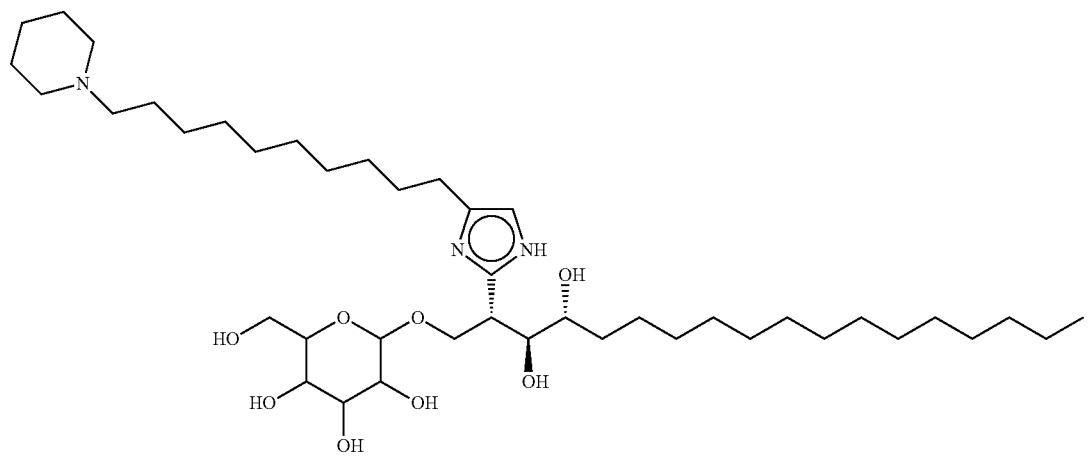
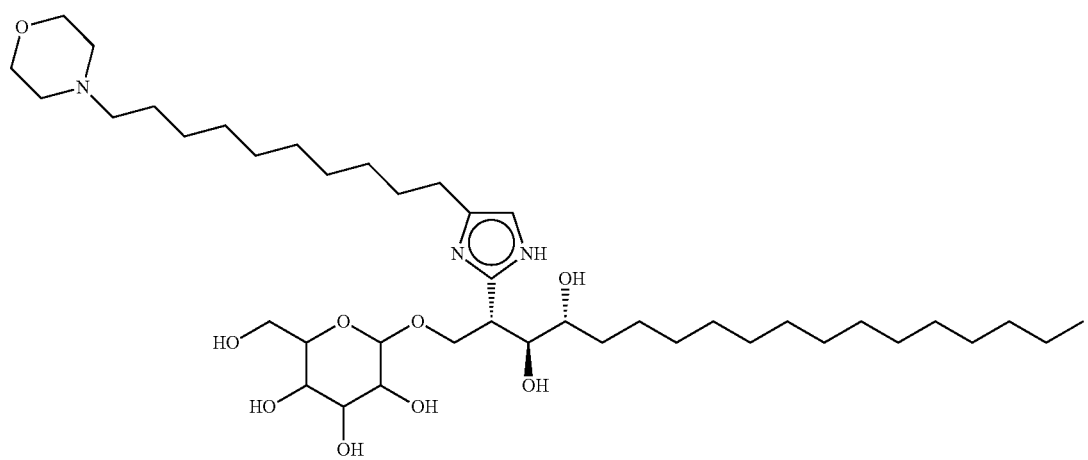

TABLE 9-continued
Imidazole Analogs
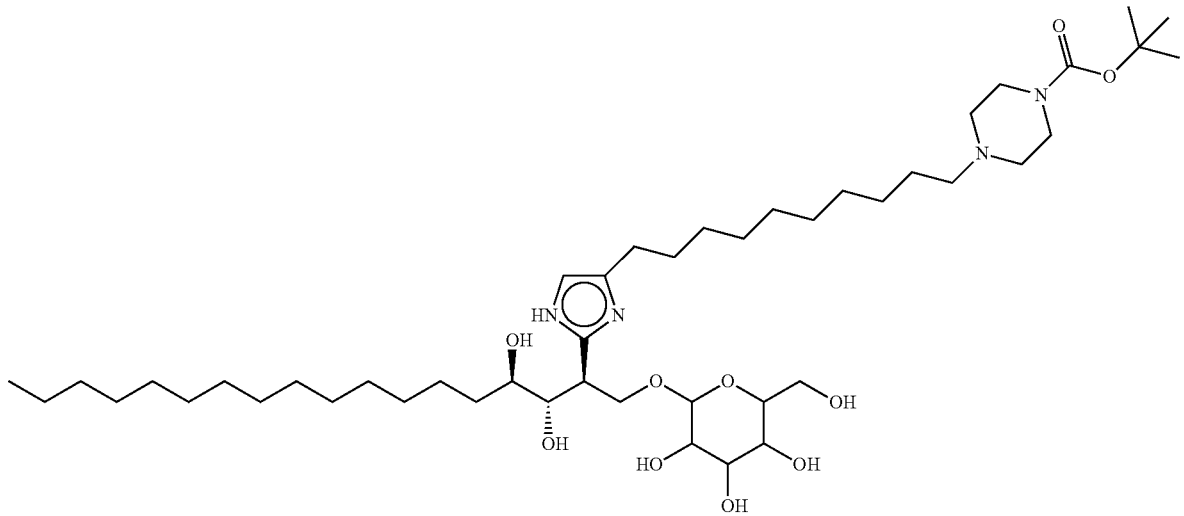
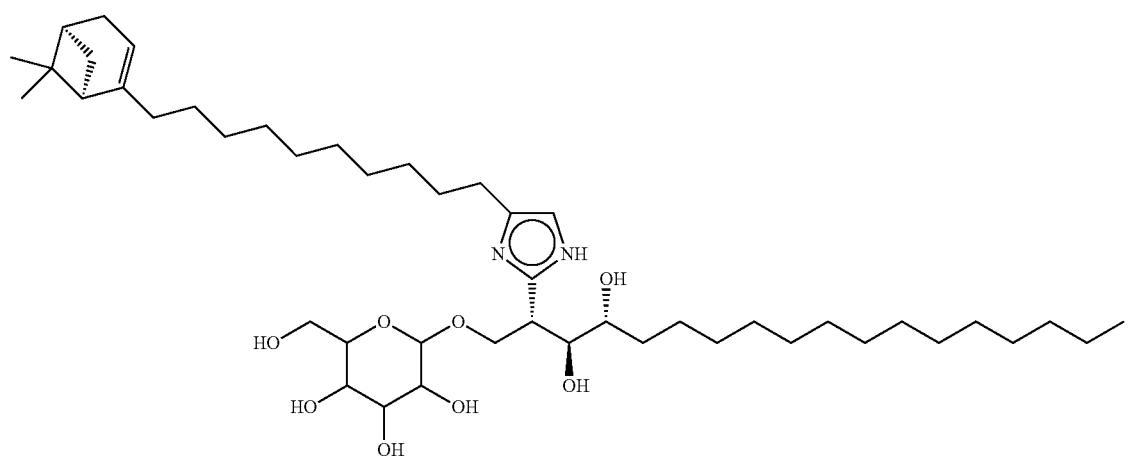
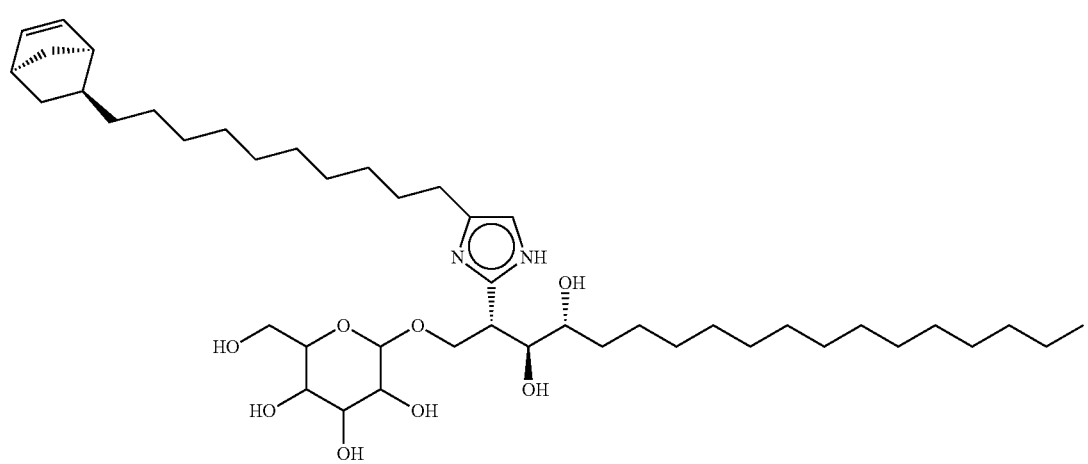

TABLE 9-continued
Imidazole Analogs
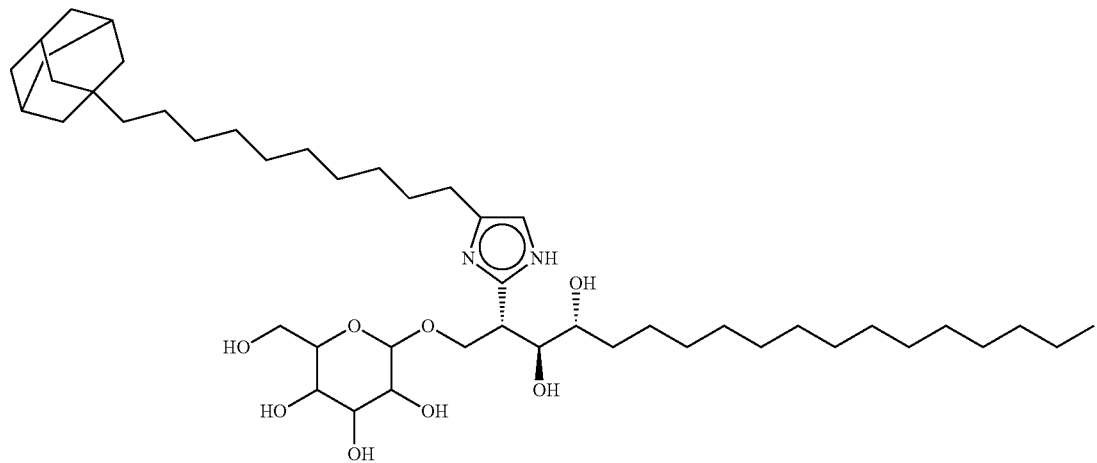
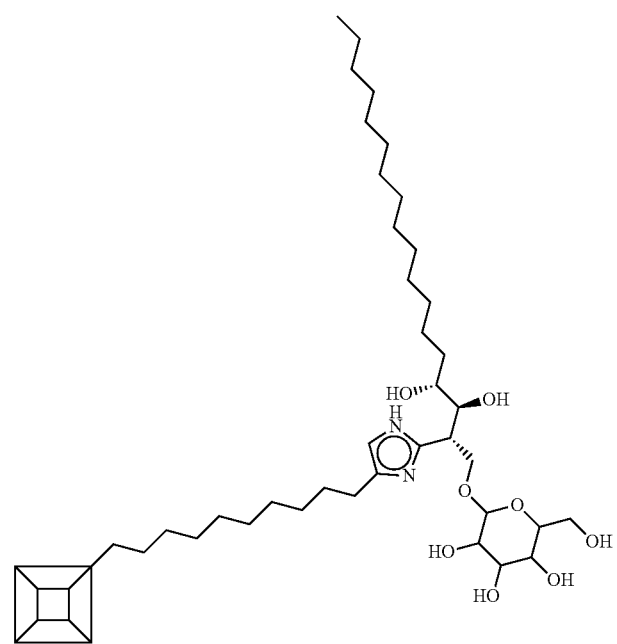

TABLE 9-continued
Imidazole Analogs
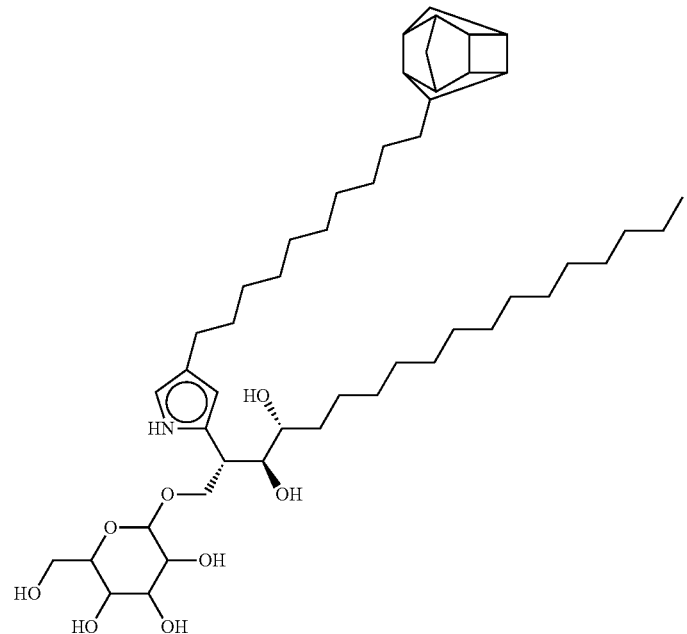
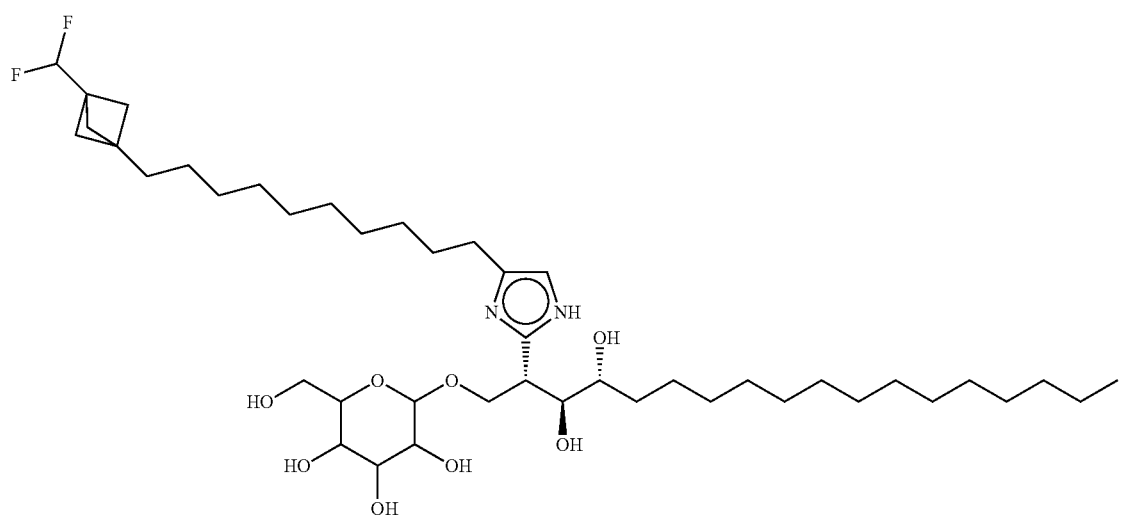

TABLE 9-continued
Imidazole Analogs
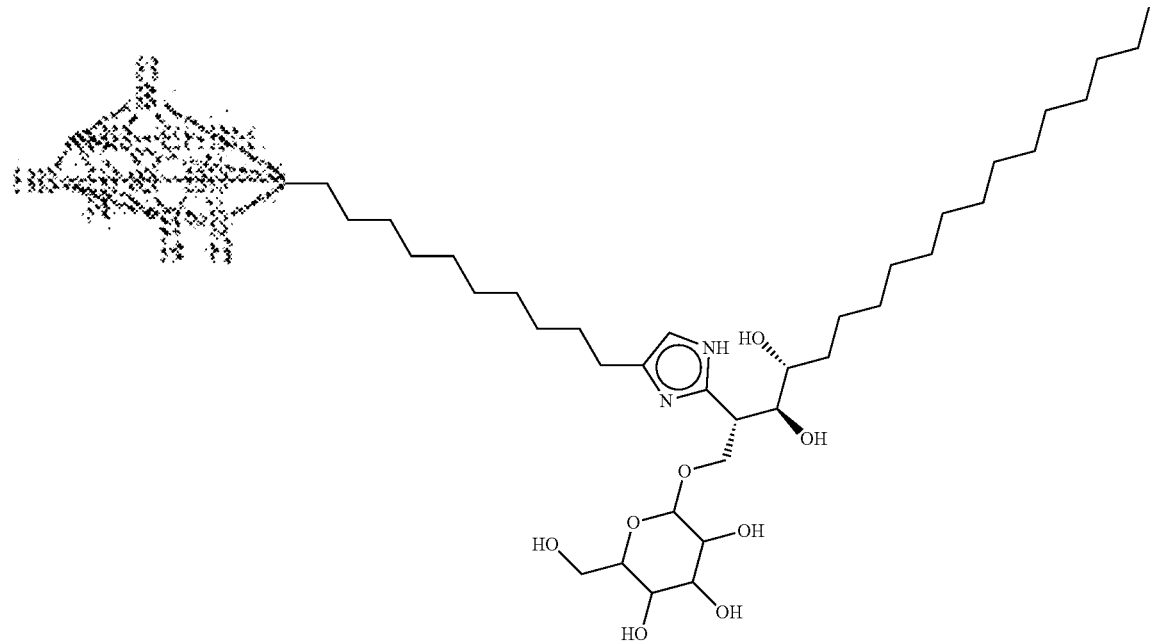
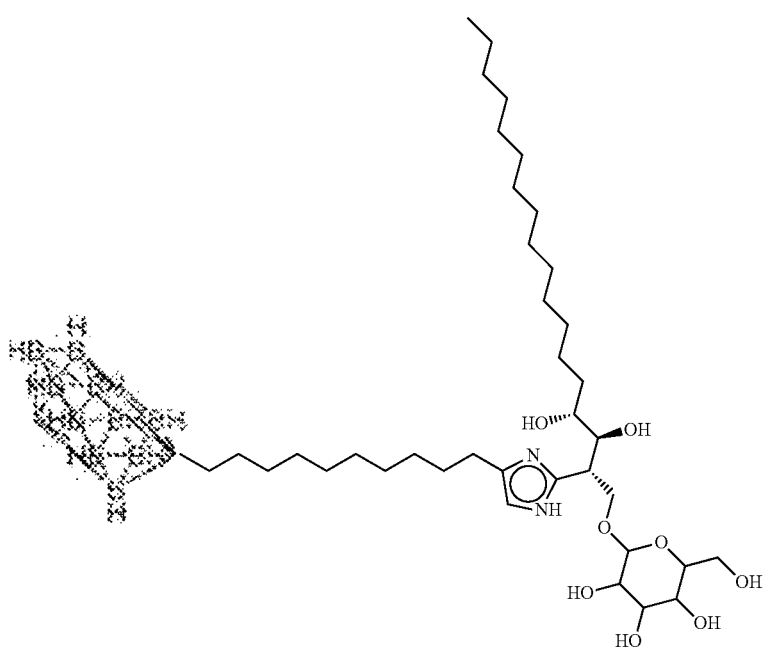

TABLE 9-continued
Imidazole Analogs
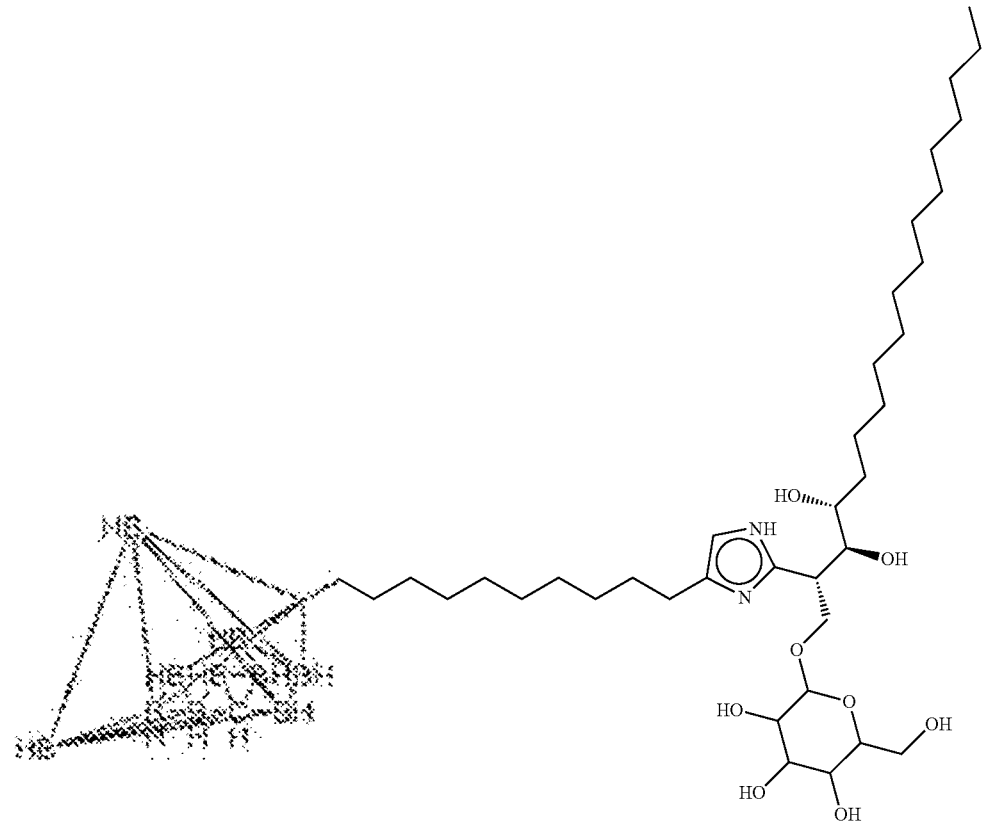
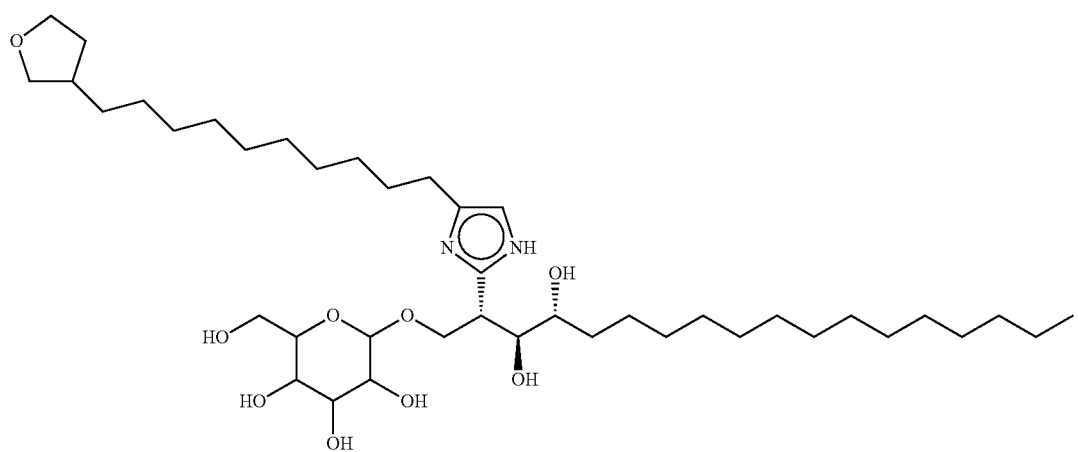

TABLE 9-continued
Imidazole Analogs
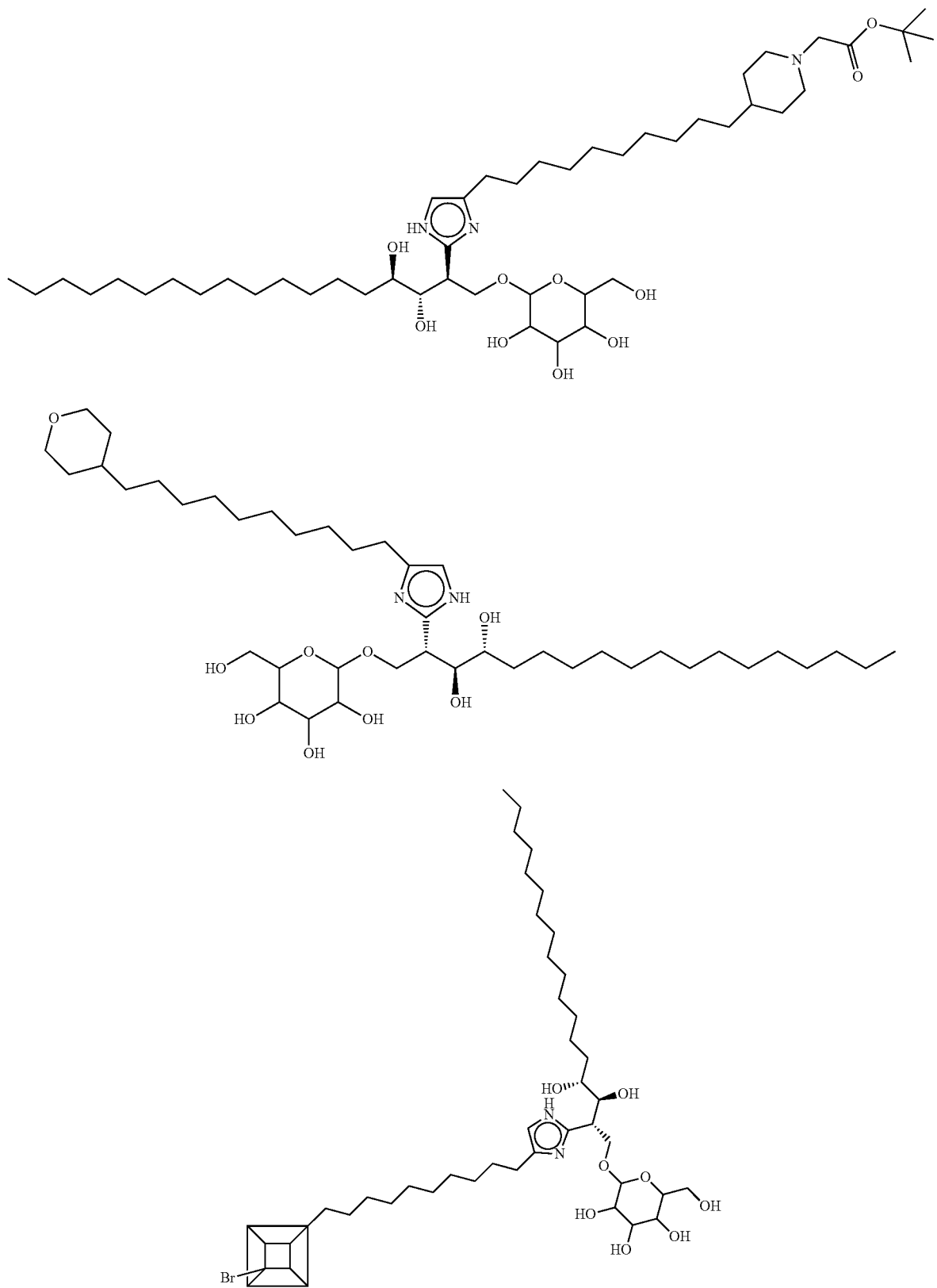

TABLE 9-continued
Imidazole Analogs
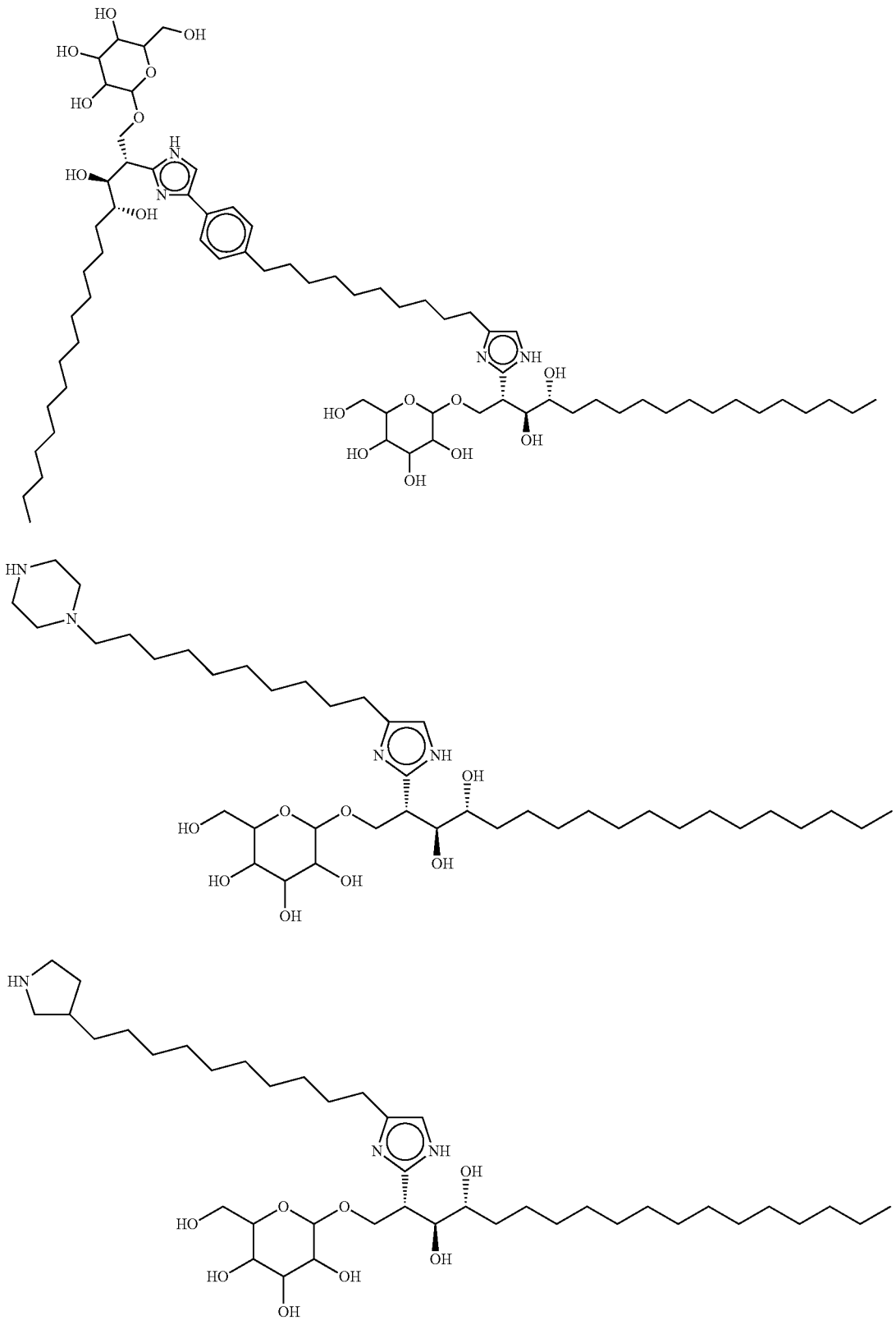

TABLE 9-continued
Imidazole Analogs
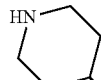
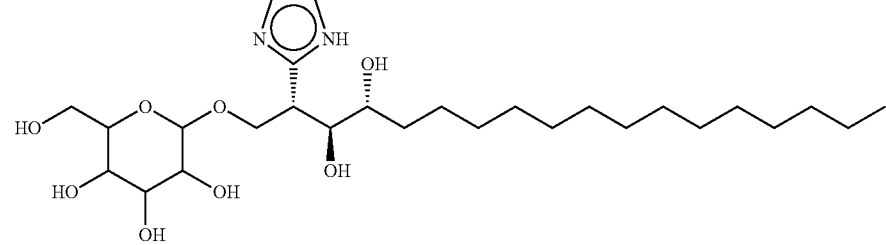
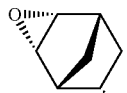
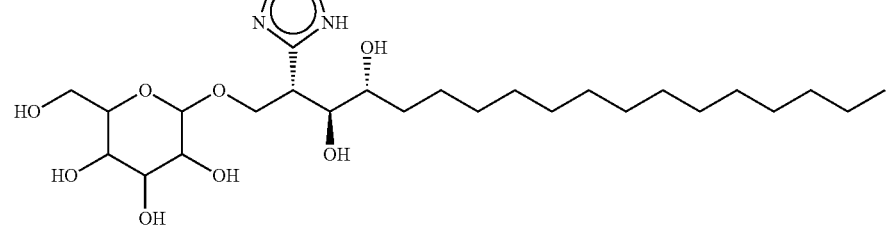
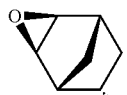
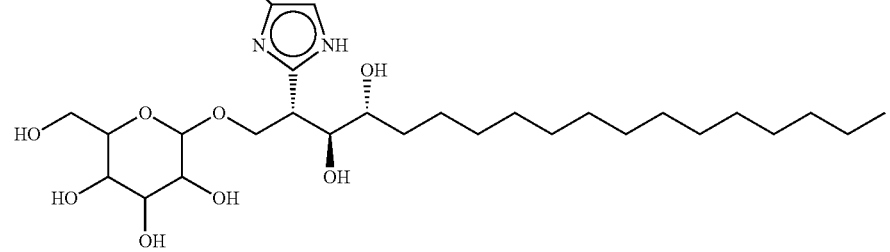

TABLE 9-continued
Imidazole Analogs
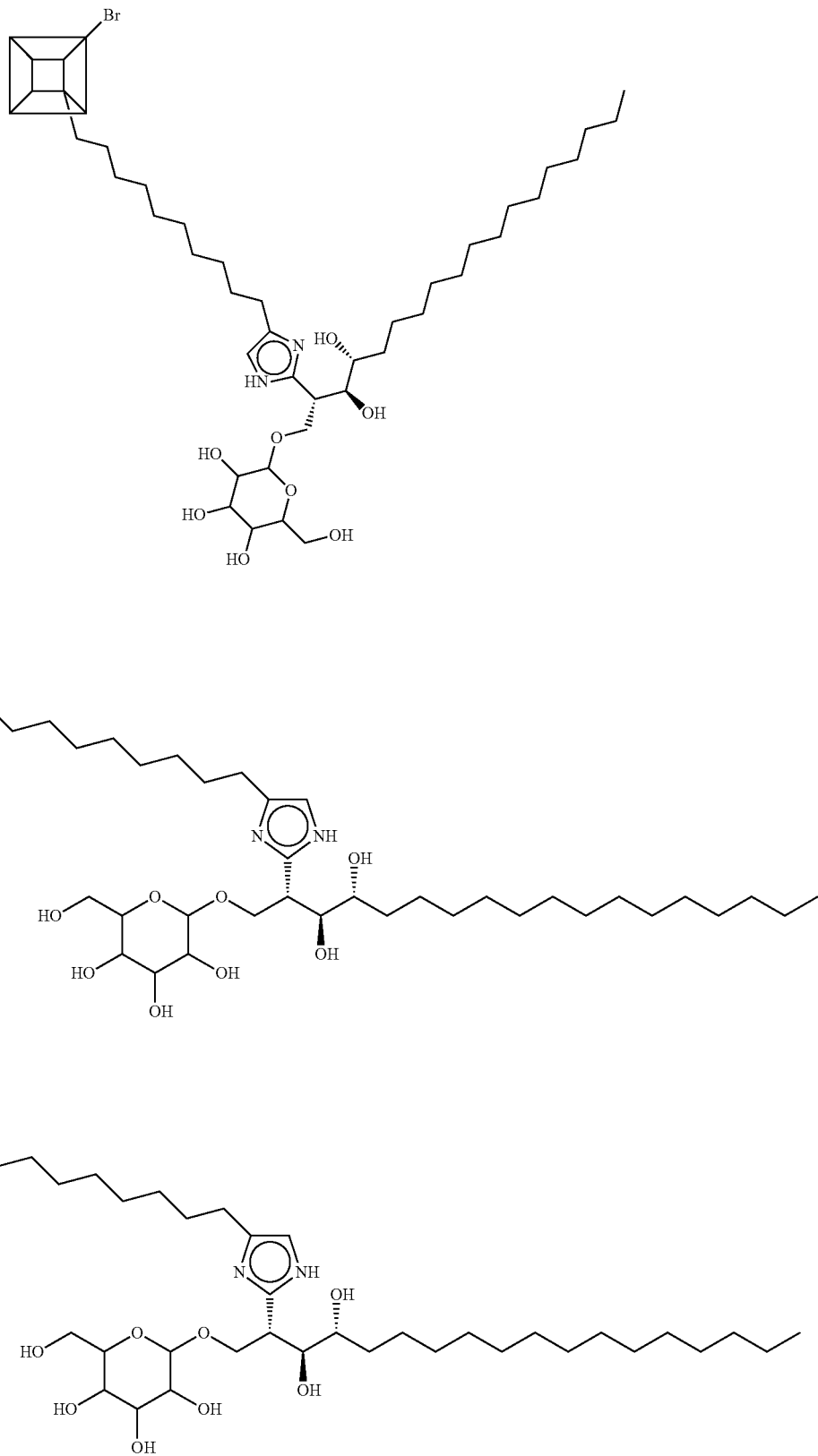

TABLE 9-continued
Imidazole Analogs
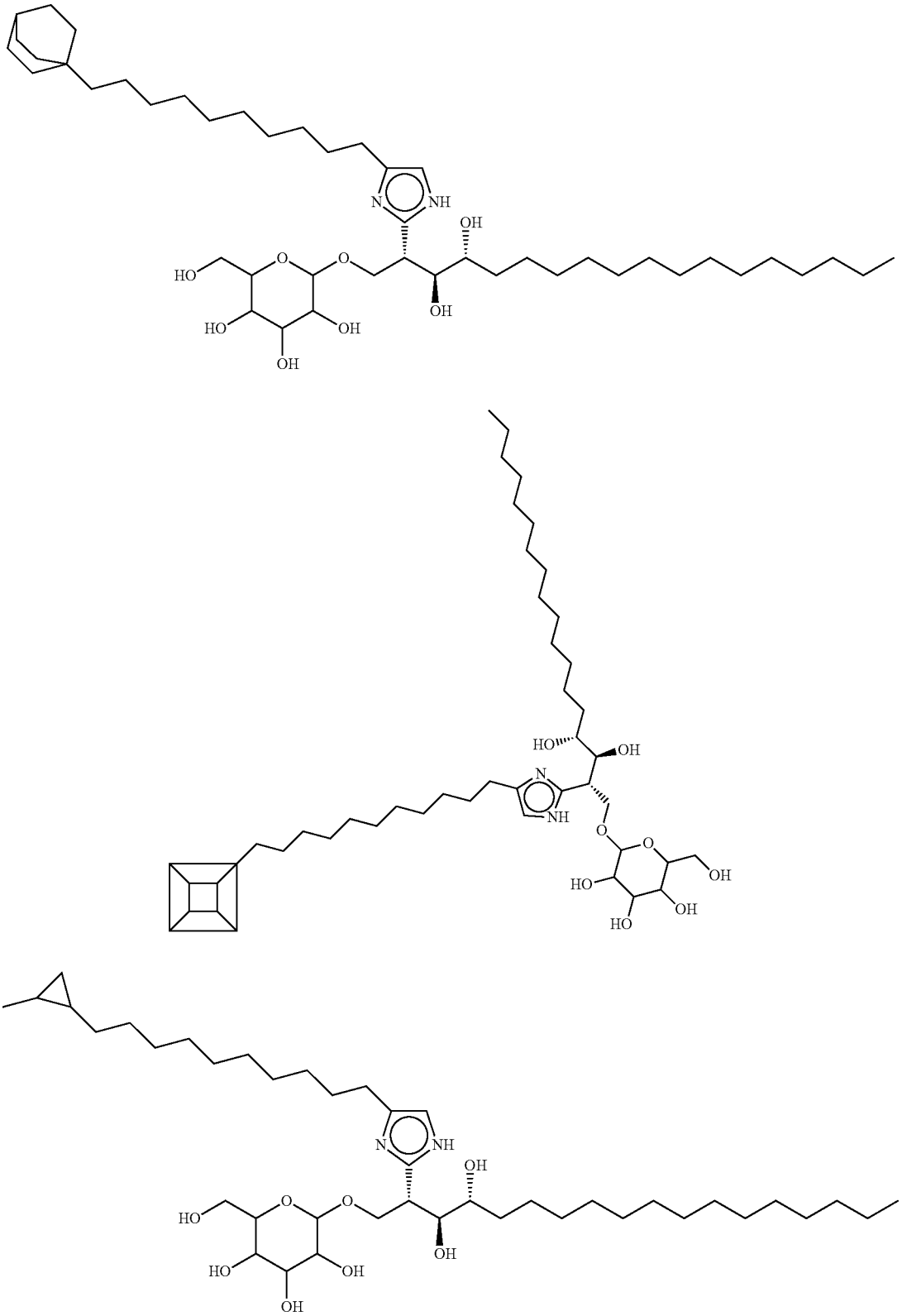

TABLE 9-continued
Imidazole Analogs
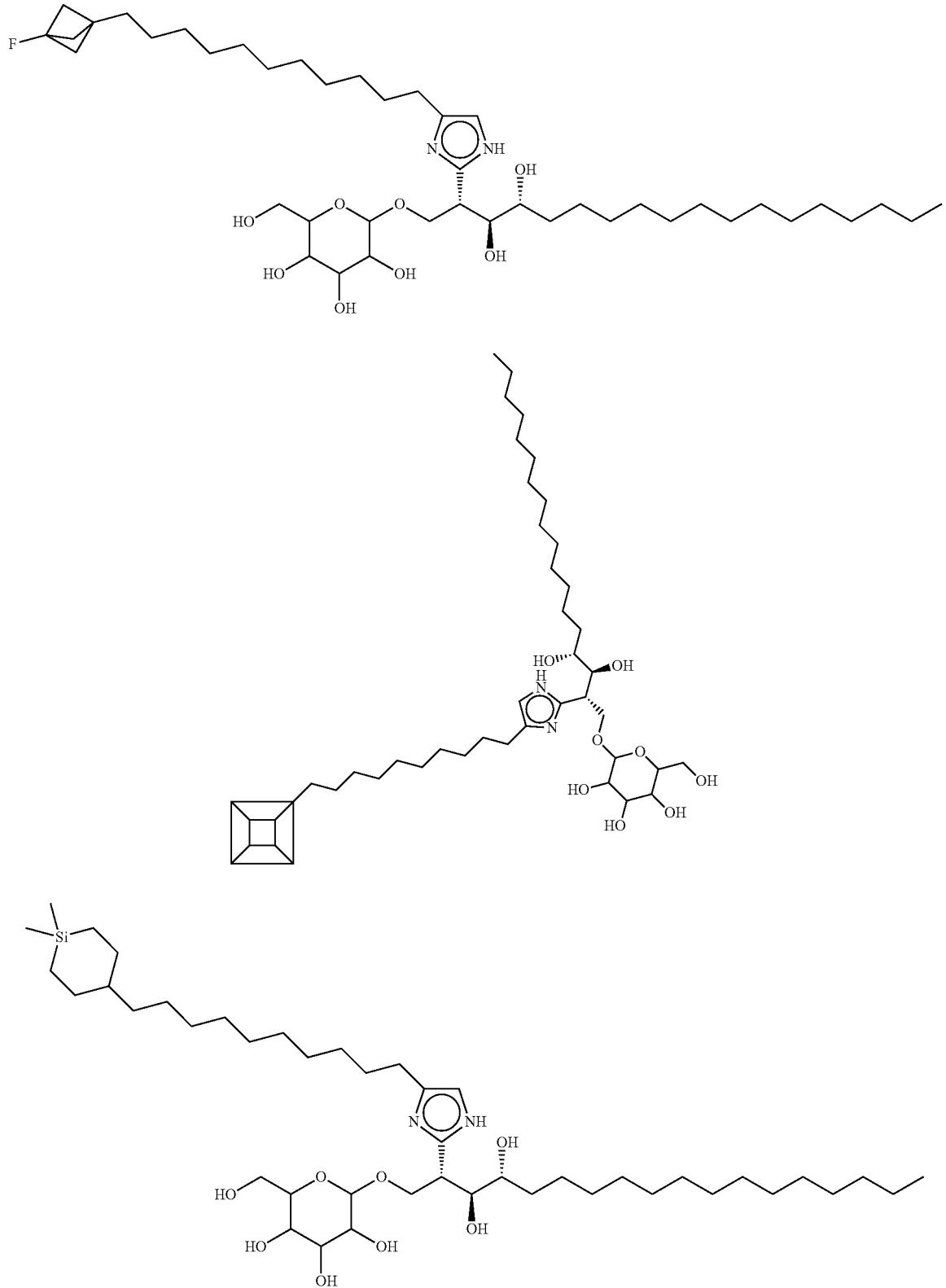

TABLE 9-continued

Imidazole Analogs

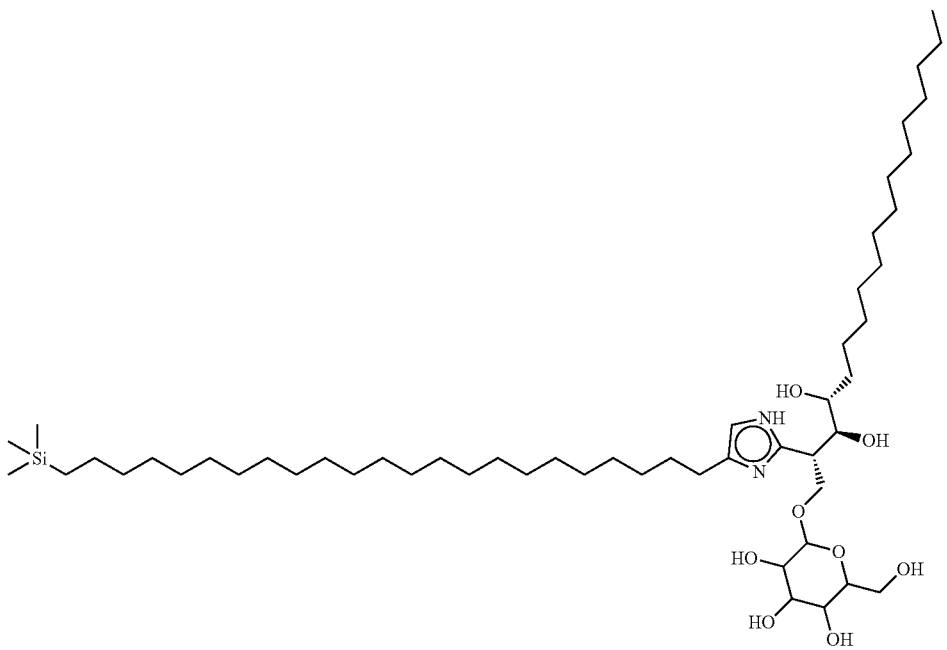

wherein ~~~ indicates the bond to the C5 to C25 alkyl; and R''' and R'' are independently selected from hydrogen, halogen, hydroxyl, substituted hydroxyl, amino, substituted amino, thiol, substituted thiol, sulfoxide, substituted sulfoxide, sulfone, substituted sulfone, sulfoximine, substituted sulfoximine, acyl, aminoacyl, alkyl, substituted alkyl; heteroalkyl, substituted heteroalkyl, cycloalkyl, substituted cycloalkyl, spiroalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

In some instances, R''' is hydrogen. In some instances, R''' is halogen. In some instances, R''' is selected from fluorine, bromine or iodine. In some instances, R'' is hydrogen. In some instances, R'' is halogen. In some instances, R'' is fluorine, bromine or iodine.

In some embodiments, compounds of interest include those shown in Tables 1-9, which are not to be construed as limitative.

Methods for Activating INKT Cells and Selectively Eliminating Senescent Cells

As summarized above, aspects of the present disclosure also include methods for activating an iNKT cell. In embodiments, methods include contacting an iNKT cell with an amount of one or more of the compounds or a pharmaceutically acceptable salt thereof described herein sufficient to activate the iNKT cell. In some instances, a source of the INKT cell is contacted in vitro. In other instances, a source of the iNKT cell is contacted in vivo (e.g., by administering to a subject as described in greater detail below). In still other instances, a source of the iNKT cell is contacted ex vivo.

In some embodiments, methods include contacting one or more of the compounds described herein with iNKT cells in a manner sufficient to activate the iNKT cells, where the activated iNKT cells induce a TH1-type cytokine response (e.g., increase production of one or more cytokines selected from IFN-γ, IL-1B, IL-2, IL-3, IL-8, IL-12, IL-15, TNF-α, GM-CSF, RANTES, MIP-1a and MCP-1). In other instances, the activated iNKT cells induce a TH2-type cytokine response (e.g., increase production of one or more cytokines selected from IL-4, IL-6, IL-8, IL-10, IL-13, RANTES, MIP-1a and MCP-1). In some instances, activating the iNKT cells with one or more of the subject compounds is sufficient to increase cytokine production by 1% or more as compared to a suitable control (e.g., iNKT cells not contacted with the compound or a control compound), such as by 2% or more, such as by 3% or more, such as by 4% or more, such as by 5% or more, such as by 10% or more, such as by 15% or more, such as by 20% or more, such as by 25% or more, such as by 50% or more, such as by 75% or more, such as by 90% or more, such as by 95% or more and including by 99% or more.

In certain instances, activating the iNKT cells with one or more of the subject compounds is sufficient to increase interleukin-2 (IL-2) production by 1% or more as compared to a suitable control (e.g., iNKT cells not contacted with the compound or a control compound), such as by 2% or more, such as by 3% or more, such as by 4% or more, such as by 5% or more, such as by 10% or more, such as by 15% or more, such as by 20% or more, such as by 25% or more, such as by 50% or more, such as by 75% or more, such as by 90% or more, such as by 95% or more and including by 99% or more. In certain instances, activating the iNKT cells with one or more of the subject compounds is sufficient to increase interleukin-4 (IL-4) production by 1% or more as compared to a suitable control (e.g., iNKT cells not contacted with the compound or a control compound), such as by 2% or more, such as by 3% or more, such as by 4% or more, such as by 5% or more, such as by 10% or more, such as by 15% or more, such as by 20% or more, such as by 25% or more, such as by 50% or more, such as by 75% or more, such as by 90% or more, such as by 95% or more and including by 99% or more. In certain instances, activating the iNKT cells with one or more of the subject compounds is sufficient to increase interleukin-6 (IL-6) production by 1% or more as compared to a suitable control (e.g., iNKT cells not contacted with the compound or a control compound), such as by 2% or more, such as by 3% or more, such as by 4% or more, such as by 5% or more, such as by 10% or more, such as by 15% or more, such as by 20% or more, such as by 25% or more, such as by 50% or more, such as by 75% or more, such as by 90% or more, such as by 95% or more and including by 99% or more. In certain instances, activating the iNKT cells with one or more of the subject compounds is sufficient to increase interferon gamma (IFNγ) production by 1% or more as compared to a suitable control (e.g., iNKT cells not contacted with the compound or a control compound), such as by 2% or more, such as by 3% or more, such as by 4% or more, such as by 5% or more, such as by 10% or more, such as by 15% or more, such as by 20% or more, such as by 25% or more, such as by 50% or more, such as by 75% or more, such as by 90% or more, such as by 95% or more and including by 99% or more. In certain instances, activating the iNKT cells with one or more of the subject compounds is sufficient to increase tumor necrosis factor (TNFα) production by 1% or more as compared to a suitable control (e.g., iNKT cells not contacted with the compound or a control compound), such as by 2% or more, such as by 3% or more, such as by 4% or more, such as by 5% or more, such as by 10% or more, such as by 15% or more, such as by 20% or more, such as by 25% or more, such as by 50% or more, such as by 75% or more, such as by 90% or more, such as by 95% or more and including by 99% or more.

In certain instances, activating the iNKT cells with one or more of the subject compounds is sufficient to increase cytokine production as compared to contacting the iNKT cells with α-galactosylceramide (α-GalCer), such as where cytokine production (e.g., increasing one or more of IFN-γ, TL-1β, IL-2, IL-3, IL-8, IL-12, IL-15, TNF-α, GM-CSF, RANTES, MIP-1α and MCP-1 or IL-4, IL-6, IL-8, IL-10, IL-13, RANTES, MIP-1α and MCP-1) is higher by activating the iNKT cells with one or more of the subject compounds than when the iNKT cells are contacted with α-galactosylceramide. In some embodiments, the compounds of the present disclosure increase cytokine production by 1% or more as compared to α-galactosylceramide, such as by 2% or more, such as by 3% or more, such as by 4% or more, such as by 5% or more, such as by 10% or more, such as by 15% or more, such as by 20% or more, such as by 25% or more, such as by 50% or more, such as by 75% or more, such as by 90% or more, such as by 95% or more and including by 99% or more as compared to α-galactosylceramide.

In some instances, the compound forms a complex with a CD1 molecule on an antigen-presenting cell. In certain instances, the CD1 molecule is a CD1d molecule. In some instances, the receptor on the T lymphocyte is a T cell receptor. In some instances, the compound stimulates at least one other lymphocyte to produce the cytokine response in some instances the at least one other lymphocyte is a T helper cell. In some embodiments, methods include activating iNKT cells with the subject compounds in a manner sufficient to modulate an immune response in a subject.

In practicing the subject methods, the iNKT cells may be contacted with the subject compounds for a duration of 1 minute or more, such as for 2 minutes or more, such as for 3 minutes or more, such as for 4 minutes or more, such as for 5 minutes or more, such as for 10 minutes or more, such as for 15 minutes or more, such as for 30 minutes or more, such as for 60 minutes or more, such as for 2 hours or more, such as for 6 hours or more, such as for 12 hours or more, such as for 18 hours or more and including for 24 hours or more. In certain embodiments, the production of one or more cytokines may be assessed (e.g., quantified) after contacting the compound with the iNKT cells. In some instances, the production of cytokines is assessed in real time (i.e., continuously monitored). In other instances, the production of cytokines is assessed at predetermined time intervals, such as every 1 minute, every 15 minutes, every 30 minutes, every 60 minutes, every 2 hours, every 4 hours, every 6 hours, every 12 hours, every 18 hours, including every 24 hours.

In some embodiments, contacting iNKT cells with one or more of the compounds of the present disclosure is sufficient to activate iNKT cells and to reduce the presence of or induce the killing of senescent cells. In certain embodiments, the senescent cells are senescent cells having an inflammatory secretome. For example, activating iNKT cells with the subject compounds according to these embodiments produces a cytotoxic effect against senescent cells. In some instances, methods include activating iNKT cells with the subject compounds in a manner sufficient to reduce the presence of or induce the killing of senescent cells in vitro. In some instances, methods include activating iNKT cells with the subject compounds in a manner sufficient to reduce the presence of or induce the killing of senescent cells in vivo (such as by administering the compound to a subject as part of a pharmaceutical composition described below). In some instances, activating iNKT cells with the subject compounds is sufficient to reduce the presence of senescent cells by 1% or more, such as by 2% or more, such as by 3% or more, such as by 4% or more, such as by 5% or more, such as by 10% or more, such as by 15% or more, such as by 20% or more, such as by 25% or more, such as by 50% or more, such as by 75% or more, such as by 90% or more, such as by 95% or more and including by 99% or more. In certain instances, the subject compounds eliminate the presence of senescent cells (e.g., where activation of iNKT cells reduces senescent present by 100%). The reduction in the presence of senescent cells may be assessed (e.g., quantified) after contacting the compound with the iNKT cells.

In some embodiments, iNKT cells activated by contact with the compounds described herein selectively reduce the presence of or selectively induce killing of senescent cells while maintaining (i.e., not killing) healthy cells. In some instances, contacting iNKT cells activated with the compounds of the present disclosure is sufficient to reduce the presence of senescent cells while maintaining 75% or more of the healthy cells, such as 80% or more, such as 85% or more, such as 90% or more, such as 95% or more, such as 97% or more, such as 99% or more, such as 99.9% or more and including 99.99% or more. In certain instances, iNKT cells activated by contact with compounds of the present disclosure selectively reduce the presence of senescent cells without any effect on healthy cells (i.e., 100% of healthy cells are maintained).

In some instances, the reduction of senescent cells may be assessed in real time (i.e., continuously monitored). In other instances, the reduction of senescent cells is assessed at predetermined time intervals, such as every 1 minute, every 15 minutes, every 30 minutes, every 60 minutes, every 2 hours, every 4 hours, every 6 hours, every 12 hours, every 18 hours, including every 24 hours.

Aspects of the present disclosure also include administering one or more of the compounds described herein to a subject in need thereof. In embodiments, the term "subject" is meant the person or organism to which the compound is administered. As such, subjects of the present disclosure may include but are not limited to mammals, e.g., humans and other primates, such as chimpanzees and other apes and monkey species, dogs, rabbits, cats and other domesticated pets; and the like, where in certain embodiments the subject are humans. The term "subject" is also meant to include a person or organism of any age, weight or other physical characteristic, where the subjects may be an adult, a child, an infant or a newborn.

In certain embodiments, the subject is diagnosed as having an autoimmune disease, fibrotic disorders (lung, kidney, liver), an allergic disease, a metabolic syndrome, type 2 diabetes. NAFLD. NASH, cancer, pathogen infection, rheumatoid arthritis, ulcerative colitis, multiple sclerosis, familial hypercholesteremia, giant cell arteritis, idiopathic pulmonary fibrosis, systemic lupus erythematosus, cachexia, glaucoma, chronic obstructive pulmonary disease, systemic sclerosis, pulmonary arterial hypertension, lipodystrophy, sarcopenia, alopecia, post myocardial infarction, vitiligo, POTS, MCAD, Sjogren's, Scleroderma, Hashimoto Disease, Ankylosing Spondylitis, Fibromyalgia, Sarcoidosis, Hepatitis, Raynauld's Syndrome, Mold Illness, Celiac, Crohn's, Pemphigus, SPS, PBC, Psoriatic Arthritis, CIDP, motor neuron disease, GPA, ALS, myasenthia gravis, and presbyopia. In some embodiments, the subject is diagnosed (e.g., by clinical laboratory test or by a qualified healthcare professional) as having or exhibiting at least one symptom of multiple sclerosis, articular rheumatism, psoriasis, Crohn's disease, leukoderma vulgaris, Behcet's disease, collagenosis, type I diabetes mellitus, uveitis, Sjogren's syndrome, autoimmune cardiomyotitis, autoimmune liver disease, autoimmune gastritis, pemphigus, Guillain-Barre syndrome, HTLV-1-related myelopathy or fulminant hepatitis.

In some embodiments, methods include administering one or more of the compounds to treat a subject for an infectious disease, such as one caused by a pathogenic microbe, including for example viruses, bacteria, fungi, protozoa and multicellular parasites. In one example, the infectious disease is by a virus selected from Retroviridae, Picornaviridae, Caliciviridae, Togaviridae, Flaviridae, Coronaviridae, Rhabdoviridae, Filoviridae, Paramyxoviridae, Orthomyxovindae, Bungaviridae, Arena viridae, Reovindae, Bimaviridae, Hepadnaviridae, Parvoviridae, Papovaviridae, Adenoviridae, Herpesviridae, Poxyiridae and Iridoviridae. In another example, the infectious disease is caused by a bacteria selected from *Helicobacter pylori, Borrelia burgdorferi, Legionella* pneumophilia, *Klebsiella pneumoniae, Mycobacteria* sps, *Staphylococcus aureus, Neisseria gonorrhoeae, Neisseria meningitidis, Listeria monocytogenes, Streptococcus pyogenes, Streptococcus agalactiae, Streptococcus, Streptococcus faecalis, Streptococcus bovis, Streptococcus pneumoniae,* pathogenic *Campylobacter* sp., *Enterococcus* sp., *Chlamydia* sp., *Haemophilus influenzae, Bacillus antracis, Corynebacterium diphtheriae, Corynebacterium* sp., *Erysipelothrix rhusiopathiae, Clostridium perfringens, Clostridium tetani, Enterobacter aerogenes. Klebsiella pneumoniae, Pasteurella multocida, Bacteroides* sp., *Fusobacterium nucleatum, Streptobacillus moniliformis, Treponema pallidium, Treponema pertenue, Leptospira, Actinomyces israelii, Sphingomonas capsulata* and *Francisella tularensis.*

Compounds as described herein may be administered to a subject by any convenient protocol, including, but not limited, to intraperitoneally, topically, orally, sublingually, parenterally, intravenously, vaginally, rectally as well as by transdermal protocols. In certain embodiments, the subject compounds are administered by intravenous injection. In certain embodiments, the subject compounds are administered by intraperitoneal injection.

Depending on the condition being treated, the amount of compound administered to the subject may vary, such as ranging from about 100 mg/day to about 10.000 mg/day, such as from about 10 mg/day to about 9000 mg/day, such as from 50 mg/day to about 8000 mg/day, such as from about 100 mg/day to about 7000 mg/day, such as from about 500 mg/day to about 6000 mg/day, including from about 600 mg/day to about 5000 mg/day. Each dosage of the compound or pharmaceutically acceptable salt administered to the subject may vary ranging from about 1 mg/kg to about 1000 mg/kg, such as from about 2 mg/kg to about 900 mg/kg, such as from about 3 mg/kg to about 800 mg/kg, such as from about 4 mg/kg to about 700 mg/kg, such as from 5 mg/kg to about 600 mg/kg, such as from 6 mg/kg to about 500 mg/kg, such as from 7 mg/kg to about 400 mg/kg, such as from about 8 mg/kg to about 300 mg/kg, such as from about 9 mg/kg to about 200 mg/kg and including from about 10 mg/kg to about 100 mg/kg.

In certain embodiments, protocols may include multiple dosage intervals. By "multiple dosage intervals" is meant that two or more dosages of the compound is administered to the subject in a sequential manner. In practicing methods of the present disclosure, treatment regimens may include two or more dosage intervals, such as three or more dosage intervals, such as four or more dosage intervals, such as five or more dosage intervals, including ten or more dosage intervals. The duration between dosage intervals in a multiple dosage interval treatment protocol may vary, depending on the physiology of the subject or by the treatment protocol as determined by a health care professional. For example, the duration between dosage intervals in a multiple dosage treatment protocol may be predetermined and follow at regular intervals. As such, the time between dosage intervals may vary and may be 1 day or longer, such as 2 days or longer, such as 4 days or longer, such as 6 days or longer, such as 8 days or longer, such as 12 days or longer, such as 16 days or longer and including 24 days or longer. In certain embodiments, multiple dosage interval protocols provide for a time between dosage intervals of 1 week or longer, such as 2 weeks or longer, such as 3 weeks or longer, such as 4 weeks or longer, such as 5 weeks or longer, including 6 weeks or longer.

The cycles of drug administration may be repeated for 1, 2, 3, 4, 5, 6, 7, 8 or more than 8 dosage cycles, for a total period of 6 months or 1 year or 2 years or 3 years or 4 years or more. In certain embodiments, one or more of the subject compounds are administered for the rest of the subject's lifetime.

In certain embodiments, compounds of the present disclosure can be administered prior to, concurrent with, or subsequent to other therapeutic agents for treating the same or an unrelated condition. If provided at the same time as another therapeutic agent, the present compounds may be administered in the same or in a different composition. Thus, the compounds of interest and other therapeutic agents can be administered to the subject by wav of concurrent therapy. By "concurrent therapy" is intended administration to a subject such that the therapeutic effect of the combination of the substances is caused in the subject undergoing therapy. For example, concurrent therapy may be achieved by administering the compounds of the present disclosure with a pharmaceutical composition having at least one other agent, such as an anti-inflammatory agent, immunosuppressant, steroid, analgesic, anesthetic, antihypertensive, chemotherapeutic, among other types of therapeutics, which in combination make up a therapeutically effective dose, according to a particular dosing regimen. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Where the compounds of the present disclosure is administered concurrently with a second therapeutic agent to treat the same condition (e.g., a chemotherapeutic, an anti-viral drug, etc.) the weight ratio of the subject compound to second therapeutic agent may range from 1:2 and 1:2.5; 1:2.5 and 1:3; 1:3 and 1:3.5 1:3.5 and 1:4; 1:4 and 1.4.5; 1.4.5 and 1:5; 1:5 and 1:10, and 1:10 and 1:25 or a range thereof. For example, the weight ratio of the subject compound to second therapeutic agent may range between 1.1 and 1:5; 1:5 and 1:10, 1:10 and 1.15; or 1:15 and 1:25. Alternatively, the weight ratio of the second therapeutic agent to the subject compound ranges between 2:1 and 2.5:1; 2.5:1 and 3:1; 3:1 and 3.5:1; 3.5:1 and 4:1; 4:1 and 4.5:1; 4.5:1 and 5:1; 5:1 and 10.1; and 10:1 and 25.1 or a range thereof. For example, the ratio of the second therapeutic agent the subject compound may range between 1:1 and 5:1, 5:1 and 10:1; 10:1 and 15:1; or 15:1 and 25:1.

Aspects of the present disclosure also include compositions having a pharmaceutically acceptable carrier and one or more of the compounds described above. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams. & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc. For example, the one or more excipients may include sucrose, starch, mannitol, sorbitol, lactose, glucose, cellulose, talc, calcium phosphate or calcium carbonate, a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange pow % der), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxy propylmethylcellulose), a diluent (e.g., water), and base wax (e.g., cocoa butter, white petrolatum or polyethylene glycol).

The compounds may be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In certain embodiments, the conjugate compounds are formulated for injection. For example, compositions of interest may be formulated for intravenous or intraperitoneal administration.

In certain embodiments, compositions of interest include liposomal or micellar compositions where the compounds described herein are liposome-based formulations or micelle-based formulations. The liposome-based formulation or micelle-based formulation of the subject compounds may be prepared by any convenient liposome or micelle forming protocol, such as for example by mechanical dispersion, solvent dispersion, or a detergent removal method. In certain instances, liposomes are formed by mechanical dispersion including by sonication. French pressure cell extrusion, freeze-thawing, lipid film hydration (e.g., by hand-shaking, mechanical agitation or freeze drying), micro-emulsification, membrane extrusion or using dried reconstituted vesicles. In certain embodiments, liposome-based formulations of the compounds described herein are prepared by thin-film rehydration followed by extrusion (e.g., through a filter of 5 nm or more, such as 10 nm or more, such as 25 nm or more, such as 50 nm or more, such as 100 nm or more, such as 150 nm or more, such as 200 nm or more, such as 250 nm or more, such as 300 nm or more and including extrusion through a filer of 500 nm or more).

In some embodiments, the liposome-based formulation or micelle-based formulation may be formed from a non-polymeric carrier material including but not limited to: sterols such as cholesterol, stigmasterol, β-sitosterol, and estradiol; cholestery esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate, $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphoethanolamine, phosphoethanolamine-PEG(2000), phosphatidylethanolamine, phosphatidylinositol, and lysoderivatives thereof; sphingosine and derivatives thereof; sphingomyelins such as stearyl, palmitoyl, and tricosanoyl sphingomyelins; ceramides such as stearyl and palmitoyl ceramides; glycosphingolipids; lanolin and lanolin alcohols; and combinations and mixtures thereof. In certain embodiments, liposome-formulated compounds include phosphatidylcholine and cholesterol.

Each component used to prepare the liposome formulation or micelle formulation may vary as desired and may be present in an amount of 0.001 wt % or more for the liposome or micelle formulation, such as 0.005 wt % or more, such as 0.010 wt % or more, such as 0.05 wt % or more, such as 0.1 wt % or more, such as 0.5 wt % or more, such as 1 wt % or more, such as 2 wt % or more, such as 3 wt % or more, such as 4 wt % or more and including where each component is present an in amount of 5 wt % or more. Where more than one component is present (e.g., a phospholipid such as phosphatidylcholine and cholesterol), the ratio of the components may range from 0.001:1 to 1:0.001, such as from 0.005:1 to 1:0.005, such as from 0.01:1 to 1:0.01, such as from 0.05:1 to 1:0.05, such as from 0.1:1 to 1:0.1, such as from 0.5:1 to 1:0.5, such as from 0.6:1 to 1:0.6, such as from 0.7:1 to 1:0.7, such as from 0.8:1 to 1:0.8, such as from 0.9:1 to 1:0.9 and including where the ratio of the components is 1:1 (e.g., phosphatidylcholine to cholesterol ratio of 1:1). In one example, the liposome or micelle formulation may include a phospholipid component (e.g., phosphatidylcholine) and cholesterol, such as in a ratio that ranges from 0.001:1 to 1:0.001, such as from 0.005:1 to 1:0.005, such as from 0.01:1 to 1:0.01, such as from 0.05:1 to 1:0.05, such as from 0.1:1 to 1:0.1, such as from 0.5:1 to 1:0.5, such as from 0.6:1 to 1:0.6, such as from 0.7:1 to 1:0.7, such as from 0.8:1 to 1:0.8, such as from 0.9:1 to 1:0.9 and including where the ratio of the components is 1:1 In certain instances, the ratio of phospholipid component to cholesterol is about 2:1.

The compounds described herein (e.g., compounds of formula DCD-(I) or DCD-(II)) may be present in the liposome or micelle formulation in an amount of 0.001 wt % or more of the formulation, such as 0.005 wt % or more, such as 0.010 wt % or more, such as 0.05 wt % or more, such as 0.1 wt % or more, such as 0.5 wt % or more, such as 1 wt % or more, such as 2 wt % or more, such as 3 wt % or more, such as 4 wt % or more and including where the active agent compound is present an in amount of 5 wt % or more. The ratio of active agent compound (e.g., compound for activating invariant natural killer T cells such as a compound of formula DCD-(I) of DCD-(II)) to each liposome component may range from 0.001:1 to 1:0.001, such as from 0.005:1 to 1:0.005, such as from 0.01:1 to 1:0.01, such as from 0.05:1 to 1:0.05, such as from 0.1:1 to 1:0.1, such as from 0.5:1 to 1:0.5, such as from 0.6:1 to 1:0.6, such as from 0.7:1 to 1:0.7, such as from 0.8:1 to 1:0.8, such as from 0.9:1 to 1:0.9 and including a ratio of the components is 1:1. In certain instances, the ratio is from 1:0.15 or 2:0.15. For example, a composition may include phosphatidylcholine, cholesterol and an active agent compound at a ratio of 2:1:0.15.

In certain embodiments, liposome formulations or micelle formulations may include an organic solvent, such for example one or more organic solvents selected from sterols such as cholesterol, stigmasterol, β-sitosterol, and estradiol; cholestery esters such as cholesteryl stearate; C12-C24 fatty acids such as lauric acid, myristic acid, palmitic acid, stearic acid, arachidic acid, behenic acid, and lignoceric acid; C18-C36 mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; C16-C18 fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphoethanolamine, phosphoethanolamine-PEG(2000), phosphatidylethanolamine, phosphatidylinositol, and lysoderivatives thereof, sphingosine and derivatives thereof; sphingomyelins such as stearyl, palmitoyl, and tricosanoyl sphingomyelins; ceramides such as stearyl and palmitoyl ceramides; glycosphingolipids; lanolin and lanolin alcohols; and combinations and mixtures thereof.

In pharmaceutical dosage forms, the compounds may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, compositions of interest include an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. In some instances, compositions of interest further include a preservative. Suitable preservatives include, but are not limited to, a benzyl alcohol, phenol, chlorobutanol, benzalkonium chloride, and the like. In many cases, the composition is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some embodiments, compositions include other additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Where the composition is formulated for injection, the compounds may be formulated by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Although the dosage used in treating a subject will vary depending on the clinical goals to be achieved, a suitable dosage range of the compound is one which provides up to about 0.0001 mg to about 5000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, from about 500 mg to about 1000 mg, or from about 1000 mg to about 5000 mg of an active agent, which can be administered in a single dose. Those of skill will readily appreciate that dose levels can vary as a function of the specific compound, the severity of the symptoms and the susceptibility of the subject to side effects.

In some embodiments, a single dose of the compound is administered. In other embodiments, multiple doses of the compound are administered. Where multiple doses are administered over a period of time, the compound may be administered, e.g., twice daily (qid), daily (qd), every other day (qod), every third day, three times per week (tiw), or twice per week (biw) over a period of time. For example, the compound may be administered qid, qd, qod, tiw, or biw over a period of from one day to about 2 years or more. For example, the compound may be administered at any of the aforementioned frequencies for one week, two weeks, one month, two months, six months, one year, or two years, or more, depending on various factors.

Dose units of the present disclosure can be made using manufacturing methods available in the art and can be of a variety of forms suitable for injection (including topical, intracisternal, intrathecal, intravenous, intramuscular, subcutaneous and dermal) administration, for example as a solution, suspension, solution, lyophilate or emulsion. The dose unit can contain components conventional in pharmaceutical preparations, e.g. one or more carriers, binders, lubricants, excipients (e.g., to impart controlled release characteristics), pH modifiers, coloring agents or further active agents.

Dose units can comprise components in any relative amounts. For example, dose units can be from about 0.1% to 99% by weight of active ingredients (i.e., compounds described herein) per total weight of dose unit. In some embodiments, dose units can be from 10% to 50%, from 20% to 40%, or about 30% by weight of active ingredients per total weight dose unit.

Aspects, including embodiments, of the subject matter described herein may be beneficial alone or in combination, with one or more other aspects or embodiments. Without limiting the description, certain non-limiting aspects of the disclosure numbered 1-99 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A compound of formula DCD-(I):

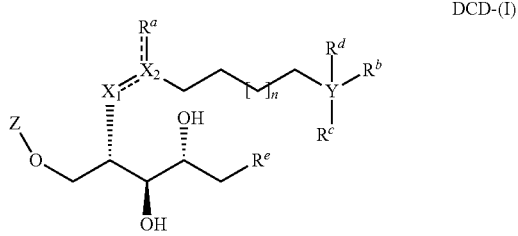

wherein:
Z is selected from:

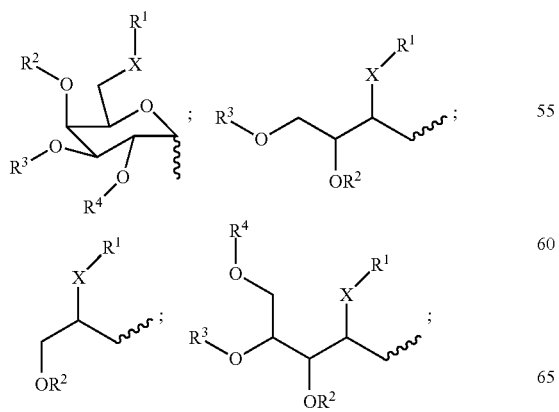

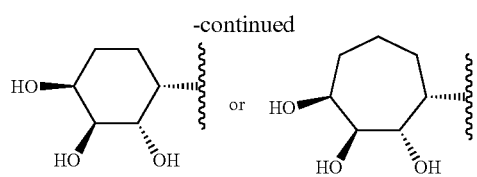

wherein ～ indicates the Z—O bond;
wherein X is —NHCO— or oxygen;
$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
$X_1$ and $X_2$ are each independently selected from —C, —NR$^j$, —O, —SR$^k$, —Si, wherein $R^j$ and $R^k$ are each independently selected from hydrogen, alkyl or substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
$R^a$ is selected from hydrogen, oxygen, fluorine, —CF$_3$, or together with $X_2$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl;
wherein ═══ indicates a double or single bond;
n is an integer from 2 to 25,
Y is selected from carbon, nitrogen or silicon;
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and
$R^e$ is alkyl or substituted alkyl,
or salt, solvate or hydrate thereof.

2. The compound according to 1, wherein $R^1$, $R^2$, $R^3$ and $R^4$ are each hydrogen.
3. The compound according to 1, wherein $R^1$ is hydrogen.
4. The compound according to any one of 1-3, wherein $R^1$ is:

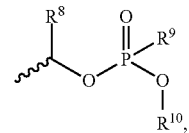

wherein ～ indicates the $R^1$—O bond;
$R^8$ is hydrogen, alkyl, substitute alkyl;
$R^9$ is —NR$^f$ or —OR$^f$, wherein $R^f$ is alkyl, substituted alkyl, acyl, alkylacyl or substituted alkylacyl, or wherein $R^f$ together with $R^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and $R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with $R^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

5. The compound according to 4, wherein $R^1$ is selected from:

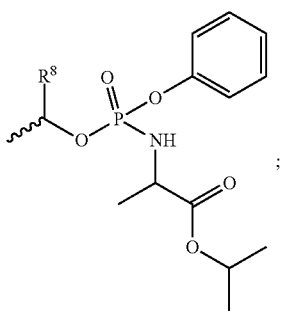

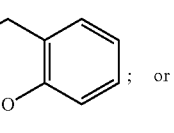 ; or 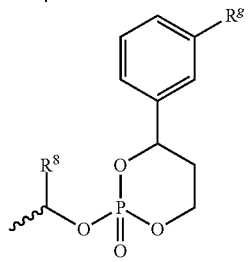

wherein ∼∼ indicates the $R^1$—O bond;

$R^8$ is hydrogen, alkyl, substitute alkyl; and $R^g$ is hydrogen or a halogen selected from fluorine, chlorine, bromine or iodine.

6. The compound according to any one of 1-3, wherein $R^1$ is:

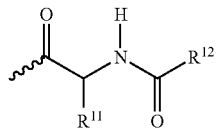

wherein:

$R^{11}$ is alkyl or substituted alkyl;

$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

7. The compound according to 6, wherein $R^1$ is:

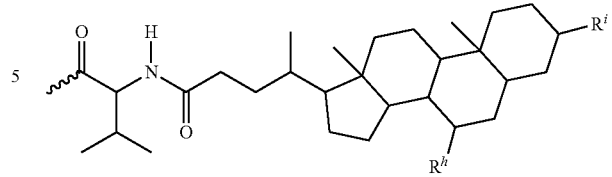

wherein $R^h$ and $R^i$ are each independently selected from hydrogen, hydroxyl or a halogen selected from F, Cl, I or Br.

8. The compound according to any one of 1-7, wherein $X_1$ is —NH.

9. The compound according to 8, wherein:
$R^a$ is O;
$X_2$ is C; and

is carbonyl.

10. The compound according to 8, wherein:
$R^a$ is O;
$X_2$ is —$SR^k$, wherein $R^k$ is methyl; and

is sulfur oxide.

11. The compound according to 8, wherein:
$R^a$ is $CF_3$; and
$X_2$ is C.

12. The compound according to 8, wherein $R^a$ together with $X^2$ form a heterocycloalkyl or substituted heterocycloalkyl.

13. The compound according to 12, wherein $R^a$ together with $X_2$ forms an oxacyclobutane.

14. The compound according to any one of 1-7, wherein:
$R^a$ is F;
$X_1$ is C;
$X_2$ is C; and
--- is a double bond.

15. The compound according to any one of 1-14, wherein $R^e$ is a C8 to C20 alkyl or substituted C8 to C20 alkyl.

16. The compound according to 19, wherein $R^e$ is a C13 alkyl.

17. The compound according to any one of 1-16, wherein $R^d$ is a C5 to C25 alkyl or a C5 to C25 alkyl substituted with a cycloalkyl group, substituted cycloalkyl group, heterocycloalkyl group, substituted heterocycloalkyl group, aryl group, substituted aryl group, arylalkyl group, substituted arylalkyl group, heteroaryl group, substituted heteroaryl group, heteroarylalkyl group, or substituted heteroarylalkyl group.

18. The compound according to 17, wherein $R^d$ is a C5 to C25 alkyl substituted with a moiety selected from the group consisting of:

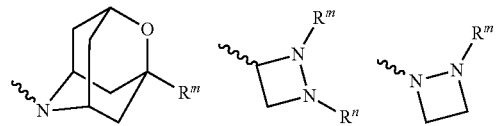

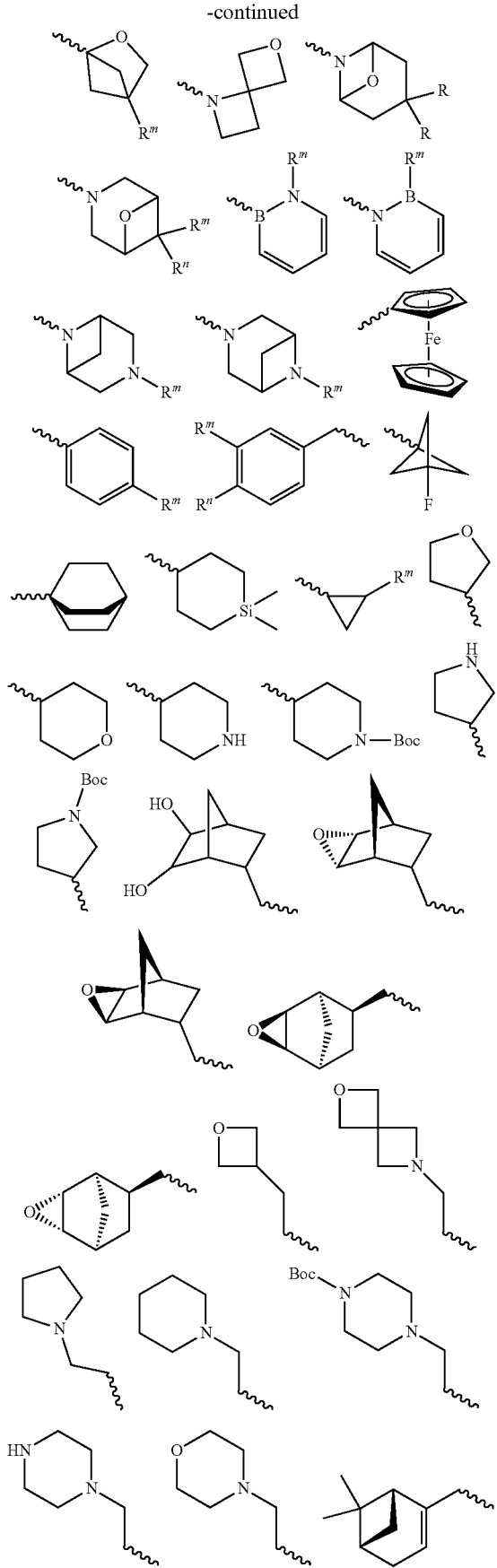
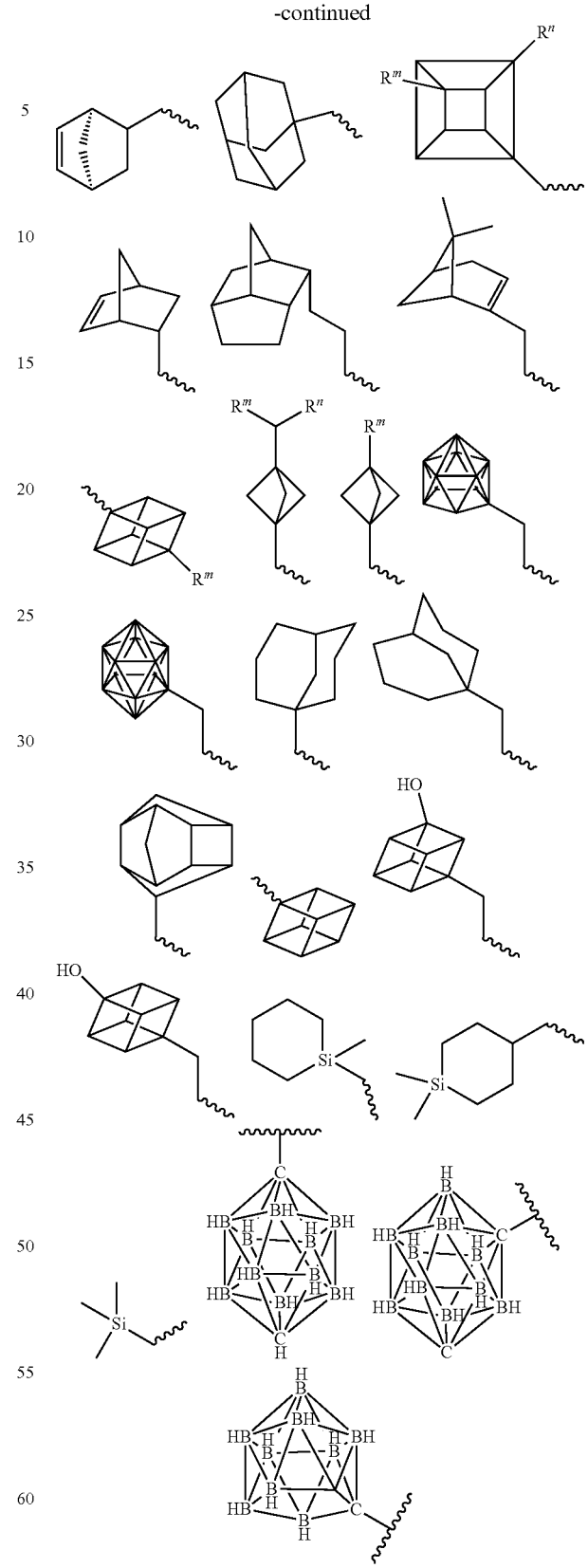
wherein ⁓ indicates the bond to the C5 to C25 alkyl; $R^m$ and $R^n$ are independently selected from hydrogen, halogen, hydroxyl, substituted hydroxyl, amino, substituted amino, thiol, substituted thiol, sulfoxide, substituted sulfoxide, sulfone, substituted sulfone, sulfoximine, substituted sulfoximine, acyl, aminoacyl, alkyl, substituted alkyl; heteroalkyl, substituted heteroalkyl, cycloalkyl, substituted cycloalkyl, spiroalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

19. The compound according to 18, wherein $R^m$ is hydrogen.
20. The compound according to 18, wherein $R^m$ is halogen.
21. The compound according to 20, wherein $R^m$ is selected from fluorine, bromine or iodine.
22. The compound according to any one of 18-21, wherein $R^n$ is hydrogen.
23. The compound according to 18-21, wherein $R^n$ is halogen.
24. The compound according to 23, wherein $R^n$ is fluorine, bromine or iodine.
25. The compound according to any one of 1-24, wherein $R^b$ is hydrogen.
26. The compound according to any one of 1-24, wherein $R^b$ is selected from the group consisting of methyl, ethyl, propyl, butyl and

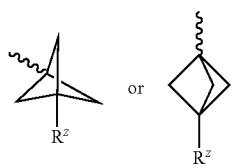

wherein ∽ indicates a bond to Y and $R^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, R is alkyl, such as a C1 to C16 alkyl or C1 to C16 substituted alkyl.

27. The compound according to any one of 1-24, wherein $R^b$ is:

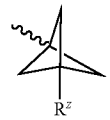

wherein ∽ indicates a bond to Y and $R^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, $R^z$ is alkyl, such as a C1 to C16 alkyl or C1 to C16 substituted alkyl.

28. The compound according to any one of 1-24, wherein $R^b$ is:

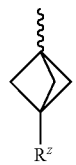

wherein ∽ indicates a bond to Y and $R^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, $R^z$ is alkyl, such as a C1 to C16 alkyl or C1 to C16 substituted alkyl.

29. The compound according to any one of 1-28, wherein $R^c$ is a C1 to C10 alkyl.
30. The compound according to 26, wherein $R^c$ is selected from the group consisting of methyl, ethyl, propyl and butyl.
31. The compound according to 1, wherein the compound is selected from the group consisting of:

| Compound No. | Structure |
|---|---|
| DCD-101 | ![structure] |
| DCD-113 | ![structure] |

| Compound No. | Structure |
|---|---|
| DCD-102 | 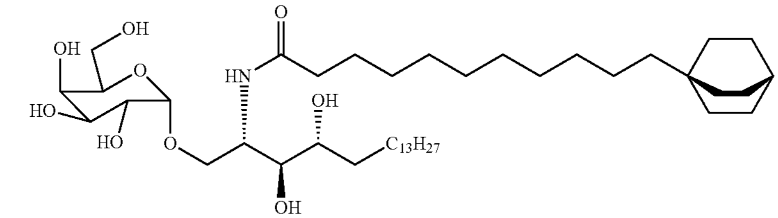 |
| DCD-103 | 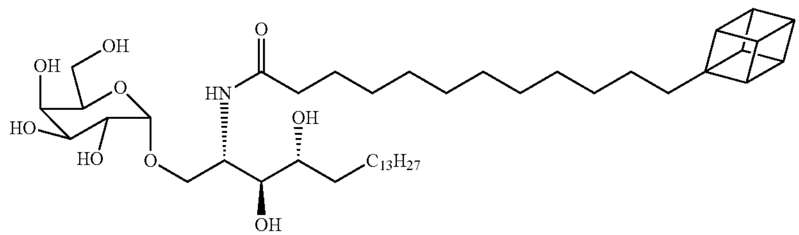 |
| DCD-106 | 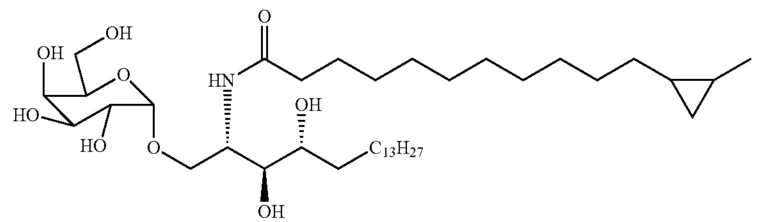 |

32. A method comprising contacting invariant natural killer T (iNKT) cells with a compound according to any one of 1-31.

33. The method according to 32, wherein the iNKT cells are contacted in vitro.

34. The method according to 32, wherein the iNKT cells are contacted in vivo.

35. The method according to any one of 32-34, wherein contacting the compound with the iNKT cells is sufficient to activate the iNKT cells.

36. The method according to 35, wherein activating the iNKT cells induce an increase in production of one or more cytokines selected from the group consisting of IFN-γ, IL-1β, IL-2, IL-3, IL-8, IL-12, IL-15, TNF-α, GM-CSF, RANTES, MIP-1α and MCP-1.

37. The method according to 35, wherein activating the iNKT cells induce an increase in production of one or more cytokines selected from the group consisting of IL-4, IL-6, IL-8, IL-10 and IL-13.

38. The method according to any one of 35-37, wherein the method further comprises contacting the activated iNKT cells with a composition comprising senescent cells, wherein contacting the activated iNKT cells reduces the presence of or eliminates the senescent cells in the composition.

39. The method according to 39, wherein the senescent cells comprise an inflammatory secretome.

40. The method according to any one of 38-39, wherein the composition further comprises healthy cells.

41. The method according to 40, wherein contacting the activated iNKT cells reduces the presence of or eliminates the senescent cells in the composition without reducing the presence of the healthy cells.

42. The method according to 41, wherein the presence of healthy cells is reduced by 5% or less when the composition is contacted with the activated iNKT cells.

43. A method comprising administering a compound according to any one of 1-31 to a subject in need thereof.

44. A method for selectively reducing the presence of or eliminating senescent cells in a subject, the method comprising administering a compound according to any one of 1-31 to a subject in need thereof.

45. The method according to 36, wherein the subject is diagnosed as having an autoimmune disease, an allergic disease, a metabolic disorder, cancer or a pathogen infection.

46. The method according to 45, wherein the subject is diagnosed as having one or more of a metabolic disorder, an eye disease, a disease of aging, fibrosis, heart disease, kidney disease.

47. A pharmaceutical composition comprising:
a compound according to any one of 1-31; and
a pharmaceutically acceptable carrier.

48. A pharmaceutical composition for selectively reducing the presence of or eliminating senescent cells in a subject, the composition comprising:
a compound according to any one of 1-31; and
a pharmaceutically acceptable carrier.

49. Use of a compound according to any one of 1-31 in the manufacture of a medicament for treating a subject in need thereof.

50. Use of a compound according to any one of 1-31 in the manufacture of a medicament for selectively reducing the presence of or eliminating senescent cells in a subject in need thereof.

51. A compound of formula DCD-(11):

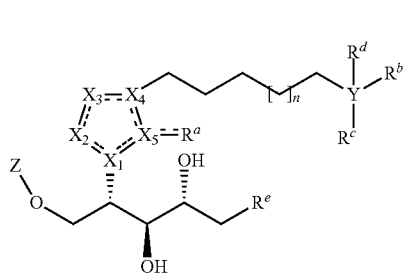

wherein:

Z is selected from:

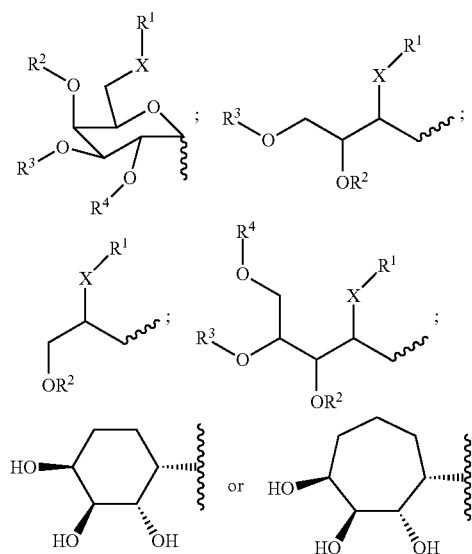

wherein ∿∿ indicates the Z—O bond;
wherein X is —NHCO— or oxygen;
$R^1$, $R^2$, $R^3$ and $R^4$ are each independently selected from hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted aryalkyl, heteroaryl, substituted heteroaryl, heteroarylalkyl, and substituted heteroarylalkyl;
$X_1$, $X_2$, $X_3$, $X_4$ and $X_5$ are each independently selected from carbon, nitrogen, oxygen or sulfur;
$R^a$ is optionally absent or when present is selected from hydrogen or oxygen;
wherein ≡≡≡ indicates a double or single bond,
n is an integer from 2 to 25;
Y is selected from carbon, nitrogen or silicon;
$R^b$, $R^c$ and $R^d$ are independently selected hydrogen, alkyl, substituted alkyl, heteroalkyl, substituted heteroalkyl, cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl, wherein when Y is nitrogen, $R^d$ is not present, or wherein $R^c$ and $R^d$ together with Y form a cycloalkyl, substituted cycloalkyl, aryl, substituted aryl, heteroaryl or substituted heteroaryl group; and $R^e$ is alkyl or substituted alkyl, or salt, solvate or hydrate thereof.

52. The compound according to 51, wherein $R^1$, $R^2$, $R^3$ and $R^4$ are each hydrogen.

53. The compound according to 52, wherein $R^1$ is hydrogen.

54. The compound according to any one of 51-53, wherein $R^1$ is:

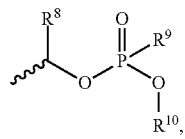

wherein ∿∿ indicates the $R^1$—O bond;
$R^d$ is hydrogen, alkyl, substitute alkyl;
$R^9$ is —$NR^f$ or —$OR^f$,
  wherein $R^f$ is alkyl, substituted alkyl, acyl, alkylacyl or substituted alkylacyl,
  or wherein $R^f$ together with $R^{10}$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl; and
$R^{10}$ is cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl or wherein $R^{10}$ together with $R^f$ form a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

55. The compound according to 54, wherein $R^1$ is selected from:

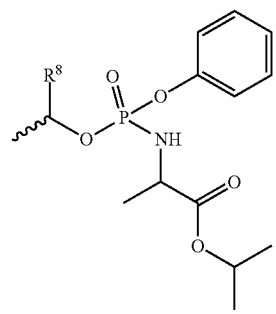

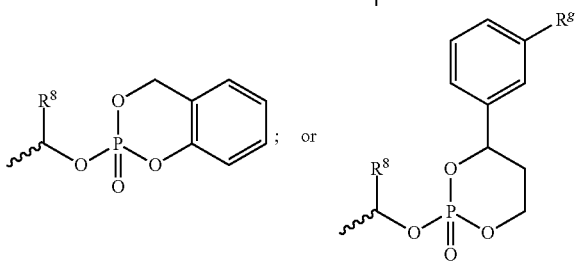

wherein ∿∿ indicates the $R^1$—O bond;
$R^8$ is hydrogen, alkyl, substitute alkyl; and
$R^g$ is hydrogen or a halogen selected from F, Cl, I or Br.

56. The compound according to any one of 51-55, wherein $R^1$ is:

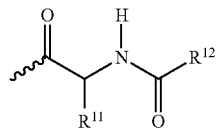

wherein:
$R^{11}$ is alkyl or substituted alkyl;
$R^{12}$ is alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

57. The compound according to 56, wherein $R^1$ is:

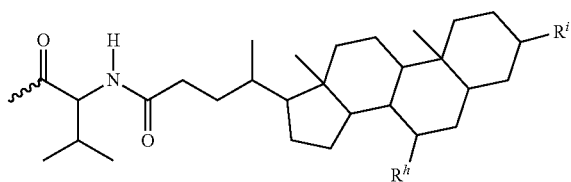

wherein $R^h$ and $R^i$ are each independently selected from hydrogen, hydroxyl or a halogen selected from F, Cl, I or Br.

58. The compound according to any one of 51-57, wherein $X_1$, $X_2$, $X_3$, $X_4$ and $X_5$ together form a pyrazole.

59. The compound according to any one of 51-57, wherein $X_1$, $X_2$, $X_3$, $X_4$ and $X_5$ together form an imidazole.

60. The compound according to any one of 51-57, wherein $X_1$, $X_2$, $X_3$, $X_4$ and $X_5$ together form a tetrazole.

61. The compound according to any one of 51-57, wherein:
$X_1$ is carbon;
$X_2$ is nitrogen;
$X_3$ is nitrogen;
$X_4$ is carbon; and
$X_5$ is carbon.

62. The compound according to any one of 51-57, wherein:
$X_1$ is carbon;
$X_2$ is nitrogen;
$X_3$ is carbon;
$X_4$ is carbon; and
$X_5$ is nitrogen.

63. The compound according to any one of 51-57, wherein:
$X_1$ is nitrogen;
$X_2$ is nitrogen;
$X_3$ is nitrogen;
$X_4$ is nitrogen;
$X_5$ is carbon;
$R^a$ is O, wherein

is carbonyl.

64. The compound according to any one of 51-63, wherein $R^e$ is a C8 to C20 alkyl or substituted C8 to C20 alkyl.

65. The compound according to 64, wherein $R^e$ is a C13 alkyl.

66. The compound according to any one of 51-65, wherein $R^d$ is a C5 to C25 alkyl or a C5 to C25 alkyl substituted with a cycloalkyl group, substituted cycloalkyl group, heterocycloalkyl group, substituted heterocycloalkyl group, aryl group, substituted aryl group, arylalkyl group, substituted arylalkyl group, heteroaryl group, substituted heteroaryl group, heteroarylalkyl group, or substituted heteroarylalkyl group 67. The compound according to 66, wherein $R^d$ is a C5 to C25 alkyl substituted with a moiety selected from the group consisting of:

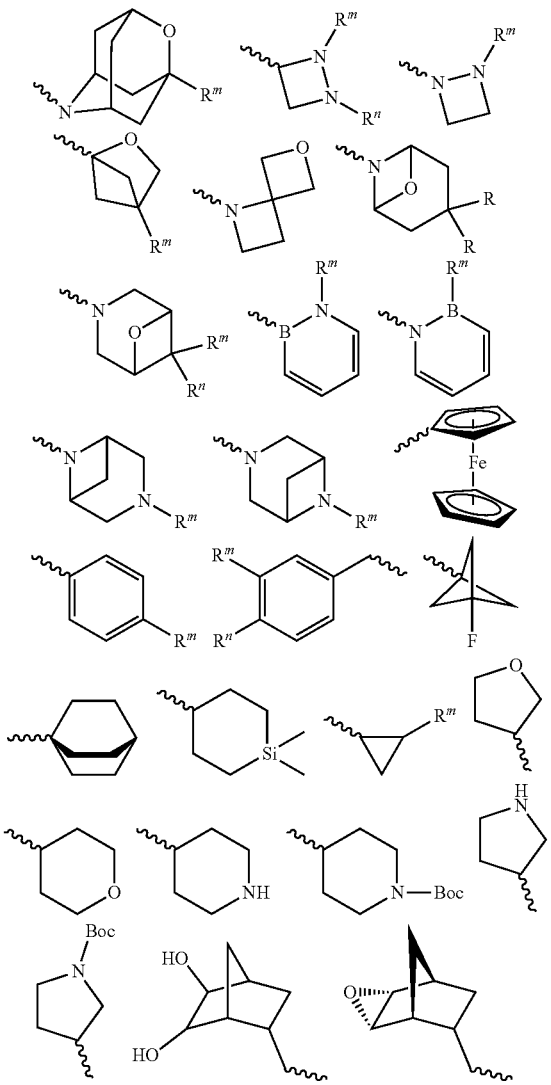

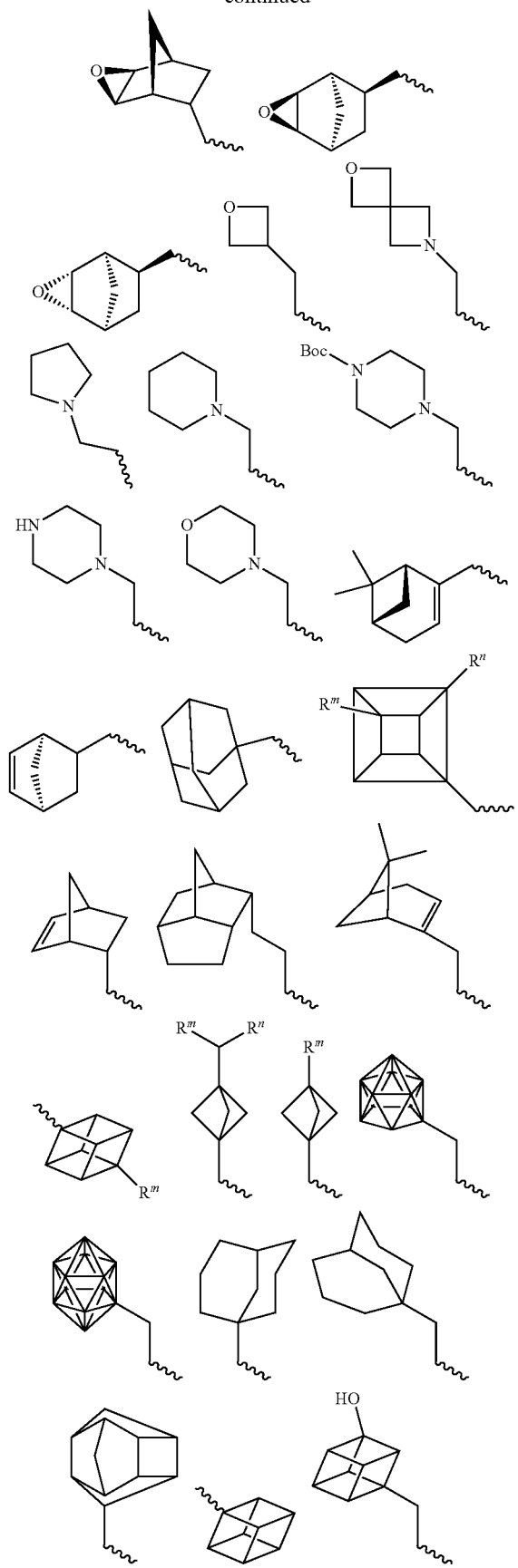

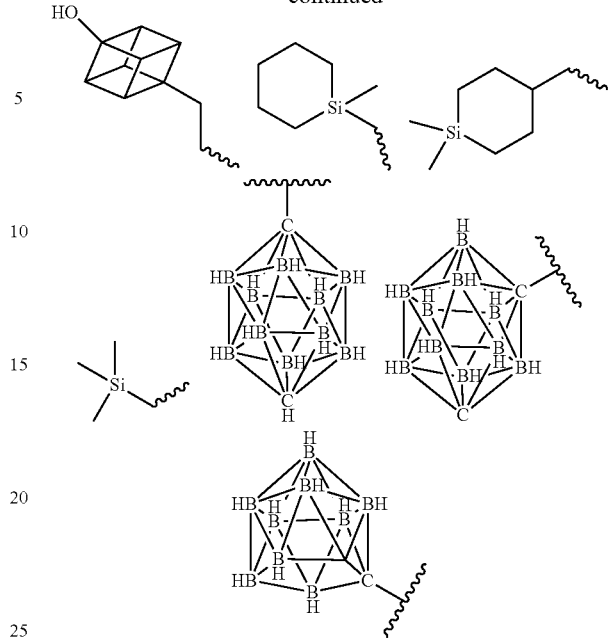

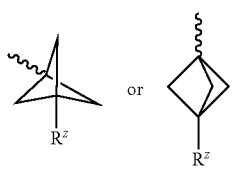

wherein ⁓ indicates the bond to the C5 to C25 alkyl; and $R^m$ and $R^n$ are independently selected from hydrogen, halogen, hydroxyl, substituted hydroxyl, amino, substituted amino, thiol, substituted thiol, sulfoxide, substituted sulfoxide, sulfone, substituted sulfone, sulfoximine, substituted sulfoximine, acyl, aminoacyl, alkyl, substituted alkyl; heteroalkyl, substituted heteroalkyl, cycloalkyl, substituted cycloalkyl, spiroalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl.

68. The compound according to 67, wherein $R^m$ is hydrogen.
69. The compound according to 67, wherein $R^m$ is halogen.
70. The compound according to 69, wherein $R^m$ is selected from fluorine, bromine or iodine.
71. The compound according to any one of 67-70, wherein $R^n$ is hydrogen.
72. The compound according to 67-70, wherein $R^n$ is halogen.
73. The compound according to 72, wherein $R^n$ is fluorine, bromine or iodine.
74. The compound according to any one of 51-73, wherein $R^b$ is hydrogen.
75. The compound according to any one of 51-73, wherein $R^b$ is selected from the group consisting of methyl, ethyl, propyl, butyl and wherein ∿ indicates a bond to Y and $R^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, $R^2$ is alkyl, such as a C1 to C16 alkyl or C1 to C16 substituted alkyl.

76. The compound according to any one of 51-73, wherein $R^b$ is:

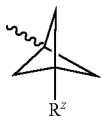

wherein ∿ indicates a bond to Y and $R^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, $R^z$ is alkyl, such as a C1 to C16 alkyl or C1 to C16 substituted alkyl.

77. The compound according to any one of 51-73, wherein $R^b$ is:

wherein ∿ indicates a bond to Y and $R^z$ is hydrogen, alkyl or alkyl substituted with a cycloalkyl, substituted cycloalkyl, heterocycloalkyl, substituted heterocycloalkyl, aryl, substituted aryl, arylalkyl, substituted arylalkyl, heteroaryl, substituted heteroaryl, heteroarylalkyl, and substituted heteroarylalkyl. In certain instances, $R^z$ is alkyl, such as a C1 to C16 alkyl or C1 to C16 substituted alkyl.

78. The compound according to any one of 51-77, wherein $R^e$ is a C1 to C10 alkyl.
79. The compound according to 78, wherein $R^e$ is selected from the group consisting of methyl, ethyl, propyl and butyl.
80. The compound according to 51, wherein the compound is selected from Compound DCD-104 and DCD-105:

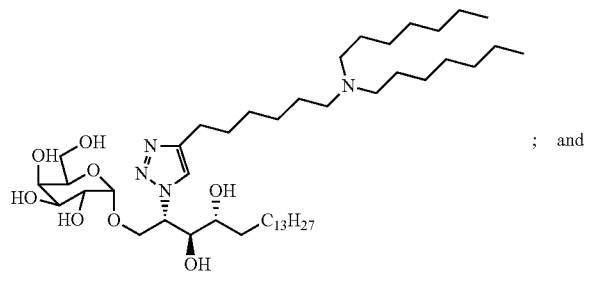

DCD-104

; and

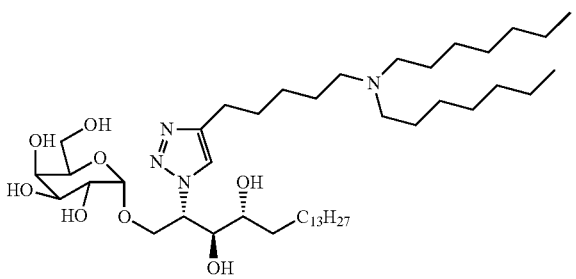

DCD-105

81. A method comprising contacting invariant natural killer T (iNKT) cells with a compound according to any one of 51-80.
82. The method according to 81, wherein the iNKT cells are contacted in vitro.
83. The method according to 81, wherein the iNKT cells are contacted in vivo.
84. The method according to any one of 81-83, wherein contacting the compound with the iNKT cells is sufficient to activate the iNKT cells.
85. The method according to 84, wherein activating the iNKT cells induce an increase in production of one or more cytokines selected from the group consisting of IFN-γ, IL-1β, IL-2, IL-3, IL-8, IL-12, IL-15, TNF-α, GM-CSF, RANTES, MIP-1α and MCP-1.
86. The method according to 84, wherein activating the iNKT cells induce an increase in production of one or more cytokines selected from the group consisting of IL-4, IL-6, IL-8, IL-10 and IL-13.
87. The method according to any one of 84-86, wherein the method further comprises contacting the activated iNKT cells with a composition comprising senescent cells, wherein contacting the activated iNKT cells reduces the presence of or eliminates the senescent cells in the composition.
88. The method according to 87, wherein the senescent cells comprise an inflammatory secretome.
89. The method according to any one of 87-88, wherein the composition further comprises healthy cells.
90. The method according to 89, wherein contacting the activated iNKT cells reduces the presence of or eliminates the senescent cells in the composition without reducing the presence of the healthy cells.
91. The method according to 90, wherein the presence of healthy cells is reduced by 5% or less when the composition is contacted with the activated iNKT cells.
92. A method comprising administering a compound according to any one of 51-80 to a subject in need thereof.
93. A method for selectively reducing the presence of or eliminating senescent cells in a subject, the method comprising administering a compound according to any one of 51-80 to a subject in need thereof.
94. The method according to 93, wherein the subject is diagnosed as having an autoimmune disease, an allergic disease, a metabolic disorder, cancer or a pathogen infection.
95. The method according to 93, wherein the subject is diagnosed as having one or more of a metabolic disorder, an eye disease, a disease of aging, fibrosis, heart disease, kidney disease.

96. A pharmaceutical composition comprising:
   a compound according to any one of 51-80; and
   a pharmaceutically acceptable carrier.
97. A pharmaceutical composition for selectively reducing the presence of or eliminating senescent cells in a subject, the composition comprising:
   a compound according to any one of 51-80; and
   a pharmaceutically acceptable carrier.
98. Use of a compound according to any one of 51-80 in the manufacture of a medicament for treating a subject in need thereof.
99. Use of a compound according to any one of 51-80 in the manufacture of a medicament for selectively reducing the presence of or eliminating senescent cells in a subject in need thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for.

Example 1—Synthesis of Compounds

General Synthetic Procedures

Many general references providing commonly known chemical synthetic schemes and conditions useful for synthesizing the disclosed compounds are available (see. e.g., Smith and March, March's Advanced Organic Chemistry: Reactions. Mechanisms, and Structure, Fifth Edition, Wiley-Interscience, 2001; or Vogel, A Textbook of Practical Organic Chemistry. Including Qualitative Organic Analysis. Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979, and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis". Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

The nomenclature used herein to name the subject compounds is illustrated in the Examples herein. When possible, this nomenclature has generally been derived using the commercially-available Auto Nom software (MDL, San Leandro. Calif.).

The compounds of the present disclosure may be prepared by various methods. Enclosed herein are exemplary methods of making compounds described herein.

Synthesis of (2S,3S,4R)-2-azidooctadecane-1,3,4-triol

Reference is made to *ChemBioChem* 2012, 13, 1689-1697 and *Eur. J. Org. Chem,* 1998, 291-229

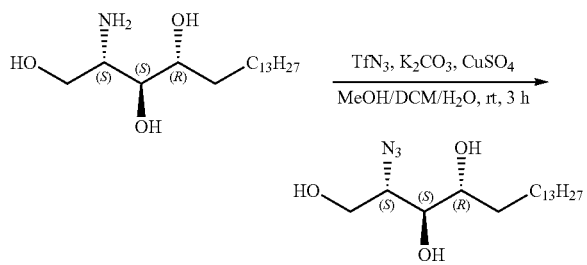

A mixture of DCM (25 mL) and H$_2$O (25 mL) containing NaN$_3$ (10 g, 153 mmol) cooled to 0° C., and Tf$_2$O (5.5 mL, 31.5 mmol) was added dropwise over 20 min. After addition, the resulting mixture was stirred at rt for 3 h. The organic layer was separated, and the aqueous portion was extracted with DCM (2×50 mL). The combined organic layers were washed with saturated aqueous Na$_2$CO$_3$ and used directly in the next step.

To a suspension of (2S,3S,4R)-2-aminooctadecane-1,3,4-triol (5 g, 15.5 mmol), K$_2$CO$_3$ (10.9 g, 79.0 mmol), and CuSO$_4$ (100 mg) in a mixture of MeOH (30 mL) and H$_2$O (30 mL) was added the above organic DCM layer, which contained TfN$_3$. More MeOH was added to make the mixture a homogeneous solution. The reaction mixture was stirred overnight at room temperature. The organic solvent was removed under vacuum and the aqueous layer was extracted with EtOAc. The organic layer was dried over anhydrous Na₂SO₄, filtered and concentrated wider reduced pressure to afford a crude residue that was purified by silica gel column chromatography (PE/EtOAc 1:1) to give (2S,3S,4R)-2-azidooctadecane-1,3,4-triol (4.5 g, 83%) as an oil.

Synthesis of (2S,3S,4R)-2-azido-1-(trityloxy)octadecane-3,4-diol

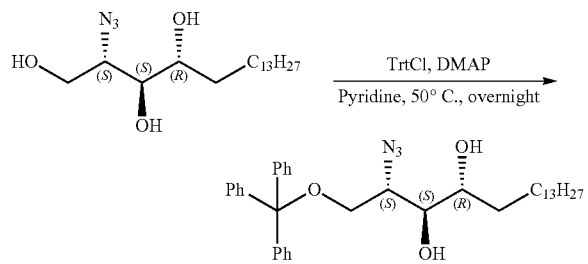

A mixture of (2S,3S,4R)-2-azidooctadecane-1,3,4-triol (6.00 g, 17.5 mmol, 1.0 eq), TrtCl (6.8 g, 24.4 mmol, 1.4 eq) and DMAP (213 mg, 1.74 mmol, 0.1 eq) in dry pyridine (100 mL) was stirred at 50° C. overnight. Pyridine was removed under reduced pressure and the residue was diluted with EtOAc (200 mL), washed with water (2×50 mL), brine (2×50 mL), dried over Na₂SO₄ and concentrated under reduced pressure. The residue was purified by column chromatography on silica gel (120 g; EtOAc/PE 1:2) to give (2S,3S,4R)-2-azido-1-(trityloxy)octadecane-3,4-diol (9 g, 88%) as an oil.

Synthesis of (((2S,3S,4R)-2-azido-3,4-bis(benzyloxy)octadecyloxy)methanetriyl)tribenzene

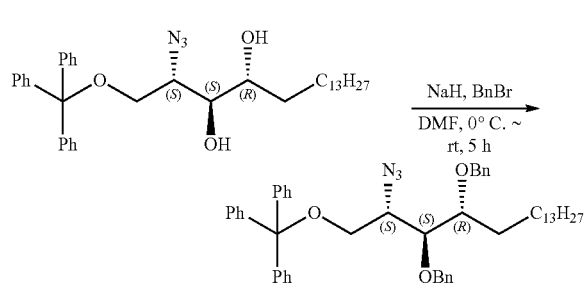

To a solution of (2S,3S,4R)-2-azido-1-(trityloxy)octadecane-3,4-diol (9.0 g, 15.4 mmol, 1.0 eq) in dry DMF (120 mL) at 0° C. was added NaH, 60% dispersion in oil (2.2 g, 55.0 mmol, 3.5 eq) in portions. After complete addition, the mixture was stirred at 0° C. for 10 min. BnBr (9.2 g, 53.8 mmol, 3.5 eq) was added and the mixture was allowed to warm to rt and stirred for an additional 5 h. It was poured into ice/water (200 mL), diluted with EtOAc (1 L), and the organic layer washed with water (4×200 mL), brine (2×200 mL), dried over Na₂SO₄ and concentrated under reduced pressure. The residue was purified by column chromatography on silica gel (120 g; EtOAc/PE 1:15) to give (((2S,3S,4R)-2-azido-3,4-bis(benzyloxy)octadecyloxy)methanetriyl)tribenzene (10 g, 85%) as an oil. LC/MS: mass calcd. for $C_{51}H_{63}N_3O_3$: 765.49, found: 788.50 [M+Na]⁺.

Synthesis of (2S,3S,4R)-2-azido-3,4-bis(benzyloxy)octadecan-1-ol

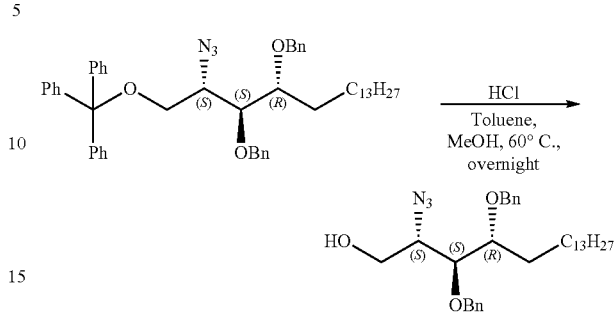

To a mixture of (((2S,3S,4R)-2-azido-3,4-bis(benzyloxy)octadecyloxy)methanetriyl)tribenzene (10 g, 13.1 mmol, 1.0 eq) in toluene (60 mL) and MeOH (60 mL) was added concentrated aqueous HCl (2 mL; 12 M). The mixture was heated to 60° C., and stirred overnight. The pH value of the aqueous phase was adjusted to ~7 used 1 M NaOH and the mixture was concentrated under reduced pressure. The crude residue was purified by column chromatography on silica gel (120 g; EtOAc/PE: 1:10) to give (2S,3S,4R)-2-azido-3,4-bis(benzyloxy)octadecan-1-ol (5 g, 73%) as an oil. LC/MS: mass calcd. for $C_{32}H_{44}N_3O_3$: 523.38, found: 546.25 [M+Na]⁺.

Synthesis of (3R,4S,5S,6R)-3,4,5-tris(benzyloxy)-6-((benzyloxy)methyl)tetrahydro-2H-pyran-2-yl Acetate

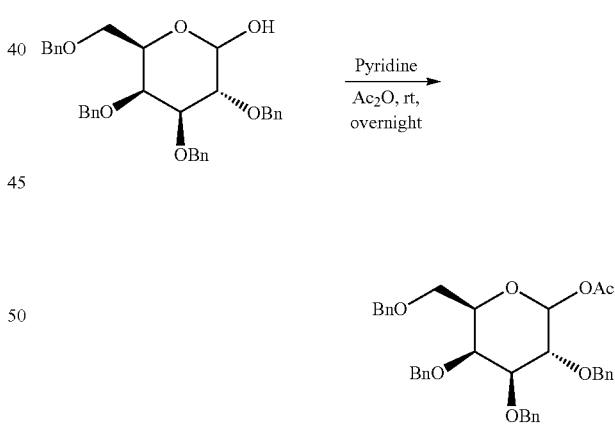

A mixture of (3R,4S,5S,6R)-3,4,5-tris(benzyloxy)-6-((benzyloxy)methyl)tetrahydro-2H-pyran-2-ol (25 g, 9.24 mmol), pyridine (60 mL) and Ac₂O (120 mL) was stirred at rt overnight. The reaction was quenched with crushed ice and the resulting mixture was extracted with DCM (3×300 mL). The combined organic layers were concentrated under reduced pressure and the crude residue was purified by column chromatography on silica gel (PE/EtOAc 1:1) to give (3R,4S,5S,6R)-3,4,5-tris(benzyloxy)-6-((benzyloxy)methyl)tetrahydro-2H-pyran-2-yl acetate (20 g, 74%) as an oil.

Synthesis of (2R,3S,4S,5R,6R)-3,4,5-tris(benzyloxy)-2-(benzyloxymethyl)-6-iodo-tetrahydro-2H-pyran

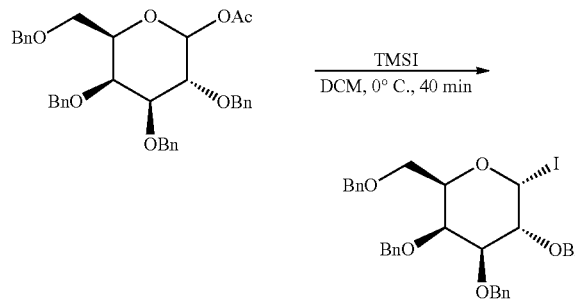

To a mixture of (3R,4S,5S,6R)-3,4,5-tris(benzyloxy)-6-(benzyloxymethyl)-tetrahydro-2H-pyran-2-yl acetate (20.0 g, 34.3 mmol, 1.0 eq) in DCM (150 mL) under an atmosphere of $N_2$ at 0° C. was added TMSI (6.9 g, 34.5 mmol, 1.0 eq). The mixture was stirred at 0° C. for 40 min, then benzene (50 mL) added and the mixture concentrated under reduced pressure to give (2R,3S,4S,5R,6R)-3,4,5-tris(benzyloxy)-2-(benzyloxymethyl)-6-iodo-tetrahydro-2H-pyran (19 g, 85%) of as an oil.

Synthesis of (2S,3R,4S,5S,6R)-2-((2S,3S,4R)-2-azido-3,4-bis(benzyloxy)octadecyloxy)-3,4,5-tris(benzyloxy)-6-(benzyloxymethyl)-tetrahydro-2H-pyran

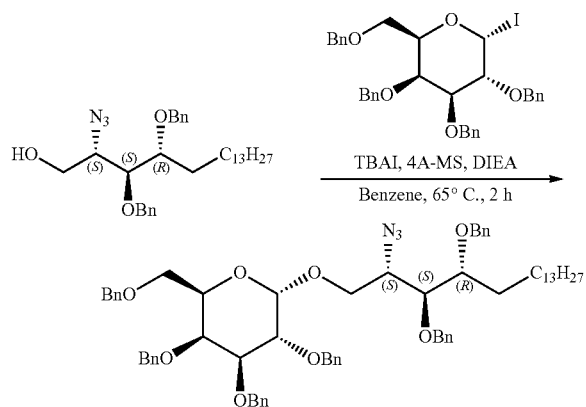

A mixture of (2S,3S,4R)-2-azido-3,4-bis(benzyloxy)octadecan-1-ol (3.0 g, 5.7 mmol, 1.0 eq), TBAI (19.0 g, 51.4 mmol, 9.0 eq), DIPEA (2.2 g, 17.0 mmol, 3.0 eq) and 4 Å-MS (2 g) in benzene (80 mL) was stirred at 65° C. for 20 min under an atmosphere of $N_2$. To this mixture was added a solution of (2R,3S,4S,5R,6R)-3,4,5-tris(benzyloxy)-2-(benzyloxymethyl)-6-iodo-tetrahydro-2H-pyran (18.6 g, 17.2 mmol, 3.0 eq) in benzene (30 mL). The mixture was stirred at 65° C. for an additional 2 h, cooled rt and EtOAc (150 mL) added. The mixture was filtered, the filtrate was washed with saturated sodium thiosulfate solution (2×80 mL), brine (2×80 mL), dried over $Na_2SO_4$ and concentrated under reduced pressure. The residue was purified by column chromatography on silica gel column (120 g; EtOAc/PE 1:5) to give (2S,3R,4S,5S,6R)-2-((2S,3S,4R)-2-azido-3,4-bis(benzyloxy)octadecyloxy)-3,4,5-tris(benzyloxy)-6-(benzyloxymethyl)-tetrahydro-2H-pyran (3 g, 50%) as an oil. LC/MS: mass calcd. for $C_{66}H_{83}N_3O_8$: 1045.62, found: 1068.60 [M+Na]$^+$.

Synthesis of (2S,3S,4R)-3,4-bis(benzyloxy)-1-((2S,3R,4S,5S,6R)-3,4,5-tris(benzyloxy)-6-(benzyloxymethyl)-tetrahydro-2H-pyran-2-yloxy)octadecan-2-amine

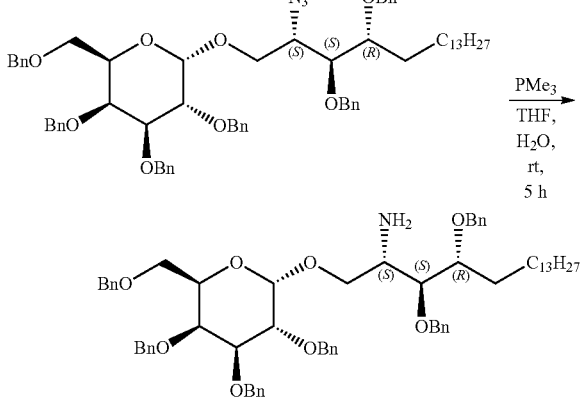

To a mixture of (2S,3R,4S,5S,6R)-2-((2S,3S,4R)-2-azido-3,4-bis(benzyloxy)octadecyloxy)-3,4,5-tris(benzyloxy)-6-(benzyloxymethyl)-tetrahydro-2H-pyran (3.0 g, 2.9 mmol, 1.0 eq) in THF (30 mL) was added 1 M $PMe_3$ in THF (3.2 mL, 3.2 mmol, 1.1 eq) at rt. The mixture was stirred at rt for 5 h, then $H_2O$ (10 mL) was added, the mixture was stirred at rt for 1 h and then concentrated under reduced pressure. The crude residue was purified by column chromatography on silica gel (MeOH/DCM 1:20) to give (2S,3S,4R)-3,4-bis(benzyloxy)-1-((2S,3R,4S,5S,6R)-3,4,5-tris(benzyloxy)-6-(benzyloxymethyl)-tetrahydro-2H-pyran-2-yloxy)octadecan-2-amine (2 g, 68%) as an oil. LC/MS: mass calcd. for $C_{66}H_{85}NO_8$: 1019.63, found: 1020.60 [M+H]$^+$.

Synthesis of (2S,3R,4S,5R,6R)-2-(((2S,3S,4R)-2-amino-3,4-dihydroxyoctadecyl)oxy)-6-(hydroxymethyl)tetrahydro-2H-pyran-3,4,5-triol

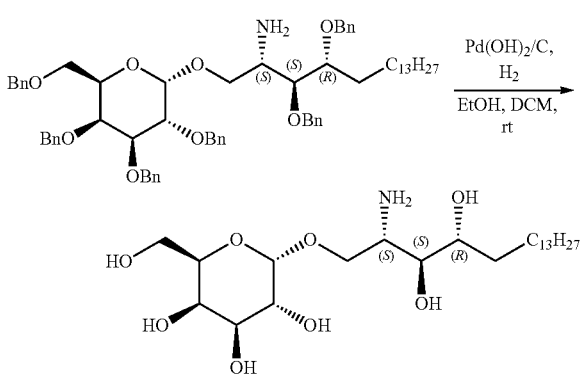

To a mixture of (2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-amine (200 mg, 0.2 mmol, 1.0 eq) in EtOH (10 mL) and DCM (3 mL) was added 20% Pd(OH)$_2$/C (0.2 g). The mixture was hydrogenated (1 atm) at rt for 16 h, then the catalyst was removed by filtration through a pad of Celite and the filter cake washed with MeOH. The filtrate was concentrated under reduced pressure to give (2S,3R,4S,5R,6R)-2-(((2S,3S,4R)-2-amino-3,4-dihydroxyoctadecyl)oxy)-6-(hydroxymethyl)tetrahydro-2H-pyran-3,4,5-triol (75 mg, 80%) as an oil.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(3-fluorobicyclo[1.1.1]pentan-1-yl)undecanamide Synthesis of 3-Fluorobicyclo[1.1.1]pentane-1-carbaldehyde

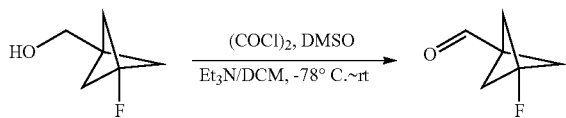 [SMILES: OCC12CC(F)(C1)C2 ; O=CC12CC(F)(C1)C2]

To a mixture of oxalyl chloride (164 mg, 1.29 mmol, 1.5 eq) in DCM (5 mL) at −78° C. under an atmosphere of N$_2$ was added DMSO (202 mg, 2.58 mmol, 3.0 eq) dropwise. The mixture was stirred for 15 min at −78° C. then (3-Fluorobicyclo[1.1.1]pentan-1-yl)methanol (100 mg, 0.86 mmol, 1.0 eq) in DCM (1 mL) was added dropwise. The mixture was stirred for 50 min at −78° C., then Et$_3$N (1 mL) was added. Stirring was continued for an additional 5 min at −78° C., and the mixture was then warmed to rt. H$_2$O (10 mL) was added and the mixture was extracted with DCM (3×20 mL). The combined organic layers were washed with H$_2$O (20 mL) and brine (20 mL), then dried over Na$_2$SO$_4$ and filtered. The filtrate was concentrated under reduced pressure to give 3-fluorobicyclo[1.1.1]pentane-1-carbaldehyde (70 mg, 71%) as an oil. The compound was used without further purification. $R_f$=0.3, PE/EtOAc 1:3.

Synthesis of (10-Carboxydecyl)triphenylphosphonium bromide

To a mixture of 11-bromoundecanoic acid (3.0 g, 11.3 mmol, 1.0 eq) in CH$_3$CN (100 mL) under an atmosphere of N$_2$ was added PPh$_3$ (3.0 g, 11.31 mmol, 1.0 eq). The mixture was heated to 90° C., and stirred for 72 h, then concentrated under reduced pressure and the crude product crystallized from EtOAc give (10-carboxydecyl)triphenylphosphonium bromide (5.8 g, 97%) as a solid. LC/MS: mass calcd. for C$_{29}$H$_{36}$BrO$_2$P: 526, found: 447 [M−Br]$^+$.

Synthesis of (E)-11-(3-Fluorobicyclo[1.1.1]pentan-1-yl)undec-10-enoic Acid

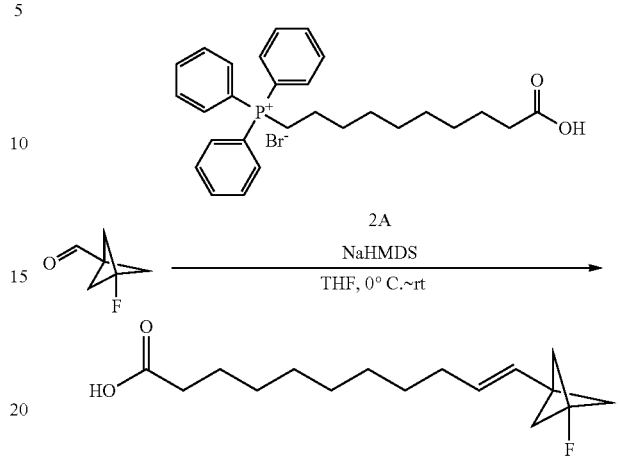

To a mixture of (9-carboxynonyl)triphenylphosphonium bromide (315 mg, 0.61 mmol, 1.0 eq) in THF (5 mL) at 0° C. under an atmosphere of N$_2$ was slowly added NaHMDS, 2 M in THF (0.61 mL, 1.22 mmol, 2 eq). The mixture was stirred at 0° C. for 1 h, then 3-fluorobicyclo[1.1.1]pentane-1-carbaldehyde (70 mg, 0.61 mmol, 1.0 eq) in THF (1 mL) was added at 0° C. The mixture was allowed to warm to rt and stirred for 16 h, then H$_2$O (10 mL) was added and the pH adjusted to 4-5 with 2N HCl. The mixture was extracted with EtOAc (20 mL×3) and the combined organic layers were concentrated under reduced pressure. The residue was purified by column chromatography on silica gel column (PE/EtOAc 2:1) to give (E)-11-(3-fluorobicyclo[1.1.1]pentan-1-yl)undec-10-enoic acid (120 mg, 73%) as a solid. LC/MS: mass calcd. for C$_{16}$H$_{25}$FO$_2$: 268, found: 267 [M−H]$^-$.

Synthesis of 11-(3-Fluorobicyclo[1.1.1]pentan-1-yl)undecanoic Acid

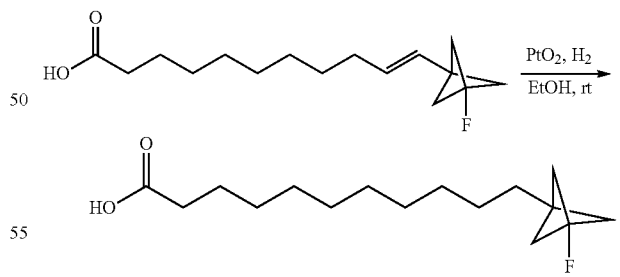

A mixture of (E)-11-(3-fluorobicyclo[1.1.1]pentan-1-yl)undec-10-enoic acid (60 mg, 0.22 mmol, 1.0 eq) and PtO$_2$ (5 mg, 0.022 mmol, 0.1 eq) in EtOH (50 mL) was hydrogenated (1 atm) at rt for 1 h. The catalyst was removed by filtration through a pad of Celite and the filter cake was rinsed with EtOH. The filtrate was concentrated under reduced pressure to give 11-(3-fluorobicyclo[1.1.1]pentan-1-yl)undecanoic acid (55 mg, 91%) as a solid. LC/MS: mass calcd. for C$_{16}$H$_{27}$FO$_2$: 270, found: 269 [M−H]$^-$.

Synthesis of N-((2S,3S,4R)-3,4-Dihydroxy-1-(((2S,3R,4S,5R,6R)-3,4,5-trihydroxy-6-(hydroxymethyl)tetrahydro-2H-pyran-2-yl)oxy)octadecan-2-yl)-11-(3-fluorobicyclo[1.1.1]pentan-1-yl)undecanamide fluorobicyclo[1.1.1]pentan-1-yl)undecanamide

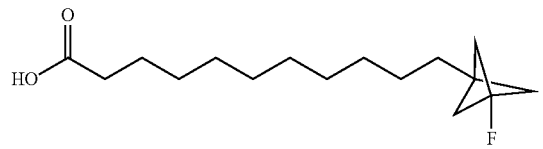
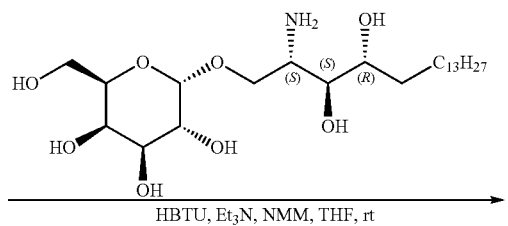
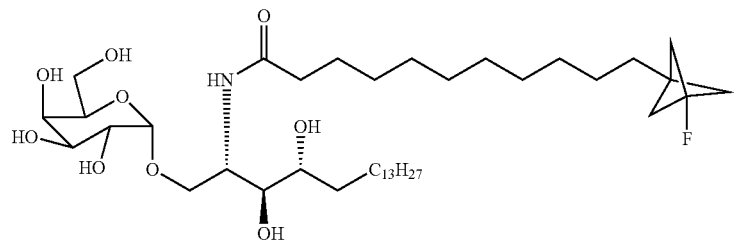

To a mixture of 11-(3-fluorobicyclo[1.1.1]pentan-1-yl)undecanoic acid (55 mg, 0.20 mmol) and (2S,3R,4S,5R,6R)-2-(((2S,3S,4R)-2-amino-3,4-dihydroxyoctadecyl)oxy)-6-(hydroxymethyl)tetrahydro-2H-pyran-3,4,5-triol (98 mg, 0.20 mmol, 1.0 eq) in THF (5 mL) under an atmosphere of $N_2$ was added HBTU (154 mg, 0.41 mmol, 2.0 eq), $Et_3N$ (41 mg, 0.41 mmol, 2.0 eq), and NMM (41 mg, 0.41 mmol, 2.0 eq) at rt. The mixture was stirred at rt for 16 h then concentrated under reduced pressure. The residue was purified by column chromatography on silica (DCM/MeOH 9:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(3-fluorobicyclo[1.1.1]pentan-1-yl)undecanamide (12.5 mg, 8%) as a solid. LC/MS: mass calcd. for $C_{40}H_{74}FNO_9$: 731.53, found: 732.45 $[M+H]^+$; $^1H$ NMR (300 MHz, MeOH-$d_4$) § 4.21 (d, J=6.0 Hz, 1H), 3.81-3.89 (m, 3H), 3.76-3.79 (m, 2H), 3.68-3.74 (m, 3H), 3.62-3.65 (m, 1H), 3.53-3.59 (m, 1H), 2.24 (t, J=7.5 Hz, 2H), 1.88 (d, J=2.7 Hz, 6H), 1.57-1.66 (m, 6H), 1.29-1.34 (m, 39H), 0.92 (t, J=6.7 Hz, 3H); 19F NMR (282 MHz, MeOH-$d_4$) δ −146.5.

Synthesis of (10-Carboxydecyl)triphenylphosphonium bromide

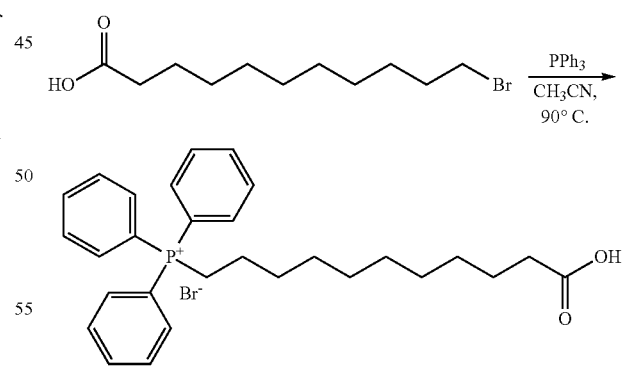

To a mixture of 11-bromoundecanoic acid (3.0 g, 11.3 mmol, 1.0 eq) in $CH_3CN$ (100 mL) under an atmosphere of $N_2$ was added $PPh_3$ (3.0 g, 11.31 mmol, 1.0 eq). The mixture was heated to 90° C. and stirred for 72 h, then concentrated under reduced pressure and the crude product crystallized from EtOAc give (10-carboxydecyl)triphenylphosphonium bromide (5.8 g, 97%) as a solid. LC/MS: mass calcd. for $C_{29}H_{36}BrO_2P$: 526, found: 447 $[M-Br]^+$.

Synthesis of (E)-12-(3-Fluorobicyclo[1.1.1]pentan-1-yl)dodec-11-enoic acid

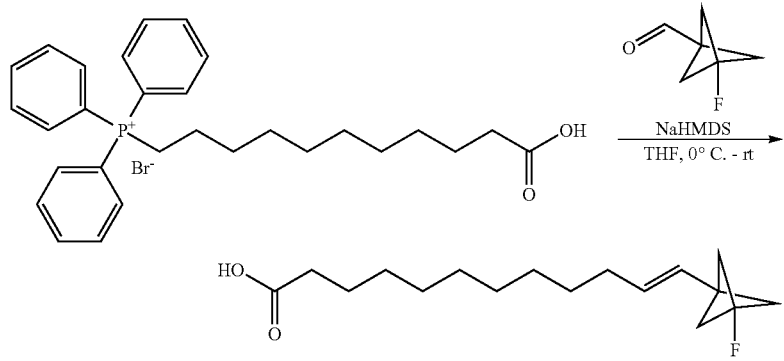

To a mixture of (10-carboxydecyl)triphenylphosphonium bromide (0.4 g, 0.76 mmol, 1.0 eq) in THF (10 mL) at 0° C. under an atmosphere of $N_2$ was slowly added NaHMDS, 2M in THF (0.8 mL, 1.6 mmol, 2.1 eq). The mixture was stirred at 0° C. for 1 h, then 3-fluorobicyclo[1.1.1]pentane-1-carbaldehyde (87 mg, 0.76 mmol, 1.0 eq) in THF (1 mL) was added at 0° C. The mixture was allowed to warm to rt and stirred for 16 h, then H2O (10 mL) added and the pH adjusted to 4~5 with 2N HCl. The mixture was extracted with EtOAc (30 mL×3) and the combined organic layers were concentrated under reduced pressure. The residue was purified by column chromatography on silica gel (PE/EtOAc 1:1) to give (E)-12-(3-fluorobicyclo[1.1.1]pentan-1-yl)dodec-11-enoic acid (0.11 g, 51%) as a solid. LC/MS: mass calcd. for $C_{17}H_{27}FO_2$: 282, found: 281 [M−H]⁻.

Synthesis of 12-(3-Fluorobicyclo[1.1.1]pentan-1-yl)dodecanoic acid

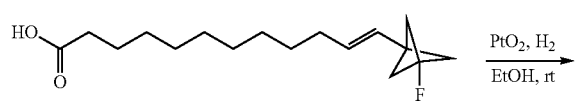

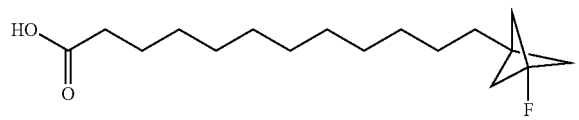

A mixture of (E)-12-(3-fluorobicyclo[1.1.1]pentan-1-yl)dodec-11-enoic acid (0.11 g, 0.39 mmol, 1.0 eq) and $PtO_2$ (10 mg, 0.04 mmol, 0.1 eq) in EtOH (70 mL) was hydrogenated (1 atm) at rt for 1 h. The catalyst was removed by filtration through a pad of Celite and the filter cake was washed with EtOH. The filtrate was concentrated under reduced pressure to give 12-(3-fluorobicyclo[1.1.1]pentan-1-yl)dodecanoic acid (0.1 g, 90%) as a solid. LC/MS: mass calcd. for $C_{17}H_{29}FO_2$: 284, found: 283 [M−H]⁻.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-12-(3-fluorobicyclo[1.1.1]pentan-1-yl)dodecanamide

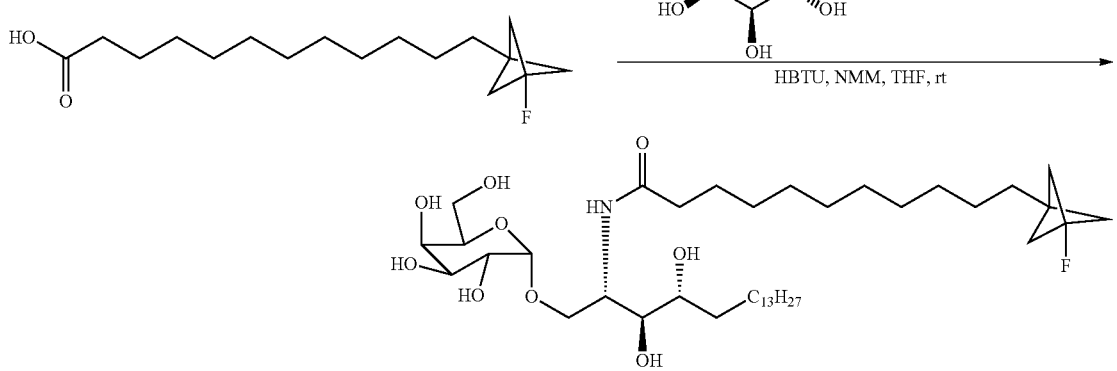

To a mixture of 12-(3-fluorobicyclo[1.1.1]pentan-1-yl)dodecanoic acid (0.1 g, 0.35 mmol, 1.0 eq) and (2S,3R,4S,5R,6R)-2-(((2S,3S,4R)-2-amino-3,4-bis(benzyloxy)octadecyl)oxy)-6-(hydroxymethyl)tetrahydro-2H-pyran-3,4,5-triol (232 mg, 0.35 mmol, 1.0 eq) in THF (6 mL) under an atmosphere of $N_2$ was added HBTU (267 mg, 0.70 mmol, 2.0 equiv), $Et_3N$ (71 mg, 0.70 mmol, 2.0 eq) and NMM (71 mg, 0.70 mmol, 2.0 eq) at rt. The mixture was stirred at rt for 16 h then concentrated under reduced pressure. The residue was purified by column chromatography on silica gel column (DCM/MeOH 8:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-12-(3-fluorobicyclo[1.1.1]pentan-1-yl)dodecanamide (15.7 mg, 6%) as a solid. LC/MS: mass calcd. for $C_{41}H_{76}FNO_9$: 745.55, found: 746.45 $[M+H]^+$; $^1H$ NMR (300 MHZ, MeOH-$d_4$) δ 4.17 (t, J=5.5 Hz, 1H), 3.81-3.89 (m, 3H), 3.74-3.77 (m, 2H), 3.66-3.72 (m, 3H), 3.59-3.63 (m, 1H), 3.52-3.57 (m, 1H), 2.22 (t, J=7.4 Hz, 2H), 1.86 (d, J=2.7 Hz, 6H), 1.56-1.65 (m, 6H), 1.27-1.35 (m, 41H), 0.95-0.85 (m, 3H); 19F NMR (282 MHZ, MeOH-$d_4$) δ −146.5.

Synthesis of 11-(Bicyclo[2.2.2]octan-1-yl)-N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)undecanamide Synthesis of (E)-11-(Bicyclo[2.2.2]octan-1-yl)undec-10-enoic acid To a mixture of 9-carboxynonyl(triphenyl)phosphonium bromide (371 mg, 0.72 mmol, 1.0 eq) in THF (5 mL) at 0° C. under an atmosphere of $N_2$ was slowly added NaHMDS, 2M in THF (0.72 mL, 1.44 mmol, 2 eq). The mixture was stirred at 0° C. for 1 h then bicyclo[2.2.2]octane-1-carbaldehyde (0.1 g, 0.72 mmol, 1.0 eq) in THF (1 mL) was added at 0° C. The mixture was warmed to rt and stirred for 16 h, then H2O added and the pH adjusted to ~4-5 with 2N HCl. The mixture was extracted with EtOAc (30 mL×3) and the combined organic layers were concentrated under reduced pressure. The residue was purified by column chromatography on silica gel (PE/EtOAc 2:1) to give (E)-11-(bicyclo[2.2.2]octan-1-yl)undec-10-enoic acid (0.15 g, 71%) as a solid. LC/MS: mass calcd. for $C_{19}H_{32}O_2$: 292, found: 291 $[M-H]^-$.

Synthesis of 11-(Bicyclo[2.2.2]octan-1-yl)undecanoic acid

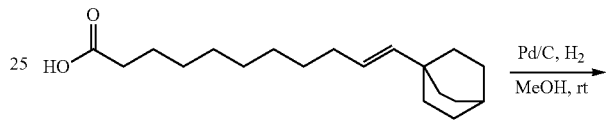

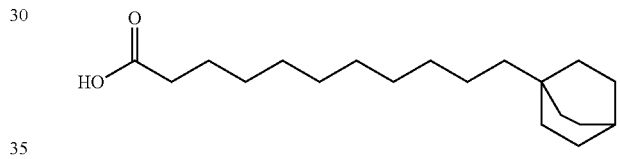

A mixture of (E)-11-(bicyclo[2.2.2]octan-1-yl)undec-10-enoic acid (0.15 g, 0.51 mmol, 1.0 eq) and 10% Pd/C (20 mg) in MeOH (10 mL) was hydrogenated (1 atm) at rt for 1 h. The catalyst was removed by filtration through a pad of Celite and the filter cake was washed with MeOH. The filtrate was concentrated under reduced pressure to give 11-(bicyclo[2.2.2]octan-1-yl)undecanoic acid (130 mg, 86%) as a solid. LC/MS: mass calcd. for $C19H_{34}O_2$: 294, found: 293 $[M-H]^-$.

Synthesis of 11-(Bicyclo[2.2.2]octan-1-yl)-N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)undecanamide

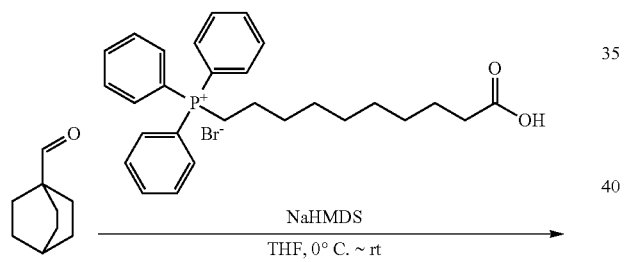

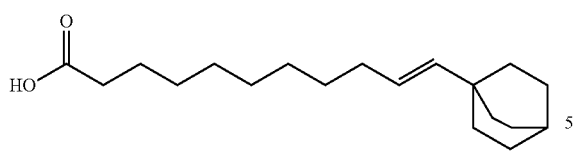

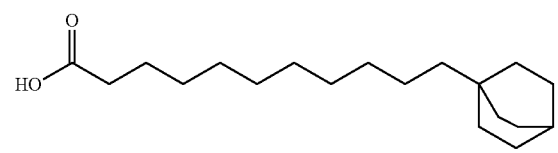

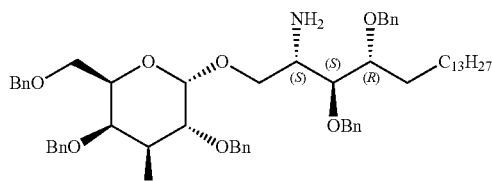

-continued

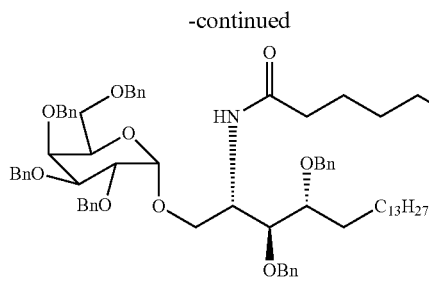

To a mixture of 11-(bicyclo[2.2.2]octan-1-yl)undecanoic acid (130 mg, 0.44 mmol, 1.0 eq) and (2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-amine (450 mg, 0.44 mmol, 1.0 eq) in DCM (5 mL) at rt were added EDCI (127 mg, 0.66 mmol, 1.5 eq) and DMAP (11 mg, 0.09 mmol, 0.2 eq). The reaction mixture was stirred at rt for 16 h, then diluted with EtOAc (10 mL) and washed with brine (5 mL). The aqueous layer was extracted with EtOAc (10 mL×2) and the combined organic layers were dried over $Na_2SO_4$, filtered and the filtrate concentrated under reduced pressure. The residue was purified by column chromatography on silica gel (PE/EtOAc 3:1) to give 11-(bicyclo[2.2.2]octan-1-yl)-N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)undecanamide (0.2 g, 35%) of as a solid. LC/MS: mass calcd. for $C_{85}H_{117}NO_9$: 1296, found: 1297 [M+H]+.

Synthesis of 11-(bicyclo[2.2.2]octan-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide A mixture of 11-(bicyclo[2.2.2]octan-1-yl)-N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)undecanamide (0.1 g, 0.08 mmol, 1.0 eq) and 20% $Pd(OH)_2$/C (0.2 g) in EtOH/DCM (10 mL/3 mL) was hydrogenated (1 atm) at rt for 16 h. The catalyst was removed by filtration through a pad of Celite and the filter cake was washed with MeOH. The filtrate was concentrated under reduced pressure and the crude residue was purified by column chromatography on silica gel column (DCM/MeOH) and preparative-HPLC to give 11-(bicyclo[2.2.2]octan-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide (8.9 mg, 15%) as a solid. LC/MS: mass calcd. for $C_{43}H_{81}NO_9$: 755.59, found: 756.50 [M+H]+; $^1$H NMR (300 MHz, CDCl3+MeOH-$d_4$) § 4.88 (d, J=3.7 Hz, 1H), 4.18 (d, J=5.0 Hz, 1H), 3.67-3.89 (m, 8H), 3.53-3.59 (m, 2H), 2.20 (t, J=7.7 Hz, 2H), 1.49-1.62 (m, 12H), 1.12-1.30 (m, 43H), 0.93-0.99 (m, 2H), 0.87 (t, J=6.4 Hz, 3H).

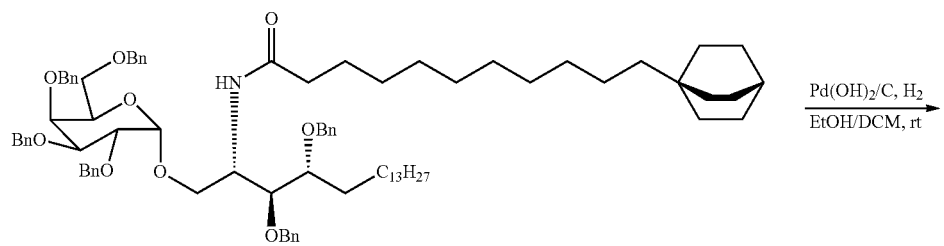

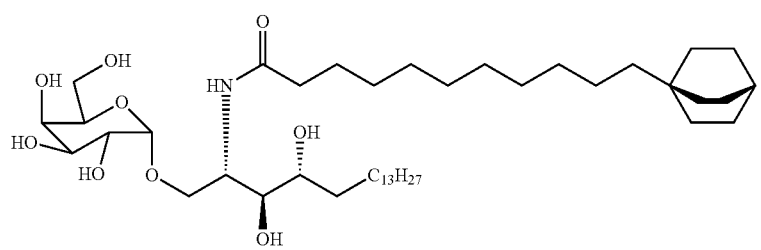

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(2-methylcyclopropyl)undecanamide

Synthesis of (E)-11-(2-Methylcyclopropyl)undec-10-enoic acid

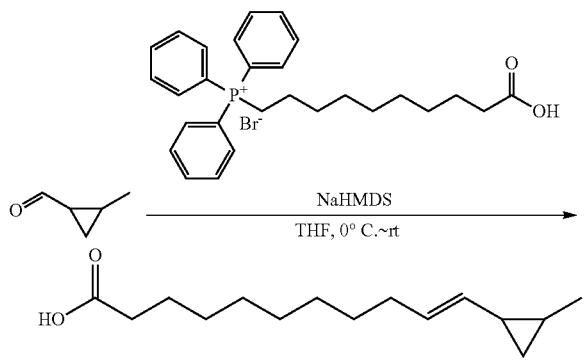

To a mixture of (9-carboxynonyl)triphenylphosphonium bromide (488 mg, 0.95 mmol, 1.0 eq) in THF (5 mL) at 0° C. under an atmosphere of $N_2$ was slowly added NaHMDS, 2M in THF (1.0 mL, 2.0 mmol, 2.0 eq). The mixture was stirred at 0° C. for 1 h, then 2-methylcyclopropane-1-carbaldehyde (80 mg, 0.95 mmol, 1.0 eq) in THF (1 mL) was added at 0° C. The mixture was warmed to rt and stirred for 16 h, then H2O (10 mL) added and the pH adjusted to ~4-5 with 2N HCl. The mixture was extracted with EtOAc (30 mL×3) and the combined organic layers were concentrated under reduced pressure. The residue was purified by column chromatography on silica gel (PE/EtOAc 2:1) to give (E)-11-(2-methylcyclopropyl)undec-10-enoic acid (120 mg, 53%) as a solid. LC/MS: mass calcd. for $C_{15}H_{26}O_2$: 238, found: 237 [M–H]⁻.

Synthesis of 11-(2-Methylcyclopropyl)undecanoic acid

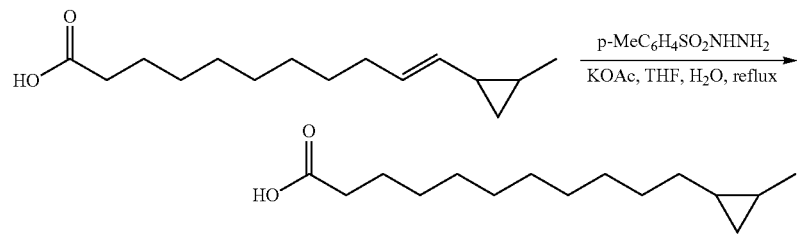

To a mixture of (E)-11-(2-methylcyclopropyl)undec-10-enoic acid (120 mg, 0.50 mmol, 1.0 eq) in THF (5 mL) and H2O (5 mL) at rt were added p-MeC$_6$H$_4$SO$_2$NHNH$_2$ (938 mg, 5.0 mmol, 10 eq) and KOAc (642 mg, 6.6 mmol, 13 eq). The mixture was heated to reflux and stirred for 5 h, cooled, and H2O added. The mixture was extracted with EtOAc (30 mL×3) and the combined organic layers were concentrated under reduced pressure. The residue was purified by column chromatography on silica gel column (PE/EtOAc) to give 11-(2-methylcyclopropyl)undecanoic acid (90 mg, 74%) as an oil. LC/MS: mass calcd. for $C_{15}H_{28}O_2$: 240, found: 239 [M–H]⁻.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(2-methylcyclopropyl)undecanamide

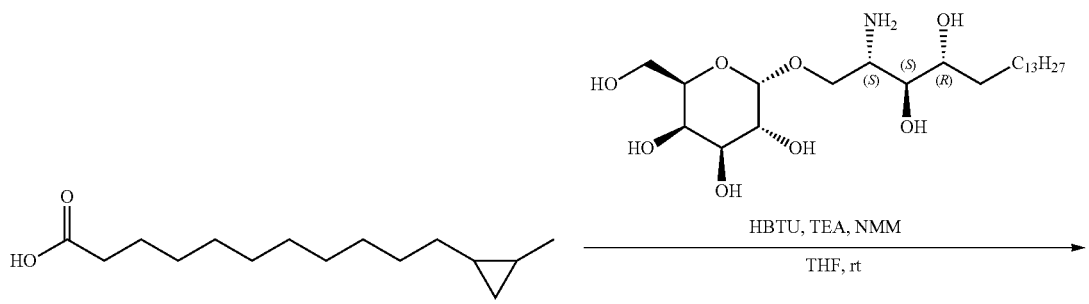

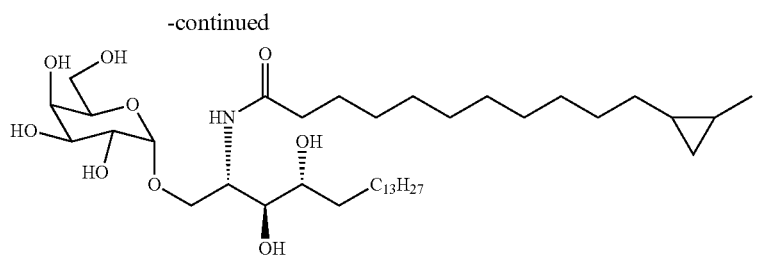

To a mixture of 11-(2-methylcyclopropyl)undecanoic acid (80 mg, 0.33 mmol, 1.0 eq) and (2S,3R,4S,5R,6R)-2-(((2S,3S,4R)-2-amino-3,4-dihydroxyoctadecyl)oxy)-6-(hydroxymethyl)tetrahydro-2H-pyran-3,4,5-triol (160 mg, 0.33 mmol, 1.0 eq) in THF (6 mL) at rt was added HBTU (252 mg, 0.66 mmol, 2.0 eq), Et$_3$N (67 mg, 0.66 mmol, 2.0 eq), and NMM (67 mg, 0.66 mmol, 2.0 eq). The mixture was stirred at rt for 16 h, then concentrated under reduced pressure and the residue was purified by column chromatography on silica gel (DCM/MeOH 8:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(2-methylcyclopropyl)undecanamide (20.7 mg, 9%) as a solid. LC/MS: mass calcd. for C$_{39}$H$_{75}$NO$_9$: 701.54, found: 702.45 [M+H]$^+$; 1H NMR (300 MHZ, MeOH-d$_4$) δ 4.18 (dd, J=6.5, 4.4 Hz, 1H), 3.80-3.89 (m, 3H), 3.74-3.78 (m, 2H), 3.66-3.72 (m, 3H), 3.60-3.64 (m, 1H), 3.52-3.57 (m, 1H), 2.22 (t, J=7.5 Hz, 2H), 1.50-1.67 (m, 4H), 1.24-1.38 (m, 41H), 1.15-1.23 (m, 2H), 0.99-1.02 (m, 3H), 0.95-0.85 (m, 3H), 0.29-0.44 (m, 1H), 0.09-0.18 (m, 1H).

Synthesis of 11-(Cuban-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide Synthesis of (E)-11-(Cuban-1-yl)undec-10-enoic acid To a mixture of (9-carboxynonyl)triphenylphosphonium bromide (0.4 g, 0.8 mmol, 1.0 eq) in THF (6 mL) at 0° C. under an atmosphere of N$_2$ was slowly added NaHMDS, 2M in THF (0.8 mL, 1.6 mmol, 2.0 eq). The mixture was stirred at 0° C. for 1 h, then cubane-1-carbaldehyde (0.1 g, 0.8 mmol, 1.0 eq) in THF (1 mL) was added at 0° C. The mixture was warmed to rt and stirred for 16 h, then H2O (10 mL) added and the pH adjusted to ~4-5 with 2N HCl. The mixture was extracted with EtOAc (20 mL×3) and the combined organic layers concentrated under reduced pressure. The residue was purified by column chromatography on silica gel column (PE/EtOAc 2:1) to give (E)-11-(cuban-1-yl)undec-10-enoic acid (0.11 g, 49%) as a solid. LC/MS: mass calcd. for C$_{19}$H$_{26}$O$_2$: 286, found: 285 [M−H]$^-$.

Synthesis of 11-(Cuban-1-yl)undecanoic acid

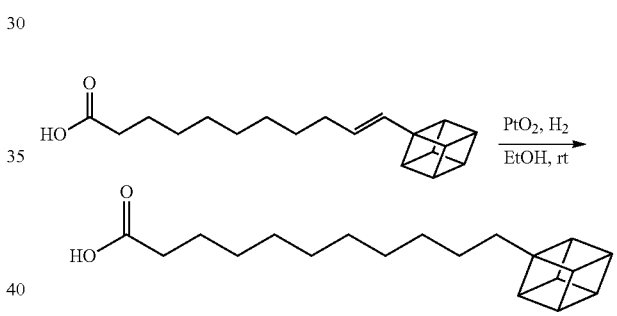

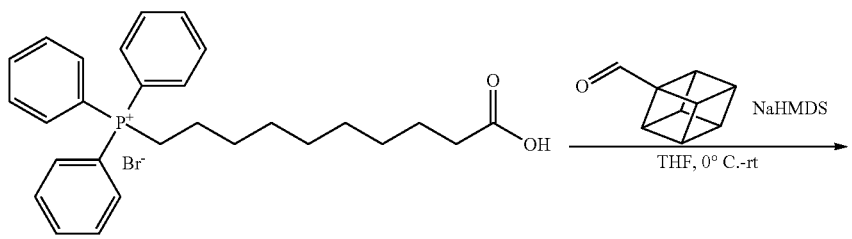

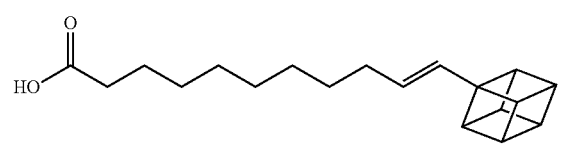

A mixture of (E)-11-(cuban-1-yl)undec-10-enoic acid (0.1 g, 0.4 mmol, 1.0 eq) and PtO$_2$ (8 mg, 0.04 mmol, 0.1 eq) in EtOH (10 mL) was hydrogenated (1 atm) at rt for 1 h. The catalyst was removed by filtration through a pad of Celite and the filter cake washed with EtOH. The filtrate was concentrated under reduced pressure to give 11-(cuban-1-yl)undecanoic acid (80 mg, 79%) as a solid. LC/MS: mass calcd. for C$_{19}$H$_{28}$O$_2$: 288 found: 287 [M–H]$^-$.

Synthesis of 11-(Cuban-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide mmol, 2.0 eq), and NMM (56 mg, 0.55 mmol, 2.0 eq). The mixture was stirred at rt for 16 h then concentrated under reduced pressure. The residue was purified by column chromatography on silica gel (DCM/MeOH) and preparative-HPLC to give 11-(cuban-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide as a solid. LC/MS: mass calcd. for C$_{43}$H$_{75}$NO$_9$: 749.54, found: 750.60 [M+H]$^+$.

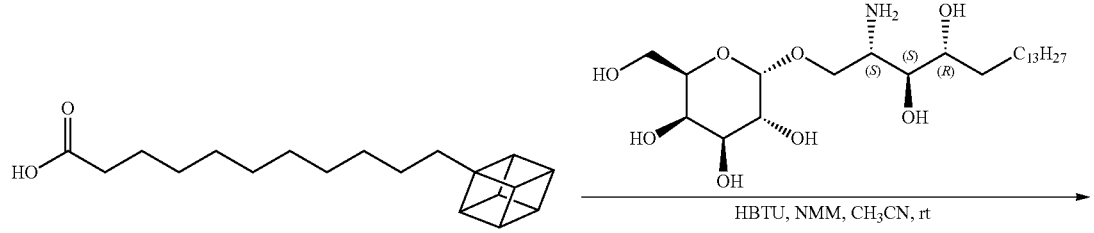

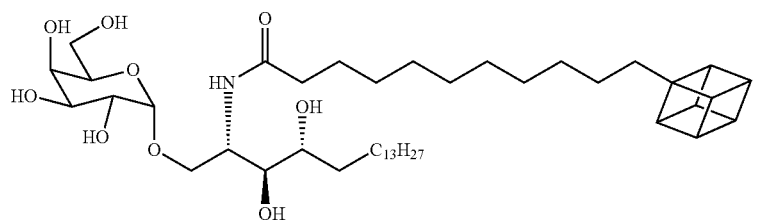

To a mixture of 11-(cuban-1-yl)undecanoic acid (80 mg, 0.3 mmol, 1.0 eq) and (2S,3R,4S,5R,6R)-2-(((2S,3S,4R)-2-amino-3,4-dihydroxyoctadecyl)oxy)-6-(hydroxymethyl)tetrahydro-2H-pyran-3,4,5-triol (130 mg, 0.3 mmol, eq) in THF (6 mL) at rt under an atmosphere of N$_2$ was added HBTU (210 mg, 0.55 mmol, 2.0 eq), Et$_3$N (56 mg, 0.55

Synthesis of 12-(Cuban-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecanamide

Synthesis of (E)-12-(Cuban-1-yl)dodec-11-enoic acid

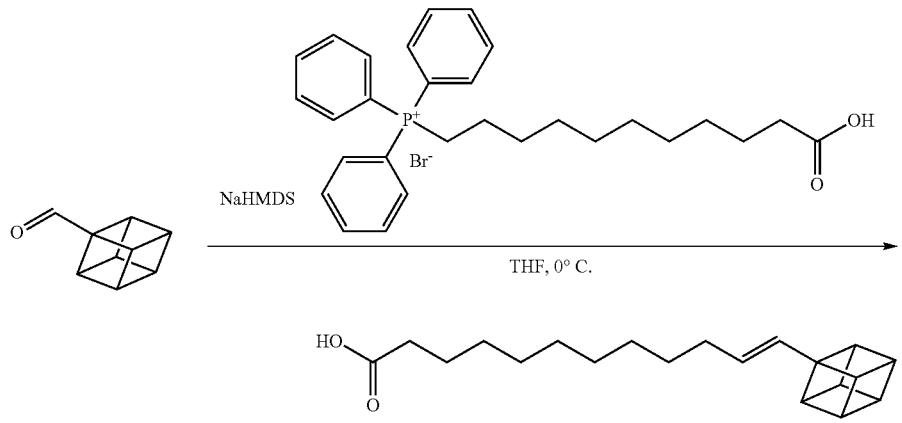

To a mixture of (10-carboxydecyl)triphenylphosphonium bromide (319 mg, 0.6 mmol, 1.0 eq) in THF (6 mL) at 0° C. under an atmosphere of $N_2$ was slowly added NaHMDS, 2M in THF (0.6 mL, 1.2 mmol, 2.0 eq). The mixture was stirred at 0° C. for 1 h, then cubane-1-carbaldehyde (80 mg, 0.6 mmol, 1.0 eq) in THF (1 mL) was added. The mixture was warmed to rt and stirred for 16 h, then H2O (10 mL) added and the pH adjusted to ~4-5 with 2N HCl. The mixture was extracted with EtOAc (20 mL×3) and the combined organic layers were concentrated under reduced pressure. The residue was purified by column chromatography on silica (PE/EtOAc 2:1) to give (E)-12-(cuban-1-yl)dodec-11-enoic acid (110 mg, 60%) as a solid. LC/MS: mass calcd. for $C_{20}H_{28}O_2$: 300, found: 299 [M–H]−.

Synthesis of 12-(Cuban-1-yl)dodecanoic acid

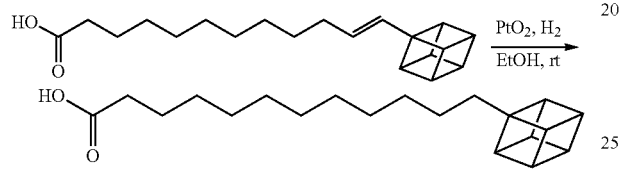

A mixture of (E)-12-(cuban-1-yl)dodec-11-enoic acid (110 mg, 0.37 mmol, 1.0 eq) and $PtO_2$ (8 mg, 0.04 mmol, 0.1 eq) in EtOH (70 mL) was hydrogenated (1 atm) at rt for 1 h. The catalyst was removed by filtration through a pad of Celite and the filter cake was washed with EtOH. The filtrate was concentrated under reduced pressure to give 12-(cuban-1-yl)dodecanoic acid (0.1 g, 90%) as a solid. LC/MS: mass calcd. for $C_{20}H_{30}O_2$: 302, found: 301 [M–H]−.

Synthesis of 12-(Cuban-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecanamide

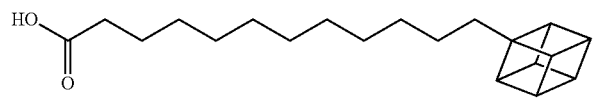

To a mixture of 12-(cuban-1-yl)dodecanoic acid (80 mg, 0.26 mmol, 1.0 eq) and (2S,3R,4S,5R,6R)-2-(((2S,3S,4R)-2-amino-3,4-bis(benzyloxy)octadecyl)oxy)-6-(hydroxymethyl)tetrahydro-2H-pyran-3,4,5-triol (175 mg, 0.26 mmol, 1.0 eq) in THF (6 mL) at rt under an atmosphere of $N_2$ was added HBTU (201 mg, 0.53 mmol, 2.0 eq) and TEA (53 mg, 0.53 mmol, 2.0 eq) and NMM (53 mg, 0.53 mmol, 2.0 eq). The mixture was stirred at rt for 16 h then concentrated under reduced pressure. The residue was purified by column chromatography on silica gel (DCM/MeOH) and preparative-HPLC to give 12-(cuban-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecanamide (8.6 mg, 4%) as a solid. LC/MS: mass calcd. for $C_{44}H_{77}NO_9$: 763.56, found: 764.60 [M+H]+; $^1H$ NMR (300 MHz, MeOH-$d_4$) δ 4.86-4.89 (m, 1H), 4.14-4.20 (m, 1H), 4.02-4.08 (m, 1H), 3.80-3.88 (m, 6H), 3.68-3.77 (m, 7H), 3.50-3.65 (m, 3H), 2.22 (t, J=7.5 Hz, 2H), 1.48-1.62 (m, 6H), 1.27-1.35 (m, 40H), 0.95-0.85 (m, 3H).

Synthesis of (2S,3R,4S,5R,6R)-2-(((2S,3S,4R)-2-(4-(5-(diheptylamino)pentyl)-1H-1,2,3-triazol-1-yl)-3,4-dihydroxyoctadecyl)oxy)-6-(hydroxymethyl)tetrahydro-2H-pyran-3,4,5-triol Synthesis of N,N-diheptylhept-6-yn-1-amine

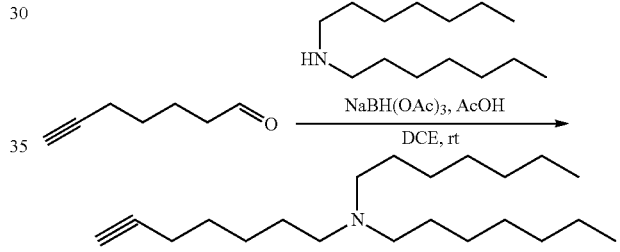

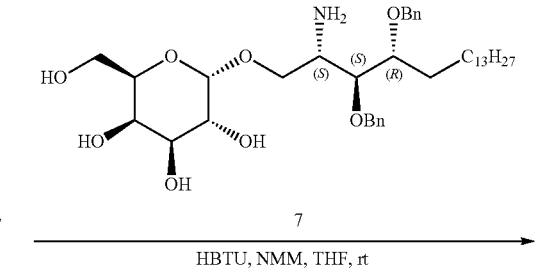

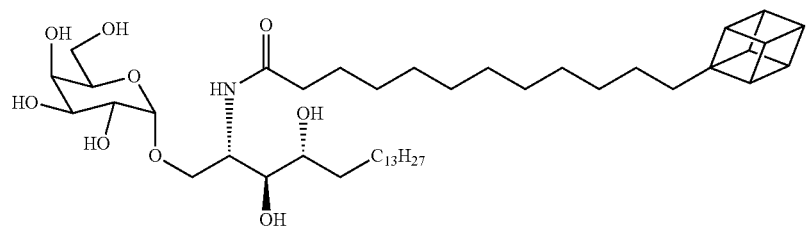

To a mixture of hept-6-ynal (0.7 g, 6.4 mmol, 1.0 eq) in DCE (10 mL) at rt under an atmosphere of $N_2$ was added diheptylamine (1.3 g, 6.4 mmol, 1.0 eq). The mixture was stirred at rt for 15 min, then $NaBH(OAc)_3$ (2.0 g, 9.5 mmol, 1.5 eq) and AcOH (0.1 mL) added. The mixture was stirred at rt for 3 h, then H2O (10 mL) added and the mixture extracted with EtOAc (30 mL×3). The combined organic layers were concentrated under reduced pressure and the residue was purified by column chromatography on silica gel column (MeOH/DCM 1:8) to give N,N-diheptylhept-6-yn-1-amine (0.7 g, 36%) as an oil. LC/MS: mass calcd. for $C_{21}H_{41}N$: 307, found: 308 $[M+H]^+$.

Synthesis of N-(5-(1-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1H-1,2,3-triazol-4-yl)pentyl)-N-heptylheptan-1-amine

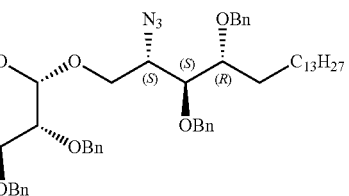

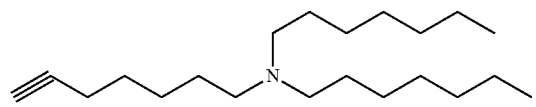

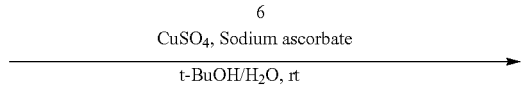

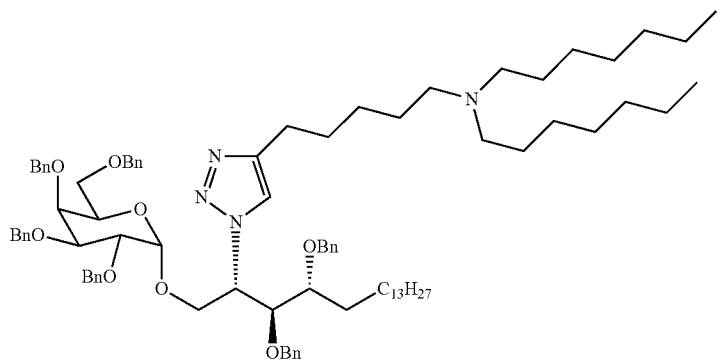

To a mixture of the N,N-diheptylhept-6-yn-1-amine (38 mg, 0.12 mmol, 1.3 eq) and (2S,3R,4S,5S,6R)-2-(((2S,3S,4R)-2-azido-3,4-bis(benzyloxy)octadecyl)oxy)-3,4,5-tris(benzyloxy)-6-((benzyloxy)methyl)tetrahydro-2H-pyran (0.1 g, 0.1 mmol, 1.0 eq) in $^t$BuOH (3 mL) and H2O (3 mL) at rt under an atmosphere of $N_2$ was added $CuSO_4$ (5 mg, 0.03 mmol, 0.3 eq) and sodium ascorbate (6 mg, 0.03 mmol, 0.3 eq). The mixture was stirred at rt for 16 h then diluted with EtOAc (10 mL), washed with brine (5 mL), and the aqueous layer extracted with EtOAc (10 mL×2). The combined organic layers were dried over $Na_2SO_4$, filtered and the filtrate concentrated under reduced pressure. The residue was purified by column chromatography on silica gel (PE/EtOAc 3:1) to give N-(5-(1-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1H-1,2,3-triazol-4-yl)pentyl)-N-heptylheptan-1-amine (0.1 g, 77%) as an oil. LC/MS: mass calcd. for $C_{87}H_{124}N_4O_8$: 1353, found: 1354 $[M+H]^+$.

Synthesis of (2S,3R,4S,5R,6R)-2-(((2S,3S,4R)-2-(4-(5-(diheptylamino)pentyl)-1H-1,2,3-triazol-1-yl)-3,4-dihydroxyoctadecyl)oxy)-6-(hydroxymethyl)tetrahydro-2H-pyran-3,4,5-triol

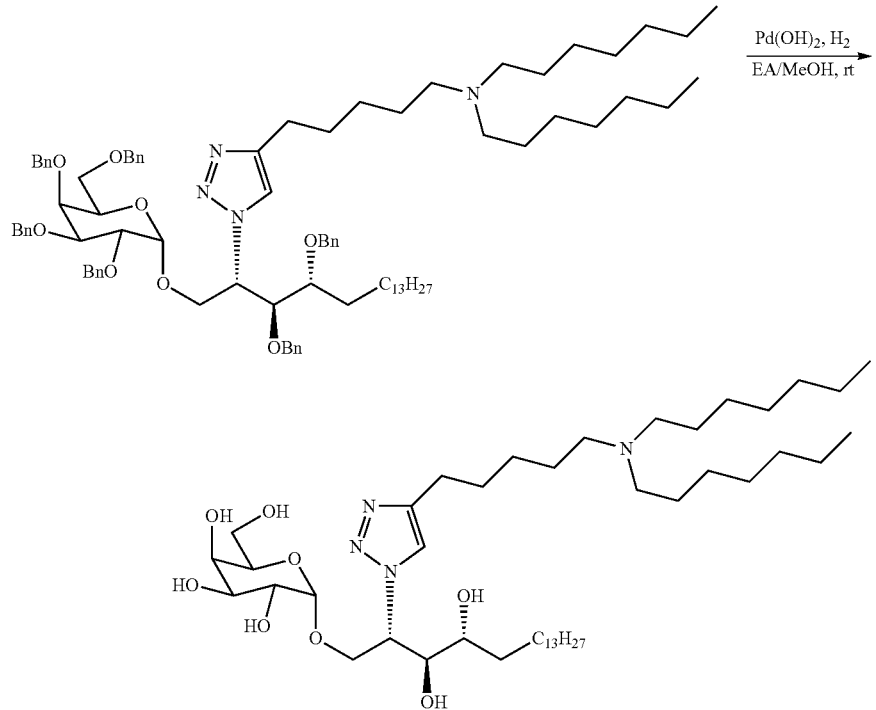

A mixture of N-(5-(1-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1H-1,2,3-triazol-4-yl)pentyl)-N-heptylheptan-1-amine (0.1 g, 0.07 mmol, 1.0 eq) in EtOH (10 mL) and DCM (3 mL) and 20% Pd(OH)$_2$/C (0.2 g) was hydrogenated (1 atm) at rt for 16 h. The catalyst was removed by filtration through a pad of Celite and the filter cake washed with EtOH/DCM(3:1). The filtrate was concentrated under reduced pressure and the residue was purified by column chromatography on silica gel (DCM/MeOH 8:1) and preparative-HPLC to give 2S,3R,4S,5R,6R)-2-(((2S,3S,4R)-2-(4-(5-(diheptylamino)pentyl)-1H-1,2,3-triazol-1-yl)-3,4-dihydroxyoctadecyl)oxy)-6-(hydroxymethyl)tetrahydro-2H-pyran-3,4,5-triol (16.2 mg, 35%) as a solid. LC/MS: mass calcd. for C$_{45}$H$_{88}$N$_4$O$_8$: 812.66, found: 813.70 [M+H]$^+$; $^1$H NMR (300 MHz, DMSO-d$_6$+D$_2$O) δ 7.86 (s, 1H), 4.90-4.96 (m, 1H), 4.63 (d, J=3.7 Hz, 1H), 4.01-4.06 (m, 1H), 3.87-3.92 (m, 1H), 3.47-3.63 (m, 2H), 3.35-3.45 (m, 2H), 3.10-3.18 (m, 1H), 2.93-2.99 (m, 6H), 2.55-2.60 (m, 2H), 1.50-1.58 (m, 9H), 1.15-1.26 (m, 46H), 0.76-0.83 (m, 9H).

Synthesis of (2S,3R,4S,5R,6R)-2-(((2S,3S,4R)-2-(4-(6-(diheptylamino)hexyl)-1H-1,2,3-triazol-1-yl)-3,4-dihydroxyoctadecyl)oxy)-6-(hydroxymethyl)tetrahydro-2H-pyran-3,4,5-triol Synthesis of N,N-diheptyloct-7-yn-1-amine

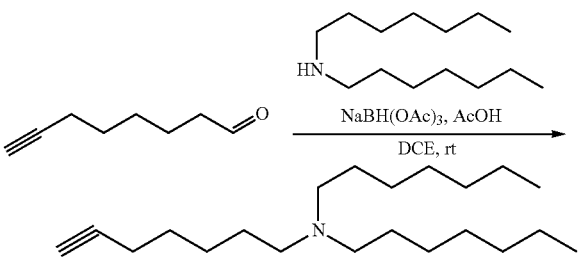

To a mixture of oct-7-ynal (0.7 g, 5.6 mmol, 1.0 eq) in DCE (10 mL) at rt under an atmosphere of N$_2$ was added diheptylamine (1.2 g, 5.6 mmol, 1.0 eq). The mixture was stirred at rt for 15 min, then NaBH(OAc)$_3$ (1.8 g, 8.5 mmol, 1.5 eq) and AcOH (0.1 mL) added. The mixture was stirred at rt for 3 h, then H2O (10 mL) added and the mixture extracted with EtOAc (30 mL×3). The combined organic layers were concentrated under reduced pressure and the residue was purified by column chromatography on silica gel (MeOH/DCM 1:8) to give N,N-diheptyloct-7-yn-1-amine (0.6 g, 33%) as an oil. LC/MS: mass calcd. for C$_{22}$H$_{43}$N: 321, found: 322 [M+H]$^+$.

Synthesis of N-(6-(1-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1H-1,2,3-triazol-4-yl)hexyl)-N-heptylheptan-1-amine

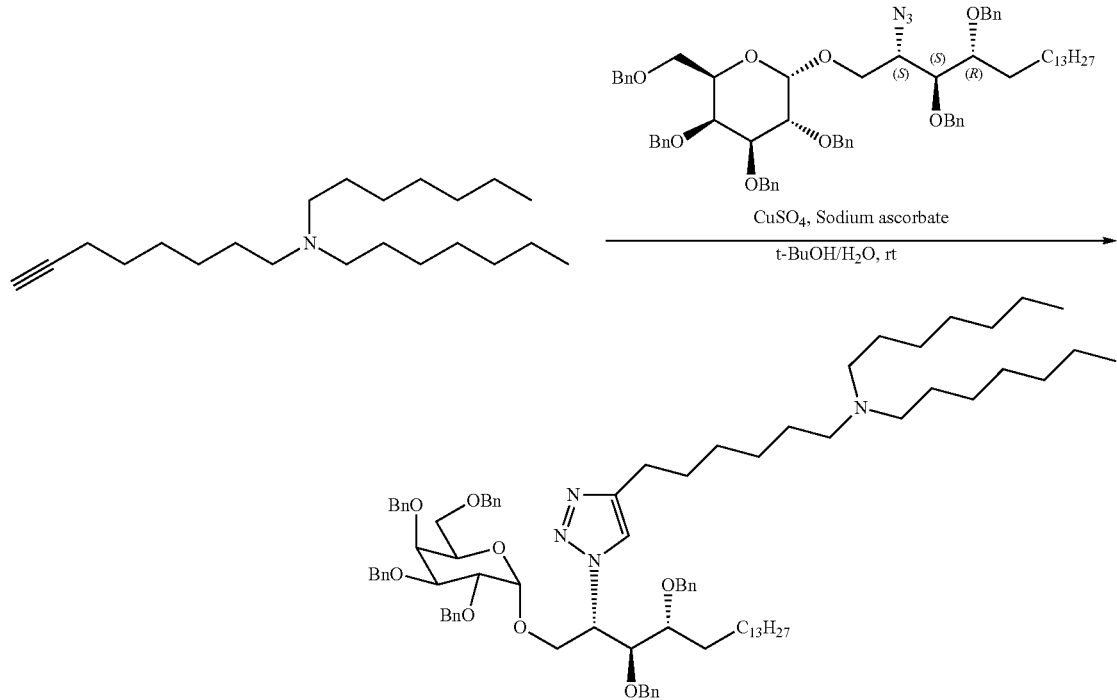

To a mixture of the N,N-diheptyloct-7-yn-1-amine (40 mg, 0.12 mmol, 1.0 eq) and (2S,3R,4S,5S,6R)-2-(((2S,3S,4R)-2-azido-3,4-bis(benzyloxy)octadecyl)oxy)-3,4,5-tris(benzyloxy)-6-((benzyloxy)methyl)tetrahydro-2H-pyran (130 mg, 0.12 mmol, 1.0 eq) in $^t$BuOH (3 mL) and H2O (3 mL) at rt was added CuSO$_4$ (6 mg, 0.04 mmol, 0.3 eq) and sodium ascorbate (7 mg, 0.04 mmol, 0.3 eq). The mixture was stirred at rt for 1 day, then diluted with EtOAc (10 mL), the mixture washed with brine and the aqueous layer extracted with EtOAc (10 mL×2). The combined organic layers were dried over Na$_2$SO$_4$, filtered and concentrated under reduced pressure. The residue was purified by column chromatography on silica gel (PE/EtOAc 3:1) to give N-(6-(1-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1H-1,2,3-triazol-4-yl)hexyl)-N-heptylheptan-1-amine (0.1 g, 59%) as an oil. LC/MS: mass calcd. for $C_{88}H_{126}N_4O_8$: 1367, found: 1368 [M+H]$^+$.

Synthesis of (2S,3R,4S,5R,6R)-2-(((2S,3S,4R)-2-(4-(6-(diheptylamino)hexyl)-1H-1,2,3-triazol-1-yl)-3,4-dihydroxyoctadecyl)oxy)-6-(hydroxymethyl)tetrahydro-2H-pyran-3,4,5-triol

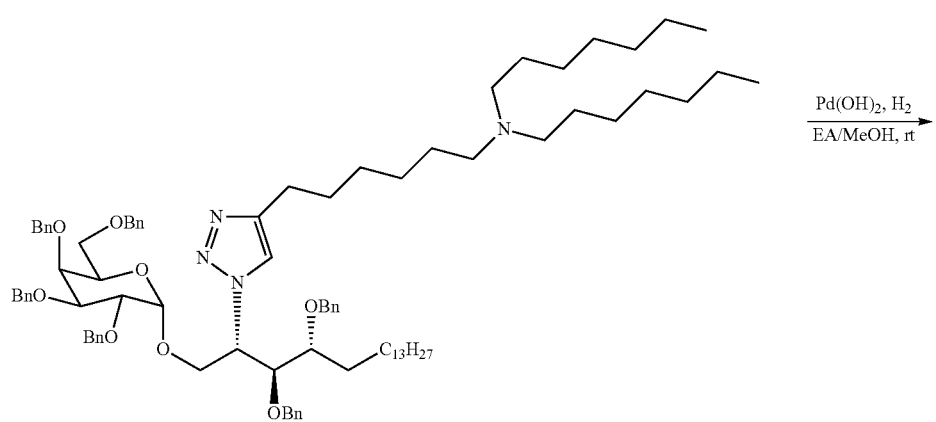

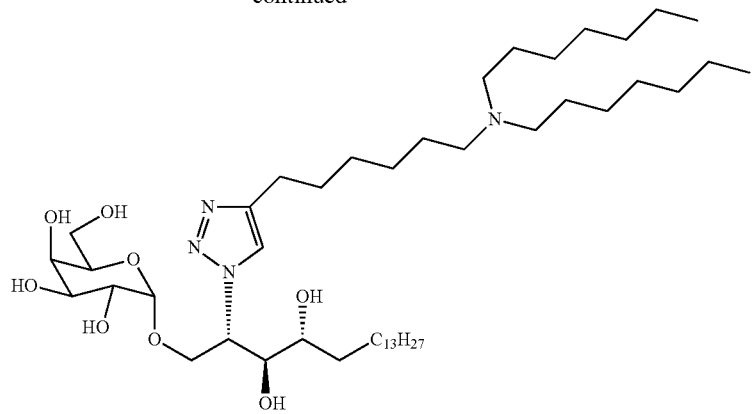

A mixture of N-(6-(1-(((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1H-1,2,3-triazol-4-yl)hexyl)-N-heptylheptan-1-amine (0.1 g, 0.07 mmol, 1.0 eq) in EtOH (10 mL) and DCM (3 mL) and 20% Pd(OH)$_2$/C (0.2 g) was hydrogenated (1 atm) at rt for 16 h. The catalyst was removed by filtration through a pad of Celite and the filter cake washed with EtOH/CH$_2$Cl$_2$ (3:1). The filtrate was concentrated under reduced pressure and the residue was purified by column chromatography on silica gel (DCM/MeOH) and preparative-HPLC to give (2S,3R,4S,5R,6R)-2-(((2S,3S,4R)-2-(4-(6-(diheptylamino)hexyl)-1H-1,2,3-triazol-1-yl)-3,4-dihydroxyoctadecyl)oxy)-6-(hydroxymethyl)tetrahydro-2H-pyran-3,4,5-triol (11.1 mg, 18%) as a solid. LC/MS: mass calcd. for C$_{46}$H$_{90}$N$_4$O$_8$: 826.68, found: 827.95 [M+H]$^+$; 1H NMR (300 MHz, DMSO-d$_6$+D$_2$O) δ 7.83 (s, 1H), 4.88-4.94 (m, 1H), 4.63 (d, J=3.8 Hz, 1H), 3.97-4.12 (m, 1H), 3.86-3.93 (m, 1H), 3.34-3.53 (m, 5H), 3.08-3.14 (m, 1H), 2.93-3.00 (m, 6H), 2.54-2.60 (m, 2H), 1.43-1.59 (m, 10H), 1.18-1.27 (m, 46H), 0.80-0.85 (m, 9H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecane-1-sulfinamide—mixture of two diastereomers

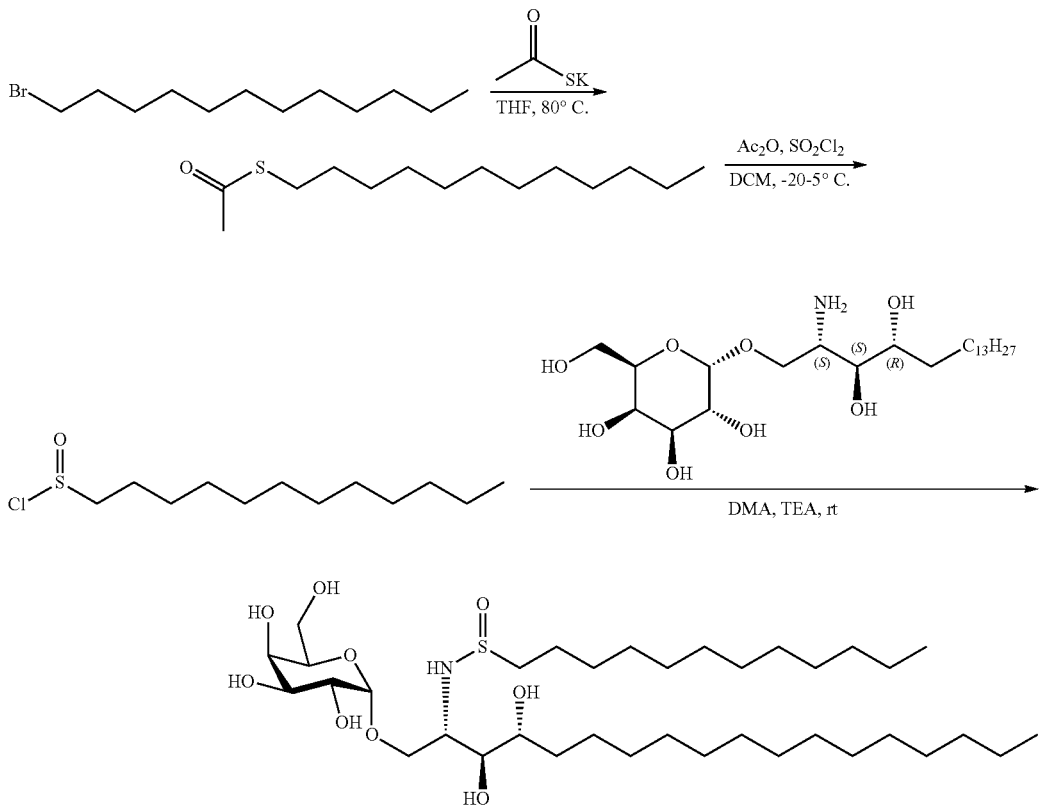

Synthesis of S-dodecyl ethanethioate

To a mixture of 1-bromododecane (0.5 g, 2.0 mmol) in THF (10 mL) at rt was added potassium ethanethioate (274 mg, 2.4 mmol). The mixture was heated to 80° C. and stirred for 3 h, then concentrated under reduced pressure and the residue was purified by column chromatography on silica gel (PE/EtOAc) to give S-dodecyl ethanethioate (382 mg, 78%) as an oil.

Synthesis of dodecane-1-sulfinic chloride

To a mixture of S-dodecyl ethanethioate (0.3 g, 1.2 mmol) in DCM (5 mL) at -20° ° C. was slowly added Ac$_2$O (126 mg, 1.2 mmol) and SO$_2$Cl$_2$ (332 mg, 2.5 mmol). The mixture was warmed to −5° C. and stirred for 2 h, then concentrated under reduced pressure to give dodecane-1-sulfinic chloride (295 mg, 95%) as an oil.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecane-1-sulfinamide—mixture of two diastereomers To a mixture of (2S,3R,4S,5R,6R)-2-(((2S,3S,4R)-2-amino-3,4-dihydroxyoctadecyl)oxy)-6-(hydroxymethyl)tetrahydro-2H-pyran-3,4,5-triol (60 mg, 0.13 mmol) in DMA (3 mL) at rt under an atmosphere of N$_2$ was added Et$_3$N (25 mg, 0.25 mmol) and dodecane-1-sulfinic chloride (47 mg, 0.19 mmol). The mixture was stirred at rt for 3 h. then H$_2$O added and the mixture was extracted with EtOAc (3×30 mL). The combined organic layers were dried over anhydrous Na$_2$SO$_4$ and filtered. The filtrate was concentrated under reduced pressure and the residue was purified twice by column chromatography on silica gel (DCM/MeOH 9:1) to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)dodecane-1-sulfinamide (3.4 mg, 3.9%) as a solid. LC/MS: mass calcd. for C$_{36}$H$_{73}$NO$_9$S: 695.50, found: 696.55 [M+H]$^+$.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-10-(3-fluorobicyclo[1.1.1]pentan-1-yl)decane-1-sulfinamide—mixture of two diastereomers

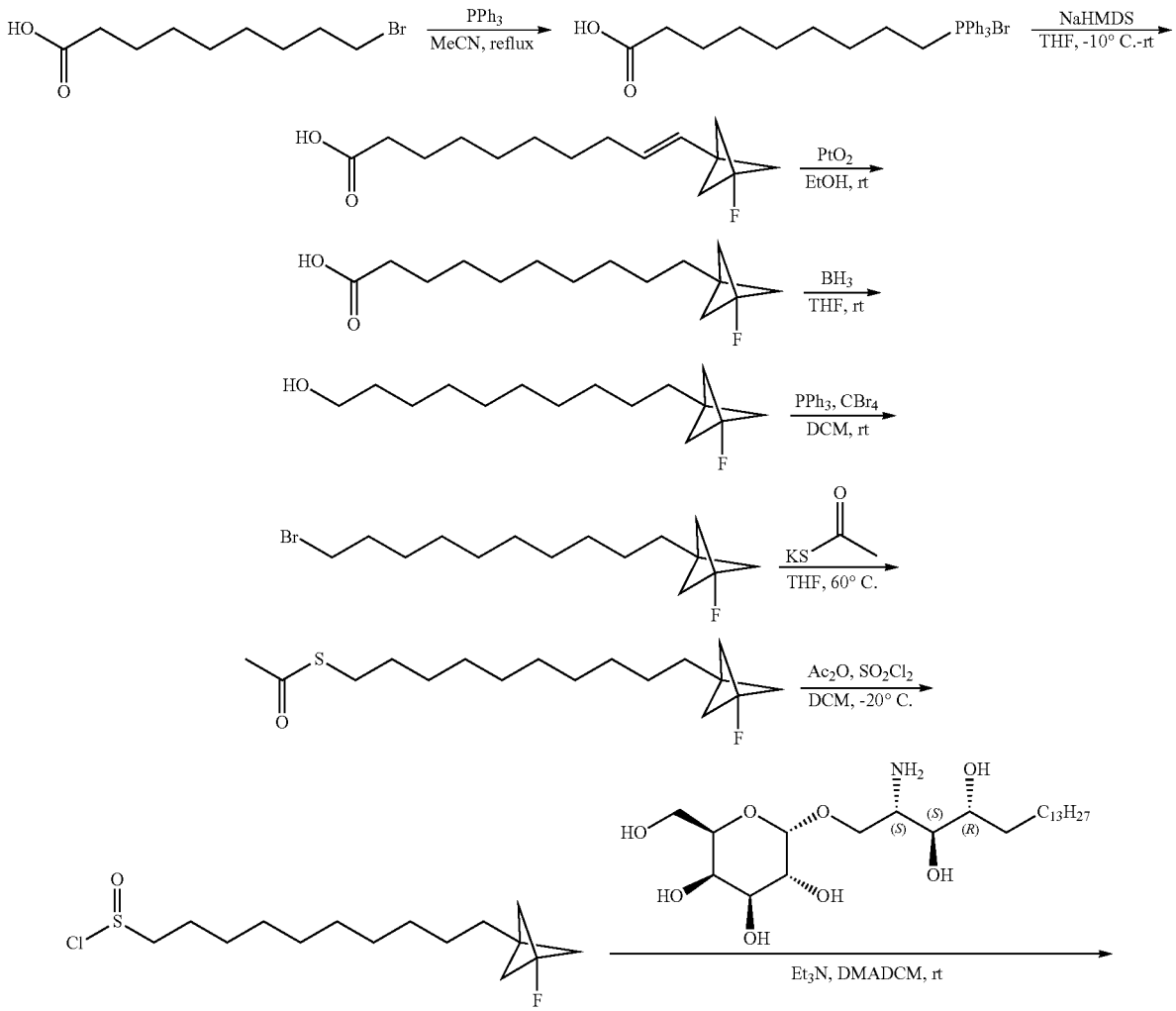

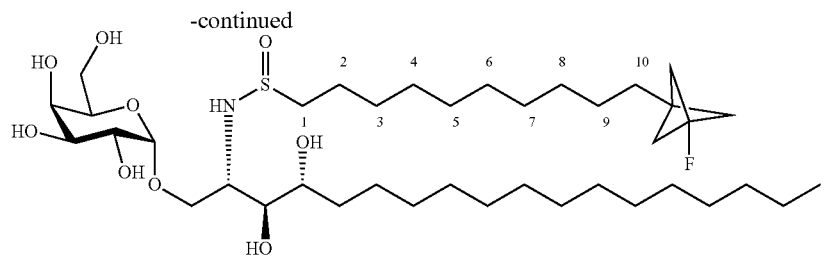

Synthesis of 9-(bromotriphenyl-lambda5-phosphanyl)nonanoic acid

A mixture of 9-bromononanoic acid (5.0 g, 21.1 mmol) and $Ph_3P$ (5.53 g, 21.1 mmol) in MeCN (50 mL) was heated to reflux and stirred for 3 days. The mixture was concentrated under reduced pressure and the residue was triturated with mixture $Et_2O$ (200 mL) and filtered to give 9-(bromotriphenyl-lambda5-phosphanyl)nonanoic acid (10.0 g, 95%) as a solid. 1H NMR (300 MHz, DMSO-$d_6$) δ 11.98 (s, 1H), 7.42-8.28 (m, 15H), 2.17 (t, J=7.3 Hz, 2H), 1.76 (td, J=6.6, 5.8, 2.5 Hz, 2H), 1.39-1.56 (m, 6H), 1.14-1.29 (m, 6H).

Synthesis of (9E)-10-[3-fluorobicyclo[1.1.1]pentan-1-yl]dec-9-enoic acid

To a mixture of 9-(bromotriphenyl-lambda5-phosphanyl) nonanoic acid (2.95 g, 5.9 mmol) in THF (50 mL) at −10° C. under an atmosphere of $N_2$ was added 2 M NaHMDS (5.9 mL, 11.8 mmol). The mixture was warmed to rt and stirred for 1 h at room temperature, then a mixture of 3-fluorobicyclo[1.1.1]pentane-1-carbaldehyde (450 mg, 3.9 mmol) in THF (5 mL) was added. The mixture was stirred at rt overnight, then 2 M HCl (20 mL) added and the mixture extracted with EtOAc (3×20 mL). The combined organic layers were washed with brine (50 mL), dried and filtered. The filtrate was concentrated under reduced pressure and the residue was purified by column chromatography on silica gel (PE/EtOAc 1:1) to give (9E)-10-[3-fluorobicyclo[1.1.1]pentan-1-yl]dec-9-enoic acid (500 mg, 50%) as an oil LC/MS: mass calcd. for $C_{15}H_{23}FO_2$: 254.2, found: 253.9 [M−H]⁻.

Synthesis of 10-[3-fluorobicyclo[1.1.1]pentan-1-yl] decanoic Acid

A mixture of (9E)-10-[3-fluorobicyclo[1.1.1]pentan-1-yl] dec-9-enoic acid (500 mg, 1.96 mmol), and $PtO_2$ (50 mg, 0.22 mmol) in EtOH (30) mL) was stirred under an atmosphere of $H_2$ (balloon) for 2 h. The mixture was filtered, the filter cake was washed with EtOH (100 mL) and the filtrate was concentrated under reduced pressure to give 10-[3-fluorobicyclo[1.1.1]pentan-1-yl]decanoic acid (500 mg, 99%) as a solid. LC/MS: mass calcd. for $C_{15}H_{25}FO_2$: 256.2, found: 255.0 [M−H]⁻.

Synthesis of 10-{3-fluorobicyclo[1.1.1]pentan-1-yl}decan-1-ol

To a mixture of 10-{3-fluorobicyclo[1.1.1]pentan-1-yl}decanoic acid (500 mg, 1.95 mmol) in THF (20 mL) under an atmosphere of $N_2$ was added 1 M $BH_3$ in THF (5.9 mL, 5.9 mmol) dropwise. The mixture was stirred at rt for 2 h, then quenched with MeOH (20 mL), concentrated under reduced pressure and the residue was purified by column chromatography on silica (PE/EtOAc 3:1) to give 10-{3-fluorobicyclo[1.1.1]pentan-1-yl}decan-1-ol (430 mg, 91%) as an oil. ¹H NMR (300 MHz, DMSO-$d_6$) δ 4.32 (t, J=5.2 Hz, 1H), 3.37 (td, J=6.5, 5.1 Hz, 2H), 1.88 (d, J=2.7 Hz, 6H), 1.60 (d, J=7.8 Hz, 2H), 1.40 (t, J=6.5 Hz, 2H), 1.25 (s, 12H).

Synthesis of 1-(10-bromodecyl)-3-fluorobicyclo[1.1.1]pentane

To a mixture of 10-{3-fluorobicyclo[1.1.1]pentan-1-yl}decan-1-ol (430 mg, 1.77 mmol) in DCM (30 mL) under an atmosphere of $N_2$ was added $Ph_3P$ (930 mg, 3.54 mmol) and $CBr_4$ (1.18 g, 3.54 mmol). The mixture was stirred at rt for 4 h, then concentrated under reduced pressure and the residue was purified by column chromatography on silica gel (PE/EtOAc 10:1) to give 1-(10-bromodecyl)-3-fluorobicyclo[1.1.1]pentane (480 mg, 89%) as an oil. ¹H NMR (400 MHz, DMSO-$d_6$) δ 3.53 (t, J=6.7 Hz, 2H), 1.88 (d, J=2.8 Hz, 6H), 1.79 (d, J=6.8 Hz, 2H), 1.59 (t, J=7.0 Hz, 2H), 1.33-1.41 (m, 2H), 1.26 (d, J=1.7 Hz, 12H).

Synthesis of 1-[(10-{3-fluorobicyclo[1.1.1]pentan-1-yl}decyl)sulfanyl]ethanone A mixture of 1-(10-bromodecyl)-3-fluorobicyclo[1.1.1] pentane (480 mg, 1.57 mmol) and 1-(potassiosulfanyl)ethanone (359 mg, 3.14 mmol) in THF (20 mL) was heated to 60° C. and stirred for 4 h, then concentrated under reduced pressure and the residue was purified by column chromatography on silicagel (PE/EtOAc 10:1) to give 1-[(10-{3-fluorobicyclo[1.1.1]pentan-1-yl}decyl)sulfanyl]ethanone (450 mg, 95%) as an oil. ¹H NMR (300 MHz, $CDCl_3$) δ 2.88 (t, J=7.3 Hz, 2H), 2.35 (s, 3H), 1.90 (d, J=2.7 Hz, 6H), 1.50-1.67 (m, 4H), 1.28 (d, J=2.7 Hz, 14H).

Synthesis of 10-{3-fluorobicyclo[1.1.1]pentan-1-yl}decane-1-sulfinyl Chloride To a mixture of 1-[(10-{3-fluorobicyclo[1.1.1]pentan-1-yl}decyl)sulfanyl]ethanone (50 mg, 0.17 mmol) in DCM (0.5 mL) under an atmosphere of $N_2$ at −20° C. was added $Ac_2O$ (17 mg, 0.17 mmol) and $SO_2Cl_2$ (45 mg, 0.33 mmol). The mixture was stirred at −20° C. for 10 min, then concentrated under reduced pressure to give 10-{3-fluorobicyclo[1.1.1]pentan-1-yl}decane-1-sulfinyl chloride (50 mg, 97%) as an oil.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-10-(3-fluorobicyclo[1.1.1]pentan-1-yl)decane-1-sulfinamide—Mixture of Two Diastereomers To a mixture of (2S,3R,4S,5R,6R)-2-{[(2S,3S,4R)-2-amino-3,4-dihydroxyoctadecyl]oxy}-6-(hydroxymethyl) oxane-3,4,5-triol (50 mg, 0.10 mmol) in DMA (3 mL) and DCM (1 mL) was added $Et_3N$ (106 mg, 1.0 mmol) and 10-(3-fluorobicyclo[1.1.1]pentan-1-yl)decane-1-sulfinyl chloride (50 mg, 0.17 mmol). The mixture was stirred at rt for 1 h, then concentrated under reduced pressure and the residue was purified by preparative-HPLC to give N-((2S,3S,4R)-3,4-dihydroxy-1-((2S,3R,4S,5R,6R)-3,4,5-trihydroxy-6-(hydroxymethyl)tetrahydro-2H-pyran-2-yl)oxy)octadecan-2-yl)-10-(3-fluorobicyclo[1.1.1]pentan-1-yl)decane-1-sulfinamide—mixture of two diastereomers (5.1 mg, 7%) as a solid. LC/MS: mass calcd. for $C_{39}H_{74}FNO_9S$: 751.51, found: 752.07 [M+H]$^+$; $^1$H NMR (400 MHz, CD$_3$OD) δ 4.10 (dd, J=9.5, 2.2 Hz, 1H), 3.85-3.98 (m, 2H), 3.65-3.85 (m, 4H), 3.55-3.65 (m, 2H), 3.45-3.55 (m, 1H), 2.89 (qt, J=13.0, 7.4 Hz, 2H), 1.88 (d, J=2.6 Hz, 6H), 1.54-1.73 (m, 6H), 1.23-1.32 (m, 40H), 0.90-0.95 (m, 3H).

Synthesis of N-[(2S,3S,4R)-3,4-dihydroxy-1-[(2S,3S)-2,3,4-trihydroxybutoxy]octadecan-2-yl]-11-[3-fluorobicyclo[1.1.1]pentan-1-yl]undecanamide

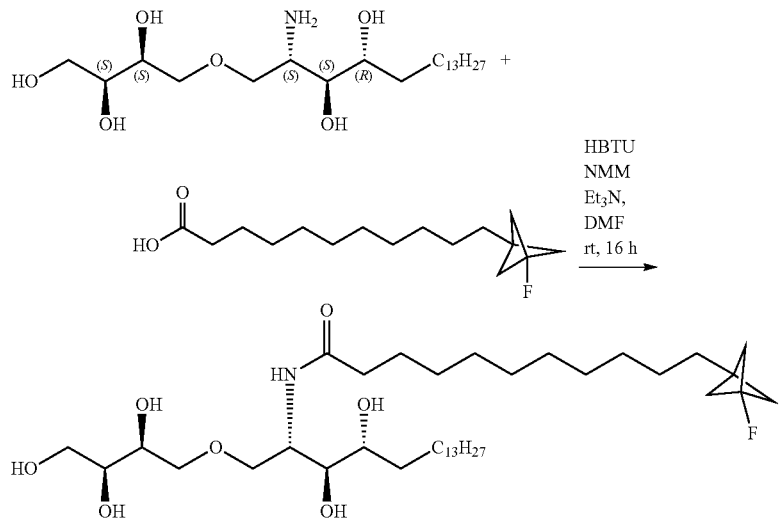

To a mixture of (2S,3S)-4-[[(2S,3S,4R)-2-amino-3,4-dihydroxyoctadecyl]oxy]butane-1,2,3-triol [Diaz et al *Tetrahedron: Asymmetry* 2009, 20, 747-753 and Jervis et al *Bioconjugate Chemistry* 2013, 24, 586-594] (50 mg, 0.12 mmol) and 11-[3-fluorobicyclo[1.1.1]pentan-1-yl]undecanoic acid (35.3 mg, 0.13 mmol) in DMF (3 mL) at rt was added HBTU (90 mg, 0.24 mmol), Et$_3$N (24 mg, 0.24 mmol) and NMM (24 mg, 0.24 mmol). The mixture was stirred at rt overnight, then purified by preparative-HPLC to afford N-[(2S,3S,4R)-3,4-dihydroxy-1-[(2S,3S)-2,3,4-trihydroxybutoxy]octadecan-2-yl]-11-[3-fluorobicyclo[1.1.1]pentan-1-yl]undecanamide (7.8 mg, 10%) as a solid. LC/MS: mass calcd. for $C_{38}H_{72}FNO_7$: 673.53, found: 674.50 [M+H]$^+$; $^1$H NMR (300 MHz, CD$_3$OD) δ 4.20 (s, 1H), 3.74-3.84 (m, 1H), 3.52-3.72 (m, 8H), 3.20-3.30 (m, 1H), 2.23 (t, J=7.5 Hz, 2H), 1.88 (s, 5H), 1.28-1.63 (m, 45H), 0.92 (t, J=6.4 Hz, 3H).

Synthesis of ((2R,3R,4S,5R,6S)-6-(((2S,3S,4R)-2-(11-(3-fluorobicyclo[1.1.1]pentan-1-yl)undecanamido)-3,4-dihydroxyoctadecyl)oxy)-3,4,5-trihydroxytetrahydro-2H-pyran-2-yl)methyl ((4R)-4-((3R,7R,10S,13R)-3,7-dihydroxy-10,13-dimethylhexadecahydro-1H-cyclopenta[a]phenanthren-17-yl)pentanoyl)-L-valinate

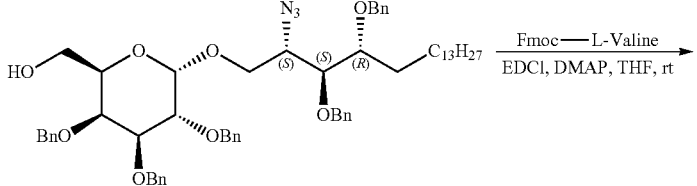

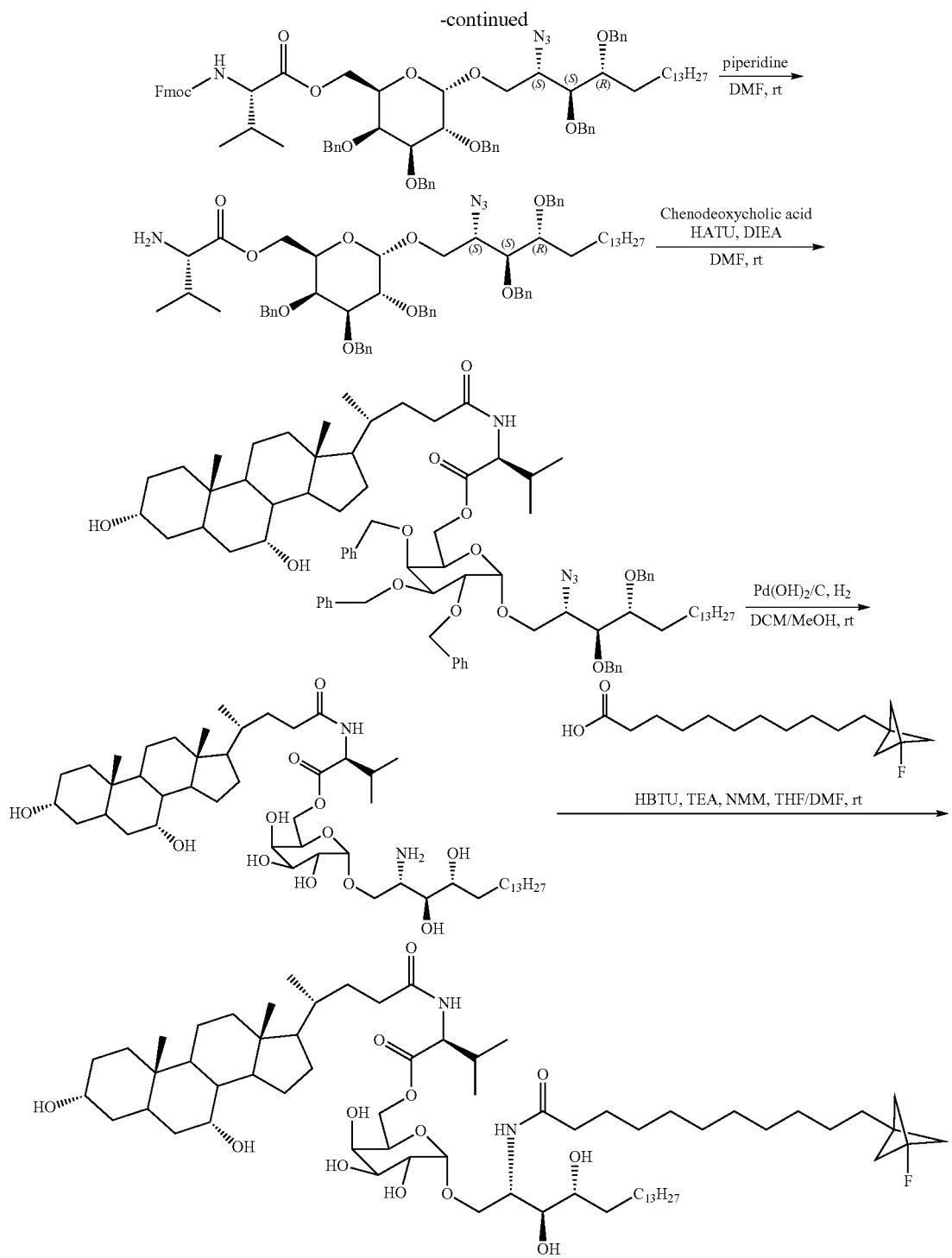

Synthesis of ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methyl (((9H-fluoren-9-yl)methoxy)carbonyl)-L-valinate To a mixture of ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methanol [*Org. Biomol. Chem.* 2011, 9, 8413] (0.7 g, 0.7 mmol) and (((9H-fluoren-9-yl)methoxy)carbonyl)-L-valine (0.5 g, 1.5 mmol) in THF (20 mL) at rt was added EDCI (210 mg, 1.10 mmol) and DMAP (179 mg, 1.46 mmol). The mixture was stirred for 16 h at rt, then concentrated under vacuum and the residue purified by silica gel column chromatography (PE/EtOAc 3:1) to give ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methyl (((9H-fluoren-9-yl)methoxy)carbonyl)-L-valinate (0.8 g, 86%) as an oil. LC/MS: mass calcd. for $C_{79}H_{96}N_4O_{11}$: 1277, found: 1278 $[M+H]^+$.

Synthesis of ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methyl L-valinate To a mixture of ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methyl (((9H-fluoren-9-yl)methoxy)carbonyl)-L-valinate (0.8 g, 0.6 mmol) in DMF (15 mL) at was added piperidine (0.3 g, 3.5 mmol). The mixture was stirred at rt for 0.5 h, then was quenched with H—O and extracted with EtOAc. The combined organic layers were washed with brine, dried over $Na_2SO_4$ and filtered. The filtrate was concentrated under reduced pressure and the residue was purified by silica gel column (PE/EtOAc 2:1) to give ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methyl L-valinate (0.6 g, 91%) as an oil. LC/MS: mass calcd. for $C_{64}H_{86}N_4O_9$: 1055, found: 1056 $[M+H]^+$.

Synthesis of ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methyl ((4R)-4-((3R,7R,10S,13R)-3,7-dihydroxy-10,13-dimethylhexadecahydro-1H-cyclopenta[a]phenanthren-17-yl)pentanoyl)-L-valinate To a mixture of ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methyl L-valinate (0.6 g, 0.6 mmol) and chenodeoxycholic acid (268 mg, 0.68 mmol) in DMF (10 mL) at rt was added HATU (324 mg, 0.85 mmol) and DIPEA (147 mg, 1.14 mmol). The mixture was stirred at rt for 6 h then $H_2O$ added and the mixture extracted with EtOAc. The combined organic layers were washed with brine, dried over $Na_2SO_4$ and filtered. The filtrate was concentrated under reduced pressure and the residue was purified by silica gel column chromatography (PE/EtOAc 3:1) to give ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methyl ((4R)-4-((3R,7R,10S,13R)-3,7-dihydroxy-10,13-dimethylhexadecahydro-1H-cyclopenta[a]phenanthren-17-yl)pentanoyl)-L-valinate (0.6 g, 74%) as an oil. LC/MS: mass calcd. for $C_{88}H_{124}N_4O_{12}$: 1429, found: 1430 $[M+H]^+$.

Synthesis of ((2R,3R,4S,5R,6S)-6-(((2S,3S,4R)-2-amino-3,4-dihydroxyoctadecyl)oxy)-3,4,5-trihydroxytetrahydro-2H-pyran-2-yl)methyl ((4R)-4-((3R,7R,10S,13R)-3,7-dihydroxy-10,13-dimethylhexadecahydro-1H-cyclopenta[a]phenanthren-17-yl)pentanoyl)-L-valinate A mixture of ((2R,3S,4S,5R,6S)-6-(((2S,3S,4R)-2-azido-3,4-bis(benzyloxy)octadecyl)oxy)-3,4,5-tris(benzyloxy)tetrahydro-2H-pyran-2-yl)methyl ((4R)-4-((3R,7R,10S,13R)-3,7-dihydroxy-10,13-dimethylhexadecahydro-1H-cyclopenta[a]phenanthren-17-yl)pentanoyl)-L-valinate (0.6 g, 0.4 mmol) and 20% $Pd(OH)_2$/C (0.6 g) in MeOH (15 mL) and DCM (15 mL) was hydrogenated (1 atm) at rt for 16 h. The mixture was filtered through a pad of Celite and the filter cake was washed with MeOH. The filtrate was concentrated under reduced pressure to give ((2R,3R,4S,5R,6S)-6-(((2S,3S,4R)-2-amino-3,4-dihydroxyoctadecyl)oxy)-3,4,5-trihydroxytetrahydro-2H-pyran-2-yl)methyl ((4R)-4-((3R,7R,10S,13R)-3,7-dihydroxy-10,13-dimethylhexadecahydro-1H-cyclopenta[a]phenanthren-17-yl)pentanoyl)-L-valinate (0.33 g, 83%) as a solid. LC/MS: mass calcd. for $C_{53}H_{96}N_2O_{12}$: 953, found: 954 $[M+H]^+$.

Synthesis of ((2R,3R,4S,5R,6S)-6-(((2S,3S,4R)-2-(11-(3-fluorobicyclo[1.1.1]pentan-1-yl)undecenamido)-3,4-dihydroxyoctadecyl)oxy)-3,4,5-trihydroxytetrahydro-2H-pyran-2-yl)methyl ((4R)-4-((3R,7R,10S,13R)-3,7-dihydroxy-10,13-dimethylhexadecahydro-1H-cyclopenta[a]phenanthren-17-yl)pentanoyl)-L-valinate To a mixture of ((2R,3R,4S,5R,6S)-6-(((2S,3S,4R)-2-amino-3,4-dihydroxyoctadecyl)oxy)-3,4,5-trihydroxytetrahydro-2H-pyran-2-yl)methyl ((4R)-4-((3R,7R,10S,13R)-3,7-dihydroxy-10,13-dimethylhexadecahydro-1H-cyclopenta[a]phenanthren-17-yl)pentanoyl)-L-valinate (100 mg, 0.11 mmol) and 11-(3-fluorobicyclo[1.1.1]pentan-1-yl)undecanoic acid (31 mg, 0.12 mmol) in THF (5 mL) and DMF (5 mL) at rt under an atmosphere of $N_2$ was added HBTU (119 mg, 0.32 mmol), $Et_3N$ (0.1 mL) and NMM (0.1 mL). The mixture was stirred at rt for 16 h, then quenched with $H_2O$ and extracted with EtOAc. The combined organic layers were washed with brine, dried over $Na_2SO_4$ and filtered. The filtrate was purified by silica gel column chromatography (DCM/MeOH) to give a crude product (50 mg), which was purified further by trituration with $CH_3CN$ to give ((2R,3R,4S,5R,6S)-6-(((2S,3S,4R)-2-(11-(3-fluorobicyclo[1.1.1]pentan-1-yl)undecanamido)-3,4-dihydroxyoctadecyl)oxy)-3,4,5-trihydroxytetrahydro-2H-pyran-2-yl)methyl ((4R)-4-((3R,7R,10S,13R)-3,7-dihydroxy-10,13-dimethylhexadecahydro-1H-cyclopenta[a]phenanthren-17-yl)pentanoyl)-L-valinate (26 mg, 21%) as a solid. LC/MS: mass calcd. for $C_{69}H_{121}FN_2O_{13}$: 1205, found: 1206 $[M+H]^+$.

Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(oxetan-3-yl)undecanamide

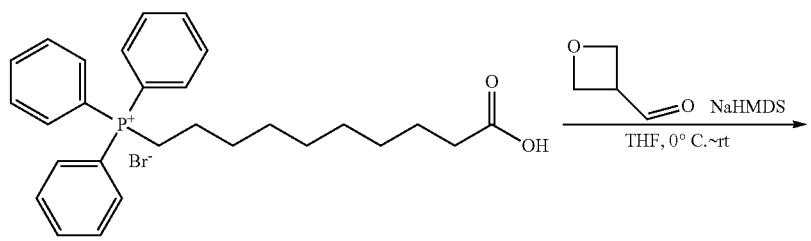

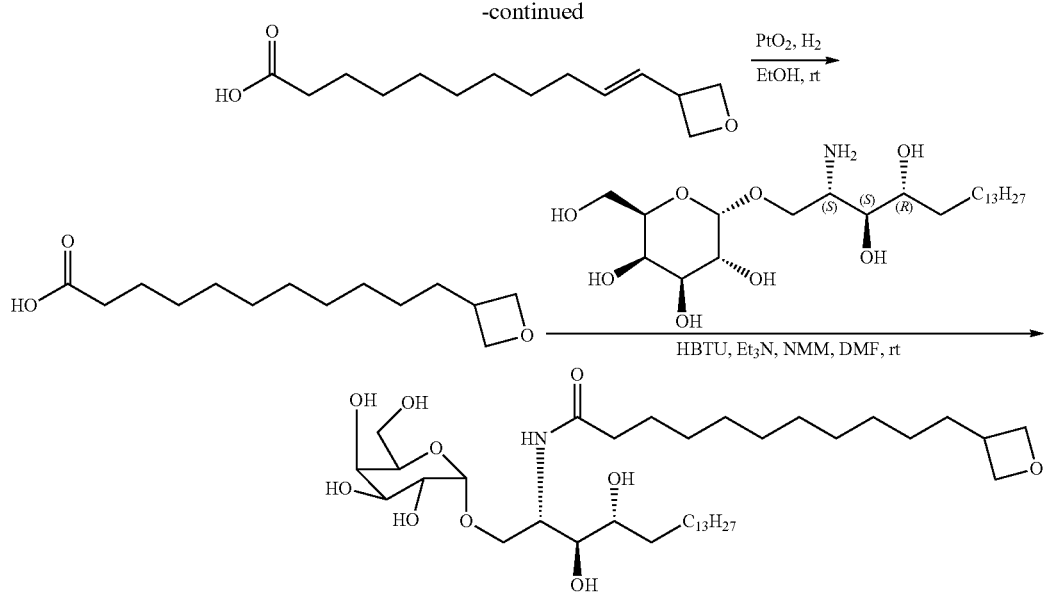

Step 1: Synthesis of 11-(oxetan-3-yl)undec-10-enoic acid

To a mixture of (9-carboxynonyl)triphenylphosphonium bromide (565 mg, 1.1 mmol) in THF (20 mL) at 0° C. under an atmosphere of $N_2$ was added NaHMDS, 2.0 M (1.1 mL, 2.2 mmol). The mixture was warmed to room temperature and stirred for 1 h, then oxetane-3-carbaldehyde (86 mg, 1.0 mmol) in THF (1 mL) was added. The mixture was stirred overnight at rt, then acidified pH ~ 1 with 1N HCl and extracted with EtOAc (3×30 mL). The combined organic layers were washed with brine (30 mL), dried over anhydrous $Na_2SO_4$, filtered, and concentrated under reduced pressure. The residue was purified by column chromatography on silica gel (PE/EtOAc 1:1] to give 11-(oxetan-3-yl)undec-10-enoic acid (100 mg, 42%) as an oil. LC/MS: mass calcd. for $C_{14}H_{24}O_3$: 240, found: 239 $[M-H]^-$.

Step 2: Synthesis of 11-(oxetan-3-yl)undecanoic

A mixture of 11-(oxetan-3-yl)undec-10-enoic acid (100 mg, 0.4 mmol), $PtO_2$ (20 mg, 0.1 mmol) and EtOH (30 mL) was stirred under an atmosphere of $H_2$ (balloon) for 1 h. The mixture was filtered through a pad of Celite and the filtrate was concentrated under reduced pressure to give 11-(oxetan-3-yl)undecanoic acid (100 mg, 99%) as a solid. LC/MS: mass calcd. for $C_{14}H_{26}O_3$: 242, found: 241 $[M-H]^-$.

Step 3: Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(oxetan-3-yl)undecanamide To a mixture of (2S,3R,4S,5R,6R)-2-(((2S,3S,4R)-2-amino-3,4-dihydroxyoctadecyl)oxy)-6-(hydroxymethyl)tetrahydro-2H-pyran-3,4,5-triol (50 mg, 0.1 mmol) in DMF (2 mL) under an atmosphere of $N_2$ was added 11-(oxetan-3-yl)undecanoic acid (25 mg, 0.1 mmol), $Et_3N$ (0.1 mL), NMM (0.1 mL) and HBTU (80 mg, 0.2 mmol). The mixture was stirred at rt for 16 h, then diluted with $H_2O$ (10 mL) and extract with EtOAc (30 mL×3). The combined organic layers were washed with brine (30 mL×2), dried over $Na_2SO_4$ and filtered. The filtrate was concentrated under reduced pressure and the residue was purified by column chromatography on silica gel (DCM/MeOH 5:1) and preparative-HPLC to give N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(oxetan-3-yl)undecanamide (13.8 mg, 19%) as a solid. LC/MS: mass calcd. for $C_{38}H_{73}NO_{10}$: 703.99, found: 704.50 $[M+H]+$. 1H NMR (300 MHz, CD3OD) δ 4.81 (dd, J=7.9, 5.8 Hz, 2H), 4.39 (t, J=6.1 Hz, 2H), 4.21 (d, J=5.7 Hz, 1H), 3.56-3.91 (m, 10H), 2.99-3.01 (m, 1H), 2.35-2.18 (m, 2H), 1.63-1.70 (m, 6H), 1.33-1.46 (m, 39H), 0.87-0.97 (m, 3H).

Synthesis of N-[(2S,3S,4R)-3,4-dihydroxy-1-{[(2,3R,4S,5R,6R)-3,4,5-trihydroxy-6-(hydroxymethyl)oxan-2-yl]oxy}octadecan-2-yl]-11-(3-methyloxetan-3-yl)undecanamide

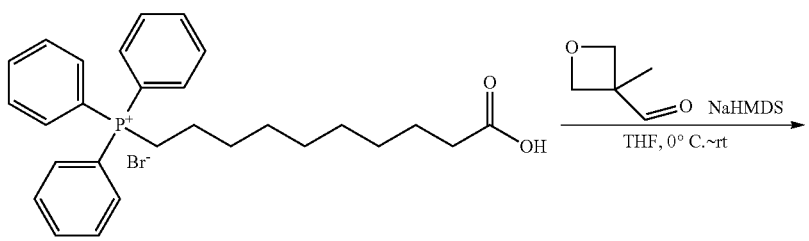

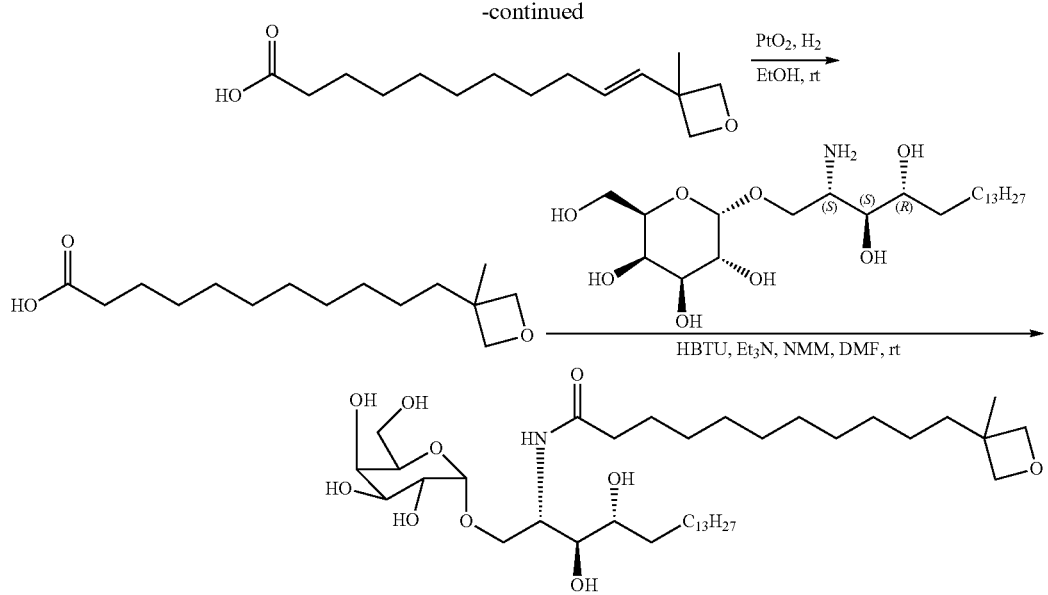

Step 1: Synthesis of 11-(3-methyloxetan-3-yl)undec-10-enoic acid

To a mixture of (9-carboxynonyl)triphenylphosphonium bromide (564 mg, 1.1 mmol) in THF (20 mL) at 0° C. under an atmosphere of $N_2$ was added 2 M NaHMDS (1.1 mL, 2.2 mmol). The mixture was warmed to rt and stirred for 1 h, then 3-methyloxetane-3-carbaldehyde (100 mg, 1.0 mmol) in THF (2 mL) was added. The mixture was stirred at rt overnight, then acidified to pH~1 with 1N HCl, and extracted with EtOAc (3×20 mL). The combined organic layers were washed with brine (30 mL), dried over anhydrous $Na_2SO_4$, filtered, and concentrated under reduced pressure. The residue was purified by column chromatography on silica gel (PE/EA 1:1) to give 11-(3-methyloxetan-3-yl)undec-10-enoic acid (110 mg, 43%) as an oil LC/MS: mass calcd. for $C_{15}H_{26}O_3$: 254, found: 253 [M−H]⁻.

Step 2: Synthesis of 11-(3-methyloxetan-3-yl)undecanoic Acid

A mixture of 11-(3-methyloxetan-3-yl)undec-10-enoic acid (110 mg, 0.4 mmol) and $PtO_2$ (20 mg, 0.1 mmol) in EtOH (30 mL) was stirred under an atmosphere of $H_2$ (balloon) for 1 h. The mixture was filtered through a pad of Celite and the filtrate was concentrated under reduced pressure to give 11-(3-methyloxetan-3-yl)undecanoic acid (110 mg, 99%) as a solid. LC/MS: mass calcd. for $C_{15}H_{28}O_3$: 256, found: 255 [M−H]⁻.

Step 3: Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide To a mixture of (2S,3R,4S,5R,6R)-2-(((2S,3S,4R)-2-amino-3,4-dihydroxyoctadecyl)oxy)-6-(hydroxymethyl)tetrahydro-2H-pyran-3,4,5-triol (50 mg, 0.1 mmol) in DMF (2 mL) under an atmosphere of $N_2$ was added 11-(3-methyloxetan-3-yl)undecanoic acid (27 mg, 0.1 mmol), $Et_3N$ (0.1 mL), NMM (0.1 mL) and HBTU (80 mg, 0.2 mmol). The mixture was stirred at rt for 16 h, then diluted with $H_2O$ (10 mL) and extract with EtOAc (30 mL×3). The combined organic layers were washed with brine (30 mL×2), dried over $Na_2SO_4$, filtered and the filtrate was concentrated under reduced pressure. The residue was purified by column chromatography on silica gel (DCM/MeOH 5.1) and preparative-HPLC to give N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide (10.2 mg, 13%) as a solid. LC/MS: mass calcd. for $C_{39}H_{75}NO_{10}$: 718.01, found: 718.50 [M+H]⁺; ¹H NMR (300 MHz, $CD_3OD$) δ 4.44 (d, J=0.1=5.6 Hz, 2H), 4.35 (d, J=5.5 Hz, 2H), 4.15-4.25 (m, 1H), 3.53-3.83 (m, 10H), 3.31-3.32 (m, 1H), 2.24 (t, J=7.5 Hz, 2H), 1.52-1.65 (m, 6H), 1.28-1.36 (m, 41H), 0.83-0.97 (m, 3H).

Synthesis of 11-((1r,3s)-adamantan-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide

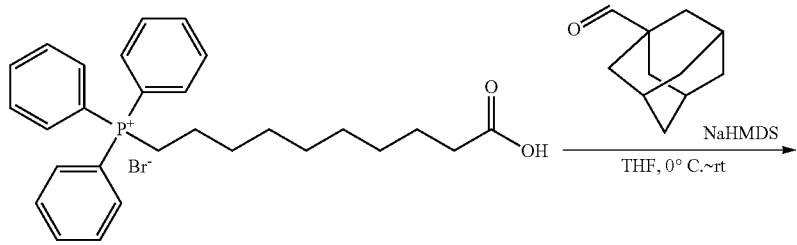

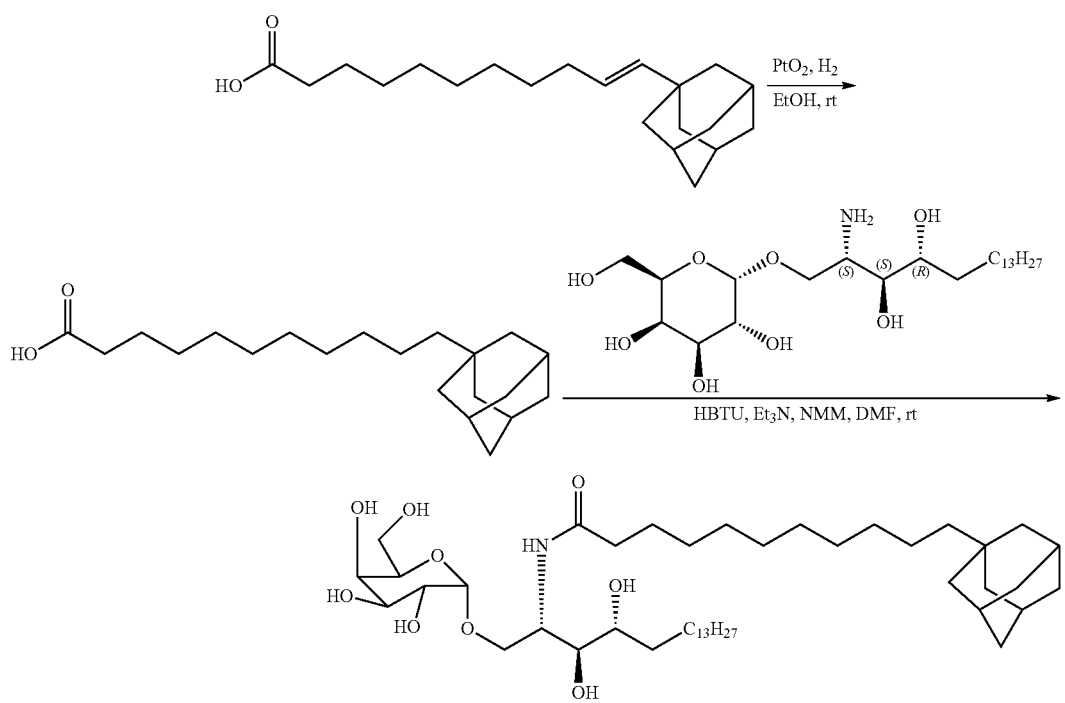

Step 1: Synthesis of (11-((1s,3s)-adamantan-1-yl)undec-10-enoic acid

Prepared in a manner similar to 11-(3-methyloxetan-3-yl)undec-10-enoic acid and purified by column chromatography on silica gel (PE/EtOAc 1:1) to give (11-((1s,3s)-adamantan-1-yl)undec-10-enoic acid (250 mg, 799%) as a solid. LC/MS: mass calcd. for $C_{21}H_{34}O_2$: 318, found: 317 [M−H]⁻.

Step 2: Synthesis of 11-((1r,3s)-adamantan-1-yl)undecanoic acid

A mixture of (11-((1s,3s)-adamantan-1-yl)undec-10-enoic acid (250 mg, 0.7 mmol) and $PtO_2$ (40 mg, 0.2 mmol) in EtOH (30 mL) was stirred under an atmosphere of $H_2$ (balloon) for 1 h. The mixture was filtered through a pad of Celite and the filtrate was concentrated under reduced pressure to give 11-((1r,3s)-adamantan-1-yl)undecanoic acid (250 mg, 99.4%) as a solid. LC/MS: mass calcd. for $C_{21}H_{36}O_2$: 320, found: 319 [M−H]⁻.

Step 3: Synthesis of 11-((1r,3s)-adamantan-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (DCM/MeOH 5:1) and preparative-HPLC to give 11-((1r,3s)-adamantan-1-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide (5.4 mg, 6.4%) as a solid. LC/MS: mass calcd. for $C_{45}H_{83}NO_9$: 782.14, found: 782.65 [M+H]⁺; ¹H NMR (300 MHZ, CD3OD) δ 4.19 (dd, J=6.7, 4.4 Hz, 1H), 3.54-3.94 (m, 10H), 3.31-3.32 (m, 1H), 2.33 (t, J=7.4 Hz, 1H), 2.24 (t, J=7.4 Hz, 1H), 1.99-1.91 (m, 4H), 1.65-1.86 (m, 11H), 1.49-1.53 (m, 7H), 1.26-1.36 (m, 34H), 1.05-1.09 (m, 3H), 0.87-0.91 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(tetrahydrofuran-3-yl)undecanamide

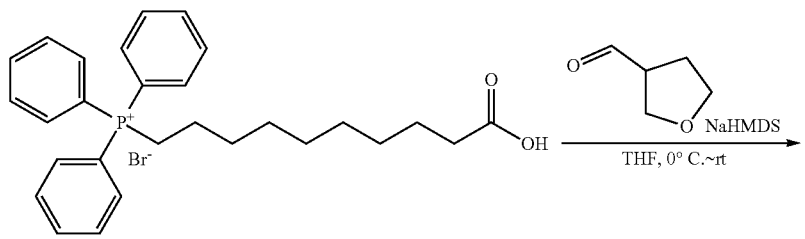

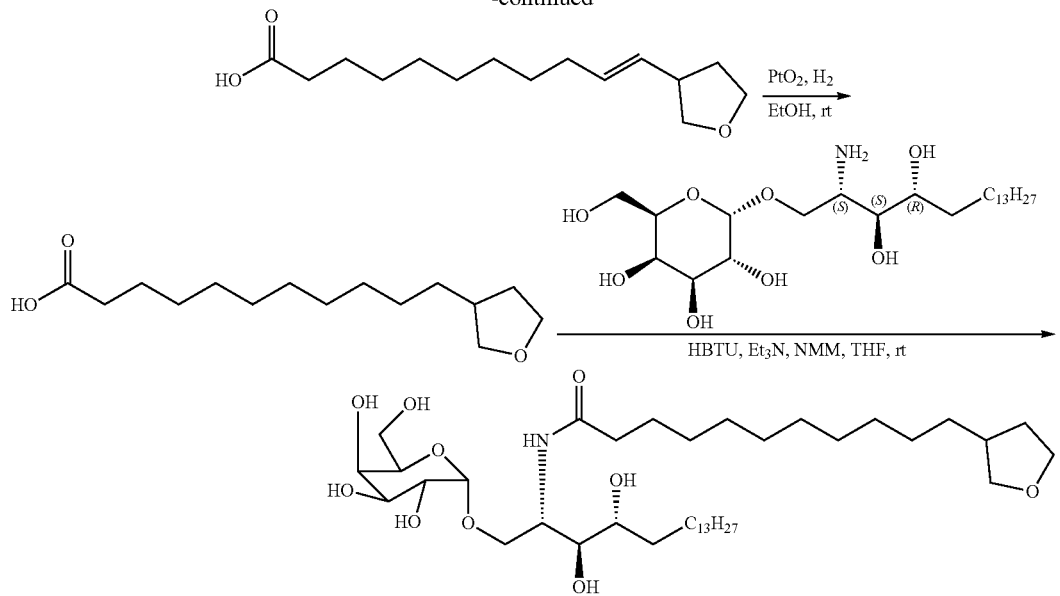

Step 1: Synthesis of 11-(tetrahydrofuran-3-yl)undec-10-enoic acid

Prepared in a manner similar to 11-(3-methyloxetan-3-yl)undec-10-enoic acid and purified by column chromatography on silica gel (PE/EtOAc 1:1) to give 11-(tetrahydrofuran-3-yl)undec-10-enoic acid (250 mg, 79%) as solid. LC/MS: mass calcd. for $C15H_{26}O_3$: 254, found: 253 [M–H]$^-$.

Step 2: Synthesis of 11-(tetrahydrofuran-3-yl)undecanoic acid

A mixture of 11-(tetrahydrofuran-3-yl)undec-10-enoic acid (200 mg, 0.7 mmol) and $PtO_2$ (40 mg, 0.2 mmol) in EtOH (30 mL) was stirred under an atmosphere of $H_2$ (balloon) for 1 h, then filtered through a pad of Celite and the filtrate was concentrated under reduced pressure to give 11-(tetrahydrofuran-3-yl)undecanoic acid (200 mg, 99%) as a solid. LC/MS: mass calcd. for $C_{15}H_{28}O_3$: 256, found: 255 [M–H]$^-$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(tetrahydrofuran-3-yl)undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(tetrahydrofuran-3-yl)undecanamide (9 mg, 8%) as a solid. LC/MS: mass calcd. for $C_{39}H_{75}NO_{10}$: 717.54, found: 718.60 [M+H]$^+$; $^1$H NMR (300 MHz, MeOHl-$d_4$) δ 4.21 (d, J=5.7 Hz, 1H), 3.56-3.92 (m, 12H), 2.15-2.20 (m, 2H), 1.63-1.70 (m, 5H), 1.33-1.46 (s, 44H), 0.87-0.97 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(tetrahydro-2H-pyran-4-yl)undecanamide

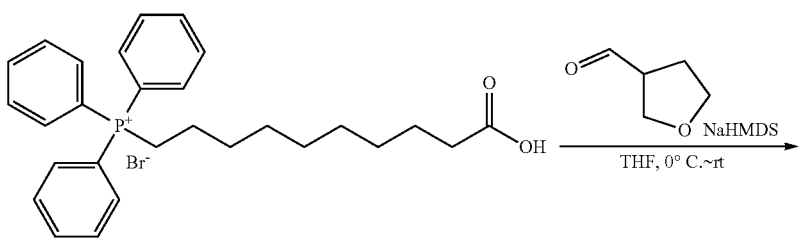

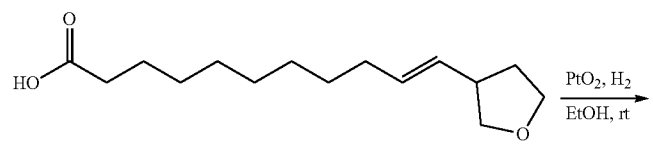

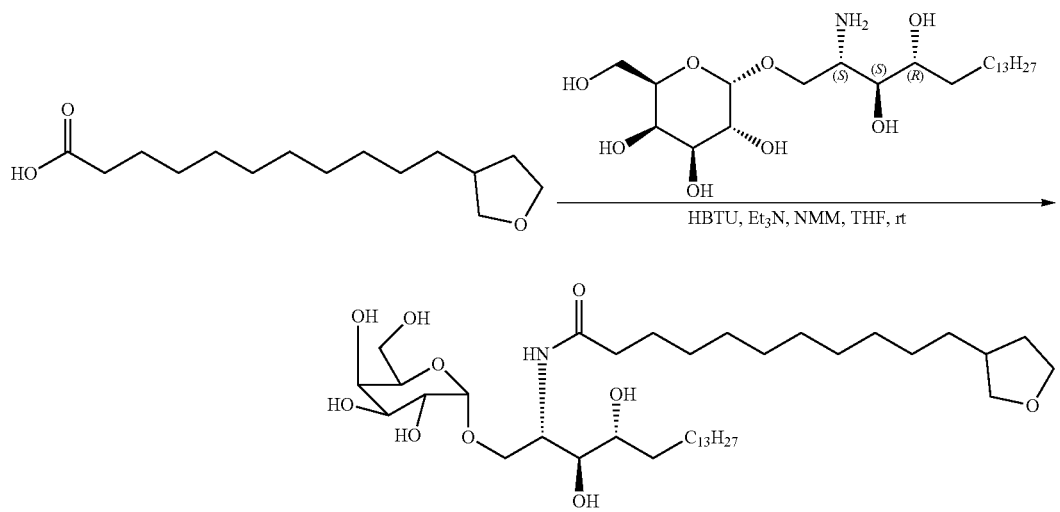

Step 1: Synthesis of 11-(tetrahydro-2H-pyran-4-yl)undec-10-enoic acid

Prepared in a manner similar to 11-(3-methyloxetan-3-yl)undec-10-enoic acid and purified by column chromatography on silica gel (PE/EtOAc 1:1) to give 11-(tetrahydro-2H-pyran-4-yl)undec-10-enoic acid (200 mg, 85%) as a solid. LC/MS: mass calcd. for $C_{16}H_{28}O_3$: 268, found: 267 [M−H]$^-$. as a solid.

Step 2: Synthesis of 11-(tetrahydro-2H-pyran-4-yl)undecanoic acid

A mixture of 11-(tetrahydro-2H-pyran-4-yl)undec-10-enoic acid (200 mg, 0.7 mmol) and PtO$_2$ (40 mg, 0.2 mmol) in EtOH (50 mL) was stirred under an atmosphere of H$_2$ (balloon) for 1h. The mixture was filtered through a pad of Celite and the filtrate was concentrated under reduced pressure to give 11-(tetrahydro-2H-pyran-4-yl)undecanoic acid (200 mg, 99%) as a solid. LC/MS: mass calcd. for $C_{16}H_{30}O_3$: 270, found: 269 [M−H]$^-$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(tetrahydro-2H-pyran-4-yl)undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(tetrahydro-2H-pyran-4-yl)undecanamide (9.6 mg, 8.7%) as a solid. LC/MS: mass calcd. for $C_{40}H_{77}NO_{10}$: 731.55, found: 732.65 [M+H]$^+$; $^1$H NMR (400 MHZ, CD3OD) δ 4.21 (d, J=5.7 Hz, 1H), 3.56-3.91 (m, 10H), 3.51-3.55 (m, 2H), 3.41-3.44 (m, 2H), 2.22-2.23 (m, 2H), 1.65-1.70 (m, 5H), 1.23-1.46 (m, 44H), 0.87-0.97 (m, 3H).

Synthesis of tert-butyl 4-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)piperidine-1-carboxylate

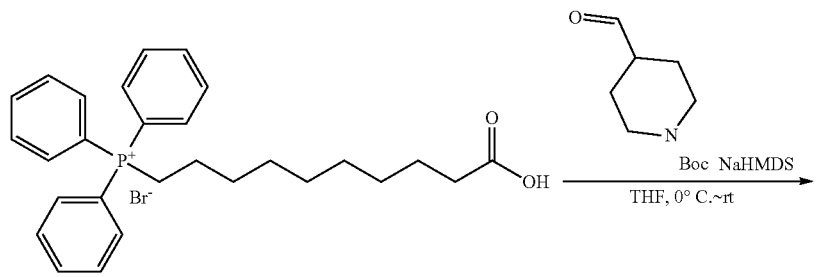

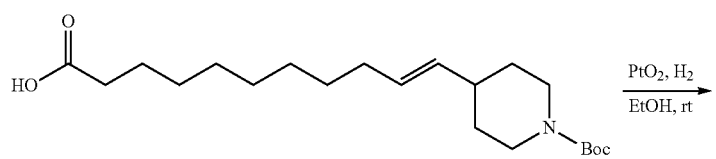

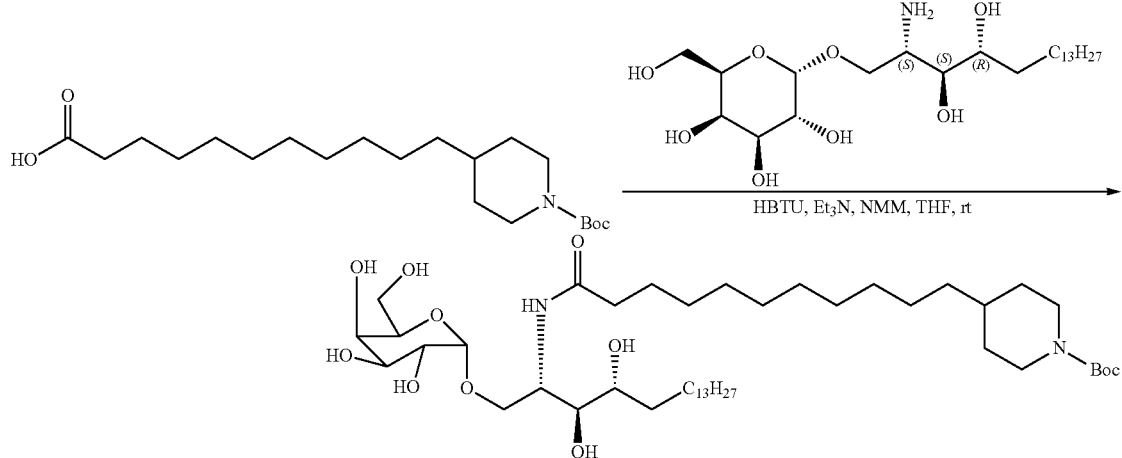

Step 1: Synthesis of 11-(1-(tert-butoxycarbonyl)piperidin-4-yl)undec-10-enoic acid Prepared in a manner similar to 11-(3-methyloxetan-3-yl)undec-10-enoic acid and purified by column chromatography on silica gel (PE/EtOAc 1:1) to give 11-(1-(tert-butoxycarbonyl)piperidin-4-yl)undec-10-enoic acid (280 mg, 76%) as a solid. LC/MS: mass calcd. for $C_{21}H_{37}NO_4$: 367, found: 366 $[M-H]^-$.

Step 2: Synthesis of 11-(1-(tert-butoxycarbonyl)piperidin-4-yl)undecanoic acid A mixture of 11-(1-(tert-butoxycarbonyl)piperidin-4-yl)undec-10-enoic acid (280 mg, 0.76 mmol) and $PtO_2$ (40 mg, 0.2 mmol) in EtOH (30 mL) was stirred under an atmosphere of $H_2$ (balloon) for 1 h. The mixture was filtered through a pad of Celite and concentrated under reduced pressure to give 11-(1-(tert-butoxycarbonyl)piperidin-4-yl)undecanoic acid (280 mg, 99%) as a solid. LC/MS: mass calcd. for $C_{21}H_{39}NO_4$: 369, found: 368 $[M-H]^-$.

Step 3: Synthesis of tert-butyl 4-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)piperidine-1-carboxylate Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (DCM/MeOH 5:1) and preparative-HPLC to give tert-butyl 4-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)piperidine-1-carboxylate (13.6 mg, 6%) as a solid. LC/MS: mass calcd. for $C_{45}H_{86}N_2O_{11}$: 830.62, found: 831.65 $[M+H]^+$; $^1H$ NMR (400 MHZ, CD3OD) δ 4.21 (d, J=5.7 Hz, 1H), 4.01-4.07 (m, 2H), 3.56-3.91 (m, 10H), 2.65-2.71 (m, 2H), 2.17-2.19 (m, 2H), 1.63-1.70 (m, 6H), 1.54 (s, 9H), 1.33-1.46 (m, 41H), 1.01-1.09 (m, 2H), 0.87-0.97 (m, 3H).

Synthesis of N-((2S,3S,4R)-3,4-dihydroxy-1-(((2,3R,4S,5R,6R)-3,4,5-trihydroxy-6-(hydroxymethyl)tetrahydro-2H-pyran-2-yl)oxy)octadecan-2-yl)-11-(piperidin-4-yl)undecanamide

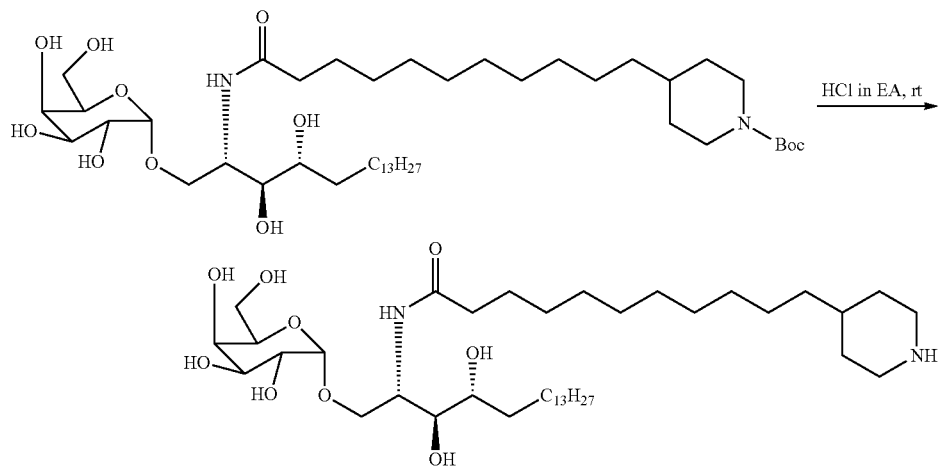

To a mixture of tert-butyl 4-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)piperidine-1-carboxylate (100 mg, 0.14 mmol) in EtOAc (3 mL) was added 2N HCl in EtOAc (3 mL). The mixture was stirred at rt for 1 h, then concentrated under reduced pressure and the residue was purified by preparative-HPLC to give to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(piperidin-4-yl)undecanamide (10.2 mg, 12.2%) as a solid. LC/MS: mass calcd. for $C_{40}H_{78}N_2O_9$: 730.57, found: 731.60 $[M+H]^+$; $^1H$ NMR (400 MHZ, CD3OD) § 4.21 (d, J=5.7 Hz, 1H), 3.46-3.91 (m, 10H), 2.89-2.99 (m, 2H), 2.35-2.41 (m, 2H), 1.90-1.97 (m, 2H), 1.63-1.70 (m, 5H), 1.33-1.46 (m, 45H), 0.87-0.97 (m, 3H).

Synthesis of tert-butyl 3-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)azetidine-1-carboxylate Step 1: Synthesis of 11-(1-(tert-butoxycarbonyl)azetidin-3-yl)undec-10-enoic acid Prepared in a manner similar to 11-(3-methyloxetan-3-yl)undec-10-enoic acid and purified by column chromatography on silica gel (PE/EtOAc 1:1) to give 11-(1-(tert-butoxycarbonyl)azetidin-3-yl)undec-10-enoic acid (180 mg, 33%) as a solid. LC/MS: mass calcd. for $C_{19}H_{33}NO_4$: 339, found: 338 $[M-H]^-$.

Step 2: Synthesis of 11-[1-(tert-butoxycarbonyl)azetidin-3-yl]undecanoic acid

A mixture of 11-(1-(tert-butoxycarbonyl)azetidin-3-yl)undec-10-enoic acid (180 mg, 0.53 mmol) and $PtO_2$ (40 mg, 0.2 mmol) in EtOH (50 mL) was stirred under an atmosphere of $H_2$ (balloon) for 1h. The mixture was filtered through a pad of Celite and the filtrate was concentrated under reduced pressure to give 11-[1-(tert-butoxycarbonyl)azetidin-3-yl]undecanoic acid (180 mg, 99%) as a solid. LC/MS: mass calcd. for $C_{19}H_{35}NO_4$: 341, found: 340 $[M-H]^-$.

Step 3: Synthesis of tert-butyl 3-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)azetidine-1-carboxylate Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column

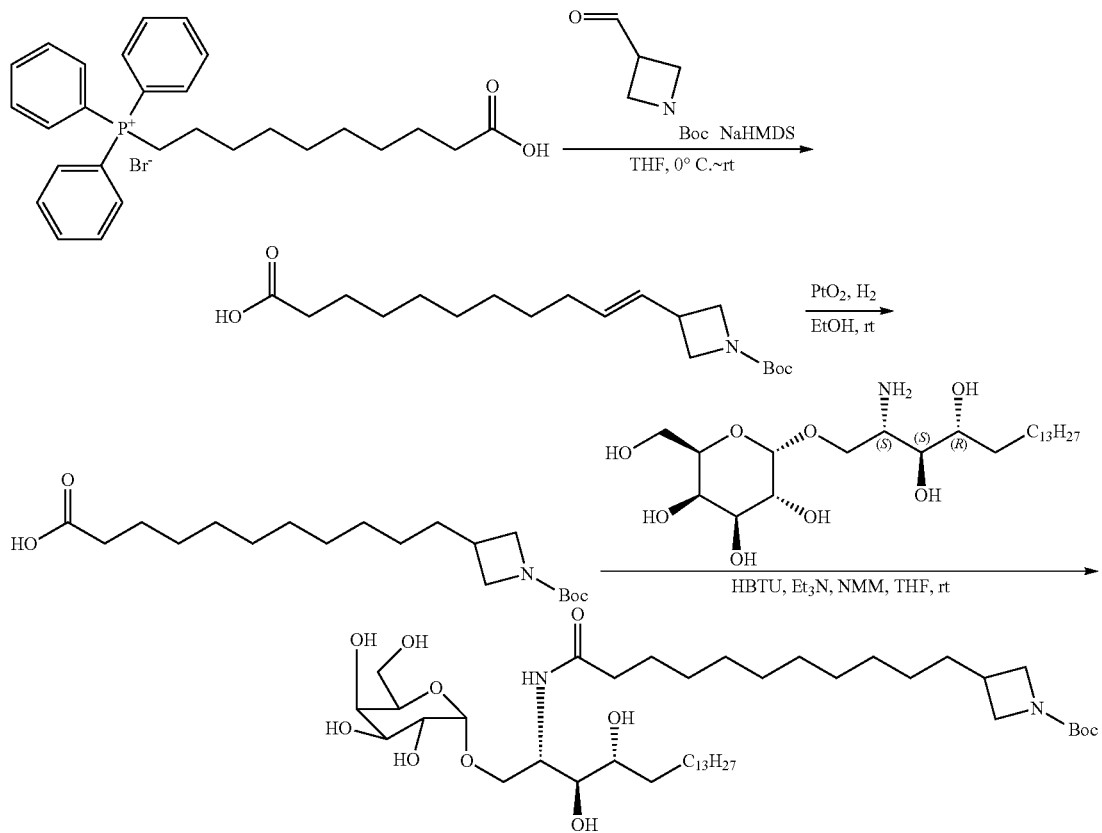

chromatography on silica gel (DCM/MeOH 5:1) and preparative-HPLC to give tert-butyl 3-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)azetidine-1-carboxylate (9.4 mg, 6.2%) as a solid. LC/MS: mass calcd. for $C_{43}H_{82}N_2O_{11}$: 802.59, found: 803.65 $[M+H]^+$; $^1H$ NMR (400 MHZ, CD3OD) δ 4.21 (d, J=5.7 Hz, 1H), 3.98-4.05 (m, 2H), 3.46-3.81 (m, 12H), 2.41-2.53 (m, 1H), 2.18-2.25 (m, 2H), 1.63-1.70 (m, 6H), 1.50 (s, 9H), 1.33-1.46 (m, 39H), 0.87-0.97 (m, 3H).

Synthesis of 11-(azetidin-3-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide

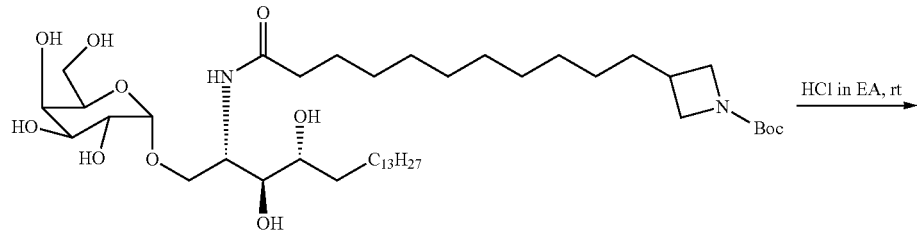

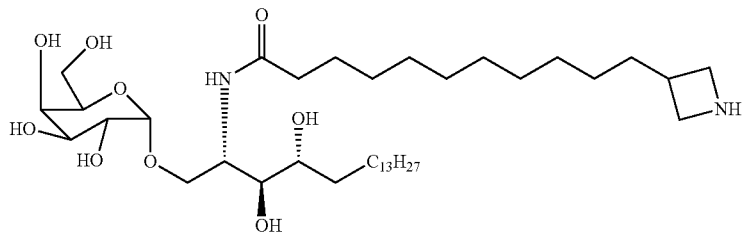

To a mixture of tert-butyl 3-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)azetidine-1-carboxylate (100 mg, 0.14 mmol) in EtOAc (3 mL) was added 2N HCl in EtOAc (3 mL). The mixture was stirred at rt for 1 h, then concentrated under reduced pressure and the residue was purified by preparative-HPLC to give 11-(azetidin-3-yl)-N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)undecanamide (7.6 mg, 8.6%) as a solid. LC/MS: mass calcd. for $C_{38}H_{74}N_2O_9$: 702.54, found: 703.60 [M+H]$^+$; $^1$H NMR (400 MHZ, CD3OD) δ 4.11-4.21 (m, 2H), 3.46-3.93 (m, 10H), 2.80-2.91 (m, 2H), 2.35-2.41 (m, 1H), 2.25-2.29 (m, 1H), 1.63-1.70 (m, 5H), 1.33-1.46 (m, 42H), 0.87-0.97 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(1,1-dioxidotetrahydro-2H-thiopyran-4-yl)undecanamide

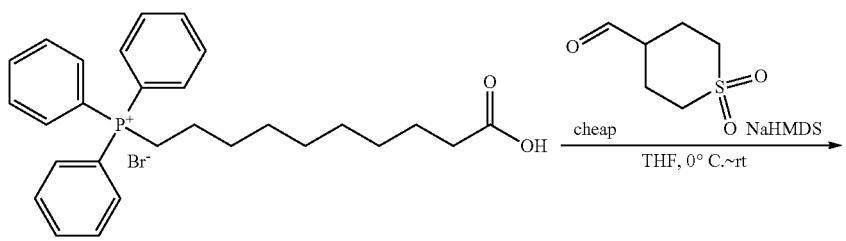

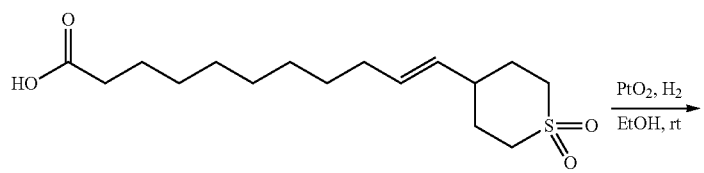

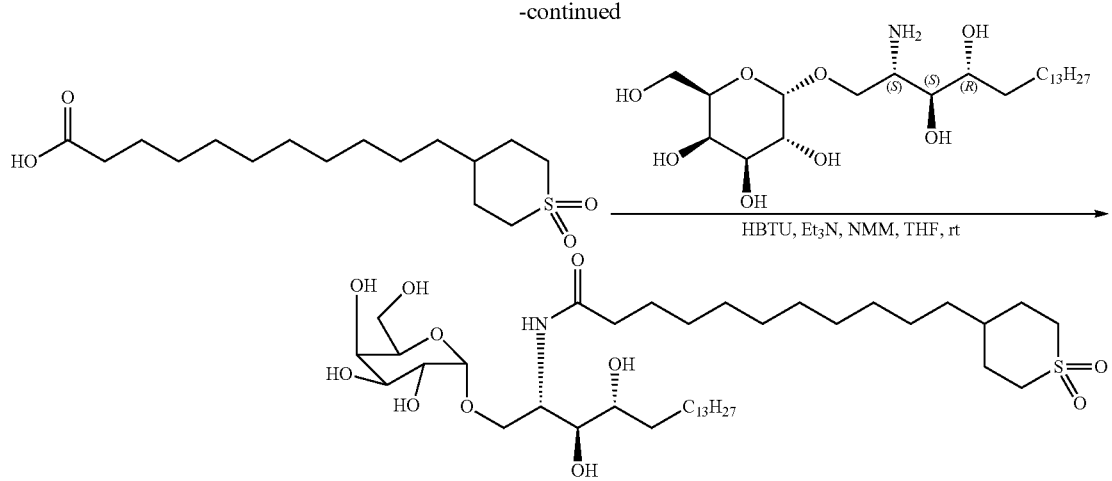

Step 1: Synthesis of 11-(1,1-dioxidotetrahydro-2H-thiopyran-4-yl)undec-10-enoic acid Prepared in a manner similar to 11-(3-methyloxetan-3-yl)undec-10-enoic acid and purified by column chromatography on silica gel (PE/EtOAc 1:1) to give 11-(1,1-dioxidotetrahydro-2H-thiopyran-4-yl)undec-10-enoic acid (100 mg, 51%) as a solid. LC/MS: mass calcd. for $C_{16}H_{28}O_4S$: 316, found: 315 [M−H]−.

Step 2: Synthesis of 11-(1,1-dioxidotetrahydro-2H-thiopyran-4-yl)undecanoic acid A mixture of 11-(1,1-dioxidotetrahydro-2H-thiopyran-4-yl)undec-10-enoic acid (80 mg, 0.3 mmol) and $PtO_2$ (20 mg, 0.1 mmol) in EtOH (30 mL) was stirred under an atmosphere of $H_2$ (balloon) for 1 h. The mixture was filtered through a pad of Celite and the filtrate was concentrated under reduced pressure to give 11-(1,1-dioxidotetrahydro-2H-thiopyran-4-yl)undecanoic acid (80 mg, 80%) as a solid. LC/MS: mass calcd. for $C_{16}H_{30}O_4S$: 318, found: 317 [M−H]−.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(1,1-dioxidotetrahydro-2H-thiopyran-4-yl)undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(1,1-dioxidotetrahydro-2H-thiopyran-4-yl)undecanamide (20.7 mg, 21%) as a solid. LC/MS: mass calcd. for $C_{40}H_{77}NO_{11}S$: 779.52, found: 780.50 [M+H]+; $^1H$ NMR (300 MHz, DMSO-$d_6$) § 4.65 (s, 1H), 3.33-3.93 (m, 12H), 2.93-3.13 (m, 4H), 2.93 (d, J=13.5 Hz, 2H), 2.04 (t, J=7.2 Hz, 2H), 1.94 (d, J=10.3 Hz, 2H), 1.38-1.53 (m, 8H), 1.10-1.32 (m, 43H), 0.87-0.97 (m, 3H).

Synthesis of tert-butyl 3-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)pyrrolidine-1-carboxylate

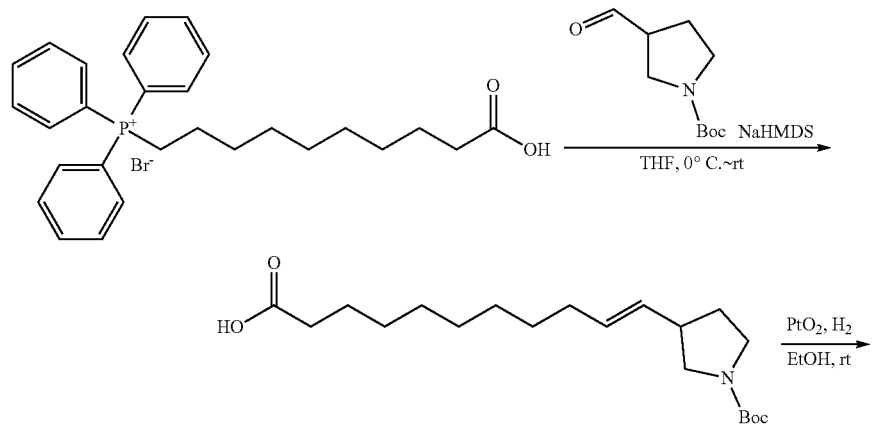

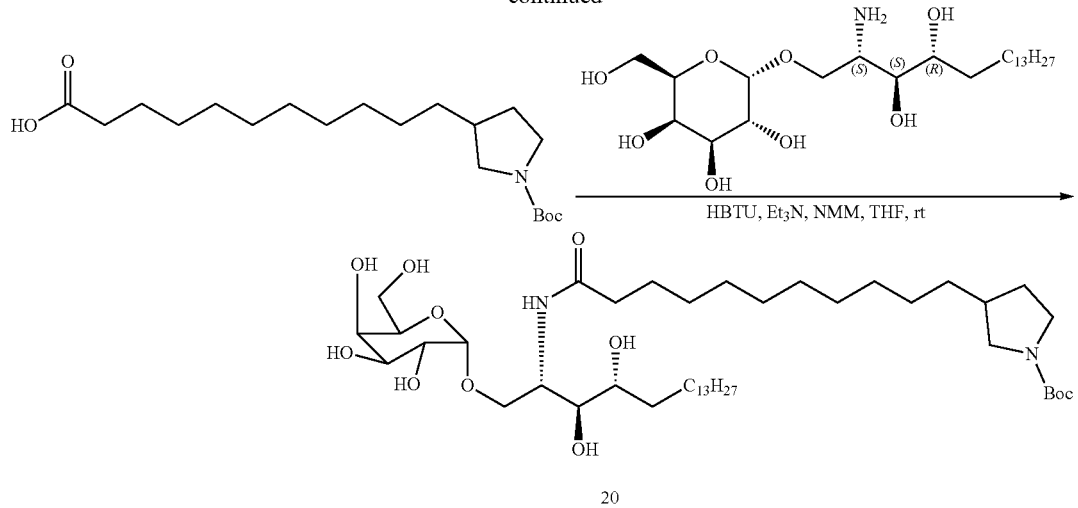

Step 1: Synthesis of 11-(1-(tert-butoxycarbonyl)pyrrolidin-3-yl)undec-10-enoic acid Prepared in a manner similar to 11-(3-methyloxetan-3-yl)undec-10-enoic acid and purified by column chromatography on silica gel (PE/EtOAc 1:1) to give 11-(1-(tert-butoxycarbonyl)pyrrolidin-3-yl)undec-10-enoic acid (150 mg, 42%) as a solid. LC/MS: mass calcd. for $C_{20}H_{35}NO_4$: 353, found: 352 [M−H]⁻.

Step 2: Synthesis of 11-(1-(tert-butoxycarbonyl)pyrrolidin-3-yl)undecanoic acid A mixture of 11-[1-(tert-butoxycarbonyl)pyrrolidin-3-yl]undec-10-enoic acid (150 mg, 0.3 mmol) and $PtO_2$ (20 mg, 0.1 mmol) in EtOH (50 mL) was stirred under an atmosphere of $H_2$ (balloon) for 1 h. The reaction mixture was filtered through a pad of Celite and the filtrate was concentrated under reduced pressure to afford 11-(1-(tert-butoxycarbonyl)pyrrolidin-3-yl)undecanoic acid (140 mg, 93%) as a solid. LC/MS: mass calcd. for $C_{20}H_{37}NO_4$: 355, found: 354 [M−H]⁻.

Step 3: Synthesis of tert-butyl 3-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)pyrrolidine-1-carboxylate Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, purified by column chromatography on silica gel (DCM/MeOH 5:1) and preparative-HPLC to give tert-butyl 3-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)pyrrolidine-1-carboxylate (6.1 mg, 3.6%) as a solid. LC/MS: mass calcd. for $C_{44}H_{84}N_2O_{11}$: 816.61, found: 839.55 [M+Na]⁺; ¹H NMR (300 MHZ, CD3OD) δ 4.18 (d, J=5.9 Hz, 1H), 3.35-3.92 (m, 11H), 3.15-3.20 (m, 2H), 2.82 (s, 1H), 1.91-2.34 (m, 4H), 1.02-1.77 (m, 54H), 0.90 (t, J=6.6 Hz, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(pyrrolidin-3-yl)undecanamide

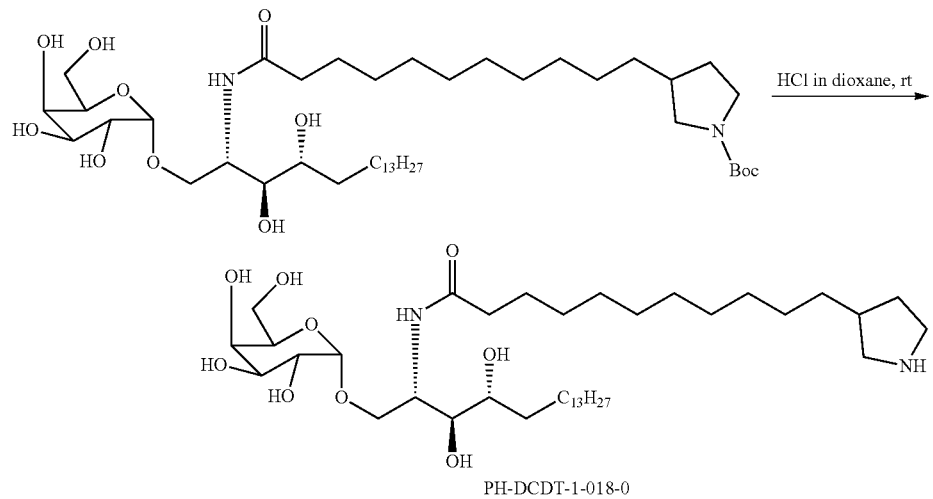

PH-DCDT-1-018-0

To a mixture of tert-butyl 3-(11-(((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)amino)-11-oxoundecyl)pyrrolidine-1-carboxylate (60 mg, 0.07 mmol) in EtOAc (3 mL) was added 2N HCl in EtOAc (3 mL). The mixture was stirred at rt for 1 h, then concentrated under reduced pressure and purified by preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(pyrrolidin-3-yl)undecanamide (15.6 mg, 28%) as an oil. LC/MS: mass calcd. for $C_{39}H_{76}N_2O_9$: 716.56, found: 717.50 [M+H]$^+$; $^1$H NMR (300 MHZ, CD3OD) & 4.21 (d, J=5.7 Hz, 1H), 3.51-3.91 (m, 14H), 3.12-3.21 (m, 4H), 2.74-2.79 (m, 1H), 2.15-2.30 (m, 3H), 1.14-1.61 (m, 42H), 0.87-0.97 (m, 3H).

Synthesis of N-[(2S,3S,4R)-3,4-dihydroxy-1-{[3,4,5-trihydroxy-6-(hydroxymethyl)oxan-2-yl]oxy}octadecan-2-yl]-11-{2-oxa-6-azaspiro[3.3]heptan-6-yl} undecanamide

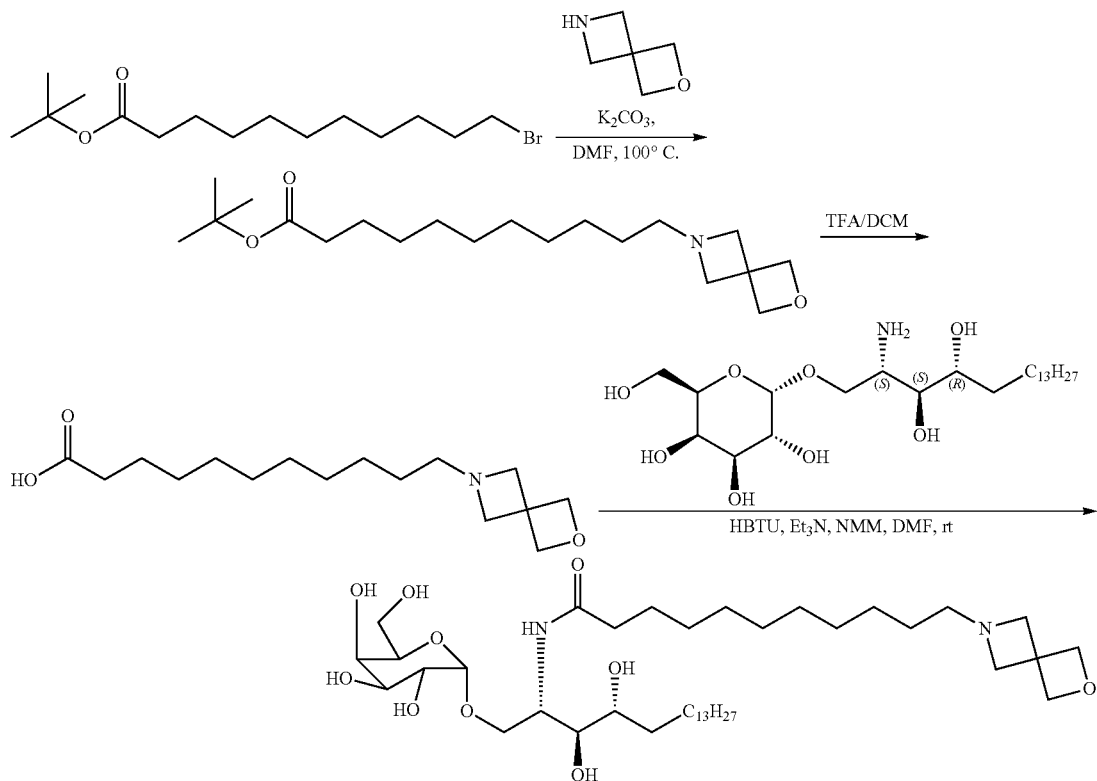

Step 1: Synthesis of tert-butyl 11-(2-oxa-6-azaspiro[3.3]heptan-6-yl)undecanoate To a mixture of 2-oxa-6-azaspiro[3.3]heptane (200 mg, 2.0 mmol) in DMF (10 mL) was added tert-butyl 11-bromoundecanoate (642 mg, 2.0 mmol) and $K_2CO_3$ (552 mg, 4.0 mmol). The mixture was heated to 100° C. and stirred for 5 h, then diluted with $H_2O$ (20 mL) and extracted with EtOAc (3×30 mL). The combined organic layers were washed with brine (50 mL), dried over anhydrous $Na_2SO_4$, filtered, and the filtrate was concentrated under reduced pressure. The residue was purified by column chromatography on silica gel (PE/EtOAc 1:1) to give tert-butyl 11-(2-oxa-6-azaspiro[3.3]heptan-6-yl)undecanoate (339 mg, 50%) as a solid. LC/MS: mass calcd. for $C_{20}H_{37}NO_3$: 339, found: 340 [M+H]$^+$.

Step 2: Synthesis of 11-(2-oxa-6-azaspiro[3.3]heptan-6-yl)undecanoic acid

A mixture of tert-butyl 11-(2-oxa-6-azaspiro[3.3]heptan-6-yl)undecanoate (220 mg, 0.6 mmol), DCM (4 mL) and TFA (2 mL) was stirred at rt for 2 h, then concentrated under reduced pressure to give 11-(2-oxa-6-azaspiro[3.3]heptan-6-yl)undecanoic acid (180 mg, 98%) as a solid.

Step 3: Synthesis of N-[(2S,3S,4R)-3,4-dihydroxy-1-{[3,4,5-trihydroxy-6-(hydroxymethyl)oxan-2-yl]oxy}octadecan-2-yl]-11-{2-oxa-6-azaspiro[3.3]heptan-6-yl}undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy)}octadecan-2-yl]-11-(3-methyloxetan-3-yl)undecanamide, purified by column chromatography on silica gel (DCM/MeOH 5:1) and preparative-HPLC to give N-[(2S,3S,4R)-3,4-dihydroxy-1-{[3,4,5-trihydroxy-6-(hydroxymethyl)oxan-2-yl]oxy}octadecan-2-yl]-11-{2-oxa-6-azaspiro[3.3]heptan-6-yl}undecanamide (8.5 mg, 6.8%) as a solid. LC/MS: mass calcd. for $C_{40}H_{76}N_2O_{10}$: 744.55, found: 745.55 [M+H]$^+$; $^1$H NMR (300 MHz, CD$_3$OD) δ 4.75 (s, 4H), 4.14-4.24 (m, 1H), 3.56-3.87 (m, 15H), 2.68-2.79 (m, 1H), 2.15-2.25 (m, 2H), 1.49-1.66 (m, 5H), 1.33-1.46 (m, 47H), 0.87-0.97 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-morpholinoundecanamide

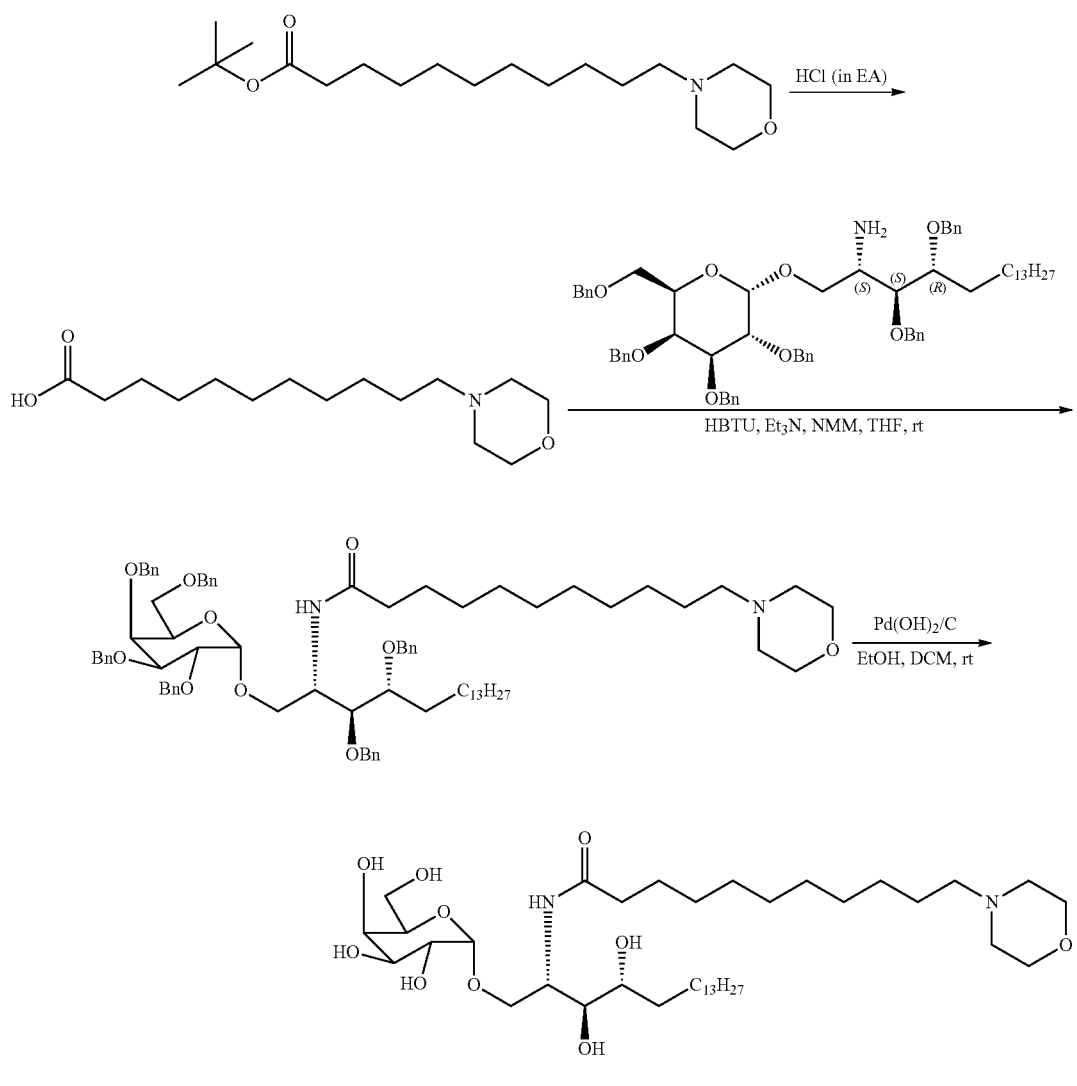

Step 1: Synthesis of tert-butyl 11-morpholinoundecanoate

Prepared in a manner similar to tert-butyl 11-(2-oxa-6-azaspiro[3.3]heptan-6-yl)undecanoate and purified by column chromatography on silica gel (PE/EtOAc 1:1) to give tert-butyl 11-morpholinoundecanoate (450 mg, 88%) as a solid. LC/MS: mass calcd. for $C_{19}H_{37}NO_3$: 327, found: 328 [M+H]$^+$.

Step 2: Synthesis of 11-morpholinoundecanoic acid

To a mixture of tert-butyl 11-(morpholin-4-yl)undecanoate (450 mg, 1.3 mmol) and EtOAc (5 mL) was added 2N HCl in EtOAc (5 mL). The mixture was stirred at rt for 1 h, then concentrated under reduced pressure to give 11-morpholinoundecanoic acid (300 mg, 77%) as a solid.

Step 3: Synthesis of N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-11-morpholinoundecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide. Purified by column chromatography on silica gel (PE/EtOAc 2:1) to give N-((2S,3S,4R)-3,4-bis(benzyloxy)-1-(((2S, 3R,4S,5S,6R)-3, 4,5-tris(benzyloxy)-6-((benzyloxy)methyl)tetrahydro-2H-pyran-2-yl)oxy)octadecan-2-yl)-11-morpholinoundecanamide (70 mg, 28%) as a solid.

Step 4: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-morpholinoundecanamide A mixture of N-((2S,3S,4R)-3,4-bis(benzyloxy)-1-(((2S, 3R,4S,5S,6R)-3,4,5-tris(benzyloxy)-6-((benzyloxy)methyl) tetrahydro-2H-pyran-2-yl)oxy)octadecan-2-yl)-11-morpholinoundecanamide (70 mg, 0.055 mmol) and Pd(OH)$_2$/C (20 mg) in DCM (5 mL) and EtOH (5 mL) was stirred under an atmosphere of H$_2$ (balloon) for 16 h. The mixture was filtered through a pad of Celite, the filtrate was concentrated under reduced pressure and the residue was purified by preparative-HPLC to give N-((2S,3S,4R)-3,4-dihydroxy-1-(((2S,3R,4S,5R,6R)-3,4,5-trihydroxy-6-(hydroxymethyl) tetrahydro-2H-pyran-2-yl)oxy)octadecan-2-yl)-11-morpholinoundecanamide (9.1 mg, 23%) as a solid. LC/MS: mass calcd. for $C_{39}H_{76}N_2O_{10}$: 732.55, found: 733.50 [M+H]$^+$. $^1$H NMR (300 MHz, CD$_3$OD) 4.21 (d, J=5.7 Hz, 1H), 4.02-4.09 (m, 2H), 3.63-3.87 (9H), 3.46-3.58 (m, 4H), 3.11-3.16 (4H), 2.22 (t, J=7.4 Hz, 2H), 1.33-1.70 (m, 43H), 0.87-0.97 (m, 3H).

Synthesis of N-((2S,3S,4R)-3,4-dihydroxy-1-(((2S, 3R,4S,5R,6R)-3,4,5-trihydroxy-6-(hydroxymethyl) tetrahydro-2H-pyran-2-yl)oxy)octadecan-2-yl)-11-(piperidin-1-yl)undecanamide Step 1: Synthesis of tert-butyl 11-(piperidin-1-yl)undecanoate Prepared in a manner similar to tert-butyl 11-(2-oxa-6-azaspiro[3.3]heptan-6-yl)undecanoate and purified by column chromatography on silica gel (PE/EtOAc 2:1) to give tert-butyl 11-(piperidin-1-yl)undecanoate (240 mg, 47%) as a solid. LC/MS: mass calcd. for $C_{20}H_{39}NO_2$: 325, found: 326 [M+H]$^+$.

Step 2: Synthesis of 11-(piperidin-1-yl)undecanoic acid

To a mixture of tert-butyl 11-(piperidin-1-yl)undecanoate (180 mg, 0.5 mmol) and EtOAc (3 mL) was added 2N HCl in EtOAc (3 mL). The mixture was stirred at rt for 1 h, then concentrated under reduced pressure to give 11-(piperidin-1-yl)undecanoic acid (140 mg, 94%) as a solid.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(piperidin-1-yl)undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl) tetrahydro-2H-pyran-2-yl)oxy)octadecan-2-yl)-11-(piperidin-1-yl)undecanamide (32 mg, 26%) as an oil. LC/MS: mass calcd. for $C_{40}H_{78}N_2O_9$: 730.57, found:

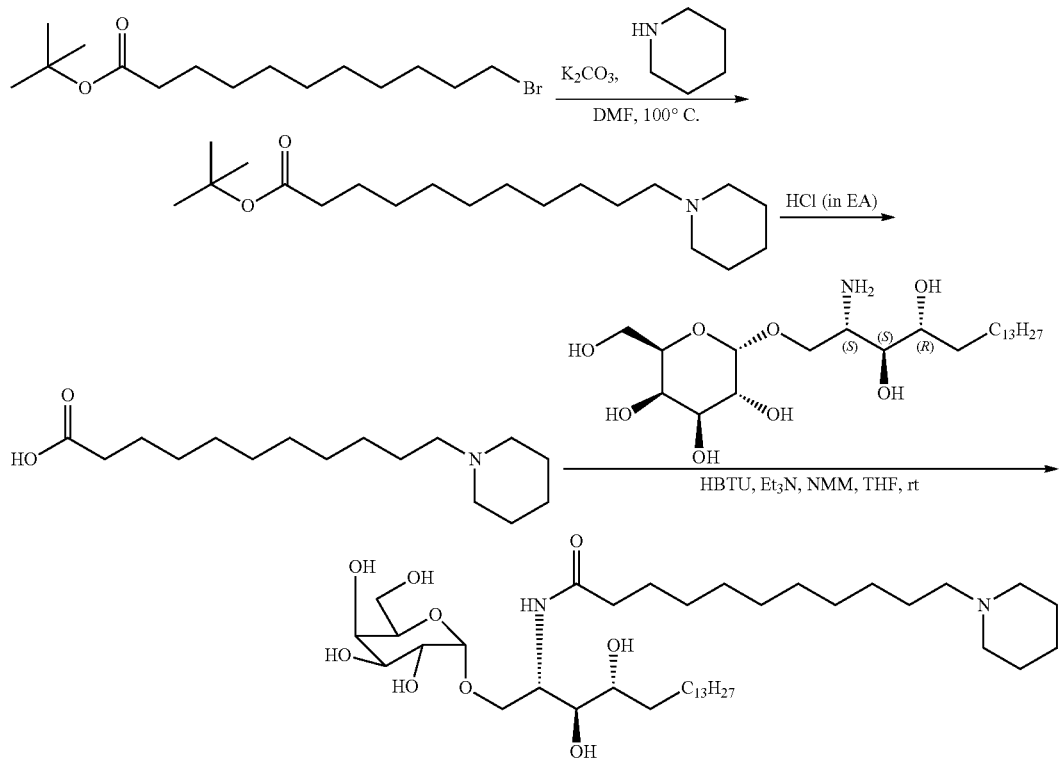

731.55 [M+H]$^+$; $^1$H NMR (400 MHZ, CD$_3$OD) δ 4.23 (q, J=4.9 Hz, 1H), 3.68-3.92 (m, 7H), 3.50-3.61 (m, 5H), 3.07-3.09 (m, 2H), 2.89-2.97 (m, 2H), 2.18-2.30 (m, 2H), 1.96-1.99 (m, 1H), 1.50-1.87 (m, 11H), 1.30-1.39 (m, 36H), 0.87-0.97 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(pyrrolidin-1-yl)undecanamide

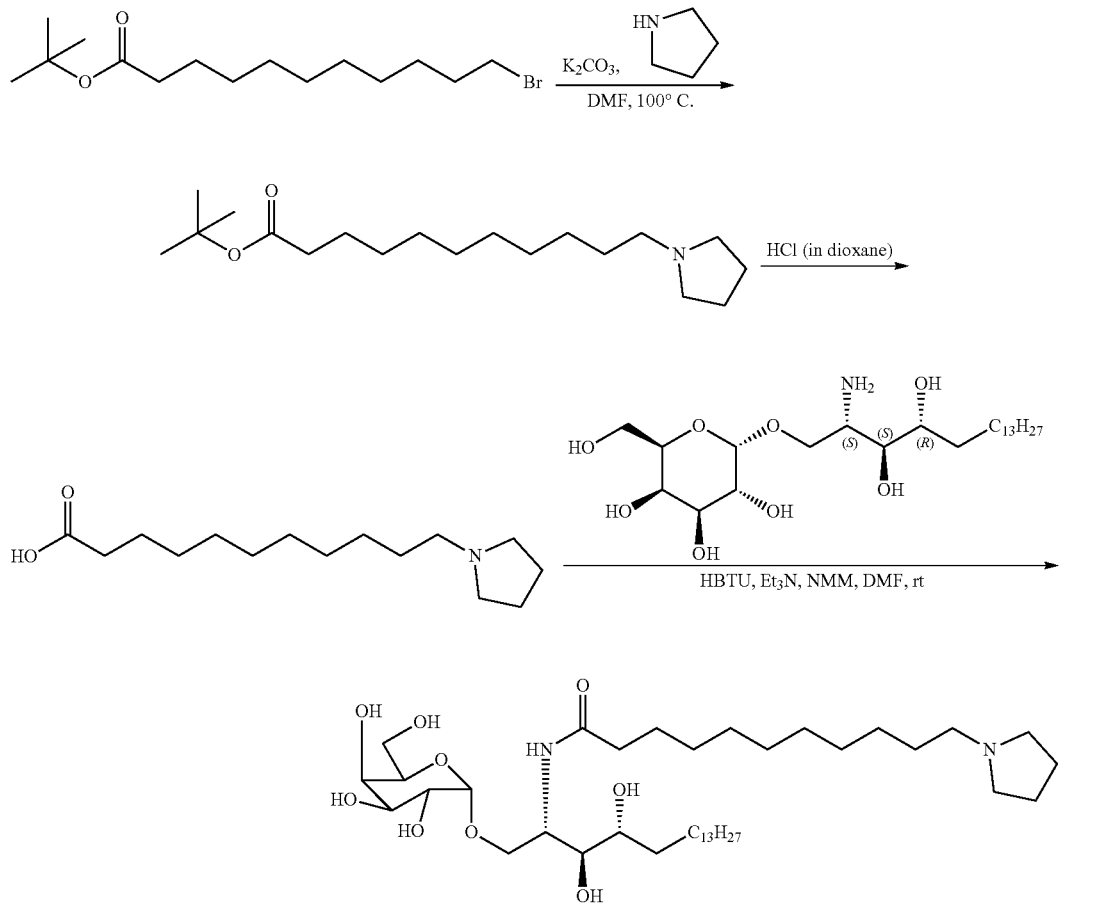

Step 1: Synthesis of tert-butyl 11-(pyrrolidin-1-yl)undecanoate

Prepared in a manner similar to tert-butyl 11-(2-oxa-6-azaspiro[3.3]heptan-6-yl)undecanoate and purified by column chromatography on silica gel (PE/EtOAc 1:1) to give tert-butyl 11-(pyrrolidin-1-yl)undecanoate (310 mg, 64%) as a solid. LC/MS: mass calcd. for C$_{19}$H$_{37}$NO$_2$: 311, found: 312 [M+H]$^+$.

Step 2: Synthesis of 11-(pyrrolidin-1-yl)undecanoic acid

To a mixture of tert-butyl 11-(pyrrolidin-1-yl)undecanoate (310 mg, 0.99 mmol) and EtOAc (3 mL) was added 2N HCl in EtOAc (3 mL). The mixture was stirred at rt for 1 h, then concentrated under reduced pressure to give 11-(pyrrolidin-1-yl)undecanoic acid (240 mg, 94%) as a solid.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(pyrrolidin-1-yl)undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(pyrrolidin-1-yl)undecanamide (15 mg, 12.4%) as an oil. LC/MS: mass calcd. for C$_{39}$H$_{76}$N$_2$O$_9$: 716.56, found: 717.50 [M+H]$^+$; $^1$H NMR (300 MHz, CD$_3$OD) δ 4.21 (d, J=5.7 Hz, 1H), 3.56-3.91 (m, 10H), 3.13-3.18 (m, 2H), 3.02-3.11 (m, 2H), 2.13-2.23 (m, 4H), 1.94-2.06 (m, 2H), 1.54-1.75 (m, 7H), 1.27-1.39 (m, 37H), 0.87-0.97 (m, 3H).

Synthesis of N-((2S,3S,4R)-3,4-dihydroxy-1-(((2S, 3R,4S,5R,6R)-3,4,5-trihydroxy-6-(hydroxymethyl) tetrahydro-2H-pyran-2-yl)oxy)octadecan-2-yl)-11- thiomorpholinoundecanamide

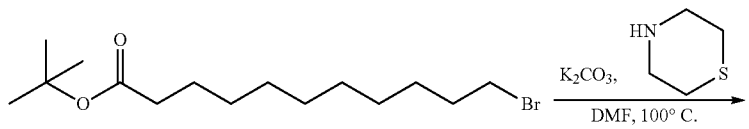

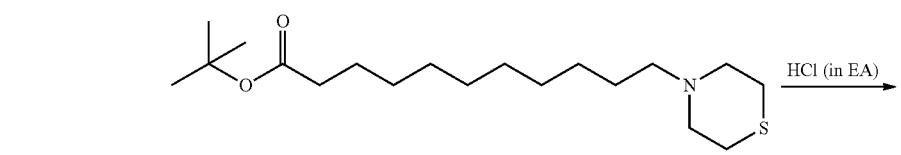

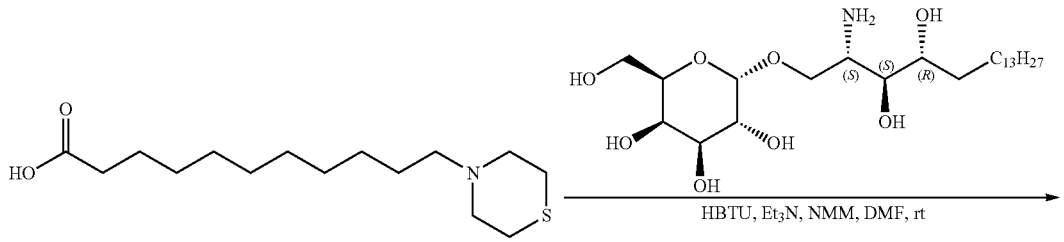

Step 1: Synthesis of tert-butyl 11-thiomorpholinoundecanoate

Prepared in a manner similar to tert-butyl 11-(2-oxa-6-azaspiro[3.3]heptan-6-yl)undecanoate and purified by column chromatography on silica gel (PE/EtOAc 2:1) to give tert-butyl 11-thiomorpholinoundecanoate (340 mg, 64%) as a solid. LC/MS: mass calcd. for $C_{19}H_{37}NO_2S$: 343, found: 344 [M+H]+.

Step 2: Synthesis of 11-thiomorpholinoundecanoic acid

To a mixture of tert-butyl 11-thiomorpholinoundecanoate (400 mg, 1.2 mmol) and EtOAc (5 mL) was added 2N HCl in EtOAc (5 mL). The mixture was stirred at rt for 1 h at then concentrated under reduced pressure to give 11-thiomorpholinoundecanoic acid (318 mg, 95%) as a solid.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-thiomorpholinoundecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl) tetrahydro-2H-pyran-2-yl)oxy)octadecan-2-yl)-11-thiomorpholinoundecanamide (17.1 mg, 13.6%) as an oil. LC/MS: mass calcd. for $C_{39}H_{76}N_2O_9S$: 748.53, found: 749.45 [M+H]+; $^1$H NMR (400 MHZ, $CD_3OD$) δ 4.23 (q, J=4.9 Hz, 1H), 3.65-3.96 (m, 10H), 3.03-3.29 (m, 6H), 2.87-2.91 (m, 3H), 2.19-2.32 (m, 2H), 1.52-1.79 (m, 6H), 1.30-1.39 (m, 39H), 0.89-0.96 (m, 3H).

Synthesis of N-[(2S,3S,4R)-3,4-dihydroxy-1-{[3,4,5-trihydroxy-6-(hydroxymethyl)oxan-2-yl]oxy}octadecan-2-yl]-11-[(1S,5S)-6,6-dimethylbicyclo[3.1.1]heptan-2-yl]undecanamide

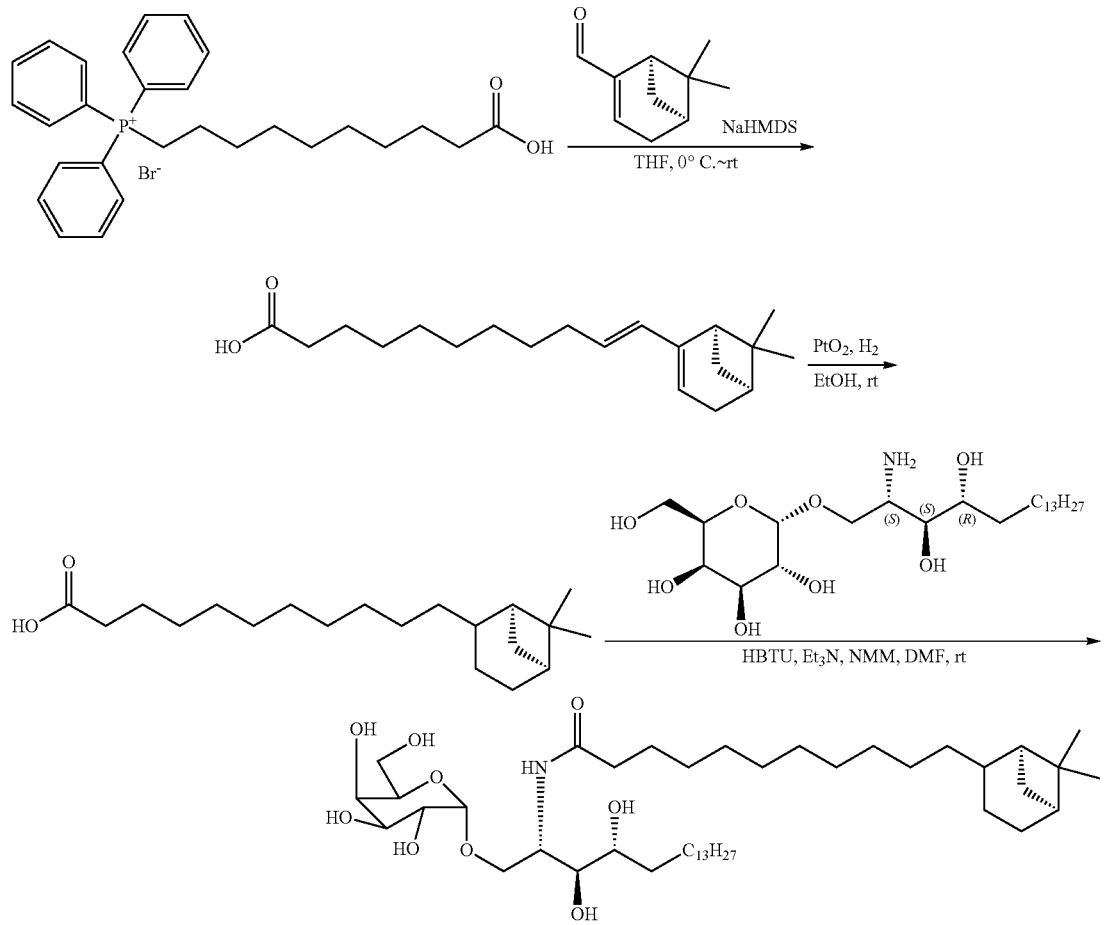

Step 1: Synthesis of 11-((1R,5S)-6,6-dimethylbicyclo[3.1.1]hept-2-en-2-yl)undec-10-enoic Acid Prepared in a manner similar to 11-(3-methyloxetan-3-yl)undec-10-enoic acid and purified by column chromatography on silica gel (PE/EtOAc 1:1) to give 11-((1R,5S)-6,6-dimethylbicyclo[3.1.1]hept-2-en-2-yl)undec-10-enoic acid (110 mg, 54%) as a solid. LC/MS: mass calcd. for $C_{20}H_{32}O_2$: 304, found: 303 [M–H]⁻.

Step 2: Synthesis of 11-((1S,5S)-6,6-dimethylbicyclo[3.1.1]heptan-2-yl)undecanoic Acid A mixture of 11-((1R,5S)-6,6-dimethylbicyclo[3.1.1]hept-2-en-2-yl)undec-10-enoic acid (100 mg, 0.3 mmol) and $PtO_2$ (20 mg, 0.1 mmol) in EtOH (50 mL) was stirred under an atmosphere of $H_2$ (balloon) for 1 h. The mixture was filtered through a pad of Celite and the filtrate was concentrated under reduced pressure to give 11-((1S,5S)-6,6-dimethylbicyclo[3.1.1]heptan-2-yl)undecanoic acid (80 mg, 79%) as a solid. LC/MS: mass calcd. for $C_{20}H_{36}O_2$: 308, found: 307 [M–H]⁻.

Step 3: Synthesis of N-[(2S,3S,4R)-3,4-dihydroxy-1-{[3,4,5-trihydroxy-6-(hydroxymethyl)oxan-2-yl]oxy}octadecan-2-yl]-11-[(1S,5S)-6,6-dimethylbicyclo[3.1.1]heptan-2-yl]undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, purified by column chromatography on silica gel (DCM/MeOH 5:1) and preparative-HPLC to give N-[(2S,3S,4R)-3,4-dihydroxy-1-{[3,4,5-trihydroxy-6-(hydroxymethyl)oxan-2-yl]oxy}octadecan-2-yl]-11-[(1S,5S)-6,6-dimethylbicyclo[3.1.1]heptan-2-yl]undecanamide (14.3 mg, 10.7%) as a solid. LC/MS: mass calcd. for $C_{44}H_{83}NO_9$: 769.61, found: 792.65 [M+Na]⁺; ¹H NMR (300 MHz, $CD_3OD$) δ 4.17 (dd, J=6.7, 4.1 Hz, 1H), 3.51-3.92 (m, 10H), 3.17-3.26 (m, 3H), 2.31-2.38 (m, 1H), 2.18-2.22 (m, 2H), 1.85-1.97 (m, 4H), 1.52-1.62 (m, 5H), 1.22-1.39 (m, 44H), 1.19 (s, 3H), 0.87-0.97 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(1,1-dioxidothiomorpholino)undecanamide

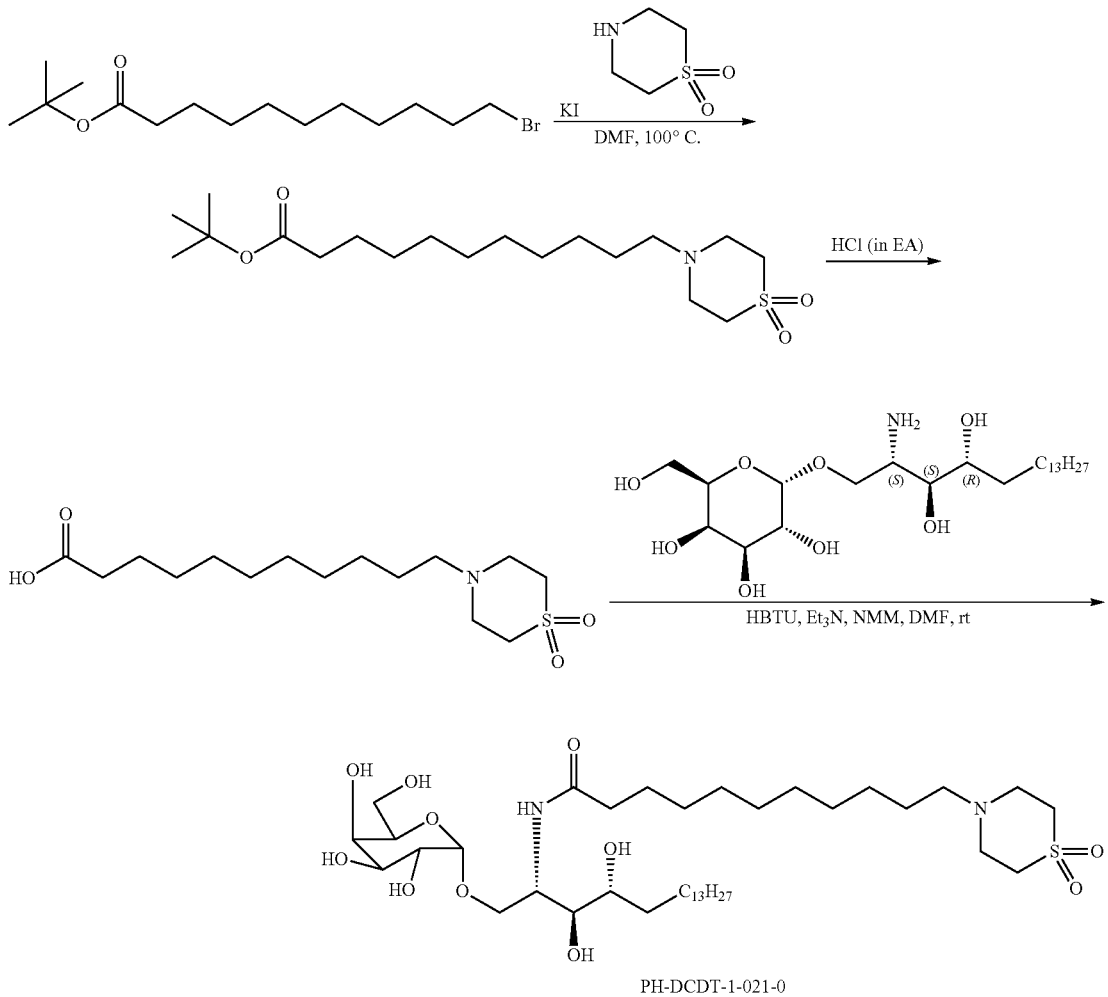

PH-DCDT-1-021-0

Step 1: Synthesis of tert-butyl 11-(2-oxa-6-azaspiro[3.3]heptan-6-yl)undecanoate Prepared in a manner similar to tert-butyl 11-(2-oxa-6-azaspiro[3.3]heptan-6-yl)undecanoate and purified by column chromatography on silica gel (PE/EtOAc 1:1) to give tert-butyl 11-(1,1-dioxidothiomorpholino)undecanoate (320 mg, 55%) as a solid. LC/MS: mass calcd. for $C_{19}H_{37}NO_4S$: 375, found: 376 [M+H]$^+$.

Step 2: Synthesis of 11-(1,1-dioxidothiomorpholino)undecanoic acid

To a mixture of tert-butyl 11-(1,1-dioxidothiomorpholino)undecanoate (300 mg, 0.79 mmol) and EtOAc (3 mL) was added 2N HCl in EtOAc (3 mL). The mixture was stirred at rt for 1 h, then concentrated under reduced pressure to give 11-(1,1-dioxidothiomorpholino)undecanoic acid (200 mg, 78%) as a solid. LC/MS: mass calcd. for $C_{15}H_{29}NO_4S$: 319, found: 318 [M–H]$^-$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(1,1-dioxidothiomorpholino)undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(1,1-dioxidothiomorpholino)undecanamide (17.3 mg, 16.2%) as a solid. LC/MS: mass calcd. for $C_{39}H_{76}N_2O_{11}S$: 780.52, found: 704.50 [M+H]$^+$; $^1$H NMR (300 MHZ, $CD_3OD$) δ 4.19 (q, J=4.8 Hz, 1H), 3.93-3.51 (m, 10H), 3.08 (q, J=4.6 Hz, 4H), 2.97 (dd, J=6.8, 3.4 Hz, 4H), 2.56-2.45 (m, 2H), 2.22 (t, J=7.5 Hz, 2H), 1.11-1.61 (m, 42H), 0.95-0.85 (m, 3H).

Synthesis of N-((2S,3S,4R)-3,4-dihydroxy-1-(((2S, 3R,4S,5R,6R)-3,4,5-trihydroxy-6-(hydroxymethyl) tetrahydro-2H-pyran-2-yl)oxy)octadecan-2-yl)-11- (isopropylsulfonyl)undecanamide

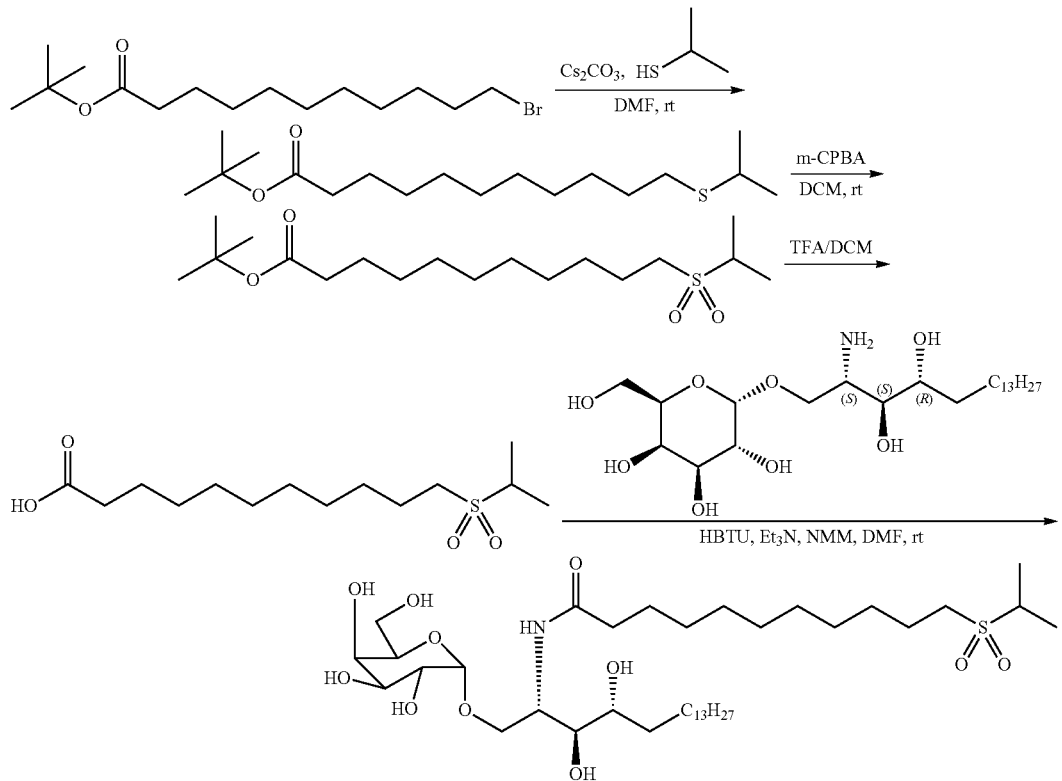

Step 1: Synthesis of tert-butyl 11-(isopropylthio)undecanoate

To a mixture of 2-propanethiol (3.5 g, 46.6 mmol) and DMF (30 mL) was added tert-butyl 11-bromoundecanoate (1.0 g, 3.1 mmol) and $Cs_2CO_3$ (2.5 g, 7.7 mmol). The mixture was stirred at rt 5 h, then diluted with $H_2O$ (60 mL) and extracted with EtOAc (3×50 mL). The combined organic layers were washed with brine (60 mL), dried over anhydrous $Na_2SO_4$, filtered, and the filtrate was concentrated under reduced pressure. The residue was purified by column chromatography on silica gel (PE/EtOAc 2:1) to give tert-butyl 11-(isopropylthio)undecanoate (900 mg, 91%) as a solid.

Step 2: Synthesis of Tert-butyl 11-(isopropylsulfonyl)undecanoate

To a mixture of tert-butyl 11-(isopropylthio)undecanoate (800 mg, 2.5 mmol) in DCM (20 mL) was added m-CPBA (870 mg, 5.0 mmol). The mixture was stirred at rt overnight, then diluted with $H_2O$ (50 mL) and extract with EtOAc (3×50 mL). The combined organic layers were washed with brine (50 mL), dried over anhydrous $Na_2SO_4$, filtered and the filtrate was concentrated under reduced pressure. The residue was purified by column chromatography on silica gel (PE/EtOAc 2:1) to give tert-butyl 11-(isopropylsulfonyl) undecanoate (600 mg, 68%) as a solid.

Step 3: Synthesis of 11-(isopropylsulfonyl)undecanoic Acid

A mixture of tert-butyl 11-(isopropylsulfonyl)undecanoate (300 mg, 0.86 mmol) in DCM (4 mL) and TFA (2 mL) was stirred at rt for 2 h, then concentrated under reduced pressure to give 11-(isopropylsulfonyl)undecanoic acid (200 mg, 79%) as a solid. LC/MS: mass calcd. for $C_{14}H_{28}O_4S$: 292, found: 291 $[M-H]^-$.

Step 4: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(isopropylsulfonyl)undecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl) tetrahydro-2H-pyran-2-yl)oxy)octadecan-2-yl)-11-(isopropylsulfonyl)undecanamide (31.3 mg, 28%) as a solid. LC/MS: mass calcd. for $C_{38}H_{75}NO_{11}S$: 753.51, found: 754.50 $[M+H]^+$; $^1H$ NMR (400 MHz, $CD_3OD$) δ 4.89 (d, J=3.7 Hz, 1H), 4.22 (q, J=4.8 Hz, 1H), 3.52-3.94 (m, 10H), 3.22-3.28 (m, 1H), 3.02-3.11 (m, 2H), 2.24 (t, J=7.5 Hz, 2H), 1.88-1.75 (m, 2H), 1.30-1.66 (m, 46H), 0.96-0.88 (m, 3H).

Synthesis of N-((2S,3S,4R)-3,4-dihydroxy-1-(((2, 3R,4S,5R,6R)-3,4,5-trihydroxy-6-(hydroxymethyl) tetrahydro-2H-pyran-2-yl)oxy)octadecan-2-yl)-10-((1,1-dioxidotetrahydro-2H-thiopyran-4-yl)oxy) decanamide

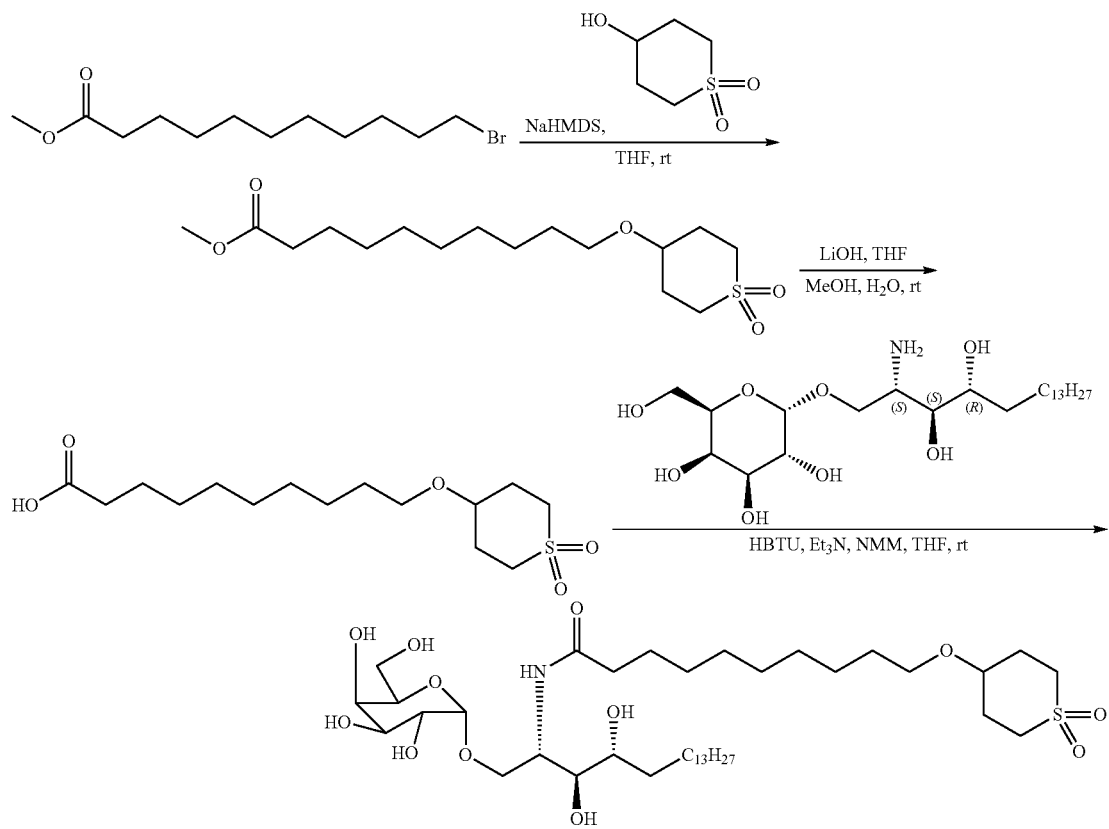

Step 1: Synthesis of methyl 10-((1,1-dioxidotetrahydro-2H-thiopyran-4-yl)oxy)decanoate To a mixture of 4-hydroxytetrahydro-2H-thiopyran 1,1-dioxide (200 mg, 1.3 mmol) and THF (10 mL) at 0° C. under an atmosphere of $N_2$ was added 2M NaHMDS (0.65 mL, 1.3 mmol). The mixture was warmed to rt and stirred for 1 h, then a solution of methyl 10-bromodecanoate (235 mg, 0.9 mmol) in THF (1.5 mL) was added. The mixture was stirred at rt overnight, then diluted with $H_2O$ (20 mL) and extracted with EtOAc (3×30 mL). The combined organic layers were washed with brine (30 mL), dried over anhydrous $Na_2SO_4$, filtered, and the filtrate was concentrated under reduced pressure. The residue was purified by column chromatography on silica gel (PE/EtOAc 1:1) to give methyl 10-((1,1-dioxidotetrahydro-2H-thiopyran-4-yl)oxy)decanoate (80 mg, 27%) as a solid. LC/MS: mass calcd. for $C_{16}H_{30}O_5S$: 334, found: 335 $[M+H]^+$.

Step 2: Synthesis of 10-((1,1-dioxidotetrahydro-2H-thiopyran-4-yl)oxy)decanoic acid To a mixture of methyl 10-((1,1-dioxidotetrahydro-2H-thiopyran-4-yl)oxy)decanoate (200 mg, 0.6 mmol) in MeOH (5 mL), THF (5 mL) and $H_2O$ (5 mL) was added LiOH (42 mg, 1.8 mmol). The mixture was stirred at rt for 2 h, then acidified pH ~3 with 1N HCl and extracted with EtOAc (3×30 mL). The combined organic layers were washed with brine (30 mL), dried over anhydrous $Na_2SO_4$, filtered, and the filtrate was concentrated under reduced pressure. The residue was purified column chromatography on by silica gel (DCM/MeOH 10:1) to give 10-((1,1-dioxidotetrahydro-2H-thiopyran-4-yl)oxy)decanoic acid (66 mg, 53%) as a solid. LC/MS: mass calcd. for $C_{15}H_{28}O_5S$: 320, found: 319 $[M-H]^-$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-10-((1,1-dioxidotetrahydro-2H-thiopyran-4-yl)oxy)decanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (DCM/MeOH 5:1) and pre-parative-HPLC to give N-((2S,3S,4R)-3,4-dihydroxy-1-(((2S,3R,4S,5R,6R)-3,4,5-trihydroxy-6-(hydroxymethyl) tetrahydro-2H-pyran-2-yl)oxy)octadecan-2-yl)-10-((1,1-dioxidotetrahydro-2H-thiopyran-4-yl)oxy)decanamide (22.2 mg, 14.5%) as an oil. LC/MS: mass calcd. for $C_{39}H_{75}NO_{12}S$: 781.50, found: 782.45 [M+H]$^+$; $^1$H NMR (400 MHZ, CD$_3$OD) δ 4.20 (dd, J=6.4, 4.5 Hz, 1H), 3.52-3.89 (m, 10H), 3.46-3.48 (m, 2H), 3.15-3.30 (m, 2H), 2.91-2.95 (m, 2H), 2.08-2.28 (m, 5H), 1.53-1.63 (m, 6H), 1.27-1.39 (m, 36H), 0.94-0.86 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-10-((tetrahydro-2H-pyran-4-yl)oxy)decanamide

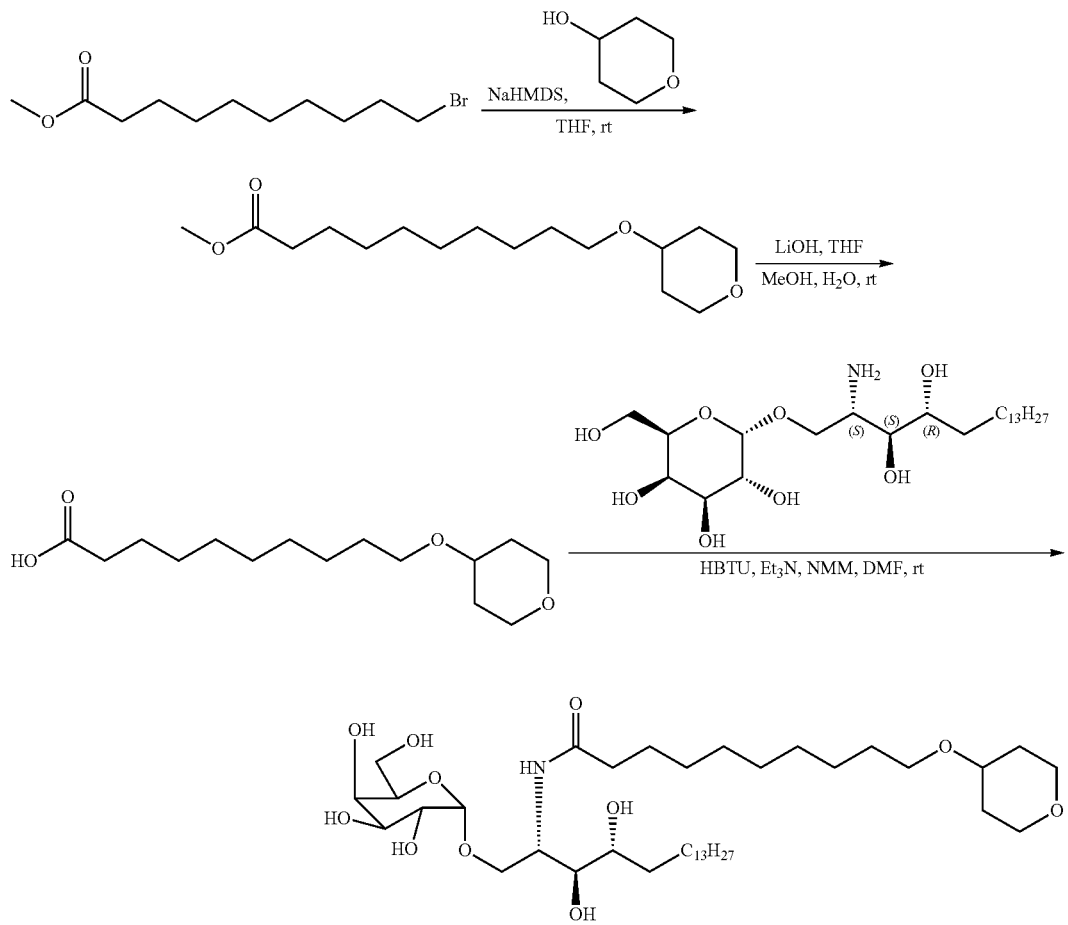

Step 1: Synthesis of methyl 10-((tetrahydro-2H-pyran-4-yl)oxy)decanoate

Prepared in a manner similar to methyl 10-((1,1-dioxidotetrahydro-2H-thiopyran-4-yl)oxy)decanoate and purified by column chromatography on silica gel (PE/EtOAc 2:1) to give methyl 10-((tetrahydro-21H-pyran-4-yl)oxy)decanoate (95 mg, 37%) as an oil.

Step 2: Synthesis of 10-((tetrahydro-2H-pyran-4-yl)oxy)decanoic Acid

Prepared in a manner similar to 10-((1,1-dioxidotetrahydro-2H-thiopyran-4-yl)oxy)decanoic and purified by column chromatography on silica gel (DCM/MeOH 10:1) to give 10-(((tetrahydro-2H-pyran-4-yl)oxy)decanoic acid (65 mg, 80%) as a solid. LC/MS: mass calcd. for $C_{15}H_{28}O_4$: 272, found: 271 [M−H]$^−$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-10-((tetrahydro-2H-pyran-4-yl)oxy)decanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyl-oxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-10-((tetrahydro-2H-pyran-4-yl)oxy)decanamide (12 mg, 13%) as an oil. LC/MS: mass calcd. for $C_{39}H_{75}NO_{11}$: 733.53, found: 734.50 [M+H]$^+$. $^1$H NMR (300 MHz, CD$_3$OD) 4.19 (q, J=4.9 Hz, 1H), 3.66-3.90 (m, 9H), 3.37-3.51 (m, 5H), 2.22 (t, J=7.5 Hz, 2H), 1.89 (dd, J=13.0, 3.8 Hz, 2H), 1.47-1.62 (m, 5H), 1.26-1.37 (m, 40H), 0.88-0.91 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-9-((tetrahydro-2H-pyran-4-yl)methoxy)nonanamide

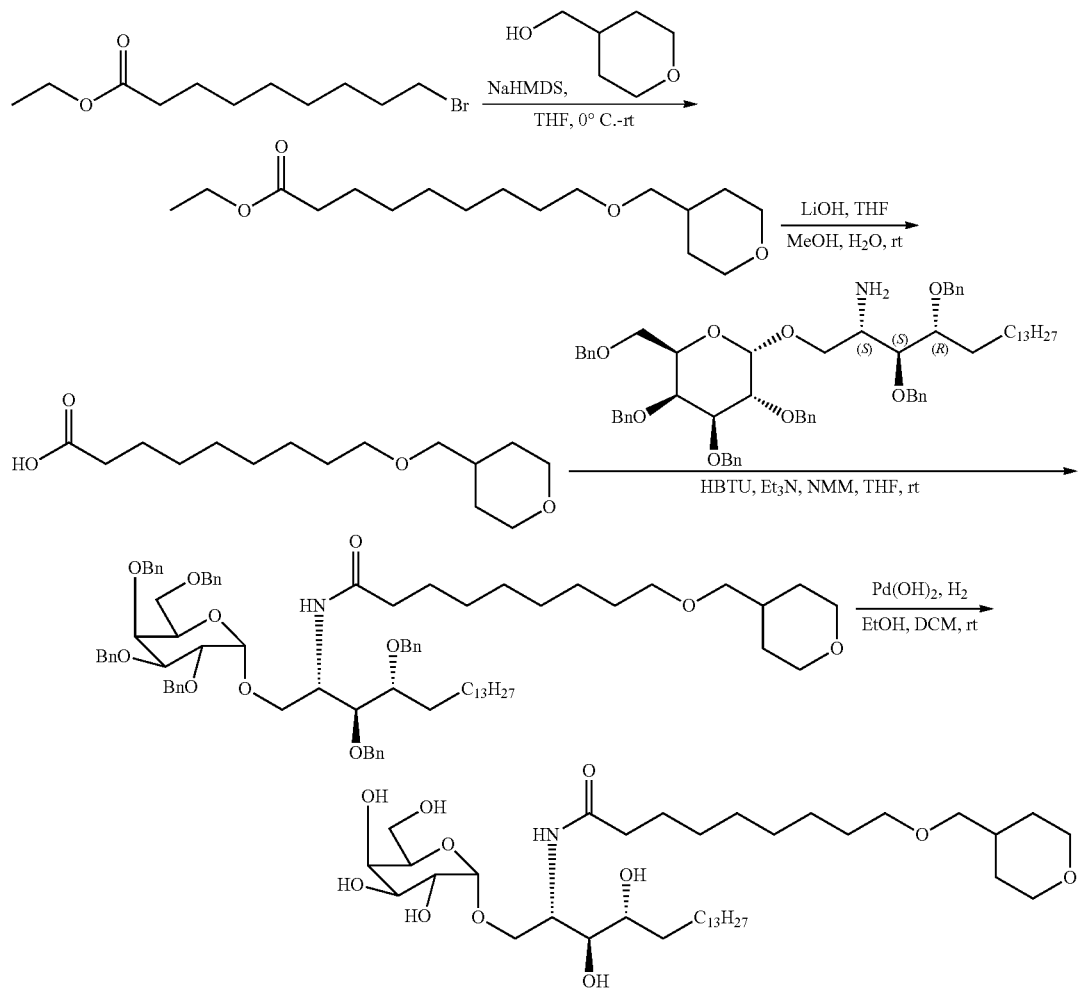

Step 1: Synthesis of ethyl 9-((tetrahydro-2H-pyran-4-yl)methoxy)nonanoate

Prepared in a manner similar to methyl 10-((1,1-dioxidotetrahydro-2H-thiopyran-4-yl)oxy)decanoate and purified by column chromatography on silica gel (PE/EtOAc 2:1) to give ethyl 9-((tetrahydro-2H-pyran-4-yl)methoxy)nonanoate (94 mg, 29%) as an oil.

Step 2: Synthesis of 9-((tetrahydro-2H-pyran-4-yl)methoxy)nonanoic acid

Prepared in a manner similar to 10-((1,1-dioxidotetrahydro-2H-thiopyran-4-yl)oxy)decanoic acid and purified by column chromatography on silica gel (DCM/MeOH 10:1) to give 9-((tetrahydro-2H-pyran-4-yl)methoxy)nonanoic acid (57 mg, 70%) as a solid. LC/MS: mass calcd. for $C_{15}H_{28}O_4$: 272, found: 271 [M−H]⁻.

Step 3: Synthesis of N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-9-((tetrahydro-2H-pyran-4-yl)methoxy)nonanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column chromatography on silica gel (PE/EtOAc 5:1) to give N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-9-((tetrahydro-2H-pyran-4-yl)methoxy)nonanamide as a solid. LC/MS: mass calcd. for $C_{81}H_{111}NO_{11}$: 1273.82, found: 1274.50 [M+H]⁺.

Step 4: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-9-((tetrahydro-2H-pyran-4-yl)methoxy)nonanamide A mixture of N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-9-((tetrahydro-2H-pyran-4-yl)methoxy)nonanamide (20 mg, 0.013 mmol) and Pd(OH)$_2$ (40 mg) in EtOH (3 mL) and DCM (3 mL) was stirred under an atmosphere of H$_2$ (balloon) for 16 h. The mixture was filtered through a pad of Celite and the filtrate was concentrated under reduced pressure to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-9-((tetrahydro-2H-pyran-4-yl)methoxy)nonanamide (6.3 mg, 54%) as a solid. LC/MS: mass calcd. for C$_{39}$H$_{75}$NO$_{11}$: 733.53, found: 734.50 [M+H]$^+$; $^1$H NMR (300 MHz, CD$_3$OD) δ 4.22 (d, J=5.8 Hz, 1H), 3.56-3.94 (m, 10H), 3.40-3.48 (m, 3H), 3.28-3.30 (m, 3H), 2.24 (t, J=7.5 Hz, 2H), 1.54-1.69 (m, 6H), 1.29-1.35 (m, 39H), 0.97-0.87 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-8-(2-(tetrahydro-2H-pyran-4-yl)ethoxy)octanamide

Step 1: Synthesis of ethyl 8-(2-(tetrahydro-2H-pyran-4-yl)ethoxy)octanoate

Prepared in a manner similar to methyl 10-((1,1-dioxidotetrahydro-2H-thiopyran-4-yl)oxy)decanoate and purified by column chromatography on silica gel (PE/EtOAc 2:1) to give ethyl 8-(2-(tetrahydro-2H-pyran-4-yl)ethoxy)octanoate (62 mg, 23%) as an oil.

Step 2: Synthesis of 8-(2-(tetrahydro-2H-pyran-4-yl)ethoxy)octanoic acid

Prepared in a manner similar to 10-((1,1-dioxidotetrahydro-2H-thiopyran-4-yl)oxy)decanoic acid and purified by column chromatography on silica gel (DCM/MeOH 10:1) to give 8-(2-(tetrahydro-2H-pyran-4-yl)ethoxy)octanoic acid (47 mg, 86%) as a solid. LC/MS: mass calcd. for C$_{15}$H$_{28}$O$_4$: 272, found: 271 [M−H]$^−$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-8-(2-(tetrahydro-2H-pyran-4-yl)ethoxy)octanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, purified by column

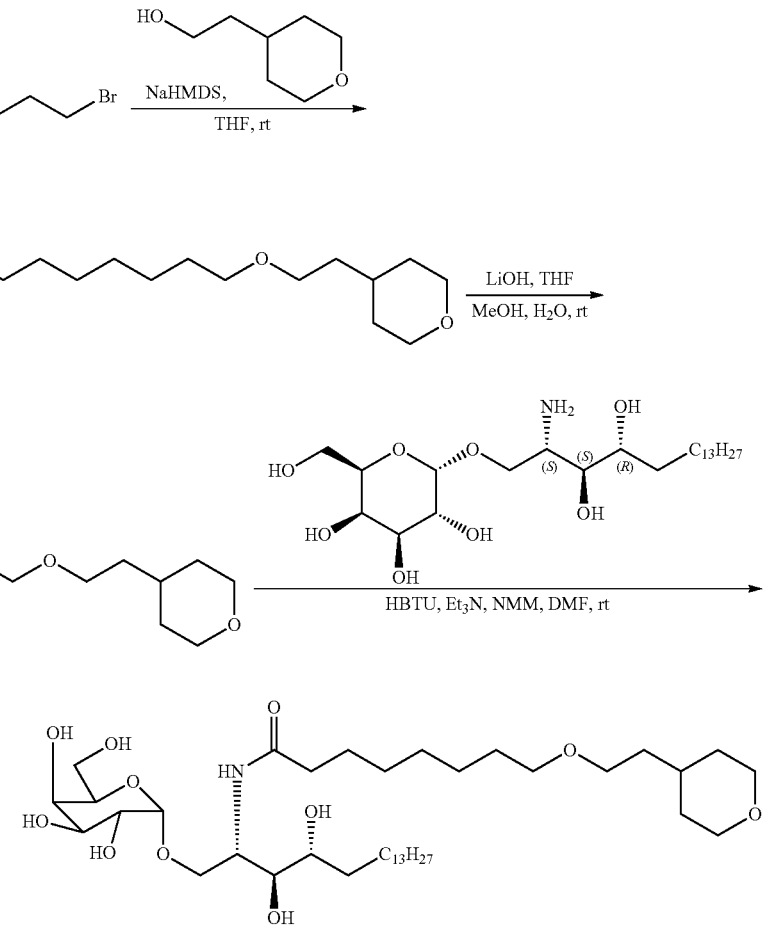

chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-8-(2-(tetrahydro-2H-pyran-4-yl)ethoxy)octanamide (7.4 mg, 8.4%) as an oil. LC/MS: mass calcd. for $C_{39}H_{75}NO_{11}$: 733.53, found: 734.45 $[M+H]^+$; $^1H$ NMR (300 MHZ, $CD_3OD$) δ 4.56-4.60 (m, 4H), 4.17-4.23 (m, 1H), 3.66-3.92 (m, 15H), 3.39-3.57 (m, 4H), 2.22 (t, J=7.5 Hz, 2H), 1.48-1.65 (m, 5H), 1.27-1.37 (m, 33H), 0.84-0.95 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-7-(3-(tetrahydro-2H-pyran-4-yl)propoxy)heptanamide gel (DCM/MeOH 10:1) to give 7-(3-(tetrahydro-2H-pyran-4-yl)propoxy)heptanoic acid (50 mg, 13%) as an oil. LC/MS: mass calcd. for $C_{15}H_{28}O_4$: 272, found: 271 $[M-H]^-$.

Step 2: Synthesis of N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-7-(3-(tetrahydro-2H-pyran-4-yl)propoxy)heptanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy-}octadecan-2-yl]-11-(3-methyloxetan-3-yl)undecanamide, except using THF a solvent. Purified by column chromatography on silica gel (PE/EtOAc

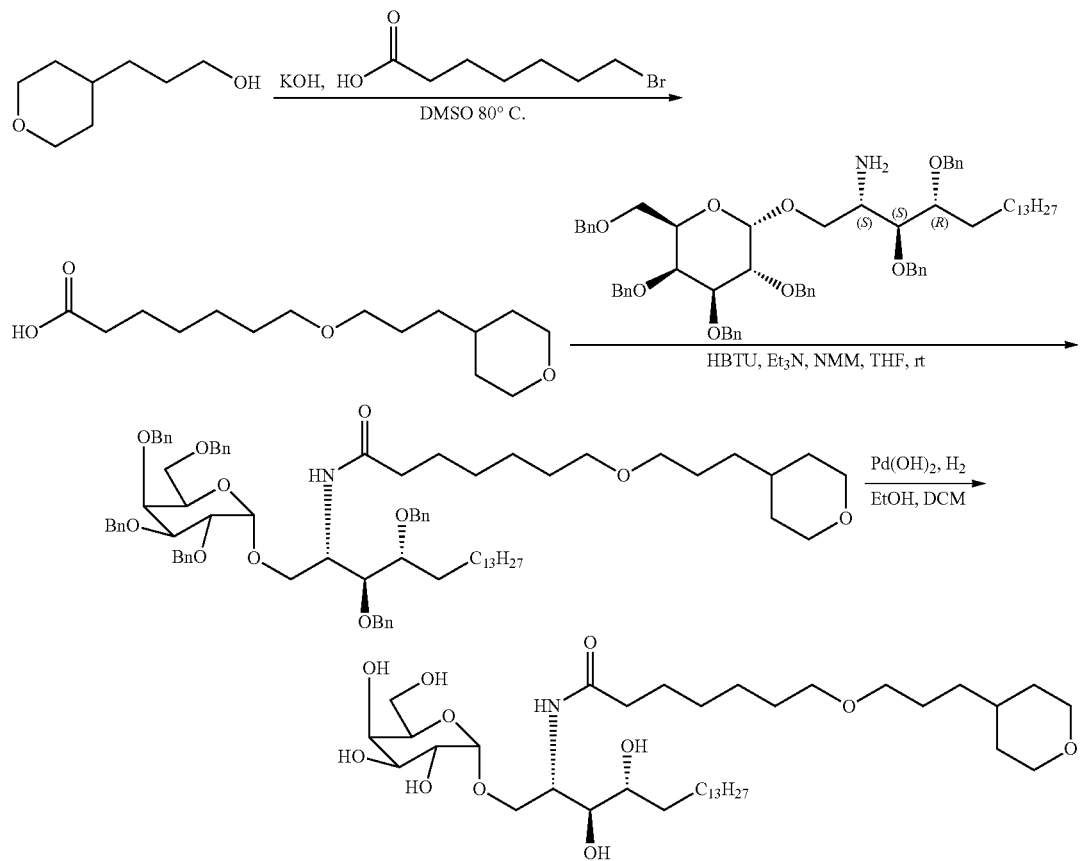

Step 1: Synthesis of 7-(3-(tetrahydro-2H-pyran-4-yl)propoxy)heptanoic acid

To a mixture of 3-(tetrahydro-2H-pyran-4-yl)propan-1-ol (1.0 g, 6.9 mmol) and DMSO (20 mL) under an atmosphere of $N_2$ was added KOH (320 mg, 5.7 mmol). The mixture was heated to 80° C. and stirred for 1 h, then 7-bromo-heptanoic acid (300 mg, 1.4 mmol) was added and the mixture stirred for at 80° C. for a further 2 h. After cooling, the mixture was acidified pH ~1 with 1N HCl and extracted with EtOAc (30 mL×3). The combined organic layers were washed with brine (30 mL), dried over anhydrous $Na_2SO_4$, filtered and the filtrate was concentrated under reduced pressure. The residue was purified by column chromatography on silica 3:1) to give N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-7-(3-(tetrahydro-2H-pyran-4-yl)propoxy)heptanamide (120 mg, 51%) as a solid. LC/MS: mass calcd. for $C_{81}H_{111}NO_{11}$: 1273.82, found: 1274.50 $[M+H]^+$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-7-(3-(tetrahydro-2H-pyran-4-yl)propoxy)heptanamide A mixture of N-((2S,3S,4R)-3,4-bis(benzyloxy)-1-(((2S,3R,4S,5S,6R)-3,4,5-tris(benzyloxy)-6-((benzyloxy)methyl)

tetrahydro-2H-pyran-2-yl)oxy)octadecan-2-yl)-7-(3-(tetrahydro-2H-pyran-4-yl)propoxy)heptanamide (24 mg, 0.019 mmol), Pd(OH)$_2$ (40 mg), EtOH (3 mL) and DCM (3 mL) was stirred under an atmosphere of H$_2$ (balloon) for 16 h. The mixture was filtered through a pad of Celite and the filtrate was concentrated under reduced pressure to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-7-(3-(tetrahydro-2H-pyran-4-yl)propoxy)heptanamide (7.1 mg, 51%) as a solid. LC/MS: mass calcd. for C$_{39}$H$_{75}$NO$_{11}$: 733.53, found: 734.50 [M+H]$^+$; $^1$H NMR (400 MHz, CD$_3$OD) δ 4.23 (q, J=4.9 Hz, 1H), 3.57-3.96 (m, 10H), 3.40-3.46 (m, 5H), 2.24 (t, J=7.8 Hz, 2H), 1.55-1.68 (m, 9H), 1.21-1.41 (m, 37H), 0.88-0.96 (m, 3H).

Synthesis of N-((2S,3S,4R)-3,4-dihydroxy-1-(((2S, 3R,4S,5R,6R)-3,4,5-trihydroxy-6-(hydroxymethyl) tetrahydro-2H-pyran-2-yl)oxy)octadecan-2-yl)-6-(4-(tetrahydro-2H-pyran-4-yl)butoxy)hexanamide Step 2: Synthesis of N-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy) octadecan-2-yl)-6-(4-(tetrahydro-2H-pyran-4-yl) butoxy)hexanamide Prepared in a manner similar to N-[(2S,3S,4R)-3,4-dihydroxy-1-{[(2,3R,4S,5R,6R)-3,4,5-trihydroxy-6-(hydroxymethyl)oxan-2-yl]oxy} octadecan-2-yl]-11-(3-methyloxetan-3-yl)undecanamide, except using THF a solvent. Purified by column chromatography on silica gel (PE/EtOAc 3:1) to give N-((2S,3S,4R)-3,4-bis(benzyloxy)-1-(((2S,3R,4S,5S, 6R)-3,4,5-tris(benzyloxy)-6-((benzyloxy)methyl)tetrahydro-2H-pyran-2-yl)oxy)octadecan-2-yl)-6-(4-(tetrahydro-2H-pyran-4-yl)butoxy)hexanamide (20 mg, 10%) as a solid. LC/MS: mass calcd. for C$_{81}$H$_{111}$NO$_{11}$: 1273.82, found: 1274.50 [M+H]$^+$.

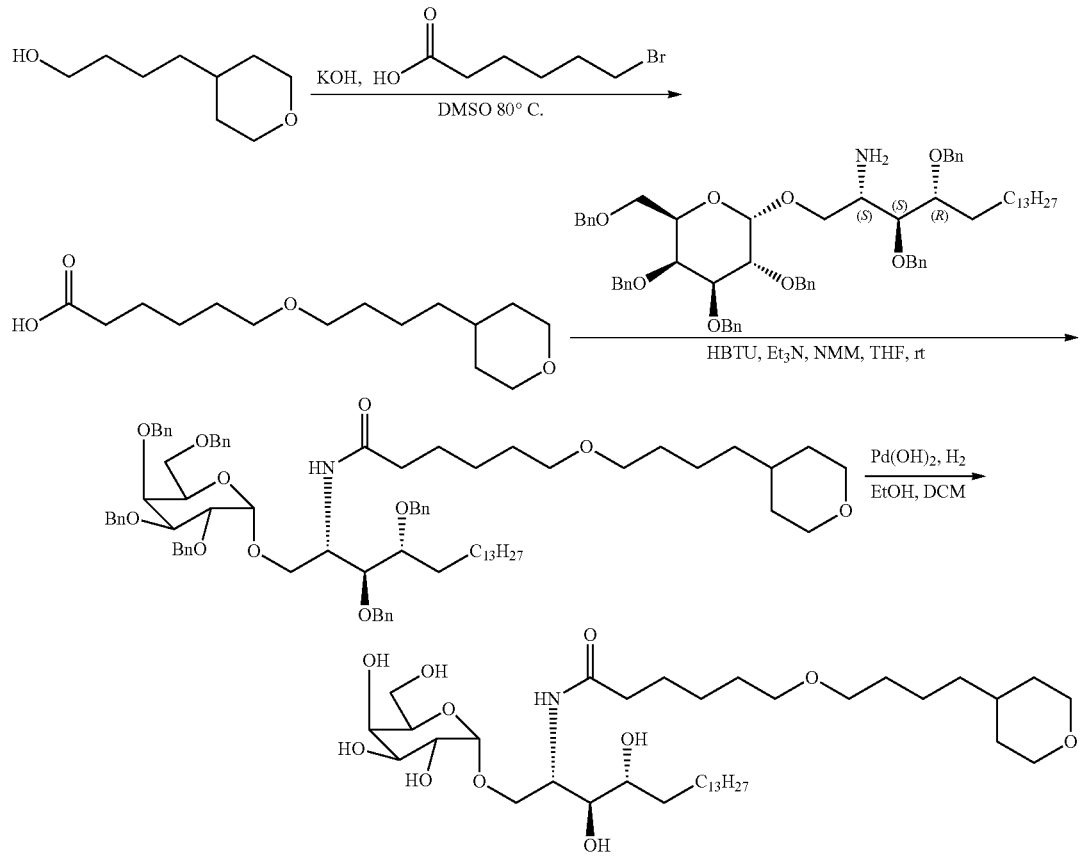

Step 1: Synthesis of 6-(4-(tetrahydro-2H-pyran-4-yl)butoxy)hexanoic acid

Prepared in a manner similar to 7-(3-(tetrahydro-2H-pyran-4-yl)propoxy)heptanoic acid and purified by column chromatography on silica gel (PE/EtOAc 2:1) to give 6-(4-(tetrahydro-2H-pyran-4-yl)butoxy)hexanoic acid (42 mg, 15%) as an oil. LC/MS: mass calcd. for C$_{15}$H$_{28}$O$_4$: 272, found: 271 [M–H]$^-$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-6-(4-(tetrahydro-2H-pyran-4-yl)butoxy) hexanamide A mixture of N-((2S,3S,4R)-3,4-bis(benzyloxy)-1-(((2S, 3R,4S,5S,6R)-3,4,5-tris(benzyloxy)-6-((benzyloxy)methyl) tetrahydro-2H-pyran-2-yl)oxy)octadecan-2-yl)-6-(4-(tetrahydro-2H-pyran-4-yl)butoxy)hexanamide (26 mg, 0.02 mmol), Pd(OH)$_2$ (40 mg), EtOH (3 mL) and DCM (3 mL) was stirred under an atmosphere of H$_2$ (balloon) for 16 h. The mixture was filtered through a pad of Celite and the filtrate was concentrated under reduced pressure to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-6-(4-(tetrahydro-2H-pyran-4-yl)butoxy)hexanamide (1.3 mg, 8.5%) as an oil. LC/MS: mass calcd. for C$_{39}$H$_{75}$NO$_{11}$: 733.53, found: 734.45 [M+H]$^+$; $^1$H NMR (400 MHZ, CD$_3$OD) δ 4.23 (q, J=5.0 Hz, 1H), 3.98-3.77 (m, 10H), 3.40-3.47 (m, 5H), 2.26 (t, J=7.6 Hz, 2H), 1.52-1.68 (m, 10H), 1.21-1.41 (m, 36H), 0.88-0.96 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-17-(3-fluorobicyclo[1.1.1]pentan-1-yl)heptadecanamide Step 2: Synthesis of 17-(3-fluorobicyclo[1.1.1]pentan-1-yl)heptadec-16-enoic Acid To a mixture of (9-carboxynonyl)triphenylphosphonium bromide (800 mg, 1.3 mmol) in THF (15 mL) at 0° C. under an atmosphere of N$_2$ was added 2 M NaHMDS (1.65 mL, 3.3 mmol). The mixture was warmed to rt and stirred for 1 h, then 3-fluorobicyclo[1.1.1]pentane-1-carbaldehyde (152 mg, 1.3 mmol) in THF (1 mL) was added. The mixture was stirred at rt overnight, then acidified pH~1 with 1N HCl and extracted with EtOAc (3×30 mL). The combined organic layers were washed with brine (30 mL), dried over anhydrous Na$_2$SO$_4$, filtered, and the filtrate was concentrated under reduced pressure. The residue was purified by column chromatography on silica gel (PE/EtOAc 2:1) to give 17-(3-fluorobicyclo[1.1.1]pentan-1-yl)heptadec-16-enoic acid (140 mg, 30%) as a solid. LC/MS: mass calcd. for C$_{22}$H$_{37}$FO$_2$: 352, found: 351 [M−H]$^-$.

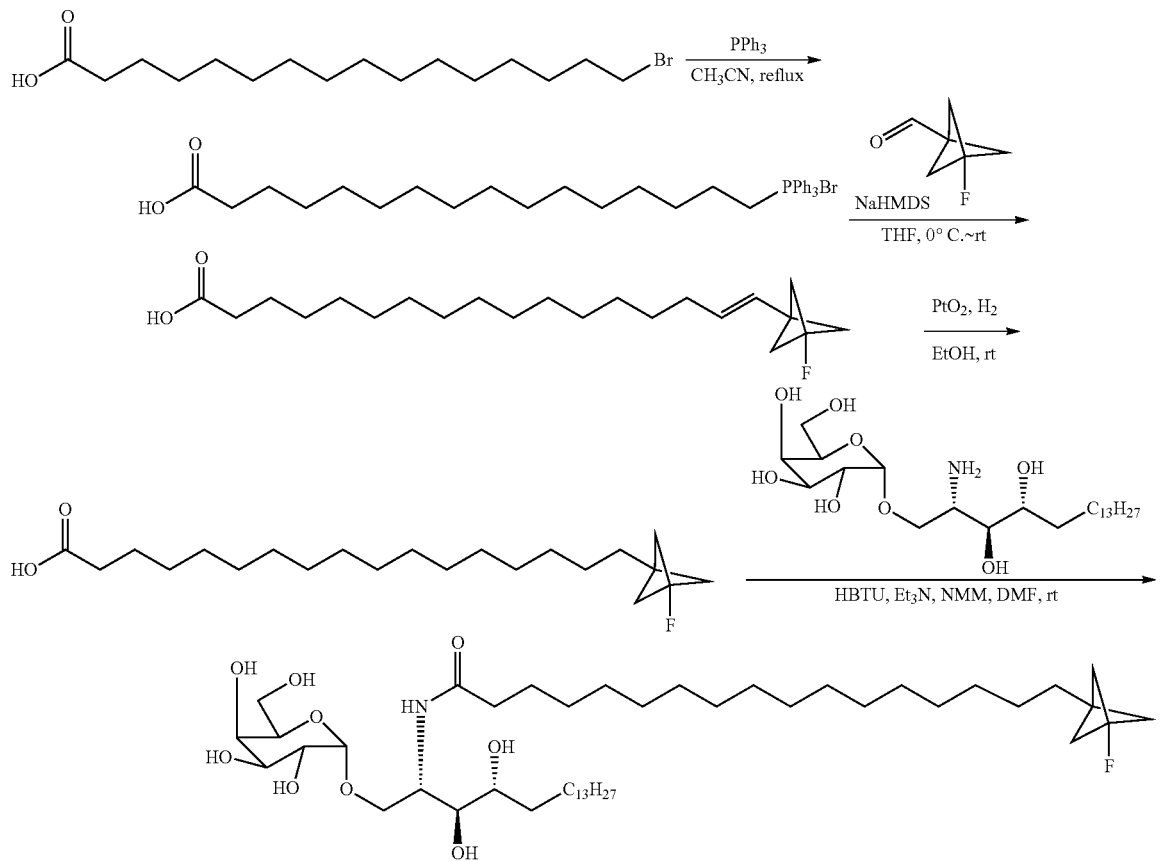

Step 1: Synthesis of (15-carboxypentadecyl)triphenylphosphonium bromide

To a mixture of 16-bromohexadecanoic acid (2.0 g, 5.9 mmol) and CH$_3$CN (30 mL) was added Ph$_3$P (1.56 g, 5.9 mmol). The mixture was heated to 90° C. and stirred for 2 days, then filtered and washed with THF to give (15-carboxypentadecyl)triphenylphosphonium bromide (3.0 g, 84%) as a solid.

Step 3: Synthesis of 17-(3-fluorobicyclo[1.1.1]pentan-1-yl)heptadecanoic Acid

A mixture of 17-(3-fluorobicyclo[1.1.1]pentan-1-yl)heptadec-16-enoic acid (140 mg, 0.39 mmol). PtO$_2$ (20 mg, 0.1 mmol) and EtOH (50 mL) was stirred under an atmosphere of H$_2$ (balloon) for 1 h. The mixture was filtered through a pad of Celite and the filtrate was concentrated under reduced pressure to give 17-(3-fluorobicyclo[1.1.1]pentan-1-yl)heptadecanoic acid (140 mg, 99%) as a solid. LC/MS: mass calcd. for C$_{22}$H$_{39}$FO$_2$: 354, found: 353 [M−H]$^-$.

Step 4: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-17-(3-fluorobicyclo[1.1.1]pentan-1-yl)heptadecanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-17-(3-fluorobicyclo[1.1.1]pentan-1-yl)heptadecanamide (18.8 mg, 15.7%) as a solid. LC/MS: mass calcd. for $C_{46}H_{86}FNO_9$: 815.63, found: 816.65 [M+H]$^+$; $^1$H NMR (400 M MHz, CD$_3$OD) δ 4.20 (dt, J=6.7, 4.4 Hz, 1H), 3.73-3.93 (m, 5H), 3.53-3.76 (m, 5H), 2.24 (t, J=7.5 Hz, 2H), 1.88 (d, J=2.6 Hz, 6H), 1.58-1.66 (m, 6H), 1.30-1.36 (m, 50H), 0.96-0.88 (m, 3H); $^{19}$F NMR (376 MHz, CD$_3$OD) δ−146.5.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-23-(3-fluorobicyclo[1.1.1]pentan-1-yl)tricosanamide

Step 1: Synthesis of (21-carboxyhenicosyl)triphenylphosphonium bromide

To a mixture of 22-bromodocosanoic acid (1.4 g, 3.4 mmol) and CH$_3$CN (30 mL) under an atmosphere of N$_2$ was added Ph$_3$P (0.91 g, 3.4 mmol). The mixture was heated to 90° C. and stirred for 2 days, then concentrated under reduced pressure to give (21-carboxyhenicosyl)triphenylphosphonium bromide (1.6 g, 68%) as a solid.

Step 2: Synthesis of 23-(3-fluorobicyclo[1.1.1]pentan-1-yl)tricos-22-enoic acid To a mixture of (21-carboxyhenicosyl)triphenylphosphonium bromide (300 mg, 0.4 mmol) in 1,4-dioxane (10 mL) under an atmosphere of N$_2$ at rt was added 4A molecular sieve (0.5 g), K$_2$CO$_3$ (245 mg, 1.7 mmol) and 3-fluorobicyclo[1.1.1]pentane-1-carbaldehyde (75 mg, 0.7 mmol). The mixture was heated to 100° C. and stirred for 16 h, then diluted with H$_2$O, the mixture adjusted to pH 4~5 with 2N HCl and extracted with EtOAc. The combined organic layers were concentrated under reduced pressure and the residue was purified by column chromatography on silica gel (PE/EtOAc 2:1) to give 23-(3-fluorobicyclo[1.1.1]pen-

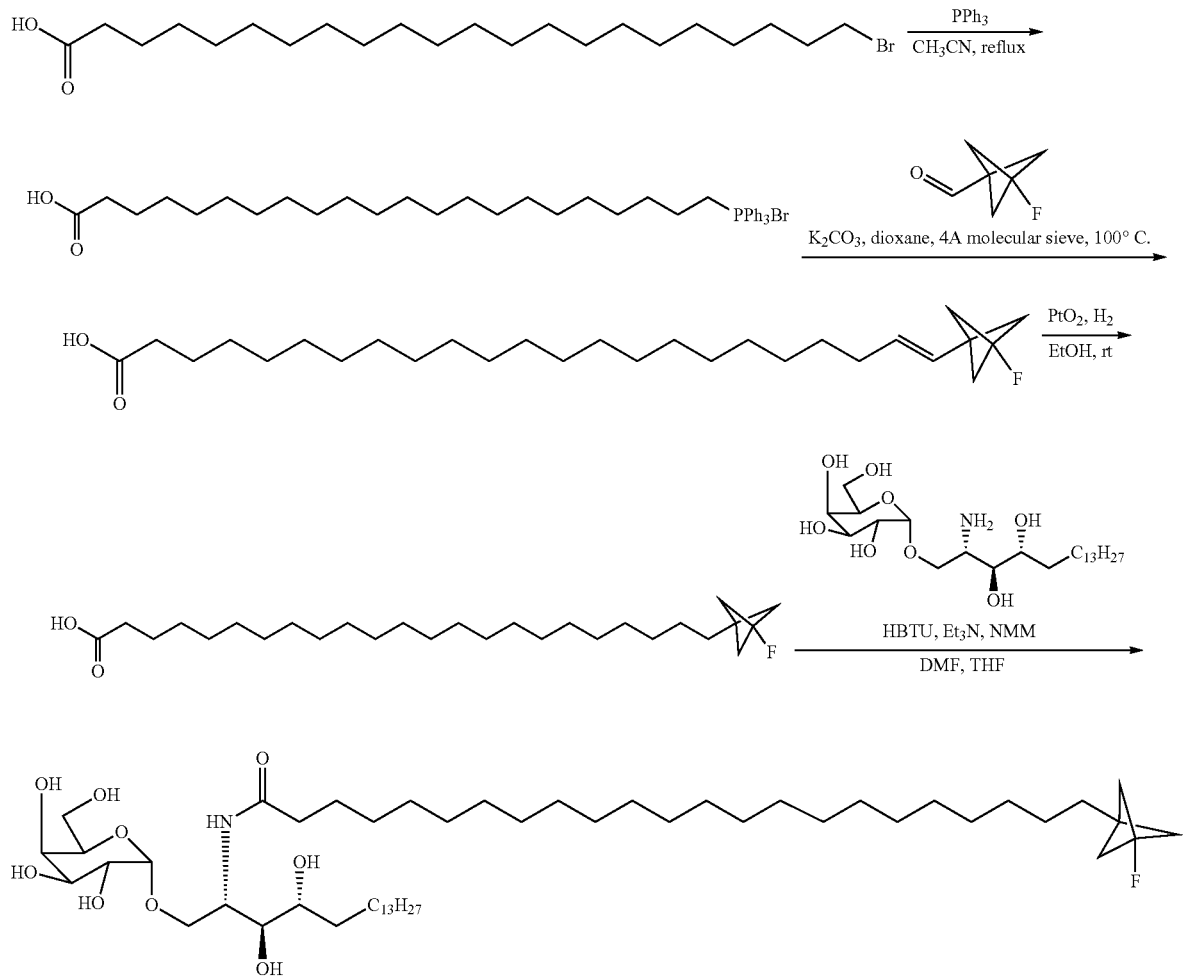

tan-1-yl)tricos-22-enoic acid (50 mg, 26%) as a solid. LC/MS: mass calcd. for $C_{28}H_{49}FO_2$: 436, found: 435 [M−H]−.

Step 3: Synthesis of 23-(3-fluorobicyclo[1.1.1]pentan-1-yl)tricosanoic acid

A mixture of 23-(3-fluorobicyclo[1.1.1]pentan-1-yl)tricos-22-enoic acid (50 mg, 0.11 mmol) and $PtO_2$ (5 mg) in EtOH (20 mL) was stirred at rt under an atmosphere of $H_2$ (1 atm) for 1 h. The mixture was filtered through a pad of Celite and the filter cake washed with EtOH. The filtrate was concentrated under reduced pressure to give 23-(3-fluorobicyclo[1.1.1]pentan-1-yl)tricosanoic acid (45 mg, 90%) as a solid. LC/MS: mass calcd. for $C_{28}H_{51}FO_2$: 438, found: 437 [M−H]−.

Step 4: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-23-(3-fluorobicyclo[1.1.1]pentan-1-yl)tricosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, except DMF/THF was used as solvent. Purified by column chromatography on silica gel (DCM/MeOH) and washed with $CH_3CN$ to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-23-(3-fluorobicyclo[1.1.1]pentan-1-yl)tricosanamide (5.2 mg, 5.2%) as a solid. LC/MS: mass calcd. for $C_{52}H_{98}FNO_9$: 899.72, found: 922.65 [M+H]+; 1H NMR (300 MHz, $CD_3OD$) δ 4.13-4.25 (m, 1H), 3.56-3.93 (m, 10H), 2.24 (t, J=7.4 Hz, 2H), 1.88 (d, J=2.6 Hz, 6H), 1.55-1.68 (m, 5H), 1.26-1.42 (m, 63H), 0.92 (t, J=6.7 Hz, 3H); 19F NMR (282 MHZ, $CD_3OD$) δ −146.5.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-21-(3-fluorobicyclo[1.1.1]pentan-1-yl)heneicosanamide

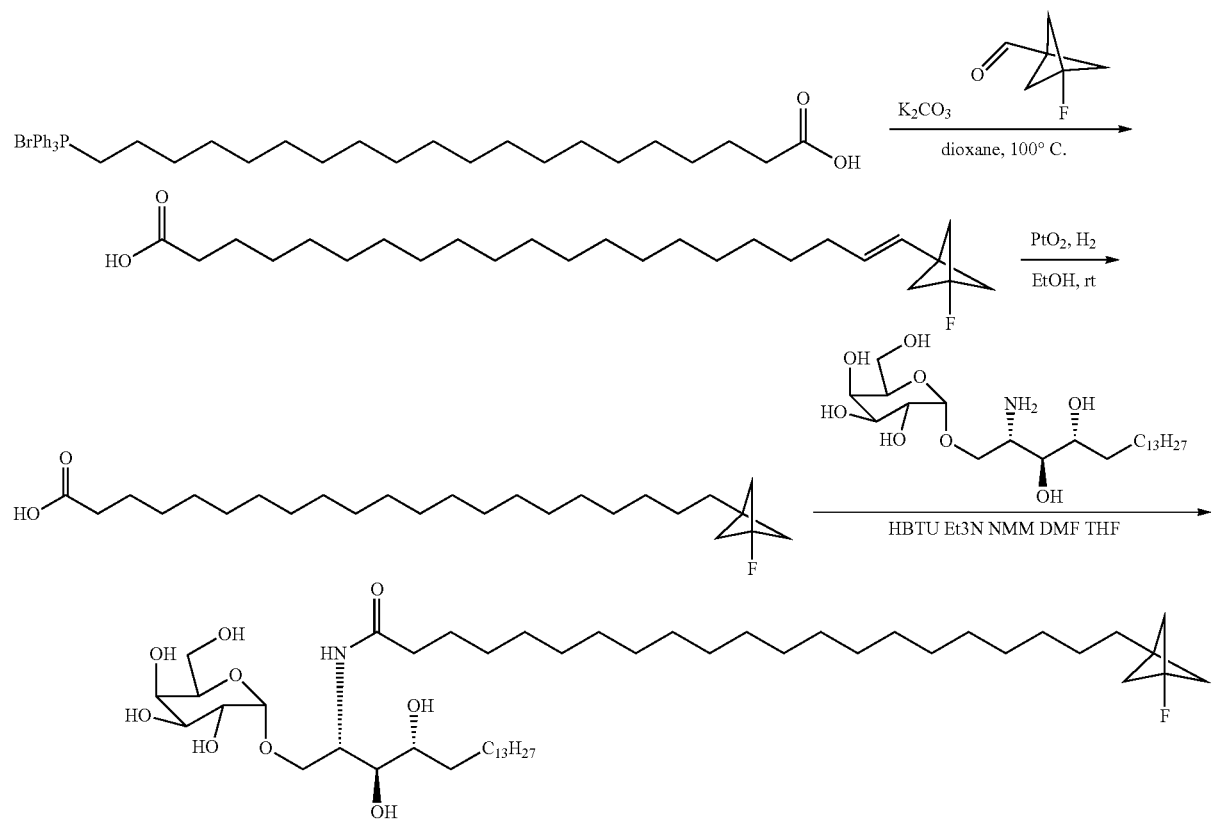

Step 1: Synthesis of 21-(3-fluorobicyclo[1.1.1]pentan-1-yl)henicos-20-enoic Acid Prepared in a manner similar to 23-(3-fluorobicyclo[1.1.1]pentan-1-yl)tricos-22-enoic acid and purified by column chromatography on silica gel (PE/EtOAc 1:1) to give 21-(3-fluorobicyclo[1.1.1]pentan-1-yl)henicos-20-enoic acid (65 mg, 35%) as a solid. LC/MS: mass calcd. for $C_{26}H_{45}FO_2$: 408, found: 407 [M−H]−.

Step 2: Synthesis of 21-(3-fluorobicyclo[1.1.1]pentan-1-yl)heneicosanoic Acid

Prepared in a similar manner to 23-(3-fluorobicyclo[1.1.1]pentan-1-yl)tricosanoic acid to give 21-(3-fluorobicyclo[1.1.1]pentan-1-yl)heneicosanoic acid (60 mg, 92%) as a solid. LC/MS: mass calcd. for $C_{26}H_{47}FO_2$: 41, found: 409 [M−H]−.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-21-(3-fluorobicyclo[1.1.1]pentan-1-yl)heneicosanamine Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, except DMF/THF was used as solvent. Purified by column chromatography on silica gel (DCM/MeOH 9:1) and washed with $CH_3CN$ to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-21-(3-fluorobicyclo[1.1.1]pentan-1-yl)heneicosanamine (4.7 mg, 3.9%) as a solid. LC/MS: mass calcd. for $C_{50}H_{94}FNO_9$: 871.69, found: 872.70 [M+H]$^+$ and 894.65 [M+Na]$^+$; $^1$H NMR (300 MHz, $CD_3OD$) δ 4.16-4.23 (m, 1H), 3.56-3.89 (m, 10H), 2.24 (t, J=7.5 Hz, 2H), 1.88 (d, J=2.6 Hz, 6H), 1.52-1.69 (m, 6H), 1.23-1.39 (m, 58H), 0.92 (t, J=6.4 Hz, 3H); $^{19}$F NMR (282 MHz, $CD_3OD$) δ −146.6.

Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-22-{3-fluorobicyclo[1.1.1]pentan-1-yl}docosanamide Step 1: Synthesis of 21-(bromotriphenyl-lambda5-phosphanyl)henicosanoic acid To a mixture of 21-bromohenicosanoic acid (1.16 g, 2.86 mmol) and $CH_3CN$ (20 mL) was added $Ph_3P$ (0.75 g, 2.86 mmol). The mixture was heated to 90° C. and stirred for 2 days, then concentrated under reduced pressure. The residue was purified by $C_{18}$ reverse-phase HPLC ($H_2O$, 5% HCl)/$CH_3OH$ 5%-100%) to give 21-(bromotriphenyl-lambda5-phosphanyl)henicosanoic acid (1.27 g, 66%) as a solid.

Step 2: Synthesis of (E)-22-(3-fluorobicyclo[1.1.1]pentan-1-yl)docos-21-enoic acid Prepared in a manner similar to 23-(3-fluorobicyclo[1.1.1]pentan-1-yl)tricos-22-enoic acid and purified by column chromatography on silica gel (PE/EtOAc 1:1) to give (E)-22-(3-fluorobicyclo[1.1.1]pentan-1-yl)docos-21-enoic acid (44 mg, 35%) as a solid. LC/MS: mass calcd. for $C_{27}H_{47}FO_2$: 422.36, found: 421.15 [M−H]$^−$.

Step 3: Synthesis of 22-(3-fluorobicyclo[1.1.1]pentan-1-yl)docosanoic acid

Prepared in a similar manner to 23-(3-fluorobicyclo[1.1.1]pentan-1-yl)tricosanoic acid to give 22-(3-fluorobi-

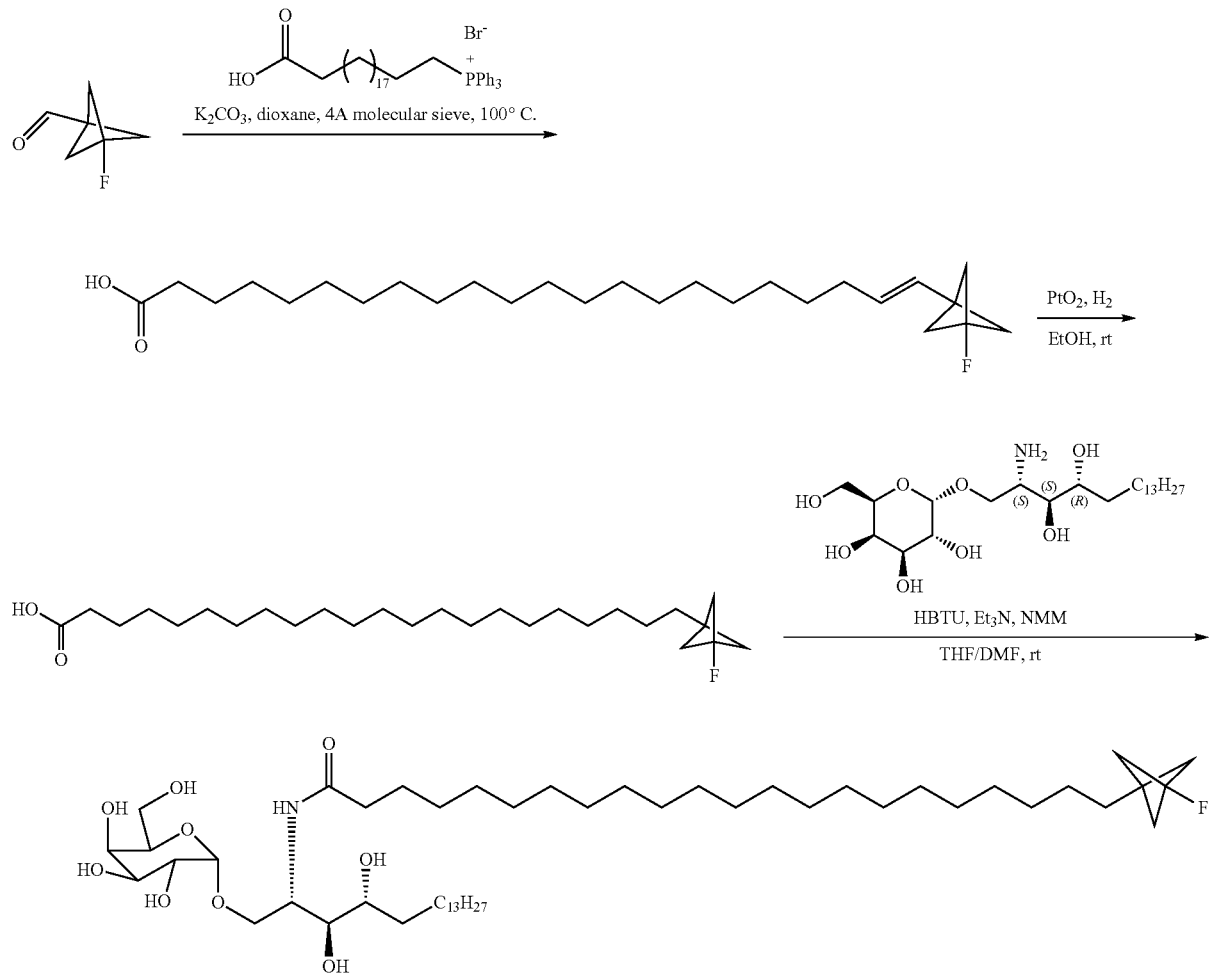

cyclo[1.1.1]pentan-1-yl)docosanoic acid (40 mg, 99%) as a solid. LC/MS: mass calcd. for $C_{27}H_{49}FO_2$: 424.37, found: 423.15 [M−H]−.

Step 4: Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-22-{3-fluorobicyclo[1.1.1]pentan-1-yl}docosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-meth- CD$_3$OD) δ 4.85-4.87 (m, 1H), 4.20 (d, J=6.6 Hz, 1H), 3.89-3.90 (m, 3H), 3.70-3.85 (m, 5H), 3.63-3.67 (m, 1H), 3.55-3.60 (m, 1H), 2.24 (t, J=7.5 Hz, 2H), 1.88 (d, J=2.6 Hz, 6H), 1.56-1.66 (m, 4H), 1.30-1.46 (m, 62H), 0.92 (t, J=6.8 Hz, 3H); 19F NMR (376 MHz, CD$_3$OD) δ −146.6.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-24-(3-fluorobicyclo[1.1.1]pentan-1-yl)tetracosanamide

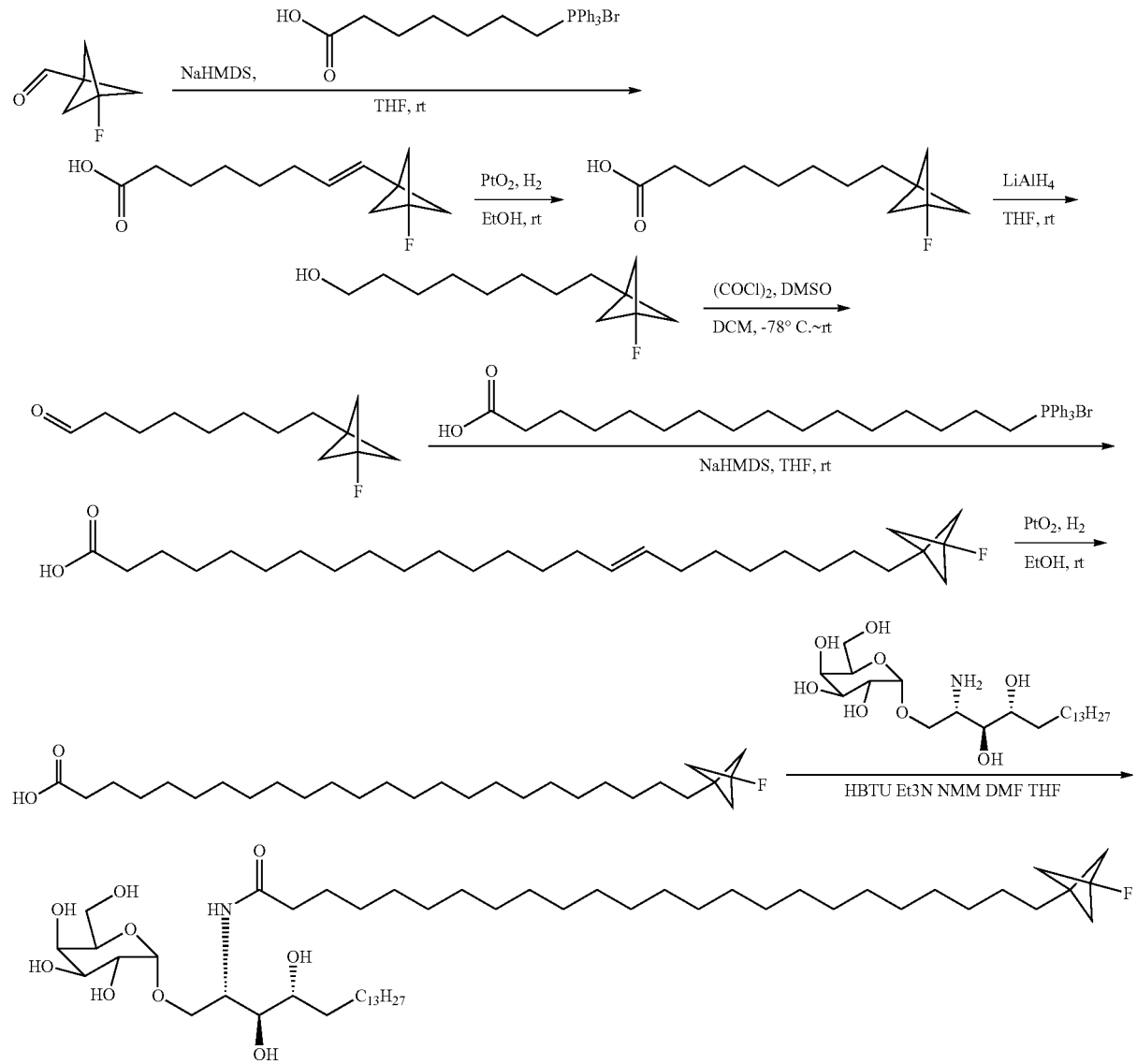

yloxetan-3-yl)undecanamide, except DMF/THF was used as solvent. Purified by column chromatography on silica gel (DCM/MeOH 9:1) and washed with CH$_3$CN to give N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-22-{3-fluorobicyclo[1.1.1]pentan-1-yl} docosanamide (22.5 mg, 18%) as a solid. LC/MS: mass calcd. for $C_{51}H_{96}FNO_9$: 885.71, found: 886.75 [M+H]+; 1H NMR (400 MHZ, Step 1: Synthesis of 8-(3-fluorobicyclo[1.1.1]pentan-1-yl)oct-7-enoic acid Prepared in a manner similar to 17-(3-fluorobicyclo[1.1.1]pentan-1-yl)heptadec-16-enoic acid and purified by column chromatography on silica gel (PE/EtOAc 1:1) to give 8-(3-fluorobicyclo[1.1.1]pentan-1-yl)oct-7-enoic acid (500 mg, 50%) as a solid. LC/MS: mass calcd. for $C_{13}H_{19}FO_2$: 226, found: 225 [M−H]−.

Step 2: Synthesis of 8-{3-fluorobicyclo[1.1.1]pentan-1-yl}octanoic Acid

A mixture of 8-(3-fluorobicyclo[1.1.1]pentan-1-yl)oct-7-enoic acid (500 mg, 2.21 mmol) and $PtO_2$ (30 mg) in EtOH (100 mL) was stirred under an atmosphere of $H_2$ (balloon) for 1 h. The mixture was filtered through a pad of Celite and the filtrate was concentrated under reduced pressure to give 8-{3-fluorobicyclo[1.1.1]pentan-1-yl}octanoic acid (500 mg, 99%) as a solid. LC/MS: mass calcd. for $C_{13}H_{21}FO_2$: 228, found: 227 [M–H]$^-$.

Step 3: Synthesis of 8-{3-fluorobicyclo[1.1.1]pentan-1-yl}octan-1-ol

To a mixture of 8-{3-fluorobicyclo[1.1.1]pentan-1-yl}octanoic acid (500 mg, 2.19 mmol) and THF (10 mL) at 0° C. under an atmosphere of $N_2$ was added LiAlH$_4$ (332 mg, 8.76 mmol). The mixture was stirred at 0° C. for 3 h, then diluted with aqueous $Na_2SO_4$ and filtered. The filtrate was washed with EtOAc, and the organic layer was dried over $Na_2SO_4$, filtered and the filtrate was concentrated under reduced pressure. The residue was purified by column chromatography on silica gel (PE/EtOAc 1:1) to give 8-{3-fluorobicyclo[1.1.1]pentan-1-yl}octan-1-ol (320 mg, 68%) as a solid.

Step 4: Synthesis of 8-(3-fluorobicyclo[1.1.1]pentan-1-yl)octanal

To a mixture of oxalyl chloride (284 mg, 2.24 mmol) and DCM (10 mL) at –78° C. under an atmosphere of $N_2$ was added DMSO (349 mg, 4.47 mmol) dropwise. The mixture was stirred at –78° C. for 15 min. then 8-{3-fluorobicyclo[1.1.1]pentan-1-yl}octan-1-ol (320 mg, 1.49 mmol) in DCM (2 mL) was added dropwise. The mixture was stirred at –78° C. for 50 min, then Et$_3$N (3 mL) was added. Stirring was continued at –78° C. for 5 min, then the mixture was warmed to rt, diluted with H$_2$O (10 mL) and extracted with DCM (3×20 mL). The combined organic layers were washed with H$_2$O (20 mL), brine (20 mL), dried over Na$_2$SO$_4$, and filtered. The filtrate was concentrated under reduced pressure to give 8-(3-fluorobicyclo[1.1.1]pentan-1-yl)octanal (300 mg, 95%) as an oil, which was used without further purification R$_f$=0.4 (PE/EtOAc=1:2).

Step 5: Synthesis of 24-(3-fluorobicyclo[1.1.1]pentan-1-yl)tetracos-16-enoic Acid To a mixture of (15-carboxy pentadecyl)triphenylphosphonium bromide (844 mg, 1.41 mmol) and THF (20 mL) at 0° C. under an atmosphere of $N_2$ was added NaHMDS (1.5 mL, 9.6 mmol). The mixture was warmed to rt and stirred for 1 h, then 8-{3-fluorobicyclo[1.1.1]pentan-1-yl}octanal (300 mg, 1.41 mmol) was added and the mixture was stirred at rt overnight. The mixture was acidified to pH~5 with 1N HCl and extracted with EtOAc (3×30 mL). The combined organic layers were washed with brine (50 mL), dried over anhydrous Na$_2$SO$_4$, filtered and the filtrate was concentrated under reduced pressure. The residue was purified by column chromatography on silica gel (PE/EtOAc 1:1) to give 24-(3-fluorobicyclo[1.1.1]pentan-1-yl)tetracos-16-enoic acid (400 mg, 63%) as a solid. LC/MS-mass calcd. for $C_{29}H_{51}FO_2$: 450, found: 449 [M–H]$^-$.

Step 6: Synthesis of 24-(3-fluorobicyclo[1.1.1]pentan-1-yl)tetracosanoic Acid Prepared in a similar manner to 23-(3-fluorobicyclo[1.1.1]pentan-1-yl)tricosanoic acid to give 24-(3-fluorobicyclo[1.1.1]pentan-1-yl)tetracosanoic acid (180 mg, 90%) as a solid. LC/MS: mass calcd. for $C_{29}H_{53}FO_2$: 452, found: 451 [M–H]$^-$.

Step 7: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-24-(3-fluorobicyclo[1.1.1]pentan-1-yl) tetracosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, except DMF/THF was used as solvent. Purified by column chromatography on silica gel (DCM/MeOH 9:1) and washed with CH$_3$CN to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-24-(3-fluorobicyclo[1.1.1]pentan-1-yl) tetracosanamide (12.0 mg, 9.4%). LC/MS: mass calcd. for $C_{53}H_{100}FNO_9$: 913.74, found: 936.80 [M+Na]$^+$; $^1$H NMR (400 MHz, CD$_3$OD) δ 4.20 (d, J=6.4 Hz, 1H), 3.53-3.93 (m, 10H), 2.09-2.36 (m, 2H), 1.88 (d, J=2.7 Hz, 6H), 1.56-1.67 (m, 6H), 0.92 (t, J=6.6 Hz, 4H); $^{19}$F NMR (376 MHz, CD$_3$OD) δ–146.5.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-25-(3-fluorobicyclo[1.1.1]pentan-1-yl)pentacosanamide

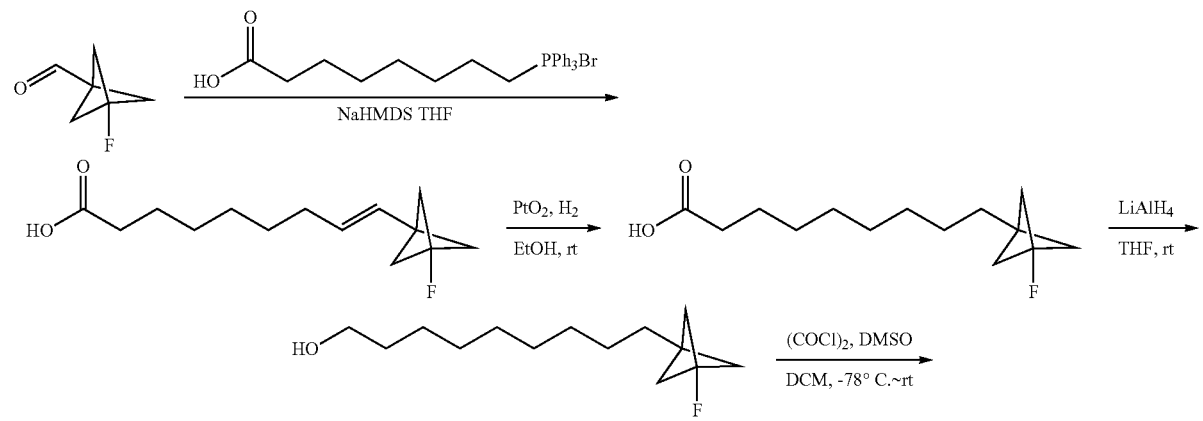

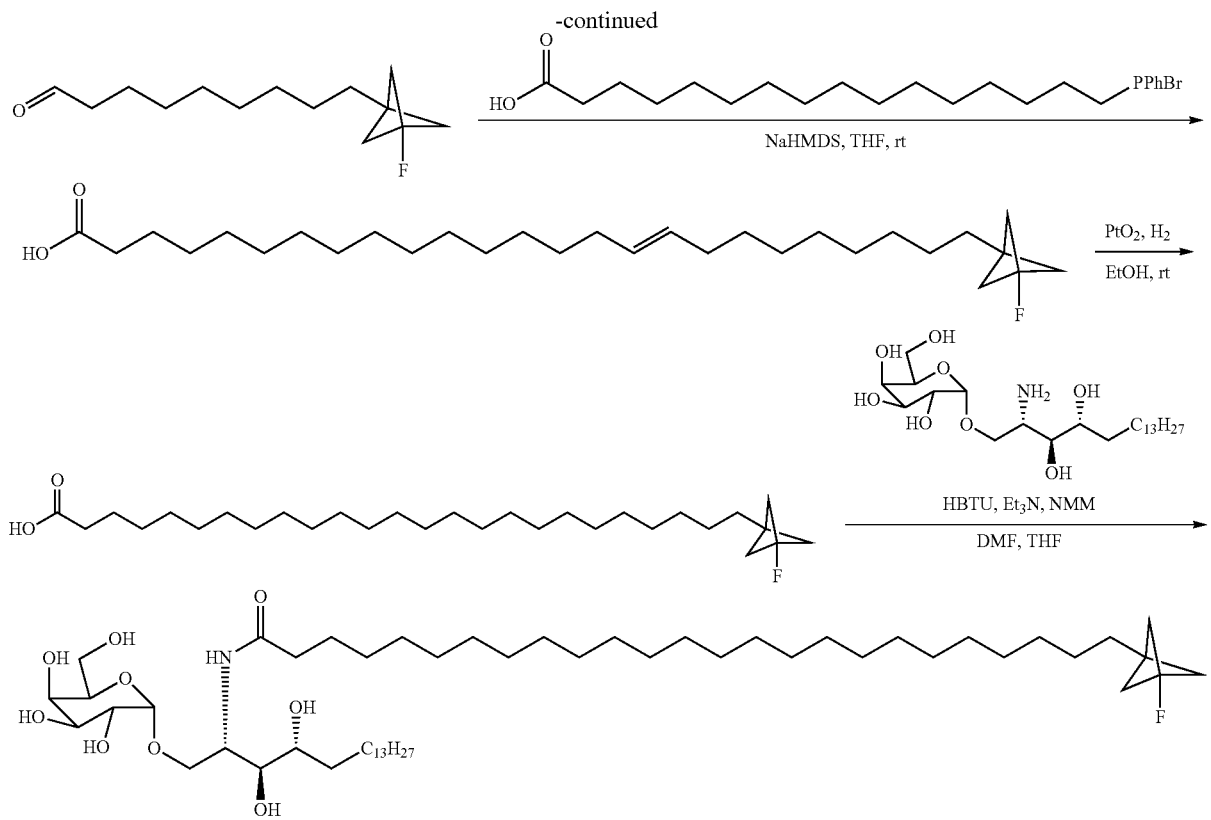

Step 1: Synthesis of 9-(3-fluorobicyclo[1.1.1]pentan-1-yl)non-8-enoic acid

Prepared in a manner similar to 17-(3-fluorobicyclo[1.1.1]pentan-1-yl)heptadec-16-enoic acid and purified by column chromatography on silica gel (PE/EtOAc 1:1) to give 9-(3-fluorobicyclo[1.1.1]pentan-1-yl)non-8-enoic acid (650 mg, 62%) as a solid. LC/MS: mass calcd. for $C_{14}H_{21}FO_2$: 240, found: 239 [M–H]$^-$.

Step 2: Synthesis of 9-{3-fluorobicyclo[1.1.1]pentan-1-yl}nonanoic acid

Prepared in a manner similar to 8-{3-fluorobicyclo[1.1.1]pentan-1-yl}octanoic acid to give 9-{3-fluorobicyclo[1.1.1]pentan-1-yl}nonanoic acid (650 mg, 99%) as a solid. LC/MS: mass calcd. for $C_{14}H_{23}FO_2$: 242, found: 240 [M–H]$^-$.

Step 3: Synthesis of 9-{3-fluorobicyclo[1.1.1]pentan-1-yl}nonan-1-ol

Prepared in a similar manner to 8-{3-fluorobicyclo[1.1.1]pentan-1-yl}octan-1-ol and purified by column chromatography on silica gel (PE/EtOAc 1:1) to give 9-{3-fluorobicyclo[1.1.1]pentan-1-yl}nonan-1-ol (400 mg, 65%) as a solid.

Step 4: Synthesis of 9-{3-fluorobicyclo[1.1.1]pentan-1-yl}nonanal

Prepared in a similar manner to 8-(3-fluorobicyclo[1.1.1]pentan-1-yl)octanal to give 9-{3-fluorobicyclo[1.1.1]pentan-1-yl}nonanal (280 mg, 94%) $R_f$=0.4. PE/EA=1:3.

Step 5: Synthesis of 25-(3-fluorobicyclo[1.1.1]pentan-1-yl)pentacos-16-enoic Acid Prepared in a similar manner to 24-(3-fluorobicyclo[1.1.1]pentan-1-yl)tetracos-16-enoic acid to give and purified by column chromatography on silica gel (PE/EtOAc 1:1) to give 25-(3-fluorobicyclo[1.1.1]pentan-1-yl)pentacos-16-enoic acid (200 mg, 35%) as a solid. LC/MS: mass calcd. for $C_{30}H_{53}FO_2$: 464, found: 463 [M–H]$^-$.

Step 6: Synthesis of 25-{3-fluorobicyclo[1.1.1]pentan-1-yl}pentacosanoic Acid

A mixture of 25-{3-fluorobicyclo[1.1.1]pentan-1-yl}pentacos-16-enoic acid (200 mg, 0.43 mmol) and $PtO_2$ (30 mg) in EtOH (100 mL) was stirred under an atmosphere of $H_2$ (balloon) for 1 h. The reaction mixture was filtered through a pad of celite and concentrated under reduced pressure to afford 25-{3-fluorobicyclo[1.1.1]pentan-1-yl}pentacosanoic acid (200 mg, 99.6%) as a white solid. LC/MS: mass calcd. for $C_{30}H_{55}FO_2$: 466, found: 465 [M–H]$^-$.

Step 7: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-25-(3-fluorobicyclo[1.1.1]pentan-1-yl)pentacosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, except DMF/THF was used as solvent. Purified by column chromatography on silica gel (DCM/MeOH 5:1) and preparative-HPLC to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-25-(3-fluorobicyclo[1.1.1]pentan-1-yl)pentacosanamide (8.8 mg, 7.7%). LC/MS: mass calcd. for C$_{54}$H$_{102}$FNO$_9$: 927.75, found: 950.85 [M+Na]$^+$; $^1$H NMR (300 MHZ, CD$_3$OD) δ 4.20 (d, J=5.5 Hz, 1H), 3.54-3.93 (m, 10H), 2.24 (t, J=7.4 Hz, 2H), 1.88 (d, J=2.7 Hz, 6H), 1.54-1.69 (m, 6H), 1.25-1.42 (m, 66H), 0.91 (t, J=8.6, 7.4 Hz, 3H); 19F NMR (282 MHZ, CD$_3$OD) δ −146.6.

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(3-tridecylbicyclo[1.1.1]pentan-1-yl)undecanamide

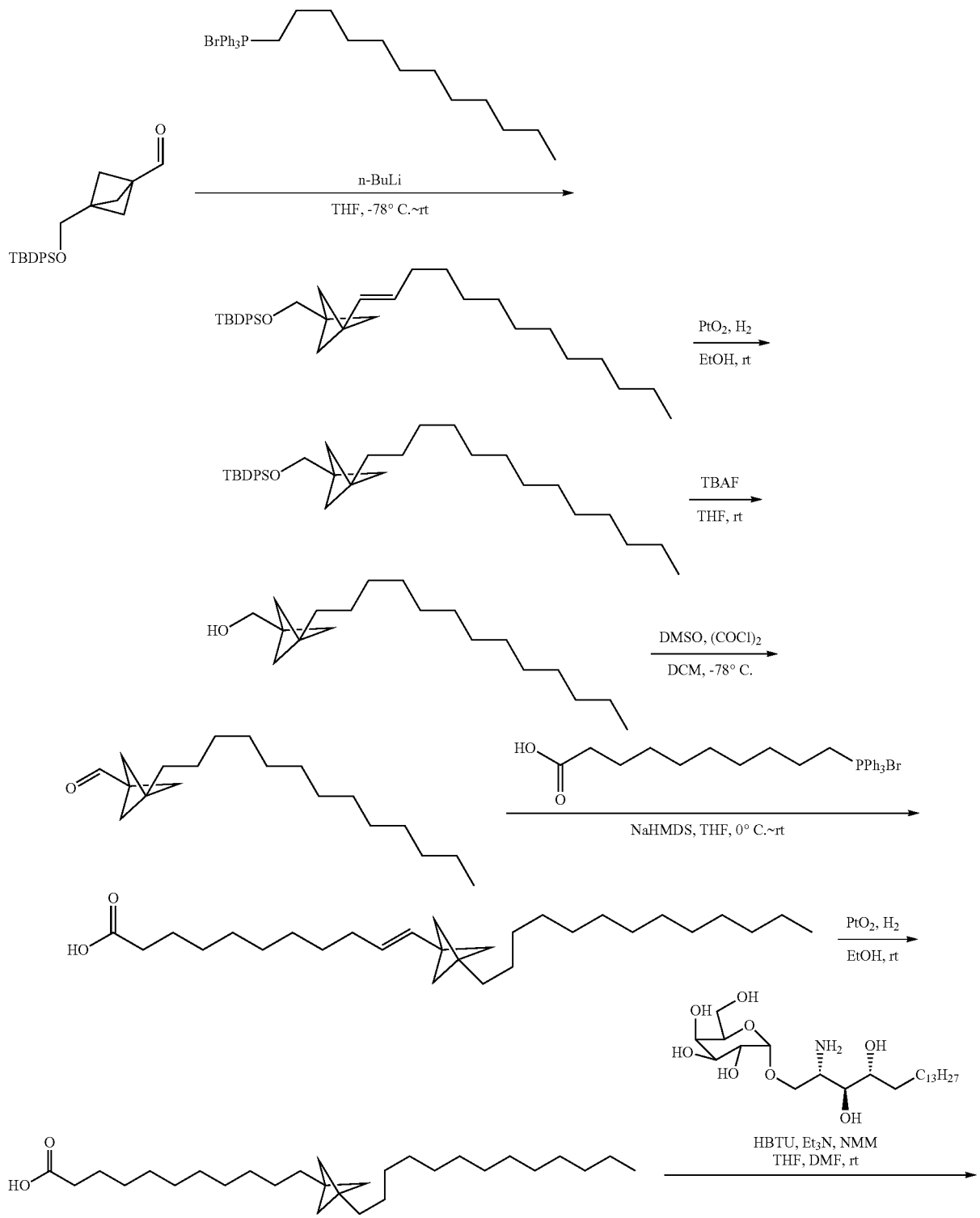

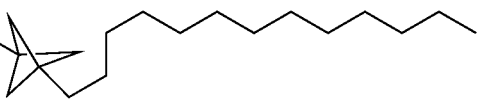
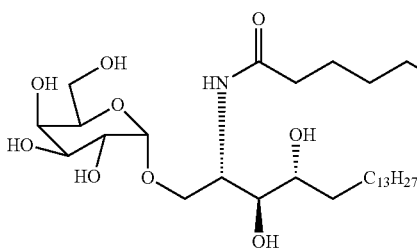

Step 1: Synthesis of tert-butyldiphenyl((3-(tridec-1-en-1-yl)bicyclo[1.1.1]pentan-1-yl)methoxy)silane To a mixture of dodecyltriphenylphosphonium bromide (2.1 g, 4.1 mmol) and THF (20 mL) at −78° C. under an atmosphere of $N_2$ was added n-BuLi (1.8 mL, 4.5 mmol). The mixture was stirred at -78° ° C. for 20 min, warmed to 0° C. and stirred 20 min, then a solution of 3-(((tert-butyldiphenylsilyl)oxy)methyl)bicyclo[1.1.1]pentane-1-carbaldehyde [CAS No: 1678528-05-6] (1.5 g, 4.1 mmol) in THF (5 mL). The mixture was warmed to rt and stirred overnight, then diluted with $H_2O$ (30 mL) and extracted with EtOAc (3×50 mL). The combined organic layers were washed with brine (50 mL), dried over anhydrous $Na_2SO_4$, filtered and the filtrate was concentrated under reduced pressure. The residue was purified by column chromatography on silica gel (PE/EtOAc 4:1) to give tert-butyldiphenyl((3-(tridec-1-en-1-yl)bicyclo[1.1.1]pentan-1-yl) methoxy)silane (1.3 g, 61%) as a solid.

Step 2: Synthesis of tert-butyldiphenyl((3-tridecyl-bicyclo[1.1.1]pentan-1-yl)methoxy)silane A mixture of tert-butyldiphenyl((3-(tridec-1-en-1-yl)bicyclo[1.1.1]pentan-1-yl)methoxy)silane (1.3 g, 2.5 mmol), $PtO_2$ (100 mg) and EtOH (100 mL) was stirred at rt under an atmosphere of $H_2$ (1 atm) for 1 h. The mixture was filtered through a pad of Celite and the filter cake was washed with EtOH. The filtrate was concentrated under reduced pressure to give tert-butyldiphenyl((3-tridecylbicyclo[1.1.1]pentan-1-yl)methoxy)silane (1.1 g, 84%) as a solid.

Step 3: Synthesis of (3-tridecylbicyclo[1.1.1]pentan-1-yl)methanol

To a mixture of tert-butyldiphenyl((3-tridecylbicyclo[1.1.1]pentan-1-yl)methoxy)silane (1.1 g, 2.1 mmol) and THF (30 mL) at rt was added TBAF (1.66 g, 6.4 mmol). The mixture was stirred at rt for 3 h, then extracted with EtOAc (3×20 mL), The combined organic layers were washed with brine (50 mL), dried over anhydrous $Na_2SO_4$, filtered and the filtrate was concentrated under reduced pressure. The residue was purified by column chromatography on silica gel (PE/EtOAc 1:1) to give (3-tridecylbicyclo[1.1.1]pentan-1-yl)methanol (500 mg, 84%) as a solid.

Step 4: Synthesis of 3-tridecylbicyclo[1.1.1]pentane-1-carbaldehyde

DMSO (267 mg, 3.4 mmol) was added dropwise to a mixture of oxalyl chloride (217 mg, 1.7 mmol) at −78° C. under an atmosphere of $N_2$. The mixture was stirred for 15 mm-78° C., then 3-tridecylbicyclo[1.1.1]pentan-1-yl)methanol (320 mg, 1.2 mmol) in DCM (2 mL) was added dropwise and the mixture was stirred at −78° C. for 50 min. $Et_3N$ (3 mL) was added at −78° C., and stirring was continued for an additional 5 min, then the mixture was warmed to rt and diluted with $H_2O$ (10 mL) and extracted with DCM (3×20 mL). The combined organic layers were washed with $H_2O$ (20 mL), brine (20 mL), dried over $Na_2SO_4$, filtered and the filtrate concentrated under reduced pressure to give 3-tridecylbicyclo[1.1.1]pentane-1-carbaldehyde (300 mg, 94%) as an oil. The product was used without further purification.

Step 5: Synthesis of 11-(3-tridecylbicyclo[1.1.1]pentan-1-yl)undec-10-enoic Acid To a mixture of 10-(bromotriphenyl-lambda5-phosphanyl)decanoic acid (553 mg, 1.0 mmol) and THF (20 mL) at 0° C. under an atmosphere of $N_2$ was added NaHMDS (1.2 mL, 2.4 mmol). The mixture was warmed to rt and stirred for 1 h, then a mixture of 3-tridecylbicyclo[1.1.1]pentane-1-carbaldehyde (300 mg, 1.0 mmol) in THF (2 mL) was added and the mixture was stirred at rt overnight. The mixture was acidified to pH~5 with 1N HCl and extracted with EtOAc (3×30 mL), The combined organic layers were washed with brine (30 mL), dried over anhydrous $Na_2SO_4$, filtered and the filtrate was concentrated under reduced pressure. The residue was purified by column chromatography on silica gel eluted (PE/EtOAc 1:1) to give 11-(3-tridecylbicyclo[1.1.1]pentan-1-yl)undec-10-enoic acid (160 mg, 34%) as a solid.

Step 6: Synthesis of 11-(3-tridecylbicyclo[1.1.1]pentan-1-yl)undecanoic Acid A mixture of 11-{3-tridecylbicyclo[1.1.1]pentan-1-yl}undec-10-enoic acid (160 mg, 0.43 mmol), $PtO_2$ (25 mg) and EtOH (50 mL) was stirred at rt under an atmosphere of $H_2$ (1 atm) for 1 h. The mixture was filtered through a pad of Celite and the filter cake was washed with EtOH. The filtrate was concentrated under reduced pressure to give 11-(3-tridecylbicyclo[1.1.1]pentan-1-yl)undecanoic acid (150 mg, 93%) as a solid.

Step 7: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(3-tridecylbicyclo[1.1.1]pentan-1-yl) undecanamide To a mixture of 11-{3-tridecylbicyclo[1.1.1]pentan-1-yl}undecanoic acid (45 mg, 0.10 mmol) and (2S,3R,4S,5R,6R)-2-(((2S,3S,4R)-2-amino-3,4-dihydroxyoctadecyl)oxy)-6-(hydroxymethyl)tetrahydro-2H-pyran-3,4,5-triol (49 mg, 0.10 mmol) in DMF (3 mL) and THF (3 mL) at rt under an atmosphere of $N_2$ was added HBTU (118 mg, 0.31 mmol), $Et_3N$ (0.1 mL) and NMM (0.1 mL). The mixture was stirred

449 at rt for 16 h, then diluted with H₂O (10 mL) and extracted with EtOAc (30 mL×3). The combined organic layers were washed with brine (30 mL×2), dried over Na₂SO₄, filtered and the filtrate was concentrated under reduced pressure. The residue was purified by column chromatography on silica gel (DCM/MeOH) and washed with CH₃CN to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-11-(3-tridecylbicyclo[1.1.1]pentan-1-yl)undecanamide (15.3 mg, 15.7%). LC/MS: mass calcd. for $C_{53}H_{101}NO_9$: 895.75, found: 918.75 [M+Na]⁺; ¹H NMR (400 MHz, CD₃OD) δ 4.17 (d, J=6.8, 4.2 Hz, 1H), 3.50-3.90 (m, 10H), 2.22 (t, J=7.5 Hz, 2H), 1.64-1.57 (m, 6H), 1.43 (s, 6H), 1.29-1.41 (m, 62H), 0.88-0.91 (m, 6H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-17-(oxetan-3-yl)heptadecanamide (hydroxymethyl)tetrahydro-2H-pyran-2-yl)oxy)octadecan-2-yl)-17-(oxetan-3-yl)heptadecanamide

450

Step 1: Synthesis of (E)-22-(3-fluorobicyclo[1.1.1]pentan-1-yl)docos-21-enoic acid Prepared in a manner similar to 17-(3-fluorobicyclo[1.1.1]pentan-1-yl)heptadec-16-enoic and purified by column chromatography on silica gel (PE/EtOAc 1:1) to give 17-(oxetan-3-yl)heptadec-16-enoic acid (60 mg, 37%) as a solid. LC/MS: mass calcd. for $C_{20}H_{36}O_3$: 324, found: 323 [M−H]⁻.

Step 2: Synthesis of 22-(3-fluorobicyclo[1.1.1]pentan-1-yl)docosanoic acid

Prepared in a similar manner to 17-(3-fluorobicyclo[1.1.1]pentan-1-yl)heptadecanoic acid to give 17-(oxetan-3-yl)heptadecanoic acid (60 mg, 99%) as a solid. LC/MS: mass calcd. for $C_{20}H_{38}O_3$: 326, found: 325 [M−H]⁻.

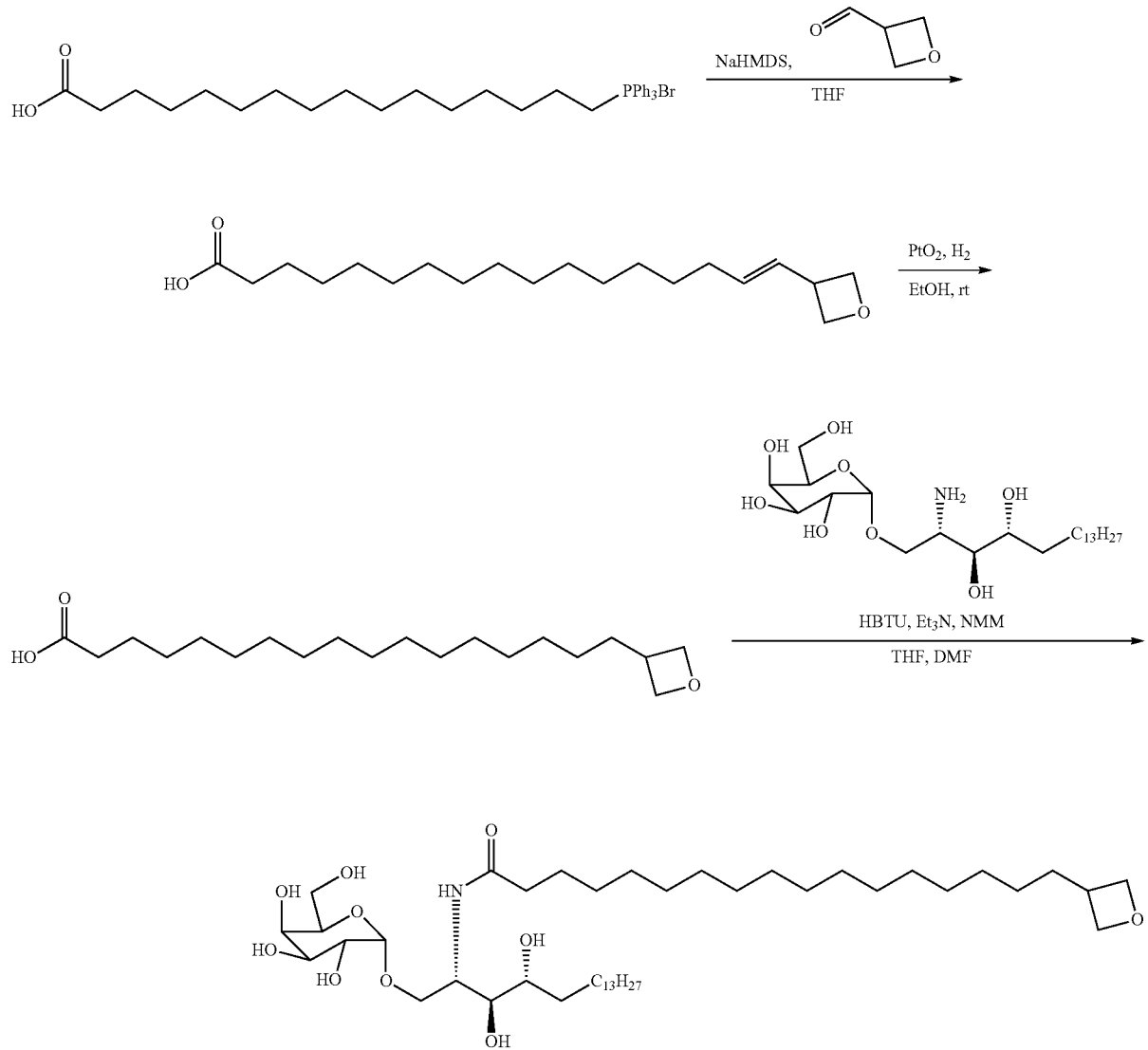

Step 3: Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-22-{3-fluorobicyclo[1.1.1]pentan-1-yl}docosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, except DMF/THF was used as solvent. Purified by column chromatography on silica gel (DCM/MeOH) and washed with $CH_3CN$ to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-17-(oxetan-3-yl)heptadecanamide (17.5 mg, 15%) as a solid. LC/MS: mass calcd. for $C_{44}H_{85}NO_{10}$: 787.62, found: 810.55 $[M+Na]^+$; $^1H$ NMR (400 MHZ, $CD_3OD$) δ 4.81 (dd, J=7.8, 5.8 Hz, 2H), 4.39 (t, J=6.1 Hz, 2H), 4.20 (q, J=4.6 Hz, 1H), 3.93-3.81 (m, 3H), 3.85-3.60 (m, 6H), 3.57 (t, J=7.4 Hz, 1H), 3.07-2.95 (m, 1H), 2.24 (t, J=7.5 Hz, 2H), 1.58-1.74 (m, 6H), 1.26-1.40 (m, 50H), 0.92 (t, J=6.7 Hz, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-21-(oxetan-3-yl)henicosanamide Step 1: Synthesis of 21-(oxetan-3-yl)henicos-20-enoic acid Prepared in a manner similar to 23-(3-fluorobicyclo[1.1.1]pentan-1-yl)tricos-22-enoic acid purified by column chromatography on silica gel (PE/EtOAc 2:1) to give 21-(oxetan-3-yl)henicos-20-enoic acid (50 mg, 29%) as a solid. LC/MS: mass calcd. for $C_{24}H_{44}O_3$: 380.33, found: 379 $[M-H]^-$.

Step 2: Synthesis of 21-(oxetan-3-yl)henicosanoic acid

Prepared in a similar manner to 23-(3-fluorobicyclo[1.1.1]pentan-1-yl)tricosanoic acid to give 21-(oxetan-3-yl)henicosanoic acid (50 mg, 90%) as a solid. LC/MS: mass calcd. for $C_{24}H_{46}O_3$: 382.34, found: 381 $[M-H]^-$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-21-(oxetan-3-yl)henicosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, except DMF/THF was used as

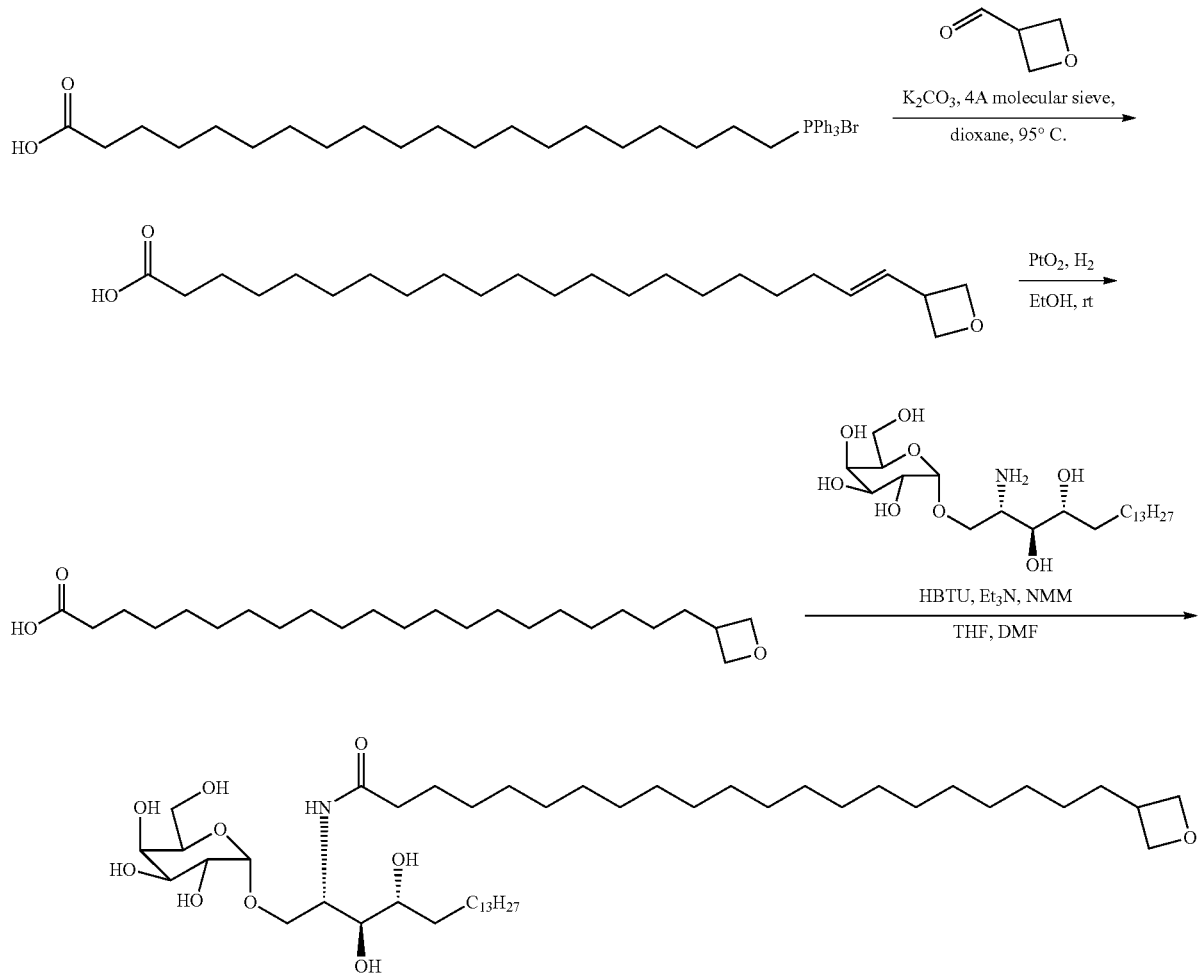

solvent. Purified by column chromatography on silica gel (DCM/MeOH) and washed with $CH_3CN$ to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-21-(oxetan-3-yl)henicosanamide (5 mg, 4.4%) as a solid. LC/MS: mass calcd. for $C_{48}H_{93}NO_{10}$: 843.68, found: 866.65 [M+Na]$^+$; $^1$H NMR (300 MHZ, $CD_3OD$) δ 4.81 (dd, J=7.8, 5.8 Hz, 2H), 4.39 (t, J=6.1 Hz, 2H), 4.20 (d, J=6.0 Hz, 1H), 3.60-3.93 (m, 9H), 2.24 (t, J=7.5 Hz, 2H), 1.57-1.79 (m, 6H), 1.13-1.38 (m, 60H), 0.87-0.93 (m, 3H).

Synthesis of N-((2S,3S,4R)-3,4-dihydroxy-1-(((2S, 3R,4S,5R,6R)-3,4,5-trihydroxy-6-(hydroxymethyl) tetrahydro-2H-pyran-2-yl)oxy)octadecan-2-yl)-23-(oxetan-3-yl)tricosanamide

Step 2: Synthesis of 23-(oxetan-3-yl)tricosanoic acid

Prepared in a similar manner to 23-(3-fluorobicyclo[1.1.1]pentan-1-yl)tricosanoic acid to give 23-(oxetan-3-yl)tricosanoic acid (55 mg, 91%) as a solid. LC/MS: mass calcd. for $C_{26}H_{50}O_3$: 410, found: 409 [M–H]$^-$.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-23-(oxetan-3-yl)tricosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-meth-

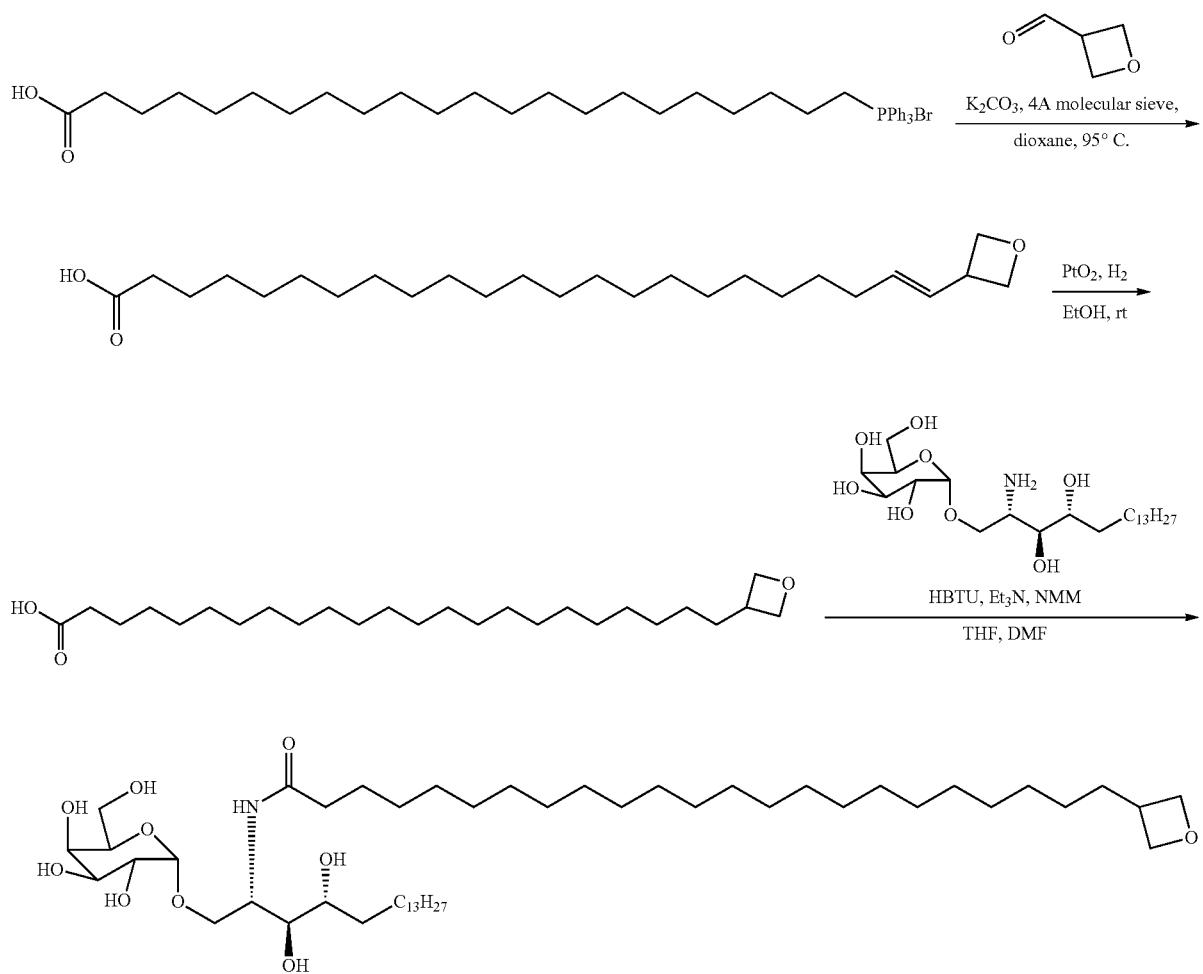

Step 1: Synthesis of 23-(oxetan-3-yl)tricos-22-enoic acid

Prepared in a manner similar to 23-(3-fluorobicyclo[1.1.1]pentan-1-yl)tricos-22-enoic acid purified by column chromatography on silica gel (PE/EtOAc 2:1) to give 23-(oxetan-3-yl)tricos-22-enoic acid (60 mg, 33%) as a solid. LC/MS: mass calcd. for $C_{26}H_{48}O_3$: 408.36: 408, found: 407 [M–H]$^-$.

yloxetan-3-yl)undecanamide, except DMF/THF was used as solvent. Purified by column chromatography on silica gel (DCM/MeOH) and washed with $CH_3CN$ to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-23-(oxetan-3-yl)tricosanamide (5.2 mg, 4.3%) as a solid. LC/MS: mass calcd. for $C_{50}H_{97}NO_{10}$: 871.71, found: 894.60 [M+Na]$^+$; $^1$H NMR (400 MHZ, $CD_3OD$) δ 4.81 (dd, J=7.8, 5.8 Hz, 2H), 4.39 (t, J=6.1 Hz, 2H), 4.20 (d, J=6.8 Hz, 1H), 3.56-3.87 (m, 10H), 2.24 (t, J=7.5 Hz, 2H), 1.54-1.71 (m, 6H), 1.24-1.38 (m, 64H), 0.85-0.96 (m, 3H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-22-(oxetan-3-yl)docosanamide

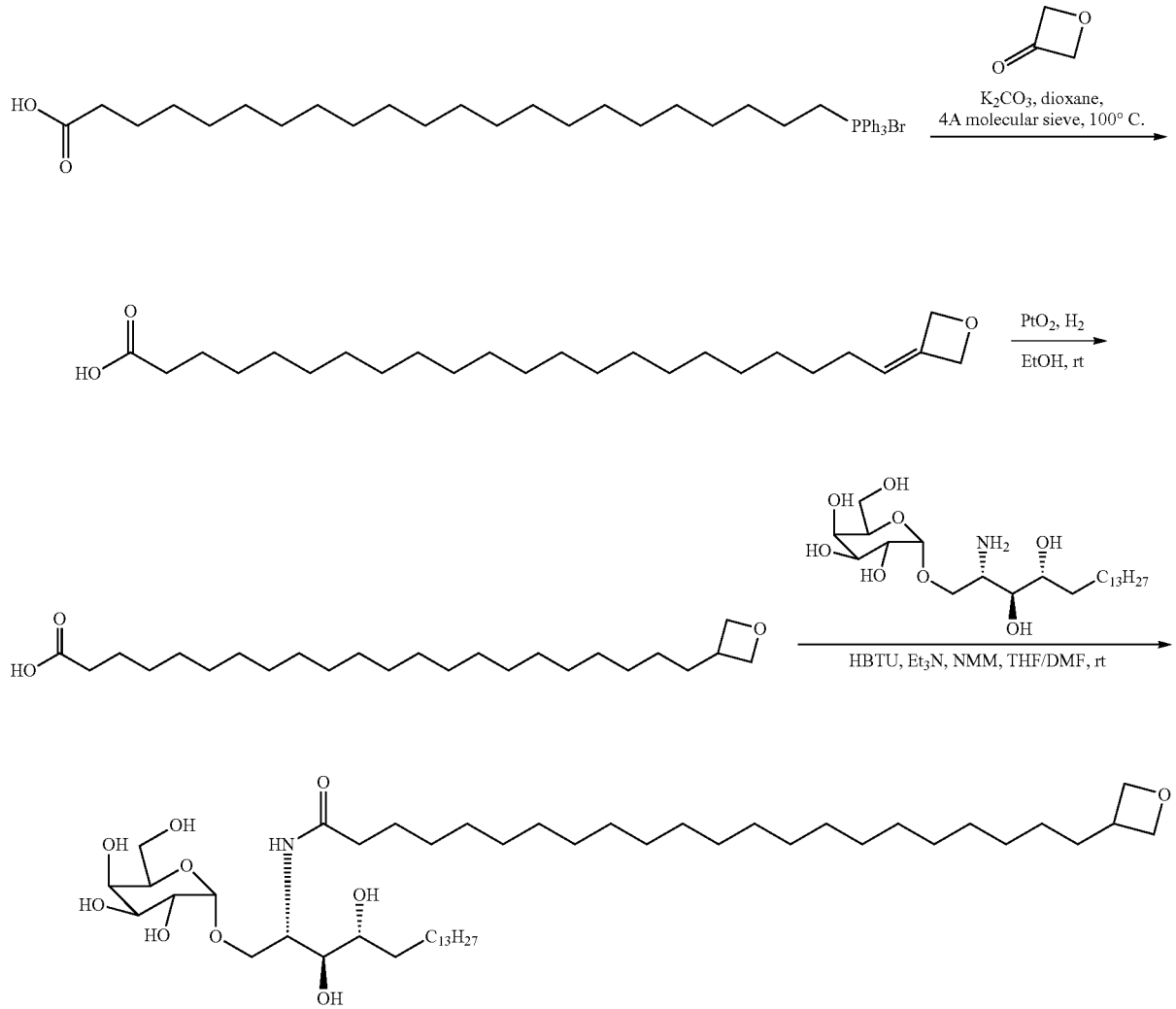

Step 1: Synthesis of 22-(oxetan-3-ylidene)docosanoic acid

Prepared in a manner similar to 23-(3-fluorobicyclo[1.1.1]pentan-1-yl)tricos-22-enoic acid purified by column chromatography on silica gel (PE/EtOAc 2:1) to give 22-(oxetan-3-ylidene)docosanoic acid (60 mg, 35%) as a solid. LC/MS: mass calcd. for $C_{25}H_{46}O_3$: 394, found: 393 [M–H]⁻.

Step 2: Synthesis of 22-(oxetan-3-yl)docosanoic acid

Prepared in a similar manner to 23-(3-fluorobicyclo[1.1.1]pentan-1-yl)tricosanoic acid to give 22-(oxetan-3-yl)docosanoic acid (55 mg, 91%) as a solid. LC/MS: mass calcd. for $C_{25}H_{48}O_3$: 396.36, found: 395 [M–H]⁻.

Step 3: Synthesis of N-((2S,3S,4R)-3,4-dihydroxy-1-(((2S,3R,4S,5R,6R)-3,4,5-trihydroxy-6-(hydroxymethyl)tetrahydro-2l-pyran-2-yl)oxy)octadecan-2-yl)-22-(oxetan-3-yl)docosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, except DMF/MIF was used as solvent. Purified by column chromatography on silica gel (DCM/MeOH) and washed with $CH_3CN$ to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-22-(oxetan-3-yl)docosanamide (6.5 mg, 5.2%) as a solid. LC/MS: mass calcd. for $C_{49}H_{95}NO_{10}$: 857.70, found: 880.65 [M+Na]⁺; ¹H NMR (400 MHz, $CD_3OD$) δ 4.80-4.84 (m, 2H), 4.81 (dd, J=7.8, 5.9 Hz, 2H), 4.16-4.22 (m, 1H), 3.54-3.96 (m, 10H), 4.14-4.28 (m, 1H), 1.54-1.73 (m, 6H), 1.28-1.41 (m, 61H), 0.86-0.99 (m, 3H).

Synthesis of N-((2S,3S,4R)-3,4-dihydroxy-1-(((2S, 3R,4S,5R,6R)-3,4,5-trihydroxy-6-(hydroxymethyl) tetrahydro-2H-pyran-2-yl)oxy)octadecan-2-yl)-24- (oxetan-3-yl)tetracosanamide

Step 3: Synthesis of 24-(oxetan-3-yl)tetracosanoic acid

Prepared in a similar manner to 23-(3-fluorobicyclo [1.1.1]pentan-1-yl)tricosanoic acid to give 24-(oxetan-3-yl)

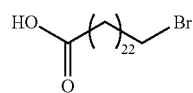 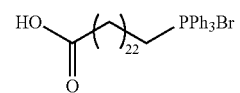 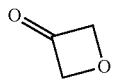

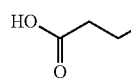 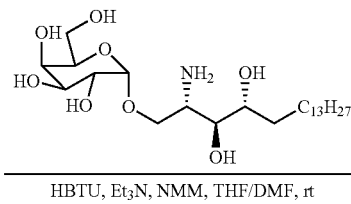

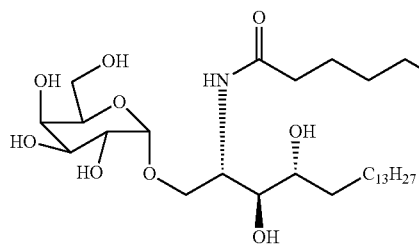

Step 1: Synthesis of (23-carboxytricosyl)triphenylphosphonium bromide

To a mixture of 24-bromotetracosanoic acid (0.6 g, 1.3 mmol) in $CH_3CN$ (10 mL) under an atmosphere of $N_2$ was added triphenylphosphine (0.34 g, 1.3 mmol, 1.0 equiv). The mixture was heated to 90° C. and stirred for 2 days, then concentrated under reduced pressure and the residue was purified by preparative-HPLC ($H_2O$ 5% HCl/$CH_3OH$ 5%-100%) to give (23-carboxytricosyl)triphenylphosphonium bromide (0.6 g, 70%) as a solid.

Step 2: Synthesis of 24-(oxetan-3-ylidene)tetracosanoic acid

Prepared in a manner similar to 23-(3-fluorobicyclo [1.1.1]pentan-1-yl)tricos-22-enoic acid purified by column chromatography on silica gel (PE/EtOAc 2:1) to give 24-(oxetan-3-ylidene)tetracosanoic acid (50 mg, 42%) as a solid. LC/MS: mass calcd. for $C_{27}H_{50}O_3$: 422, found: 421 [M–H]$^-$.

tetracosanoic acid (50 mg, 100%) as a solid. LC/MS: mass calcd. for $C_{27}H_{52}O_3$: 424, found: 423 [M–H]$^-$.

Step 4: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-24-(oxetan-3-yl)tetracosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, except DMF/THF was used as solvent. Purified by column chromatography on silica gel (DCM/MeOH) and washed with $CH_3CN$ to give N-((2S,3S, 4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-24-(oxetan-3-yl)tetracosanamide (7 mg, 6.7%) as a solid. LC/MS: mass calcd. for $C_{51}H_{99}NO_{10}$: 885.73, found: 908.70 [M+Na]$^+$; $^1$H NMR (400 MHZ, $CD_3OD$) δ 4.79-4.83 (m, 2H), 4.37-4.42 (m, 2H), 4.17-4.21 (m, 1H), 3.56-3.91 (m, 10H), 2.21-2.28 (m, 2H), 1.54-1.74 (m, 6H), 1.30-1.38 (m, 65H), 0.90-0.93 (m, 3H).

Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-25-(oxetan-3-yl)pentacosanamide

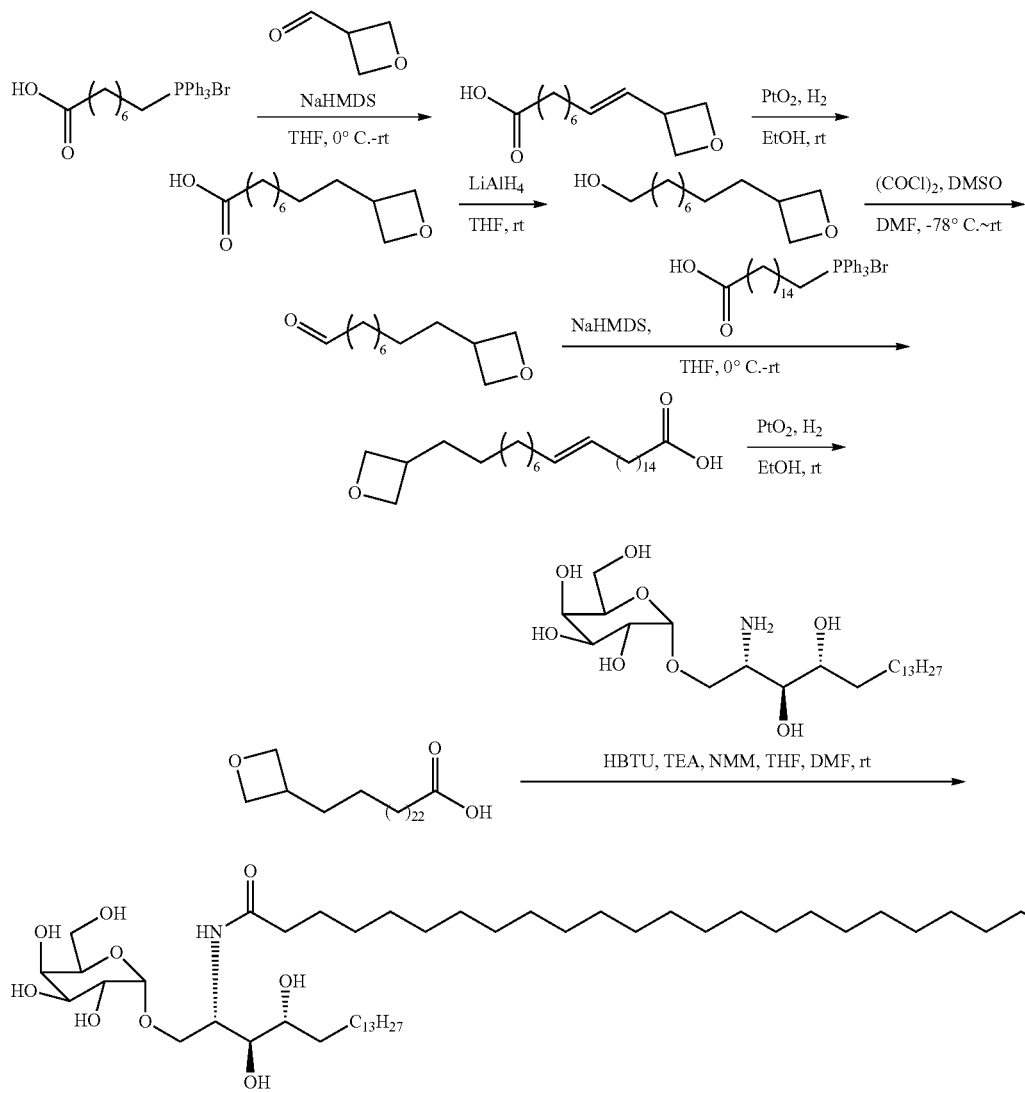

Step 1: Synthesis of 9-(oxetan-3-yl)non-8-enoic Acid

Prepared in a manner similar to 17-(3-fluorobicyclo[1.1.1]pentan-1-yl)heptadec-16-enoic purified by column chromatography on silica gel (PE/EtOAc 1:1) to give 9-(oxetan-3-yl)non-8-enoic acid (1.4 g, 58%) as a solid. LC/MS: mass calcd. for $C_{12}H_{20}O_3$: 212, found: 211 [M–H]+.

Step 2: Synthesis of 9-(oxetan-3-yl)nonanoic Acid

Prepared in a similar manner to 17-(3-fluorobicyclo[1.1.1]pentan-1-yl)heptadecanoic acid to give 9-(oxetan-3-yl)nonanoic acid (1.2 g, 100%) as a solid. LC/MS: mass calcd. for $C_{12}H_{22}O_3$: 214, found: 213 [M+H]+.

Step 3: Synthesis of 9-(oxetan-3-yl)nonan-1-ol

Prepared in a manner similar to 8-{3-fluorobicyclo[1.1.1]pentan-1-yl}octan-1-ol and purified by column chromatography on silica gel (PE/EtOAc 2:1) to give 9-(oxetan-3-yl)nonan-1-ol (500 mg, 76%) as an oil.

Step 4: Synthesis of 9-(oxetan-3-yl)nonanal

Prepared in a manner similar to 8-(3-fluorobicyclo[1.1.1]pentan-1-yl)octanal to give 9-(oxetan-3-yl)nonanal (300 mg, 61%) as an oil, that was used directly in the next step, without further purification.

Step 5: Synthesis of 25-(oxetan-3-yl)pentacos-16-enoic Acid

Prepared in a manner similar to 2443-fluorobicyclo[1.1.1]pentan-1-yl)tetracos-16-enoic acid and purified by column chromatography on silica gel (PE/EtOAc 1:1) to give 25-

(oxetan-3-yl)pentacos-16-enoic acid (230 mg, 35%) as a solid. LC/MS: mass calcd. for $C_{28}H_{52}O_3$: 436, found: 435 [M+H]$^+$.

Step 6: Synthesis of 25-(oxetan-3-yl)pentacosanoic Acid

Prepared in a manner similar to 23-(3-fluorobicyclo[1.1.1]pentan-1-yl)tricosanoic acid give 25-(oxetan-3-yl)pentacosanoic acid (230 mg, 100%) as a solid. LC/MS: mass calcd. for $C_{28}H_{54}O_3$: 438, found: 437 [M+H]$^+$.

Step 7: Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-25-(oxetan-3-yl)pentacosanamide 6-(hydroxymethyl)oxan-2-yl]oxy}octadecan-2-yl]-25-(oxetan-3-yl)pentacosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide, except DMF/THF was used as solvent. Purified by column chromatography on silica gel (DCM/MeOH 9:1) and washed with $CH_3CN$ to give N-[(2S, 3S,4R)-3,4-dihydroxy-1-{[(2S,3R,4S,5R,6R)-3,4,5-trihydroxy-6-(hydroxymethyl)oxan-2-yl]oxy} octadecan-2-yl]-25-(oxetan-3-yl)pentacosanamide (28.4 mg, 13%). LC/MS: mass calcd. for $C_{52}H_{101}NO_{10}$: 899.74, found: 922.80 [M+Na]$^+$; $^1$H NMR (400 MHZ, $CD_3OD$) δ 4.79 (dd, J=7.8, 5.8 Hz, 2H), 4.36 (t, J=6.1 Hz, 2H), 4.08-4.24 (m, 1H), 3.54-3.87 (m, 10H), 2.22 (t, J=7.4 Hz, 2H), 1.53-1.72 (m, 5H), 1.27-1.37 (m, 68H), 0.88-0.92 (m, 3H).

Synthesis of N-((2S,3S,4R)-3,4-dihydroxy-1-(((2S, 3R,4S,5R,6R)-3,4,5-trihydroxy-6-(hydroxymethyl)tetrahydro-2H-pyran-2-yl)oxy)octadecan-2-yl)-7-(dimethyl(octadecyl)silyl)heptanamide

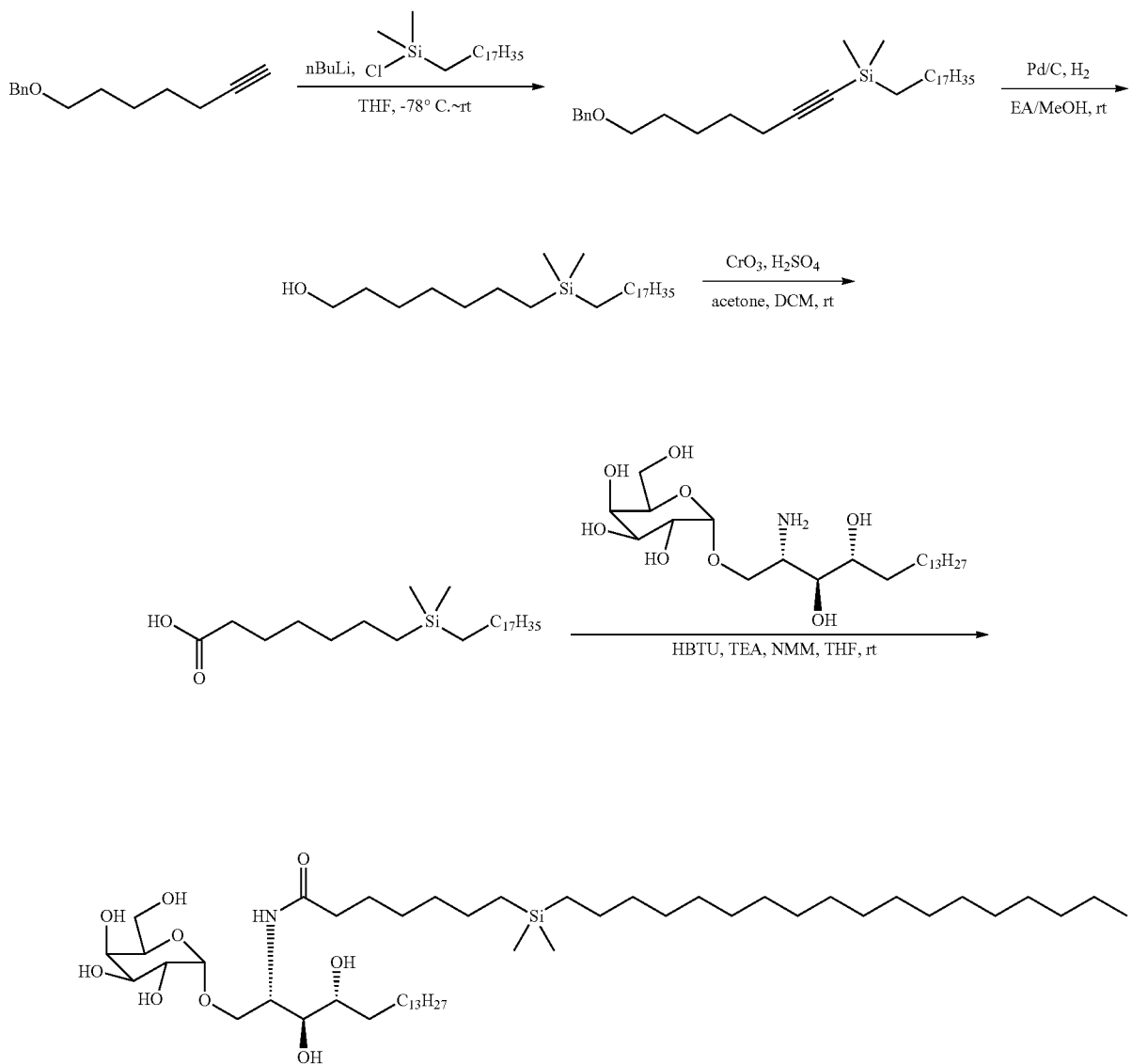

Step 1: Synthesis of (7-(benzyloxy)hept-1-yn-1-yl)dimethyl(octadecyl)silane

To a mixture of ((hept-6-yn-1-yloxy)methyl)benzene (1.0 g, 4.9 mmol) in THF (20 mL) at −78° C. under an atmosphere of $N_2$ was added n-BuLi, 2.5 M, in hexane (2.2 mL, 5.4 mmol). The mixture was stirred at -78° ° C. for 0.5 h, then chlorodimethyl(octadecyl)silane (1.7 g, 4.9 mmol) was added and the mixture was warmed to rt and stirred overnight. $H_2O$ (30 mL) was added and the mixture was extracted with EtOAc (50 mL×3). The combined organic layers were washed with brine (30 mL), dried over anhydrous $Na_2SO_4$, filtered and the filtrate was concentrated under reduced pressure. The residue was purified by column chromatography on silica gel (PE/EtOAc 3:1) to give (7-(benzyloxy)hept-1-yn-1-yl)dimethyl(octadecyl)silane (1.0 g, 39%) as an oil.

Step 2: Synthesis of 7-(dimethyl(octadecyl)silyl)heptan-1-ol

A mixture of [7-benzyloxy)hept-1-yn-1-yl]dimethyloctadecylsilane (1.0 g, 1.95 mmol), Pd/C (100 mg), MeOH (6 mL) and EtOAc (18 mL) was stirred at rt under an atmosphere of $H_2$ (1 atm) for 16 h. The mixture was filtered through a pad of Celite and the filter cake was washed with MeOH. The filtrate was concentrated under reduced pressure to give 7-(dimethyl(octadecyl)silyl)heptan-1-ol (300 mg, 36%) as a solid.

Step 3: Synthesis of 7-[dimethyl(octadecyl)silyl]heptanoic Acid

A mixture of $CrO_3$ (281 mg, 2.8 mmol), $H2SO_4$ (1 mL) and $H_2O$ (2 mL) under an atmosphere of $N_2$ was stirred at rt for 10 min, then 7-[dimethyl(octadecyl)silyl]heptan-1-ol (300 mg, 0.7 mmol), acetone (24 mL) and DCM (8 mL) were added, and the mixture was stirred at rt overnight. The solvent was removed under reduced pressure, $H_2O$ (30 mL) was added and the mixture was extracted with DCM (50 mL×4). The combined organic layers were washed with brine (30×3 mL), dried over $Na_2SO_4$, filtered and the filtrate was concentrated under reduced pressure. The residue was purified by column chromatography on silica gel (PE/EtOAc 1:1) to give 7-[dimethyl(octadecyl)silyl]heptanoic acid (160 mg, 52%) as a solid.

Step 4: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-7-(dimethyl(octadecyl)silyl)heptanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide. Purified by column chromatography on silica gel (DCM/MeOH 9:1) and washed with $CH_3CN$ to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-7-(dimethyl(octadecyl)silyl)heptanamide (9 mg, 9%). LC/MS: mass calcd. for $C_{51}H_{103}NO_9Si$: 901.74, found: 924.75 [M+Na]$^+$, $^1H$ NMR (300 MHz, $CD_3OD$) δ 4.20 (d, J=6.2 Hz, 1H), 3.56-3.93 (m, 10H), 2.24 (t, J=7.5 Hz, 2H), 1.53-1.70 (m, 5H), 1.19-1.41 (m, 61H), 0.90-0.94 (m, 6H), 0.49-0.55 (m, 4H), 0.01 (s, 6H).

Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-8-(heptadecyldimethylsilyl)octanamide

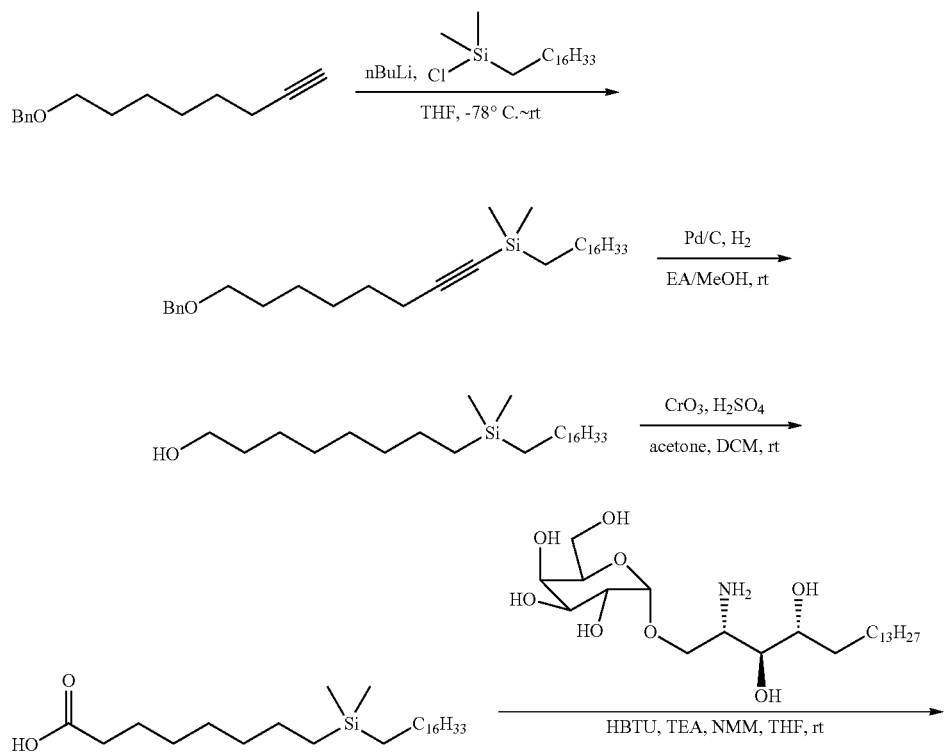

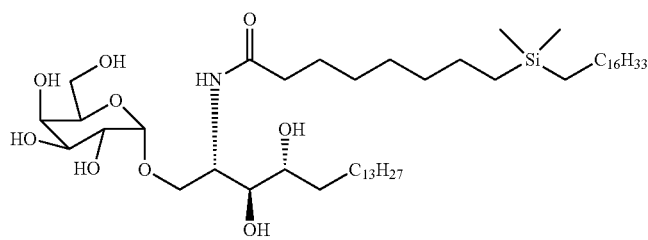

Step 1: Synthesis of [8-(benzyloxy)oct-1-yn-1-yl](heptadecyl)dimethylsilane

Prepared in a similar manner to (7-(benzyloxy)hept-1-yn-1-yl)dimethyl(octadecyl)silane and purified by column chromatography on silica gel (PE/EtOAc 3:1) to give [8-(benzyloxy)oct-1-yn-1-yl](heptadecyl)dimethylsilane (800 mg, 38%) as an oil.

Step 2: Synthesis of 8-(heptadecyldimethylsilyl)octan-1-ol

Prepared in a manner similar to 7-(dimethyl(octadecyl)silyl)heptan-1-ol to give 8-(heptadecyldimethylsilyl)octan-1-ol (150 mg, 36%) as a solid.

Step 3: Synthesis of 8-(heptadecyldimethylsilyl)octanoic acid

Prepare in a manner similar to 7-[dimethyl(octadecyl)silyl]heptanoic acid. Purified by column chromatography on silica gel (PE/EtOAc 1:1) to give 8-(heptadecyldimethylsilyl)octanoic acid (80 mg, 52%) as a solid.

Step 4: Synthesis of N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-8-(heptadecyldimethylsilyl)octanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-11-(3-methyloxetan-3-yl)undecanamide. Purified by column chromatography on silica gel (DCM/MeOH 9:1) and washed with CH$_3$CN to give N-[(2S,3S,4R)-3,4-dihydroxy-1-{[(2S,3R,4S,5R,6R)-3,4,5-trihydroxy-6-(hydroxymethyl)oxan-2-yl]oxy} octadecan-2-yl]-8-(heptadecyldimethylsilyl)octanamide (11.9 mg, 9.0%). LC/MS: mass calcd. for C$_{51}$H$_{103}$NO$_9$Si: 901.74, found: 924.85 [M+Na]$^+$; $^1$H NMR (400 MHZ, CD$_3$OD) δ 4.19 (dt, J=6.9, 4.4 Hz, 1H), 3.53-3.93 (m, 10H), 2.24 (t, J=7.5 Hz, 2H), 1.56-1.68 (m, 5H), 1.28-1.44 (m, 61H), 0.90-0.94 (m, 6H), 0.51-0.55 (m, 4H), 0.01 (s, 6H).

Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-24-(trimethylsilyl)tetracosanamide

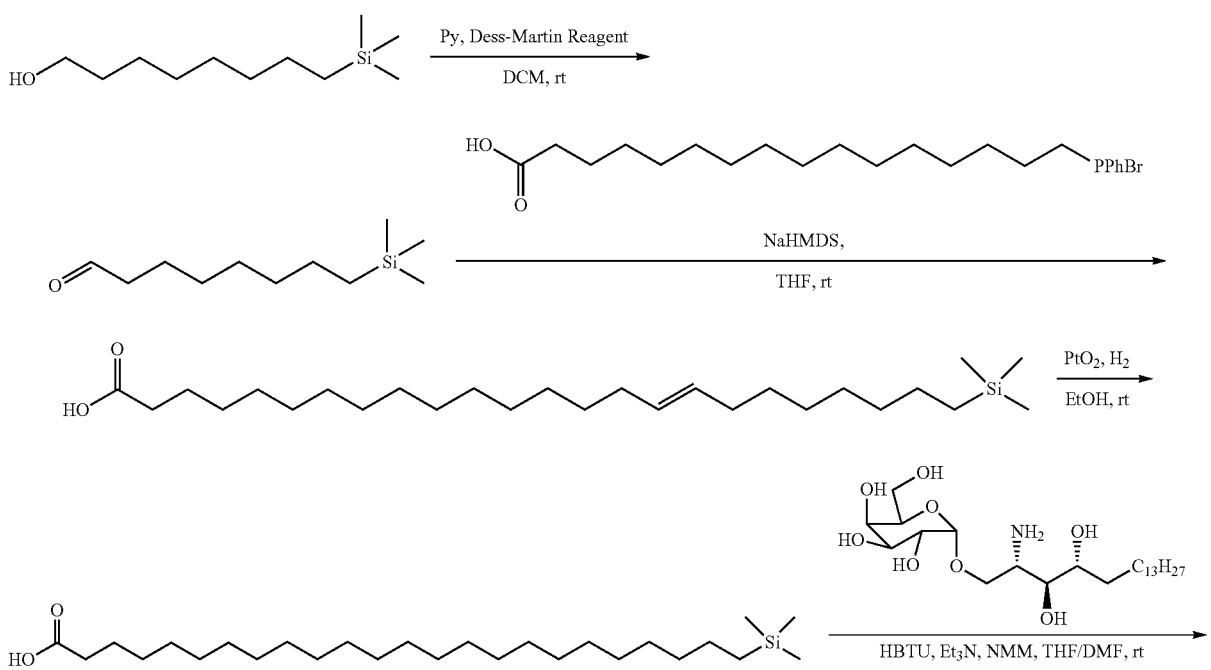

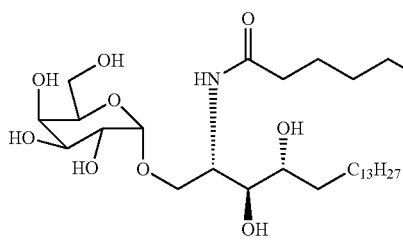

Step 1: Synthesis of 8-(trimethylsilyl)octanal

To a mixture of 8-(trimethylsilyl)octan-1-ol [CAS No: 473844-91-6] (600 mg, 2.96 mmol) and pyridine (467 mg, 5.93 mmol) in DCM (20 mL) was added Dess-Martin periodinane (1.88 g, 4.44 mmol). The mixture was stirred at rt for 3 h, then purified directly by column chromatography on silica gel (PE/EtOAc 5:1) to give 8-(trimethylsilyl) octanal (450 mg, 76%) as an oil.

Step 2: Synthesis of 24-(trimethylsilyl)tetracos-16-enoic acid

To a mixture of (15-carboxypentadecyl)triphenylphosphonium bromide (995 mg, 2.24 mmol), THF (10 mL) at 0° C. under an atmosphere of $N_2$ was added 2 M NaHMDS (2.48 mL, 4.94 mmol). The mixture was warmed to rt and stirred for 1 h, then 8-(trimethylsilyl)octanal (450 mg, 2.24 mmol) was added and the mixture was stirred overnight at rt, then acidified to pH~6 with 1N HCl. The mixture was extracted with EtOAc (3×20 mL), the combined organic layers were washed with brine (50 mL), dried over anhydrous $Na_2SO_4$, filtered and the filtrate was concentrated under reduced pressure. The residue was purified by column chromatography on silica gel (PE/EtOAc 1:1) to give 24-(trimethylsilyl)tetracos-16-enoic acid (100 mg, 10%) as a solid. $^1$H NMR (400 MHz, $CDCl_3$) δ 5.33-5.43 (m, 2H), 2.37 (t, J=7.5 Hz, 2H), 2.04 (q, J=6.4 Hz, 4H), 1.65 (q, J=7.3 Hz, 2H), 1.29 (d, J=10.0 Hz, 32H), 1.24 (s, 2H), 0.53-0.45 (m, 2H), 0.09 (s, 9H).

Step 3: Synthesis of 24-(trimethylsilyl)tetracosanoic Acid

A mixture of 24-(trimethylsilyl)tetracos-16-enoic acid (100 mg, 0.22 mmol). $PtO_2$ (2.5 mg) and EtOH (30 mL) were stirred under an atmosphere of $H_2$ (balloon) for 1 h, then filtered through a pad of Celite and the filtrate was concentrated under reduced pressure to give 24-(trimethylsilyl)tetracosanoic acid (100 mg, 100%) as a solid. $^1$H NMR (400 MHz, $CDCl_3$) δ 2.23-2.36 (m, 2H), 1.55-1.60 (m, 2H), 1.27-1.32 (m, 40H), 0.48-0.51 (m, 2H), 0.01 (s, 9H).

Step 4: Synthesis of N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-24-(trimethylsilyl)tetracosanamide Prepared in a manner similar to N-[(2S,3S,4R)-3,4-dihydroxy-1-{[(2S,3R,4S,5R,6R)-3,4,5-trihydroxy-6-(hydroxymethyl)oxan-2-yl]oxy}octadecan-2-yl]-11-(3-methyloxetan-3-yl)undecanamide, except DMF/THF was used as solvent. Purified by column chromatography on silica gel (DCM/MeOH) and washed with $CH_3CN$ to give N-((2S,3S,4R)-3,4-dihydroxy-1-(((2S,3R,4S,5R,6R)-3,4,5-trihydroxy-6-(hydroxymethyl)tetrahydro-2H-pyran-2-yl)oxy)octadecan-2-yl)-24-(trimethylsilyl)tetracosanamide (4.1 mg, 2.7%). LC/MS: mass calcd. for $C_{51}H_{103}NO_9Si$: 901.74, found: 924.80 [M+Na]$^+$; $^1$H NMR (300 MHz, $CD_3OD$) δ 4.17 (d, J=6.2 Hz, 1H), 3.54-3.93 (m, 10H), 2.22 (t, J=7.4 Hz, 2H), 1.50-1.69 (m, 6H), 1.26-1.39 (m, 62H), 0.88 (t, J=8.8, 7.2 Hz, 3H), 0.45-0.53 (m, 2H), 0.01 (s, 9H).

Synthesis of 1-allyl-4-((2S,3S,4R)-3,4-bis(benzyloxy)-1-(((2S,3R,4S,5S,6R),3,4,5-tris(benzyloxy)-6-((benzyloxy)methyl)tetrahydro-2H-pyran-2-yl)oxy)octadecan-2-yl)-1,4-dihydro-5H-tetrazol-5-one

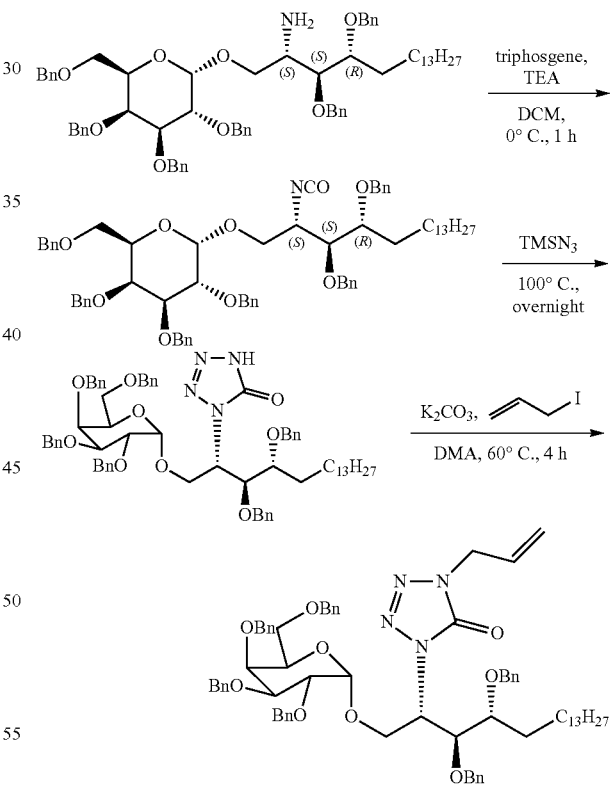

Step 1: Synthesis of (2R,3S,4S,5R,6S)-3,4,5-tris(benzyloxy)-2-((benzyloxy)methyl)-6-(((2S,3S,4R)-3,4-bis(benzyloxy)-2-isocyanatooctadecyl)oxy)tetrahydro-2H-pyran To a mixture of (2S,3S,4R)-3,4-bis(benzyloxy)-1-(((2S,3R,4S,5S,6R)-3,4,5-tris(benzyloxy)-6-((benzyloxy)methyl) tetrahydro-2H-pyran-2-yl)oxy)octadecan-2-amine (700 mg, 0.68 mmol) and Et$_3$N (84 mg, 0.83 mmol) in DCM (20 mL) at 0° C. was added triphosgene (224 mg, 0.75 mmol). The mixture was stirred at 0° C. for 1 h, then diluted with H$_2$O (20 mL) and extracted with DCM (3×30 mL). The combined organic layers were dried over anhydrous Na$_2$SO$_4$, filtered and the filtrate was concentrated under reduced pressure to give (2R,3S,4S,5R,6S)-3,4,5-tris(benzyloxy)-2-((benzyloxy)methyl)-6-(((2S,3S,4R)-3,4-bis(benzyloxy)-2-isocyanatooctadecyl)oxy)tetrahydro-2H-pyran (700 mg, 98%) as a solid. LC/MS: mass calcd. for C$_{67}$H$_{83}$NO$_9$: 1045.61, found: 1068.50 [M+Na]$^+$.

Step 2: Synthesis of 1-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1,4-dihydro-5H-tetrazol-5-one A mixture of (2R,3S,4S,5R,6S)-3,4,5-tris(benzyloxy)-2-((benzyloxy)methyl)-6-(((2S,3S,4R)-3,4-bis(benzyloxy)-2-isocyanatooctadecyl)oxy)tetrahydro-2H-pyran (700 mg, 0.67 mmol) and TMSN$_3$ (20 mL) was heated to 100° C., and stirred overnight. After cooling, the mixture was concentrated under the reduced pressure and the residue was purified by column chromatography on silica gel (PE/EtOAc 2:1) to give 1-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1,4-dihydro-5H-tetrazol-5-one (400 mg, 55%) as a solid. LC/MS: mass calcd. for C$_{67}$H$_{84}$N$_4$O$_9$: 1088.62, found: 1111.50 [M+Na]$^+$.

Step 3: Synthesis of 1-allyl-4-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1,4-dihydro-5H-tetrazol-S-one To a mixture of 1-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1,4-dihydro-5H-tetrazol-5-one (50 mg, 0.05 mmol), K$_2$CO$_3$ (26 mg, 0.19 mmol) and DMA (3 mL) was added 3-iodoprop-1-ene (12 mg, 0.071 mmol) in DMA (0.1 mL). The mixture was heated to 60° C., and stirred for 4 h, then diluted with EtOAc (60 mL) and the mixture washed with H$_2$O (4×15 mL), brine (2×15 mL), dried over Na$_2$SO$_4$, filtered and the filtrate was concentrated under reduced pressure to give 1-allyl-4-((2S,3S,4R)-3,4-bis(benzyloxy)-1-(((2S,3R,4S,5S,6R)-3,4,5-tris(benzyloxy)-6-((benzyloxy)methyl)tetrahydro-2H-pyran-2-yl)oxy)octadecan-2-yl)-1,4-dihydro-5H-tetrazol-5-one (30 mg, 58%) as a solid. LC/MS: mass calcd. for C$_{70}$H$_{88}$N$_4$O$_9$: 1128.66, found: 1151.55 [M+Na]$^+$.

Example 2—In Vitro Activation of Human iTCR Through a Jurkat Reporter Cell Line

In order to determine the human iTCR activation potential induced by the compounds described herein, a jurkat cell line (JiNKT) was transfected with the human iTCR, and GFP under the NFkB promoter (cell line licensed from the Medical University of Vienna). A BWS147 cell line (BWSTIM) was also transfected with CD80 and CD1d to act as the antigen-presenting cell.

Methods

DCD molecules or α-GalCer were both dissolved in DMSO at a 5 mg/mL stock solution. BWSTIM cells were loaded with DCD molecules or α-GalCer at varying concentrations for 4 hours at 37° C. at a concentration of 20 k cells/well in 200 μL of media in a u-bottom 96 well dish. BWSTIM cells were washed 2× with media, then incubated with JiNKT cells at a concentration of 80 k cells/well in a u-bottom 96 well dish Cells were co-cultured for 18 to 24 hours. The percentage of cells expressing high levels of GFP was measured through flow cytometry (after gating out the mCD45+BWSTIM cells).

Results

FIG. 1 depicts results from the activation of human iTCR study with the Jurkat reporter cell line at different concentrations of compounds DCD-101, DCD-102, DCD-103, DCD-104, DCD-105, DCD-106, DCD-108, DCD-112, DCD-113, DCD-114, DCD115, and DCD-116, DCD118, DCD-119, DCD-120, DCD-121, DCD-122, DCD-123, DCD-124, DCD-125, DCD-126, DCD-127, DCD-128, DCD-129, DCD-130, DCD-131, DCD-132, DCD-133, DCD-134, DCD-135, DCD-136, DCD-137, DCD-138, DCD-139, DCD-140, DCD-141, DCD-142, DCD-143, DCD-144, DCD-145, DCD-146, DCD-147, DCD-148, DCD-149, DCD-150, DCD-151, DCD-152, DCD-153, DCD-154, DCD-155, DCD-156, DCD-157, DCD-158, and DCD-159. Alphagalactosylceramide (α-GalCer) was also tested for comparison.

FIG. 1 shows DCD-127, DCD-141, DCD-143, DCD-144, DCD-136, DCD-133, DCD-122, DCD-155, DCD-118, DCD-121, DCD-101, DCD-138, DCD-153, DCD-119, DCD-149, DCD-150, DCD-139, DCD-125, DCD-148, DCD-103, DCD-113, DCD-106, DCD-114, DCD-151, DCD-137, DCD-128, DCD156, DCD-104, DCD-130, DCD-140, DCD-157 all had lower EC50s compared to α-GalCer.

Conclusions

Compound DCD-127 demonstrated the highest % GFP+ at the lowest concentration.

Example 3—In Vitro Activation of Mouse iTCR Through a DN3-a4.1.2 iNKT Hybridoma Cell Line In order to determine the mouse iTCR activation potential induced by the compounds described herein, a mouse iNKT hybridoma cell line (DN3.2) from the La Jolla Institute for Allergy and Immunology were used as the iNKT. The BWS147 cell line (BWSTIM) with CD80 and CD1d acted as the antigen-presenting cell.

Methods

DCD molecules or α-GalCer were both dissolved in DMSO at a 5 mg/mL stock solution. BWSTIM cells were loaded with DCD molecules or α-GalCer of varying concentrations for 4 hours at 37° C. at a concentration of 20 k cells/well in 200 μL of media in a u-bottom 96 well dish. BWSTIM cells were washed 2× with media, then incubated with DN3.2 cells at a concentration of 80 k cells/well in a u-bottom 96 well dish. Cells were co-cultured for 48 hours. Media was collected and IL-2 was measured using the CisBio HTRF ELISA detection kit.

Results

FIG. 2 depicts results from the activation of the mouse iTCR activation study with the DN3.2 reporter cell line. The amount of IL-2 secretion in response to incubation with DCD-101, DCD-102, DCD-104, DCD105, DCD-106 and α-GalCer is shown. No drug loading was also tested and is shown in FIG. 2 as well. FIG. 2 shows that when drug was loaded at a concentration of 0.01 μg/mL, each of DCD-101, DCD-102 and DCD-106 exhibited greater IL-2 secretion than α-GalCer.

Conclusions

Compounds DCD101, showed the highest IL-2 secretion at the lowest concentrations.

Example 4—Cytokine Secretion of Primary Human iNKT Cells

In order to determine the activation profile induced by the compounds described herein, primary human iNKT cells were co-cultured with drug-loaded BWSTIM cells Methods Day 0: PBMCs were isolated from human blood using the STEMCELL TECHNOLOGIES™ SepMate™ PBMC isolation system. iNKT cells were then selected using the Miltenyi NKT magnetic cell separation kit.

Day 2: DCD molecules or α-GalCer were both dissolved in DMSO at a 5 mg/mL stock solution. BWSTIM cells were fixed with mitomycin C, then loaded with 10 µg/mL of DCD molecules or α-GalCer for 4 hours at 37° C. at a concentration of 20 k cells/well in 200 µL of media in a u-bottom 96 well dish. Cells were co-cultured with 80 k 6B11+ selected primary human iNKT cells.

D4: Media was collected. Cytokines were measured using the Satorious 4 Plex kit on the iQue3 cytometer.

Results

Figure 3A:
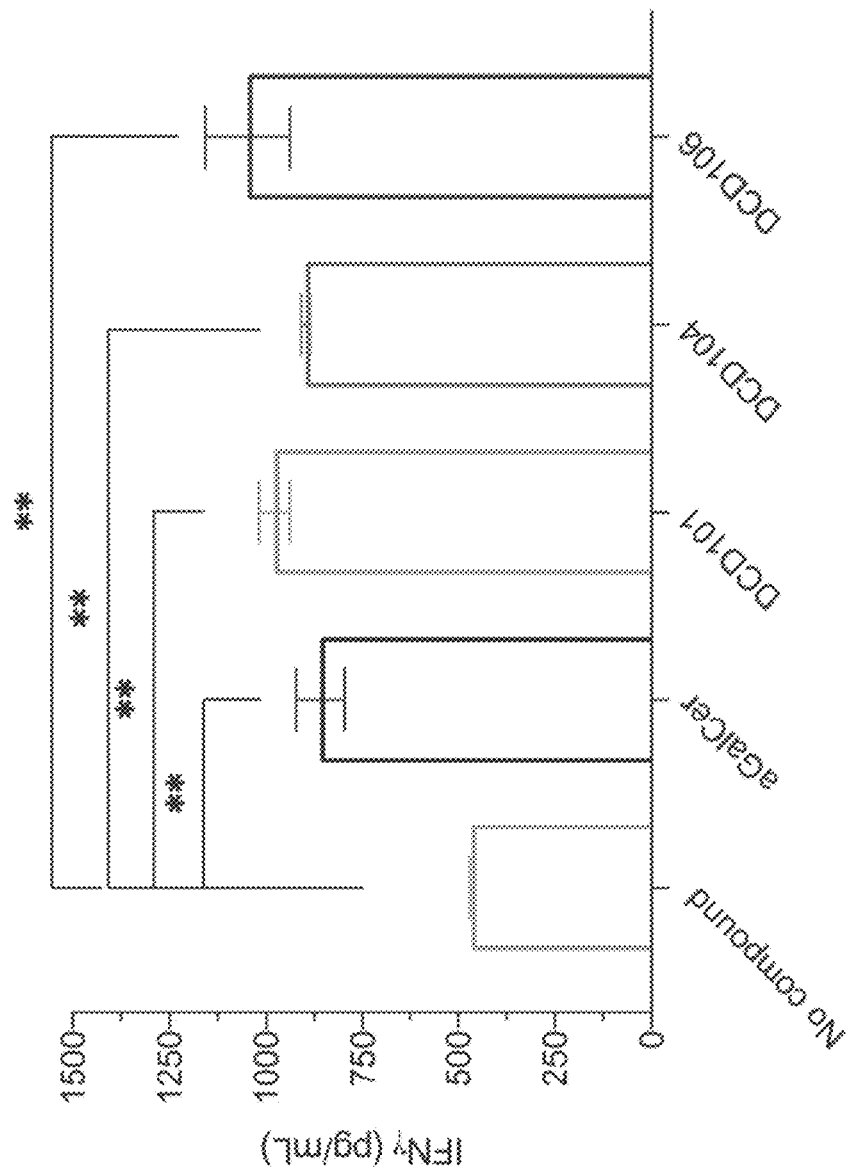
FIG. 3A depicts the secretion of the cytokine interferon gamma (IFNγ) in response to activation by compounds DCD-101, DCD-104, DCD-106 and α-GalCer.
Figure 3B:
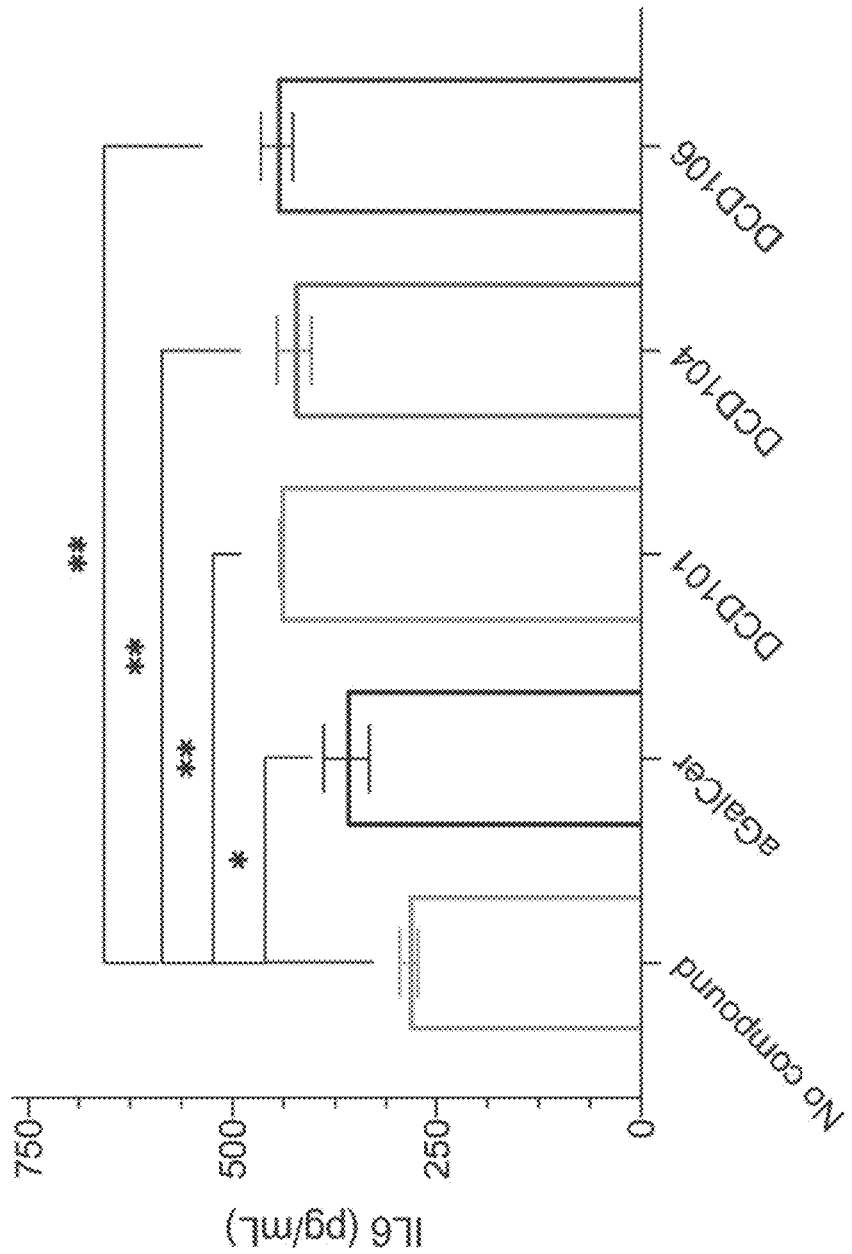
FIG. 3B depicts the secretion of the cytokine interleukin-6 (IL-6) in response to activation by compounds DCD-101, DCD-104, DCD-106 and α-GalCer.
Figure 3C:
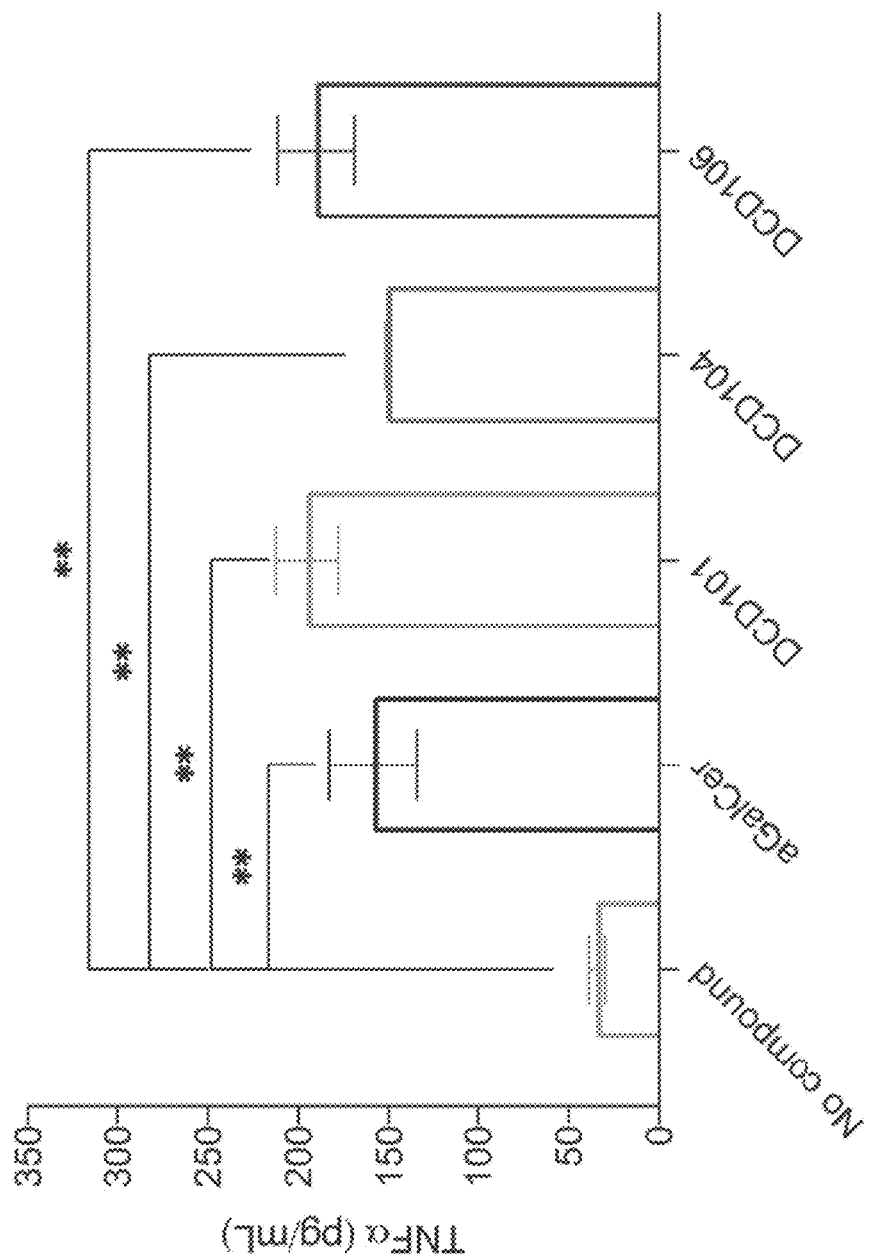
FIG. 3C depicts the secretion of the cytokine tumor necrosis factor alpha (TNFα) in response to activation by compounds DCD-101, DCD-104, DCD-106 and α-GalCer.

FIG. 3A depicts the secretion of the cytokine interferon gamma (IFNγ) in response to activation by compounds DCD-101, DCD-104, DCD-106 and α-GalCer. FIG. 3B depicts the secretion of the cytokine interleukin-6 (IL-6) in response to activation by compounds DCD-101, DCD-104, DCD-106 and α-GalCer. FIG. 3C depicts the secretion of the cytokine tumor necrosis factor alpha (TNFα) in response to activation by compounds DCD-101, DCD-104, DCD-106 and α-GalCer.

Conclusions

DCD-101, DCD-104, and DCD-106 all induce significantly higher levels of IFNγ. IL6, and TNFα compared to the no-compound control. (**p<0.01; *p<0.05)

Example 5—In Vivo IFNγ Activation and iNKT Cell Expansion in C57BL/6J Mice

In order to determine the expansion induced by the molecules described herein, molecules were injected into C57BL/6J mice. Serum IFNγ levels and the expansion of iNKT cells within splenocytes was measured 4 days post-IP injection.

Methods

Eight weeks old C57BL/6J mice were injected (I.P.) with 2 µg of α-GalCer or DCD molecules. Molecules were either dissolved in DMSO at a 5 mg/mL stock solution, or formulated into liposomes through thin-film rehydration, then extrusion through 200 nm filters. Liposome-based formulations were constructed using soy phosphatidylcholine, cholesterol, and DCD or α-GalCer in a 2.1:0.15 ratio. Twenty hours post-injection, blood was collected from the tail to measure the level of serum IFNγ using an ELISA kit from Biolegend. Four days post-injection, the mice were sacrificed and the splenocytes were isolated. The percentage of iNKT cells within the spleens was measured using flow cytometry, selecting for live cells and mouse CD1d-α-GalCer tetramer+ cells.

Results

FIG. 4A depicts the activation of immune cells, as measured by the amount of serum IFNγ using ELISA, in response to injection of the compounds DCD-101, DCD-119, DCD-123, DCD125, DCD127, DCD-128, DCD-134, DCD-142, DCD-145, DCD-146, DCD-147, DCD-148, DCD-149, DCD-150, DCD-151, DCD-152, DCD-153, DCD-154, DCD-155, DCD-156, DCD-157, DCD-158, and DCD-159 with comparison to α-GalCer twenty hours after injection.

Figure 4B:
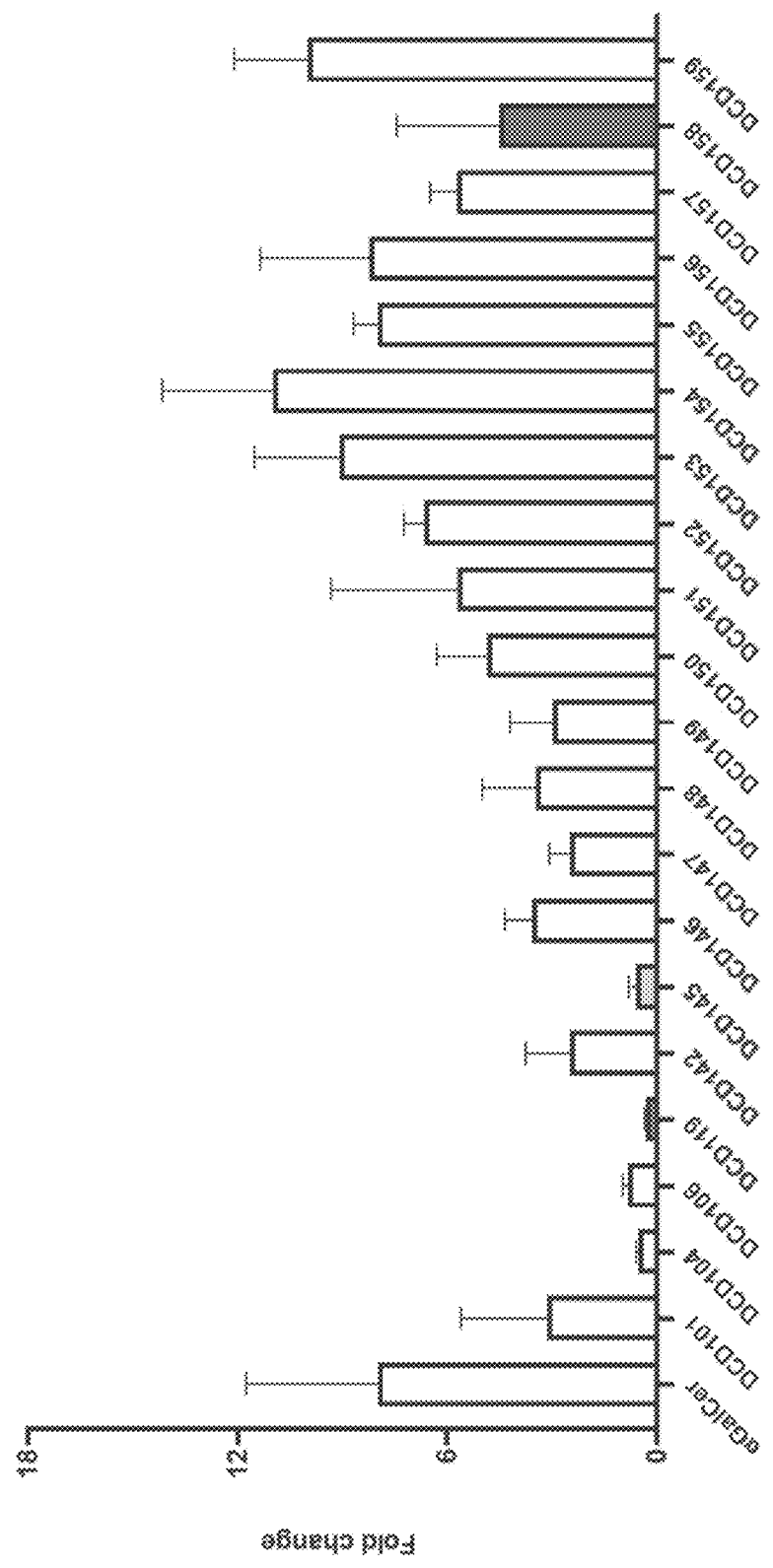
FIG. 4B depicts the expansion of iNKT cells in the C57BL/6J mouse spleen in response to injection of the compounds DCD-101, DCD-104, DCD-106, DCD-119, DCD-142, DCD-145, DCD-146, DCD-147, DCD-148, DCD-149, DCD-150, DCD-151, DCD-152, DCD-153, DCD-154, DCD-155, DCD-156, DCD-157, DCD-158, and DCD-159 with comparison to αGalCer.

FIG. 4B depicts the expansion of iNKT cells in the mouse spleen in response to injection of the compounds DCD-101, DCD-104, DCD-106, DCD-119, DCD-142, DCD-145, DCD-146, DCD-147, DCD-148, DCD-149, DCD-150, DCD-151, DCD-152, DCD-153, DCD-154, DCD-155, DCD-156, DCD-157, DCD-158, and DCD-159 with comparison to α-GalCer.

Conclusions

The average serum IFNγ collected in the DCD-152, DCD-153, DCD-154, DCD-155.

DCD-156, and DCD-157 is all higher than the average serum IFNγ of C57BL/6J mice treated with α-GalCer.

The average iNKT cell isolated from the spleen of C57BL/6J mice treated with DCD-153 or DCD-154 are both higher than mice treated with α-GalCer.

Example 6—Diet Induced Obesity (HFD) Mouse Model Study

Senescence is a feature of pre-adipocytes in obese individuals. To study the efficacy of the molecules described herein in decreasing senescence in fat, a diet induced obesity high fat diet (HFD) mouse model was used. 22-week-old HFD mice were injected with α-GalCer as a control and compared with the compounds of the present disclosure. The blood and spleen (or adipose tissue) were collected to measure iNKT activation and expansion, respectively. Cells in the eWAT (adipose tissue) were also collected and measured for % senescent cells. HFD mice were compared to non-HFD (normal diet) mice.

Methods 22-week-old C57BL/6J mice on a chow or high-fat diet (HFD) were injected (I.P) with 2 µg of α-GalCer, compound DCD-101 or compound DCD-154. Molecules were either dissolved in DMSO at a 5 mg/mL stock solution, or formulated into liposomes through thin-film rehydration, then extrusion through 200 nm filters. Liposome-based formulations were constructed using soy phosphatidylcholine, cholesterol, and DCD or α-GalCer in a 2:1.0.15 ratio. Two or twenty hours post-injection, blood was collected from the tail to measure the level of IFNγ using ELISA. Four days post-injection, mice were sacrificed to collect eWAT or spleen. Spleen was used to measure the number of iNKT cells, and eWAT was used to measure the number of iNKT cells and senescent cells using flow cytometry, iNKT cells were identified in the digested adipose tissue by gating live cells and mouse CD1d-α-GalCer tetramer+ cells. Senescent cells were measured within the processes adipose tissue by selecting mCD45– cells, and C12FDG$^{HIGH}$ cells.

Results

FIG. 5A depicts the expansion of immune cells in the spleen of: 1) mice on a normal diet; 2) mice on a high fat diet injected with diluent; 3) mice on a high fat diet injected with α-GalCer and 4) mice on a high fat diet injected with compound DCD-101. Both α-GalCer and compound DCD-101 caused expansion of immune cells in HFD mouse spleen, at four days post-injection.

Figure 5B:
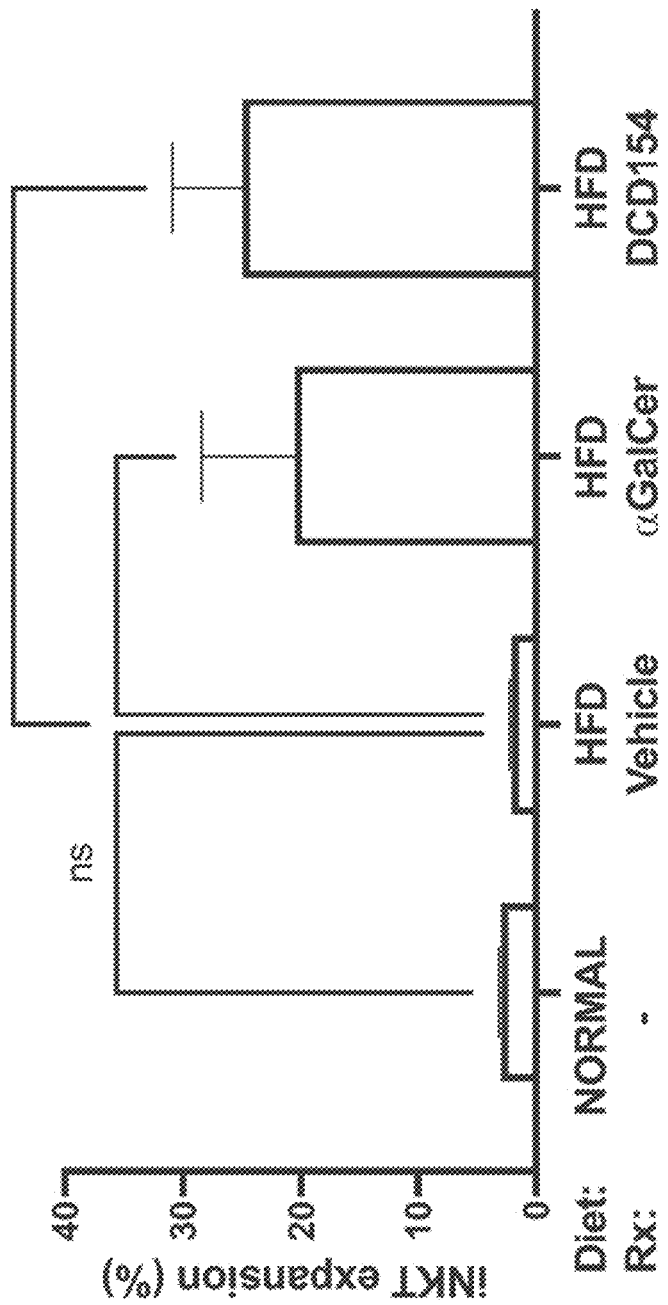
FIG. 5B depicts the expansion of iNKT cells caused by αGalCer or DCD-154 in the HFD mouse model eWAT, as measured by flow cytometry.

FIG. 5B depicts the expansion of immune cells in the eWAT of: 1) mice on a normal diet; 2) mice on a high fat diet injected with diluent; 3) mice on a high fat diet injected with α-GalCer and 4) mice on a high fat diet injected with compound DCD-154 Both α-GalCer and compound DCD- 154 caused expansion of immune cells in HFD mouse eWAT, as measured by flow cytometry of the percent iNKT cells of live cells in the mouse eWAT.

Figure 5C:
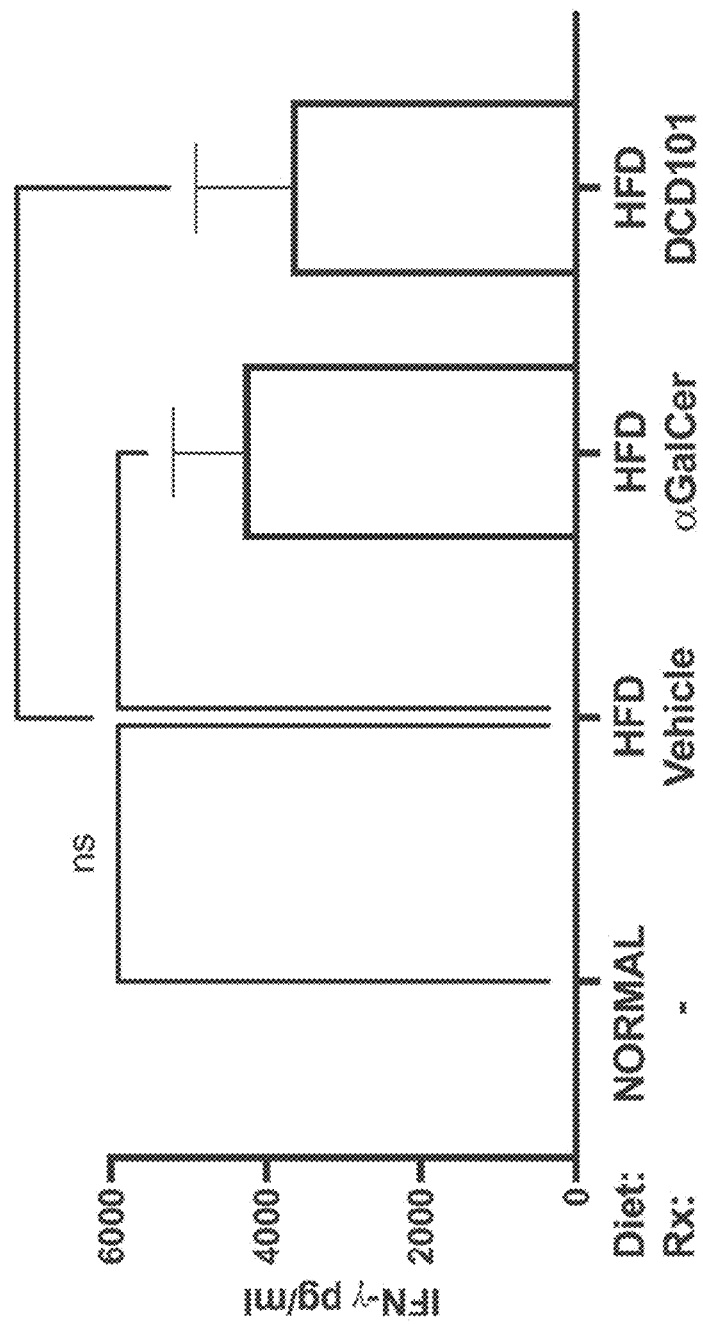
FIG. 5C depicts the amount of IFNγ in blood serum generated in the HFD mouse model in response to αGalCer or DCD-101 two hours after injection.

FIG. 5C depicts the activation of immune cells, as measured by the levels of serum IFNγ using ELISA. Both α-GalCer and DCD-101 significantly increased levels of IFNγ in the HFD model two hours post injection.

Figure 5D:
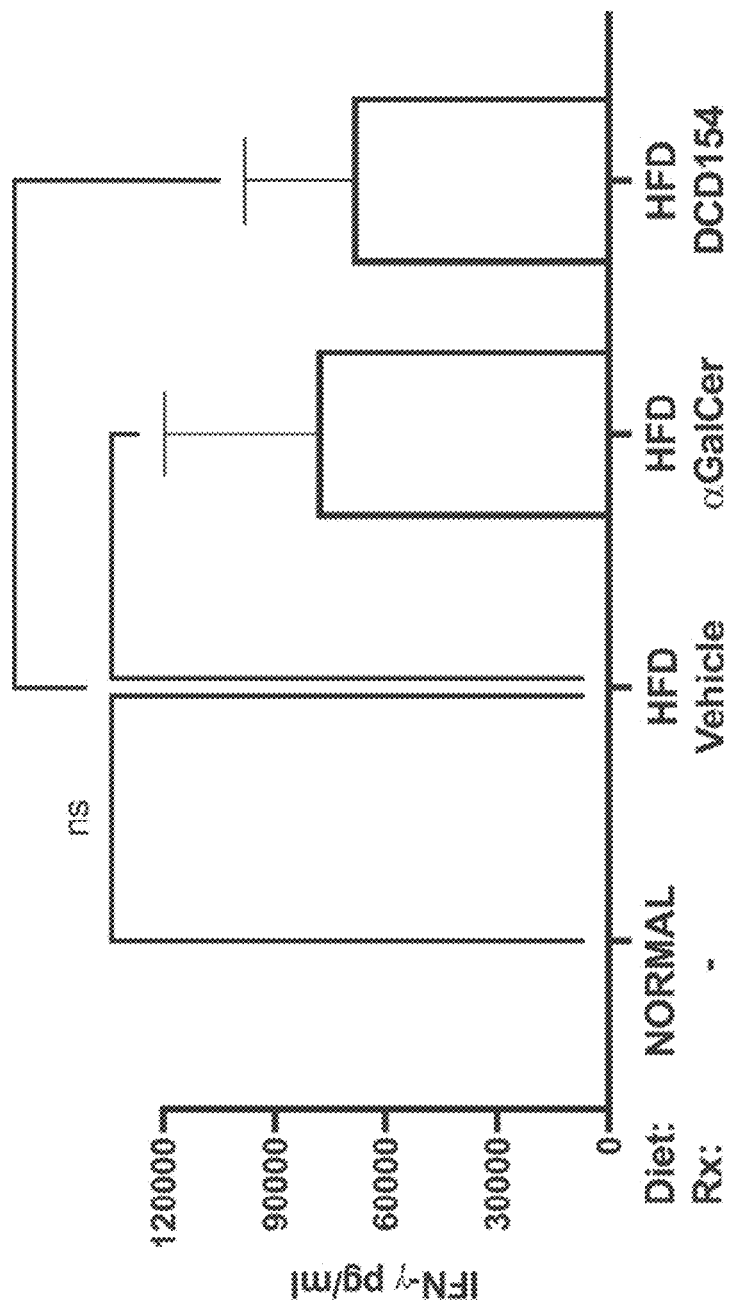
FIG. 5D depicts the amount of IFNγ in blood serum generated in the HFD mouse model in response to αGalCer or DCD-154.20 hours after injection.

FIG. 5D depicts the activation of immune cells, as measured by the secretion of IFNγ using ELISA. Both α-GalCer and DCD-154 significantly increased levels of IFNγ in the HFD model twenty hours post injection.

Figure 5E:
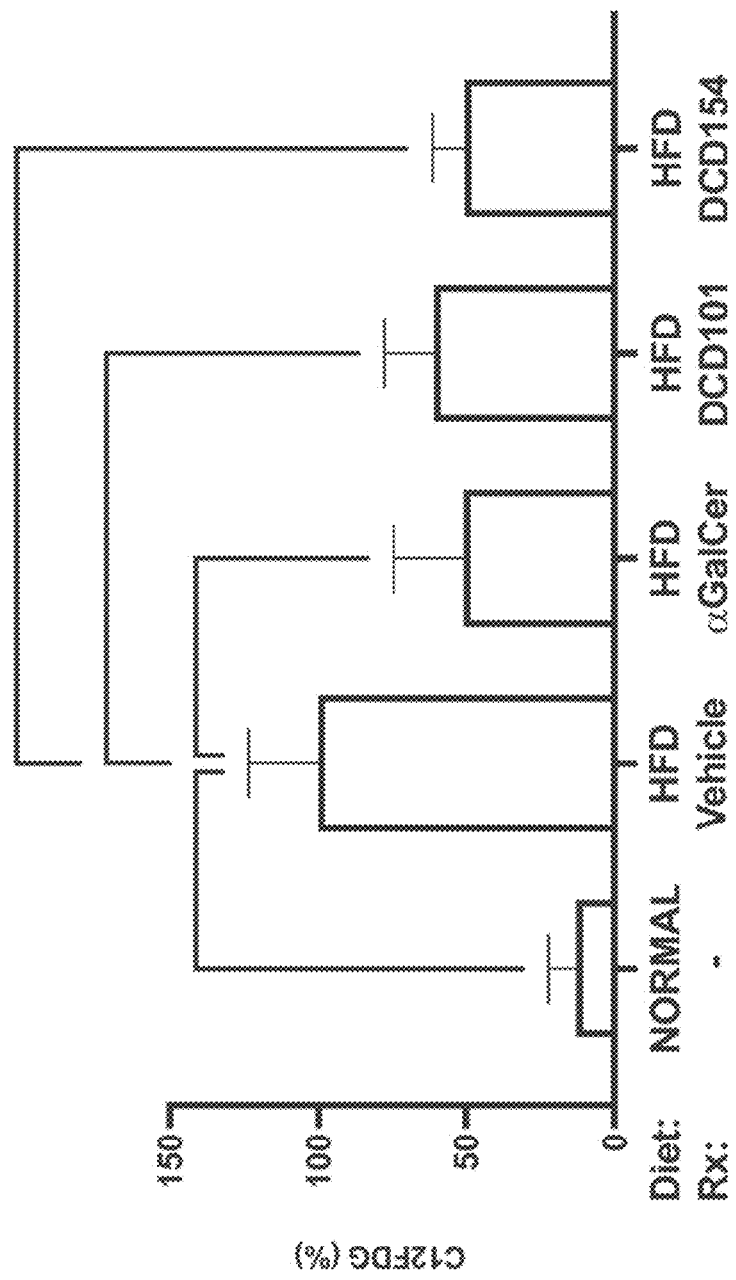
FIG. 5E depicts the reduction in accumulated senescent cells in eWAT in response to treatment with compound DCD-101, DCD-154 and αGalCer. Values were collected from multiple experiments and normalized to the HFD-vehicle condition.

Non-immune C12FDG+ cells from eWAT were identified via flow cytometry. Decrease in the number of C12FDG positive cells indicate a decrease in the number of senescent cells in eWAT. HFD mice treated with DCD-101, DCD-154 and α-GalCer were effective in decreasing the accumulation of senescent cells in eWAT. (FIG. 5E). (**p<0.0001; *P<0.001, **p<0.01)

Conclusions

In the HFD mouse model, DCD-101 and DCD-154 expand iNKT cells in the spleen or adipose tissue respectively, 4 days post-treatment. Both DCD-101 and DCD-154 induce secretion of IFNγ between two and twenty hours post-treatment. Senescent cell reduction in adipose tissue is observed in both DCD-101 and DCD-154.

Example 7—Inactivity of Compounds in In Vitro Studies with Human and Mouse iTCR in Jurkat Reporter and DN3-a4.1.2 iNKT Hybridoma Cell Lines A jurkat cell line (JiNKT) was transfected with the human iTCR, and GFP under the NFKB promoter. A BWS147 cell line (BWSTIM) was also transfected with CD80 and CD1d to act as the antigen-presenting cell. A mouse iNKT hybridoma cell line (DN3.2) was also used as the iNKT. The BWS147 cell line (BWSTIM) with CD80 and CD1d acted as the antigen-presenting cell.

Compounds tested:

1a

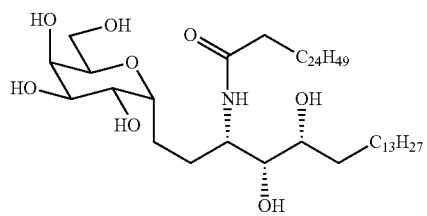

GVK1a

1b

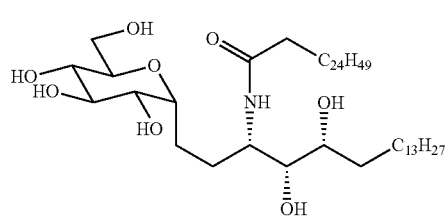

GVK1b

1c

-continued

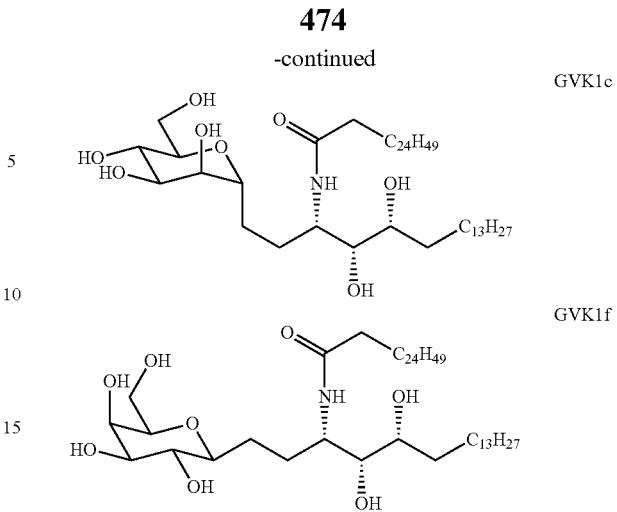

GVK1c

GVK1f

GFP Expression Studies
Methods

GVK molecules or α-GalCer were both dissolved in DMSO at a 5 mg/mL stock solution. BWSTIM cells were loaded with compounds for 4 hours at 37° C. at a concentration of 20 k cells/well in 200 uL of media in a u-bottom 96 well dish. BWSTIM cells were washed 2× with media, then incubated with JiNKT cells at a concentration of 80 k cells/well in a u-bottom 96 well dish. Cells were co-cultured for 24 hours. The percentage of cells expressing high levels of GFP was measured through flow cytometry. 1 ug/mL of molecule GVK1a, GVK1b, GVK1c, or GVK1f was incubated with BWSTIM+JiNKT, and compared to α-GalCer.

Results

As shown in FIG. 6A, compound GVK1a, GVK1b, GVK1c, and GVK1f did not induce GFP expression higher than the negative control, while α-GalCer induction remained high. (****p<0.000)

IL-2 Expression Studies
Methods

GVK molecules or α-GalCer were both dissolved in DMSO at a 5 mg/mL stock solution. BWSTIM cells were loaded with compounds for 4 hours at 37° C. at a concentration of 20 k cells/well in 200 μL of media in a u-bottom 96 well dish. BWSTIM cells were washed 2× with media, then incubated with DN3.2 cells at a concentration of 80 k cells/well in a u-bottom 96 well dish. Cells were co-cultured for 48 hours. Media was collected and IL-2 was measured using the CisBio HTRF ELISA detection kit.

Results

FIG. 6B depicts IL-2 expression by compounds GVK1a, GVK1b and GVK1f in the DN3.2 cell line when loaded on BWSTIM CD1d. As shown in FIG. 6B, each of compounds GVK1b, GVK1d and GVK1f did not induce expression of IL-2. (****p<0.0001)

Cytokine Secretion Studies

In order to determine the activation profile induced by the compounds described herein, primary human iNKT cells were co-cultured with drug-loaded BWSTIM cells.

Methods

GVK molecules or α-GalCer were both dissolved in DMSO at a 5 mg/mL stock solution. BWSTIM cells were loaded with compounds for 4 hours at 37° C. at a concentration of 20 k cells/well in 200 μL of media in a u-bottom 96 well dish. Cells were co-cultured with 100 k 6B11+ selected primary human iNKT cells. Media was collected 2 days later. Cytokines were measured using the Satorious 4 Plex kit on the iQue3 cytometer.

Results

Figure 6C:
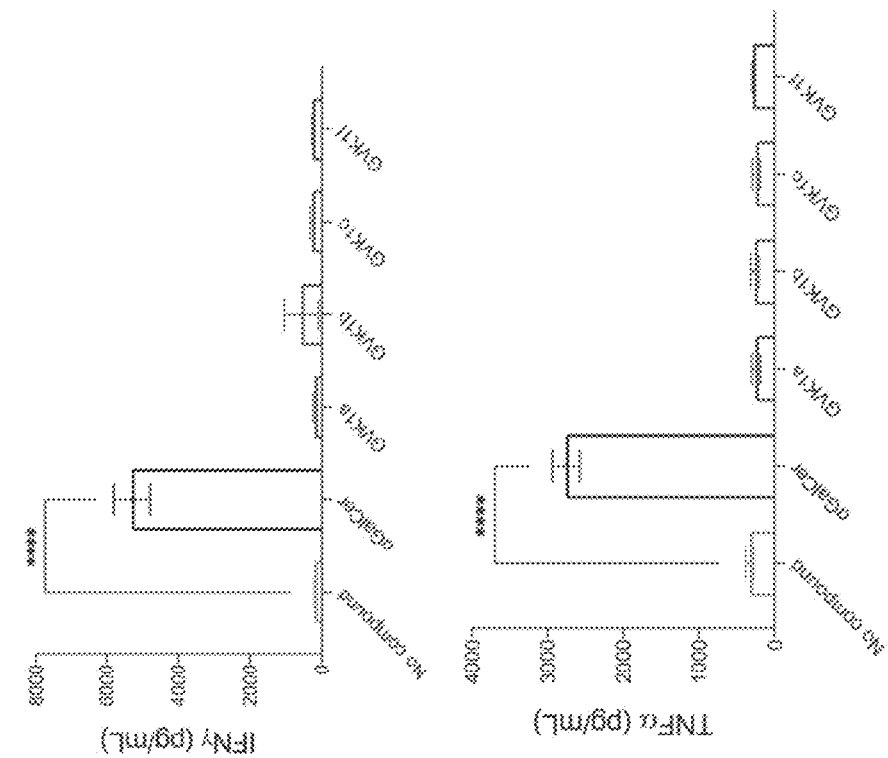
FIG. 6C depicts the secretion of the cytokine interferon gamma (IFNγ), tumor necrosis factor alpha (TNFα), interleukin-4 (IL-4) and interleukin-6 (IL-6) in response to incubation with compounds GVK1a, GVK1b, GVK1c and GVK1f and α-GalCer.
Figure 6C:
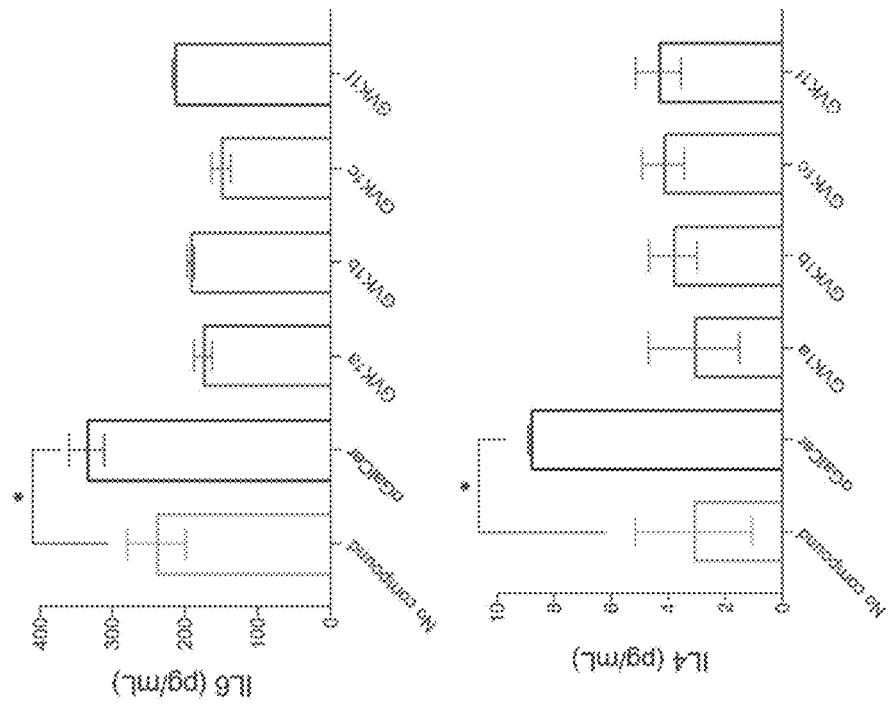

FIG. 6C depicts the secretion of the cytokine interferon gamma (IFNγ), tumor necrosis factor alpha (TNFα), interleukin-4 (IL-4) and interleukin-6 (IL-6) in response to incubation with compounds GVK1a, GVK1b, GVK1c and GVK1f and α-GalCer. The secretion was compared to secretion by cells in the absence of drug loading as a negative control. As shown in FIG. 8F, loading with each of compounds GVK1a, GVK1b, GVK1c and GVK1f did not increase secretion of IFNγ, TNF, IL-4 or IL-6 as compared to cells in the absence of drug loading. Loading with α-GalCer exhibited a significantly greater increase in the secretion of each of IFNγ, TNFα, IL4 or IL-6 as compared with GVK1a GVK1b, GVK1c and GVK1f. (****p<0.0001; *p<0.05)

TABLE 1

Summary of Experiments with Compounds GVK1a, GVK1b, GVK1c and GVK1f

| Compound | % GFP hiNKT binding (BWSTIM + JiNKT) 1 µg/mL | % GFP hiNKT binding (recombinant protein CD1d + JiNKT) | IL-2 Secretion (A20 + DN3.2) | Primary iNKT cytokine release |
|---|---|---|---|---|
| α-GalCer | %40-70 | %30 | | |
| GVK1a | %<5 away from negative control | %<5 away from negative control | Activated DN3.2 to release IL-2 | No activation of primary iNKT to release IL-4, IL-6, IFNγ or TNFα cytokines |
| GVK1b | %<5 away from negative control | %<5 away from negative control | Does not activate DN3.2 to release IL-2 | No activation of primary iNKT to release IL-4, IL-6, IFNγ or TNFα cytokines |
| GVK1c | %<5 away from negative control | %<5 away from negative control | Does not activate DN3.2 to release IL-2 | No activation of primary iNKT to release IL-4, IL-6, IFNγ or TNFα cytokines |
| GVK1f | %<5 away from negative control | %<5 away from negative control | Does not activate DN3.2 to release IL-2 | No activation of primary iNKT to release IL-4, IL-6, IFNγ or TNFα cytokines |

Example 8—Activation of iNKT Cells Selectively Kills Senescent Cells In Vitro

Figure 7B:
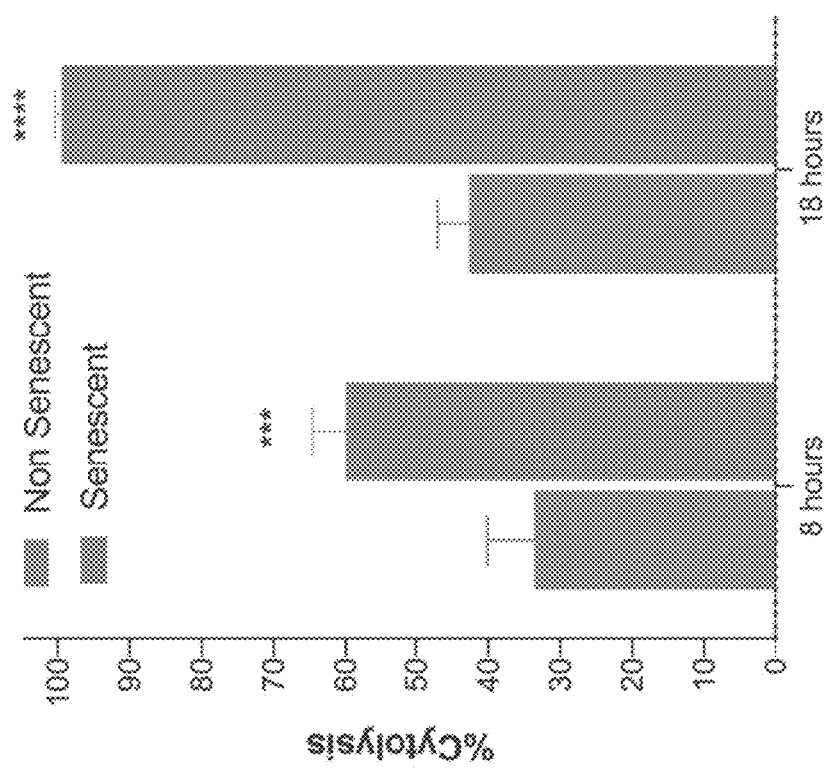
FIG. 7B depicts a comparison between cytolysis of senescent cells and healthy cells by activated iNKT cells after incubation for 8 hours and 18 hours.

Selective reduction in the presence of senescent cells by iNKT mediated killing in an in vitro sample was demonstrated using α-GalCer. Human iNKT cells were isolated and activated by incubation with α-GalCer. Activated iNKT cells were combined with samples containing healthy cells and senescent cells. As shown in FIGS. 7A, incubation of senescent cells with activated iNKT cells resulted in a reduction in the presence of senescent cells over time whereas non-senescent cells were maintained. FIG. 7B demonstrates that senescent cells were selectively killed whereas non-senescent cells were maintained in the presence of activated iNKT cells when evaluated after 8 hours and 18 hours.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future. i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a feature in the claim only when the exact phrase "means for" or the exact phrase "step for" is recited at the beginning of such feature in the claim; if such exact phrase is not used in a feature in the claim, then 35 U.S.C. § 112(f) or 35 U.S.C. § 112(6) is not invoked.

What is claimed is:
1. A compound selected from the group consisting of:
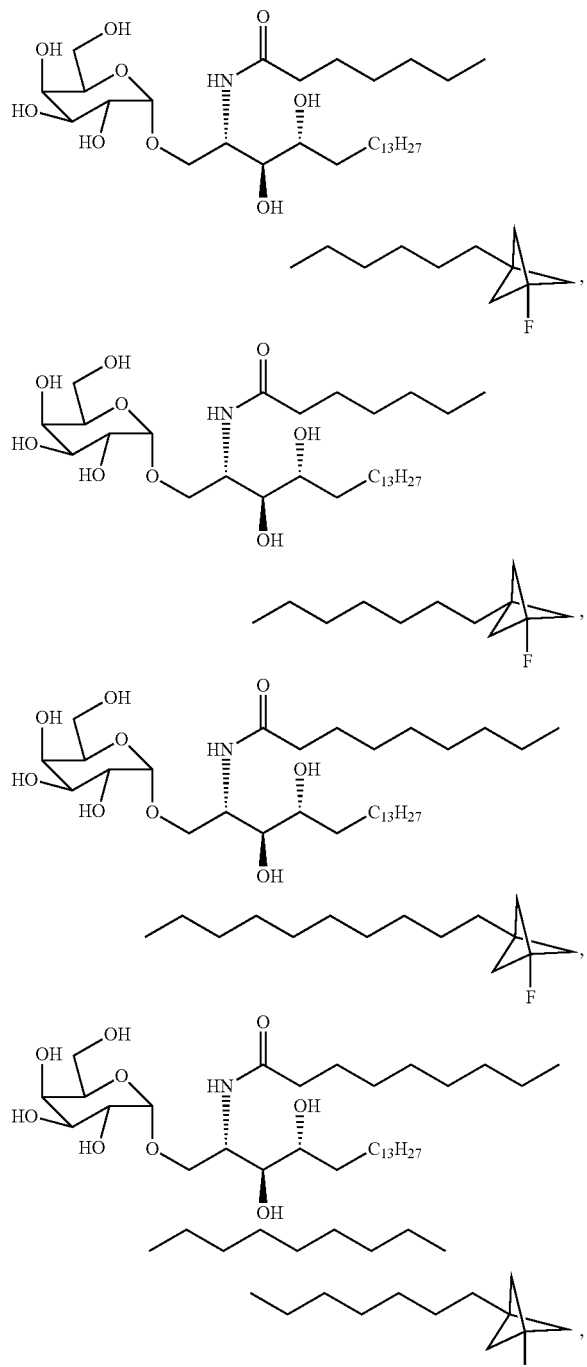
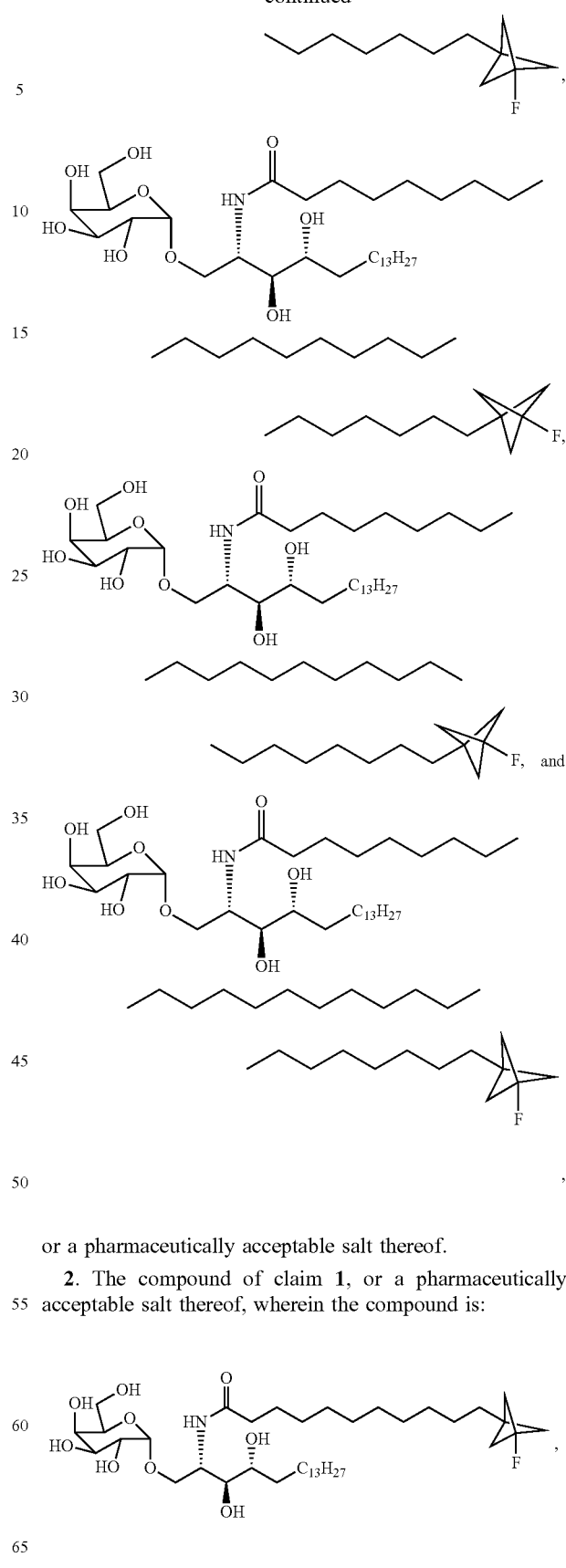
or a pharmaceutically acceptable salt thereof.
2. The compound of claim 1, or a pharmaceutically acceptable salt thereof, wherein the compound is:
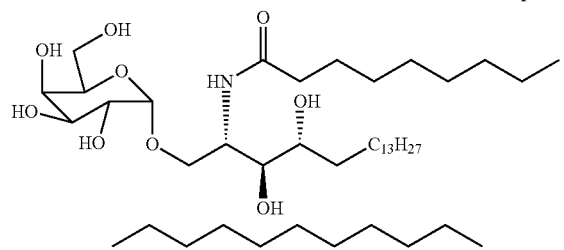
or a pharmaceutically acceptable salt thereof.

3. The compound of claim 1, or a pharmaceutically acceptable salt thereof, wherein the compound is:

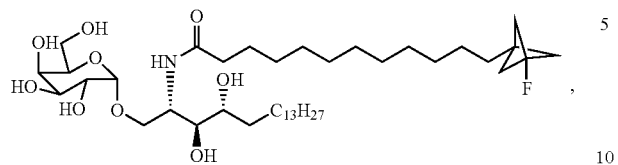

or a pharmaceutically acceptable salt thereof.

4. The compound of claim 1, or a pharmaceutically acceptable salt thereof, wherein the compound is:

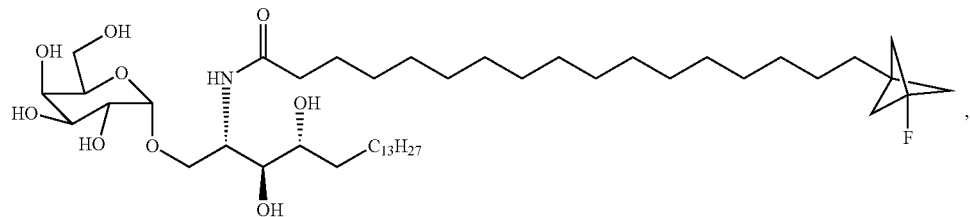

or a pharmaceutically acceptable salt thereof.

5. The compound of claim 1, or a pharmaceutically acceptable salt thereof, wherein the compound is:

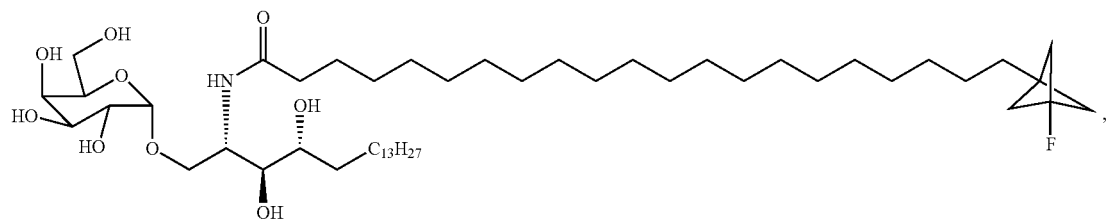

or a pharmaceutically acceptable salt thereof.

6. The compound of claim 1, or a pharmaceutically acceptable salt thereof, wherein the compound is:

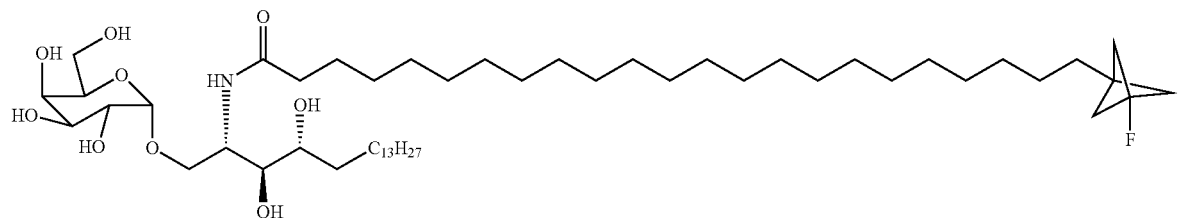

or a pharmaceutically acceptable salt thereof.

7. The compound of claim 1, or a pharmaceutically acceptable salt thereof, wherein the compound is:

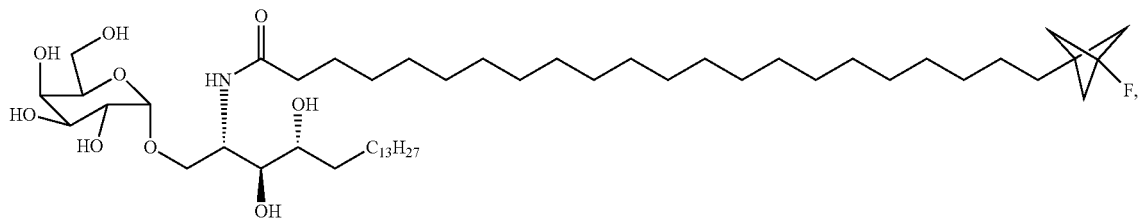

or a pharmaceutically acceptable salt thereof.

8. The compound of claim 1, or a pharmaceutically acceptable salt thereof, wherein the compound is:

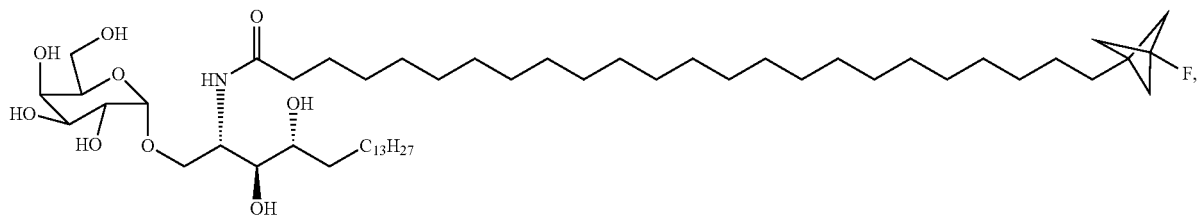

or a pharmaceutically acceptable salt thereof.

9. The compound of claim 1, or a pharmaceutically acceptable salt thereof, wherein the compound is:

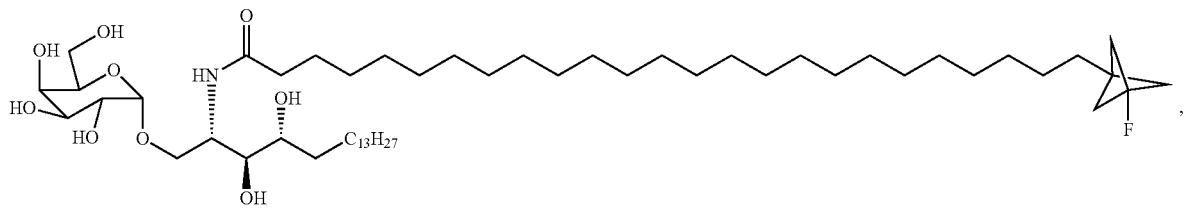

or a pharmaceutically acceptable salt thereof.

10. A pharmaceutical composition, comprising:
    a compound of claim 1, or a pharmaceutically acceptable salt thereof; and
    at least one pharmaceutically acceptable carrier.
11. A pharmaceutical composition, comprising:
    a compound of claim 2, or a pharmaceutically acceptable salt thereof; and
    at least one pharmaceutically acceptable carrier.
12. A pharmaceutical composition, comprising:
    a compound of claim 3, or a pharmaceutically acceptable salt thereof; and
    at least one pharmaceutically acceptable carrier.
13. A pharmaceutical composition, comprising:
    a compound of claim 4, or a pharmaceutically acceptable salt thereof; and
    at least one pharmaceutically acceptable carrier.
14. A pharmaceutical composition, comprising:
    a compound according to claim 5, or a pharmaceutically acceptable salt thereof; and
    at least one pharmaceutically acceptable carrier.
15. A pharmaceutical composition, comprising:
    a compound of claim 6, or a pharmaceutically acceptable salt thereof; and
    at least one pharmaceutically acceptable carrier.
16. A pharmaceutical composition, comprising:
    a compound of claim 7, or a pharmaceutically acceptable salt thereof; and
    at least one pharmaceutically acceptable carrier.
17. A pharmaceutical composition, comprising:
    a compound of claim 8, or a pharmaceutically acceptable salt thereof; and
    at least one pharmaceutically acceptable carrier.
18. A pharmaceutical composition, comprising:
    a compound of claim 9, or a pharmaceutically acceptable salt thereof; and
    at least one pharmaceutically acceptable carrier.

* * * * *